United States Patent
Barrett et al.

(10) Patent No.: US 10,729,810 B2
(45) Date of Patent: *Aug. 4, 2020

(54) METHODS, SYSTEMS, AND COMPOSITIONS FOR PROMOTING BONE GROWTH

(71) Applicants: Cayman Chemical Company, Inc., Ann Arbor, MI (US); Myometrics, LLC, New London, CT (US)

(72) Inventors: Stephen Douglas Barrett, Hartland, MI (US); Joseph Michael Colombo, Ann Arbor, MI (US); Bradlee David Germain, Ann Arbor, MI (US); Andriy Kornilov, Ypsilanti, MI (US); James Bernard Kramer, Sylvania, OH (US); Adam Uzieblo, Farmington Hills, MI (US); Gregory William Endres, Saline, MI (US); Fred Lawrence Ciske, Dexter, MI (US); Thomas Allen Owen, Pompton Plains, NJ (US); James Paul O'Malley, Dunedin (NZ)

(73) Assignees: CAYMAN CHEMICAL COMPANY, INC, Ann Arbor, MI (US); MYOMETRICS LLC, New London, CT (US)

( * ) Notice: Subject to any disclaimer, the term of this patent is extended or adjusted under 35 U.S.C. 154(b) by 926 days.

This patent is subject to a terminal disclaimer.

(21) Appl. No.: 14/905,663

(22) PCT Filed: Jul. 18, 2014

(86) PCT No.: PCT/US2014/047138
§ 371 (c)(1),
(2) Date: Jan. 15, 2016

(87) PCT Pub. No.: WO2015/009991
PCT Pub. Date: Jan. 22, 2015

(65) Prior Publication Data
US 2016/0158413 A1    Jun. 9, 2016

Related U.S. Application Data

(60) Provisional application No. 61/856,370, filed on Jul. 19, 2013, provisional application No. 61/928,843, filed on Jan. 17, 2014.

(51) Int. Cl.
| | | |
|---|---|---|
| A61K 31/4015 | (2006.01) |
| A61K 31/4025 | (2006.01) |
| C07D 207/12 | (2006.01) |
| C07D 207/273 | (2006.01) |
| C07D 207/26 | (2006.01) |
| C07D 409/06 | (2006.01) |
| A61L 27/36 | (2006.01) |
| A61L 27/42 | (2006.01) |
| A61L 27/54 | (2006.01) |
| A61L 27/24 | (2006.01) |

(52) U.S. Cl.
CPC .......... *A61L 27/3608* (2013.01); *A61L 27/24* (2013.01); *A61L 27/365* (2013.01); *A61L 27/425* (2013.01); *A61L 27/54* (2013.01); *A61L 2300/22* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,975,399 A | 8/1976 | DeFranco et al. |
| 4,073,934 A | 2/1978 | Skuballa et al. |
| 4,177,346 A | 12/1979 | Nelson |
| 4,268,522 A | 5/1981 | Eggler et al. |
| 4,456,613 A | 6/1984 | Wang |
| 5,737,437 A | 4/1998 | Nakao et al. |
| 6,043,275 A | 3/2000 | Maruyama et al. |
| 6,462,081 B1 | 10/2002 | Maruyama et al. |
| 6,573,294 B1 | 6/2003 | Old et al. |
| 6,642,266 B2 | 11/2003 | Cameron et al. |
| 6,849,657 B2 | 2/2005 | Elworthy et al. |
| 6,891,062 B2 | 5/2005 | Oida et al. |
| 6,894,175 B1 | 5/2005 | DeLong |
| 7,169,807 B2 | 1/2007 | Donde |

(Continued)

FOREIGN PATENT DOCUMENTS

| | | |
|---|---|---|
| CA | 1085859 | 9/1980 |
| EP | 0046082 B1 | 6/1985 |

(Continued)

OTHER PUBLICATIONS

Okamoto et al. Journal of Bone and Mineral Research, vol. 21, No. 7, 2006, 1022-1033.*

(Continued)

*Primary Examiner* — Julie Wu
*Assistant Examiner* — Douglas F White
(74) *Attorney, Agent, or Firm* — Barnes & Thornburg LLP

(57) ABSTRACT

The present invention relates to novel bone compositions for locally delivering a therapeutic agent to the site of a bone defect. Therapeutic agents may promote repair of the bone defect and/or treat conditions or disorders such as pain, inflammation, cancer, and infection. The compositions include calcium phosphate cements and a demineralized bone matrix or a collagen sponge. The compositions are useful for implantation in a patient at the site of a bone defect.

16 Claims, 6 Drawing Sheets

(56) References Cited

U.S. PATENT DOCUMENTS

| | | |
|---|---|---|
| 7,196,054 B1 | 3/2007 | Drohan et al. |
| 7,208,179 B1 | 4/2007 | Drohan et al. |
| 7,256,211 B1 | 8/2007 | Kambe et al. |
| 7,276,531 B2 | 10/2007 | Araldi et al. |
| 7,402,605 B2 | 7/2008 | Tani et al. |
| 7,410,991 B2 | 8/2008 | Araldi et al. |
| 7,419,999 B2 | 9/2008 | Araldi et al. |
| 7,517,539 B1 | 4/2009 | Lee et al. |
| 7,621,963 B2 * | 11/2009 | Simon ............ A61L 27/56 424/422 |
| 7,652,063 B2 | 1/2010 | Donde |
| 7,683,094 B2 | 3/2010 | Tani et al. |
| 7,754,246 B2 | 7/2010 | Moseley et al. |
| 9,180,116 B2 | 11/2015 | Barrett et al. |
| 9,440,919 B2 | 9/2016 | Barrett et al. |
| 9,487,478 B2 | 11/2016 | Barrett et al. |
| 2001/0047105 A1 | 11/2001 | Cameron et al. |
| 2002/0040149 A1 | 4/2002 | Cameron et al. |
| 2002/0187104 A1 * | 12/2002 | Li ............ A61K 38/02 424/44 |
| 2003/0176479 A1 | 9/2003 | Cameron et al. |
| 2005/0020686 A1 | 1/2005 | Maruyama et al. |
| 2005/0124577 A1 | 6/2005 | Tani et al. |
| 2006/0039949 A1 | 2/2006 | Nycz |
| 2006/0057184 A1 | 3/2006 | Nycz et al. |
| 2006/0167081 A1 | 7/2006 | Billot et al. |
| 2007/0191319 A1 | 8/2007 | Ke et al. |
| 2008/0021021 A1 | 1/2008 | Okada et al. |
| 2008/0234337 A1 | 9/2008 | Kuwahara et al. |
| 2009/0112332 A1 | 4/2009 | Shelokov |
| 2009/0324683 A1 | 12/2009 | Evans et al. |
| 2010/0216689 A1 | 8/2010 | Takigawa et al. |
| 2010/0280250 A1 | 11/2010 | Im et al. |
| 2012/0121660 A1 * | 5/2012 | Akella ............ A61L 24/0063 424/400 |
| 2012/0283293 A1 | 11/2012 | Andreasson |
| 2014/0179606 A1 | 6/2014 | Kanaji et al. |
| 2016/0031811 A1 | 2/2016 | Barrett et al. |
| 2016/0060216 A1 | 3/2016 | Barrett et al. |
| 2016/0340306 A1 | 11/2016 | Barrett et al. |

FOREIGN PATENT DOCUMENTS

| | | |
|---|---|---|
| EP | 0567391 A1 | 10/1993 |
| EP | 1121939 A2 | 8/2001 |
| EP | 0878465 B1 | 7/2003 |
| EP | 1348451 A1 | 10/2003 |
| GB | 1553595 A1 | 10/1979 |
| GB | 1583163 A1 | 1/1981 |
| JP | 2009137977 A | 6/2009 |
| JP | 2012523853 A | 10/2012 |
| KR | 10-2006-0013354 A | 2/2006 |
| WO | WO 96/14335 A1 | 5/1996 |
| WO | WO 2001/046140 A1 | 6/2001 |
| WO | WO 2002/024647 A1 | 3/2002 |
| WO | WO 2002/042268 A2 | 5/2002 |
| WO | WO 2003/007941 A1 | 1/2003 |
| WO | WO 2003/008377 A1 | 1/2003 |
| WO | WO 2003/047417 A2 | 6/2003 |
| WO | WO 2003/047513 A2 | 6/2003 |
| WO | WO 2003/077910 A1 | 9/2003 |
| WO | WO 2003/103604 A2 | 12/2003 |
| WO | WO 2004/037786 A2 | 5/2004 |
| WO | WO 2005/032461 A2 | 4/2005 |
| WO | WO 2006/130455 A2 | 12/2006 |
| WO | WO 2007/030616 A2 | 3/2007 |
| WO | WO 2009/055289 A2 | 4/2009 |
| WO | WO 2010/011599 A2 | 1/2010 |
| WO | WO 2010/025135 A2 | 3/2010 |
| WO | WO 2011/003058 A1 | 1/2011 |
| WO | WO 2011/127149 A1 | 10/2011 |
| WO | WO 2012/058042 A2 | 5/2012 |
| WO | WO 2012/063207 A1 | 5/2012 |
| WO | WO 2013/018837 A1 | 2/2013 |
| WO | WO 2014/015246 A1 | 1/2014 |
| WO | WO 2014/015247 A1 | 1/2014 |

OTHER PUBLICATIONS

Arisan, V., et al., "Injectable calcium phosphate cement as a bone-graft material around peri-implant dehiscence defects: a dog study," Int J Oral Maxillofac Implants, Nov.-Dec. 2008; 23(6):1053-62.

Aspenberg, P., et al., "Fibroblast growth factor stimulates bone formation. Bone induction studied in rats," Acta orthopaedica Scandinavica, 1989, 60(4):473-6.

Ballantyne, J.C., et al., "Bone Cancer Pain," IASP Pain Clinical Updates, vol. XVII, Issue 2, 6 pages (Jun. 2009).

Benghuzzi, Ham, et al., "The effects of sustained delivery of estrogen and demineralized bone matrix proteins on bone in ovariectomized female rats," Biomedical Sciences Instrumentation 2013, 49:85-93. (Abstract only).

Billot, X. et al. "Discovery of a Potent and Selective Agonist of the Prostaglandin EP4 Receptor," Biorganic & Medicinal Chemistry Letters, 2003, 13, 1129-1132.

Bodei, Lisa, et al., "EANM procedure guideline for treatment of refractory metastatic bone pain," Eur J Nucl Med Mol Imaging, 7 pages (2008).

Brochure: "Comprehensive Bone Regeneration Solutions," BioHorizons Science Innovation Service, 2009, www.biohorizons.com, 12 pgs.

Brochure: "JRF STIMUBLAST™ Demineralized Bone Matrix," Arthrex Inc., 2011, http://biologics.arthrex.com, 6 pgs.

Brochure: "Managing Pain Related to Cancer and Bone," A Publication of The Bone and Cancer Foundation, 7 pages (2011).

Brömme, Dieter, et al., "Cathepsin K Inhibitors for osteoporosis and potential off-target effects," Expert Opin Investig Drugs, 18(5):585-600 (2009).

Cameron, K.O. et al. "Discovery of Highly Selective EP4 Receptor Agonists That Stimulate New Bone Formation and Restore Bone Mass in Ovariectomized Rats," Biorganic & Medicinal Chemistry Letters, 2006, 16, 1799-1802.

Chen, Lei, et al., "Loading of VEGF to the heparin cross-linked demineralized bone matrix improves vascularization of the scaffold," Journal of Materials Science: Materials in Medicine, 2010, 21(1):309-317.

Chow, L.C., et al., "A dual constant-composition titration system as an in vitro resorption model for comparing dissolution rates of calcium phosphate biomaterials," J Biomed Mater Res B Appl Biomater, May 15, 2003; 65(2):245-51.

Clokie Cameron, M.L., et al., "Closure of critical sized defects with allogenic and alloplastic bone substitutes," The Journal of craniofacial surgery, 2002, 13(1):111-21, discussion 122-3.

Constantz, B.R., et al., "Histological, chemical, and crystallographic analysis of four calcium phosphate cements in different rabbit osseous sites," J Biomed Mater Res., 1998 Winter; 43(4):451-61.

Davies, J.E., "Bone bonding at natural and biomaterial surfaces," Biomaterials, Dec. 2007; 28(34):5058-67, Epub Aug. 13, 2007.

Doi, Y., et al., "Development of a new calcium phosphate cement that contains sodium calcium phosphate," Biomaterials, Apr. 2001; 22(8):847-54.

Dorozhkin, S.V. et al. "Calcium Orthophsphate Cements and Concretes," Materials, 2009, 2, 221-291.

Duarte, Afonso M.S., et al., "Tracking Down a New Putative Drug Target for Osteoporosis: Structure of an Essential Region of the Proton Translocation Channel of $H^+$-Vo-ATPase," Chapter XV in Antibiotic Resistance . . . , Nova Science Publishers, Inc., Editors: A.R. Bonilla and K.P. Muniz, pp. 345-369 (2009).

Elsner, A., et al., "Augmentation of intraarticular calcaneal fractures with injectable calcium phosphate cement: densitometry, histology, and functional outcome of 18 patients," J Foot Ankle Surg, Sep.-Oct. 2005; 44(5):390-5.

Elworthy, T.R. et al. "Lactams as EP4 Prostanoid Receptor Agonists. 3. Discovery of N-Ethylbenzoic Acid 2-Pyrrolidinones as Subtype Selective Agents," J. Med. Chem., 2004, 20, 6124-6127.

(56) References Cited

OTHER PUBLICATIONS

Elworthy, T.R. et al. "Lactams as EP4 Prostanoid Receptor Subtype Selective Agonists. Part 1: 2-Pyrrolidinones-Stereochemical and Lower Side-Chain Optimization," Biorganic & Medicinal Chemistry Letters, 2004, 14, 1655-1659.
Elworthy, T.R. et al. "Lactams as Prostanoid Receptor Ligands. Part 4: 2-Piperidones as Selective EP4 Receptor Agonists," Biorganic & Medicinal Chemistry Letters, 2005, 15, 2523-2526.
Espanol, M. et al. "Intrinsic Porosity of Calcium Phosphate Cements and Its Significance for Drug Delivery and Tissue Engineering Applications," Acta Biomaterialia, 2009, 5, 2752-2762.
Frankenburg, E.P., et al., "Biomechanical and histological evaluation of a calcium phosphate cement," J Bone Joint Surg Am., Aug. 1998; 80(8):1112-24.
Fukuyama, T., et al., "Effects of alpha-DT cement with hydroxypropyl cellulose on bone augmentation within a titanium cap in the rabbit calvarium," Dent Mater J., Mar. 2010; 29(2):160-6.
Fustero, S. et al. "A New Tandem Cross Metathesis-Intramolecular Aza-Michael Reaction for the Synthesis of α,α-Difluorinated Lactams," Synthesis, 2012, 44, 1863-1873.
Galjour, Chris, et al., "Stimulation of fracture healing by continuous delivery of demineralized bone matrix proteins and tobramycin," Biomedical Sciences Instrumentation, 2005, 41:122-127.
Ginebra, M.P. et al. "Calcium Phosphate Cements as Bone Drug Delivery Systems: A Review," J. Controlled Release, 2006, 113, 102-110.
Ginebra, M-P. et al. "Calcium Phosphate Cements: Competitive Drug Carriers for the Musculoskeletal System?" Biomaterials, 2006, 27, 2171-2177.
Goff, Thomas, et al., "Use of bone graft substitutes in the management of tibial plateau fractures," Injury, 2013, 44 Suppl 1S86-94.
Gombotz, Wayne R., et al., "Controlled release of TGF-β1 from a biodegradable matrix for bone regeneration," Journal of Biomaterials Science, Polymer Edition, 1993, 5(1-2):49-63.
Gowri, Sindhu, "Use of Calcium Phosphate Bone Cement for Fracture Fixations in Osteoporotic Patients," San Jose State University, 21 pages, downloaded from internet Jul. 3, 2013.
Haddad, Albert J., et al., "Closure of rabbit calvarial critical-sized defects using protective composite allogeneic and alloplastic bone substitutes," The Journal of craniofacial surgery, 2006, 17(5):926-34.
Hannink, G., et al., "In vivo behavior of a novel injectable calcium phosphate cement compared with two other commercially available calcium phosphate cements," J Biomed Mater Res B Appl Biomater, May 2008; 85(2):478-88.
Hayashi, K. et al. "Effect of a Prostaglandin EP4 Receptor Agonist on Early Fixation of Hydroxyapatite/Titanium Composite- and Titanium-Coated Rough-Surfaced Implants in Ovariectomized Rats," J. Biomedical Materials Research Part A, 2009, 1202-1209.
Hayashi, K. et al. "Prostaglandin EP4 Receptor Agonist Augments Fixation of Hydroxyapatite-Coated Implants in a Rat Model of Osteoporosis," J. Bone and Joint Surgery, 2005, 87-B, 1150-1156.
He, Jie, et al., "Injectable compound scaffold of fibrin gel/demineralized bone matrix to delay early osteoarthritis in rabbits," Zhongguo Zuzhi Gongcheng Yanjiu Yu Linchuang Kangfu, 2010, 14(29):5334-5338. (Abstract only).
Heinemann, S., et al., "Bioactive silica-collagen composite xerogels modified by calcium phosphate phases with adjustable mechanical properties for bone replacement," Acta Biomater, Jul. 2009; 5(6):1979-90, doi: 10.1016/j.actbio.2009.02.029, Epub Feb. 28, 2009.
Hertzberg, Brian P., et al., "An evaluation of carrier agents for desferoxamine, an up-regulator of vascular endothelial growth factor," Journal of biomaterials applications, 2013, 27(8):1046-54.
Holt, Dolly J., et al., "Demineralized bone matrix as a vehicle for delivering endogenous and exogenous therapeutics in bone repair," Advanced Drug Delivery Reviews, 2012, 64(12):1123-1128.
Hu, K-Z et al., "SmI2-Mediated Intermolecular Coupling of γ-Lactam N-α-Radicals with Activated Alkenes: Asymmetric Synthesis of 11-Hydroxylated Analogues of the Lead Compounds CP-734432 and PF-04475270," J. Org. Chem., 2013, 78, 1790-1801.
International Preliminary Report on Patentability for International Patent Application No. PCT/US2014/047138, dated Jan. 19, 2016 (10 pages).
International Search Report and Written Opinion for corresponding International Patent Application No. PCT/US2013/051263, dated Oct. 2, 2013 (10 pages).
International Search Report and Written Opinion for corresponding International Patent Application No. PCT/US2014/029093, dated Jun. 30, 2014 (9 pages).
International Search Report and Written Opinion for International Patent Application No. PCT/US2014/029057, dated Sep. 17, 2014 (9 pages).
Iwaniec, U.T. et al. "A Comparative Study of the Bone-Restorative Efficacy of Anabolic Agents in Aged Ovariectomized Rats," Osteoporos. Int., 2007, 18, 351-362.
Kambe, T. et al. "Synthesis and Evaluation of γ-lactam Analogs of PGE2 as EP4 and EP2/EP4 Agonists," Bioorganic & Medicinal Chemistry, 2012, 20, 3502-3522.
Kim, H., et al., "In vivo bone tissue formation induced by calcium phosphate paste composite with demineralized bone matrix," Key Engineering Materials, 2007, 330-332(Pt. 2, Bioceramics):1091-1094.
Kim, J.S., et al., "Titanium-reinforced Polytetrafluoroethylene Membrane Combined With Inorganic Polyphosphate Induces Exophytic Bone Formation in Rabbit Calvaria," Key Engineering Materials, vols. 330-332, pp. 1075-1078 (2007).
Kim, Young-Woo, et al., "Effect of saline solution on the development of compressive strength in apatite based bone cement containing demineralized bone matrix," Key Engineering Materials, 2009, 396-398(Bioceramics 21):229-232.
Kimoto, T., et al., "Continuous administration of basic fibroblast growth factor (FGF-2) accelerates bone induction on rat calvaria—an application of a new drug delivery system," Journal of Dental Research, 1998, 77(12):1965-1969.
Knepper-Nicolai, B., et al., "Influence of osteocalcin and collagen I on the mechanical and biological properties of Biocement D," Biomol Eng., Aug. 2002; 19(2-6):227-31.
Kobayashi, N., et al., "Histological and mechanical evaluation of self-setting calcium phosphate cements in a sheep vertebral bone void model," J Biomed Mater Res A, Jun. 15, 2007; 81(4):838-46.
Kuang, G.M., et al., "An effective approach by a chelate reaction in optimizing the setting process of strontium-incorporated calcium phosphate bone cement," J Biomed Mater Res B Appl Biomater, Apr. 2012; 100(3):778-87, doi: 10.1002/jbm.b.32511, Epub Feb. 14, 2012.
Kuemmerle, J.M., et al., "Assessment of the suitability of a new brushite calcium phosphate cement for cranioplasty—an experimental study in sheep," J Craniomaxillofac Surg., Feb. 2005; 33(1):37-44, Epub Jan. 11, 2005.
Ladd, A.L., et al., "Use of bone-graft substitutes in distal radius fractures," The Journal of the American Academy of Orthopaedic Surgeons, 1999, 7(5):279-90.
Lanao, RP Félix, et al., "RANKL delivery from calcium phosphate containing PLGA microspheres," J Biomed Mater Res A Nov. 25, 2013; 101(11):3123-30. Epub Mar. 25, 2013, doi: 10.1002/jbm.a.34623.
Le Nihouannen, D., et al., "Bioactivity of bone resorptive factor loaded on osteoconductive matrices: stability post-dehydration," Eur J Pharm Biopharm, Nov. 2008; 70(3):813-8, doi: 10.1016/j.ejpb.2008.07.018, Epub Aug. 14, 2008.
Le Nihouannen, D., et al., "The use of RANKL-coated brushite cement to stimulate bone remodeling," Biomaterials, Aug. 2008; 29(22):3253-9, doi: 10.1016/j.biomaterials.2008.03.035, Epub May 1, 2008.
Lee, K.-Y., et al., "Preparation of calcium phosphate paste composites with demineralized bone matrix," Key Engineering Materials, 2007, 330-332(Pt. 2, Bioceramics):803-806.
Li, B-H. et al. "Rational and Practical Synthesis of α,α-difluoro-γ-lactams," J. Fluorine Chemistry, 2012, 133, 163-166.
Li, D., et al., "A histological evaluation on osteogenesis and resorption of methotrexate-loaded calcium phosphate cement in vivo," Biomed Mater, Apr. 2010; 5(2):25007, doi: 10.1088/1748-6041/5/2/025007, Epub Mar. 25, 2010.

(56) References Cited

OTHER PUBLICATIONS

Li, M. et al. "Prostaglandin E2 Receptors in Bone Formation," International Orthopaedics, 2007, 31, 767-772.
Li, Qiang, et al., "Vascular Endothelial Growth Factor Release from Alginate Microspheres Under Simulated Physiological Compressive Loading and the Effect on Human Vascular Endothelial Cells," Tissue Engineering, Part A, 2011, 17(13 and 14): 1777-1785.
Lucas, P.A., et al., "Ectopic induction of cartilage and bone by water-soluble proteins from bovine bone using a polyanhydride delivery vehicle," Journal of biomedical materials research, 1990, 24(7):901-11.
Lucas, Paul A., et al., "Ectopic induction of cartilage and bone by water-soluble proteins from bovine bone using a collagenous delivery vehicle," Journal of Biomedical Materials Research, 1989, 23(Suppl. A1):23-39.
Ma, Y., et al., "In vivo osteogenic functions of injectable biological bone cement," Zhonghua Yi Xue Za Zhi, Jun. 21, 2011; 91(23):1649-53.
Mancini, Isabelle, et al., "Efficacy and Safety of Ibandronate in the Treatment of Opioid-Resistant Bone Pain Associated with Metastatic Bone Disease: A Pilot Study," J Clin Oncol 22(17):3587-3592 (2004).
Marie, Pierre J., et al., "Osteoblasts in osteoporosis: past, emerging, and future anabolic targets," European Journal of Endocrinology, 165:1-10 (2011).
Marks, Tyler, et al., "Histological and radiographic comparison of allograft substitutes using a continuous delivery model in segmental defects," Biomedical sciences instrumentation, 2007, 43194-9. (Abstract only).
Maruyama, T. et al. "Design and Synthesis of a Highly Selective EP4-Receptor Agonist. Part 1: 3,7-DithiaPG Derivatives With High Selectivity," Bioorganic & Medicinal Chemistry Letters, 2001, 11, 2029-2031.
Maruyama, T. et al. "Design and Synthesis of a Highly Selective EP4-Receptor Agonist. Part 2: 5-Thia and 9β-HaloPG Derivatives With Improved Stability," Bioorganic & Medicinal Chemistry Letters, 2001, 11, 2033-2035.
Maruyama, T. et al. "Design and Synthesis of a Selective EP4-Receptor Agonist. Part 1: Discovery of 3,7-DithiaPGE1 Derivatives and Identification of Their ω Chains," Bioorganic & Medicinal Chemistry, 2002, 10, 975-988.
Maruyama, T. et al. "Design and Synthesis of a Selective EP4-Receptor Agonist. Part 2: 3,7-DithiaPGE1 Derivatives With High Selectivity," Bioorganic & Medicinal Chemistry, 2002, 10, 989-1008.
Maruyama, T. et al. "Design and Synthesis of a Selective EP4-Receptor Agonist. Part 3: 16-Phenyl-5thiaPGE1 and 9-β-Halo Derivatives With Improved Stability," Bioorganic & Medicinal Chemistry, 2002, 10, 1743-1759.
Maruyama, T. et al. "Design and Synthesis of a Selective EP4-Receptor Agonist. Part 4: Practical Synthesis and Biological Evaluation of a Novel Highly Selective EP4-Receptor Agonist," Bioorganic & Medicinal Chemistry, 2002, 10, 2103-2110.
McMillan, J., et al., "Osteoinductivity of demineralized bone matrix in immunocompromised mice and rats is decreased by ovariectomy and restored by estrogen replacement," Bone (San Diego, CA, United States), 2007, 40(1):111-121.
Millard, Melissa, et al., "Integrin Targeted Therapeutics," Theranostics, 1:154-188 (2011).
Miyamoto, Y., et al., "Tissue response to fast-setting calcium phosphate cement in bone," J Biomed Mater Res., Dec. 15, 1997; 37(4):457-64.
Moghadam, Hassan G., et al., "Histomorphometric evaluation of bone regeneration using allogeneic and alloplastic bone substitutes," Journal of oral and maxillofacial surgery : official journal of the American Association of Oral and Maxillofacial Surgeons, 2004, 62(2):202-13.
Montazerolghaem, Maryam, et al., "Sustained release of simvastatin from premixed injectable calcium phosphate cement," J Biomed Mater Res Part A 2013: 00A:000-000.

Nair S.K. et al. "Novel Synthesis of CP-734432, an EP4 Agonist, Using Sharpless Asymmetric Dihydroxylation," Tetrahedron Letters, 2010, 51, 1451-1454.
Nakagawa, K. et al. "Prostaglandin E2 EP4 Agonist (ONO-4819) Accelerates BMP-induced Osteoblastic Differentiation," Bone, 2007, 41, 543-548.
Namikawa, T., et al., "Enhancing effects of a prostaglandin EP4 receptor agonist on recombinant human bone morphogenetic protein-2 mediated spine fusion in a rabbit model," SPINE, 32(21):2294-2299 (2007).
Nyman, Jonas, "Potential of the Osteoclast's Proton Pump as a Drug Target in Osteoporosis," Turun Yliopisto, University of Turku, 84 pages (2011).
Offer, L., et al., "Phosphoserine-modified calcium phosphate cements: bioresorption and substitution," J Tissue Eng Regen Med, Jan. 2011; 5(1):11-9, doi: 10.1002/term.283.
Oh, S.A., et al., "Osteoclastic cell behaviors affected by the α-tricalcium phosphate based bone cements," J Mater Sci Mater Med, Nov. 2010; 21(11):3019-27, doi: 10.1007/s10856-010-4152-z, Epub Sep. 21, 2010.
Ooms, E.M., et al., "Histological evaluation of the bone response to calcium phosphate cement implanted in cortical bone," Biomaterials, Mar. 2003; 24(6):989-1000.
Ooms, E.M., et al., "Trabecular bone response to injectable calcium phosphate (Ca-P) cement," J Biomed Mater Res., Jul. 2002; 61(1):9-18.
Orlovskii, V.P. et al. "Hydroxyapatite and Hydroxyapatite-Based Ceramics," Inorganic Materials, 2002, 38, 973-984.
Panzavolta, S., et al., "Alendronate and Pamidronate calcium phosphate bone cements: setting properties and in vitro response of osteoblast and osteoclast cells," J Inorg Biochem, Jan. 2009; 103(1):101-6, doi: 10.1016/j.jinorgbio.2008.09.012, Epub Oct. 1, 2008.
Panzavolta, S., et al., "Functionalization of biomimetic calcium phosphate bone cements with alendronate," J Inorg Biochem, Oct. 2010; 104(10):1099-106, doi: 10.1016/j.jinorgbio.2010.06.008, Epub Jun. 26, 2010.
Pinholt, E.M., et al., "Bone induction by composites of bioresorbable carriers and demineralized bone in rats: a comparative study of fibrincollagen paste, fibrin sealant, and polyorthoester with gentamicin," Journal of oral and maxillofacial surgery : official journal of the American Association of Oral and Maxillofacial Surgeons, 1992, 50(12): 1300-4.
Prasanna, G. et al. "Ocular Pharmacokinetics and Hypotensive Activity of PF-04475270, an EP4 Prostaglandin Agonist in Preclinical Models," Experimental Eye Research, 2009, 89, 608-617.
Prisell, P.T., et al., "Insulin-like growth factor I increases bone formation in old or corticosteroid treated rats," Acta orthopaedica Scandinavica, 1997, 68(6):586-92.
Qiang, Ya-Wei, et al., "Bortezomib induces osteoblast differentiation via Wnt-independent activation of β-catenin/TCF signaling," Blood, 113:4319-4330 (2009).
Rochet, N., et al. "Differentiation and activity of human preosteoclasts on chitosan enriched calcium phosphate cement," Biomaterials. Sep. 2009, 30(26):4260-7, doi: 10.1016/j.biomaterials.2009.04.044, Epub May 23, 2009.
Rosenberg, A., et al., "In vitro and in vivo evaluation of a calcium phosphate and demineralized bone matrix composite biomaterial," Journal of Biomimetics, Biomaterials, and Tissue Engineering, 2010, 5:1-12.
Saeki, T. et al. "Effects of Prostanoid EP Agonists on Mouse Intraocular Pressure," IOVS, 2009, 50, 2201-2208.
Schilling, A.F., et al., "Resorbability of bone substitute biomaterials by human osteoclasts," Biomaterials, Aug. 2004; 25(18):3963-72.
Schneiders, W., et al., "Effect of chondroitin sulphate on material properties and bone remodelling around hydroxyapatite/collagen composites," J Biomed Mater Res A, Jun. 1, 2008; 85(3):638-45.
Schneiders, W., et al., "In vivo effects of modification of hydroxyapatite/collagen composites with and without chondroitin sulphate on bone remodeling in the sheep tibia," J Orthop Res, Jan. 2009; 27(1):15-21, doi: 10.1002/jor.20719.
Sheraly, A.R., et al., "Use of gastrointestinal proton pump inhibitors to regulate osteoclast-mediated resorption of calcium phosphate cements in vivo," Curr Drug Deliv., Apr. 2009; 6(2):192-8.

(56) References Cited

OTHER PUBLICATIONS

Smartt, J.M., Jr., et al., "Repair of the immature and mature craniofacial skeleton with a carbonated calcium phosphate cement: assessment of biocompatibility, osteoconductivity, and remodeling capacity," Plast Reconstr Surg., May 2005; 115(6):1642-50.
Smith, R.L. et al. "Prostaglandin Isosteres. 1. (8-Aza-, 8,10-Diaza-, and 8-Aza-11-thia)-9-oxoprostanoic Acids and Their Derivatives," J. Med. Chem., 1977, 20, 1292-1299.
Sugawara, A., et al., "Histological analysis of calcium phosphate bone grafts for surgically created periodontal bone defects in dogs," Dent Mater J., Nov. 2008; 27(6):787-94.
Sun, L., "Fast setting calcium phosphate cement-chitosan composite: mechanical properties and dissolution rates," J Biomater Appl, Jan. 2007; 21(3):299-315, Epub Mar. 16, 2006.
Tanaka, Masahiro, et al., "Prostaglandin $E_2$ receptor (EP4) selective agonist (ONO-4819.CD) accelerates bone repair of femoral cortex after drill-hole injury associated with local upregulation of bone turnover in mature rats," Bone 34:940-948 (2004).
Tofighi, Aliassghar, "Calcium phosphate bone cement (CPBC): development, commercialization and future challenges," Key Engineering Materials, 2012, 493-494(Bioceramics 23):349-354.
Toyoda, H. et al. "Augmentation of Bone Morphogenetic Protein-Induced Bone Mass by Local Delivery of a Prostaglandin E EP4 Receptor Agonist," Bone, 2005, 555-562.
Tucci, Michelle, et al., "Comparison of segmental fracture healing in young and old rats that were treated with bone stimulators—biomed 2009," Biomedical sciences instrumentation, 2009, 45407-12. (Abstract only).
Visentin, Luciano, et al., "A selective inhibitor of the osteoclastic V-H+-ATPase prevents bone loss in both thyroparathyroidectomized and ovariectomized rats," J. Clin. Invest. 106(2):309-318 (2000).
Wang, C-L.J. et al. "Azaprostanoids I. Synthesis of (RAC)-8-Aza-11-Deoxy-15-Deoxy-16-Hydroxy-16-Methylprostaglandins," Tetrahedron Letters, 1982, 10, 1067-1070.
Wang, J.S., "Basic fibroblast growth factor for stimulation of bone formation in osteoinductive or conductive implants," Acta orthopaedica Scandinavica, Supplementum, 1996, 2691-33.
Wang, Y., et al., "Selective local delivery of RANK siRNA to bone phagocytes using bone augmentation biomaterials," Biomaterials, Nov. 2012; 33(33):8540-7, doi: 10.1016/j.biomaterials.2012.07.039, Epub Sep. 3, 2012.
Wingerter, Scott, et al., "Evaluation of short-term healing following sustained delivery of osteoinductive agents in a rat femur drill defect model," Biomedical Sciences Instrumentation, 2007, 43:188-193. (Abstract only).
Winkler, T., et al., "Osteoclastic bioresorption of biomaterials: two- and three-dimensional imaging and quantification," Int J Artif Organs, Apr. 2010; 33(4):198-203.
Wu, C.C., et al. "Calcium phosphate cement delivering zoledronate decreases bone turnover rate and restores bone architecture in ovariectomized rats," Biomed Mater, Jun. 2012; 7(3):035009, doi: 10.1088/1748-6041/7/3/035009. Epub Mar. 15, 2012.
Xia, Z., et al., "In vitro biodegradation of three brushite calcium phosphate cements by a macrophage cell-line," Biomaterials, Sep. 2006; 27(26):4557-65, Epub May 23, 2006.
Xiao, Y. et al. "Discovery of Novel Prostaglandin Analogs of PGE2 as Potent and Selective EP2 and EP4 Receptor Agonists," Biorganic & Medicinal Chemistry Letters, 2007, 17, 4323-4327.
Xiao, Y. et al. "Synthesis and Evaluation of a γ-lactam as a Highly Selective EP2 and EP4 Receptor Agonist," Biorganic & Medicinal Chemistry Letters, 2008, 18, 821-824.
Yang, Z.P., et al., "Release kinetics of methotrexate loaded calcium phosphate cement and histological evaluation of the osteogenesis in rabbits," Zhongguo Yi Xue Ke Xue Yuan Xue Bao, Oct. 2010; 32(5):543-8, doi: 10.3881/j.issn.1000-503X.2010.05.014. (Abstract only).
Yokoyama, U. et al. "Chronic Activation of the Prostaglandin Receptor EP4 Promotes Hyaluronan-Medicated Neointimal Formation in the Ductus Arteriosus," J. Clin. Inves., 2006, 116, 3026-3034.
Yoshida, K. et al., "Stimulation of bone formation and prevention of bone loss by prostaglandin E EP4 receptor activation," *PNAS*, 2014, 99(7) 4580-4585.
Yuan, H., et al., "Tissue responses of calcium phosphate cement: a study in dogs," Biomaterials, Jun. 2000; 21(12):1283-90.
Zaffe, D., "Some considerations on biomaterials and bone," Micron, 2005; 36(7-8):583-92, Epub Sep. 2, 2005.
Zhao, Yannan, et al., "The osteogenic effect of bone morphogenetic protein-2 on the collagen scaffold conjugated with antibodies," Journal of Controlled Release, 2010, 141(1): 30-37.
Zimecki, Michal, "Potential therapeutic interventions via EP2/EP4 prostaglandin receptors," Postepy Hig Med Dosw (online), 66:287-294 (2012).

\* cited by examiner

METHODS, SYSTEMS, AND COMPOSITIONS FOR PROMOTING BONE GROWTH

RELATED APPLICATIONS

This application is the U.S. National Phase under 35 U.S.C. § 371 of International Patent Application No. PCT/US2014/047138, filed Jul. 18, 2014, which claims priority to and the benefit of U.S. Provisional Application Ser. No. 61/856,370, filed Jul. 19, 2013, and 61/928,843, filed Jan. 17, 2014. The entire contents of these patent applications are hereby incorporated herein by reference.

FIELD OF THE INVENTION

The present invention relates to bone matrix compositions, systems, and methods for local release of pharmaceutical agents, particularly agents that promote bone growth.

BACKGROUND OF THE INVENTION

All references, including patents and patent applications, are hereby incorporated by reference in their entireties.

Bone defects such as through fractures or other causes can be treated with autologous bone grafts (i.e., bone taken from another part of a patient's body). The graft can act as a scaffold to aid in the bone regeneration process. This approach to treating bone defects, however, has several drawbacks including the requirement for additional surgery and the morbidity to the donor site.

As an alternative to autologous bone grafts, various biocompatible synthetic bone fillers have been developed such as the calcium phosphate cements (CPCs) and the acrylic bone cement polymethylmethacrylate.

Synthetic bone fillers have additionally been investigated as drug delivery systems. For example, zoledronate-impregnated CPC blocks implanted in the greater momentum were found to decrease bone turnover and to restore bone architecture in ovariectomized rats. Treating a localized bone defect in this fashion, however, results in potentially unnecessary systemic exposure to a drug. In another study, simvastatin β-hydroxy acid in CPC was released over one week and promoted osteogenesis using in vitro assay systems. This relatively quick release of drug over just one week may be of insufficient duration where the promotion of bone growth is required for longer periods of time.

Thus, there exists a need for improved compositions, systems, and methods for locally delivering a bone-repairing drug over extended periods of time to promote bone growth and repair bone defects.

SUMMARY OF THE INVENTION

The present invention provides improved compositions and methods related to bone repair and local delivery into a bone of a therapeutic agent. The therapeutic agent may be a bone-repairing drug to repair bone defects and otherwise promote bone growth, an agent that treats bone-related pain, an anti-inflammatory agent to treat an inflammation-related condition (e.g., arthritis), an anti-cancer drug to treat bone cancer, or an antimicrobial agent to treat or prevent infection at the treatment site.

One aspect of the invention provides a bone composition that includes a drug-carrier mixture and a bone matrix or collagen sponge. According to this aspect, the drug-carrier mixture includes a therapeutic agent and a calcium phosphate cement, and the bone matrix is at least partially demineralized.

Another aspect of the invention provides a bone repair composition that includes a drug-carrier mixture and a bone matrix or collagen sponge. According to this aspect of the invention, the drug-carrier mixture includes a bone-repairing drug and a calcium phosphate cement, and the bone matrix is at least partially demineralized.

Another aspect of the invention provides a method of repairing bone or increasing bone density by locally delivering a bone-repairing drug to a bone defect in a patient. The bone-repairing drug is delivered from a bone repair composition that includes a drug-carrier mixture and a bone matrix that is at least partially demineralized.

Another aspect of the invention provides a bone composition that includes a solid insert comprising a therapeutic agent that is embedded in a set non-ceramic calcium phosphate cement, the therapeutic agent being distributed substantially homogeneously throughout the set non-ceramic calcium phosphate cement.

Still another aspect of the invention provides bone repair composition that includes a solid insert comprising a bone-repairing drug that is embedded in a set non-ceramic calcium phosphate cement, the therapeutic agent being distributed substantially homogeneously throughout the set non-ceramic calcium phosphate cement.

Yet another aspect of the invention provides a method of repairing bone or increasing bone density by locally delivering a bone-repairing drug to the bone of a patient with a bone repair composition that includes a solid insert comprising a bone-repairing drug that is embedded in a set non-ceramic calcium phosphate cement, the therapeutic agent being distributed substantially homogeneously throughout the set non-ceramic calcium phosphate cement.

In certain aspects of the invention, the bone-repairing drug comprises a compound that activates osteoblasts. In other aspects, the bone-repairing drug inhibits osteoclasts. In still other aspects, the bone-repairing drug comprises one or more of PGE1, PGE2, an EP2 agonist, EP4 receptor agonist, an EP2/EP4 dual agonist, an organic bisphosphonate; a cathepsin K inhibitor; an estrogen or an estrogen receptor modulator; calcitonin; an inhibitor of osteoclast proton ATPase; an inhibitor of HMG-CoA reductase; an integrin receptor antagonist; a RANKL inhibitor; a bone anabolic agent; a bone morphogenetic agent; Vitamin D or a synthetic Vitamin D analogue; an androgen or an androgen receptor modulator; a SOST inhibitor; platelet-derived growth factor; and the pharmaceutically acceptable salts and mixtures thereof.

In certain aspects of the invention, the bone-repairing drug comprises a compound of formula (I),

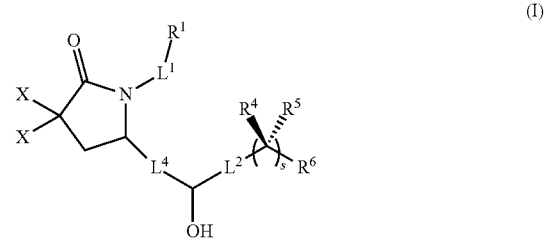

or a pharmaceutically acceptable salt thereof, wherein:
both X are either hydrogen or fluoro;

$L^1$ is a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;

b) —$(CH_2)_t$-G-$(CH_2)_p$—; wherein t is 0, 1, or 2, p is 0, 1, 2, or 3, and t+p=0, 1, 2, 3, or 4; or c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{13}$)=C($R^{13}$)-$G^2$-, wherein n is 1, 2, 3, 4, or 5, p is 0, 1, 2, or 3, and n+p=1, 2, 3, 4, 5, or 6;

G is

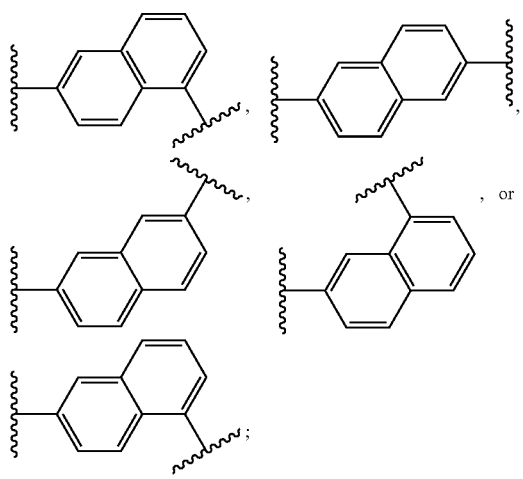

$G^1$ is O, C(O), S, S(O), S(O)$_2$, or $NR^8$; wherein $R^8$ is H, $C_1$-$C_4$ alkyl, or $C_1$-$C_4$alkylcarbonyl;

$G^2$ is

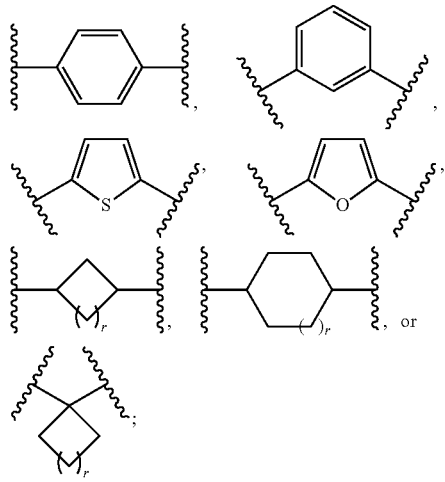

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^1$ is COO$R^{10}$, CON$R^{10}R^{11}$, $CH_2OR^{10}$, $SO_3R^{10}$, $SO_2NR^{10}R^{11}$, PO(O$R^{10}$)$_2$, or tetrazol-5-yl;

$R^{10}$ is H, $C_1$-$C_4$ alkyl, or aryl;

$R^{11}$ is H, $C_1$-$C_4$ alkyl, CO$R^{12}$, O$R^{10}$, or SO$_2R^{12}$;

$R^{12}$ is $C_1$-$C_4$ alkyl;

$R^{13}$, at each occurrence, is independently H or $C_1$-$C_4$alkyl;

$L^4$ is —C($R^2$)$_2$—C($R^3$)$_2$—, —C($R^2$)=C($R^3$)—, —C≡C—, or

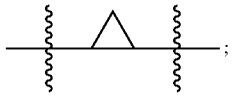;

wherein $R^2$ and $R^3$ are each H, $CH_3$, fluoro, or chloro;

$L^2$ is —$CH_2$— or a bond;

$R^4$ and $R^5$ are each independently H, F, $CF_3$, or $C_1$-$C_4$ alkyl; or $R^4$ and $R^5$ together with the carbon to which they are attached form a $C_3$-$C_5$ cycloalkyl,

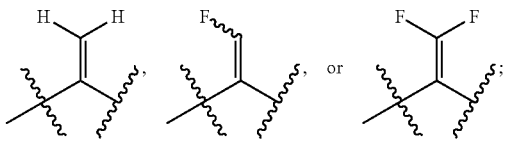

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy; and wherein the $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, and $C_3$-$C_{10}$haloalkynyl are optionally substituted with a substituent selected from the group consisting of COO$R^{10'}$, CON$R^{10'}R^{11'}$, $CH_2OR^{10'}$, $SO_3R^{10'}$, $SO_2NR^{10'}R^{11'}$, PO(O$R^{10'}$)$_2$, and tetrazol-5-yl;

$R^{10'}$ is H, $C_1$-$C_4$ alkyl, or aryl;

$R^{11'}$ is H, $C_1$-$C_4$ alkyl, CO$R^{12'}$, O$R^{10'}$, or SO$_2R^{12'}$;

$R^{12'}$ is $C_1$-$C_4$ alkyl;

$L^3$ is $C_1$-$C_6$alkylene, $C_2$-$C_6$alkenylene, $C_2$-$C_6$alkynylene, —$(CH_2)_m$-$G^3$-$(CH_2)_q$—, —$(CH_2)_m$-$G^4$-$(CH_2)_q$—, or -$G^5$-C≡C—; wherein the $C_1$-$C_6$alkylene, $C_2$-$C_6$alkenylene, and $C_2$-$C_6$alkynylene are optionally substituted with 1, 2, 3, or 4 fluoro substituents; and wherein m and q are each independently 0, 1, 2, or 3 and m+q=0, 1, 2, 3, or 4;

$G^3$ is O, C(O), S, S(O), S(O)$_2$, or $NR^9$; wherein $R^9$ is H, $C_1$-$C_4$ alkyl, or $C_1$-$C_4$alkylcarbonyl;

$G^4$ is

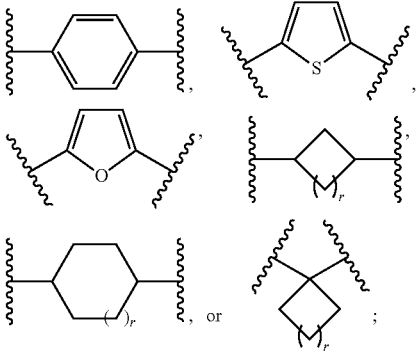

wherein $G^4$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$G^5$ is

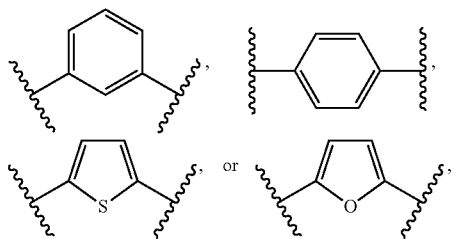

wherein $G^5$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy;

r is 0 or 1; and
s is 0 or 1.

In another aspect of the invention, the bone-repairing drug comprises a compound of formula (Ia)

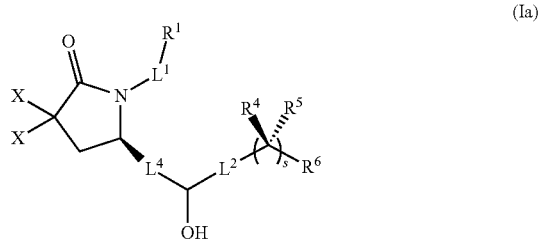

(Ia)

or a pharmaceutically acceptable salt thereof, wherein X, $R^1$, $R^4$, $R^5$, $R^6$, $L^1$, $L^2$, $L^4$, and s are as defined herein.

In another aspect of the invention the bone-repairing drug comprises a compound of formula (II)

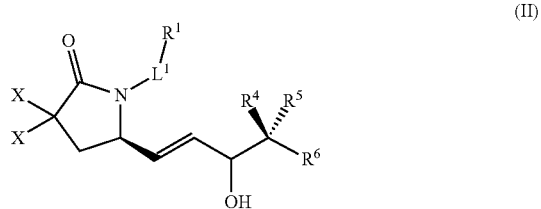

(II)

or a pharmaceutically acceptable salt thereof, wherein X, $R^1$, $R^4$, $R^5$, $R^6$, and $L^1$ are as defined herein.

DETAILED DESCRIPTION

Bone Compositions and Delivery Methods

Figure 1:
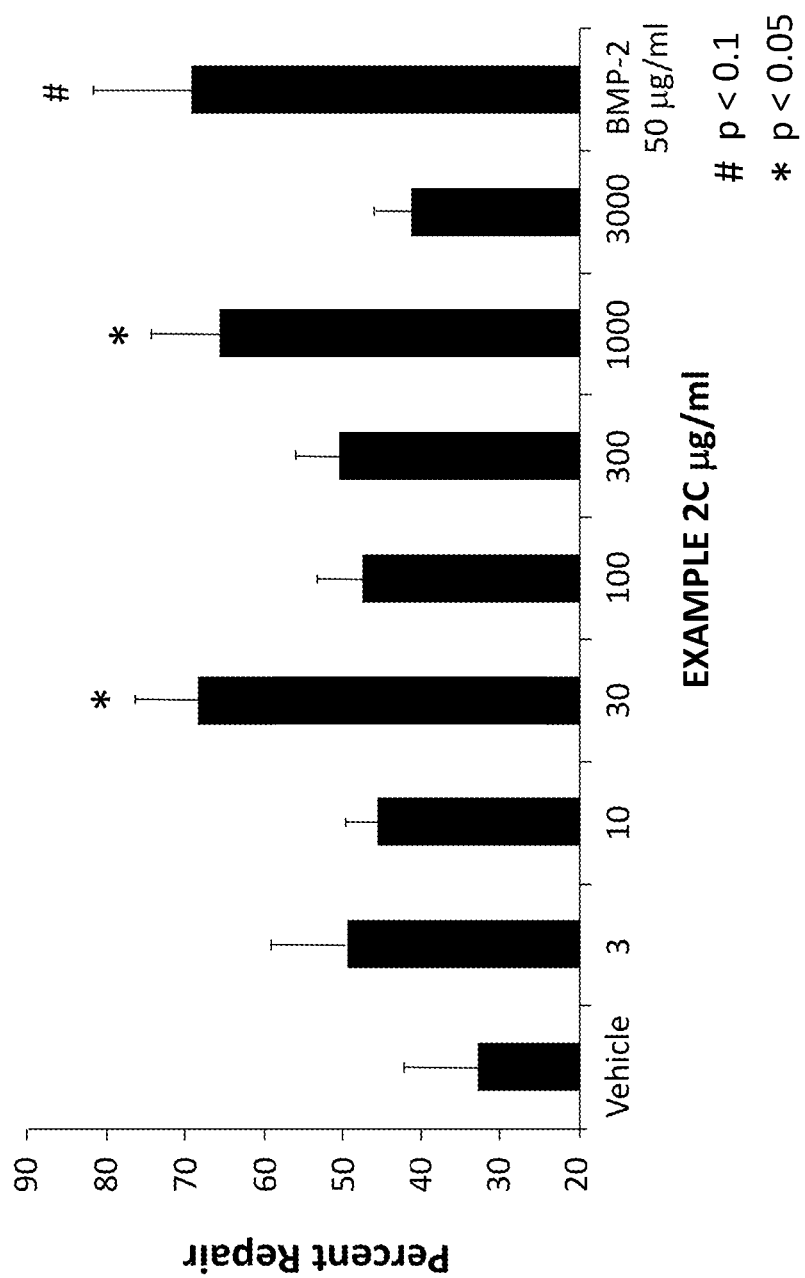
FIG. 1 depicts data showing the effect of Compound 2C on stimulation of bone growth in the rat calvarial defect model.

In certain embodiments, the bone compositions of the invention include a drug-carrier mixture and a bone matrix that is at least partially demineralized or a collagen sponge. In other embodiments, the bone matrix component/collagen sponge is omitted from the bone composition. In the latter case, the drug-carrier mixture is in the form of a solid insert of a set non-ceramic calcium phosphate cement with a drug embedded substantially homogeneously throughout the cement. Drugs included in the drug-carrier mixture include agents that are capable of stimulating, promoting, enhancing, or inducing bone formation, or inhibiting bone resorption. Bone-repairing drugs or other agents may alleviate pain and/or inflammation at the treatment site, or treat cancer or treat or prevent a microbial infection. The drug-carrier mixture provides for the release of drug at a treatment site. Preferably, the drug-carrier mixture sustains release of the drug for prolonged periods of time.

As described below in greater detail, the drug-carrier mixture is prepared by mixing a drug with a suitable carrier material such as, for example, a calcium phosphate cement powder. Depending on the particular embodiment, the mixture may be further processed by setting and grinding it into a ground powder. The drug-carrier mixture may be combined with a suitable bone matrix material, as described below, to form a bone composition of the invention. Alternatively, the bone-repair compositions may include a collagen sponge. The bone composition may then be applied to a treatment site, such as, for example, by implantation or injection at the site of a bone defect.

1.0 Calcium Phosphate Cements

Calcium Phosphate cements (CPCs) that can be used in the compositions include tri-calcium phosphate mixtures such as α-tri-calcium phosphate (α-TCP) and β-tri-calcium phosphate (β-TCP). Other CPCs that may be used include combinations of dicalcium phosphate and tetracalcium phosphate. Commercially available calcium phosphate cement may also be used such as Hydroset (sold by Stryker Corp), which was used in the Examples disclosed herein. Hydroset is a soft tri-calcium phosphate cement that has the characteristics of a mixture of α-TCP and β-TCP (1:3). In some embodiments the calcium phosphate cements and mixtures thereof may also be seeded with hydroxyapatite (e.g., 2.5% wt./wt. hydroxyapatite crystals). α-TCP and β-TCP may be used in various ratios. For example, in some embodiments the CPC comprises a mixture of α-TCP and 3-TCP (1:3) and optionally a seed of hydroxyapatite. In other embodiments, α-TCP and 3-TCP may be used in ratios of 1:1 or 1:0. In other embodiments, the CPC is α-TCP cement seeded with 2.5% hydroxyapatite, which produces a harder cement upon setting.

2.0 Demineralized Bone Matrix

The bone compositions of the invention may include a bone matrix that is at least partially demineralized. The bone matrix may be a demineralized bone matrix putty, or an intact bone matrix that is either partially or wholly demineralized. An intact bone matrix may be used in a bone graft procedure and act as a scaffold for delivery of a bone-repairing drug. Without being bound by a particular theory, a bone matrix may facilitate repair of a bone defect by attracting osteoblasts and stimulating their differentiation to promote bone formation and mineralization. A bone matrix may have osteooconductive, osteoinductive and osteogenic capabilities.

2.1 Demineralized Bone Matrix Putty

Human demineralized bone matrix putty can be obtained from commercial sources such as Puros Demineralized Bone Matrix Putty manufactured by RTI Biologics (Alachua, Fla.). Demineralized bone matrix putty can also be made by the method described by Urist & Dowell (Inductive Substratum for Osteogenesis in Pellets of Particulate Bone Matrix, Clin. Orthop. Relat. Res., 1968, 61, 61-78). The method involves bone demineralization and defatting and cutting the solid demineralized bone into small pieces that are ground into a course powder under liquid nitrogen. Upon thawing, the ground demineralized bone matrix takes on the consistency of a putty.

2.2 Intact Demineralized Bone Matrix

Intact demineralized bone matrix (DBM) can be made by the method described by Urist & Dowell (1968). After removal from the donor animal the bone is cleaned of attached tissue and placed in a 0.3 N HCL solution overnight at 4° C. The following day the bone is imaged on a cone beam X-ray CT scanner (Vatech Pax3-Duo) and the extent of mineralization is assessed. If any remaining mineralization is observed the bone is placed in a fresh acid solution and incubated overnight at 4° C. This process is repeated until no remaining mineral is observed.

The demineralized bone is then defatted by incubating in a 100% ethanol solution for 4 h on a rotator at room temperature. Following defatting, the demineralized bone is stored at 4° C. in phosphate buffered saline until use.

The demineralization and defatting procedure creates dosing spaces into which a drug-CPC mixture may be loaded. One example of a typical dosing space is a hole drilled into the matrix either before or after demineralization of the bone.

In addition to complete demineralization, the bone material may alternatively be partially demineralized.

2.3 Setting Solutions

Setting solutions for tricalcium phosphate cement powders are well known in the art and include solutions of $Na_2HPO_4$ between 2.5% w/v or commercially available solutions. See Dorozhkin, Materials 2009, 2, 221-291.

3.0 Drug-Loaded Calcium Phosphate Cement (drug-CPC mixture)

Drug-CPC mixtures can be prepared by dissolving a drug in an appropriate solvent such as, for example, ethanol and adding the solution to a calcium phosphate cement powder. After the solvent has been vented off, the cement powder is mixed to distribute the drug evenly (i.e., homogeneously) throughout the powder and is then wetted with the setting solution appropriate for each cement. The cement-drug mix is mixed thoroughly for about 1 minute as the cement begins to set. The mixing and setting process results in the drug being embedded substantially homogeneously throughout the set CPC, rather than simply adsorbed onto the surface. If the drug is to be delivered from ground cement either suspended in demineralized bone matrix putty or with collagen sponge the cement is allowed to set overnight at room temperature before being ground to a fine powder in a mortar and pestle. Amounts of drug that may be loaded into CPC range from about 3 ng drug per gram of CPC to about 3 mg of drug per gram of CPC. The CPC serves to encapsulate the drug so that it is released slowly over time to sustain the therapeutic effects of the drug.

Depending on the particular type of CPC employed, the setting procedure may convert the CPC into hydroxyapatite by a dissolution-precipitation process. For example, α-tricalcium phosphate can convert to hydroxyapatite during the setting procedure. This conversion may be assisted by the addition of seed crystals of hydroxyapatite. Conversely, β-tricalcium phosphate does not convert to hydroxyapatite. Thus, by varying the proportion of a and (3 tricalcium phosphate in the original powder, the amount of hydroxyapatite in the final product is also proportionally changed. The dissolution-precipitation process may produce a crystalline CPC or a crystalline hydroxyapatite.

In some embodiments, the setting process produces a set non-ceramic calcium phosphate cement. The cement may be in whole, or in part, a set non-ceramic hydroxyapatite, depending on the type of starting calcium phosphate cement used. In some embodiments, the set CPC may be resorbed after implantation at the treatment site (e.g., a bone defect or area of low bone density) and replaced by bone.

Following setting of the CPC, the drug-CPC mixture may be used either as a solid insert or ground to a powder, depending on the particular application. The solid insert of drug-CPC may be shaped as desired for implantation. For example, prior to implantation, the solid insert of drug-CPC may be cut or abraded by any suitable technique, such as, for example, trimming with a scalpel, grinding, filing, etc. A solid insert of drug-CPC may be implanted directly into a trephined bone or into an intact demineralized bone matrix as described below.

4.0 Bone Composition and Delivery Method 1a

In one embodiment of the invention, a bone composition comprises a mixture of a drug-CPC mixture with DBM putty. The ratio of drug-CPC mixture:DBM putty may be from about 1:20 wt (mg)/vol(µL) to about 1:4 wt (mg)/vol (µL) and any ratios in between. In some embodiments, the ratio may range from 1:19 wt (mg)/vol(µL) to about 1:6.7 wt (mg)/vol(µL). In one embodiment, the ratio of drug-CPC mixture:DBM putty is about 1:8 wt (mg)/vol(µL). Outside the stated ranges, the inclusion of greater amounts of drug-CPC mixture tends to cause aggregation of the cement leading to less effective dispersal and turnover with time. Lesser amounts of cement tend to release the bone-repairing drug more quickly rather than in a sustained release fashion. A bone composition can be made, for example, by adding a fine powder of a drug-CPC mixture to (DBM) putty in amounts of 1 mg of drug-CPC mix to 8 µL of putty, followed by thorough mixing. The drug-CPC-DBM mixture is then stored at 4° C. until use. In use, the drug-CPC-DBM putty is applied to a bone defect (e.g., by injection) in sufficient quantity so as to fill the bone defect. Preferably the defect is filled entirely.

In certain embodiments, a method of repairing bone or increasing bone density includes locally delivering a bone-repairing drug to a bone of a patient where the drug is locally delivered by a mixture of drug-CPC-DBM putty or drug-CPC-collagen sponge, either of which may be implanted into the bone in need of repair or increased density. In other embodiments, one or more of a pain-relieving drug, an anti-inflammatory agent, an antimicrobial agent, or an anti-cancer agent is locally delivered from the mixture of drug-CPC-DBM putty or drug-CPC-collagen sponge.

In some embodiments, the CPC used in the composition is made from a mixture of α-TCP and β-TCP (1:3), with optional hydroxyapatite, and the drug-CPC mixture:DBM putty ratio is about 1:8 wt (mg)/vol(µL). In other embodiments, the ratio of α-TCP to β-TCP is 1:1 or 1:0. In further embodiments, the drug in the foregoing composition is a bone-repairing drug, as defined and described herein. In some embodiments, for example, the bone-repairing drug is an EP4 agonist.

4.1 Bone Composition and Delivery Method 1b

In another embodiment of the invention, a bone composition comprises a mixture of a drug-CPC mixture with a collagen sponge. For example, a bone composition according to this embodiment may be prepared by dampening a collagen sponge with a physiological salt solution and applying a drug-CPC mixture to adhere the cement powder to the outside of the sponge. The loaded sponge may then be inserted into the bone defect.

In some embodiments, the CPC used in the composition is made from a mixture of α-TCP and β-TCP (1:3), with optional hydroxyapatite. In other embodiments, the ratio of α-TCP to β-TCP is 1:1 or 1:0. In further embodiments, the drug in the foregoing composition is a bone-repairing drug, as defined and described herein. In some embodiments, for example, the bone-repairing drug is an EP4 agonist.

4.2 Bone Composition and Delivery Method 2

In another embodiment of the invention, a bone composition comprises a mixture of a drug-CPC mixture with intact DBM (IDBM). The drug-CPC-IDBM is created by loading a drug-CPC mixture into the dosing spaces of intact solid demineralized bone matrix. In practice, fresh drug-CPC powder is prepared and then set with the appropriate setting solution. During the setting phase the drug-cement mixture is placed into the dosing space created in the intact demineralized bone matrix. The cement is allowed to set in situ at 4° C. overnight in a water-saturated atmosphere after which the drug-CPC-IDBM is stored in a water-saturated atmosphere at 4° C. until use. Alternatively, the drug-CPC mixture may be prepared as a solid insert that may be loaded into a dosing space created in the IDBM.

In some embodiments, the CPC used in the drug-CPC-IDBM is made from a mixture of α-TCP and β-TCP (1:3), with optional hydroxyapatite. In other embodiments, the ratio of α-TCP to β-TCP is 1:1 or 1:0. In further embodiments, the drug in the foregoing composition is a bone-repairing drug, as defined and described herein. In some embodiments, for example, the bone-repairing drug is an EP4 agonist.

The intact DBM is suitable for use in repairing a large bone defect. For example, the drug-CPC-IDBM may be used in the replacement of a piece of missing bone that is both highly shaped and all of the original bone is lost, e.g. craniofacial injury or long bone injury over 3 cm. In one embodiment, a piece of donor bone which matches the defect would be demineralized as described herein, loaded with the drug-CPC mixture and the mixture set. The drug-CPC-IDBM may then be surgically implanted at the site of the missing bone. Alternatively, the drug-CPC-IDBM may be used to replace missing bone in which some of the original bone structure is still present, e.g. alveolar ridge augmentation. In this embodiment, a block of drug-CPC-IDBM would be trimmed to the desired shape by the surgeon before placement at the bone defect site. In yet another alternative embodiment, the drug-CPC-IDBM may be used in procedures that are more routine, e.g. vertebral fusion where the surgeon would be supplied with a pre-shaped piece of drug-CPC-IDBM which would be placed in the surgical site.

An alternative use for the intact DBM would be to roughly shred it after loading with drug. In this embodiment, the drug-CPC-IDBM can be used to fill large defects in which the surgeon has poor access or the surgeon would prefer a filling material that is moldable, e.g. sinus lift. In this embodiment, the superior osteoconductive activity of the solid DBM is still maintained but because the DBM is now shredded into smaller pieces it has the filling activity more like that of a putty. Shredded drug-CPC-IDBM may be combined with DBM putty to make a moldable void filler like putty but with much of the superior osteoconductive activity associated with the intact DBM. In other embodiments, the drug-CPC-IDBM may be formed (e.g. cut) into chips. In other embodiments, the drug-CPC-IDBM may be formed into strips.

In certain embodiments, a method of repairing bone or increasing bone density includes locally delivering a bone-repairing drug to a bone of a patient where the drug is locally delivered by a composition of drug-CPC-IDBM, which may be implanted into the bone in need of repair or increased density. In other embodiments, one or more of a pain-relieving drug, an anti-inflammatory agent, an antimicrobial agent, or an anti-cancer agent is locally delivered from the mixture of drug-CPC-IDBM.

4.3 Bone Composition and Delivery Method 3

In another embodiment of the invention, a bone composition comprises a mixture of a drug-CPC mixture with intact partially demineralized bone matrix (PDBM). The drug-CPC-PDBM is created in the same fashion as described above for IDBM except that partially demineralized bone matrix is used instead. In some embodiments, the CPC used in the drug-CPC-PDBM is made from a mixture of α-TCP and β-TCP (1:3), with optional hydroxyapatite. In other embodiments, the ratio of α-TCP to β-TCP is 1:1 or 1:0. In further embodiments, the drug in the foregoing composition is a bone-repairing drug, as defined and described herein. In some embodiments, for example, the bone-repairing drug is an EP4 agonist.

The drug-CPC-PDBM may generally be used in the same fashion as that described above for the drug-CPC-IDBM. The drug-CPC-PDBM may be preferred in the treatment of a very large bone defect where the mechanical strength of the newly placed insert is important for maintaining space and shape (e.g. loss of long bone greater than 3 cm). An implant made from PDBM has greater mechanical strength since only the outer layers of bone are demineralized and the inner part remains mineralized. In this embodiment, the demineralized bone offers a substrate for osseointegration with the host and the mineralized bone provides rigidity to the insert for mechanical support while integration occurs.

In certain embodiments, a method of repairing bone or increasing bone density includes locally delivering a bone-repairing drug to a bone of a patient where the drug is locally delivered by a composition of drug-CPC-PDBM, which may be implanted into the bone in need of repair or increased density. In other embodiments, one or more of a pain-relieving drug, an anti-inflammatory agent, an antimicrobial agent, or an anti-cancer agent is locally delivered from the mixture of drug-CPC-PDBM.

4.4 Bone Composition and Delivery Method 4

In another embodiment of the invention, a drug-CPC mixture may be cast as a solid insert for direct insertion into bone. For example, the solid insert may be adapted for insertion into a trephined bone by forming the solid insert into a shape that is complementary to the insertion site. The shaping of the solid insert includes, for example, the cutting and abrading methods discussed above.

In some embodiments, the CPC used as a solid insert is made from a mixture of α-TCP and β-TCP (1:3), with optional hydroxyapatite. In other embodiments, the ratio of α-TCP to β-TCP is 1:1 or 1:0. In further embodiments, the drug in the foregoing composition is a bone-repairing drug, as defined and described herein. In some embodiments, for example, the bone-repairing drug may be an EP4 agonist.

In the solid inserts of this embodiment, the drug is embedded substantially homogeneously throughout the set calcium phosphate cement as a consequence of the mixing and setting procedure. The mixing and setting process produces a calcium phosphate cement that is non-ceramic. In certain embodiments, the set non-ceramic calcium phosphate cement is a crystalline calcium phosphate. In other embodiments, the set non-ceramic calcium phosphate cement contains some amount of crystalline hydroxyapatite, depending on the type(s) of calcium phosphate cement used in the setting procedure.

In one embodiment, a method of repairing bone or increasing bone density in a patient includes locally delivering a bone-repairing drug to a bone in the patient where the bone repairing drug is delivered from a solid insert comprising a therapeutically effective amount of the bone-repairing drug embedded substantially homogeneously throughout the set non-ceramic calcium phosphate cement. In other embodiments, the bone is a trephined bone and the bone repair composition (solid insert) is implanted into the trephined bone. In other embodiments, one or more of a pain-relieving drug, an anti-inflammatory agent, an antimicrobial agent, or an anti-cancer agent is locally delivered from the solid insert bone repair composition.

5.0 Principles of Operation

In operation, the compositions of the invention provide a vehicle for release of drugs at a treatment site following a procedure to repair a bone defect. Preferably the release is a sustained release. The sustained release of a drug at the treatment site prolongs the therapeutic drug effect in order to promote healing at the treatment site.

Figure 3:
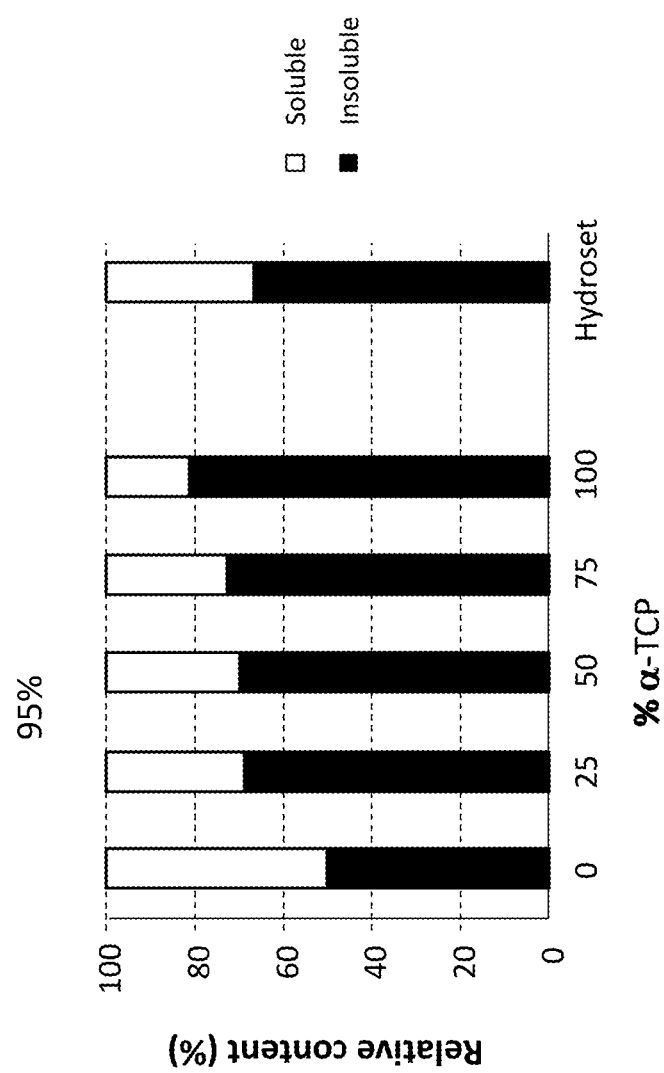
FIG. 3 illustrates the effect of varying proportions of α-tricalcium phosphate cement and α-tricalcium phosphate cement on cement dissolution rate in a physiological medium.

Without being bound by a particular theory, drug release from the drug-CPC mixture may be controlled by one or both of: (1) dissolution of the cement in the surrounding physiological medium; and (2) degradation of the cement by osteoclasts. β-TCP has greater solubility in physiological solutions than α-TCP and so greater proportions of β-TCP in the drug-CPC mixture may result in a greater degree of drug release by a dissolution mechanism. It has been found that increasing the proportion of α-TCP in a CPC mixture of α-TCP and β-TCP decreases the extent of CPC dissolution after 2 days at 37° C. in phosphate buffered saline (FIG. 3). Thus, using greater proportions of a more soluble cement may result in greater amounts of drug being released by a dissolution process. Conversely, using greater proportions of a harder and less soluble cement (e.g., α-TCP) may decrease the extent of drug release by dissolution and proportionally increase the amount released by degradation. Since the rates of dissolution and degradation differ, the rate of drug release may be varied by adjusting the proportions of the particular cements used in the drug-CPC mixture.

Since both dissolution and degradation are expected to be dependent on the surface area to volume ratio, an increase in particle size is expected to result in slowing of both processes.

The release of drug by dissolution is a passive process that is primarily dependent on the solubility of the cement and not on the structure of the drug. Thus, dissolution-mediated release is expected to take place independent of the structure or functionalities present in a particular drug. For this reason, the rate of release of most drugs by dissolution is expected to be approximately the same, with the release rate being governed by the choice of cement. However, since release of drug by the degradation process is expected to be mediated by osteoclast activity, drugs that inhibit osteoclast activity (e.g., bisphosphonates, estrogen receptor modulators) may slow the degradative release of the drug from the drug-CPC mixture. The inclusion of an osteoclast-inhibiting drug in the drug-CPC mixture provides for more sustained release of drug, particularly where the CPC has higher percentages of a harder, less soluble CPC (e.g., α-TCP).

The foregoing discussion illustrates that drug release rates may be controlled by adjusting the surface area to volume ratio, by manipulating the proportions of soluble and insoluble cements, and by the inclusion of osteoclast-inhibiting drugs in the drug-CPC mixture. Depending on the choice of drug and the particular condition being treated, one may adjust the variables accordingly to achieve a desired drug release rate. As an example, decreasing the rate of drug release by any of the foregoing mechanisms is preferred for treatments requiring longer term therapy such as in the treatment of bone cancer or osteoporosis. For bone cancer and osteoporosis, it is preferable to embed the therapeutic drug in a solid cement implant (as opposed to ground cement) to slow the drug release.

Because of the acidic pH created by osteoclasts, it is preferred that a drug be stable to pH 4-5 where a greater proportion is released by the osteoclast-mediated degradation mechanism. Drugs with greater sensitivity to the osteoclast environment are preferably embedded in CPCs having a higher proportion of soluble CPC such as β-TCP. This allows the drug to be released by the passive dissolution process and thereby avoid significant degradation at pH 4-5.

Release of drug from drug-CPC-IDBM/PDBM operates according to the same principles as release from CPC-DBM putty. However, because the CPC set inside the IDBM/PDBM is a solid block, the surface area/volume ratio is much smaller than the ground cement in DBM putty and the rate of CPC turnover is lower in IDBM than in DBM putty.

At a treatment site, the CPC is removed/resorbed and replaced by newly formed bone. The drug released in the removal/resorption of the CPC may enhance the rate of new bone formation by modulating osteoblast and osteoclast activity. For example, a drug that increases osteoblast numbers may result in the increased osteoblast population continuing to repair/fill a defect for weeks after the drug has dissipated from the site.

In the bone compositions made from DBM putty, the DBM has no three-dimensional structure and so serves as the raw material for making new bone soft tissue. IDBM/PDBM, however, possess much of the three-dimensional structure of the original tissue by virtue of being prepared from whole bone. As such the IDBM/PDBM may serve as a scaffold for the formation of new bone. IDBM/PDBM may thus be remineralized by the host prior to significant resorption/replacement of the DBM. Eventually, it is expected that the DBM material would nonetheless be replaced by the host over a longer time course than with DBM putty.

Drugs released by the bone compositions may promote bone formation by increasing osteoblast activity. Certain classes of drugs are known to increase osteoblast activity such as, for example, PGE2, parathyroid hormone, strontium ranelate, EP4 agonists, and activators of Wnt/β-catenin signaling (e.g. a GSK-3 inhibitor, a sclerostin antagonist, a SOST inhibitor). Alternatively, other classes of drugs are known to inhibit osteoclast activity such as, for example, estrogen, estrogen-receptor modulators, organic bis-phosphonates, RANKL inhibitors, cathepsin K inhibitors, inhibitors of osteoclast proton ATPase (e.g., SB242784); inhibitors of HMG-CoA reductase (i.e. a statin), and αvβ3integrin receptor antagonists.

Bone-repairing drugs, in addition to beneficial effects on bone formation, may incidentally reduce pain at the treatment site as a consequence of effects on bone remodeling. Thus, by increasing bone strength, a bone repair drug may also alleviate bone pain. Antiresorptive therapies (e.g., bisphosphonates) may also reduce pain by impairing osteoclast function, which is believed to contribute to bone cancer pain.

A bone-repairing drug may also be loaded in the CPC with one or more pain relieving agents, anti-inflammatory agents, antimicrobial agents, or anti-cancer agents. The pain relieving agents may be released from the CPC in the same manner as a bone-repairing drug to provide local relief of bone pain. In like fashion, anti-inflammatory drugs may be released from the CPC to reduce local inflammation. Antimicrobial agents (e.g., antibacterials, antifungals) may also be released from the CPC to prevent or counter infection that may occur during installation of the bone composition. Anti-cancer agents may be released from the compositions to treat bone cancer.

6.0 Salt Forms, Adjuvants, and Excipients

The bone compositions comprise compounds described herein, pharmaceutically acceptable salts thereof, or solvates of either. The bone compositions comprising the compound, salt, or solvate described herein may be formulated together with one or more non-toxic pharmaceutically acceptable carriers, either alone or in combination with one or more other medicaments as described hereinabove.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Compounds described herein can exist in unsolvated as well as solvated forms, including hydrated forms, such as hemi-hydrates. In general, the solvated forms, with pharmaceutically acceptable solvents such as water and ethanol, among others, are equivalent to the unsolvated forms.

7.0 Methods of Treatment

The bone compositions are useful in treating low bone density due to osteoporosis (Cameron, K. O. et al, *Bioorganic and Medicinal Chemistry Letters*, 2006, 16, 1799-1802) or glucocorticoid treatment, bone fracture, and bone loss due to periodontal disease, surgical procedures, cancer, or trauma. Further uses of the compositions of the invention include use in increasing bone density in preparation of bone for receiving dental or orthopedic implants, coating of implants for enhanced osseointegration, and use in all forms of spinal fusion.

The present invention provides methods of treatment comprising administering to a patient in need thereof a bone composition containing a therapeutically effective amount of a bone-repairing drug, as described herein. The methods of treatment generally include stimulating, promoting, enhancing, or inducing bone formation, or inhibiting bone resorption. The methods of treatment also include, for example, promoting bone remodeling, activating osteoblasts, promoting osteoblast differentiation, inhibiting osteoclasts, increasing the number and activity of osteoblasts, enhancing mean wall thickness, enhancing trabecular bone volume, improving bone architecture, improving trabecular connectivity, increasing cortical thickness, inhibiting bone loss, maintaining/improving bone strength, increasing total bone volume, or volume of the osteoid. The methods of treatment also include treating one or more of osteoporosis, bone fracture, low bone density, or periodontal disease.

In one embodiment of the method of treatment, one or more bone-repairing drugs is administered by release from a CPC-DBM mixture as described herein. In another embodiment, a bone-repairing drug is administered from a CPC-DBM mixture in combination with another therapeutic agent administered systemically (e.g., orally). For example, a bone-repairing drug may be administered with a bone composition in combination with one or more additional therapeutic agents to treat bone loss or osteoporosis administered systemically.

The methods of treatment further comprise administration of bone compositions to humans, other mammals, and birds locally to the desired site of action; for example, into a bone void such as a tooth socket defect, adjacent to an alveolar bone, or a bone defect caused by surgery, trauma, or disease.

The invention also provides methods of treating bone-related pain, inflammation, infection and/or bone cancer comprising administering a bone composition containing a therapeutically effective amount of an analgesic, anti-inflammatory agent, an anti-cancer agent, and/or an antimicrobial agent. The methods of treating pain, inflammation, cancer, and/or infection may be combined with any of the foregoing methods of treating bone disorders.

The phrase "therapeutically effective amount" means sufficient amounts of the compounds to treat disorders, at a reasonable benefit/risk ratio applicable to any medical treatment. It is understood, however, that the total dosage of the compounds in the compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the rate of drug release from the composition, the age, body weight, general health and prior medical history, sex and diet of the patient; the delivery method; drugs used in combination or coincidental with the specific compound employed; and like factors well-known in the medical arts. Actual dosage levels of active ingredients in the pharmaceutical compositions can be varied so as to obtain an amount of the active compound(s) that is effective to achieve the desired therapeutic response for a particular patient and a particular mode of administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a bone composition having a fixed ratio of each active ingredient, or each agent can be administered in separate dosage formulations. For example, a patient may be treated by a bone composition delivering an active drug locally at the site of a bone defect in combination with another drug administered systemically. Where separate dosage formulations are used, the present compounds and one or more additional pharmaceutical agents can be administered at essentially the same time (e.g., concurrently) or at separately staggered times (e.g., sequentially).

In one aspect of the invention, drugs delivered by the compositions of the invention, or a pharmaceutically acceptable salts thereof, or a solvates of either are administered as the active pharmaceutical agent. In another aspect, drugs delivered by compositions of the invention or a pharmaceutically acceptable salt thereof, or a solvate of either are administered to a subject and the administered compounds are converted to the active pharmaceutical agent in the subject by chemical or biotransformation.

Definition of Terms

The term "bone matrix" as used herein refers to a demineralized bone matrix putty, intact demineralized bone, or intact partially demineralized bone.

The term "bone-repairing drug" as used herein refers to an agent that is capable of stimulating, promoting, enhancing, or inducing bone formation, or inhibiting bone resorption. Thus, a bone-repairing drug may be an anabolic drug or an anticatabolic drug. A bone repairing drug may do one or more of the following: promote bone remodeling, activate osteoblasts, promote osteoblast differentiation, inhibit osteoclasts, increase the number and activity of osteoblasts, enhance mean wall thickness, enhance trabecular bone volume, improve bone architecture, improve trabecular connectivity, increase cortical thickness, inhibit bone loss, maintain/improve bone strength, increase total bone volume, or volume of the osteoid. A bone-repairing drug includes, but is not limited to, prostaglandin E2; an EP2 agonist; an EP4 agonist; an EP2/EP4 dual agonist; an organic bisphosphonate (e.g., alendronic acid or sodium alendronate); a cathepsin K inhibitor; an estrogen or an estrogen receptor modulator; calcitonin; an inhibitor of osteoclast proton ATPase; an inhibitor of HMG-CoA reductase (i.e., a statin); an αvβ3integrin receptor antagonist; a RANKL inhibitor such as denosumab; a bone anabolic agent, such as parathyroid hormone; a bone morphogenic protein (e.g., BMP-2, BMP-4, BMP-7); Vitamin D or a synthetic Vitamin D analogue such as ED-70; an androgen or an androgen receptor modulator; an activator of Wnt/α-catenin signaling (e.g. a GSK-3 inhibitor, a sclerostin antagonist, a SOST inhibitor); bortezomib; strontium ranelate; platelet-derived growth factor; and the pharmaceutically acceptable salts and mixtures thereof. Bone-repairing drugs preferably are not degraded to an inactive form when exposed to a pH of between about 4-5.

The term "calcium phosphate cement" or "calcium phosphate cement composition" as used herein refers to a composition that includes a di-calcium phosphate, a tri-calcium phosphate (e.g., α-tri-calcium phosphate and β-tri-calcium phosphate) or a tetra-calcium phosphate, or refers to a composition that is made from any of the foregoing, or mixtures thereof by setting. A calcium phosphate cement or calcium phosphate cement composition may also include hydroxyapatite incorporated in with a calcium phosphate compound.

The term "drug-carrier mixture" as used herein refers to a mixture of a drug incorporated into a calcium phosphate cement composition.

The term "agonist" as used herein refers to a compound, the biological effect of which is to mimic the action of the natural agonist PGE2. An agonist may have full efficacy (i.e., equivalent to PGE2), partial efficacy (lower maximal efficacy compared to PGE2), or super maximal efficacy (higher maximal efficacy compared to PGE2). An agonist with partial efficacy is referred to as a "partial agonist." An agonist with super maximal efficacy is referred to as a "super agonist."

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, means a straight or branched chain hydrocarbon and containing at least one carbon-carbon triple bond. Representative examples include propynyl, butynyl, pentynyl, and the like.

The term "alkylene," as used herein, means a divalent group derived from a straight or branched chain hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and —CH$_2$CH(CH$_3$)CH(CH$_3$)CH$_2$—.

The term "alkenylene," as used herein, means a divalent group derived from a straight or branched chain hydrocarbon and containing at least one carbon-carbon double bond. Representative examples of alkenylene include, but are not limited to —CH=CH—, —CH$_2$CH=CH—, and —CH$_2$CH=CH(CH$_3$)—.

The term "alkynylene," as used herein, means a divalent group derived from a straight or branched chain hydrocarbon and containing at least one carbon-carbon triple bond. Representative examples of alkynylene include, but are not limited to —CH$_2$—C≡C—, —CH$_2$CH$_2$—C≡C—, and —C≡C—CH$_2$CH(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkylcarbonyl" as used herein, means an alkyl group, as defined herein, appended to the parent molecular moiety through a C(O) group.

The terms "haloalkyl," "haloalkenyl," and "haloalkynyl" as used herein, mean, respectively an alkyl, alkenyl, or alkynyl group, as defined herein, in which one, two, three, four, five, six, or seven hydrogen atoms are replaced by halogen. For example, representative examples of haloalkyl include, but are not limited to, 2-fluoroethyl, 2,2-difluoroethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "heteroaryl," as used herein, means a monocyclic heteroaryl or a fused bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is an 8- to 12-membered ring system having a monocyclic heteroaryl fused to an additional ring; wherein the additional ring may be aromatic or partially saturated, and may contain additional heteroatoms. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, furopyridinyl, indolyl, indazolyl, isoquinolinyl, naphthyridinyl, oxazolopyridine, quinolinyl, thienopyridinyl, 5,6,7,8-tetrahydroquinolinyl, 6,7-dihydro-5H-cyclopenta[b]pyridinyl, and 2,3-dihydrofuro[3,2-b]pyridinyl. The monocyclic and the bicyclic heteroaryl groups are connected to the parent molecular moiety through any substitutable carbon atom or any substitutable nitrogen atom contained within the groups.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

The term "heterocycle" or "heterocyclic" as used herein, refers to a monocyclic heterocycle, a bicyclic heterocycle, or a spirocyclic heterocycle. The monocyclic heterocycle is a 3, 4, 5, 6, 7, or 8-membered ring containing at least one heteroatom selected from O, N, or S. The 3 or 4 membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The bicyclic heterocycle is a 5-12-membered ring system having a monocyclic heterocycle fused to a phenyl, a saturated or partially saturated carbocyclic ring, or another monocyclic heterocyclic ring. Representative examples of bicyclic heterocycle include, but are not limited to, 1,3-benzodioxol-4-yl, 1,3-benzodithiolyl, 3-azabicyclo [3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4, 5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. Examples of a spiroheterocycle include, but are not limited to, 5-oxaspiro[3,4]octane and 8-azaspiro[4.5]decane. The monocyclic and bicyclic heterocycle groups of the present invention may contain an alkylene bridge of 1, 2, 3, or 4 carbon atoms, linking two non-adjacent atoms of the group. Examples of such a bridged heterocycle include, but are not limited to, 2-azabicyclo[2.2.1]heptanyl, 2-azabicyclo[2.2.2]octanyl, 1,2,3,4-tetrahydro-1,4-methanoisoquinolinyl, and oxabicyclo[2.2.1]heptanyl. The monocyclic, bicyclic, and spirocyclic heterocycle groups are connected to the parent molecular moiety through any substitutable carbon atom or any substitutable nitrogen atom contained within the group.

Terms such as "alkyl," "cycloalkyl," "alkylene," etc. may be preceded by a designation indicating the number of atoms present in the group in a particular instance (e.g., "$C_3$-$C_{10}$alkyl," "$C_3$-$C_{10}$cycloalkyl," "$C_2$-$C_6$alkynylene," "$C_2$-$C_6$alkenylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_3$-$C_{10}$," the members of the group that follows may have any number of carbon atoms falling within the recited range. A "$C_3$-$C_{10}$alkyl," for example, is an alkyl group having from 3 to 10 carbon atoms, however arranged.

Drugs

Classes of pain relieving agents that may be released from the compositions include sodium channel blockers (e.g., Nav 1.8 inhibitors, Nav1.9 inhibitors, ropivacaine, bupivacaine, etc.), TRPV 1 antagonists, endothelin antagonists (e.g., atrasentan, zibotentan), bradykinin antagonists, ASIC inhibitors, TrkA inhibitors, and radionuclides ($^{89}$Sr, $^{153}$Sm-lexidronam, $^{186}$Re-etidronate).

Classes of anti-inflammatory agents that may be released from the compositions include NSAIDS, corticosteroids, and cytokine inhibitors (e.g., inhibitors of TNF-α, IL-1β, etc.).

Classes of antimicrobial agents that may be released from the compositions include antibacterials and antifungals. Antibacterials include well-known agents like cephems, cephalosporins, quinolone antibiotics (e.g., ciprofloxacin, levofloxacin, etc.), macrolides (e.g., azithromycin, clarithromycin, erythromycin, etc.). Antifungals include fluconazole, clotrimazole, itraconazole, etc.

Classes of anti-cancer agents that may be released from the compositions include vincristine, doxorubicin, etoposide, gemcitabine, methotrexate, SRC kinase inhibitors described by Saad in Cancer Treat Rev. 2010, 36(2) 177-84 (e.g., dasatinib, saracatinib, bosutinib).

A bone repairing drug may be prostaglandin E1, prostaglandin E2, strontium ranelate, calcitonin, parathyroid hormone, Vitamin D, or a synthetic Vitamin D analogue (e.g., ED-70), BMP-2, BMP-4, BMP-7, or platelet-derived growth factor.

A bone repairing drug may also be an organic bisphosphonate. Organic bisphosphonates include, for example, alendronic acid, sodium alendronate, ibandronate, risedronate, zoledronate, zoledronic acid, etidronate, pamidronate, tiludronate, neridronate, and olpadronate.

A bone repairing drug may also be a cathepsin K inhibitor including, for example, compounds disclosed and cited by Brömme in Expert Opin. Investig. Drugs 2009, 18(5) 585-600, (e.g., odanacatib).

A bone repairing drug may be an estrogen or an estrogen receptor modulator including, for example, raloxifene, bazedoxifene, and lasofoxifene, including compounds described at http://en.wikipedia.org/wiki/Selective_estrogen-receptor_modulator.

A bone repairing drug may be an androgen or an androgen receptor modulator including, for example, testosterone.

A bone repairing drug may be an inhibitor of osteoclast proton ATPase, including, for example, compounds described by Nyman in *Potential of the Osteoclast's Proton Pump as a Drug Target in Osteoporosis*, Annales Universitatis Turkuensis 2011, e.g., SB242784, a bafilomycin (e.g., bafilomycin A1), concanamycin A, apicularen, archazolides, benzolactone enamides (salicylihalamide A, lobatamide A), FR 167356, FR177995, and diphyllin.

A bone repairing drug may be an inhibitor of HMG-CoA reductase (i.e., a statin) including, for example those described at http://en.wikipedia.org/wiki/Statin, e.g., atorvastatin, cerivastatin, fluvastatin, lovastatin, mevastatin, pitabastatin, pravastatin, rosuvastatin, and simvastatin.

A bone repairing drug may be an αvβ3integrin receptor antagonist including, for example, compounds described by Millard et al. in Integrin Targeted Therapeutics, Theranostics 2011, 154-188, e.g., cilengitide (EMD 121974), L000845704, SB2730005.

A bone repairing drug may be a RANKL inhibitor such as denosumab.

A bone repairing drug may be an EP2 agonist such as, for example, ONO-AE1-259-01 and CP-533536.

A bone repairing drug may be an EP2/EP4 dual agonist such as, for example, those described in Bioorganic & Medicinal Chemistry Letters, 2012, 22(1), 396-401, U.S. Pat. Nos. 7,402,605, and 7,608,637. An exemplary dual EP2/EP4 agonist is 2-((2-((R)-2-((S,E)-3-hydroxy-4-(m-tolyl)but-1-en-1-yl)-5-oxopyrrolidin-1-yl)ethyl)thio)thiazole-4-carboxylic acid (CAS #494223-86-8).

A bone repairing drug may be an EP4 receptor agonist including, but are not limited to, compounds disclosed in U.S. Pat. Nos. 6,043,275, 6,462,081, 6,737,437, 7,169,807, 7,276,531, 7,402,605, 7,419,999, 7,608,637; WO 2002/024647; Bioorganic & Medicinal Chemistry Letters, 2001, 11 (15), 2029-2031; Bioorganic & Medicinal Chemistry Letters, 2002, 10(4), 989-1008; Bioorganic & Medicinal Chemistry Letters, 2002, 10(6), 1743-1759; Bioorganic & Medicinal Chemistry Letters, 2002, 10(7), 2103-2110); Journal of Medicinal Chemistry, 2004, 47(25), 6124-6127; Bioorganic & Medicinal Chemistry Letters, 2005, 15(10), 2523-2526; Bioorganic & Medicinal Chemistry Letters, 2003, 13(6), 1129-1132; Medicinal Chemistry Letters, 2006, 16(7), 1799-1802; Bioorganic & Medicinal Chemistry Letters, 2004, 14(7), 1655-1659; Bioorganic & Medicinal Chemistry Letters, 2003, 13(6), 1129-1132; Journal of Medicinal Chemistry, 1977, 20(10), 1292-1299; Bioorganic & Medicinal Chemistry Letters, 2008, 18(2), 821-824; Bioorganic & Medicinal Chemistry Letters, 2007, 17(15), 4323-4327; Bioorganic & Medicinal Chemistry Letters, 2006, 16(7), 1799-1802; Tetrahedron Letters, 2010, 51(11), 1451-1454; Osteoporosis International, 2007, 18(3), 351-362; Journal of Bone and Mineral Research, 2007, 22(6), 877-888; Heterocycles, 2004, 64, 437-445.

Particular EP4 agonists include, but are not limited to, CP-734432, ONO-4819 (i.e., rivenprost), AE1-329, L-902, 688.

In some embodiments, bone-repairing drugs included in the bone compositions are one or more of alendronic acid, sodium alendronate, ibandronate, risedronate, zoledronate, zoledronic acid, etidronate, pamidronate, tiludronate, neridronate, and olpadronate, odanacatib, raloxifene, bazedoxifene, lasofoxifene, atorvastatin, cerivastatin, fluvastatin, lovastatin, mevastatin, pitabastatin, pravastatin, rosuvastatin, simvastatin, strontium ranelate, calcitonin, parathyroid hormone, or bone morphogenic protein-2.

In other embodiments, bone-repairing drugs included in the bone compositions are one or more of an EP2 agonist, an EP2/EP4 dual agonist, an EP4 agonist, an organic bisphosphonate, an estrogen receptor modulator, an inhibitor of HMG-CoA reductase, and strontium ranelate.

Bone-repairing EP4 agonist drug compounds may have also the structures set forth in formula (I), (Ia), or (II).

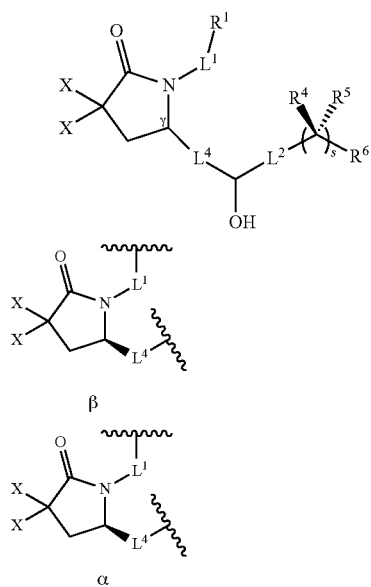

Formula (I) refers to compounds having either β stereochemistry or a substantially equal mixture of β and a stereochemistries at the γ-position of the lactam ring. Excluded are compounds having pure or substantially pure a stereochemistry at the γ-position, as compounds possessing the α stereochemistry at the γ-position have been found to lack appreciable activity as $EP_4$ receptor agonists.

In some embodiments of the invention, $L^1$ is $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents. In other embodiments, $L^1$ is $C_3$-$C_7$alkylene, optionally substituted. In some groups of compounds, $L^1$ is n-pentylene, n-hexylene, or n-heptylene each optionally substituted with 1, 2, 3, or 4 fluoro substituents. In subgroups of compounds, $L^1$ is n-hexylene.

In other embodiments, $L^1$ is —(CH$_2$)$_t$-G-(CH$_2$)$_p$—; wherein t, p, and G are as defined herein. In some groups of compounds, t and p are both 0. In other groups of compounds, t is 0 and p is 0, 1, 2, or 3. In still other groups of compounds, p is 0 and t is 0, 1, or 2.

In other embodiments, $L^1$ is —(CH$_2$)$_n$-G$^1$-(CH$_2$)$_p$—, wherein G$^1$ is as defined herein, n is 1, 2, 3, 4, or 5 and p is 1, 2, or 3.

In still other embodiments, $L^1$ is —(CH$_2$)$_n$-G$^2$-(CH$_2$)—, —(CH$_2$)$_n$—C≡C-G$^2$-, or —(CH$_2$)$_n$—C(H)═C(H)-G$^2$- wherein G$^2$, n and p are as defined herein.

In still other embodiments, $L^1$ is —(CH$_2$)$_3$-G$^2$-(CH$_2$)$_p$—, —CH$_2$—C≡C-G$^2$-, or —(CH$_2$)$_n$—C(H)═C(H)-G$^2$-.

In still other embodiments, $L^1$ is —(CH$_2$)$_3$-G$^2$-, —CH$_2$—C≡C-G$^2$-, or —CH$_2$—C(H)═C(H)-G$^2$-.

In some embodiments $L^1$ is —(CH$_2$)$_n$-G$^2$-(CH$_2$)$_p$—. For example, in some groups of compounds, G$^2$ is

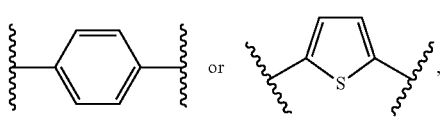

n is 2 and p is 0. In other groups, G$^2$ is

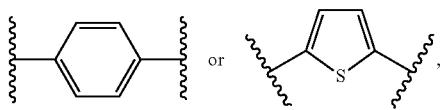

n is 3 and p is 0. In still other groups, G$^2$ is

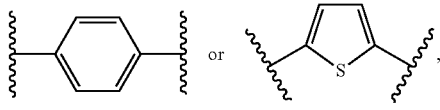

n is 2 and p is 0, 1, 2, or 3. In yet other groups, G$^2$ is

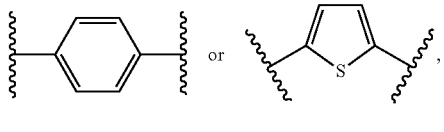

p is 0, and n is 2, 3, 4, or 5. In some subgroups, G$^2$ is

n is 2 and p is 0. In other subgroups, G$^2$ is

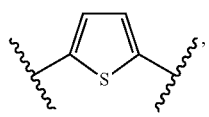 [SMILES: *c1ccc(*)s1]

n is 3 and p is 0. In other subgroups, $G^2$ is

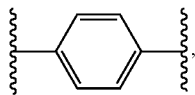 [SMILES: *c1ccc(*)cc1]

In still other embodiments, $L^1$ is —$(CH_2)_n$—C≡C-$G^2$- or —$(CH_2)_n$—C(H)=C(H)-$G^2$-. For example, in some groups of compounds $G^2$ is

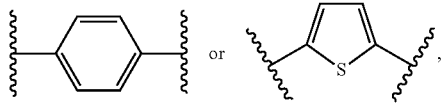 [SMILES: *c1ccc(*)cc1 ; *c1ccc(*)s1]

and n is 1. In certain subgroups of compounds $G^2$ is

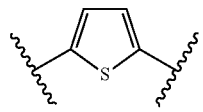 [SMILES: *c1ccc(*)s1]

and n is 1. In other subgroups, $L^1$ is —$(CH_2)_n$—C≡C-$G^2$-, $G^2$ is

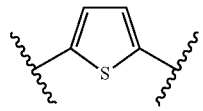 [SMILES: *c1ccc(*)s1]

and n is 1. In still other subgroups, $L^1$ is —$(CH_2)_n$—C(H)=C(H)-$G^2$-, $G^2$ is

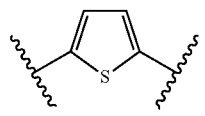 [SMILES: *c1ccc(*)s1]

and n is 1.

In compounds of formula (I), (Ia), or (II), $R^1$ is $COOR^{10}$, $CONR^{10}R^{11}$, $CH_2OR^{10}$, $SO_3R^{10}$, $SO_2NR^{10}R^{11}$, $PO(OR^1)_2$, or tetrazol-5-yl; wherein $R^{10}$ is H, $C_1$-$C_4$ alkyl (e.g., methyl, ethyl) or aryl (e.g., phenyl) and $R^{11}$ is H, $C_1$-$C_4$ alkyl (e.g., methyl, ethyl), $COR^{12}$, $OR^{10}$, or $SO_2R^{12}$; wherein $R^{12}$ is $C_1$-$C_4$ alkyl (e.g., methyl, ethyl). In one group of compounds, $R^1$ is COOH or $COOCH_3$. In another group of compounds, $R^1$ is COOH.

In compounds of formula (I) or (Ia), $L^4$ is —$C(R^2)_2$—$C(R^3)_2$—, —$C(R^2)$=$C(R^3)$—, —C≡C—, or

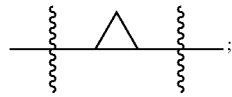

wherein $R^2$ and $R^3$ are each H, $CH_3$, fluoro, or chloro. In some embodiments, $L^4$ is —$C(R^2)_2$—$C(R^3)_2$— and $R^2$ and $R^3$ are each hydrogen. In other embodiments, $L^4$ is —$C(R^2)$=$C(R^3)$— and $R^2$ and $R^3$ are each independently H, $CH_3$, fluoro or chloro. In some groups of compounds, $L^4$ is —$C(R^2)$=$C(R^3)$— and $R^2$ and $R^3$ are hydrogen. In certain subgroups, $L^4$ is

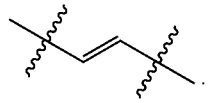

In other embodiments, $L^4$ is —C≡C—. In yet other embodiments, $L^4$ is

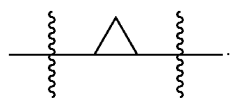

In compounds of formula (I) or (Ia), $L^2$ is —$CH_2$— or a bond. In some embodiments, $L^2$ is a bond.

In compounds of formula (I), (Ia), or (II), $R^4$ and $R^5$ are each independently H, F, $CF_3$, or $C_1$-$C_4$ alkyl (e.g., methyl, ethyl, etc.); or $R^4$ and $R^5$ together with the carbon to which they are attached form a $C_3$-$C_5$ cycloalkyl (e.g., cyclopropyl),

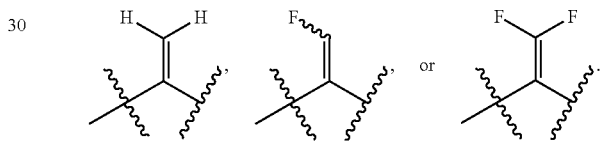

In some embodiments, $R^4$ and $R^5$ are each independently hydrogen or $CH_3$. In other embodiments $R^4$ is $C_1$-$C_4$ alkyl (e.g., methyl, ethyl, etc.) and $R^5$ is hydrogen. In yet other embodiments, $R^4$ is hydrogen and $R^5$ is $C_1$-$C_4$ alkyl (e.g., methyl, ethyl, etc.). In still other embodiments, $R^4$ and $R^5$ are fluoro. In some embodiments, $R^4$ is methyl and $R^5$ is hydrogen. In other embodiments, $R^4$ is hydrogen and $R^5$ is methyl.

In the compounds of formula (I), (Ia), or (II), the stereochemistry of the hydroxyl group on the lower chain may be either α or β or a mixture of α and β.

Formula (I) and (Ia) lower chain

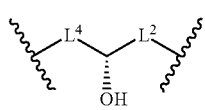
α

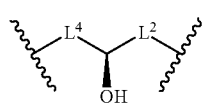
β

Formula (II) lower chain

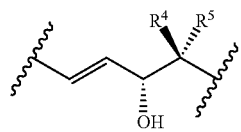
α

β

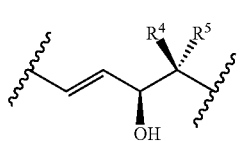

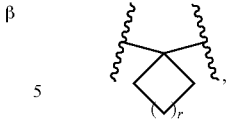

In some embodiments of the invention, $R^6$ is aryl or heteroaryl, each optionally substituted as described herein. In some groups of compounds, $R^6$ is aryl, optionally substituted as described herein. In some groups of compounds, $R^6$ is phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$). In other embodiments of the invention, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, each optionally substituted as described herein. In other embodiments, $R^6$ is $C_3$-$C_{10}$alkyl (e.g., propyl, butyl, pentyl, octyl, etc.). In some groups of compounds, $R^6$ is n-propyl, n-butyl, or n-pentyl. In a particular subgroups of compounds, $R^6$ is n-butyl. In other embodiments, $R^6$ is $C_3$-$C_{10}$alkynyl (e.g., propynyl, butynyl, pentynyl, hexynyl, etc.). In some groups of compounds, $R^6$ is but-2-yn-1-yl, pent-2-yn-1-yl, or hex-2-yn-1-yl. In particular subgroups, $R^6$ is pent-2-yn-1-yl.

In some embodiments, $R^6$ is $L^3$-$R^1$, where $L^3$ and $R^7$ are as defined herein. In other embodiments, $L^3$ is $C_1$-$C_6$alkylene, $C_2$-$C_6$alkenylene, or $C_2$-$C_6$alkynylene. The $C_1$-$C_6$alkylene, $C_2$-$C_6$alkenylene, and $C_2$-$C_6$alkynylene are optionally substituted with 1, 2, 3, or 4 fluoro substituents. In further embodiments, $L^3$ is $C_1$-$C_6$alkylene (e.g., propylene, butylene, pentylene, etc.), optionally substituted. In further embodiments, $L^3$ is $C_1$-$C_6$alkylene, where the $C_1$-$C_6$alkylene is a straight chain alkylene group. For, example, in some groups of compounds, $L^3$ is n-propylene, n-butylene, or n-pentylene. In still other embodiments, $L^3$ is $C_2$-$C_6$alkenylene (e.g., propenylene, butenylene, etc.). In other embodiments $L^3$ is $C_2$-$C_6$alkynylene (e.g., propynylene, butynylene, etc.). In other embodiments, $L^3$ is —$CH_2$—C≡C—.

In still further embodiments $L^3$ is —$(CH_2)_m$-$G^3$-$(CH_2)_q$—, —$(CH_2)_m$-$G^4$-$(CH_2)_q$—, or -$G^5$-C≡C—; wherein m and q are each independently 0, 1, 2, or 3 and m+q=0, 1, 2, 3, or 4. In one embodiment, $L^3$ is —$(CH_2)_m$-$G^3$-$(CH_2)_q$— and m, q, and $G^3$ are as defined herein. In another embodiment, $L^3$ is —$(CH_2)_m$-$G^4$-$(CH_2)_q$— and m, q, and $G^4$ are as defined herein. In one embodiment, $G^4$ is

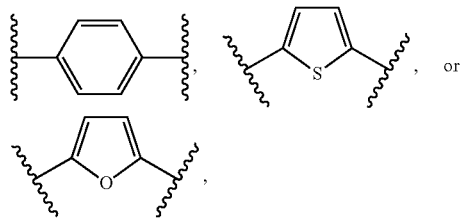

each optionally substituted as described herein. In another embodiment, $G^4$ is

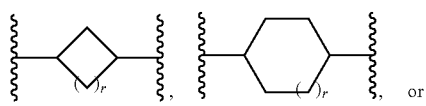

each optionally substituted as described herein. In another embodiment, $L^3$ is -$G^5$-C≡C—, wherein $G^5$ is as defined herein. In one embodiment, $G^5$ is

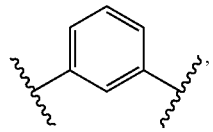 [SMILES: *c1cccc(*)c1]

optionally substituted as described herein. In another embodiment, $G^5$ is

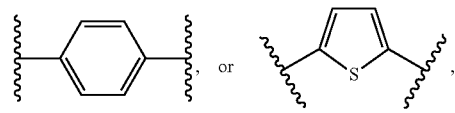 [SMILES: *c1ccc(*)cc1 ; *c1ccc(*)s1]

each optionally substituted as described herein. In another embodiment, $G^5$ is

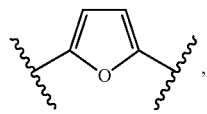 [SMILES: *c1ccc(*)o1]

optionally substituted as described herein.

In compounds of formula (I), (Ia), or (II), $R^7$ is $C_3$-$C_8$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein $R^7$ is optionally substituted as described herein. In some embodiments, $R^7$ is aryl, optionally substituted. In other embodiments, $R^7$ is phenyl, optionally substituted. In some groups of compounds, $R^7$ is phenyl.

In one aspect of the invention are compounds of formula (I), (Ia), or (II), wherein $L^1$-$R^1$ is $C_3$-$C_7$alkylene-$R^1$, wherein the $C_3$-$C_7$alkylene is optionally substituted with 1, 2, 3, or 4 fluoro substituents; or $L^1$-$R^1$ is —$(CH_2)_n$-$G^2$-$(CH_2)_p$—$R^1$, —$(CH_2)_n$—C≡C-$G^2$-$R^1$, or —$(CH_2)_n$—C(H)=C(H)-$G^2$-$R^1$, wherein n is 1, 2, 3, 4, or 5, p is 0, 1, 2, or 3, and n+p=1, 2, 3, 4, 5, or 6; $G^2$ is

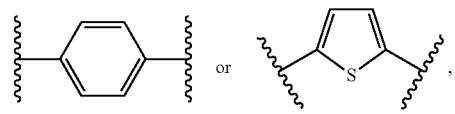

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy; $R^1$ is $COOR^{10}$; and $R^{10}$ is H or $C_1$-$C_4$ alkyl. In one embodiment of this aspect of the invention $L^1$-$R^1$ is n-hexylene-COOR$^{10}$, —(CH$_2$)$_n$-G$^2$-(CH$_2$)$_p$—COOR$^{10}$, —(CH$_2$)$_n$—C≡C-G$^2$-COOR$^{10}$, or —(CH$_2$)$_n$—C(H)=C(H)-G$^2$-COOR$^{10}$; wherein n is 1, 2 or 3, p is 0 or 1; G$^2$ is

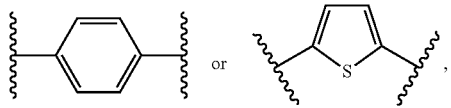 [SMILES: *c1ccc(*)cc1 ; *c1ccc(*)s1]

and R$^{10}$ is H or CH$_3$.

In one embodiment of this aspect of the invention, $L^1$-$R^1$ is C$_3$-C$_7$alkylene-R$^1$ and the C$_3$-C$_7$alkylene is optionally substituted with 1-4 fluoro substituents. In one group of compounds, for example, $L^1$-$R^1$ is n-pentylene-COOR$^{10}$, n-hexylene-COOR$^{10}$, n-heptylene-COOR$^{10}$, etc., and R$^{10}$ is H or CH$_3$. In one embodiment, $L^1$-$R^1$ is n-hexylene-COOH or n-hexylene-COOCH$_3$.

In another embodiment of this aspect of the invention, $L^1$-$R^1$ is —(CH$_2$)$_n$-G$^2$-(CH$_2$)$_p$—R$^1$; and G$^2$ is

In another embodiment, $L^1$-$R^1$ is —(CH$_2$)$_n$-G$^2$-COOR$^{10}$ (i.e., p is 0), G$^2$ is

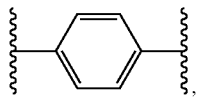

n is 2 or 3, and R$^{10}$ is H or CH$_3$. In one embodiment, $L^1$-$R^1$ is

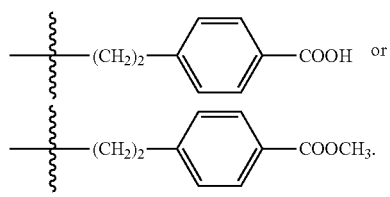

In another embodiment, $L^1$-$R^1$ is

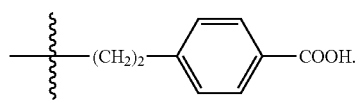

In another embodiment of this aspect of the invention $L^1$-$R^1$ is —(CH$_2$)$_n$-G$^2$-(CH$_2$)$_p$—R$^1$ and G$^2$ is

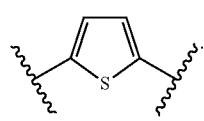

In another embodiment, $L^1$-$R^1$ is —(CH$_2$)$_n$-G$^2$-COOR$^{10}$ (i.e., p is 0), G$^2$ is

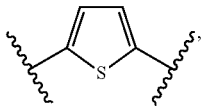 [SMILES: *c1ccc(*)s1]

n is 2 or 3; and R$^{10}$ is H or CH$_3$. In still another embodiment, $L^1$-$R^1$ is

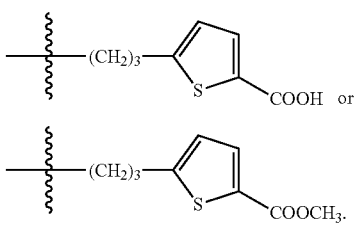

In yet another embodiment, $L^1$-$R^1$ is

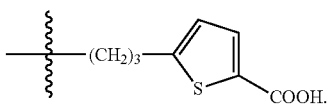

In another embodiment, $L^1$-$R^1$ is —CH$_2$-G$^2$-CH$_2$—COOR$^{00}$, G$^2$ is

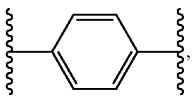

and R$^{10}$ is H or CH$_3$. In another embodiment, $L^1$-$R^1$ is —CH$_2$-G$^2$-CH$_2$—COOR$^{10}$, G$^2$ is

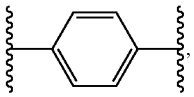

and R$^9$ is H.

In still another embodiment of this aspect of the invention, $L^1$-$R^1$ is —(CH$_2$)$_n$—C≡C-G$^2$-COOR$^{10}$ and G$^2$ is

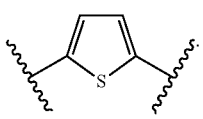 [SMILES: *c1ccc(*)s1]

In yet another embodiment, $L^1$-$R^1$ is —(CH$_2$)$_n$—C≡C-G$^2$-COOR$^{10}$, G$^2$ is

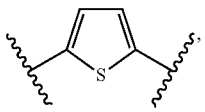 [SMILES: *c1ccc(*)s1]

n is 1, and $R^{10}$ is H or $CH_3$. In another embodiment, $L^1$-$R^1$ is —$(CH_2)_n$—C≡C-$G^2$-COO$R^{10}$, $G^2$ is

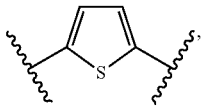 [SMILES: *c1ccc(*)s1]

n is 1, and $R^{10}$ is H.

In another embodiment of this aspect of the invention, $L^1$-$R^1$ is —$(CH_2)_n$—C(H)=C(H)-$G^2$-COO$R^{10}$ and $G^2$ is

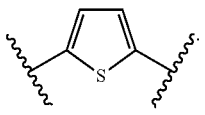 [SMILES: *c1ccc(*)s1]

In another embodiment, $L^1$-$R^1$ is —$(CH_2)_n$—C(H)=C(H)-$G^2$-COO$R^{10}$, $G^2$ is

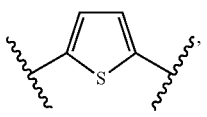

n is 1, and $R^{10}$ is H or $CH_3$. In another embodiment, $L^1$-$R^1$ is —$(CH_2)_n$—C(H)=C(H)-$G^2$-COO$R^{10}$, $G^2$ is

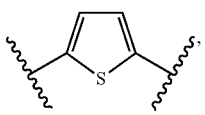 [SMILES: *c1ccc(*)s1]

n is 1, and $R^{10}$ is H.

In another aspect of the invention are compounds of formula (I) or (Ia), wherein

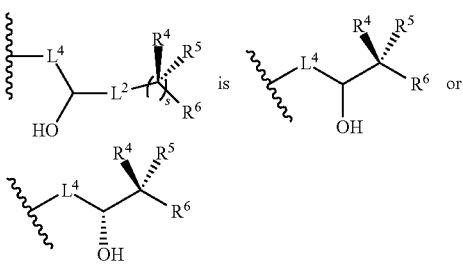

(i.e., $L^2$ is a bond and s is 1), $R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, (each optionally substituted as described herein) and $L^4$, $R^4$, and $R^5$ are as defined herein. In a first embodiment of this aspect of the invention, $L^4$ is

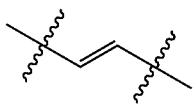 [SMILES: */C=C/*]

and $R^4$ and $R^5$ are independently H or $CH_3$. In one group of compounds according to the first embodiment, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl. In another group of compounds of this embodiment, $R^6$ is $C_3$-$C_{10}$alkyl (e.g., propyl, butyl, pentyl, octyl, etc.). In a subgroup of compounds, $R^6$ is n-propyl, n-butyl, or n-pentyl. In another subgroup, $R^6$ is n-butyl. In another group of compounds of the first embodiment, $R^6$ is $C_3$-$C_{10}$alkynyl (e.g., propynyl, butynyl, pentynyl, hexynyl, etc.). In a subgroup of compounds, $R^6$ is but-2-yn-1-yl, pent-2-yn-1-yl, or hex-2-yn-1-yl. In another subgroup, $R^6$ is pent-2-yn-1-yl. In another group of compounds according to the first embodiment, $R^6$ is aryl or heteroaryl, each optionally substituted as described herein. In one group of compounds, $R^6$ is phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$). In a second embodiment of this aspect of the invention, $L^4$ is —$CH_2$—$CH_2$— and $R^4$ and $R^5$ are independently H or $CH_3$. In a third embodiment of this aspect of the invention $L^4$ is —C≡C— and $R^4$ and $R^5$ are independently H or $CH_3$. In a fourth embodiment of this aspect of the invention, $L^4$ is

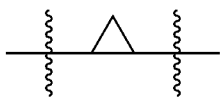 [SMILES: *C1CC1*]

and $R^4$ and $R^5$ are independently H or $CH_3$. Groups of compounds according to the second, third, and fourth embodiments include those where $R^6$ is $C_3$-$C_{10}$alkyl (e.g., propyl, butyl, pentyl, octyl, etc.), $C_3$-$C_{10}$alkynyl (e.g., propynyl, butynyl, pentynyl, hexynyl, etc.), or phenyl optionally substituted with halogen (e.g., fluoro, chloro), $C_1$-$C_3$haloalkyl (e.g., $CF_3$), or —$C_1$-$C_3$alkylene-$C_1$-$C_3$alkoxy (e.g., $CH_2OCH_3$).

In another aspect of the invention are compounds of formula (I) or (Ia), wherein

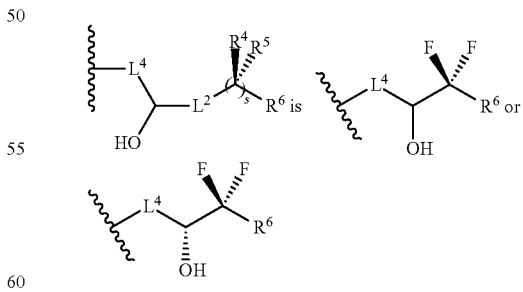

(i.e., $L^2$ is a bond, s is 1, and $R^4$ and $R^5$ are fluoro), $R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl, (each optionally substituted as described herein), and $L^4$ is as defined herein. In a first embodiment according to this aspect of the invention, $L^4$ is

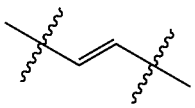 [SMILES: */C=C/*]

and $R^6$ is aryl, optionally substituted as describe herein. In one group of compounds according to the first embodiment $R^6$ is phenyl, optionally substituted. In another group of compounds $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl.

In another aspect of the invention are compounds of formula (I) or (Ia), wherein

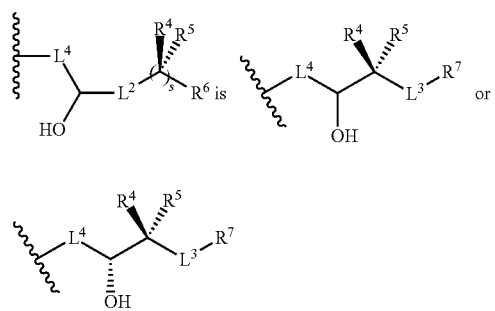

(i.e., $L^2$ is a bond, s is 1, and $R^6$ is $L^3$-$R^7$), $L^3$ is $C_1$-$C_6$alkylene, $C_2$-$C_6$alkenylene, or $C_2$-$C_6$alkynylene (each optionally substituted with 1, 2, 3, or 4 fluoro substituents), and $L^4$, $R^4$, $R^5$, and $R^7$ are as defined herein. In a first embodiment of this aspect of the invention, $L^4$ is

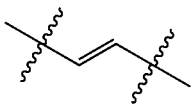 [SMILES: */C=C/*]

and $R^4$ and $R^5$ are independently H or $CH_3$. In one group of compounds according to the first embodiment, $R^7$ is $C_3$-$C_8$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein $R^7$ is optionally substituted as described herein. In one group of compounds of this embodiment, $L^3$ is $C_1$-$C_6$alkylene (e.g., propylene, butylene, pentylene, etc.) and $R^7$ is phenyl, naphthyl, thienyl, or cyclohexyl, each optionally substituted. In another group of compounds of this embodiment, $L^3$ is $C_1$-$C_6$alkylene (e.g., propylene, butylene, pentylene, etc.), where the $C_1$-$C_6$alkylene is a straight chain alkylene group, and $R^7$ is phenyl optionally substituted. In a subgroup of compounds $L^3$ is n-propylene, n-butylene, or n-pentylene and $R^7$ is phenyl. In another group of compounds of this embodiment, $L^3$ is $C_2$-$C_6$alkenylene (e.g., propenylene, butenylene, etc.) and $R^7$ is phenyl, naphthyl, thienyl, or cyclohexyl, each optionally substituted. In another group of compounds of this embodiment, $L^3$ is $C_2$-$C_6$alkynylene (e.g., propynylene, butynylene, etc.) and $R^7$ is phenyl, naphthyl, thienyl, or cyclohexyl, each optionally substituted. In a subgroup of compounds, $L^3$ is —$CH_2$—C≡C—, and $R^7$ is phenyl. In a second embodiment of this aspect of the invention, $L^4$ is —$CH_2$—$CH_2$— and $R^4$ and $R^5$ are independently H or $CH_3$. In a third embodiment of this aspect of the invention $L^4$ is —C≡C— and $R^4$ and $R^5$ are independently H or $CH_3$. In a fourth embodiment of this aspect of the invention, $L^4$ is

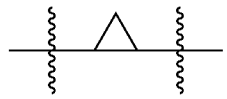 [SMILES: *C1CC1*]

and $R^4$ and $R^5$ are independently H or $CH_3$. Groups of compounds according to the second, third, and fourth embodiments include those where $L^3$ is $C_2$-$C_6$alkylene (e.g., propylene, butylene, pentylene, etc.), $C_2$-$C_6$alkenylene (e.g., propenylene, butenylene, etc.), or $C_2$-$C_6$alkynylene (e.g., propynyl, butynyl, etc.), and $R^7$ is phenyl, naphthyl, thienyl, or cyclohexyl, each optionally substituted.

In another aspect of the invention,

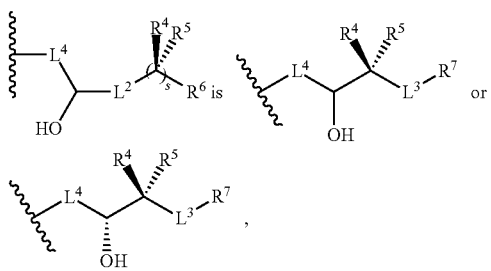

$L^3$ is —$(CH_2)_m$-$G^3$-$(CH_2)_q$—, —$(CH_2)_m$-$G^4$-$(CH_2)_q$—, or -$G^5$-C≡C—; and $L^4$, $G^3$, $G^4$, $G^5$, $R^4$, $R^5$, $R^7$, m, and q are as defined herein. In a first embodiment of this aspect of the invention, $L^4$

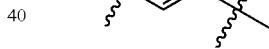

and $R^4$ and $R^5$ are independently H or $CH_3$. In one group of compounds according to the first embodiment, $L^3$ is -$G^5$-C≡C—, $G^5$ is

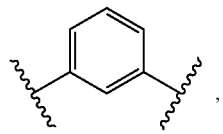 [SMILES: *c1cccc(*)c1]

and $R^7$ is $C_3$-$C_8$cycloalkyl (e.g., cyclopropyl, cyclopentyl, cyclohexyl), aryl (e.g., phenyl, naphthyl), heteroaryl (e.g., thienyl, furanyl), or heterocyclyl (e.g., tetrahydrofuranyl); wherein $R^7$ is optionally substituted as described herein.

In another aspect of the invention

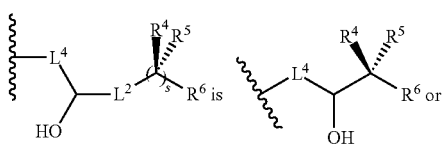

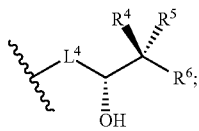

$L^4$ is —C(R)=C($R^3$)—; $R^2$ and $R^3$ are each hydrogen; $R^4$ and $R^5$ are independently H or $C_1$-$C_4$ alkyl; $R^6$ is $C_3$-$C_{10}$alkyl, $C_3$-$C_{10}$alkynyl, or $L^3$-$R^7$; $L^3$ is $C_1$-$C_6$alkylene or $C_2$-$C_6$alkynylene; wherein the $C_1$-$C_6$alkylene and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In another aspect of the invention are compounds of formula (I) or (Ia), wherein:

$L^1$-$R^1$ is $C_3$-$C_7$alkylene-$R^1$, wherein the $C_3$-$C_7$alkylene is optionally substituted with 1, 2, 3, or 4 fluoro substituents; or $L^1$-$R^1$ is —(CH$_2$)$_n$-$G^2$-(CH$_2$)$_p$—$R^1$, —(CH$_2$)$_n$—C≡C-$G^2$-$R^1$, or —(CH$_2$)$_n$—C(H)=C(H)-$G^2$-$R^1$, wherein n is 1, 2, 3, 4, or 5, p is 0, 1, 2, or 3, and n+p=1, 2, 3, 4, 5, or 6; $G^2$ is

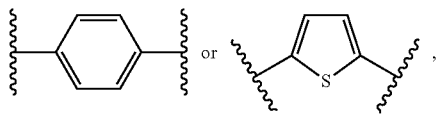

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy; $R^1$ is COOR$^{10}$; $R^{10}$ is H or $C_1$-$C_4$ alkyl; and

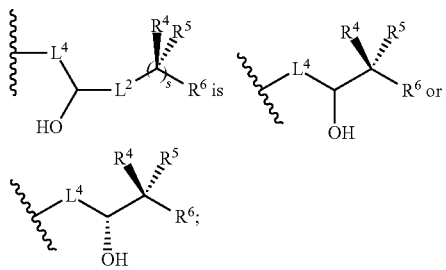

$L^4$ is —C($R^2$)$_2$—C($R^3$)$_2$—, —C($R^2$)=C($R^3$)—, —C≡C—, or

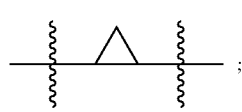

wherein $R^2$ and $R^3$ are each H, CH$_3$, fluoro, or chloro; $R^4$ and $R^5$ are each independently H, F, CF$_3$, or $C_1$-$C_4$ alkyl; or $R^4$ and $R^5$ together with the carbon to which they are attached form a $C_3$-$C_5$ cycloalkyl; $R^6$ is aryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; $L^3$ is $C_1$-$C_6$alkylene, $C_2$-$C_6$alkenylene, or $C_2$-$C_6$alkynylene wherein the $C_1$-$C_6$alkylene, $C_2$-$C_6$alkenylene, and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In one embodiment according to the foregoing aspect of the invention, $L^4$ is

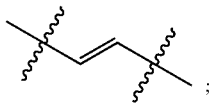 [SMILES: */C=C/*]

$R^4$ and $R^5$ are independently H or $C_1$-$C_4$ alkyl; $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; $L^3$ is $C_1$-$C_6$alkylene, $C_2$-$C_6$alkenylene, or $C_2$-$C_6$alkynylene; wherein the $C_1$-$C_6$alkylene, $C_2$-$C_6$alkenylene, and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In one group of compounds according to the foregoing embodiment, $L^1$-$R^1$ is $C_3$-$C_7$alkylene-$R^1$; or $L^1$-$R^1$ is —(CH$_2$)$_n$-$G^2$-(CH$_2$)$_p$—$R^1$, —(CH$_2$)$_n$—C≡C-$G^2$-$R^1$, or —(CH$_2$)$_n$—C(H)=C(H)-$G^2$-$R^1$, wherein n is 1, 2 or 3, p is 0, 1, or 2, and n+p=1, 2, 3 or 4; $G^2$ is

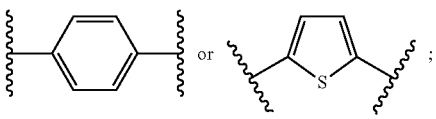

$R^1$ is COOR$^{10}$; $R^{10}$ is H or $C_1$-$C_4$ alkyl; $R^4$ and $R^5$ are independently H or CH$_3$; $L^3$ is ethynylene, propynylene, or butynylene; and $R^6$ is phenyl or $C_1$-$C_6$alkyl, wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy.

In one group of compounds according to the foregoing embodiment, $L^1$-$R^1$ is $C_3$-$C_7$alkylene-$R^1$; or $L^1$-$R^1$ is —(CH$_2$)$_n$-$G^2$-(CH$_2$)$_p$—$R^1$, wherein n is 2 or 3 and p is 0; $G^2$ is

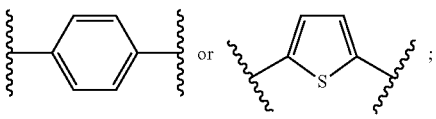 [SMILES: *c1ccc(*)cc1 ; *c1ccc(*)s1]

$R^1$ is COOR$^{10}$; and $R^{10}$ is H or $C_1$-$C_4$ alkyl.

In one group of compounds according to the foregoing embodiment, $R^4$ and $R^5$ are independently H or CH$_3$; $R^6$ is $C_3$-$C_{10}$alkyl, $C_3$-$C_{10}$alkynyl, or $L^3$-$R^7$; $L^3$ is $C_1$-$C_6$alkylene or $C_2$-$C_6$alkynylene; wherein the $C_1$-$C_6$alkylene and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy. In one subgroup of compounds, $L^1$ is $C_3$-$C_7$alkylene or —(CH$_2$)$_n$-G$^2$-(CH$_2$)$_p$—, wherein n is 2 or 3 and p is 0; and G$^2$ is

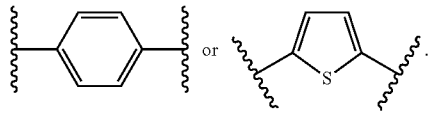 [SMILES: *c1ccc(*)cc1 ; *c1ccc(*)s1]

In another subgroup of compounds, $L^1$ is $C_3$-$C_7$alkylene or —(CH$_2$)$_n$-G$^2$-; n is 2 or 3; G$^2$ is

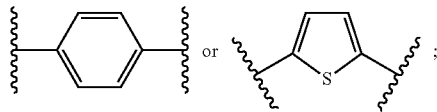 [SMILES: *c1ccc(*)cc1 ; *c1ccc(*)s1]

$R^6$ is propyl, butyl, pentyl, propynyl, butynyl, pentynyl, hexynyl, or $L^3$-$R^7$; $L^3$ is propylene, butylene, pentylene, propynylene, or butynylene; and $R^7$ is phenyl or phenyl optionally substituted. In another subgroup of compounds, $L^1$ is $C_3$-$C_7$alkylene and $R^6$ is propyl, butyl, pentyl, propynyl, butynyl, pentynyl, or hexynyl. In another subgroup of compounds, $L^1$ is $C_3$-$C_7$alkylene and $R^6$ is $L^3$-$R^7$; $L^3$ is propylene, butylene, pentylene, propynylene, or butynylene; and $R^7$ is phenyl or phenyl optionally substituted. In another subgroup of compounds, $L^1$ is —(CH$_2$)$_n$-G$^2$-, wherein n is 2 or 3; G$^2$ is

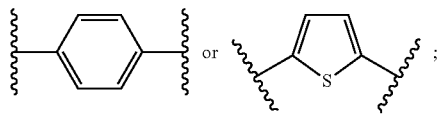 [SMILES: *c1ccc(*)cc1 ; *c1ccc(*)s1]

and $R^6$ is propyl, butyl, pentyl, propynyl, butynyl, pentynyl, or hexynyl. In another subgroup of compounds, $L^1$ is —(CH$_2$)$_n$-G$^2$-, wherein n is 2 or 3; G$^2$ is

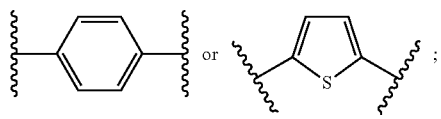 [SMILES: *c1ccc(*)cc1 ; *c1ccc(*)s1]

and $R^6$ is $L^3$-$R^7$; $L^3$ is propylene, butylene, pentylene, propynylene, or butynylene; and $R^7$ is phenyl or phenyl optionally substituted. In a further subgroup, $L^1$ is n-hexylene or —(CH$_2$)$_n$-G$^2$-, wherein n is 2 or 3; G$^2$ is

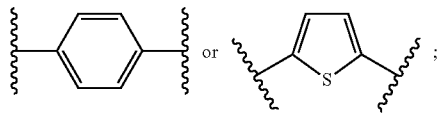 [SMILES: *c1ccc(*)cc1 ; *c1ccc(*)s1]

$R^1$ is COOR$^{10}$; $R^{10}$ is H or CH$_3$; $R^6$ is n-butyl, but-2-yn-1-yl, pent-2-yn-1-yl, hex-2-yn-1-yl, or $L^3$-$R^7$; $L^3$ is n-propylene, n-butylene, or n-pentylene or —CH$_2$—C≡C—; and $R^7$ is phenyl or phenyl optionally substituted. In another subgroup of compounds, $L^1$ is n-hexylene; $R^1$ is COOR$^{10}$; $R^{10}$ is H or CH$_3$; and $R^6$ is n-butyl, but-2-yn-1-yl, pent-2-yn-1-yl, or hex-2-yn-1-yl. In another subgroup of compounds, $L^1$ is n-hexylene; $R^1$ is COOR$^{10}$; $R^{10}$ is H or CH$_3$; and $R^6$ is $L^3$-$R^7$; $L^3$ is n-propylene, n-butylene, n-pentylene or —CH$_2$—C≡C—; and $R^7$ is phenyl or phenyl optionally substituted. In another subgroup of compounds, $L^1$ is —(CH$_2$)$_n$-G$^2$-, wherein n is 2 or 3; G$^2$ is

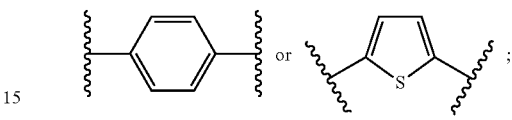

$R^1$ is COOR$^{10}$; $R^{10}$ is H or CH$_3$; and $R^6$ is n-butyl, but-2-yn-1-yl, pent-2-yn-1-yl or hex-2-yn-1-yl. In another subgroup of compounds, $L^1$ is —(CH$_2$)$_n$-G$^2$-, wherein n is 2 or 3; G$^2$ is

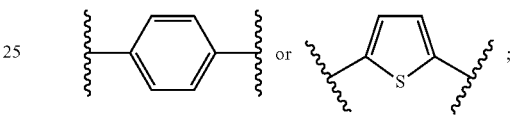

$R^1$ is COOR$^{10}$; $R^{10}$ is H or CH$_3$; and $R^6$ is $L^3$-R; $L^3$ is n-propylene, n-butylene, n-pentylene or —CH$_2$—C≡C—; and $R^7$ is phenyl or phenyl optionally substituted.

In another group of compounds according to the foregoing embodiment, $R^6$ is $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, or $C_3$-$C_{10}$haloalkynyl. In a subgroup of compounds, $L^1$ is $C_3$-$C_7$alkylene, wherein the alkylene is optionally substituted with 1, 2, 3, or 4 fluoro substituents. In a further subgroup, $R^6$ is $C_3$-$C_{10}$alkyl, $C_3$-$C_{10}$alkenyl, or $C_3$-$C_{10}$alkynyl; and $L^1$ is $C_3$-$C_7$alkylene. In another subgroup, $L^1$ is —(CH$_2$)$_n$-G$^2$-(CH$_2$)$_p$—, —(CH$_2$)$_n$—C≡C-G$^2$-, or —(CH$_2$)$_n$—C(H)=C(H)-G$^2$-, wherein n is 1, 2, 3, 4, or 5, p is 0, 1, 2, or 3, and n+p=1, 2, 3, 4, 5, or 6; and G$^2$ is

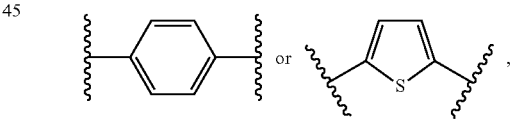

wherein G$^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In a further subgroup, $R^6$ is $C_3$-$C_{10}$alkyl, $C_3$-$C_{10}$alkenyl, or $C_3$-$C_{10}$alkynyl; and $L^1$ is —(CH$_2$)$_n$-G-(CH$_2$)$_p$—, wherein n is 2 or 3 and p is 0; and G$^2$ is

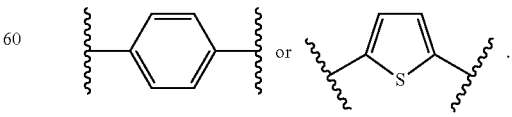

In yet another group of compounds according to the foregoing embodiment, $R^6$ is $L^3$-$R^7$; $L^3$ is $C_1$-$C_6$alkylene, $C_2$-$C_6$alkenylene, or $C_2$-$C_6$alkynylene; wherein the $C_1$-$C_6$alkylene, $C_2$-$C_6$alkenylene, and $C_2$-$C_6$alkynylene are optionally substituted with 1, 2, 3, or 4 fluoro substituents; and $R^7$ is aryl, wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy. In one subgroup of compounds, $L^1$ is $C_3$-$C_7$alkylene, wherein the $C_3$-$C_7$alkylene is optionally substituted with 1, 2, 3, or 4 fluoro substituents. In a further subgroup of compounds, $R^6$ is $L^3$-$R^7$; $L^3$ is $C_1$-$C_6$alkylene, $C_2$-$C_6$alkenylene, or $C_2$-$C_6$alkynylene; $R^7$ is aryl or optionally substituted aryl; and $L^1$ is $C_3$-$C_7$alkylene. In still another subgroup $R^6$ is $L^3$-$R^7$; $L^3$ is $C_1$-$C_6$alkylene, $C_2$-$C_6$alkenylene, or $C_2$-$C_6$alkynylene; $R^7$ is phenyl or phenyl optionally substituted; and $L^1$ is $C_3$-$C_7$alkylene. In another subgroup, $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

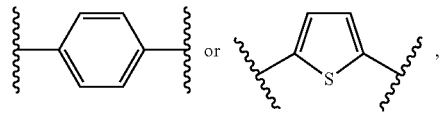

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In a further subgroup of compounds, $R^6$ is $L^3$-$R^7$; $L^3$ is $C_1$-$C_6$alkylene, $C_2$-$C_6$alkenylene, or $C_2$-$C_6$alkynylene; $R^7$ is aryl; $L^1$ is —$(CH_2)_n$-$G^2$-$(CH_2)_p$—, wherein n is 2 or 3, and p is 0; and $G^2$ is

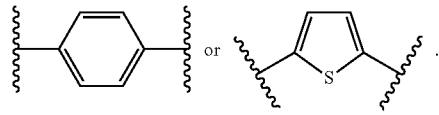

In still another subgroup $R^6$ is $L^3$-$R^7$; $L^3$ is $C_1$-$C_6$alkylene, $C_2$-$C_6$alkenylene, or $C_2$-$C_6$alkynylene; $R^7$ is phenyl or phenyl optionally substituted; and $L^1$ is —$(CH_2)_n$-$G^2$-$(CH_2)_p$—, wherein n is 2 or 3, and p is 0; and $G^2$ is

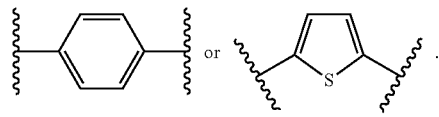 [SMILES: *c1ccc(*)cc1 ; *c1ccc(*)s1]

In still another group of compounds according to the foregoing embodiment, $L^1$ is $C_3$-$C_7$alkylene, wherein the $C_3$-$C_7$alkylene is optionally substituted with 1, 2, 3, or 4 fluoro substituents.

In another group of compounds according to the foregoing embodiment, $L^1$ is —$(CH_2)_n$-$G^2$-$(CH_2)_p$—, —$(CH_2)_n$—C≡C-$G^2$-, or —$(CH_2)_n$—C(H)=C(H)-$G^2$-, wherein n is 1, 2, 3, 4, or 5, p is 0, 1, 2, or 3, and n+p=1, 2, 3, 4, 5, or 6; and $G^2$ is

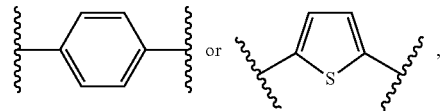

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy. In one subgroup of compounds, $L^1$ is —$(CH_2)_n$-$G^2$-$(CH_2)_p$—, wherein n is 2 or 3, p is 0, and $G^2$ is

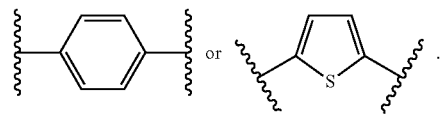 [SMILES: *c1ccc(*)cc1 ; *c1ccc(*)s1]

In another aspect of the invention are bone-repairing compounds of formula (II)

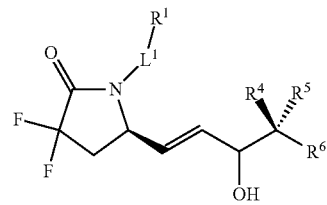

(II)

wherein:

$L^1$ is a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;

b) —$(CH_2)_t$-G-$(CH_2)_p$—; wherein t is 0, 1, or 2, p is 0, 1, 2, or 3, and t+p=0, 1, 2, 3, or 4; or c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{13}$)=C($R^{13}$)-$G^2$-, wherein n is 1, 2, 3, 4, or 5, p is 0, 1, 2, or 3, and n+p=1, 2, 3, 4, 5, or 6;

$G^1$ is

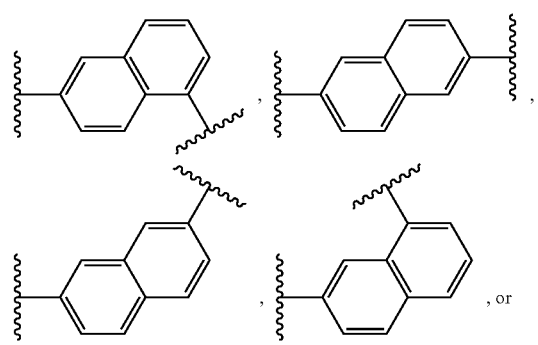

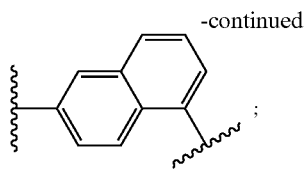

$G^1$ is O, C(O), S, S(O), S(O)$_2$, or NR$^8$; wherein R$^8$ is H, C$_1$-C$_4$ alkyl, or C$_1$-C$_4$alkylcarbonyl;
$G^2$ is

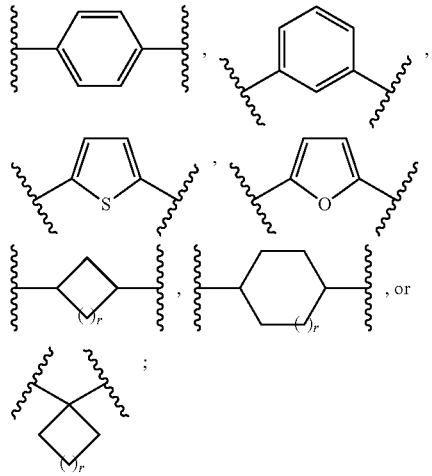

wherein G$^2$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;

R$^1$ is COOR$^{10}$, CONR$^{11}$R$^{11}$, CH$_2$OR$^{10}$, SO$_3$R$^{10}$, SO$_2$NR$^{10}$R$^{11}$, PO(OR$^{10}$)$_2$, or tetrazol-5-yl;

R$^{10}$ is H, C$_1$-C$_4$ alkyl, or aryl;

R$^{11}$ is H, C$_1$-C$_4$ alkyl, COR$^{12}$, OR$^{10}$, or SO$_2$R$^{12}$;

R$^{12}$ is C$_1$-C$_4$ alkyl;

R$^{13}$, at each occurrence, is independently H or C$_1$-C$_4$alkyl;

R$^4$ and R$^5$ are each independently H, F, CF$_3$, or C$_1$-C$_4$ alkyl; or R$^4$ and R$^5$ together with the carbon to which they are attached form a C$_3$-C$_5$ cycloalkyl,

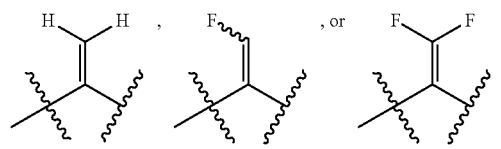

R$^6$ is aryl, heteroaryl, C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, C$_3$-C$_{10}$haloalkynyl, or L$^3$-R$^7$; wherein the aryl and heteroaryl are optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy; and —C$_1$-C$_3$alkylene-C$_1$-C$_3$alkoxy; and wherein the C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, and C$_3$-C$_{10}$haloalkynyl are optionally substituted with a substituent selected from the group consisting of COOR$^{10}$, CONR$^{10}$R$^{11}$, CH$_2$OR$^{10}$, SO$_3$R$^{10}$, SO$_2$NR$^{10}$R$^{11}$, PO(OR$^{10}$)$_2$, and tetrazol-5-yl;

L$^3$ is C$_1$-C$_6$alkylene, C$_2$-C$_6$alkenylene, C$_2$-C$_6$alkynylene, —(CH$_2$)$_m$-G$^3$-(CH$_2$)$_q$—, —(CH$_2$)$_m$-G$^4$-(CH$_2$)$_q$—, or -G$^5$-C≡C—; wherein the C$_1$-C$_6$alkylene, C$_2$-C$_6$alkenylene, and C$_2$-C$_6$alkynylene are optionally substituted with 1, 2, 3, or 4 fluoro substituents; and wherein m and q are each independently 0, 1, 2, or 3 and m+q=0, 1, 2, 3, or 4;

G$^3$ is O, C(O), S, S(O), S(O)$_2$, or NR$^9$; wherein R$^9$ is H, C$_1$-C$_4$ alkyl, or C$_1$-C$_4$alkylcarbonyl;

G$^4$ is

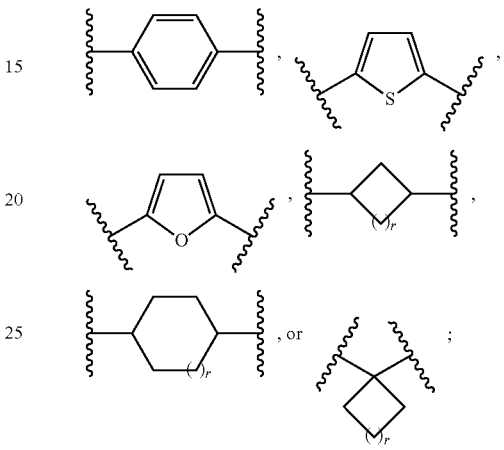

wherein G$^4$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;

G$^5$ is

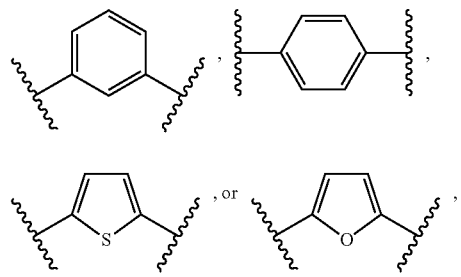

wherein G$^5$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;

R$^7$ is C$_3$-C$_8$cycloalkyl, aryl, heteroaryl, or heterocyclyl; wherein R$^7$ is optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy, and —C$_1$-C$_3$alkylene-C$_1$-C$_3$alkoxy; and r is 0 or 1.

In one embodiment according to the foregoing aspect, L$^1$ is C$_3$-C$_7$alkylene, —(CH$_2$)$_n$-G$^2$-(CH$_2$)$_p$—, —(CH$_2$)$_n$—C≡C-G$^2$-, or —(CH$_2$)$_n$—C(H)=C(H)-G$^2$-, wherein n is 1, 2, 3, 4, or 5, p is 0, 1, 2, or 3, and n+p=1, 2, 3, 4, 5, or 6; G$^2$ is

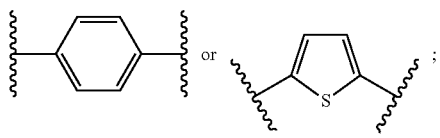 [SMILES: *c1ccc(*)cc1 ; *c1ccc(*)s1]

$R^1$ is $COOR^{10}$; $R^{10}$ is H or $C_1$-$C_4$ alkyl; $R^4$ and $R^5$ are each independently H or $C_1$-$C_4$ alkyl; $R^6$ is $C_3$-$C_{10}$alkyl, $C_3$-$C_{10}$alkenyl, $C_3$-$C_{10}$alkynyl, or $L^3$-$R^7$; $L^3$ is $C_1$-$C_6$alkylene, $C_2$-$C_6$alkynylene, or $C_2$-$C_6$alkynylene; and $R^7$ is aryl, optionally substituted as described herein.

In another embodiment according to the foregoing aspect, $L^1$ is $C_3$-$C_7$alkylene or —$(CH_2)_n$-$G^2$-$(CH_2)_p$—, wherein n is 2, 3, 4, or 5, p is 0, 1, 2, or 3, and n+p=2, 3, 4, 5, or 6; $G^2$

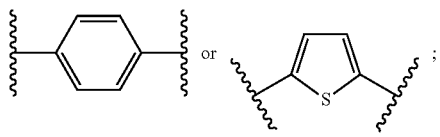 [SMILES: *c1ccc(*)cc1 ; *c1ccc(*)s1]

$R^1$ is $COOR^{10}$; $R^{10}$ is H or $C_1$-$C_4$ alkyl; $R^4$ and $R^5$ are each independently H or $C_1$-$C_4$ alkyl; $R^6$ is $C_3$-$C_{10}$alkyl, $C_3$-$C_{10}$alkenyl, $C_3$-$C_{10}$alkynyl, or $L^3$-$R^7$; $L^3$ is $C_1$-$C_6$alkylene, $C_2$-$C_6$alkynylene, or $C_2$-$C_6$alkynylene; and $R^7$ is aryl, optionally substituted as described herein.

In another embodiment, $L^1$ is $C_3$-$C_7$alkylene or —$(CH_2)_n$-$G^2$-$(CH_2)_p$—, wherein n is 2 or 3, p is 0; $G^2$ is

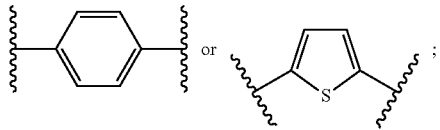 [SMILES: *c1ccc(*)cc1 ; *c1ccc(*)s1]

$R^1$ is $COOR^{10}$; $R^{10}$ is H or $C_1$-$C_4$ alkyl; $R^4$ and $R^5$ are each independently H or $C_1$-$C_4$ alkyl; $R^6$ is $C_3$-$C_{10}$alkyl, $C_3$-$C_{10}$alkynyl, or $L^3$-$R^7$; $L^3$ is $C_1$-$C_6$alkylene, $C_2$-$C_6$alkynylene, or $C_2$-$C_6$alkynylene; and $R^7$ is aryl, optionally substituted as described herein.

In another aspect, bone-repairing EP4 agonist drug compounds are selected from the group consisting of:

methyl 7-((R)-3,3-difluoro-5-((3S,4S,E)-3-hydroxy-4-methyloct-1-en-6-yn-1-yl)-2-oxopyrrolidin-1-yl)heptanoate;
methyl 7-((R)-3,3-difluoro-5-((3S,4R,E)-3-hydroxy-4-methyloct-1-en-6-yn-1-yl)-2-oxopyrrolidin-1-yl)heptanoate;
methyl 7-((5R)-3,3-difluoro-5-((3R,E)-3-hydroxy-4-methyloct-1-en-6-yn-1-yl)-2-oxopyrrolidin-1-yl)heptanoate;
methyl 7-((R)-3,3-difluoro-5-((3R,4S,E)-3-hydroxy-4-methyloct-1-en-6-yn-1-yl)-2-oxopyrrolidin-1-yl)heptanoate;
methyl 7-((R)-3,3-difluoro-5-((3R,4R,E)-3-hydroxy-4-methyloct-1-en-6-yn-1-yl)-2-oxopyrrolidin-1-yl)heptanoate;
7-((R)-3,3-difluoro-5-((3S,4S,E)-3-hydroxy-4-methyloct-1-en-6-yn-1-yl)-2-oxopyrrolidin-1-yl)heptanoic acid;
7-((R)-3,3-difluoro-5-((3S,4R,E)-3-hydroxy-4-methyloct-1-en-6-yn-1-yl)-2-oxopyrrolidin-1-yl)heptanoic acid;
7-((R)-3,3-difluoro-5-((3R,4S,E)-3-hydroxy-4-methyloct-1-en-6-yn-1-yl)-2-oxopyrrolidin-1-yl)heptanoic acid;
7-((R)-3,3-difluoro-5-((3R,4R,E)-3-hydroxy-4-methyloct-1-en-6-yn-1-yl)-2-oxopyrrolidin-1-yl)heptanoic acid;
methyl 7-((R)-3,3-difluoro-5-((3S,4S,E)-3-hydroxy-4-methylnon-1-en-6-yn-1-yl)-2-oxopyrrolidin-1-yl)heptanoate;
methyl 7-((R)-3,3-difluoro-5-((3R,4S,E)-3-hydroxy-4-methylnon-1-en-6-yn-1-yl)-2-oxopyrrolidin-1-yl)heptanoate;
7-((R)-3,3-difluoro-5-((3S,4S,E)-3-hydroxy-4-methylnon-1-en-6-yn-1-yl)-2-oxopyrrolidin-1-yl)heptanoic acid;
7-((R)-3,3-difluoro-5-((3R,4S,E)-3-hydroxy-4-methylnon-1-en-6-yn-1-yl)-2-oxopyrrolidin-1-yl)heptanoic acid;
Methyl 7-((5R)-3,3-difluoro-5-((E)-3-hydroxy-4-methyldec-1-en-6-yn-1-yl)-2-oxopyrrolidin-1-yl)heptanoate;
Methyl 7-((5R)-3,3-difluoro-5-((E)-3-hydroxy-4-methyl-7-phenylhept-1-en-6-yn-1-yl)-2-oxopyrrolidin-1-yl)heptanoate;
Methyl 7-((5R)-3,3-difluoro-5-((E)-3-hydroxy-4-methyloct-1-en-1-yl)-2-oxopyrrolidin-1-yl)heptanoate;
methyl 7-((R)-3,3-difluoro-5-((3S,4S,E)-3-hydroxy-4-methyl-7-phenylhept-1-en-1-yl)-2-oxopyrrolidin-1-yl)heptanoate;
methyl 7-((R)-3,3-difluoro-5-((3S,4R,E)-3-hydroxy-4-methyl-7-phenylhept-1-en-1-yl)-2-oxopyrrolidin-1-yl)heptanoate;
methyl 7-((5R)-3,3-difluoro-5-((3R,E)-3-hydroxy-4-methyl-7-phenylhept-1-en-1-yl)-2-oxopyrrolidin-1-yl)heptanoate;
7-((R)-3,3-difluoro-5-((3S,4S,E)-3-hydroxy-4-methyl-7-phenylhept-1-en-1-yl)-2-oxopyrrolidin-1-yl)heptanoic acid;
7-((R)-3,3-difluoro-5-((3S,4R,E)-3-hydroxy-4-methyl-7-phenylhept-1-en-1-yl)-2-oxopyrrolidin-1-yl)heptanoic acid;
7-((5R)-3,3-difluoro-5-((3R,E)-3-hydroxy-4-methyl-7-phenylhept-1-en-1-yl)-2-oxopyrrolidin-1-yl)heptanoic acid;
Methyl 7-((5R)-3,3-difluoro-5-((E)-3-hydroxynon-1-en-6-yn-1-yl)-2-oxopyrrolidin-1-yl)heptanoate;
Methyl 7-((5R)-3,3-difluoro-5-((E)-3-hydroxy-7-phenylhept-1-en-6-yn-1-yl)-2-oxopyrrolidin-1-yl)heptanoate;
methyl 7-((R)-3,3-difluoro-5-((S,E)-3-hydroxyoct-1-en-1-yl)-2-oxopyrrolidin-1-yl)heptanoate;
methyl 7-((R)-3,3-difluoro-5-((R,E)-3-hydroxyoct-1-en-1-yl)-2-oxopyrrolidin-1-yl)heptanoate;
7-((R)-3,3-difluoro-5-((S,E)-3-hydroxyoct-1-en-1-yl)-2-oxopyrrolidin-1-yl)heptanoic acid;
7-((R)-3,3-difluoro-5-((R,E)-3-hydroxyoct-1-en-1-yl)-2-oxopyrrolidin-1-yl)heptanoic acid;
methyl 7-((R)-3,3-difluoro-5-((S,E)-3-hydroxy-7-phenylhept-1-en-1-yl)-2-oxopyrrolidin-1-yl)heptanoate;
methyl 7-((R)-3,3-difluoro-5-((R,E)-3-hydroxy-7-phenylhept-1-en-1-yl)-2-oxopyrrolidin-1-yl)heptanoate;
7-((R)-3,3-difluoro-5-((S,E)-3-hydroxy-7-phenylhept-1-en-1-yl)-2-oxopyrrolidin-1-yl)heptanoic acid;
7-((R)-3,3-difluoro-5-((R,E)-3-hydroxy-7-phenylhept-1-en-1-yl)-2-oxopyrrolidin-1-yl)heptanoic acid;
methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate;
methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate;
methyl 4-(2-((5R)-3,3-difluoro-5-((3R,E)-3-hydroxy-4-methylnon-1-en-6-yn-1-yl)-2-oxopyrrolidin-1-yl)ethyl)benzoate;
4-(2-((R)-3,3-difluoro-5-((3S,4S,E)-3-hydroxy-4-methylnon-1-en-6-yn-1-yl)-2-oxopyrrolidin-1-yl)ethyl)benzoic acid;

4-(2-((R)-3,3-difluoro-5-((3S,4R,E)-3-hydroxy-4-methyl-non-1-en-6-yn-1-yl)-2-oxopyrrolidin-1-yl)ethyl)benzoic acid;

4-(2-((5R)-3,3-difluoro-5-((3R,E)-3-hydroxy-4-methylnon-1-en-6-yn-1-yl)-2-oxopyrrolidin-1-yl)ethyl)benzoic acid;

4-(2-((R)-3,3-Difluoro-5-((3S,4S,E)-3-hydroxy-4-methyl-dec-1-en-6-yn-1-yl)-2-oxopyrrolidin-1-yl)ethyl)benzoic acid;

4-(2-((R)-3,3-Difluoro-5-((3S,4S,E)-3-hydroxy-4-methyl-7-phenylhept-1-en-6-yn-1-yl)-2-oxopyrrolidin-1-yl)ethyl)benzoic acid;

4-(2-((R)-3,3-difluoro-5-((3S,4S,E)-3-hydroxy-4-methyl-oct-1-en-1-yl)-2-oxopyrrolidin-1-yl)ethyl)benzoic acid;

4-(2-((R)-3,3-Difluoro-5-((3S,4S,E)-3-hydroxy-4-methyl-7-phenylhept-1-en-1-yl)-2-oxopyrrolidin-1-yl)ethyl)benzoic acid;

4-(2-((R)-3,3-Difluoro-5-((S,E)-3-hydroxyoct-1-en-6-yn-1-yl)-2-oxopyrrolidin-1-yl)ethyl)benzoic acid;

4-(2-((R)-3,3-Difluoro-5-((S,E)-3-hydroxynon-1-en-6-yn-1-yl)-2-oxopyrrolidin-1-yl)ethyl)benzoic acid;

4-(2-((R)-3,3-Difluoro-5-((S,E)-3-hydroxydec-1-en-6-yn-1-yl)-2-oxopyrrolidin-1-yl)ethyl)benzoic acid;

4-(2-((R)-3,3-Difluoro-5-((S,E)-3-hydroxy-7-phenylhept-1-en-6-yn-1-yl)-2-oxopyrrolidin-1-yl)ethyl)benzoic acid;

methyl 4-(2-((R)-3,3-difluoro-5-((S,E)-3-hydroxyoct-1-en-1-yl)-2-oxopyrrolidin-1-yl)ethyl)benzoate;

methyl 4-(2-((R)-3,3-difluoro-5-((R,E)-3-hydroxyoct-1-en-1-yl)-2-oxopyrrolidin-1-yl)ethyl)benzoate;

4-(2-((R)-3,3-difluoro-5-((S,E)-3-hydroxyoct-1-en-1-yl)-2-oxopyrrolidin-1-yl)ethyl)benzoic acid;

4-(2-((R)-3,3-difluoro-5-((R,E)-3-hydroxyoct-1-en-1-yl)-2-oxopyrrolidin-1-yl)ethyl)benzoic acid;

4-(2-((R)-3,3-Difluoro-5-((S,E)-3-hydroxy-7-phenylhept-1-en-1-yl)-2-oxopyrrolidin-1-yl)ethyl)benzoic acid;

5-(3-((R)-3,3-Difluoro-5-((3S,4S,E)-3-hydroxy-4-methyl-oct-1-en-6-yn-1-yl)-2-oxopyrrolidin-1-yl)propyl)thiophene-2-carboxylic acid;

methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate;

methyl 5-(3-((R)-3,3-difluoro-5-((3 S,4R,E)-3-hydroxy-4-methylnon-1-en-6-yn-1-yl)-2-oxopyrrolidin-1-yl)propyl)thiophene-2-carboxylate;

methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate;

5-(3-((R)-3,3-difluoro-5-((3S,4S,E)-3-hydroxy-4-methyl-non-1-en-6-yn-1-yl)-2-oxopyrrolidin-1-yl)propyl)thiophene-2-carboxylic acid;

5-(3-((R)-3,3-difluoro-5-((3S,4R,E)-3-hydroxy-4-methyl-non-1-en-6-yn-1-yl)-2-oxopyrrolidin-1-yl)propyl)thiophene-2-carboxylic acid;

5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylic acid;

5-(3-((R)-3,3-Difluoro-5-((3S,4S,E)-3-hydroxy-4-methyl-dec-1-en-6-yn-1-yl)-2-oxopyrrolidin-1-yl)propyl)thiophene-2-carboxylic acid;

5-(3-((R)-3,3-Difluoro-5-((3S,4S,E)-3-hydroxy-4-methyl-7-phenylhept-1-en-6-yn-1-yl)-2-oxopyrrolidin-1-yl)propyl)thiophene-2-carboxylic acid;

5-(3-((R)-3,3-Difluoro-5-((3S,4S,E)-3-hydroxy-4-methyl-oct-1-en-1-yl)-2-oxopyrrolidin-1-yl)propyl)thiophene-2-carboxylic acid;

methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate;

methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate;

5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid;

5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylic acid;

methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate;

methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate;

5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylic acid;

5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylic acid;

5-(3-((S)-3,3-difluoro-5-((3R,4S)-3-hydroxy-4-methyl-7-phenylheptyl)-2-oxopyrrolidin-1-yl)propyl)thiophene-2-carboxylic acid;

5-(3-((R)-3,3-Difluoro-5-((S,E)-3-hydroxyoct-1-en-6-yn-1-yl)-2-oxopyrrolidin-1-yl)propyl)thiophene-2-carboxylic acid;

5-(3-((R)-3,3-Difluoro-5-((S,E)-3-hydroxynon-1-en-6-yn-1-yl)-2-oxopyrrolidin-1-yl)propyl)thiophene-2-carboxylic acid;

5-(3-((R)-3,3-Difluoro-5-((S,E)-3-hydroxydec-1-en-6-yn-1-yl)-2-oxopyrrolidin-1-yl)propyl)thiophene-2-carboxylic acid;

5-(3-((R)-3,3-Difluoro-5-((S,E)-3-hydroxy-7-phenylhept-1-en-6-yn-1-yl)-2-oxopyrrolidin-1-yl)propyl)thiophene-2-carboxylic acid;

methyl 5-(3-((R)-3,3-difluoro-5-((S,E)-3-hydroxyoct-1-en-1-yl)-2-oxopyrrolidin-1-yl)propyl)thiophene-2-carboxylate;

methyl 5-(3-((R)-3,3-difluoro-5-((R,E)-3-hydroxyoct-1-en-1-yl)-2-oxopyrrolidin-1-yl)propyl)thiophene-2-carboxylate;

5-(3-((R)-3,3-difluoro-5-((S,E)-3-hydroxyoct-1-en-1-yl)-2-oxopyrrolidin-1-yl)propyl)thiophene-2-carboxylic acid;

5-(3-((R)-3,3-difluoro-5-((R,E)-3-hydroxyoct-1-en-1-yl)-2-oxopyrrolidin-1-yl)propyl)thiophene-2-carboxylic acid;

5-(3-((R)-3,3-Difluoro-5-((S,E)-3-hydroxy-7-phenylhept-1-en-1-yl)-2-oxopyrrolidin-1-yl)propyl)thiophene-2-carboxylic acid;

methyl 5-(3-((R)-3,3-difluoro-5-((3R,4S,E)-3-hydroxy-4-phenylpent-1-en-1-yl)-2-oxopyrrolidin-1-yl)propyl)thiophene-2-carboxylate;

methyl 5-(3-((R)-3,3-difluoro-5-((3S,4S,E)-3-hydroxy-4-phenylpent-1-en-1-yl)-2-oxopyrrolidin-1-yl)propyl)thiophene-2-carboxylate;

5-(3-((R)-3,3-difluoro-5-((3R,4S,E)-3-hydroxy-4-phenyl-pent-1-en-1-yl)-2-oxopyrrolidin-1-yl)propyl)thiophene-2-carboxylic acid;

5-(3-((R)-3,3-difluoro-5-((3S,4S,E)-3-hydroxy-4-phenyl-pent-1-en-1-yl)-2-oxopyrrolidin-1-yl)propyl)thiophene-2-carboxylic acid;

methyl 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylate;

methyl 5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylate;

5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylic acid;

5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylic acid;

methyl 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylate;

methyl 5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylate;

5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylic acid;

5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylic acid;

methyl 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylate;

methyl 5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylate;

5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylic acid;

5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylic acid;

methyl 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylate;

methyl 5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylate;

5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylic acid;

5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylic acid;

methyl 7-((2R)-2-((3S,4R/S,E)-3-hydroxy-4-methyloct-1-en-6-yn-1-yl)-5-oxopyrrolidin-1-yl)heptanoate;

methyl 7-((2R)-2-((3R,4R/S,E)-3-hydroxy-4-methyloct-1-en-6-yn-1-yl)-5-oxopyrrolidin-1-yl)heptanoate;

7-((2R)-2-((3S,4R/S,E)-3-hydroxy-4-methyloct-1-en-6-yn-1-yl)-5-oxopyrrolidin-1-yl)heptanoic acid;

7-((2R)-2-((3R,4R/S,E)-3-hydroxy-4-methyloct-1-en-6-yn-1-yl)-5-oxopyrrolidin-1-yl)heptanoic acid;

7-((R)-2-((3S,4S,E)-3-hydroxy-4-methyloct-1-en-6-yn-1-yl)-5-oxopyrrolidin-1-yl)heptanoic acid;

7-((R)-2-((3S,4R,E)-3-hydroxy-4-methyloct-1-en-6-yn-1-yl)-5-oxopyrrolidin-1-yl)heptanoic acid;

methyl 7-((2R)-2-((3S,4R/S,E)-3-hydroxy-4-methylnon-1-en-6-yn-1-yl)-5-oxopyrrolidin-1-yl)heptanoate;

methyl 7-((2R)-2-((3R,4R/S,E)-3-hydroxy-4-methylnon-1-en-6-yn-1-yl)-5-oxopyrrolidin-1-yl)heptanoate;

7-((2R)-2-((3S,4R/S,E)-3-hydroxy-4-methylnon-1-en-6-yn-1-yl)-5-oxopyrrolidin-1-yl)heptanoic acid;

7-((2R)-2-((3R,4R/S,E)-3-hydroxy-4-methylnon-1-en-6-yn-1-yl)-5-oxopyrrolidin-1-yl)heptanoic acid;

7-((R)-2-((3S,4S,E)-3-hydroxy-4-methylnon-1-en-6-yn-1-yl)-5-oxopyrrolidin-1-yl)heptanoic acid;

7-((R)-2-((3S,4R,E)-3-hydroxy-4-methylnon-1-en-6-yn-1-yl)-5-oxopyrrolidin-1-yl)heptanoic acid;

methyl 7-((2R)-2-((3S,4S,E)-3-hydroxy-4-methylnon-1-en-6-yn-1-yl)-5-oxopyrrolidin-1-yl)heptanoate;

methyl 7-((2R)-2-((3R,4S,E)-3-hydroxy-4-methylnon-1-en-6-yn-1-yl)-5-oxopyrrolidin-1-yl)heptanoate;

methyl 7-((2R)-2-((3S,4R/S,E)-3-hydroxy-4-methyldec-1-en-6-yn-1-yl)-5-oxopyrrolidin-1-yl)heptanoate;

methyl 7-((2R)-2-((3R,4R/S,E)-3-hydroxy-4-methyldec-1-en-6-yn-1-yl)-5-oxopyrrolidin-1-yl)heptanoate;

7-((2R)-2-((3S,4R/S,E)-3-hydroxy-4-methyldec-1-en-6-yn-1-yl)-5-oxopyrrolidin-1-yl)heptanoic acid;

7-((2R)-2-((3R,4R/S,E)-3-hydroxy-4-methyldec-1-en-6-yn-1-yl)-5-oxopyrrolidin-1-yl)heptanoic acid;

methyl 7-((2R)-2-((3S,4R/S,E)-3-hydroxy-4-methyl-7-phenylhept-1-en-6-yn-1-yl)-5-oxopyrrolidin-1-yl)heptanoate;

methyl 7-((2R)-2-((3R,4R/S,E)-3-hydroxy-4-methyl-7-phenylhept-1-en-6-yn-1-yl)-5-oxopyrrolidin-1-yl)heptanoate;

7-((2R)-2-((3S,4R/S,E)-3-hydroxy-4-methyl-7-phenylhept-1-en-6-yn-1-yl)-5-oxopyrrolidin-1-yl)heptanoic acid;

7-((2R)-2-((3R,4R/S,E)-3-hydroxy-4-methyl-7-phenylhept-1-en-6-yn-1-yl)-5-oxopyrrolidin-1-yl)heptanoic acid;

methyl 7-((2R)-2-((3S,E)-3-hydroxy-7-phenylhept-1-en-6-yn-1-yl)-5-oxopyrrolidin-1-yl)heptanoate;

methyl 7-((2R)-2-((3R,E)-3-hydroxy-7-phenylhept-1-en-6-yn-1-yl)-5-oxopyrrolidin-1-yl)heptanoate;

7-((R)-2-((3S,E)-3-hydroxy-7-phenylhept-1-en-6-yn-1-yl)-5-oxopyrrolidin-1-yl)heptanoic acid;

7-((R)-2-((3R,E)-3-hydroxy-7-phenylhept-1-en-6-yn-1-yl)-5-oxopyrrolidin-1-yl)heptanoic acid;

methyl 7-((R)-2-((R,E)-3-hydroxyhept-1-en-4-yn-1-yl)-5-oxopyrrolidin-1-yl)heptanoate;

methyl 7-((R)-2-((S,E)-3-hydroxyhept-1-en-4-yn-1-yl)-5-oxopyrrolidin-1-yl)heptanoate;

7-((R)-2-((R,E)-3-hydroxyhept-1-en-4-yn-1-yl)-5-oxopyrrolidin-1-yl)heptanoic acid;

7-((R)-2-((S,E)-3-hydroxyhept-1-en-4-yn-1-yl)-5-oxopyrrolidin-1-yl)heptanoic acid;

methyl 7-((R)-2-((R,E)-3-hydroxy-5-phenylpent-1-en-4-yn-1-yl)-5-oxopyrrolidin-1-yl)heptanoate;

methyl 7-((R)-2-((S,E)-3-hydroxy-5-phenylpent-1-en-4-yn-1-yl)-5-oxopyrrolidin-1-yl)heptanoate;

7-((R)-2-((R,E)-3-hydroxy-5-phenylpent-1-en-4-yn-1-yl)-5-oxopyrrolidin-1-yl)heptanoic acid;

7-((R)-2-((S,E)-3-hydroxy-5-phenylpent-1-en-4-yn-1-yl)-5-oxopyrrolidin-1-yl)heptanoic acid;

methyl 4-(2-((2R)-2-((3S,4R/S,E)-3-hydroxy-4-methyloct-1-en-6-yn-1-yl)-5-oxopyrrolidin-1-yl)ethyl)benzoate;

methyl 4-(2-((2R)-2-((3R,4R/S,E)-3-hydroxy-4-methyloct-1-en-6-yn-1-yl)-5-oxopyrrolidin-1-yl)ethyl)benzoate;

4-(2-((2R)-2-((3S,4R/S,E)-3-hydroxy-4-methyloct-1-en-6-yn-1-yl)-5-oxopyrrolidin-1-yl)ethyl)benzoic acid;

4-(2-((2R)-2-((3R,4R/S,E)-3-hydroxy-4-methyloct-1-en-6-yn-1-yl)-5-oxopyrrolidin-1-yl)ethyl)benzoic acid;

ethyl 4-(2-((R)-2-((3S,4S,E)-3-hydroxy-4-methylnon-1-en-6-yn-1-yl)-5-oxopyrrolidin-1-yl)ethyl)benzoate;

ethyl 4-(2-((R)-2-((3R,4S,E)-3-hydroxy-4-methylnon-1-en-6-yn-1-yl)-5-oxopyrrolidin-1-yl)ethyl)benzoate;

4-(2-((R)-2-((3S,4S,E)-3-hydroxy-4-methylnon-1-en-6-yn-1-yl)-5-oxopyrrolidin-1-yl)ethyl)benzoic acid;

4-(2-((R)-2-((3R,4S,E)-3-hydroxy-4-methylnon-1-en-6-yn-1-yl)-5-oxopyrrolidin-1-yl)ethyl)benzoic acid;

ethyl 4-(2-((R)-2-((3S,4R/S,E)-3-hydroxy-4-methyldec-1-en-6-yn-1-yl)-5-oxopyrrolidin-1-yl)ethyl)benzoate;

ethyl 4-(2-((R)-2-((3R,4R/S,E)-3-hydroxy-4-methyldec-1-en-6-yn-1-yl)-5-oxopyrrolidin-1-yl)ethyl)benzoate;

4-(2-((2R)-2-((3S,E)-3-hydroxy-4-methyldec-1-en-6-yn-1-yl)-5-oxopyrrolidin-1-yl)ethyl)benzoic acid;
4-(2-((2R)-2-((3R,E)-3-hydroxy-4-methyldec-1-en-6-yn-1-yl)-5-oxopyrrolidin-1-yl)ethyl)benzoic acid;
methyl 4-(2-((2R)-2-((3S,4R/S,E)-3-hydroxy-4-methyl-7-phenylhept-1-en-6-yn-1-yl)-5-oxopyrrolidin-1-yl)ethyl)benzoate;
methyl 4-(2-((2R)-2-((3R,4R/S,E)-3-hydroxy-4-methyl-7-phenylhept-1-en-6-yn-1-yl)-5-oxopyrrolidin-1-yl)ethyl)benzoate;
4-(2-((2R)-2-((3S,4R/S,E)-3-hydroxy-4-methyl-7-phenylhept-1-en-6-yn-1-yl)-5-oxopyrrolidin-1-yl)ethyl)benzoic acid;
4-(2-((2R)-2-((3R,4R/S,E)-3-hydroxy-4-methyl-7-phenylhept-1-en-6-yn-1-yl)-5-oxopyrrolidin-1-yl)ethyl)benzoic acid;
methyl 2-(4-(((2R)-2-((3S,4R/S,E)-3-hydroxy-4-methyloct-1-en-6-yn-1-yl)-5-oxopyrrolidin-1-yl)methyl)phenyl)acetate;
methyl 2-(4-(((2R)-2-((3R,4R/S,E)-3-hydroxy-4-methyloct-1-en-6-yn-1-yl)-5-oxopyrrolidin-1-yl)methyl)phenyl)acetate;
2-(4-(((2R)-2-((3S,4R/S,E)-3-hydroxy-4-methyloct-1-en-6-yn-1-yl)-5-oxopyrrolidin-1-yl)methyl)phenyl)acetic acid;
2-(4-(((2R)-2-((3R,4R/S,E)-3-hydroxy-4-methyloct-1-en-6-yn-1-yl)-5-oxopyrrolidin-1-yl)methyl)phenyl)acetic acid;
methyl 5-(3-((2R)-2-((3S,E)-3-hydroxy-4-methylnon-1-en-6-yn-1-yl)-5-oxopyrrolidin-1-yl)prop-1-yn-1-yl)thiophene-2-carboxylate;
methyl 5-(3-((2R)-2-((3R,E)-3-hydroxy-4-methylnon-1-en-6-yn-1-yl)-5-oxopyrrolidin-1-yl)prop-1-yn-1-yl)thiophene-2-carboxylate;
5-(3-((2R)-2-((3S,E)-3-hydroxy-4-methylnon-1-en-6-yn-1-yl)-5-oxopyrrolidin-1-yl)prop-1-yn-1-yl)thiophene-2-carboxylic acid;
5-(3-((2R)-2-((3R,E)-3-hydroxy-4-methylnon-1-en-6-yn-1-yl)-5-oxopyrrolidin-1-yl)prop-1-yn-1-yl)thiophene-2-carboxylic acid;
methyl 5-(3-((2R)-2-((3S,E)-3-hydroxy-4-methyl-7-phenylhept-1-en-6-yn-1-yl)-5-oxopyrrolidin-1-yl)prop-1-yn-1-yl)thiophene-2-carboxylate;
methyl 5-(3-((2R)-2-((3R,E)-3-hydroxy-4-methyl-7-phenylhept-1-en-6-yn-1-yl)-5-oxopyrrolidin-1-yl)prop-1-yn-1-yl)thiophene-2-carboxylate;
5-((Z)-3-((2R)-2-((3S,E)-3-hydroxy-4-methyl-7-phenylhept-1-en-6-yn-1-yl)-5-oxopyrrolidin-1-yl)prop-1-en-1-yl)thiophene-2-carboxylic acid;
5-((Z)-3-((2R)-2-((3R,E)-3-hydroxy-4-methyl-7-phenylhept-1-en-6-yn-1-yl)-5-oxopyrrolidin-1-yl)prop-1-en-1-yl)thiophene-2-carboxylic acid;
methyl 5-((Z)-3-((2R)-2-((3S,4R/S,E)-3-hydroxy-4-methylnon-1-en-6-yn-1-yl)-5-oxopyrrolidin-1-yl)prop-1-en-1-yl)thiophene-2-carboxylate;
methyl 5-((Z)-3-((2R)-2-((3R,4R/S,E)-3-hydroxy-4-methylnon-1-en-6-yn-1-yl)-5-oxopyrrolidin-1-yl)prop-1-en-1-yl)thiophene-2-carboxylate;
5-((Z)-3-((2R)-2-((3S,4R/S,E)-3-hydroxy-4-methylnon-1-en-6-yn-1-yl)-5-oxopyrrolidin-1-yl)prop-1-en-1-yl)thiophene-2-carboxylic acid;
5-((Z)-3-((2R)-2-((3R,4R/S,E)-3-hydroxy-4-methylnon-1-en-6-yn-1-yl)-5-oxopyrrolidin-1-yl)prop-1-en-1-yl)thiophene-2-carboxylic acid;
methyl 5-((Z)-3-((2R)-2-((3S,4R/S,E)-3-hydroxy-4-methyl-7-phenylhept-1-en-6-yn-1-yl)-5-oxopyrrolidin-1-yl)prop-1-en-1-yl)thiophene-2-carboxylate;
methyl 5-((Z)-3-((2R)-2-((3R,4R/S,E)-3-hydroxy-4-methyl-7-phenylhept-1-en-6-yn-1-yl)-5-oxopyrrolidin-1-yl)prop-1-en-1-yl)thiophene-2-carboxylate;
5-((Z)-3-((2R)-2-((3S,4R/S,E)-3-hydroxy-4-methyl-7-phenylhept-1-en-6-yn-1-yl)-5-oxopyrrolidin-1-yl)prop-1-en-1-yl)thiophene-2-carboxylic acid;
5-((Z)-3-((2R)-2-((3R,4R/S,E)-3-hydroxy-4-methyl-7-phenylhept-1-en-6-yn-1-yl)-5-oxopyrrolidin-1-yl)prop-1-en-1-yl)thiophene-2-carboxylic acid;
methyl 5-(3-((R)-2-((3S,4S,E)-3-hydroxy-4-methylnon-1-en-6-yn-1-yl)-5-oxopyrrolidin-1-yl)propyl)thiophene-2-carboxylate;
methyl 5-(3-((R)-2-((3S,4R,E)-3-hydroxy-4-methylnon-1-en-6-yn-1-yl)-5-oxopyrrolidin-1-yl)propyl)thiophene-2-carboxylate;
methyl 5-(3-((2R)-2-((3R,E)-3-hydroxy-4-methylnon-1-en-6-yn-1-yl)-5-oxopyrrolidin-1-yl)propyl)thiophene-2-carboxylate;
5-(3-((R)-2-((3S,4S,E)-3-hydroxy-4-methylnon-1-en-6-yn-1-yl)-5-oxopyrrolidin-1-yl)propyl)thiophene-2-carboxylic acid;
5-(3-((R)-2-((3S,4R,E)-3-hydroxy-4-methylnon-1-en-6-yn-1-yl)-5-oxopyrrolidin-1-yl)propyl)thiophene-2-carboxylic acid;
5-(3-((R)-2-((3S,E)-3-hydroxy-4-methylnon-1-en-6-yn-1-yl)-5-oxopyrrolidin-1-yl)propyl)thiophene-2-carboxylic acid;
5-(3-((R)-2-((3R,E)-3-hydroxy-4-methylnon-1-en-6-yn-1-yl)-5-oxopyrrolidin-1-yl)propyl)thiophene-2-carboxylic acid;
methyl 5-(3-((2R)-2-((3S,E)-3-hydroxy-4-methyl-7-phenylhept-1-en-6-yn-1-yl)-5-oxopyrrolidin-1-yl)propyl)thiophene-2-carboxylate;
methyl 5-(3-((2R)-2-((3R,E)-3-hydroxy-4-methyl-7-phenylhept-1-en-6-yn-1-yl)-5-oxopyrrolidin-1-yl)propyl)thiophene-2-carboxylate;
5-(3-((2R)-2-((3S,E)-3-hydroxy-4-methyl-7-phenylhept-1-en-6-yn-1-yl)-5-oxopyrrolidin-1-yl)propyl)thiophene-2-carboxylic acid;
5-(3-((2R)-2-((3R,E)-3-hydroxy-4-methyl-7-phenylhept-1-en-6-yn-1-yl)-5-oxopyrrolidin-1-yl)propyl)thiophene-2-carboxylic acid;
methyl 7-((R)-2-((S,E)-3-hydroxy-7-phenylhept-1-en-1-yl)-5-oxopyrrolidin-1-yl)heptanoate;
methyl 7-((R)-2-((R,E)-3-hydroxy-7-phenylhept-1-en-1-yl)-5-oxopyrrolidin-1-yl)heptanoate;
7-((R)-2-((S,E)-3-hydroxy-7-phenylhept-1-en-1-yl)-5-oxopyrrolidin-1-yl)heptanoic acid;
7-((R)-2-((R,E)-3-hydroxy-7-phenylhept-1-en-1-yl)-5-oxopyrrolidin-1-yl)heptanoic acid;
methyl 7-((2R)-2-((3S,E)-3-hydroxy-4-methyl-7-phenylhept-1-en-1-yl)-5-oxopyrrolidin-1-yl)heptanoate;
methyl 7-((2R)-2-((3R,E)-3-hydroxy-4-methyl-7-phenylhept-1-en-1-yl)-5-oxopyrrolidin-1-yl)heptanoate;
7-((2R)-2-((3S,E)-3-hydroxy-4-methyl-7-phenylhept-1-en-1-yl)-5-oxopyrrolidin-1-yl)heptanoic acid;
7-((2R)-2-((3R,E)-3-hydroxy-4-methyl-7-phenylhept-1-en-1-yl)-5-oxopyrrolidin-1-yl)heptanoic acid;
7-((R)-2-((3S,4S,E)-3-hydroxy-4-methyl-7-phenylhept-1-en-1-yl)-5-oxopyrrolidin-1-yl)heptanoic acid;
7-((R)-2-((3S,4R,E)-3-hydroxy-4-methyl-7-phenylhept-1-en-1-yl)-5-oxopyrrolidin-1-yl)heptanoic acid;
methyl 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylate;

methyl 5-(3-((2R)-2-((3R,E)-3-hydroxy-4-methyl-7-phenyl-hept-1-en-1-yl)-5-oxopyrrolidin-1-yl)prop-1-yn-1-yl) thiophene-2-carboxylate;

5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylic acid;

5-(3-((2R)-2-((3R,E)-3-hydroxy-4-methyl-7-phenylhept-1-en-1-yl)-5-oxopyrrolidin-1-yl)prop-1-yn-1-yl)thiophene-2-carboxylic acid;

methyl 5-(3-((2R)-2-((3S,E)-3-hydroxy-4-methyl-7-phenyl-hept-1-en-1-yl)-5-oxopyrrolidin-1-yl)propyl)thiophene-2-carboxylate;

methyl 5-(3-((2R)-2-((3R,E)-3-hydroxy-4-methyl-7-phenyl-hept-1-en-1-yl)-5-oxopyrrolidin-1-yl)propyl)thiophene-2-carboxylate;

5-(3-((2R)-2-((3S,E)-3-hydroxy-4-methyl-7-phenylhept-1-en-1-yl)-5-oxopyrrolidin-1-yl)propyl)thiophene-2-carboxylic acid;

5-(3-((2R)-2-((3R,E)-3-hydroxy-4-methyl-7-phenylhept-1-en-1-yl)-5-oxopyrrolidin-1-yl)propyl)thiophene-2-carboxylic acid;

5-(3-((R)-2-((3S,4S,E)-3-hydroxy-4-methyl-7-phenylhept-1-en-1-yl)-5-oxopyrrolidin-1-yl)propyl)thiophene-2-carboxylic acid;

5-(3-((R)-2-((3S,4R,E)-3-hydroxy-4-methyl-7-phenylhept-1-en-1-yl)-5-oxopyrrolidin-1-yl)propyl)thiophene-2-carboxylic acid;

5-(3-((R)-2-((3S,4S,E)-3-hydroxy-4-methyl-6-phenylhex-1-en-1-yl)-5-oxopyrrolidin-1-yl)propyl)thiophene-2-carboxylic acid;

5-(3-((R)-2-((3R,4S,E)-3-hydroxy-4-methyl-6-phenylhex-1-en-1-yl)-5-oxopyrrolidin-1-yl)propyl)thiophene-2-carboxylic acid;

5-(3-((R)-2-((3S,4R,E)-3-hydroxy-4-methyl-6-phenylhex-1-en-1-yl)-5-oxopyrrolidin-1-yl)propyl)thiophene-2-carboxylic acid;

5-(3-((R)-2-((3R,4R,E)-3-hydroxy-4-methyl-6-phenylhex-1-en-1-yl)-5-oxopyrrolidin-1-yl)propyl)thiophene-2-carboxylic acid;

5-(3-((R)-2-((3S,4S,E)-3-hydroxy-4-methyl-8-phenyloct-1-en-1-yl)-5-oxopyrrolidin-1-yl)propyl)thiophene-2-carboxylic acid;

5-(3-((R)-2-((3R,4S,E)-3-hydroxy-4-methyl-8-phenyloct-1-en-1-yl)-5-oxopyrrolidin-1-yl)propyl)thiophene-2-carboxylic acid;

5-(3-((R)-2-((3S,4R,E)-3-hydroxy-4-methyl-8-phenyloct-1-en-1-yl)-5-oxopyrrolidin-1-yl)propyl)thiophene-2-carboxylic acid;

5-(3-((R)-2-((3R,4R,E)-3-hydroxy-4-methyl-8-phenyloct-1-en-1-yl)-5-oxopyrrolidin-1-yl)propyl)thiophene-2-carboxylic acid;

5-(3-((R)-2-((3S,4S,E)-3-hydroxy-4-methyl-9-phenylnon-1-en-1-yl)-5-oxopyrrolidin-1-yl)propyl)thiophene-2-carboxylic acid;

5-(3-((R)-2-((3R,4S,E)-3-hydroxy-4-methyl-9-phenylnon-1-en-1-yl)-5-oxopyrrolidin-1-yl)propyl)thiophene-2-carboxylic acid;

5-(3-((R)-2-((3S,4R,E)-3-hydroxy-4-methyl-9-phenyloct-non-1-en-1-yl)-5-oxopyrrolidin-1-yl)propyl)thiophene-2-carboxylic acid;

5-(3-((R)-2-((3R,4R,E)-3-hydroxy-4-methyl-9-phenylnon-1-en-1-yl)-5-oxopyrrolidin-1-yl)propyl)thiophene-2-carboxylic acid;

or a pharmaceutically acceptable salt thereof.

The invention also provides for bone compositions that include combinations of any of the drugs or classes of drugs described herein. For example, one or more drugs that activate osteoblasts may be combined with one or more drugs that inhibit osteoclasts. Alternatively, multiple drugs that either activate osteoblasts or inhibit osteoclasts may be combined together.

In some embodiments, bone compositions may include an EP4 agonist with any one or more of the following: a bisphosphonate; a cathepsin K inhibitor; an estrogen or an estrogen receptor modulator; calcitonin; an inhibitor of osteoclast proton ATPase; an inhibitor of HMG-CoA reductase (i.e., a statin); an αvβintegrin receptor antagonist; a RANKL inhibitor such as denosumab; a bone anabolic agent, such as parathyroid hormone; a bone morphogenic protein (e.g., BMP-2, BMP-4, BMP-7); Vitamin D or a synthetic Vitamin D analogue such as ED-70; an androgen or an androgen receptor modulator; an activator of Wnt/α-catenin signaling (e.g. a GSK-3 inhibitor, a sclerostin antagonist, a SOST inhibitor); bortezomib; strontium ranelate; platelet-derived growth factor.

In some embodiments, for example, an EP4 agonist is combined with one or more bisphosphonates selected from alendronic acid, sodium alendronate, ibandronate, risedronate, zoledronate, zoledronic acid, etidronate, pamidronate, tiludronate, neridronate, and olpadronate.

In other embodiments, an EP4 agonist is combined with one or more of raloxifene, bazedoxifene, and lasofoxifene.

In other embodiments, an EP4 agonist is combined with a bone morphogenic protein, e.g., BMP-2, BMP-4, or BMP-7. For example, one combination includes CP-734432 with either BMP-2 or BMP-7. Another combination includes ONO-4819 (rivenprost) with BMP-2 or BMP-7. Yet another combination includes AE1-329 with BMP-2 or BMP-7. Still another combination includes L-902,688 with BMP-2 or BMP-7. A further combination includes 7-((R)-3,3-difluoro-5-((3S,4S,E)-3-hydroxy-4-methylnon-1-en-6-yn-1-yl)-2-oxopyrrolidin-1-yl)heptanoic acid with BMP-2 or BMP-7. Another combination includes 7-((R)-2-((3S,4S,E)-3-hydroxy-4-methylnon-1-en-6-yn-1-yl)-5-oxopyrrolidin-1-yl)heptanoic acid with BMP-2 or BMP-7.

In other embodiments, an EP4 agonist is combined with strontium ranelate.

In other embodiments, an EP4 agonist is combined with an EP2 agonist.

In still other embodiments, an EP4 agonist is combined with a statin such as, for example, atorvastatin, cerivastatin, fluvastatin, lovastatin, mevastatin, pitabastatin, pravastatin, rosuvastatin, and simvastatin.

In still other embodiments, a bisphosphonate is combined with an estrogen receptor modulator. For example, one or more of alendronic acid, sodium alendronate, ibandronate, risedronate, zoledronate, zoledronic acid, etidronate, pamidronate, tiludronate, neridronate, and olpadronate is combined with one or more of raloxifene, bazedoxifene, and lasofoxifene. In other embodiments, a bisphosphonate and/or an estrogen receptor modulator is combined with a statin. Any of the foregoing classes or compounds could, alternatively or in addition to, be combined with strontium ranelate and/or a bone morphogentic protein.

According to any of the foregoing combinations, the EP4 agonist may be a compound of formula (I) or any other EP4 agonist according to the description contained herein. Exemplary preferred EP4 agonists include CP-734432, ONO-4819 (i.e., rivenprost), AE1-329, L-902,688, 7-((R)-3,3-difluoro-5-((3S,4S,E)-3-hydroxy-4-methylnon-1-en-6-yn-1-yl)-2-oxopyrrolidin-1-yl)heptanoic acid, and 7-((R)-2-((3S,4S,E)-3-hydroxy-4-methylnon-1-en-6-yn-1-yl)-5-oxopyrrolidin-1-yl)heptanoic acid.

The foregoing drug combinations are intended for illustration purposes only and should not be construed as limiting the invention to the explicitly recited combinations.

CHEMISTRY AND EXAMPLES

Compounds described herein may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The various stereoisomers (including enantiomers and diastereomers) and mixtures thereof of the compounds described are also contemplated. Individual stereoisomers of compounds described may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. All various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae within this specification can represent only one of the possible tautomeric forms. It is to be understood that encompassed herein are any tautomeric form, and mixtures thereof, and is not to be limited merely to any one tautomeric form utilized within the naming of the compounds or formulae.

Additionally, unless otherwise stated, the structures depicted herein are also meant to include compounds that differ only in the presence of one or more isotopically enriched atoms. For example, compounds having the present structures except for the replacement of hydrogen by deuterium or tritium, or the replacement of a carbon by a 13C- or $^{14}$C-enriched carbon are within the scope of this invention. Such compounds are useful, for example, as analytical tools, probes in a biological assay, or as $EP_4$ receptor agonists.

Also contemplated as part of the invention are compounds formed by synthetic means or formed in vivo by biotransformation or by chemical means. For example, certain compounds of the invention may function as prodrugs that are converted to other compounds of the invention upon administration to a subject.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well-known and commonly used in the art.

It will be appreciated that the synthetic schemes and specific examples are illustrative and are not to be read as limiting the scope of the invention. Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. The skilled artisan will also appreciate that not all of the substituents in the compounds of formula (I) will tolerate certain reaction conditions employed to synthesize the compounds. Routine experimentation, including appropriate manipulation of the reaction conditions, reagents and sequence of the synthetic route, protection and deprotection may be required in the case of particular compounds. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3 d ed.), John Wiley & Sons, NY (1999), which is incorporated herein by reference in its entirety.

Furthermore, the skilled artisan will appreciate that in some cases, the order in which moieties are introduced may vary. The particular order of steps required to produce the compounds of formula (I) is dependent upon the particular compounds being synthesized, the starting compound, and the relative stability of the substituted moieties. Thus, synthesis of the present compounds may be accomplished by methods analogous to those described in the synthetic schemes described herein and in the specific examples, with routine experimentation (e.g., manipulation of the reaction conditions, reagents, and sequence of the synthetic steps).

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Systematic names of compound structures have been generated by the Convert-Structure-to-Name function of Chem & Bio Draw 12.0 Ultra by CambridgeSoft®, which uses the Cahn-Ingold-Prelog rules for stereochemistry. When discussing individual atomic positions of compound structures, an alternative continuous numbering scheme for the lactams as described below may be used.

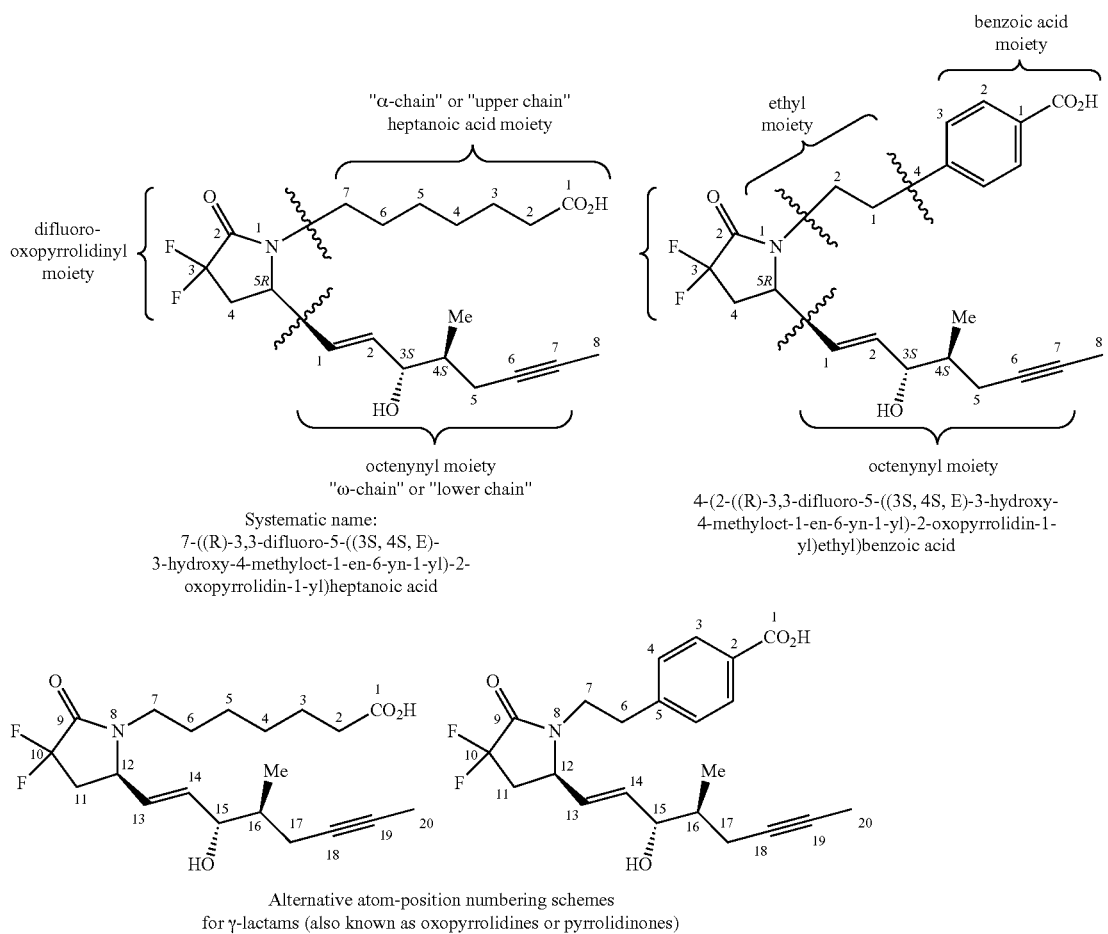

Alternative atom-position numbering schemes for γ-lactams (also known as oxopyrrolidines or pyrrolidinones)

Liquid chromatography—mass spectra (LC/MS) were obtained using an Agilent LC/MSD G1946D or an Agilent 1100 Series LC/MSD Trap G1311A or G2435A. Quantifications were obtained on a Cary 50 Bio UV-visible spectrophotometer.

$^1$H, $^{13}$C, and $^{19}$F Nuclear magnetic resonance (NMR) spectra were obtained using a Varian INOVA nuclear magnetic resonance spectrometer at 400, 100, and 376 MHz, respectively.

High performance liquid chromatography (HPLC) analytical separations were performed on an Agilent 1100 or Agilent 1200 HPLC analytical system and followed by an Agilent Technologies G1315B Diode Array Detector set at or near the $UV_{max}$ @ 260 nm.

High performance liquid chromatography (HPLC) preparatory separations were performed on a Gilson preparative HPLC system or an Agilent 1100 preparative HPLC system and followed by an Agilent Technologies G1315B Diode Array Detector set at or near the $UV_{max}$ @ 260 nm.

Analytical chiral HPLC separations were performed on an Agilent 1100 analytical system and followed by an Agilent Technologies G1315B Diode Array Detector set at or near the $UV_{max}$ @ 260 nm.

Thin layer chromatography (TLC) analyses were performed on Uniplate™ 250μ silica gel plates (Analtech, Inc. Catalog No. 02521) and were typically developed for visualization using 50 volume % concentrated sulfuric acid in water spray unless otherwise indicated.

When used in the present application, the following abbreviations have the meaning set out below:
Ac is acetyl;
ACN is acetonitrile;
BBr$_3$ is boron tribromide;
Bn is benzyl;
BnNH$_2$ is benzylamine;
BSA is bovine serum albumin;
CH$_2$Cl$_2$ is dichloromethane;
CHCl$_3$ is chloroform;
CDCl$_3$ is deuterochloroform;
CSA is camphorsulfonic acid;
DCC is N,N'-dicyclohexylcarbodiimide;
DME is 1,2-dimethoxyethane;
DMF is N,N-dimethylformamide;
DMP is 2,2-dimethoxypropane (also called, acetone dimethyl acetal);
DMSO is dimethyl sulfoxide;
DBU is 1,8-diazabicyclo[5.4.0]undec-7-ene;
DIA is diisopropylamine;
DMAP is 4-dimethylaminopyridine;
EDC/EDAC is N-(3-dimethylaminopropyl)-N'-ethylcarbodiimide hydrochloride;
EDTA is ethylenediaminetetraacetic acid;
EE is ethoxyeth-1-yl;
ee is enantiomeric excess;
EIA is enzyme immunoassay;
Et is ethyl;

EtOAc is ethyl acetate;
EtOH is ethanol;
Et₃N is triethylamine;
HCl is hydrogen chloride;
HOBt is 1-hydroxybenzotriazole;
Me is methyl;
MeOH is methanol;
MTBE is methyl tert-butyl ether;
NaOMe is sodium methoxide;
nBuLi or n-BuLi is n-butyllithium;
NFSi is N-fluorobenzenesulfonimide;
NHS is N-hydroxysuccinimide;
NMP is 1-methyl-2-pyrrolidinone;
PG is a protecting group;
Ph is phenyl;
Pd(PPh₃)₄ is tetrakis(triphenylphosphine)palladium;
PhMe is toluene;
rt is room temperature;
TBAF is tetrabutylammonium fluoride;
TBS or TBDMS is tert-butyldimethylsilyl;
tBu or t-Bu is tert-butyl;
TEA is triethylamine;
TFA is trifluoroacetic acid;
THF is tetrahydrofuran;
TMS is trimethylsilyl; and
Tris-HCl is 2-amino-2-(hydroxymethyl)-1,3-propanediol hydrochloride.

A γ-lactam scaffold common to various compounds used in the present invention may be derived from the difluorooxopyrrolidinyl intermediate, (R)-3,3-difluoro-5-(hydroxymethyl)pyrrolidin-2-one ((R)-8), which may be prepared from commercially available (R)-(+)-5-oxopyrrolidine-2-carboxylic acid (D-pyroglutamic acid) (1) as illustrated in Scheme 1.

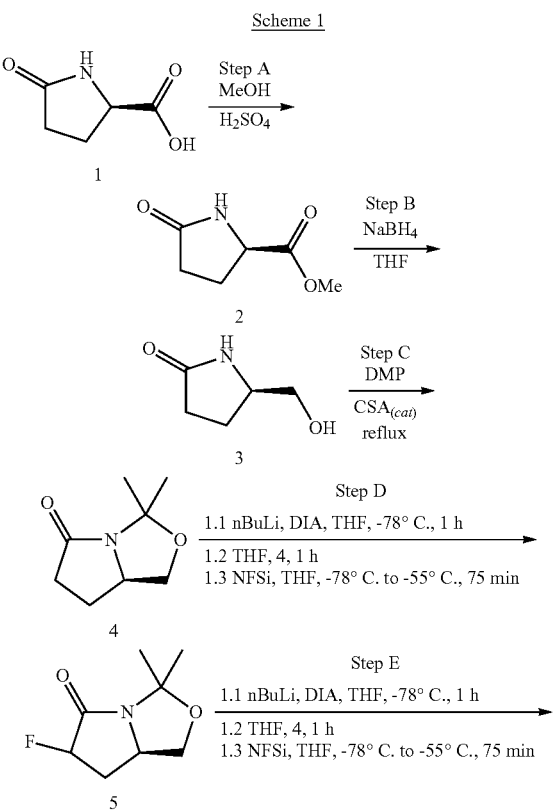

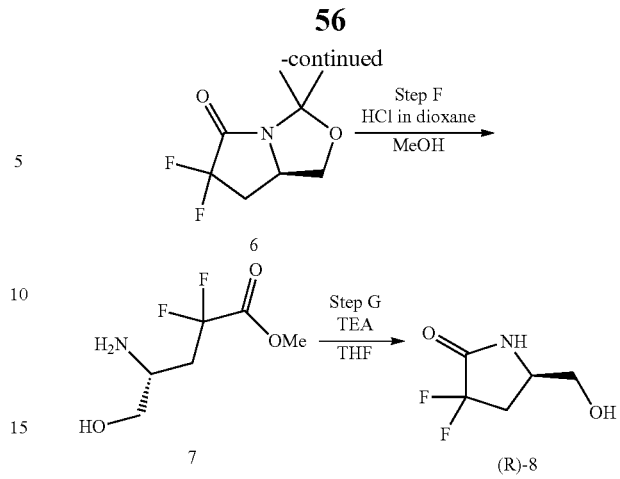

D-pyroglutamic acid (1) may undergo acid-catalyzed esterification in an alcohol solvent, such as methanol, as illustrated in Step A. The resulting ester intermediate (2) may be reduced with sodium borohydride in a solvent, such as THF, to the alcohol intermediate (R)-5-(hydroxymethyl)pyrrolidin-2-one (3) as shown for Step B. The followings Steps C, D, E, F, and G may be carried out according to the procedures described in US 2009/0275537. Simultaneous protection of the alcohol and amide groups of intermediate 3 by the acid-catalyzed addition of 2,2-dimethoxypropane (Step C) provides protected intermediate 4. Subsequent repeat stepwise deprotonation followed by addition of electrophilic fluorine using NFSi (Steps D and E) affords the α,α-difluoropyrrolidone intermediate 6. Treatment of intermediate 6 with HCl in 1,4-dioxane and methanol (Step F) removes the protecting group and opens the lactam ring to provide intermediate 7. Annulation (Step G) is achieved with the use of a base, such as triethylamine, to provide (R)-3,3-difluoro-5-(hydroxymethyl)pyrrolidin-2-one ((R)-8).

An alternative preparation of (R)-8 is illustrated in Scheme 1A.

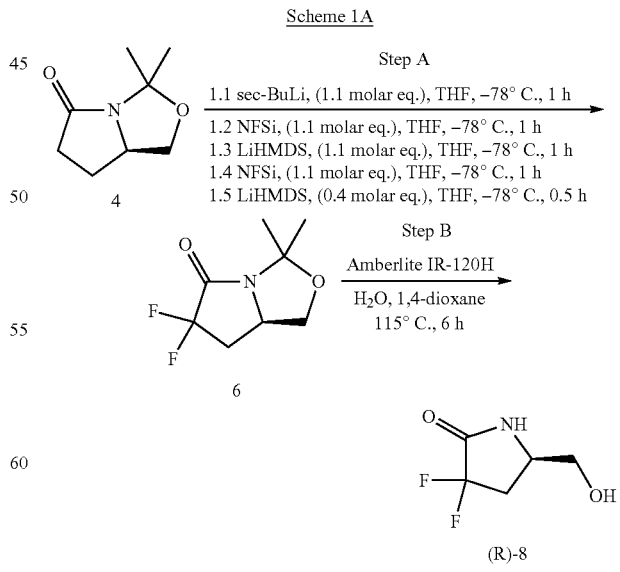

Intermediate (R)-3,3-dimethyltetrahydro-3H,5H-pyrrolo[1,2-c]oxazol-5-one (4) may be converted directly to its difluoro analog (R)-6,6-difluoro-3,3-dimethyltetrahydro-3H,5H-pyrrolo[1,2-c]oxazol-5-one (6) in a one-pot method (Step A) comprising the addition of a solution comprising sec-butyllithium in (about 1.1 molar equivalents of sec-butyllithium) to a solution comprising 4 (limiting reagent) in THF at −78° C., stirring for about an hour at −78° C., subsequent addition of a solution comprising NFSi (about 1.1 molar equivalents of NFSi), stirring for about another hour at −78° C., addition of a solution comprising LiHMDS (about 1.1 molar equivalents), stirring for about another hour at −78° C., subsequent addition of a solution comprising NFSi (about 1.1 molar equivalents of NFSi), stirring for about another hour at −78° C., addition of a solution comprising LiHMDS (about 0.4 molar equivalent), and stirring for about 30 minutes. Intermediate 5 may subsequently be converted directly to (R)-8 by treatment (Step B) with a strongly acid gel-type ion-exchange resin.

Compounds used in the present invention may be prepared from 8 or O-protected 8 by general routes illustrated in Scheme 2.

Compounds of the present invention, (I), may be prepared from 8 or protected 8, for example, by a process that comprises first installing the upper chain with a nitrogen-carbon bond forming reaction (using 8 or an O-protected 8), wherein the nitrogen atom of the γ-lactam ring of 8 forms a covalent bond with the appropriate upper chain carbon atom to provide the corresponding 8+upper chain intermediate shown in Scheme 2. In some aspects of the present invention, the nitrogen-carbon forming reaction comprises an alkylation reaction between 8 or an oxygen-protected analog of 8 and an alkylating agent comprising the upper chain moiety and a leaving group as illustrated in Scheme 2A. In some aspects of the present invention, the alkylating agent is an alkyl halide such as an alkyl iodide, alkyl bromide, or alkyl triflate. In other aspects of the present invention, the alkylating agent is an allyl bromide. In other aspects of the present invention, the alkylating agent is a propargyl halide such as a propargyl bromide.

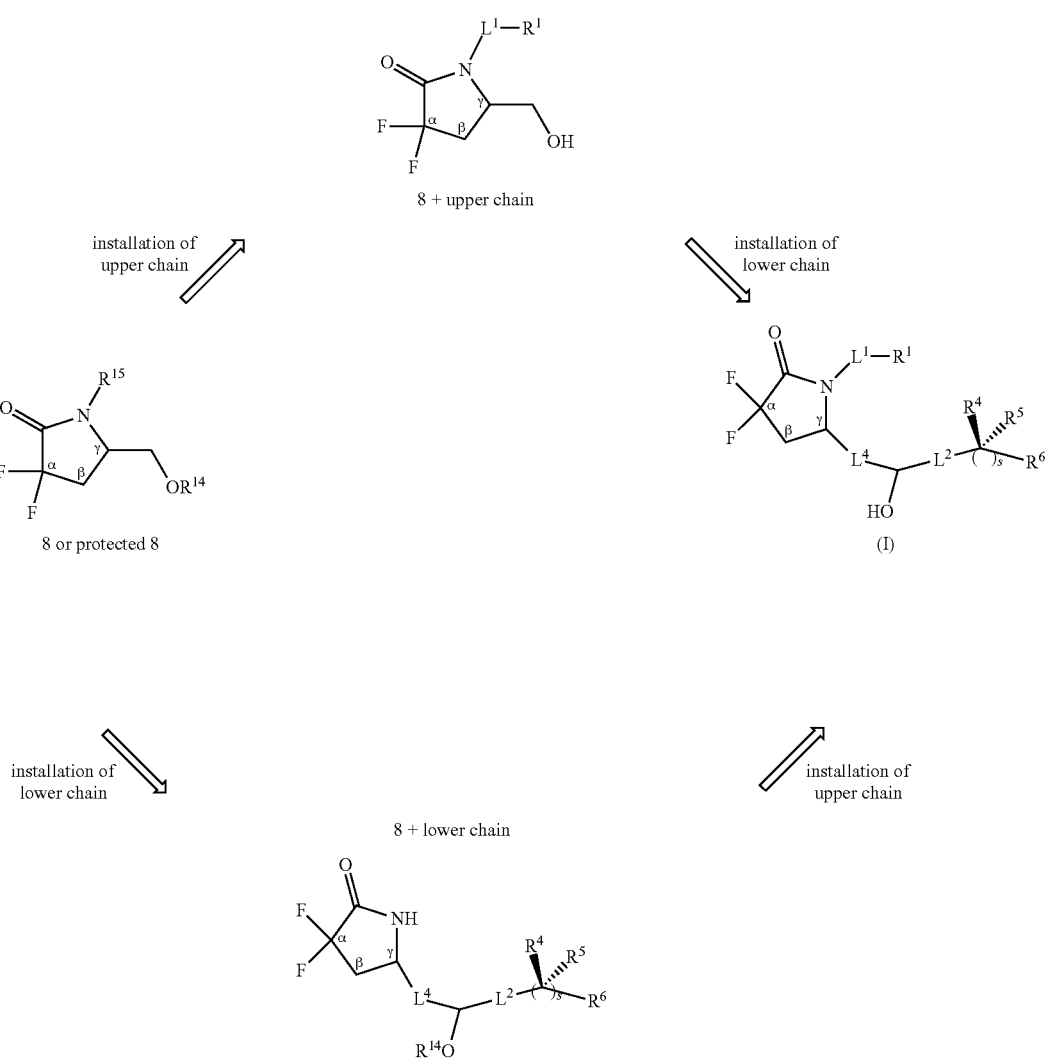

$R^{14}$ is hydrogen or an oxygen protecting group.
$R^{15}$ is hydrogen or a nitrogen protecting group.

Scheme 2A

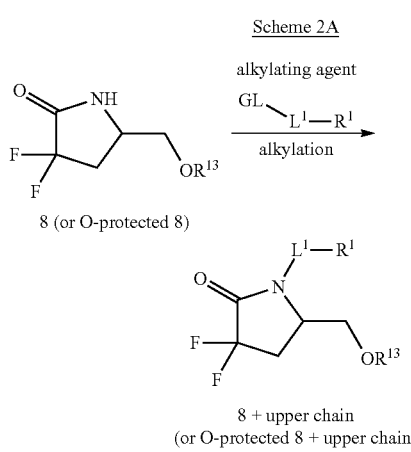

8 (or O-protected 8)

8 + upper chain
(or O-protected 8 + upper chain)

Leaving group "LG" is, for example, iodo, bromo, chloro, trifluoromethanesulfonyl, methanesulfonylate toluenesulfonylate, or 4-nitrobenzenesulfonylate. $R^{13}$ is hydrogen or an oxygen protecting group.

The installation of the upper chain may be followed by a process that comprises installation of the lower chain by way of a carbon-carbon bond forming reaction, wherein the hydroxymethyl group carbon atom attached to the γ-position of the lactam ring of intermediate 8+upper chain forms a covalent bond (carbon-carbon single, double, or triple bond) with the appropriate lower chain carbon atom to provide the corresponding compound (I). In some aspects of the present invention, the intermediate 8+upper chain (directly from the alkylation reaction or its O-protected analog having undergone subsequent deprotection) is oxidized to the corresponding aldehyde intermediate, which may be subsequently subjected to Horner-Wadsworth-Emmons reaction conditions in the presence of a β-keto phosphonate ester coupling partner to, after subsequent reduction of the resulting ketone to the corresponding alcohol, provide compounds (I) of the present invention, wherein $L^4$ is a carbon-carbon double bond, as illustrated in Scheme 1B.

Scheme 1B

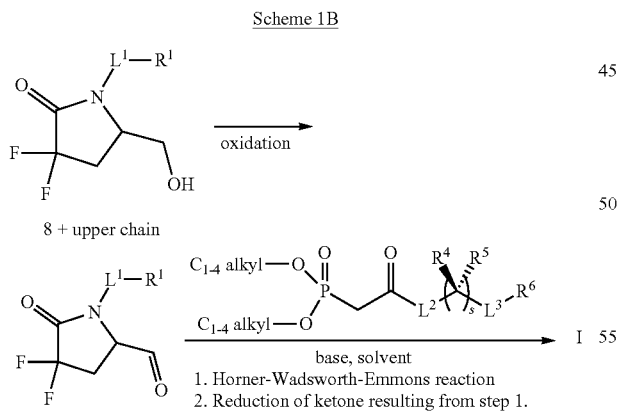

Alternatively, compounds of the present invention, (I), may be prepared from 8 or protected 8, for example, by a process that comprises first installing the lower chain with a carbon-carbon bond forming reaction (using 8 or an N-protected 8), wherein the hydroxymethyl group carbon atom attached to the γ-position of the lactam ring of intermediate 8 forms a covalent bond (carbon-carbon single, double, or triple bond) with the appropriate lower chain carbon atom to provide the corresponding 8+lower chain intermediate shown in Scheme 2. The installation of the lower chain may be followed by a process that comprises installation of the upper chain by way of nitrogen-carbon bond forming reaction, wherein the nitrogen atom of the γ-lactam ring of 8+lower chain forms a covalent bond with the appropriate upper chain carbon atom to provide the corresponding compound (I).

In some aspects of the present invention, the synthetic route to a compound (I) comprises a process wherein certain intermediates 8+upper chain may undergo chemical reaction or a series of chemical reactions, which are known in the art or disclosed herein, that chemically modify the upper chain such that chemical installation and/or modification of the lower chain is facilitated.

In further aspects of the present invention, the synthetic route to a compound (I) comprises a process wherein a certain intermediate 8+upper chain may undergo chemical reaction or a series of chemical reactions, which are known in the art or disclosed herein, that chemically modify the upper chain such that at least one particular functional group or other structural feature not incorporated into said intermediate is incorporated into the structure of invention compound (I).

In some aspects of the present invention, the synthetic route to a compound (I) comprises a process wherein certain intermediates 8+lower chain may undergo chemical reaction or a series of chemical reactions, which are known in the art or disclosed herein, that chemically modify the lower chain such that chemical installation and/or modification of the upper chain is facilitated.

In further aspects of the present invention, the synthetic route to a compound (I) comprises a process wherein a certain intermediate 8+lower chain may undergo chemical reaction or a series of chemical reactions, which are known in the art or disclosed herein, that chemically modify the lower chain such that at least one particular functional group or other structural feature not incorporated into said intermediate is incorporated into the structure of invention compound (I). For some embodiments of compound (I) wherein $L^4$ is a carbon-carbon single bond, the synthesis may comprise a sequence of steps as shown in Scheme 2C.

Scheme 2C

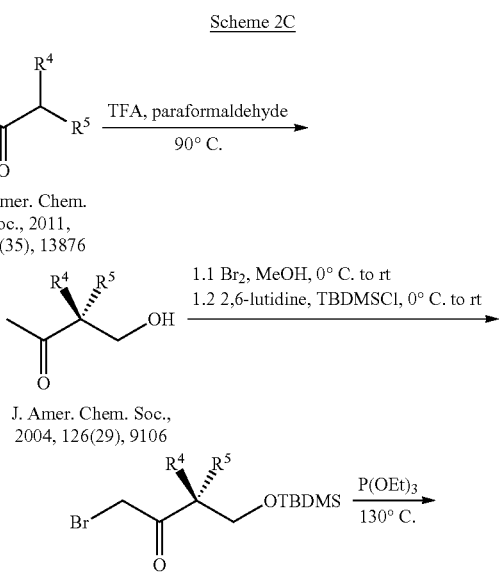

J. Amer. Chem. Soc., 2011, 133(35), 13876

J. Amer. Chem. Soc., 2004, 126(29), 9106

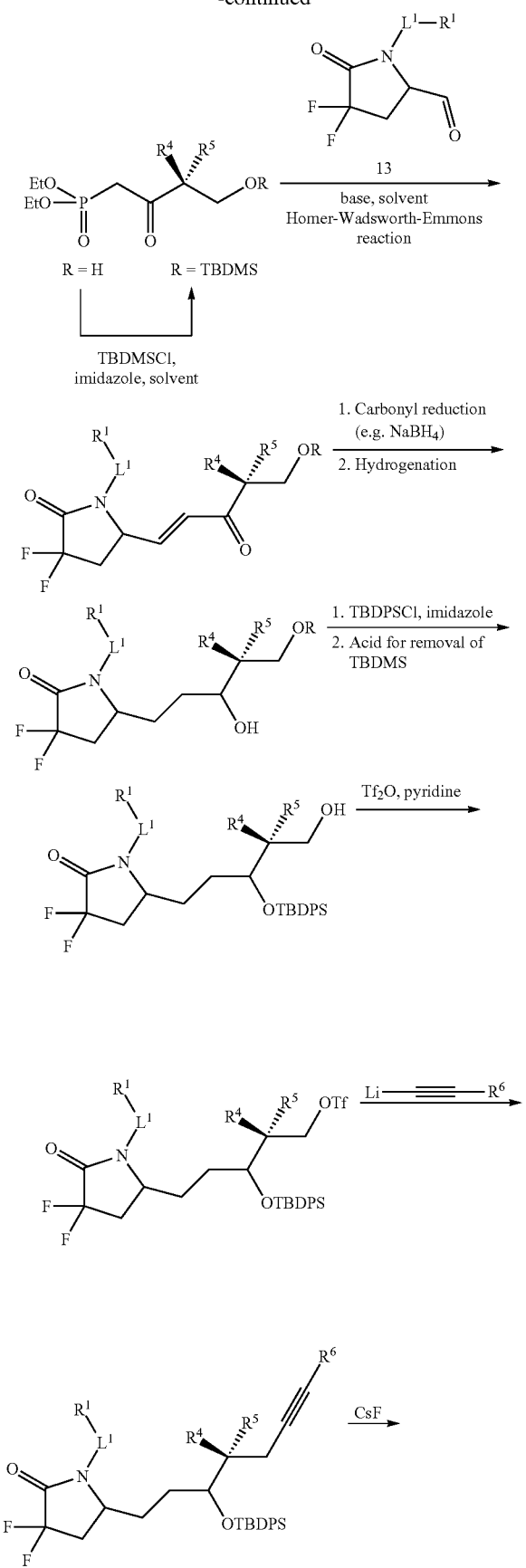

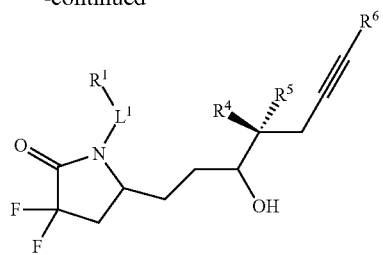

Omission of the hydrogenation step of Scheme 2C may provide compounds of Formula (I) wherein $L^4$ is a carbon-carbon double bond and wherein various $R^4$ and $R^5$ may be incorporated. In some aspects, $R^4$ and $R^5$ are determined by the starting ketone used in the chemical route sequence. Some ketones that may be utilized for this purpose and are commercially available include butan-2-one, pentan-2-one, 3-methyl-2-butanone (Aldrich), cyclopropyl methyl ketone (Aldrich), cyclobutyl methyl ketone (Aldrich), and 1-cyclopentyl-ethanone (Aldrich). Starting ketones and substituted acetylenes may also be available according to published procedures or methods well known to those skilled in the art.

Synthetic routes utilized to prepare compounds of the present invention typically proceed through a carbon-carbon double bond formation (olefination) step to install the compound's lower chain. The olefination may be accomplished by the interaction of an appropriate aldehyde intermediate with an appropriate nucleophilic carbanion species. Such methods may include Wittig reactions, wherein the nucleophilic carbanion species is an appropriate organic phosphonium ylide. Another carbon-carbon bond forming reaction that may be employed is a Horner-Wadsworth-Emmons reaction, wherein the coupling partner with the aldehyde is an appropriate organic phosphonate carbanion. Published reviews describing the general scope and mechanism along with various protocols for these types of olefination reactions include the following:

Boutagy, J. and Thomas, R. *Chemical Reviews,* 1974, 74, 87-99.

Wadsworth, W. S., Jr. *Organic Reactions,* 1977, 25, 73-253.

Walker, B. J. in *Organophosphorous Reagents in Organic Synthesis,* Cadogan, J. I. G., Ed.; Academic Press: New York, 1979, pp. 155-205.

Schlosser, M. et al., *Phosphorous and Sulfur and the Related Elements,* 1983, 18(2-3), 171-174.

Maryanoff, B. E. and Reitz, A. B. *Chemical Reviews,* 1989, 89(4), 863-927.

Kelly, S. E. in *Comprehensive Organic Synthesis,* Trost, B. M. and Fleming, I. Ed.; Pergamon: Oxford, 1991, Vol. 1, pp. 729-817.

Kolodiazhnyi, O. I., *Phosphorus Ylides, Chemistry and Application in Organic Synthesis*; Wiley-VCH: New York, 1999.

Another carbon-carbon bond forming reaction that may be used to install the lower chain is the Peterson olefination reaction, which is reviewed by Ager, D. J. *Organic Reactions,* 1990, 38, 1-223.

Aldehydes that may be used in the olefination step involved in preparation of compounds of the present invention include, but are not limited to, intermediates 13a-f, which can be generally prepared from (R)-3,3-difluoro-5-(hydroxymethyl)pyrrolidin-2-one ((R)-8), as shown in Scheme 3.

Scheme 3

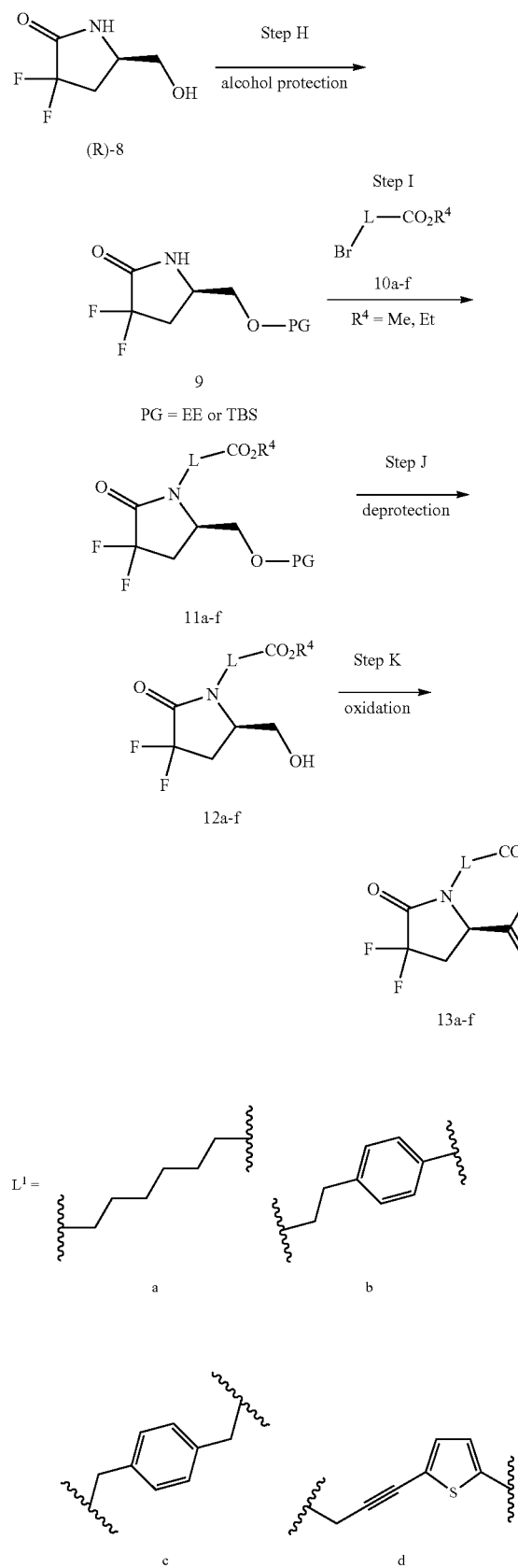

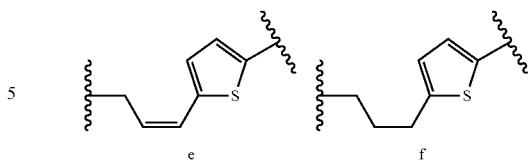

The hydroxyl moiety of intermediate (R)-8 may be protected (Step H) by reacting with ethyl vinyl ether (EVE) in the presence of TFA or tert-butyldimethylsilyl chloride (TBDMSCl) in the presence of a base, such as imidazole, to provide the EE-protected or TBS-protected species (9), respectively. N-alkylation of one of the protected α,α-difluoropyrrolidone intermediates (9) with an alkylating agent, such as one of 10a-f, affords the corresponding intermediate 11a-f (Step I). Alcohol deprotection (Step J) and subsequent controlled alcohol oxidation (Step K) provides the corresponding aldehyde intermediates 13a-f that may be employed in the subsequent olefination step.

Aldehyde intermediate 13f may alternatively be acquired by the hydrogenation of protected alcohol intermediates 11d or 11e to 11f or the unprotected alcohol intermediates 12d or 12e to 12f, followed by the subsequent deprotection (for 11f) and controlled oxidation to 13f. One hydrogenation reaction example is illustrated in Scheme 4. Palladium-catalyzed reduction of the internal carbon-carbon double bond of intermediate 12e (Scheme 4) to provide alcohol intermediate 12f followed by the controlled oxidation of the alcohol affords aldehyde intermediate 13f as illustrated in Scheme 3, Step K.

Scheme 4

Detailed procedures for preparing the aldehyde intermediates is described below.

Preparation of (R)-methyl 7-(3,3-difluoro-5-formyl-2-oxopyrrolidin-1-yl)heptanoate (13a)

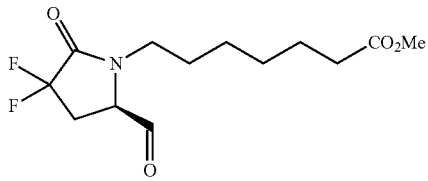 [SMILES: COC(=O)CCCCCCN1C(=O)C(F)(F)C[C@@H]1C=O]

Scheme 1, Step A: Preparation of (R)-methyl 5-oxopyrrolidine-2-carboxylate (2) from (R)-5-oxopyrrolidine-2-carboxylic acid (1)

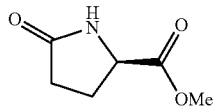

To a solution consisting of (R)-5-oxopyrrolidine-2-carboxylic acid (1,D-pyroglutamic acid from Chem-Impex International, 12.6 g, 97.4 mmol) in methanol (100 mL) was added sulfuric acid (1 mL) and the mixture was stirred at room temperature for 24 hours. The solvent was evaporated from the mixture, and the residue was purified by silica gel chromatography. Elution with acetone-dichloromethane (3:7 v/v) afforded the title intermediate (13.3 g, 95%) as a clear oil; TLC $R_f$ 0.42 (solvent system: 3:7 v/v acetone-dichloromethane); $^1$H-NMR (CDCl$_3$) δ 4.25 (t, 1H), 3.73 (s, 3H), 2.5-2.2 (m, 4H).

Scheme 1, Step B: Preparation of (R)-5-(hydroxymethyl)pyrrolidin-2-one (3)

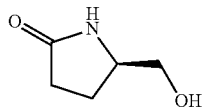

To a solution consisting of (R)-methyl 5-oxopyrrolidine-2-carboxylate (intermediate 2, 13.2 g, 115 mmol) in methanol (100 mL) at 0° C. was added sodium borohydride (10.5 g, 278 mmol) in portions. The reaction mixture was stirred at 0° C. until completion, at which time, acetic acid (3 mL) was added. The reaction mixture was concentrated and the residue was purified on silica gel, eluting with methanol-chloroform (1:9 v/v) to afford the title intermediate (12.9 g, 97%) as a colorless solid; TLC $R_f$ 0.33 (solvent system: 1:9 v/v methanol-chloroform); $^1$H-NMR (CDCl$_3$) δ 7.17 (s, 1H), 3.92 (s, 1H), 3.85-3.75 (m, 1H), 3.64-3.40 (m, 2H), 2.42-2.35 (m, 2H), 2.2-2.05 (m, 1H), 1.88-1.7 (m, 1H).

Scheme 1, Step C: Preparation of (R)-3,3-dimethyltetrahydropyrrolo[1,2-c]oxazol-5(3H)-one (4)

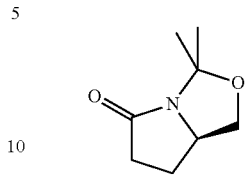

To a solution consisting of (R)-5-hydroxymethyl-2-pyrrolidinone (Alfa Aesar, 5.3 g, 46 mmol) in 2,2-dimethoxypropane (DMP) (40 mL, 326 mmol) was added camphorsulfonic acid (530 mg). The mixture was brought to reflux at 75° C. for 4 hours, and was subsequently concentrated in vacuo. Fresh DMP (40 mL) was then added and the mixture was brought to reflux overnight. After concentration, the remaining residue was purified by silica gel chromatography. Elution with ethyl acetate-heptanes (1:2 v/v) afforded the title intermediate (3.6 g) as a clear oil; TLC $R_f$ 0.20 (solvent system 50:50 v/v heptanes:ethyl acetate); $^1$H-NMR (CDCl$_3$) δ 4.3-4.2 (1H, m), 4.1 (1H, dd), 3.5 (1H, t), 2.9-2.7 (1H, m), 2.6-2.5 (1H, m), 2.2-2.1 (1H, m), 1.9-1.7 (1H, m), 1.7 (3H, s), 1.5 (3H, s); MS (ESI$^+$) m/z 156.2 (M+1).

Scheme 1, Step C: First Alternative Preparation of (R)-3,3-dimethyltetrahydropyrrolo[1,2-c]oxazol-5(3H)-one (4)

To a mixture consisting of (R)-5-hydroxymethyl-2-pyrrolidinone (20 g, 174 mmol) in 2,2-dimethoxypropane (1.4 L, 11,400 mmol) was added camphorsulfonic acid (1.0 g, 4.3 mmol). The stirring mixture was heated to 75° C. for 20 hours. The reaction mixture was treated with a saturated aqueous solution of sodium bicarbonate, diluted with water, and extracted with ethyl acetate. The combined organic phase was washed with a saturated aqueous solution of sodium chloride, dried over sodium sulfate, filtered, and concentrated. The residue was purified by silica gel chromatography. Elution with methanol-dichloromethane (1:70 v/v) afforded the title compound as a white solid (21.2 g, 78%); TLC $R_f$ 0.6 (solvent system: 25:75 v/v ethyl acetate-hexane); MS (ESI$^+$) m/z 156.1 (M+H)$^+$, 178.1 (M+Na)$^+$; $^1$H-NMR (CDCl$_3$) δ 4.3-4.2 (m, 1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Scheme 1, Step C: Second Alternative Preparation of (R)-3,3-dimethyltetrahydropyrrolo[1,2-c]oxazol-5(3H)-one (4)

To a mixture consisting of (R)-5-hydroxymethyl-2-pyrrolidinone (50.0 g, 434 mmol) in 2,2-dimethoxypropane (533 mL, 4300 mmol) was added camphorsulfonic acid (2.85 g, 10.8 mmol). The stirring mixture was brought to reflux at 88° C. for 1.5 hours, while removing methanol by distillation. The reaction mixture was subsequently heated to 95° C. for one hour, cooled to room temperature, treated with triethylamine (5 mL), and stirred for 5 minutes. The mixture was then diluted with hexanes-ethyl acetate (500 mL, 1:3 v/v) and washed sequentially with a 50% aqueous solution of sodium chloride and a saturated aqueous solution of sodium chloride. The organic phase was dried over sodium sulfate, filtered, and concentrated. The residue was purified by crystallization from hexanes to afford the title compound as white crystalline solid (30.48 g, 45%); TLC R$_f$ 0.4 (solvent system: 5:95 v/v methanol:dichloromethane) MS (ESI$^+$) m/z 156.1 (M+H)$^+$, 178.1 (M+Na)$^+$; $^1$H-NMR (CDCl$_3$) δ 4.3-4.2 (m, 1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Scheme 1, Step D: Preparation of (R)-6-fluoro-3,3-dimethyltetrahydropyrrolo [1,2-c]oxazol-5(3H)-one (5)

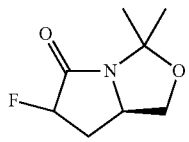

To a mixture consisting of diisopropylamine (6.5 mL, 46 mmol) and THF (75 mL) at −78° C. was added dropwise a solution of nBuLi (2.5 M in hexanes, 18 mL, 44 mmol), and the resulting solution stirred for one hour. A solution consisting of (R)-3,3-dimethyltetrahydropyrrolo[1,2-c]oxazol-5 (3H)-one (intermediate 4, 3.6 g, 23 mmol) in THF (25 mL) was added dropwise, and the resulting solution stirred for one hour. A solution consisting of N-fluorobenzenesulfonimide (9.5 g, 30 mmol) in THF (50 mL) was added dropwise, and the resulting solution was allowed to stir for 75 minutes below −55° C., and was subsequently quenched with the addition of a saturated aqueous ammonium chloride solution and warmed to room temperature. The organic material was extracted twice with ethyl acetate. The combined organic phase was dried over anhydrous sodium sulfate, filtered, and concentrated. The residue was dissolved in ethyl acetate, filtered, and the filtrate was concentrated to a gold oil, which was purified by silica gel chromatography. Elution with ethyl acetate:heptanes (1:3 v/v) afforded an approximately 1:1 mixture of the diastereomers of the title intermediate (1.54 g) as a clear oil; TLC R$_f$ 0.40 (solvent system 50:50 v/v heptanes:ethyl acetate); $^1$H-NMR (CDCl$_3$) δ 5.4-5.2 (m, 1H), 5.2-5.0 (m, 1H), 4.5-4.4 (m, 1H), 4.2-4.1 (m, 2H), 4.0-3.9 (m, 1H), 3.5 (t, 1H), 3.4 (t, 1H), 2.8-2.7 (m, 1H), 2.5-2.3 (m, 1H), 2.1-1.8 (m, 2H), 1.7 (s, 3H), 1.7 (s, 3H), 1.5 (s, 3H) 1.5 (s, 3H); $^{19}$F-NMR (CDCl$_3$, 376 MHz) δ −102.2 (dd, −0.5F, J=264.2, 13.2 Hz), −103.5 (ddd, −0.5F, J=264.3, 26.5, 14.6 Hz); MS (ESI$^+$) m/z 174.1 (M+1).

Scheme 1, Step D: Alternative Preparation of (7aR)-6-fluoro-3,3-dimethyltetrahydropyrrolo[1,2-c]oxazol-5(3H)-one (5)

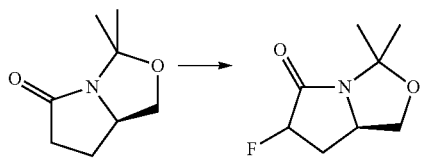

To a solution consisting of (R)-3,3-dimethyltetrahydropyrrolo[1,2-c]oxazol-5(3H)-one (intermediate 4, 18.5 g, 119 mmol) in dry THF (400 mL) at −75° C. was added lithium diisopropylamide (74.5 mL, 149 mmol, 2 M in heptanes/THF/ethylbenzene from Sigma Aldrich) dropwise over 20 minutes, then stirred for one hour. The reaction mixture was then treated with a solution consisting of N-fluorobenzenesulfonimide (56.6 g, 167 mmol, NFSi, from Oakwood Chemical) in THF (300 mL) with steady addition over 30 minutes, and the resulting mixture was stirred for 16 hours, warming to room temperature. To the reaction mixture was added a saturated aqueous solution of ammonium chloride. The organic material was extracted twice with ethyl acetate. The organic layer was washed with a 50% aqueous solution of sodium chloride, followed by a saturated solution of sodium chloride, and dried over sodium sulfate, filtered, and concentrated. The residue was redissolved in ethyl acetate (200 mL) and treated with heptane (200 mL), causing the formation of a white precipitate. The precipitate was filtered and washed with 50% ethyl acetate in heptane. The combined filtrate was concentrated. The residue was dissolved in ethyl acetate (200 mL) and treated with heptane (200 mL), forming a second precipitate. The second precipitate was filtered and washed with 50% ethyl acetate in heptane. The filtrate was concentrated and the residue (31 g) was purified by silica gel chromatography. Elution with ethyl acetate-hexanes (1:3 v/v) afforded pure samples of each of the two diastereomers of the title compound as tan solids (4.1 g of each) and a portion of mixed diastereomers (3.8 g of an approximately 1:1 ratio). The total mass of the two diastereomer products isolated was 12.0 g (65% total yield).

(6S,7aR)-6-fluoro-3,3-dimethyltetrahydropyrrolo[1, 2-c]oxazol-5(3H)-one (5.1α) and (6R,7aR)-6-fluoro-3,3-dimethyltetrahydropyrrolo[1,2-c]oxazol-5 (3H)-one (5.1β)

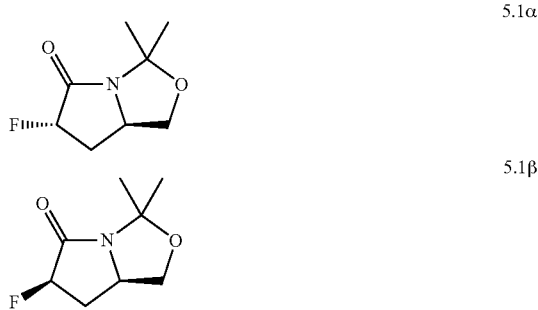

Separation of the two isomers by chromatography, as described above, provided the two pure diastereomers.

(5.1α) TLC R$_f$ 0.55 (solvent system: 60:40 v/v ethyl acetate-hexanes); HPLC on an Agilent 1100 instrument, ultraviolet detector at 210 nm, stationary phase Gemini 3μ C18, 50×2 mm column, mobile phase, water-methanol-acetic acid gradient over 4 min (90:10:0.1 to 10:90:0.1), retention time 2.33 minutes; MS (ESI$^+$) m/z 174.1 (M+H)$^+$; 1H-NMR (CDCl$_3$) δ 5.085 (ddd, J=51.6, 6.0, 0.8 Hz, 1H) 4.5-4.4 (m, 1H), 4.15 (dd, 1H), 3.4 (dd, 1H), 2.5-2.3 (m, 1H), 2.1-1.7 (m, 1H), 1.65 (s, 3H), 1.5 (s, 3H); $^{19}$F-NMR (CDCl$_3$, 376 MHz) δ −184.5 (ddd, J=52, 41, 22 Hz, 1F).

(5.1β) TLC R 0.45 (solvent system: 60:40 v/v ethyl acetate-hexanes); HPLC on an Agilent 1100 instrument, ultraviolet detector at 210 nm, stationary phase Gemini 3 μC18, 50×2 mm column, mobile phase, water-methanol-acetic acid gradient over 4 min (90:10:0.1 to 10:90:0.1), retention time 1.69 minutes; MS (ESI$^+$) m/z 174.1 (M+H)$^+$; 1H-NMR (CDCl$_3$) δ 5.325 (ddd, J=52.4, 9.9, 7.7 Hz, 1H) 4.2

(dd, 1H), 4.0-3.9 (m, 1H), 3.5 (dd, 1H), 2.8-2.7 (m, 1H), 2.0-1.9 (m, 1H), 1.7 (s, 3H), 1.5 (s, 3H); $^{19}$F-NMR (CDCl$_3$, 376 MHz) δ-185.9 (dd, J=52, 23 Hz, 1F).

Scheme 1, Step E: Preparation of (R)-6,6-difluoro-3,3-dimethyltetrahydropyrrolo [1,2-c]oxazol-5(3H)-one (6)

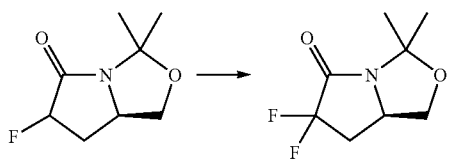

To a solution consisting of (7aR)-6-fluoro-3,3-dimethyl-tetrahydropyrrolo[1,2-c]oxazol-5(3H)-one (8.0 g, 46.2 mmol, mixture of diastereomers of 5.1) in dry THF (300 mL) at −75° C. was added lithium bis(trimethylsilyl)amide (50.8 mL, 50.8 mmol, LiHMDS 1 M in THF) dropwise over ten minutes, then stirred for one hour. The reaction mixture was then treated with a solution consisting of N-fluorobenzenesulfonimide (17.5 g, 55.4 mmol) in THF (100 mL) with steady addition over ten minutes. The resulting mixture was stirred for 30 minutes. Lithium bis(trimethylsilyl)amide (10.0 mL, 10 mmol) was added, and the reaction stirred for 16 hours, warming to room temperature. To the reaction mixture was added a 50% aqueous solution of ammonium chloride. The organic material was extracted with ethyl acetate-heptane (5:1). The organic layer was washed sequentially with a 50% aqueous solution of sodium chloride, water, and a saturated solution of sodium chloride, then dried over sodium sulfate, filtered, and concentrated. The residue was purified by silica gel chromatography. Elution with ethyl acetate-hexanes (1:5 v/v) afforded the title compounds as a tan solid (7.39 g; 79%); TLC R$_f$ 0.70 (solvent system: 50:50 v/v ethyl acetate-hexanes); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 1, Step E: Preparation of (R)-6,6-difluoro-3,3-dimethyltetrahydropyrrolo [1,2-c]oxazol-5(3H)-one (6)

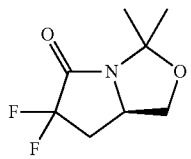

To a mixture consisting of diisopropylamine (2.2 mL, 8.9 mmol) and THF (40 mL) at −78° C. was added dropwise a solution of nBuLi (2.5 M in hexanes, 6.0 mL, 15 mmol), and the resulting solution stirred for one hour. A solution consisting of (7aR)-6-fluoro-3,3-dimethyltetrahydropyrrolo[1,2-c]oxazol-5(3H)-one (intermediate 5, 1.54 g, 8.90 mmol) in THF (25 mL) was added dropwise, and the resulting solution stirred for one hour. A solution consisting of N-fluorobenzenesulfonimide (3.5 g, 11 mmol) in THF (25 mL) was added dropwise, and the resulting mixture was allowed to stir for 75 minutes below −55° C. The reaction mixture was subsequently quenched with the addition of a saturated aqueous ammonium chloride solution and warmed to room temperature. The organic material was extracted twice with ethyl acetate. The combined organic phase was dried over anhydrous sodium sulfate, filtered, and concentrated. The residue was dissolved in ethyl acetate, filtered, and the filtrate was concentrated to a gold oil which was purified by silica gel chromatography. Elution with ethyl acetate:heptanes (1:5 v:v) afforded the title intermediate (1.28 g, 75%) as a clear oil; TLC R$_f$ 0.60 (solvent system 50:50 v/v heptanes:ethyl acetate); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H); MS (ESI$^+$) m/z 192.1 (M+1).

Scheme 1A, Step A: Alternative Preparation of (R)-6,6-difluoro-3,3-dimethyltetrahydropyrrolo [1,2-c]oxazol-5(3H)-one (6)

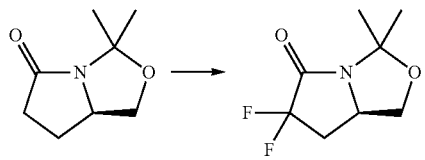

To a mixture consisting of (R)-3,3-dimethyltetrahydropyrrolo[1,2-c]oxazol-5(3H)-one (4) (15.5 g, 100 mmol) in dry THF (300 mL) at −78° C. was added sec-butyllithium (78.5 mL, 110 mmol, 1.4 M in cyclohexane, from Sigma Aldrich) dropwise over 5 minutes. The resulting reaction mixture was stirred for one hour and was subsequently treated with a mixture consisting of N-fluorobenzene sulfonimide (35 g, 111 mmol, NFSi, from Oakwood) in THF (100 mL) with steady addition over five minutes. The resulting reaction mixture was stirred for another hour, after which time a lithium bis(trimethylsilyl)amide solution (LiHMDS, 110 mL, 110 mmol, 1.0 M in THF, from Sigma Aldrich) was added dropwise over five minutes. The resulting reaction mixture was stirred for another hour, after which time a mixture consisting of NFSi (34.4 g, 109 mmol) in THF (100 mL) was added over five minutes. The resulting reaction mixture was stirred for two hours, after which time was added lithium bis(trimethylsilyl)amide (40 mL, 40 mmol, 1M in THF) to the −78° C. reaction mixture, which was subsequently stirred for 30 minutes. The cooling bath was removed and a saturated aqueous solution of ammonium chloride added. The reaction mixture was allowed to warm to room temperature, and the organic material was extracted with ethyl acetate. The organic layer was sequentially washed with water, a 50% saturated aqueous solution of sodium chloride, and a saturated solution of sodium chloride, dried over sodium sulfate, filtered, and concentrated. The residue was purified by silica gel chromatography. Elution with ethyl acetate-hexanes (1:3 v/v) afforded of the title compound as a solid (11.64 g; 61%); TLC R$_f$ 0.4 (solvent system: 5:95 v/v methanol-dichloromethane); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 1, Step F: Preparation of (R)-methyl 4-amino-2,2-difluoro-5-hydroxypentanoate (7)

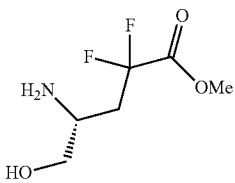 [SMILES: COC(=O)C(F)(F)C[C@@H](N)CO]

To an ice-cooled solution consisting of (R)-6,6-difluoro-3,3-dimethyltetrahydropyrrolo [1,2-c]oxazol-5(3H)-one (intermediate 6, 1.28 g, 6.70 mmol) in methanol (20 mL) was added dropwise 4N HCl in dioxane (3.0 mL, 12 mmol) and stirred at room temperature for 16 hours. The resulting mixture was concentrated and the product concentrate used without purification; TLC $R_f$ 0.60 (solvent system 93:7 v/v dichloromethane-methanol).

Scheme 1, Step G: Preparation of (R)-3,3-difluoro-5-(hydroxymethyl)pyrrolidin-2-one ((R)-8)

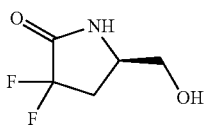

To a solution consisting of (R)-methyl 4-amino-2,2-difluoro-5-hydroxypentanoate (intermediate 7, 6.70 mmol) in THF (25 mL) was added triethylamine (6 mL) and the reaction mixture was stirred overnight. The reaction mixture was concentrated to give a crude residue, which was purified by silica gel chromatography. Elution with methanol:dichloromethane (1:20 v/v) afforded the title intermediate (540 mg) as a clear oil; TLC $R_f$ 0.40 (solvent system 93:7 v/v dichloromethane:methanol); $^1$H-NMR (CDCl$_3$) δ 3.7-3.6 (w, 1H), 3.6-3.4 (m, 2H), 3.4-3.2 (m, 1H), 2.7-2.4 (m, 1H), 2.4-2.1 (m, 1H); MS (ESI$^+$) m/z 152.1 (M+1); (ESI$^-$) m/z 150.1 (M−1).

Scheme 1A, Step B: Alternative Preparation of (R)-3,3-difluoro-5-(hydroxymethyl)pyrrolidin-2-one ((R)-8)

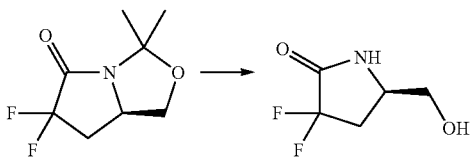

To a solution consisting of (R)-6,6-difluoro-3,3-dimethyltetrahydropyrrolo[1,2-c]oxazol-5(3H)-one (intermediate 6, 12.5 g, 65.4 mmol) in water-1,4-dioxane (300 mL, 1:1 v/v) was added Amberlite IR-120H* (6.23 g). The reaction mixture was heated to 115° C. for 6 hours and was subsequently filtered through Celite and washed with methanol. The filtrate was concentrated under reduced pressure, using toluene and ethanol additives to help drive off water, to provide a residue. The residue was washed with diethyl ether to afford the title compound as a tan solid (8.8 g; 89%), which was carried on without further purification; TLC $R_f$ 0.25 (solvent system: 70:30 v/v ethyl acetate:hexanes).

*Amberlite IR-120H ion-exchange resin, strongly acid gel-type resin with sulfonic acid functionality, CAS: 39389-20-3.75 g of Amberlite was washed and decanted three times with deionized water. The fourth wash was filtered using suction filtration and the semi-dry resin was quickly washed with 2-propanol then diethyl ether. The resin was dried to give 54 g of free flowing dark brown bead resin.

Scheme 3, Step H: Preparation of (5R)-5-((1-ethoxyethoxy)methyl)-3,3-difluoropyrrolidin-2-one (9; PG=EE)

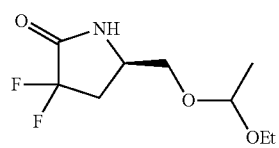

To a solution consisting of (R)-3,3-difluoro-5-(hydroxymethyl)pyrrolidin-2-one (intermediate 8, 540 mg, 3.57 mmol) in dichloromethane (20 mL) and THF (10 mL) was added ethyl vinyl ether (1.4 mL, 15 mmol) followed by trifluoroacetic acid (20 mg). The reaction mixture was stirred at room temperature for 16 hours. The reaction mixture was diluted with ethyl acetate (150 mL) and washed with a saturated aqueous solution of sodium bicarbonate (10 mL) and brine (5 mL) before being dried over sodium sulfate, filtered, and concentrated. The residue was purified by silica gel chromatography. Elution with methanol:dichloromethane (1:60 v/v) afforded the title intermediate (726 mg) as a clear oil; TLC $R_f$ 0.60 (solvent system: 93:7 v/v dichloromethane:methanol); $^1$H-NMR (CDCl$_3$) δ 4.8-4.6 (m, 1H), 4.0-3.8 (m, 1H), 3.7-3.5 (m, 2H), 3.5-3.4 (m, 2H), 2.8-2.6 (m, 1H), 2.4-2.2 (m, 1H), 1.3 (d, 3H), 1.2 (t, 3H); MS (ESI$^+$) m/z 241.1 (M+NH$_3$), 246.1 (M+Na); (ESI$^-$) m/z 222.1 (M−1).

Scheme 3, Step H: Preparation of (R)-5-(((tert-butyldimethylsilyl)oxy)methyl)-3,3-difluoropyrrolidin-2-one (9; PG=TBS)

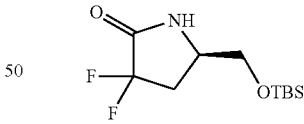

To a solution consisting of (R)-3,3-difluoro-5-(hydroxymethyl)pyrrolidin-2-one (intermediate 8, 880 mg, 3.57 mmol) in DMF (10 mL) and THF (10 mL) was added tert-butyldimethylchlorosilane (1.40 g, 9.23 mmol) followed by imidazole (800 mg, 6.55 mmol). The reaction mixture was stirred at room temperature for 16 hours. The reaction mixture was diluted with water (10 mL) and extracted thrice with ethyl acetate (55 ml, 2×25 ml). The combined organics were washed with 1:1 water:brine (3×10 mL) and brine (5 mL) before being dried over sodium sulfate, filtered, and concentrated. The residue was purified by silica gel chromatography. Elution with methanol:dichloromethane (1:50 v/v) afforded the title intermediate (1528 mg, 99%) as a clear oil; TLC $R_f$ 0.60 (solvent system: 95:5 v/v dichloromethane-methanol); ¹H-NMR (CDCl₃) δ 3.8-3.7 (m, 1H), 3.7-3.6 (m, 1H), 3.5-3.4 (m, 1H), 2.6-2.5 (m, 1H), 2.3-2.1 (m, 1H), 0.8 (s, 9H), 0.0 (s, 6H); MS (ESI+) m/z 266.1 (M+1).

Scheme 3, Step 1: Preparation of methyl 7-((5R)-5-((1-ethoxyethoxy)methyl)-3,3-difluoro-2-oxopyrrolidin-1-yl)heptanoate (11a)

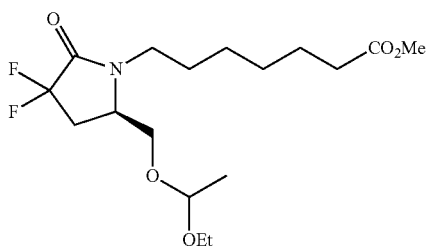 [SMILES: CCOC(C)OC[C@H]1CC(F)(F)C(=O)N1CCCCCCC(=O)OC]

To a suspension consisting of sodium hydride (60% in mineral oil, 18 mg, 0.45 mmol) and sodium iodide (74 mg, 0.49 mmol) in DMF (5 mL) was added dropwise a solution of (5R)-5-((1-ethoxyethoxy)methyl)-3,3-difluoropyrrolidin-2-one (intermediate 9; PG=EE, 100 mg, 0.45 mmol) in DMF (5 mL). The mixture was stirred at room temperature for two hours followed by 50° C. for 30 minutes. To the reaction mixture was added dropwise methyl 7-bromoheptanoate (10a, Alfa Aesar, 120 mg, 0.538 mmol) and stirring continued overnight at 50° C. The mixture was diluted with ethyl acetate (200 mL) and washed sequentially with 0.5N hydrochloric acid (20 mL), a 5% aqueous solution of sodium thiosulfate (10 mL), 50% brine (4×25 mL), and brine (25 mL). The organic phase was dried over sodium sulfate, filtered, and concentrated. The residue was purified by silica gel chromatography. Elution with methanol:dichloromethane (1:100 v/v) afforded the title intermediate (128 mg, 78%) as a clear oil; TLC $R_f$ 0.95 (solvent system: 93:7 v/v dichloromethane:methanol); ¹H-NMR (CDCl₃) δ 4.7 (dq, 1H), 3.85-3.75 (m, 1H), 3.75-3.4 (m, 8H), 3.15-3.05 (m, 1H), 2.65-2.35 (m, 1H), 2.3 (t, 2H), 1.7-1.4 (m, 4H), 1.4-1.3 (m, 4H), 1.3 (d, 3H), 1.2 (t, 3H); MS (ESI⁺) m/z 383.2 (M+NH₃), 388.1 (M+Na).

Alternative Preparation of 11a:

To a suspension consisting of sodium hydride (60% in mineral oil, 108 mg, 2.7 mmol) and sodium iodide (450 mg, 3.0 mmol) in DMF (30 mL) was added dropwise a solution consisting of (5R)-5-((1-ethoxyethoxy)methyl)-3,3-difluoropyrrolidin-2-one (intermediate 9; PG=EE, 600 mg, 2.68 mmol) in DMF (30 mL). The reaction mixture was stirred at room temperature for two hours followed by 50° C. for 30 minutes. To the reaction mixture was added dropwise methyl 7-bromoheptanoate (available from Alfa Aesar, 720 mg, 2.23 mmol) and stirring continued overnight at 50° C. The mixture was diluted with ethyl acetate and washed sequentially with 0.5 N hydrochloric acid, a 5% aqueous solution of sodium thiosulfate, 50% saturate aqueous solution of sodium chloride, and saturate aqueous solution of sodium chloride. The organic phase was dried over sodium sulfate, filtered, and concentrated. The residue was purified by silica gel chromatography. Elution with methanol:dichloromethane (1:125 v/v) afforded the title intermediate (888 mg, 90%) as a tan solid; TLC $R_f$ 0.95 (solvent system: 93:7 v/v dichloromethane-methanol); MS (ESI⁺) m/z 383.2 (M+NH₄)⁺, 388.1 (M+Na)⁺.

Scheme 3, Step J: Preparation of (R)-methyl 7-(3,3-difluoro-5-(hydroxymethyl)-2-oxopyrrolidin-1-yl)heptanoate (12a)

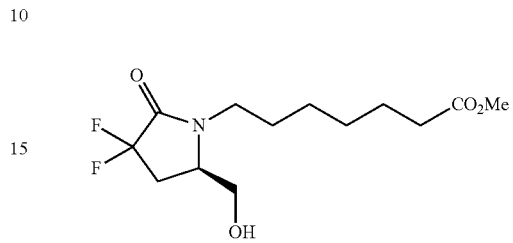

To a solution consisting of methyl 7-((5R)-5-((1-ethoxyethoxy)methyl)-3,3-difluoro-2-oxopyrrolidin-1-yl)heptanoate (intermediate 11a, 113 mg, 0.310 mmol) in methanol (10 mL) was added p-toluenesulfonic acid monohydrate (2 mg) and the mixture was stirred at room temperature for 18 hours. The reaction mixture was concentrated to give a crude residue that was purified by silica gel chromatography. Elution with methanol-dichloromethane (1:80 v/v) afforded the title intermediate (86 mg, 95%) as a pale yellow oil; TLC $R_f$ 0.55 (solvent system: 7:93 v/v methanol-dichloromethane); ¹H-NMR (CDCl₃) δ 3.85-3.6 (m, 4H), 3.65 (s, 3H), 3.2-3.1 (m, 1H), 2.6-2.4 (m, 2H), 2.3 (t, 2H), 1.7-1.4 (m, 4H), 1.4-1.2 (m, 4H); MS (ESI⁺) m/z 311.2 (M+⁺NH₄), 316.1 (M+Na).

Scheme 3, Step K: Preparation of (R)-methyl 7-(3,3-difluoro-5-formyl-2-oxopyrrolidin-1-yl) heptanoate (13a)

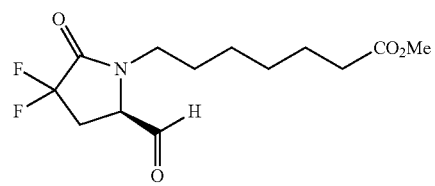 [SMILES: COC(=O)CCCCCCN1C(=O)C(F)(F)C[C@@H]1C=O]

To a solution consisting of (R)-methyl 7-(3,3-difluoro-5-(hydroxymethyl)-2-oxopyrrolidin-1-yl)heptanoate (intermediate 12a, 85 mg, 0.29 mmol) in dichloromethane (10 ml) was added Dess-Martin periodinate (150 mg, 0.348 mmol), and the reaction mixture was stirred for four hours. The reaction mixture was filtered and the filtrate was subsequently concentrated. Without further workup, the residue was purified by silica gel chromatography. Elution with methanol-dichloromethane (1:200 v/v) afforded the title intermediate (76.6 mg, 91%) as a pale yellow oil; TLC $R_f$ 0.60 (solvent system: 7:93 v/v methanol-dichloromethane).

Preparation of (R)-methyl 4-(2-(3,3-difluoro-5-formyl-2-oxopyrrolidin-1-yl)ethyl)benzoate (13b)

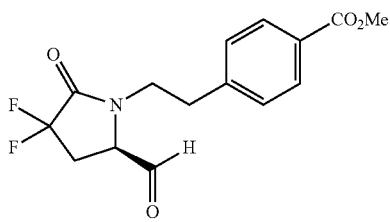 [SMILES: COC(=O)c1ccc(CCN2C(=O)C(F)(F)C[C@@H]2C=O)cc1]

Scheme 3, Step I: Preparation of (R)-methyl 4-(2-(5-(((tert-butyldimethylsilyl)oxy)methyl)-3,3-difluoro-2-oxopyrrolidin-1-yl)ethyl)benzoate (11b; PG=TBS)

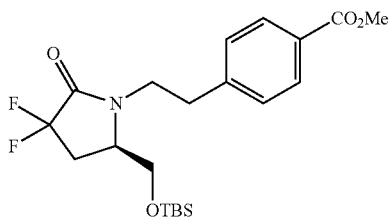 [SMILES: COC(=O)c1ccc(CCN2C(=O)C(F)(F)C[C@@H]2CO[Si](C)(C)C(C)(C)C)cc1]

To a suspension consisting of sodium hydride (60% in mineral oil, 61 mg, 1.5 mmol) and sodium iodide (251 mg, 1.67 mmol) in DMF (40 mL) was added dropwise a solution consisting of (R)-5-(((tert-butyldimethylsilyl)oxy)methyl)-3,3-difluoropyrrolidin-2-one (intermediate 9; PG=TBS, 370 mg, 1.39 mmol) in DMF (5 mL). The mixture was stirred at room temperature for two hours followed by 50° C. for 30 minutes. To the reaction mixture was added dropwise methyl 4-(2-bromoethyl)benzoate (406 mg, 1.67 mmol) in DMF (5 mL), and stirring continued overnight at 50° C. The mixture was diluted with ethyl acetate and washed sequentially with 0.5 N hydrochloric acid, a 5% aqueous solution of sodium thiosulfate, 50% brine, and brine. The organic phase was dried over sodium sulfate, filtered, and concentrated. The residue was purified by silica gel chromatography. Elution with ethyl acetate:heptane (increasing solvent strength, 1:50 v/v to 1:10 v/v) followed by eluting with methanol-dichloromethane (1:50 v/v) afforded the title intermediate (39 mg, 6.6%); TLC $R_f$ 0.6 (solvent system: 70:30 v/v heptane:ethyl acetate); $^1$H-NMR (CDCl$_3$) δ 7.9 (d, 2H), 7.28 (d, 2H), 3.98-3.91 (m, 1H), 3.9 (s, 3H), 3.74-3.48 (m, 2H), 3.46-3.35 (m, 2H), 3.1-2.9 (m, 2H), 2.48-2.18 (m, 2H), 0.8 (s, 9H), 0.0 (s, 6H); MS (ESI$^+$) m/z 445.1 (M+NH$_3$).

Significant improvement of the yield (in relation to (R)-5-(((tert-butyldimethylsilyl)oxy)methyl)-3,3-difluoropyrrolidin-2-one) was realized by repeated additions of sodium hydride and methyl 4-(2-bromoethyl)benzoate to the reaction mixture.

Scheme 3, Step J: (R)-methyl 4-(2-(3,3-difluoro-5-(hydroxymethyl)-2-oxopyrrolidin-1-yl)ethyl)benzoate (12b)

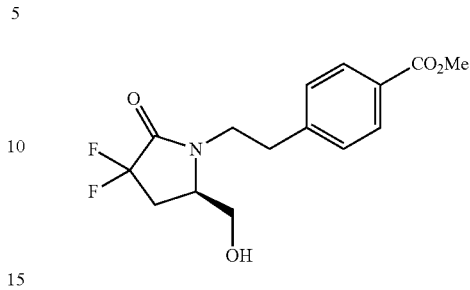

To a solution consisting of (R)-methyl 4-(2-(5-(((tert-butyldimethylsilyl)oxy)methyl)-3,3-difluoro-2-oxopyrrolidin-1-yl)ethyl)benzoate (11b, 180 mg, 0.42 mmol) in THF (10 mL) was added tetrabutylammonium fluoride (0.55 mL, 1M in THF), and the reaction mixture was stirred overnight. The reaction mixture was diluted with ethyl acetate and washed with 1:1 brine-water (3×15 mL) and once with brine. The organic phase was dried over sodium sulfate, filtered, and concentrated. The crude residue was purified by silica gel chromatography. Elution with methanol-dichloromethane (increasing solvent strength, 1:200 v/v to 1:30 v/v) afforded the title intermediate (147 mg); TLC $R_f$ 0.5 (solvent system: 5:95 v/v methanol-dichloromethane); $^1$H-NMR (CDCl$_3$) δ 7.9 (d, 2H), 7.24 (d, 2H), 3.98-3.91 (m, 1H), 3.87 (s, 3H), 3.74-3.48 (m, 2H), 3.51-3.46 (m, 2H), 3.1-2.8 (m, 2H), 2.48-2.22 (m, 2H); MS (ESI$^+$) nm/z 331 (M+$^+$NH$_4$).

Scheme 3, Step K: Preparation of (R)-methyl 4-(2-(3,3-difluoro-5-formyl-2-oxopyrrolidin-1-yl)ethyl)benzoate (13b)

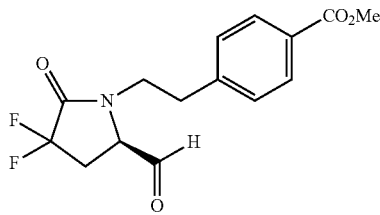 [SMILES: COC(=O)c1ccc(CCN2C(=O)C(F)(F)C[C@@H]2C=O)cc1]

(R)-methyl 4-(2-(3,3-difluoro-5-formyl-2-oxopyrrolidin-1-yl)ethyl)benzoate was prepared from 12b using the oxidation procedure (Step K) described for the preparation of intermediate 13a from intermediate 12a; TLC $R_f$ 0.4 (solvent system: 95:5 v/v dichloromethane-methanol); $^1$H-NMR (CDCl$_3$) δ 9.2 (s, 1H), 7.9 (dd, 2H), 7.24 (dd, 2H), 3.98-3.91 (m, 1H), 3.87 (s, 3H), 3.74-3.48 (m, 2H), 3.51-3.46 (m, 2H), 3.1-2.8 (m, 2H), 2.48-2.22 (m, 2H).

Preparation of (R)-methyl 5-(3-(3,3-difluoro-5-formyl-2-oxopyrrolidin-1-yl)prop-1-yn-1-yl)thiophene-2-carboxylate (13d)

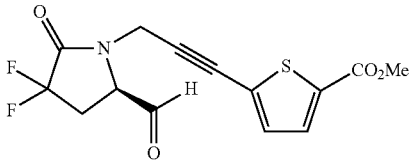 [SMILES: COC(=O)c1ccc(C#CCN2C(=O)C(F)(F)C[C@@H]2C=O)s1]

(R)-Methyl 5-(3-(3,3-difluoro-5-formyl-2-oxopyrrolidin-1-yl)prop-1-yn-1-yl)thiophene-2-carboxylate is prepared in the manner as that described for the preparation of intermediate 13a except that methyl 5-(3-bromoprop-1-yn-1-yl)thiophene-2-carboxylate (10d) is used in Step I instead of methyl 7-bromoheptanoate.

Preparation of (R,Z)-methyl 5-(3-(3,3-difluoro-5-formyl-2-oxopyrrolidin-1-yl)prop-1-en-1-yl)thiophene-2-carboxylate (13e)

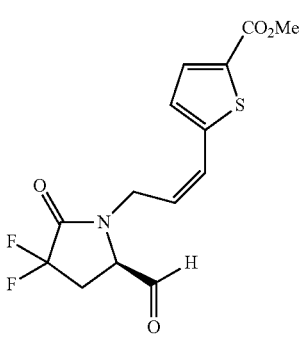 [SMILES: COC(=O)c1ccc(/C=C\CN2C(=O)C(F)(F)C[C@@H]2C=O)s1]

(R,Z)-Methyl 5-(3-(3,3-difluoro-5-formyl-2-oxopyrrolidin-1-yl)prop-1-en-1-yl)thiophene-2-carboxylate is prepared in the manner as that described for the preparation of intermediate 13a except that (Z)-methyl 5-(3-bromoprop-1-en-1-yl)thiophene-2-carboxylate (10e) is used in Step I instead of methyl 7-bromoheptanoate.

Preparation of (R)-methyl 5-(3-(3,3-difluoro-5-formyl-2-oxopyrrolidin-1-yl)propyl)thiophene-2-carboxylate (13f)

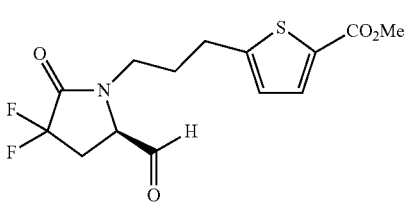 [SMILES: COC(=O)c1ccc(CCCN2C(=O)C(F)(F)C[C@@H]2C=O)s1]

Preparation of methyl 5-bromothiophene-2-carboxylate

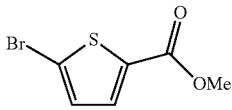

To an iced-cooled solution consisting of 5-bromo-2-thiophene carboxylic acid (Oakwood Products, 5.1 g, 25 mmol) in ethyl acetate (200 mL) and methanol (20 mL) was added TMS diazomethane (2M in diethyl ether, 20 ml, 40 mmol) over 20 minutes. Gas evolution was observed and the reaction mixture was stirred for one hour. The mixture was then allowed to warm to room temperature overnight. The volatile material was removed and the residue was purified by silica gel chromatography. Elution with ethyl acetate-heptane (1:50 v/v) afforded the title intermediate (5.4 g, 98%) as a white solid; TLC $R_f$ 0.60 (solvent system 90:10 v/v heptanes:ethyl acetate); $^1$H-NMR (CDCl$_3$) δ 7.5 (d, 1H), 7.1 (d, 1H), 4.9 (s, 3H).

Preparation of methyl 5-(3-hydroxyprop-1-yn-1-yl)thiophene-2-carboxylate

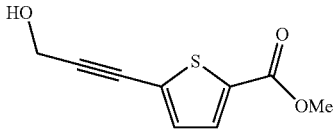 [SMILES: COC(=O)c1ccc(C#CCO)s1]

To a solution consisting of methyl 5-bromo-2-thiophene carboxylate (5.4 g, 24 mmol) in benzene (60 mL) was added tetrakis(triphenylphosphine)palladium (0) (676 mg, 0.6 mmol) and the reaction mixture was stirred for 30 minutes. To the reaction mixture was then added, quickly in one portion, a solution consisting of copper iodide (360 mg, 1.8 mmol) and n-butylamine (5.0 ml, 48 mmol in benzene (10 mL) followed by slow addition of propargyl alcohol (2.2 mL, 36 mmol) in benzene (30 ml) over 15 minutes. The reaction mixture was stirred for five days and was quenched with a saturated solution of ammonium chloride (200 mL). The organic material was extracted with diethyl ether (3×300 mL). The combined organic phase was washed with water (100 mL) and brine (2×50 mL) before drying over sodium sulfate and concentrating to a dark brown oil. The residue was purified by silica gel chromatography. Elution with ethyl acetate-heptane—(1:9 v:v) afforded the title intermediate (4.39 g, 93%); TLC $R_f$ 0.7 (solvent system 50:50 v/v heptanes:ethyl acetate); $^1$H-NMR (CDCl$_3$). δ 7.6 (d, 1H), 7.1 (d, 1H), 4.5 (s, 2H), 3.9 (s, 3H), 2.0 (br t, 1H).

Preparation of methyl 5-(3-hydroxypropyl)thiophene-2-carboxylate

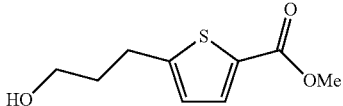 [SMILES: COC(=O)c1ccc(CCCO)s1]

To a solution consisting of methyl 5-(3-hydroxyprop-1-yn-1-yl)thiophene-2-carboxylate (700 mg, 3.57 mmol) in methanol (10 ml) was added palladium on calcium carbonate, 5% (2.0 g). The reaction atmosphere was replaced with hydrogen and the reaction mixture was stirred vigorously for two hours. The mixture was then filtered through Celite and the solvent removed. The residue was purified by silica gel chromatography. Elution with methanol-dichloromethane (1:100 v:v) afforded the title intermediate (650 mg, 91%); TLC $R_f$ 0.60 (solvent system 93:7 v/v dichloromethane-methanol); $^1$H-NMR (CDCl$_3$) δ 7.2 (d, 1H), 6.8 (d, 1H), 3.9 (s, 3H), 3.7 (t, 2H), 2.9 (t, 2H), 2.0-1.9 (m, 2H), 1.8-1.7 (br m, 1H); MS (ESI$^+$) nm/z 201.1 (M+1), 223.0 (M+Na).

Preparation of methyl 5-(3-bromopropyl)thiophene-2-carboxylate (10f)

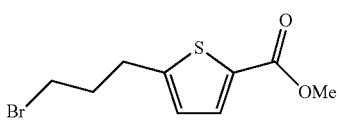 [SMILES: COC(=O)c1ccc(CCCBr)s1]

To a solution consisting of methyl 5-(3-hydroxypropyl) thiophene-2-carboxylate (633 mg, 3.17 mmol) in dichloromethane (25 mL) at 0° C. was added carbon tetrabromide (1.56 g, 4.43 mmol) and triphenylphosphine (1.23 g, 4.43 mmol). The reaction mixture was stirred for two hours. The solvent was removed and the residue was purified by silica gel chromatography. Elution with ethyl acetate-heptane (1:20 v:v) afforded the title intermediate (2.56 g); TLC $R_f$ 0.60 (solvent system 75:25 v/v heptane-ethyl acetate); MS (ESI$^+$) m/z 263.0 (M+1); $^1$H-NMR (CDCl$_3$) δ 7.6 (d, 1H), 6.8 (d, 1H), 3.9 (s, 3H), 3.85 (t, 2H), 2.95 (t, 2H), 2.0-1.9 (m, 2H).

Alternative preparation of methyl 5-(3-bromopropyl)thiophene-2-carboxylate (10f)

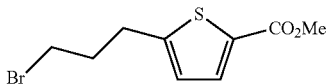 [SMILES: COC(=O)c1ccc(CCCBr)s1]

Preparation of 5-(3-bromopropyl)thiophene-2-carboxylic acid

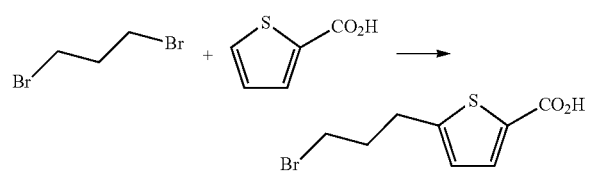

To a solution consisting of thienoic acid (10 g, 78 mmol) in THF (150 mL) at −78° C. was added an LDA solution (85 mL, 170 mmol, 2 M in heptanes/THF/ethylbenzene, Sigma-Aldrich) dropwise over 20 minutes, and the reaction mixture was stirred 40 minutes. To the reaction mixture was then added dibromopropane (23.8 g, 117 mmol) in one portion, and the reaction mixture was allowed to warm to room temperature and was stirred for 3 days. To the reaction mixture was added 50 mL each of a saturated aqueous solution of ammonium chloride, a saturated aqueous solution of sodium chloride, and 6 N HCl. The organic material was extracted with ethyl acetate and the organic layer was dried over sodium sulfate, filtered, and concentrated to afford the title compound as a yellow oil (24.0 g). The product was used without further purification; TLC $R_f$ 0.5 (solvent system: 30:70:1 v/v ethyl acetate-hexanes-acetic acid).

Preparation of methyl 5-(3-bromopropyl)thiophene-2-carboxylate (10f)

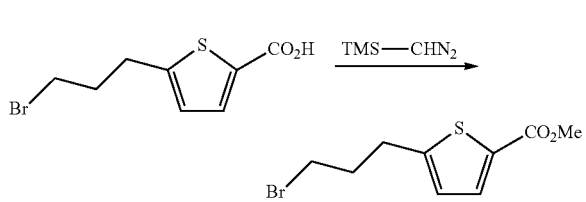

To a solution consisting of 5-(3-bromopropyl) thiophene-2-carboxylic acid (from procedure above, 24 g, 78 mmol) in ethyl acetate (150 mL) and methanol (15 mL) at 0° C. was added TMS-diazomethane (50 mL, 100 mmol, 2 M) dropwise over one hour. The reaction mixture was then allowed to warm to room temperature and was stirred for 16 hours, The reaction mixture was concentrated under reduced pressure without workup. The residue was purified by silica gel chromatography. Elution with ethyl acetate-heptane (1:80 v/v) afforded the title compound as a white solid (4.95 g; 24% over two steps); TLC $R_f$ 0.45 (solvent system: 15:85 v/v ethyl acetate-hexanes); MS (ESI$^+$) m/z 263, 265 (isotopic bromines, each (M+H)$^+$); $^1$HNMR (CDCl$_3$) δ 7.5 (d, 1H), 6.7 (d, 1H), 3.75 (s, 3H), 3.3 (t, 2H), 2.9 (t, 2H), 2.1-2.0 (m, 2H).

Scheme 3, Step I: Preparation of (R)-methyl 5-(3-(5-(((tert-butyldimethyl silyl)oxy)methyl)-3,3-difluoro-2-oxopyrrolidin-1-yl)propyl)thiophene-2-carboxylate (11f; PG=TBS)

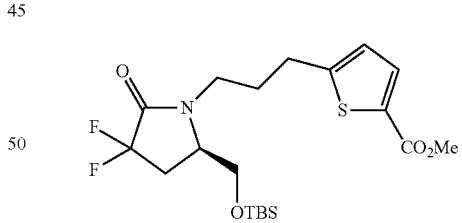

To a suspension consisting of sodium hydride (60% in mineral oil, 458 mg, 11.5 mmol) and sodium iodide (1.79 g, 12.0 mmol) in DMF (60 mL) was added dropwise a solution consisting of (R)-5-(((tert-butyldimethylsilyl)oxy)methyl)-3,3-difluoropyrrolidin-2-one (5; PG=TBS, 2.9 g, 10.9 mmol) in DMF (10 mL). The mixture was stirred at room temperature for 90 minutes, after which time was added dropwise a mixture consisting of methyl 5-(3-bromopropyl) thiophene-2-carboxylate (10f, 3.16 g, 12.0 mmol, preparation described above) in DMF, and stirring was continued at 50° C. for 16 hours. The mixture was treated with an aqueous solution of ammonium chloride and extracted with 2:1 ethyl acetate-heptane. The combined organics were washed with a 50% saturated aqueous solution of sodium chloride, followed by a saturated aqueous solution of sodium chloride, and was dried over sodium sulfate. The residue was purified by silica gel chromatography. Elution with ethyl acetate-heptane (1:5 v/v) afforded the title intermediate (4.6 g; 93%); TLC $R_f$ 0.30 (solvent system: 75:25 v/v heptanes:ethyl acetate); $^1$H-NMR (CDCl$_3$) δ 7.6 (d, 1H), 6.8 (d, 1H), 3.8 (s, 3H), 3.7-3.6 (m, 1H), 3.6-3.5 (m, 1H), 3.3-3.1 (m, 1H), 2.8 (t, 2H), 2.6-2.4 (m, 1H), 2.4-2.2 (m, 1H), 2.0 (s, 3H), 1.2 (t, 1H), 0.8 (s, 9H), 0.0 (s, 6H); MS (ESI$^+$) m/z 465.1 (M+NH$_4$)$^+$.

Scheme 3, Step J: Preparation of (R)-methyl 5-(3-(3,3-difluoro-5-(hydroxymethyl)-2-oxopyrrolidin-1-yl)propyl)thiophene-2-carboxylate (12f)

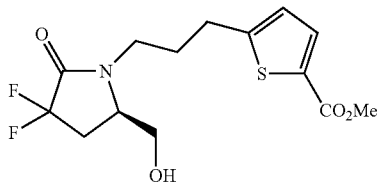 [SMILES: COC(=O)c1ccc(CCCN2C(=O)C(F)(F)C[C@@H]2CO)s1]

To a solution consisting of (R)-methyl 5-(3-(5-(((tert-butyldimethylsilyl)oxy)methyl)-3,3-difluoro-2-oxopyrrolidin-1-yl)propyl)thiophene-2-carboxylate (11f; PG=TBS, 5.15 g, 11.5 mmol) in THF (20 mL) was added TBAF (1 M in THF, 14.96 mL, 14.96 mmol) over two hours and the mixture was stirred at room temperature for 16 hours. The mixture was treated with an aqueous solution of ammonium chloride and extracted with ethyl acetate. The combined organic phase was washed with a 50% saturated aqueous solution of sodium chloride, followed by a saturated aqueous solution of sodium chloride and was dried over sodium sulfate, filtered, and concentrated. The residue was purified by silica gel chromatography. Elution with methanol-dichloromethane (1:80 v/v) afforded the title intermediate as a pale yellow oil (3.4 g; 88%); TLC $R_f$ 0.5 (solvent system: 5:95 v/v methanol-dichloromethane); $^1$H-NMR (CDCl$_3$) δ 7.6 (d, 1H), 6.8 (d, 1H), 3.85 (s, 3H), 3.8-3.6 (m, 4H), 3.3-3.1 (m, 1H), 2.85 (t, 2H), 2.6-2.4 (m, 2H), 2.1-1.9 (m, 2H); MS (ESI$^+$) m/z 351.0 (M+NH$_4$)$^+$.

Scheme 3, Step J: Alternative Preparation of (R)-methyl 5-(3-(3,3-difluoro-5-(hydroxymethyl)-2-oxopyrrolidin-1-yl)propyl)thiophene-2-carboxylate (12f)

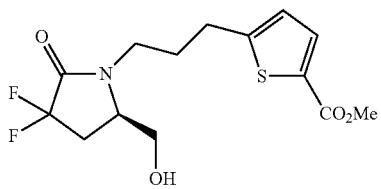 [SMILES: COC(=O)c1ccc(CCCN2C(=O)C(F)(F)C[C@@H]2CO)s1]

To a solution consisting of (R)-methyl 5-(3-(5-(((tert-butyldimethylsilyl)oxy)methyl-3,3-difluoro-2-oxopyrrolidin-1-yl)propyl)thiophene-2-carboxylate (11f; PG=TBS, 305 mg, 0.682 mmol) in methanol (10 mL) was added 1 M HCl (1 mL) and the reaction mixture was stirred overnight. The mixture was concentrated under reduced pressure to provide a residue, which was purified by silca gel chromatography. Elution with 5:95 (v/v) methanol-dichloromethane afforded the title intermediate (178 mg, 78.4%) as an oil; TLC $R_f$ 0.4, solvent system: 5:95 (v/v) methanol-dichloromethane.

Scheme 3, Step K: Preparation of (R)-methyl 5-(3-(3,3-difluoro-5-formyl-2-oxopyrrolidin-1-yl)propyl) thiophene-2-carboxylate (13f

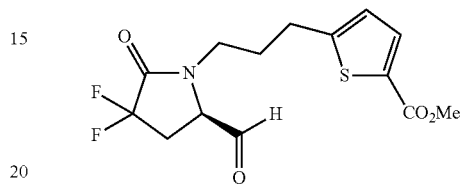

(R)-Methyl 5-(3-(3,3-difluoro-5-formyl-2-oxopyrrolidin-1-yl)propyl)thiophene-2-carboxylate was prepared from 12f using the oxidation procedure (Step K) described for the preparation of intermediate 13a from intermediate 12a to afford the title intermediate (80 mg) as a pale yellow oil; TLC $R_f$ 0.60 (solvent system: 7:93 v/v methanol-dichloromethane).

Organic β-keto phosphonate esters such as

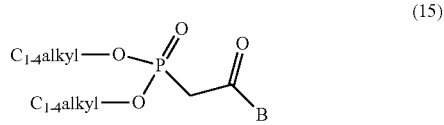

(15)

may be used as reaction coupling partners with aldehydes such as 13a-f in a Horner-Emmons-Wadsworth-type process to install the lactam lower-chain scaffold. Such (β-keto phosphonate esters may be prepared by coupling an appropriate carboxylic ester

(14)

with lithiated/deprotonated dialkyl methylphosphonate according to the general reaction illustrated in Scheme 6 and variations thereof. Tables A—P/Q of Lower Chains (below) describe various lower-chain components B of the exemplary embodiments.

Carboxylic esters 14 may be commercially available or prepared from commercially-available starting materials as shown in Schemes 7a-g. The numbering system, comprising various numerical, lower-case alphabetical, and lower-case Roman numeral descriptors, for intermediates comprising component B, such as carboxylic esters 14, β-keto phosphonate esters 15, NHS esters 18, amides 19, carboxylic acids 20, and (S)-3-(B-carbonyl)-4-benzyloxazolidin-2-ones 21 found in Schemes, Tables, and Examples herein shall be interpreted in the following manner. Intermediates comprising component B, such as in the formulae shown below,

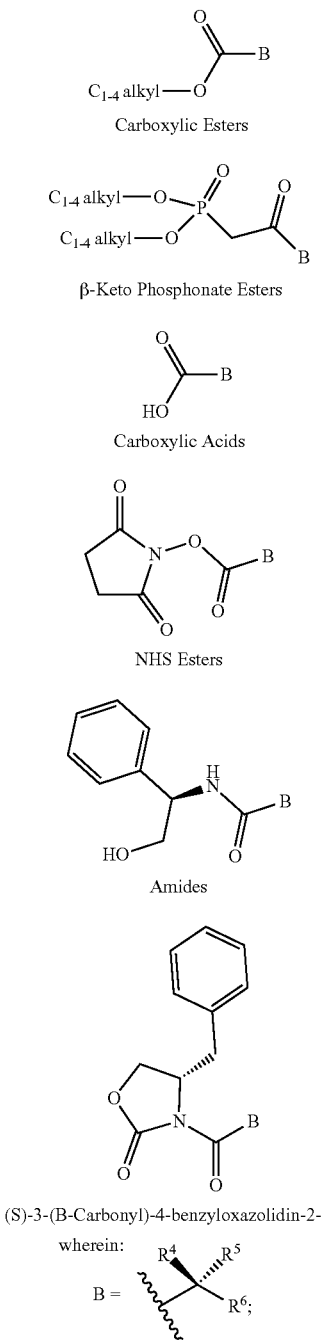

shall be expressed as a formula having three or four moieties which define the functionality of the intermediate and the $R^4$, $R^5$ and $R^6$ substituents of B comprising the intermediate. The first moiety is expressed as an Arabic numeral which represents the type of intermediate with its compound structure in accordance with the descriptions herein (e.g., 14 is a carboxylic ester; 15 is a β-keto phosphonate ester; 18 is an NHS ester; 19 is an amide; 20 is a carboxylic acid, etc.). The second moiety is expressed as a lower case letter that represents the structure of the $R^6$ group in accordance with the descriptions herein. A particular genus of intermediates having a range of $R^6$ substituents is shown by replacing the first moiety by a letter range enclosed within parentheses (e.g., (a-o)). The third moiety is expressed as a lower case letter that represents the nature of the $R^4$ and $R^5$ substitutions as follows: a (wherein both $R^4$ and $R^5$ are hydrogen); b (wherein $R^4$ is $C_1$-$C_4$ alkyl, $R^5$ is hydrogen); c (wherein $R^4$ is hydrogen, $R^5$ is $C_1$-$C_4$ alkyl; d (wherein both $R^4$ and $R^5$ are $C_1$-$C_4$ alkyl; and e (wherein $R^4$ and $R^5$ with the carbon to which they are bound form a $C_3$-$C_5$ cycloalkyl. In addition, a third moiety designation of "b/c" represents a mixture of the b and c stereoisomers. The fourth moiety is expressed as a lower-case Roman numeral in parentheses that represents the size and structure of the $R^4$ and/or $R^5$ $C_1$-$C_4$ alkyl group or groups, if present, or the size of the $C_3$-$C_5$ cycloalkyl ring, if present, in accordance with the descriptions herein. In the case where both $R^4$ and $R^5$ are hydrogen (e.g. 14aa), no lower-case Roman numeral in parentheses is present. This descriptor only takes into account embodiments for which only one of $R^4$ and $R^5$ is $C_1$-$C_4$ alkyl, both $R^4$ and $R^5$ are identical $C_1$-$C_4$ alkyl, or $R^4$ and $R^5$ with the carbon to which they are bound form a $C_3$-$C_5$ cycloalkyl, and does not take into account embodiments for which both $R^4$ and $R^5$ are $C_1$-$C_4$ alkyl that are different one from another. However, $R^4$ and $R^5$ may both be $C_1$-$C_4$ alkyl groups that are not the same. Although no examples of these embodiments are represented in these tables, their absence infers no limitation in scope. Table A lists some intermediates with defined B substituents ($R^4$, $R^5$ and $R^6$) as well as indicating the partial formulae notations for each listed combination of $R^4$, $R^5$ and $R^6$. By way of example, a carboxylic ester of formula 14 with $R^4$ as H, $R^5$ as Me and $R^6$ as

is expressed as 14ac(i) when the hereinabove defined notations are used. Similarly, a genus of carboxylic esters wherein $R^4$ and $R^5$ are each H and $R^6$ is varied can be envisaged when expressed by the formula 14(a-o)a in view of Tables A through O as provided herein.

A carboxylic ester, 14(a-o)a or 14(a-o)b/c(i-viii), may be prepared in two steps from commercially available diethyl malonate or an appropriate commercially available diethyl 2-($C_1$-$C_4$ alkyl) malonate starting material. Reaction of the malonate starting material with an appropriate lithium amide base, such as LDA or LiHMDS, or an appropriate hydride base, such as sodium hydride, or alkoxide base, such as sodium ethoxide, followed with an appropriate alkylating agent $R^6$—$X^1$, as illustrated in Scheme 7a, Step A, affords the corresponding 2-$R^6$-substituted diethyl malonate 16. Subsequent decarboxylation (Step B) provides the corresponding carboxylic ester intermediate 14, wherein both $R^4$ and $R^5$ are hydrogen, or wherein one of $R^4$ and $R^5$ is a $C_1$-$C_4$ alkyl group (alkyl groups (i) through (viii) represent methyl, ethyl, n-propyl, 2-propyl, n-butyl, iso-butyl, sec-butyl, and tert-butyl, respectively) and the other is a hydrogen. Examples of commercially available diethyl ($C_1$-$C_4$alkyl) malonates include diethyl methyl malonate, diethyl ethyl malonate, diethyl isopropyl malonate, diethyl n-propyl malonate, diethyl n-butyl malonate (all from Sigma-Aldrich, Acros Organics, or Alfa Aesar), diethyl isobutyl malonate, and diethyl sec-butyl malonate (both from Alfa Aesar). Methods for preparing the starting diethyl ($C_1$-$C_4$ alkyl) malonates are known in the art; for example, diethyl malonate may be combined with a base such as potassium carbonate and an appropriate alkylating agent such as methyl iodide, ethyl iodide, n-propyl bromide, or n-butyl bromide under microwave irradiation in the method described by Keglevich et al. in *Letters in Organic Chemistry*, 2008, 5(3), 224-228 and in Green Chemistry, 2006, 8(12), 1073-1075. Other methods that may be used to prepare the diethyl ($C_1$-$C_4$ alkyl) malonates include the reaction of diethyl malonate with an appropriate alkylating agent such as ethyl iodide, isopropyl bromide, isobutyl bromide, or sec-butyl bromide in the presence of a base such as sodium ethoxide in an organic solvent such as ethanol as described in Patel and Ryono in *Bioorganic and Medicinal Chemistry Letters*, 1992, 2(9), 1089-1092 and elsewhere.

Carboxylic ester intermediates 14 possessing a gem-dimethyl substitution at the carbon atom α to the ester carbonyl group (both $R^4$ and $R^5$ are methyl), such as 14(a-o)d(i), may be prepared by the methylation of the corresponding mono-α-methyl ester intermediate (stereochemical mixture) 14(a-o)b/c(i) as shown in Scheme 7b and reported in Shibasaki, M. et al, in *Chemical and Pharmaceutical Bulletin*, 1989, 37(6), 1647-1649.

Scheme 7c illustrates mono-alkylations of commercially available or prepared carboxylic esters 14(a-o)a with an alkylating agent $R^4/R^5$—$X^1$, wherein the $R^4/R^5$ group is a $C_1$-$C_4$ alkyl group and $X^1$ is a leaving group such as iodide or bromide to provide the corresponding mono-alkylated analogs 14(a-o)b/c, respectively. The mono-alkylated carboxylic ester analogs may be alkylated a second time; for example, mono-methylated carboxylic acid esters (stereochemical mixture) 14(a-o)b/c(i) may be methylated a second time to provide the corresponding gem-dimethyl substituted esters 14(a-o)d(i), as illustrated in Scheme 7d.

Scheme 7e illustrates the preparation of 1-$R^6$-substituted $C_3$-$C_5$ cycloalkylcarboxylic acids and their $C_1$-$C_4$ alkyl esters 14(a-o)e(ix-xi). Similar transformations are described in Yang, D. et. al. in *Journal of Organic Chemistry*, 2009, 74(22), 8726-8732; Cowling, S. J. and Goodby, J. W. in *Chemical Communications* (Cambridge, United Kingdom), 2006, 39, 4107-4709; Araldi, G. L. et. al. in WO 2003/103604; and others.

Stereopure carboxylic esters 14(a-o)b(i-viii) and their stereoisomers, 14(a-o)c(i-viii) may be prepared according to the route illustrated in Scheme 7f. Alkylation of an appropriately-substituted carboxylic acid starting material, such as propionic acid ($R^4/R^5$ is a methyl group), at the carbon position alpha to the acid carbonyl group by treatment of the acid with an appropriate base, such as lithium diisopropylamide (about two molar equivalents) in the presence of a suitable solvent, such as THF, with an alkylating agent $R^6$—$X^1$ (Step A) provides the corresponding carboxylic acid intermediates 20(a-o)b/c(i-viii). Subsequent coupling of the carboxylic acid intermediate with N-hydroxysuccinimide (NHS) forms the corresponding NHS ester (an activated ester) stereoisomeric mixture 18(a-o)b/c(i-viii) (Step B). Treatment of the activated ester stereoisomeric mixture 18(a-o)b/c(i-viii) with (R)-2-amino-2-phenylethanol in THF results in the mixture of two amide diastereomers 19(a-o)b(i-viii) and 19(a-o)c(i-viii) (Step C), which may be separated by chromatography to provide each pure diastereomer (Step D). Recrystallization of the individual diastereomers may provide amides with even greater de purity. Amide hydrolysis of each diastereomer to its corresponding carboxylic acid 20(a-o)b(i-viii) and 20(a-o)c(i-viii), respectively (Step E), and subsequent esterification (Step F) provides corresponding individual carboxylic ester stereoisomers 14(a-o)b(i-viii) and 14(a-o)c(i-viii), respectively.

Scheme 7g shows a synthetic pathway to stereopure carboxylic esters 14(a-o)b(i-vii) ($R^5$ is hydrogen) employing the use of the chiral auxiliary to generate "(S)-3-(B-carbonyl)-4-benzyloxazolidin-2-ones" 21(a-o)a (both $R^4$ and $R^5$ are hydrogen) for more-efficient (asymmetric) alkylation in Step C to provide the corresponding alkylated. "(S)-3-(B-carbonyl)-4-benzyloxazolidin-2-ones" analogs enriched in the 21(a-o)b(i-vii) stereoisomer over the 21(a-o)c(i-vii) stereoisomer. Removal of the chiral auxiliary (Step D) following alkylation and subsequent chiral amide derivatization (Steps E and F) provides the diastereomers 19(a-o)b(i-vii) separable by chromatography and further purified by crystallization (Step G). Acid-catalyzed amide hydrolysis (Step H) to the corresponding stereopure carboxylic acid 20(a-o)b(i-vii) and subsequent esterification (Step I) provide the desired stereopure carboxylic ester intermediates 14(a-o)b(i-vii), which can be carried onto their corresponding stereopure (β-keto phosphonate esters 15(a-o)b(i-vii).

Scheme 8 illustrates the conversions of acetylenic carboxylic esters 14(a-f)a and 14(a-f)(b-e)(i-xi) to the corresponding β-keto phosphonates by the previously-described general manner (Step A) and subsequent catalytic hydrogenation (Step B) to provide the corresponding saturated analogs.

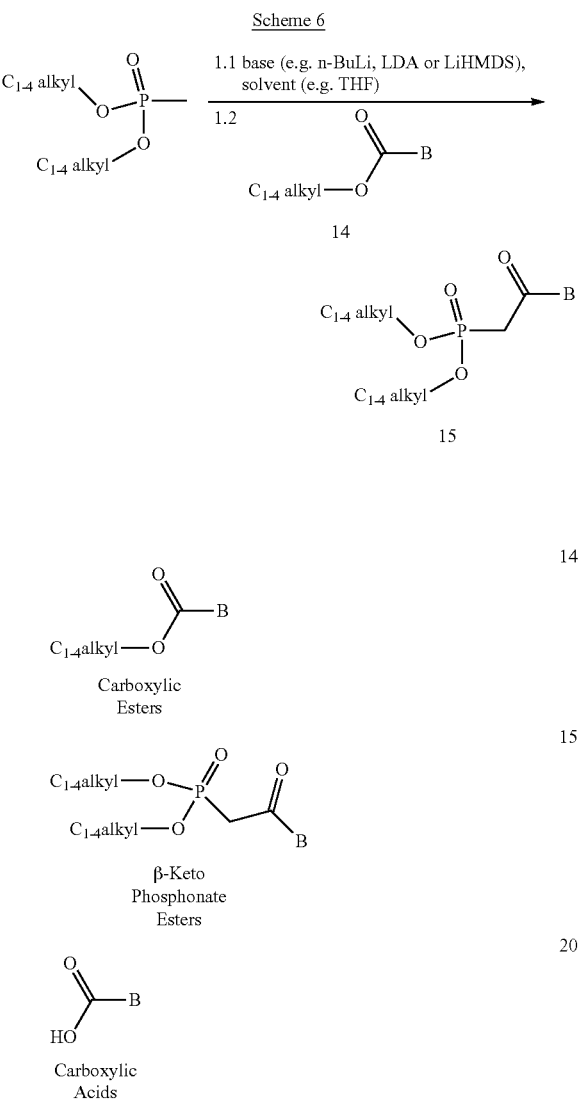

Scheme 6

14

15

14

Carboxylic Esters

15

β-Keto Phosphonate Esters

20

Carboxylic Acids

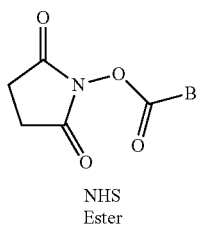

NHS
Ester

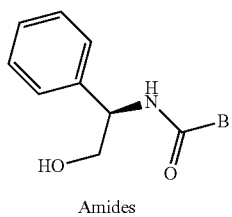

Amides

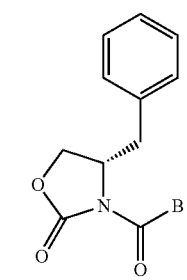

(S)-3-(B-Carbonyl)-
4-benzyloxazolidin-2-ones

TABLE A

| | of Lower Chains | | |
|---|---|---|---|
| B | R⁴ | R⁵ | R⁶ |
| aa | H | H | ⌇—≡—Me (pent-alkyne group shown) |
| ab(i) | Me | H | |
| ac(i) | H | Me | |
| ad(i) | Me | Me | |
| ab(ii) | Et | H | |
| ac(ii) | H | Et | |
| ad(ii) | Et | Et | |
| ab(iii) | n-Pr | H | |
| ac(iii) | H | n-Pr | |
| ad(iii) | n-Pr | n-Pr | |
| ab(iv) | i-Pr | H | |
| ac(iv) | H | i-Pr | |
| ad(iv) | i-Pr | i-Pr | |
| ab(v) | n-Bu | H | |
| ac(v) | H | n-Bu | |
| ad(v) | n-Bu | n-Bu | |
| ab(vi) | i-Bu | H | |
| ac(vi) | H | i-Bu | |
| ad(vi) | i-Bu | i-Bu | |
| ab(vii) | sec-Bu | H | |
| ac(vii) | H | sec-Bu | |
| ad(vii) | sec-Bu | sec-Bu | |
| ab(viii) | tert-Bu | H | |
| ac(viii) | H | tert-Bu | |
| ad(viii) | tert-Bu | tert-Bu | |
| ae(ix) | —CH₂—CH₂— (bridging) | | |

TABLE A-continued

| | of Lower Chains | | |
|---|---|---|---|
| B | R⁴ | R⁵ | R⁶ |
| ae(x) | —(CH₂)₂—CH₂— (bridging) | | |
| ae(xi) | —(CH₂)₃—CH₂— (bridging) | | |

B = (carbon bearing R⁴, R⁵, R⁶)

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu (R⁴/R⁵ cyclic) = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

C₁₋₄alkyl—O—C(=O)—B

Carboxylic
Esters (C₁₋₄alkyl—O)₂P(=O)—CH₂—C(=O)—B

β-Keto
Phosphonate
Esters

HO—C(=O)—B

Carboxylic
Acids (NHS ester structure)

NHS
Ester

-continued

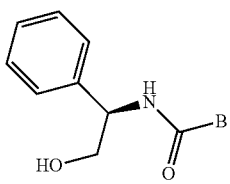

Amides

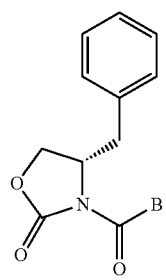

(S)-3-(B-Carbonyl)-
4-benzyloxazolidin-2-ones

TABLE B of Lower Chains

| B | R⁴ | R⁵ | R⁶ |
|---|---|---|---|
| ba | H | H | |
| bb(i) | Me | H | |
| bc(i) | H | Me | |
| bd(i) | Me | Me | |
| bb(ii) | Et | H | |
| bc(ii) | H | Et | |
| bd(ii) | Et | Et | |
| bb(iii) | n-Pr | H | |
| bc(iii) | H | n-Pr | |
| bd(iii) | n-Pr | n-Pr | |
| bb(iv) | i-Pr | H | |
| bc(iv) | H | i-Pr | |
| bd(iv) | i-Pr | i-Pr | |
| bb(v) | n-Bu | H | |
| bc(v) | H | n-Bu | |
| bd(v) | n-Bu | n-Bu | |
| bb(vi) | i-Bu | H | |
| bc(vi) | H | i-Bu | |
| bd(vi) | i-Bu | i-Bu | |
| bb(vii) | sec-Bu | H | |
| bc(vii) | H | sec-Bu | |
| bd(vii) | sec-Bu | sec-Bu | |
| bb(viii) | tert-Bu | H | |
| bc(viii) | H | tert-Bu | |
| bd(viii) | tert-Bu | tert-Bu | |
| be(ix) | —CH₂—CH₂— | | |
| be(x) | —(CH₂)₂—CH₂— | | |
| be(xi) | —(CH₂)₃—CH₂— | | |

TABLE B-continued of Lower Chains

| B | R⁴ | R⁵ | R⁶ |
|---|---|---|---|

$B = $ 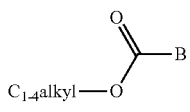

$R^4$ and/or $R^5 = C_1$-$C_4$ alkyl*

(i) Me
  (ii) Et
  (iii) n-Pr
  (iv) i-Pr
  (v) n-Bu
  (vi) i-Bu
  (vii) sec-Bu
  (viii) tert-Bu

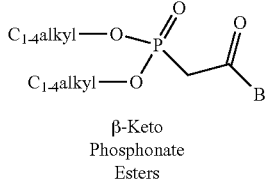 $= C_3$-$C_5$ cycloalkyl (ix) cyclopropyl
  (x) cyclobutyl
  (xi) cyclopentyl

*$R^4$ and $R^5$ may both be $C_1$-$C_4$ alkyl groups that are not the same. Although no examples of these embodiments are represented in these tables, their absence infers no limitation in scope.

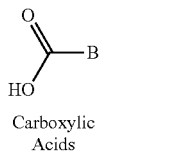

Carboxylic
Esters

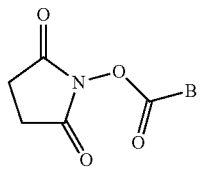

β-Keto
Phosphonate
Esters

HO—C(=O)—B

Carboxylic
Acids

NHS Ester structure

NHS
Ester

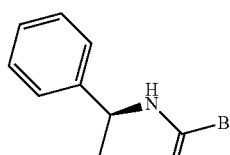

Amides

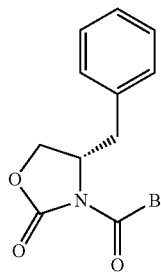

(S)-3-(B-Carbonyl)-
4-benzyloxazolidin-2-ones

TABLE C of Lower Chains

| B | $R^4$ | $R^5$ | $R^6$ |
|---|---|---|---|
| ca | H | H | |
| cb(i) | Me | H | |
| cc(i) | H | Me | |
| cd(i) | Me | Me | |
| cb(ii) | Et | H | |
| cc(ii) | H | Et | |
| cd(ii) | Et | Et | |
| cb(iii) | n-Pr | H | |
| cc(iii) | H | n-Pr | |
| cd(iii) | n-Pr | n-Pr | |
| cb(iv) | i-Pr | H | |
| cc(iv) | H | i-Pr | |
| cd(iv) | i-Pr | i-Pr | |
| cb(v) | n-Bu | H | |
| cc(v) | H | n-Bu | |
| cd(v) | n-Bu | n-Bu | |
| cb(vi) | i-Bu | H | |
| cc(vi) | H | i-Bu | |
| cd(vi) | i-Bu | i-Bu | |
| cb(vii) | sec-Bu | H | |
| cc(vii) | H | sec-Bu | |
| cd(vii) | sec-Bu | sec-Bu | |
| cb(viii) | tert-Bu | H | |
| cc(viii) | H | tert-Bu | |
| cd(viii) | tert-Bu | tert-Bu | |
| ce(ix) | —CH₂—CH₂— | | |
| ce(x) | —(CH₂)₂—CH₂— | | |
| ce(xi) | —(CH₂)₃—CH₂— | | |

TABLE C-continued of Lower Chains

| B | $R^4$ | $R^5$ | $R^6$ |
|---|---|---|---|

$B = $ with $R^4, R^5, R^6$ $R^4$ and/or $R^5 = C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu $= C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

14

$C_{1-4}$alkyl—O—C(O)—B

Carboxylic
Esters

15

$C_{1-4}$alkyl—O—P(O)(O—$C_{1-4}$alkyl)—CH₂—C(O)—B

β-Keto
Phosphonate
Esters

20

HO—C(O)—B

Carboxylic
Acids

18

NHS
Ester

19

Amides

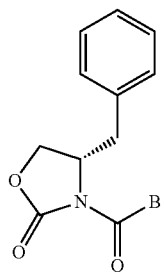

(S)-3-(B-Carbonyl)-
4-benzyloxazolidin-2-ones

TABLE D of Lower Chains

| B | $R^4$ | $R^5$ | $R^6$ |
|---|---|---|---|
| da | H | H | |
| db(i) | Me | H | |
| dc(i) | H | Me | |
| dd(i) | Me | Me | |
| db(ii) | Et | H | |
| dc(ii) | H | Et | |
| dd(ii) | Et | Et | |
| db(iii) | n-Pr | H | |
| dc(iii) | H | n-Pr | |
| dd(iii) | n-Pr | n-Pr | |
| db(iv) | i-Pr | H | |
| dc(iv) | H | i-Pr | |
| dd(iv) | i-Pr | i-Pr | |
| db(v) | n-Bu | H | |
| dc(v) | H | n-Bu | |
| dd(v) | n-Bu | n-Bu | |
| db(vi) | i-Bu | H | |
| dc(vi) | H | i-Bu | |
| dd(vi) | i-Bu | i-Bu | |
| db(vii) | sec-Bu | H | |
| dc(vii) | H | sec-Bu | |
| dd(vii) | sec-Bu | sec-Bu | |
| db(viii) | tert-Bu | H | |
| dc(viii) | H | tert-Bu | |
| dd(viii) | tert-Bu | tert-Bu | |
| de(ix) | —CH₂—CH₂— | | |
| de(x) | —(CH₂)₂—CH₂— | | |
| de(xi) | —(CH₂)₃—CH₂— | | |

TABLE D-continued of Lower Chains

B = structure with $R^4$, $R^5$, $R^6$ substituents $R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu $R^4$, $R^5$ = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

Carboxylic Esters

β-Keto Phosphonate Esters

Carboxylic Acids

NHS Ester

Amides

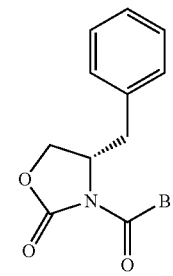

(S)-3-(B-Carbonyl)-
4-benzyloxazolidin-2-ones

TABLE E of Lower Chains

| B | R⁴ | R⁵ | R⁶ |
|---|----|----|----|
| ea | H | H | |
| eb(i) | Me | H | |
| ec(i) | H | Me | |
| ed(i) | Me | Me | |
| eb(ii) | Et | H | |
| ec(ii) | H | Et | |
| ed(ii) | Et | Et | |
| eb(iii) | n-Pr | H | |
| ec(iii) | H | n-Pr | |
| ed(iii) | n-Pr | n-Pr | |
| eb(iv) | i-Pr | H | |
| ec(iv) | H | i-Pr | |
| ed(iv) | i-Pr | i-Pr | |
| eb(v) | n-Bu | H | |
| ec(v) | H | n-Bu | |
| ed(v) | n-Bu | n-Bu | |
| eb(vi) | i-Bu | H | |
| ec(vi) | H | i-Bu | |
| ed(vi) | i-Bu | i-Bu | |
| eb(vii) | sec-Bu | H | |
| ec(vii) | H | sec-Bu | |
| ed(vii) | sec-Bu | sec-Bu | |
| eb(viii) | tert-Bu | H | |
| ec(viii) | H | tert-Bu | |
| ed(viii) | tert-Bu | tert-Bu | |
| ee(ix) | —CH₂—CH₂— | | |
| ee(x) | —(CH₂)₂—CH₂— | | |
| ee(xi) | —(CH₂)₃—CH₂— | | |

B = 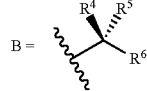

TABLE E-continued of Lower Chains

| B | R⁴ | R⁵ | R⁶ |
|---|----|----|----|

R⁴ and/or R⁵ = C₁-C₄ alkyl*

(i) Me
(ii) Et
(iii) n-Pr
(iv) i-Pr
(v) n-Bu
(vi) i-Bu
(vii) sec-Bu
(viii) tert-Bu = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

Carboxylic Esters

β-Keto Phosphonate Esters

Carboxylic Acids

NHS Ester

Amides

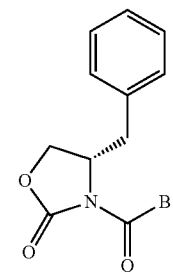

(S)-3-(B-Carbonyl)-
4-benzyloxazolidin-2-ones

TABLE F of Lower Chains

| B | R⁴ | R⁵ | R⁶ |
|---|----|----|----|
| fa | H | H | |
| fb(i) | Me | H | |
| fc(i) | H | Me | |
| fd(i) | Me | Me | |
| fb(ii) | Et | H | |
| fc(ii) | H | Et | |
| fd(ii) | Et | Et | |
| fb(iii) | n-Pr | H | |
| fc(iii) | H | n-Pr | |
| fd(iii) | n-Pr | n-Pr | |
| fb(iv) | i-Pr | H | |
| fc(iv) | H | i-Pr | |
| fd(iv) | i-Pr | i-Pr | |
| fb(v) | n-Bu | H | |
| fc(v) | H | n-Bu | |
| fd(v) | n-Bu | n-Bu | |
| fb(vi) | i-Bu | H | |
| fc(vi) | H | i-Bu | |
| fd(vi) | i-Bu | i-Bu | |
| fb(vii) | sec-Bu | H | |
| fc(vii) | H | sec-Bu | |
| fd(vii) | sec-Bu | sec-Bu | |
| fb(viii) | tert-Bu | H | |
| fc(viii) | H | tert-Bu | |
| fd(viii) | tert-Bu | tert-Bu | | fe(ix)  —CH₂—CH₂— fe(x)   —(CH₂)₂—CH₂— fe(xi)  —(CH₂)₃—CH₂—

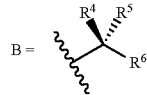

TABLE F-continued of Lower Chains

| B | R⁴ | R⁵ | R⁶ |
|---|----|----|----|

R⁴ and/or R⁵ = C₁-C₄ alkyl*

(i) Me
(ii) Et
(iii) n-Pr
(iv) i-Pr
(v) n-Bu
(vi) i-Bu
(vii) sec-Bu
(viii) tert-Bu = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

14

C₁₋₄alkyl—O—C(O)—B

Carboxylic
Esters

15

C₁₋₄alkyl—O—P(O)—CH₂—C(O)—B
C₁₋₄alkyl—O

β-Keto
Phosphonate
Esters

20

HO—C(O)—B

Carboxylic
Acids

18

NHS
Esters

19

Amides

-continued

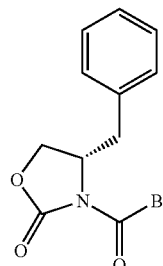

(S)-3-(B-Carbonyl)-
4-benzyloxazolidin-2-ones

TABLE G of Lower Chains

| B | R⁴ | R⁵ | R⁶ |
|---|---|---|---|
| ga | H | H | |
| gb(i) | Me | H | |
| gc(i) | H | Me | |
| gd(i) | Me | Me | |
| gb(ii) | Et | H | |
| gc(ii) | H | Et | |
| gd(ii) | Et | Et | |
| gb(iii) | n-Pr | H | |
| gc(iii) | H | n-Pr | |
| gd(iii) | n-Pr | n-Pr | |
| gb(iv) | i-Pr | H | |
| gc(iv) | H | i-Pr | |
| gd(iv) | i-Pr | i-Pr | |
| gb(v) | n-Bu | H | |
| gc(v) | H | n-Bu | |
| gd(v) | n-Bu | n-Bu | |
| gb(vi) | i-Bu | H | |
| gc(vi) | H | i-Bu | |
| gd(vi) | i-Bu | i-Bu | |
| gb(vii) | sec-Bu | H | |
| gc(vii) | H | sec-Bu | |
| gd(vii) | sec-Bu | sec-Bu | |
| gb(viii) | tert-Bu | H | |
| gc(viii) | H | tert-Bu | |
| gd(viii) | tert-Bu | tert-Bu | |
| ge(ix) | —CH₂—CH₂— | | |
| ge(x) | —(CH₂)₂—CH₂— | | |
| ge(xi) | —(CH₂)₃—CH₂— | | |

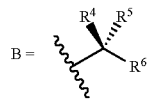

TABLE G-continued of Lower Chains

| B | R⁴ | R⁵ | R⁶ |
|---|---|---|---|

R⁴ and/or R⁵ = C₁-C₄ alkyl*

(i) Me
(ii) Et
(iii) n-Pr
(iv) i-Pr
(v) n-Bu
(vi) i-Bu
(vii) sec-Bu
(viii) tert-Bu = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

Carboxylic Esters

β-Keto Phosphonate Esters

Carboxylic Acids

NHS Esters

Amides

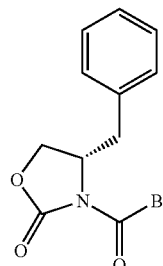

(S)-3-(B-Carbonyl)-
4-benzyloxazolidin-2-ones

TABLE H of Lower Chains

| B | R$^4$ | R$^5$ | R$^6$ |
|---|---|---|---|
| ha | H | H | |
| hb(i) | Me | H | |
| hc(i) | H | Me | |
| hd(i) | Me | Me | |
| hb(ii) | Et | H | |
| hc(ii) | H | Et | |
| hd(ii) | Et | Et | |
| hb(iii) | n-Pr | H | |
| hc(iii) | H | n-Pr | |
| hd(iii) | n-Pr | n-Pr | |
| hb(iv) | i-Pr | H | |
| hc(iv) | H | i-Pr | |
| hd(iv) | i-Pr | i-Pr | |
| hb(v) | n-Bu | H | |
| hc(v) | H | n-Bu | |
| hd(v) | n-Bu | n-Bu | |
| hb(vi) | i-Bu | H | |
| hc(vi) | H | i-Bu | |
| hd(vi) | i-Bu | i-Bu | |
| hb(vii) | sec-Bu | H | |
| hc(vii) | H | sec-Bu | |
| hd(vii) | sec-Bu | sec-Bu | |
| hb(viii) | tert-Bu | H | |
| hc(viii) | H | tert-Bu | |
| hd(viii) | tert-Bu | tert-Bu | |
| he(ix) | —CH$_2$—CH$_2$— | | |
| he(x) | —(CH$_2$)$_2$—CH$_2$— | | |
| he(xi) | —(CH$_2$)$_3$—CH$_2$— | | |

$B = $ [structure with R$^4$, R$^5$, R$^6$]

TABLE H-continued of Lower Chains

| B | R$^4$ | R$^5$ | R$^6$ |
|---|---|---|---|

R$^4$ and/or R$^5$ = C$_1$-C$_4$ alkyl*

(i) Me
(ii) Et
(iii) n-Pr
(iv) i-Pr
(v) n-Bu
(vi) i-Bu
(vii) sec-Bu
(viii) tert-Bu

[structure] = C$_3$-C$_5$ cycloalkyl (ix) cyclopropyl
(x) cyclobutyl
(xi) cyclopentyl

*R$^4$ and R$^5$ may both be C$_1$-C$_4$ alkyl groups that are not the same. Although no examples of these embodiments are represented in these tables, their absence infers no limitation in scope.

C$_{1-4}$alkyl—O—C(O)—B

Carboxylic
Esters

C$_{1-4}$alkyl—O—P(O)(—O—C$_{1-4}$alkyl)—CH$_2$—C(O)—B

β-Keto
Phosphonate
Esters

HO—C(O)—B

Carboxylic
Acids

[NHS ester structure]—O—C(O)—B

NHS
Esters

[phenyl-CH(HOCH$_2$-)-NH—C(O)—B structure]

Amides

103
-continued

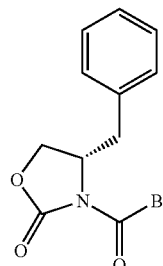

(S)-3-(B-Carbonyl)-
4-benzyloxazolidin-2-ones

TABLE I of Lower Chains

| B | $R^4$ | $R^5$ | $R^6$ |
|---|---|---|---|
| ia | H | H | |
| ib(i) | Me | H | |
| ic(i) | H | Me | |
| id(i) | Me | Me | |
| ib(ii) | Et | H | |
| ic(ii) | H | Et | |
| id(ii) | Et | Et | |
| ib(iii) | n-Pr | H | |
| ic(iii) | H | n-Pr | |
| id(iii) | n-Pr | n-Pr | |
| ib(iv) | i-Pr | H | |
| ic(iv) | H | i-Pr | |
| id(iv) | i-Pr | i-Pr | |
| ib(v) | n-Bu | H | |
| ic(v) | H | n-Bu | |
| id(v) | n-Bu | n-Bu | |
| ib(vi) | i-Bu | H | |
| ic(vi) | H | i-Bu | |
| id(vi) | i-Bu | i-Bu | |
| ib(vii) | sec-Bu | H | |
| ic(vii) | H | sec-Bu | |
| id(vii) | sec-Bu | sec-Bu | |
| ib(viii) | tert-Bu | H | |
| ic(viii) | H | tert-Bu | |
| id(viii) | tert-Bu | tert-Bu | |
| ie(ix) | —CH₂—CH₂— | | |
| ie(x) | —(CH₂)₂—CH₂— | | |
| ie(xi) | —(CH₂)₃—CH₂— | | |

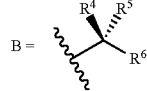

TABLE I-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

$C_{1-4}$alkyl—O—(C=O)—B

Carboxylic
Esters $C_{1-4}$alkyl—O—P(=O)(—O—$C_{1-4}$alkyl)—CH₂—(C=O)—B

β-Keto
Phosphonate
Esters

HO—(C=O)—B

Carboxylic
Acids

NHS
Esters

Amides

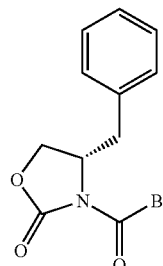

(S)-3-(B-Carbonyl)-
4-benzyloxazolidin-2-ones

TABLE J of Lower Chains

| B | R⁴ | R⁵ | R⁶ |
|---|---|---|---|
| ja | H | H | |
| jb(i) | Me | H | |
| jc(i) | H | Me | |
| jd(i) | Me | Me | |
| jb(ii) | Et | H | |
| jc(ii) | H | Et | |
| jd(ii) | Et | Et | |
| jb(iii) | n-Pr | H | |
| jc(iii) | H | n-Pr | |
| jd(iii) | n-Pr | n-Pr | |
| jb(iv) | i-Pr | H | |
| jc(iv) | H | i-Pr | |
| jd(iv) | i-Pr | i-Pr | |
| jb(v) | n-Bu | H | |
| jc(v) | H | n-Bu | |
| jd(v) | n-Bu | n-Bu | |
| jb(vi) | i-Bu | H | |
| jc(vi) | H | i-Bu | |
| jd(vi) | i-Bu | i-Bu | |
| jb(vii) | sec-Bu | H | |
| jc(vii) | H | sec-Bu | |
| jd(vii) | sec-Bu | sec-Bu | |
| jb(viii) | tert-Bu | H | |
| jc(viii) | H | tert-Bu | |
| jd(viii) | tert-Bu | tert-Bu | |
| je(ix) | —CH₂—CH₂— | | |
| je(x) | —(CH₂)₂—CH₂— | | |
| je(xi) | —(CH₂)₃—CH₂— | | |

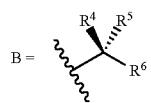

TABLE J-continued of Lower Chains

| B | R⁴ | R⁵ | R⁶ |
|---|---|---|---|

R⁴ and/or R⁵ = C₁-C₄ alkyl*

(i) Me
(ii) Et
(iii) n-Pr
(iv) i-Pr
(v) n-Bu
(vi) i-Bu
(vii) sec-Bu
(viii) tert-Bu $\underset{R^4\ R^5}{\diagup\!\!\!\diagdown}$ = C₃-C₅ cycloalkyl (ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

14

C₁₋₄alkyl—O—C(=O)—B

Carboxylic
Esters

15

C₁₋₄alkyl—O—P(=O)(O—C₁₋₄alkyl)—CH₂—C(=O)—B

β-Keto
Phosphonate
Esters

20

HO—C(=O)—B

Carboxylic
Acids

18

NHS ester structure with B

NHS
Esters

19

Amide structure with phenyl, HO-CH₂, NH, C(=O)-B

Amides

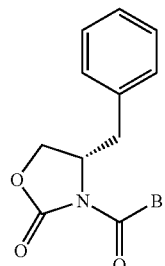

(S)-3-(B-Carbonyl)-
4-benzyloxazolidin-2-ones

TABLE K of Lower Chains

| B | $R^4$ | $R^5$ | $R^6$ |
|---|---|---|---|
| ka | H | H | |
| kb(i) | Me | H | |
| kc(i) | H | Me | |
| kd(i) | Me | Me | 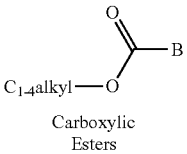 |
| kb(ii) | Et | H | |
| kc(ii) | H | Et | |
| kd(ii) | Et | Et | |
| kb(iii) | n-Pr | H | |
| kc(iii) | H | n-Pr | |
| kd(iii) | n-Pr | n-Pr | |
| kb(iv) | i-Pr | H | |
| kc(iv) | H | i-Pr | |
| kd(iv) | i-Pr | i-Pr | |
| kb(v) | n-Bu | H | |
| kc(v) | H | n-Bu | |
| kd(v) | n-Bu | n-Bu | |
| kb(vi) | i-Bu | H | |
| kc(vi) | H | i-Bu | |
| kd(vi) | i-Bu | i-Bu | |
| kb(vii) | sec-Bu | H | |
| kc(vii) | H | sec-Bu | |
| kd(vii) | sec-Bu | sec-Bu | |
| kb(viii) | tert-Bu | H | |
| kc(viii) | H | tert-Bu | |
| kd(viii) | tert-Bu | tert-Bu | |
| ke(ix) | —CH$_2$—CH$_2$— | | |
| ke(x) | —(CH$_2$)$_2$—CH$_2$— | | |
| ke(xi) | —(CH$_2$)$_3$—CH$_2$— | | |

B = 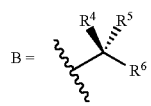

TABLE K-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu

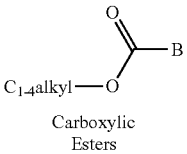 = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

14

$C_{1-4}$alkyl—O—(C(=O))—B

Carboxylic
Esters

15

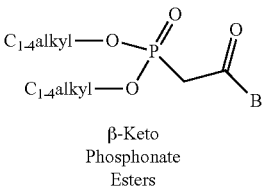

β-Keto
Phosphonate
Esters

18

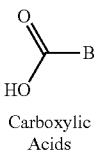

Carboxylic
Acids

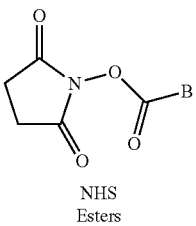

NHS
Esters

19

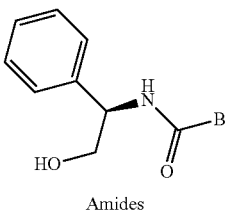

Amides

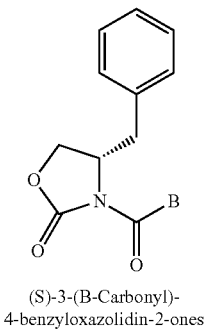

(S)-3-(B-Carbonyl)-
4-benzyloxazolidin-2-ones

TABLE L of Lower Chains

| B | $R^4$ | $R^5$ | $R^6$ |
|---|---|---|---|
| Ia | H | H | |
| Ib(i) | Me | H | |
| Ic(i) | H | Me | |
| Id(i) | Me | Me | |
| Ib(ii) | Et | H | |
| Ic(ii) | H | Et | |
| Id(ii) | Et | Et | |
| Ib(iii) | n-Pr | H | |
| Ic(iii) | H | n-Pr | |
| Id(iii) | n-Pr | n-Pr | |
| Ib(iv) | i-Pr | H | |
| Ic(iv) | H | i-Pr | |
| Id(iv) | i-Pr | i-Pr | |
| Ib(v) | n-Bu | H | |
| Ic(v) | H | n-Bu | |
| Id(v) | n-Bu | n-Bu | |
| Ib(vi) | i-Bu | H | |
| Ic(vi) | H | i-Bu | |
| Id(vi) | i-Bu | i-Bu | |
| Ib(vii) | sec-Bu | H | |
| Ic(vii) | H | sec-Bu | |
| Id(vii) | sec-Bu | sec-Bu | |
| Ib(viii) | tert-Bu | H | |
| Ic(viii) | H | tert-Bu | |
| Id(viii) | tert-Bu | tert-Bu | |
| Ie(ix) | —CH₂—CH₂— | | |
| Ie(x) | —(CH₂)₂—CH₂— | | |
| Ie(xi) | —(CH₂)₃—CH₂— | | |

B = (structure with $R^4$, $R^5$, $R^6$)

TABLE L-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu (structure) = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

(phenylpropyl structure)

14

(carboxylic ester structure: $C_{1-4}$alkyl—O—C(=O)—B)

Carboxylic
Esters

15

(β-keto phosphonate structure: $C_{1-4}$alkyl—O—P(=O)(—O—$C_{1-4}$alkyl)—CH₂—C(=O)—B)

β-Keto
Phosphonate
Esters

20

(HO—C(=O)—B)

Carboxylic
Acids

18

(NHS ester structure)

NHS
Esters

19

(amide structure with phenyl, HO-CH₂, NH-C(=O)-B)

Amides

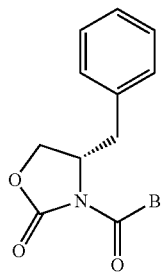

(S)-3-(B-Carbonyl)-
4-benzyloxazolidin-2-ones

TABLE M of Lower Chains

| B | $R^4$ | $R^5$ | $R^6$ |
|---|---|---|---|
| ma | H | H | |
| mb(i) | Me | H | |
| mc(i) | H | Me | |
| md(i) | Me | Me | |
| mb(ii) | Et | H | |
| mc(ii) | H | Et | |
| md(ii) | Et | Et | |
| mb(iii) | n-Pr | H | |
| mc(iii) | H | n-Pr | |
| md(iii) | n-Pr | n-Pr | |
| mb(iv) | i-Pr | H | |
| mc(iv) | H | i-Pr | |
| md(iv) | i-Pr | i-Pr | |
| mb(v) | n-Bu | H | |
| mc(v) | H | n-Bu | |
| md(v) | n-Bu | n-Bu | |
| mb(vi) | i-Bu | H | |
| mc(vi) | H | i-Bu | |
| md(vi) | i-Bu | i-Bu | |
| mb(vii) | sec-Bu | H | |
| mc(vii) | H | sec-Bu | |
| md(vii) | sec-Bu | sec-Bu | |
| mb(viii) | tert-Bu | H | |
| mc(viii) | H | tert-Bu | |
| md(viii) | tert-Bu | tert-Bu | |
| me(ix) | —CH₂—CH₂— | | |
| me(x) | —(CH₂)₂—CH₂— | | |
| me(xi) | —(CH₂)₃—CH₂— | | |

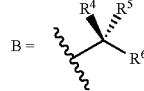

TABLE M-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

14

$C_{1-4}$alkyl—O—C(=O)—B

Carboxylic
Esters

15

$C_{1-4}$alkyl—O—P(=O)—CH₂—C(=O)—B
$C_{1-4}$alkyl—O

β-Keto
Phosphonate
Esters

20

HO—C(=O)—B

Carboxylic
Acids

18

NHS
Esters

19

Amides

-continued

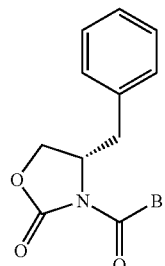

(S)-3-(B-Carbonyl)-
4-benzyloxazolidin-2-ones

TABLE N of Lower Chains

| B | $R^4$ | $R^5$ | $R^6$ |
|---|---|---|---|
| na | H | H | |
| nb(i) | Me | H | |
| nc(i) | H | Me | |
| nd(i) | Me | Me | |
| nb(ii) | Et | H | |
| nc(ii) | H | Et | |
| nd(ii) | Et | Et | |
| nb(iii) | n-Pr | H | |
| nc(iii) | H | n-Pr | |
| nd(iii) | n-Pr | n-Pr | |
| nb(iv) | i-Pr | H | |
| nc(iv) | H | i-Pr | |
| nd(iv) | i-Pr | i-Pr | |
| nb(v) | n-Bu | H | |
| nc(v) | H | n-Bu | |
| nd(v) | n-Bu | n-Bu | |
| nb(vi) | i-Bu | H | |
| nc(vi) | H | i-Bu | |
| nd(vi) | i-Bu | i-Bu | |
| nb(vii) | sec-Bu | H | |
| nc(vii) | H | sec-Bu | |
| nd(vii) | sec-Bu | sec-Bu | |
| nb(viii) | tert-Bu | H | |
| nc(viii) | H | tert-Bu | |
| nd(viii) | tert-Bu | tert-Bu | | ne(ix)  ⸺CH₂—CH₂⸺ ne(x)  ⸺(CH₂)₂—CH₂⸺ ne(xi)  ⸺(CH₂)₃—CH₂⸺

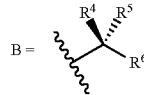

TABLE N-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu $R^4$, $R^5$ = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

$C_{1-4}$alkyl—O—C(=O)—B

Carboxylic
Esters $C_{1-4}$alkyl—O—P(=O)(—O—$C_{1-4}$alkyl)—CH₂—C(=O)—B

β-Keto
Phosphonate
Esters

HO—C(=O)—B

Carboxylic
Acids

NHS
Esters

Amides

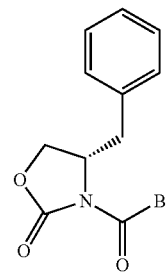

(S)-3-(B-Carbonyl)-
4-benzyloxazolidin-2-ones

TABLE O of Lower Chains

| B | $R^4$ | $R^5$ | $R^6$ |
|---|---|---|---|
| oa | H | H | |
| ob(i) | Me | H | |
| oc(i) | H | Me | |
| od(i) | Me | Me | |
| ob(ii) | Et | H | |
| oc(ii) | H | Et | |
| od(ii) | Et | Et | |
| ob(iii) | n-Pr | H | |
| oc(iii) | H | n-Pr | |
| od(iii) | n-Pr | n-Pr | |
| ob(iv) | i-Pr | H | |
| oc(iv) | H | i-Pr | |
| od(iv) | i-Pr | i-Pr | |
| ob(v) | n-Bu | H | |
| oc(v) | H | n-Bu | |
| od(v) | n-Bu | n-Bu | |
| ob(vi) | i-Bu | H | |
| oc(vi) | H | i-Bu | |
| od(vi) | i-Bu | i-Bu | |
| ob(vii) | sec-Bu | H | |
| oc(vii) | H | sec-Bu | |
| od(vii) | sec-Bu | sec-Bu | |
| ob(viii) | tert-Bu | H | |
| oc(viii) | H | tert-Bu | |
| od(viii) | tert-Bu | tert-Bu | |
| oe(ix) | —CH₂—CH₂— | | |
| oe(x) | —(CH₂)₂—CH₂— | | |
| oe(xi) | —(CH₂)₃—CH₂— | | |

B = 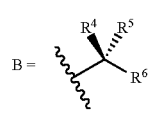

TABLE O-continued of Lower Chains

| B | $R^4$ | $R^5$ | $R^6$ |
|---|---|---|---|

$R^4$ and/or $R^5$ = $C_1$-$C_4$ alkyl*

(i) Me
(ii) Et
(iii) n-Pr
(iv) i-Pr
(v) n-Bu
(vi) i-Bu
(vii) sec-Bu
(viii) tert-Bu

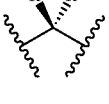 = $C_3$-$C_5$ cycloalkyl (ix) cyclopropyl
(x) cyclobutyl
(xi) cyclopentyl

*$R^4$ and $R^5$ may both be $C_1$-$C_4$ alkyl groups that are not the same. Although no examples of these embodiments are represented in these tables, their absence infers no limitation in scope.

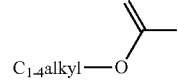

Carboxylic
Esters

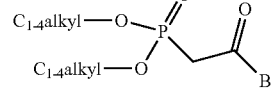

β-Keto
Phosphonate
Esters

Carboxylic
Acids

TABLE P/Q of Lower Chains

| B |
|---|
| p 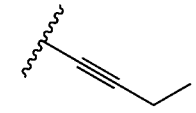 [SMILES: *C#CCC] |
| q 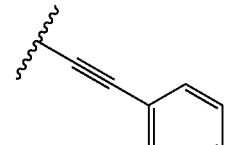 |

Scheme 7a
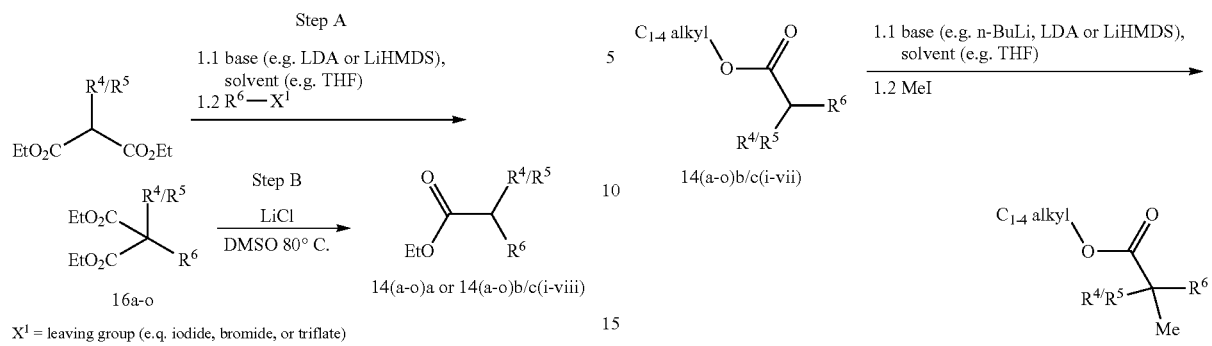
$X^1$ = leaving group (e.q. iodide, bromide, or triflate)
Scheme 7b
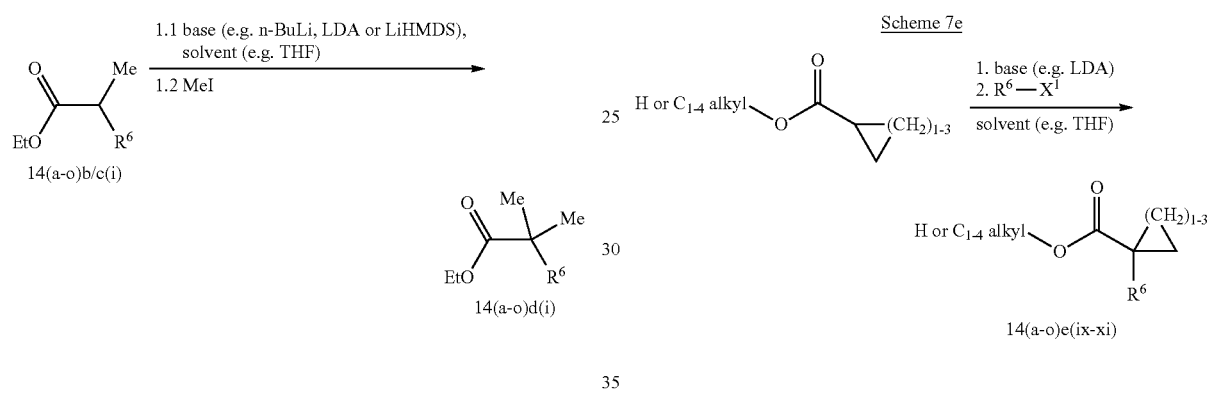
Scheme 7c
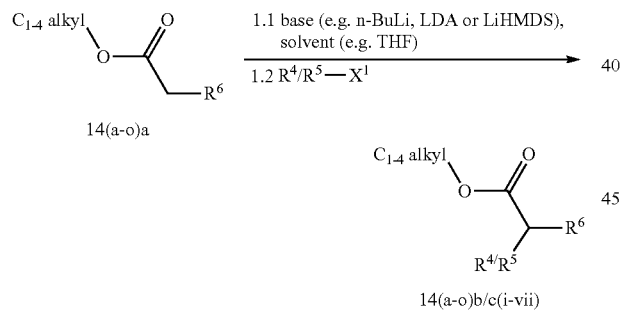
$X^1$ = leaving group
(e.g. bromide, iodide, or triflate)
Scheme 7d
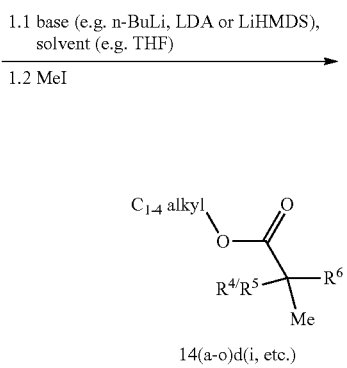
Scheme 7e Scheme 7f
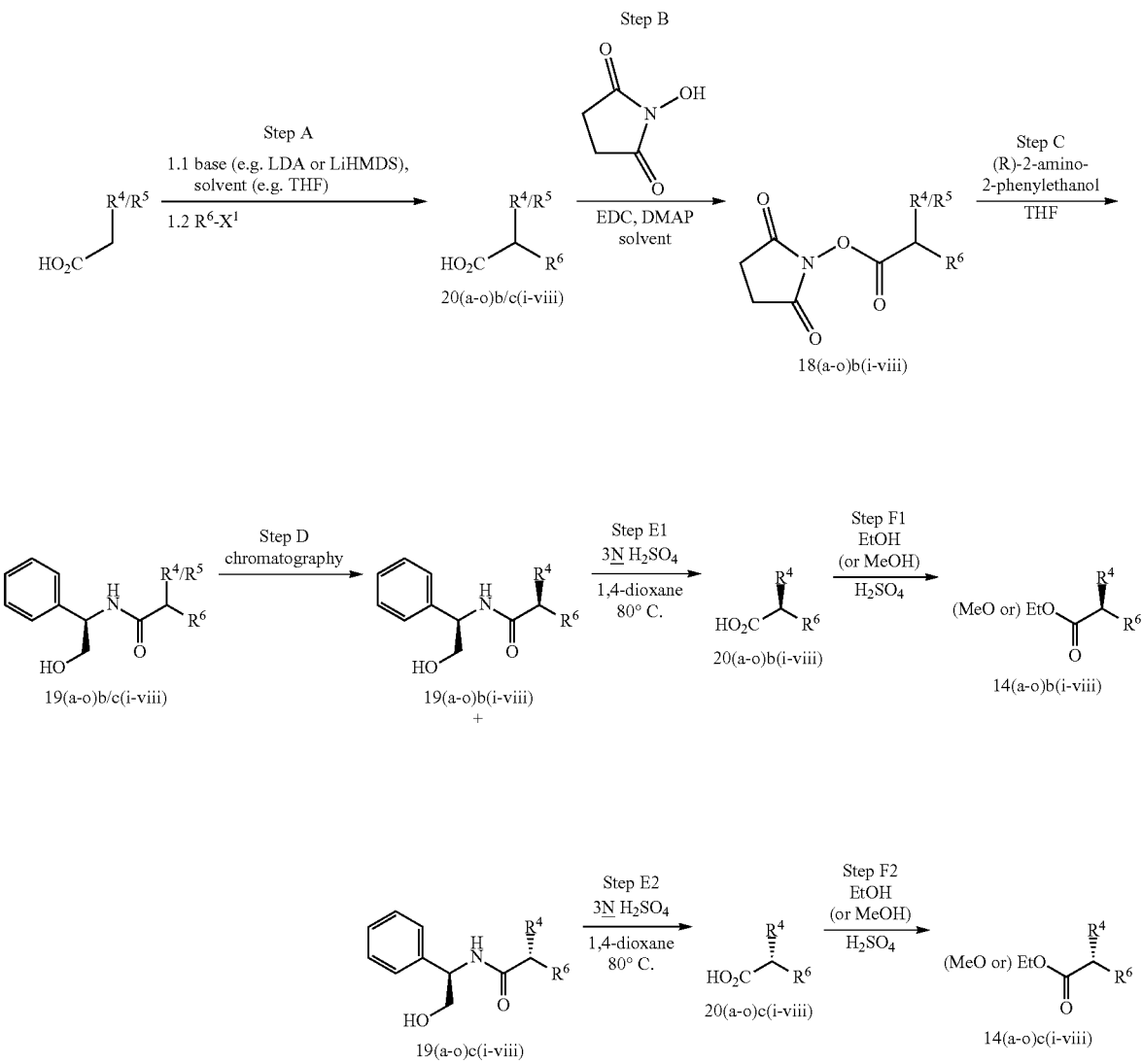
$X^1$ = leaving group (e.g. bromide, iodide, or triflate)
Scheme 7g
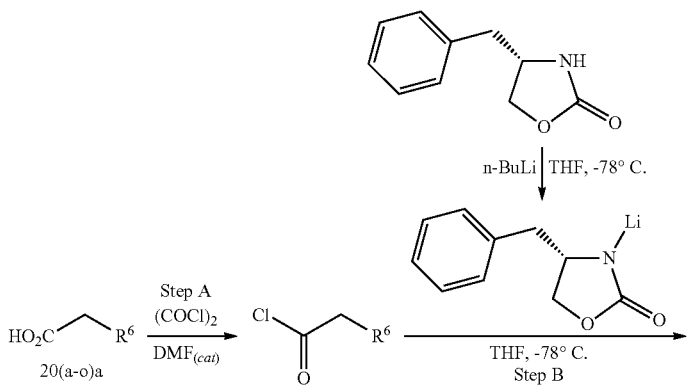

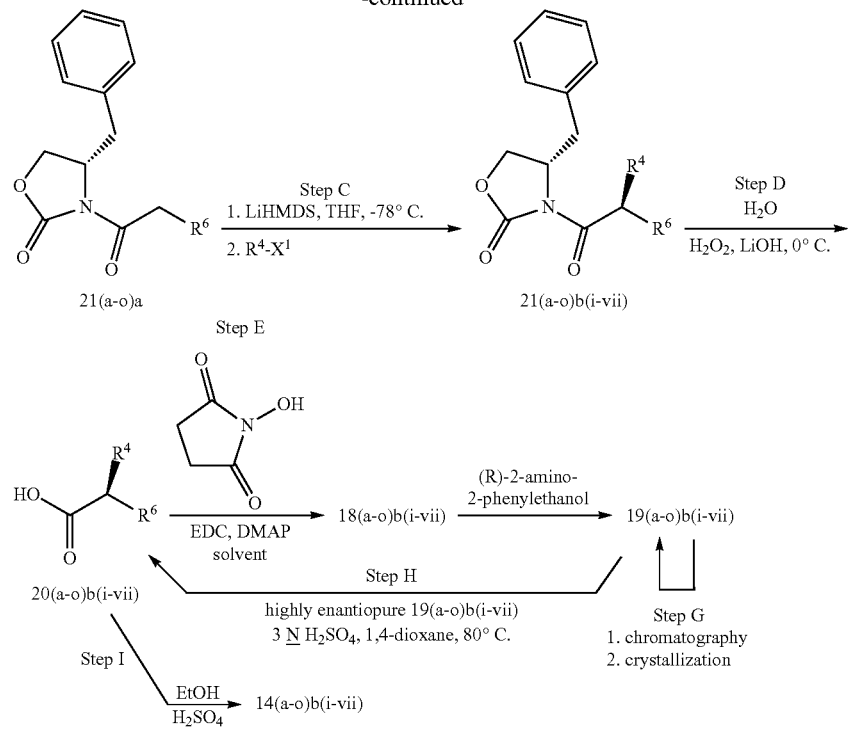

$X^1$ = leaving group (e.g. bromide, iodide, or triflate)

Scheme 8

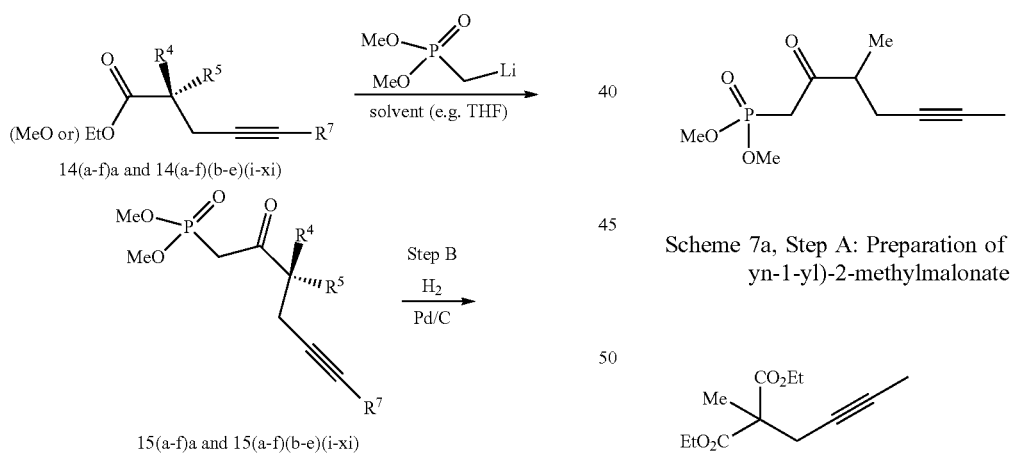

(+)-Dimethyl (3-methyl-2-oxohept-5-yn-1-yl)phosphonate (15ab(i)/15ac(i))

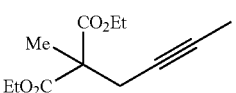

Scheme 7a, Step A: Preparation of diethyl 2-(but-2-yn-1-yl)-2-methylmalonate (16a(i))

To a stirring mixture consisting of diethyl 2-methylmalonate (Sigma-Aldrich, 34.8 g, 200 mmol) in THF (50 mL) at −78° C. was added lithium bis-(trimethylsilyl)amide (1M in THF, 200 mL, 200 mmol) and the resulting reaction mixture was stirred at −78° C. for 30 minutes. To the reaction mixture was added a mixture consisting of 1-bromobut-2-yne (GFS, 25 g, 190 mmol) in THF (50 mL), and the mixture was stirred for another hour at −78° C., and was then allowed to warm to room temperature. The mixture was treated with 10% aqueous sodium hydrogen sulfate, diluted with brine (800 mL), and extracted with ethyl acetate (300 mL). The organic phase was washed with brine (2×250 mL), dried over sodium sulfate, filtered, and concentrated. The residue (brown oil) was purified by silica gel chromatography. Elution with ethyl acetate-hexane (1:9 v/v) afforded the title intermediate (41.5 g, 97.6%); TLC R$_f$ 0.52 (solvent system: 1:9 v/v ethyl acetate-hexane).

Scheme 7a, Step B: Preparation of (±)-ethyl 2-methylhex-4-ynoate (14ab(i)/14ac(i))

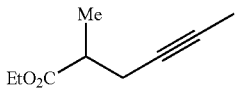

To a mixture consisting of diethyl-2-(but-2-yn-1-yl)-methylmalonate (41.5 g, 184 mmol) in DMSO (150 mL) was added lithium chloride (8.05 g, 190 mmol) and water (6.2 mL), and the stirring mixture was heated at 160° C. overnight. The reaction mixture was cooled and diluted with brine, and the organic material was extracted with ethyl acetate (250 mL). The organic phase was washed with brine (2×200 mL), dried over sodium sulfate, filtered, and concentrated. The residue (dark brown oil) was filtered through a pad of silica gel, using ethyl acetate-hexane (1:4 v/v) to flush the column. The filtrate was concentrated to give the title intermediate (22.3 g, 78.9%) as a colorless oil; TLC R$_f$ 0.37 (solvent system: 1:4 v/v ethyl acetate:hexanes).

Scheme 8, Step A: Preparation of (±)-dimethyl (3-methyl-2-oxohept-5-yn-1-yl)phosphonate (15ab(i)/15ac(i))

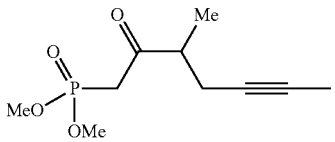

To a stirring mixture consisting of dimethyl methylphosphonate (21.7 g, 175 mmol) in THF (200 mL) at −78° C. was added n-butyllithium (1.6 M in hexanes, 106.2 mL, 169.9 mmol) and the mixture was allowed to continue stirring at −78° C. for one hour. To the reaction mixture was added dropwise (±)-ethyl 2-methylhex-4-ynoate (22.3 g, 145 mmol) and the resulting mixture was stirred at −78° C. for three hours. The reaction mixture was treated with 10% sodium hydrogen sulfate to achieve pH 4, diluted with brine (800 mL), and extracted with ethyl acetate (250 mL). The organic phase was washed with brine (2×150 mL), dried over sodium sulfate, filtered, and concentrated. The residue was purified by silica gel chromatography. Elution with ethyl acetate afforded the title intermediate (24.12 g, 71.6%) as a colorless oil; TLC R$_f$ 0.31 (solvent system: ethyl acetate); MS (ESI$^+$) m/z 233 (M+1).

Preparation of (S)-(+)-dimethyl (3-methyl-2-oxo-hept-5-yn-1-yl)phosphonate (15ab(i))

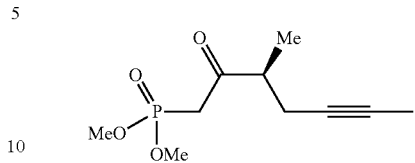

(S)-(+)-Dimethyl (3-methyl-2-oxohept-5-yn-1-yl)phosphonate was prepared in the same manner as that described for the preparation of intermediate 15bb(i) except that intermediate (S)-2-methylhex-4-ynoic acid was prepared instead of (S)-2-methylhept-4-ynoic acid and used to complete the synthesis of the title compound 15ab(i) as a clear oil; TLC R$_f$ 0.27 (solvent system: 4:1 v/v ethyl acetate-hexane); $^1$H-NMR (CDCl$_3$) δ 3.80 (s, 3H), 3.77 (s, 3H), 3.11-3.27 (m, 2H), 2.86-2.95 (m, 1H), 2.23-2.42 (m, 2H), 1.71-1.77 (m, 3H), 1.18 (d, 3H); MS (ESI$^+$) m/z 233 (M+1); [α]$^{20}$D=+44° (c=1, CHCl$_3$).

Preparation of (±)-dimethyl (3-methyl-2-oxooct-5-yn-1-yl)phosphonate (15bb(i)/15bc(i))

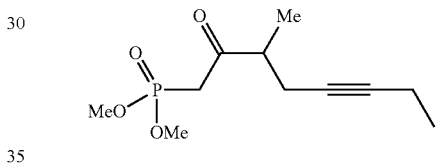

(±)-Dimethyl (3-methyl-2-oxooct-5-yn-1-yl)phosphonate was prepared in the same manner as that described for the preparation of intermediate 15ab(i)/15ac(i) except that 1-bromopent-2-yne was used instead of 1-bromobut-2-yne; chiral analytical HPLC (stationary phase: Chiralcel OJ-H normal phase 250×4.6 mm; mobile phase: 85:15 hexane/1-propanol; flow rate: 1 mL/min): two peaks each of essentially equal area, fast peak having retention time of 5.8 min, slow peak having a retention time of 6.5 min; MS (ESI$^+$) m/z 247.1 (M+1).

Preparation of (S)-(+)-dimethyl (3-methyl-2-oxooct-5-yn-1-yl)phosphonate (15bb(i))

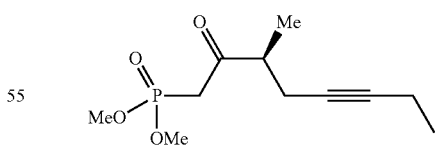

(S)-(+)-Dimethyl (3-methyl-2-oxooct-5-yn-1-yl)phosphonate was prepared by following the sequence of reaction steps described in Scheme 7a, 7f and Scheme 8, Step A. The intermediate 2-methylhept-4-ynoic acid was prepared according to a method described in WO 2011/003058 A1. (S)-(+)-Diethyl (3-methyl-2-oxooct-5-yn-1-yl)phosphonate was prepared according to the method described in the *Journal of Medicinal Chemistry*, 1986, 29(3), 313-315, except that 2,5-dioxopyrrolidin-1-yl 2-methylhept-4-ynoate (N-hydroxysuccinimide 2-methylhept-4-ynoate) was prepared as an activated acyl species (activated ester) instead of 2-methylhept-4-ynoyl chloride to make the intermediate diastereomeric pair N—((R)-2-hydroxy-1-phenylethyl)-2-methylhept-4-ynamide. The diastereomers were separated by silica gel chromatography and the desired diastereomer was manipulated as described to afford the title intermediate as a clear oil. The absolute stereochemistry of the title intermediate was proven by determination of its specific rotation. $[\alpha]^T_\lambda = \alpha/cl$, $[\alpha]^{21.9}_D = +0.574/(0.025 \text{ g}/1 \text{ mL})(0.5) = +45.830$ (c=1, CHCl$_3$). Literature reported specific rotation from *Liebigs Annalen der Chemie*, 1989, 11, 1081-1083; $[\alpha]^{20}_D = +37.7°$ (c=1, CHCl$_3$); chiral analytical HPLC (stationary phase: Chiralcel OJ-H normal phase 250×4.6 mm; mobile phase: 85:15 hexane/1-propanol; flow rate: 1 mL/min) retention time 6.4 min, 100% purity; TLC R$_f$ 0.32 (solvent system: 4:1 v/v ethyl acetate-hexane); $^1$H-NMR (CDCl$_3$) δ 3.76-3.80 (m, 6H), 3.11-3.29 (m, 2H), 2.86-2.95 (m, 1H), 2.36-2.44 (m, 1H), 2.26-2.33 (m, 1H), 2.09-2.16 (m, 2H), 1.16-1.20 (m, 3H), 1.06-1.11 (m, 3H); MS (ESI$^+$) m/z 247 (M+1).

A second preparation of the title intermediate by the same process described above afforded the title intermediate wherein the specific rotation (c=1, CHCl$_3$) is +49°.

Preparation of (R)-(−)-dimethyl (3-methyl-2-oxooct-5-yn-1-yl)phosphonate

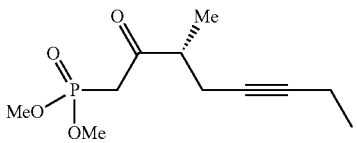

(R)-(−)-Dimethyl (3-methyl-2-oxooct-5-yn-1-yl)phosphonate was prepared by the same method described for the preparation of the (S) isomer above, except that the (R)—N—((R)-2-hydroxy-1-phenylethyl)-2-methylhept-4-ynamide diastereomer collected from the silica gel chromatography was taken on to afford the title phosphonate intermediate; $[\alpha]^T_\lambda = \alpha/cl$, $[\alpha]^{21.9}_D = -0.306/(0.01925 \text{ g}/1.5 \text{ mL})(0.5) = -47.69°$ (c=1.28, CHCl$_3$); TLC R$_f$ 0.347 (solvent system: 85:15 v/v ethyl acetate-heptane); MS (ESI$^+$) m/z 247 (M+H)$^+$.

Preparation of (±)-dimethyl (3-methyl-2-oxonon-5-yn-1-yl)phosphonate (15cb(i)/15cc(i))

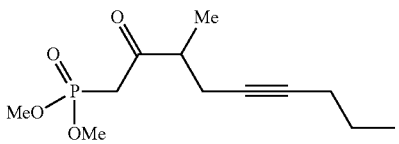 [SMILES: CCCC#CCC(C)C(=O)CP(=O)(OC)OC]

(±)-Dimethyl (3-methyl-2-oxonon-5-yn-1-yl)phosphonate was prepared in the same manner as that described for the preparation of intermediate 15ab(i)/15ac(i) except that 1-bromohex-2-yne (prepared from the corresponding commercially available alcohol using PBr$_3$/pyridine) was used instead of 1-bromobut-2-yne; MS (ESI$^+$) m/z 261 (M+1).

Preparation of (S)-(+)-dimethyl (3-methyl-2-oxonon-5-yn-1-yl)phosphonate (15cb(i))

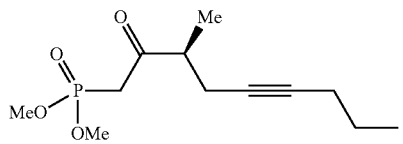 [SMILES: CCCC#CC[C@H](C)C(=O)CP(=O)(OC)OC]

(S)-(+)-Dimethyl (3-methyl-2-oxonon-5-yn-1-yl)phosphonate was prepared in the same manner as that described for the preparation of intermediate 15bb(i) except that intermediate (S)-2-methyloct-4-ynoic acid was prepared instead of (S)-2-methylhept-4-ynoic acid and used to complete the synthesis of the title compound 15cb(i) as a clear oil; TLC R$_f$ 0.12 (solvent system: 3:2 v/v ethyl acetate-hexane); $^1$H-NMR (CDCl$_3$) δ 3.76-3.80 (m, 6H), 3.11-3.29 (m, 2H), 2.86-2.95 (m, 1H), 2.27-2.45 (m, 2H), 2.04-2.12 (m, 2H), 1.39-1.55 (m, 2H), 1.13-1.24 (m, 3H), 0.94 (m, 3H); MS (ESI$^+$) m/z 261 (M+1); $[\alpha]^{20}_D = +48.80$ (c=1, CHCl$_3$).

Preparation of (±)-dimethyl (3-methyl-2-oxo-6-phenylhex-5-yn-1-yl)phosphonate (15db(i)/15dc(i))

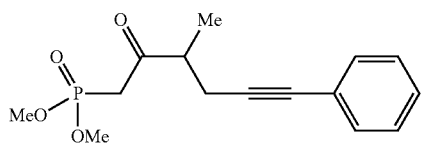 [SMILES: COP(=O)(CC(=O)C(C)CC#Cc1ccccc1)OC]

(±)-Dimethyl (3-methyl-2-oxo-6-phenylhex-5-yn-1-yl)phosphonate was prepared in the same manner as that described for the preparation of intermediate 15ab(i)/15ac(i) except that (3-bromoprop-1-yn-1-yl)benzene (prepared from the corresponding commercially available alcohol using PBr$_3$/pyridine) was used instead of 1-bromobut-2-yne to afford 2.4 g of a clear oil; $^1$H-NMR (CDCl$_3$) δ 7.35-7.45 (m, 2H), 7.2-7.3 (m, 3H), 3.85-3.75 (m, 6H), 3.25 (d, 2H), 3.0-3.2 (m, 1H), 2.5-2.7 (m, 2H), 1.25 (d, 3H); MS (ESI$^+$) m/z 295.1 (M+1).

Preparation of (S)-(+)-dimethyl (3-methyl-2-oxo-6-phenylhex-5-yn-1-yl)phosphonate (15db(i))

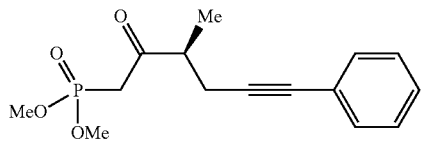 [SMILES: COP(=O)(CC(=O)[C@@H](C)CC#Cc1ccccc1)OC]

(S)-(+)-Dimethyl (3-methyl-2-oxo-6-phenylhex-5-yn-1-yl)phosphonate was prepared in the same manner as that described for the preparation of intermediate 15bb(i) except that intermediate (S)-2-methyl-5-phenylpent-4-ynoic acid was prepared instead of (S)-2-methylhept-4-ynoic acid and used to complete the synthesis of the title compound 15db(i) as a clear oil; TLC R$_f$ 0.22 (solvent system: 4:1 v/v ethyl acetate-hexane); MS (ESI$^+$) m/z 295 (M+1).

Preparation of (+)-dimethyl (3-methyl-2-oxo-6-phenylhexyl)phosphonate (15mb(i)/15mc(i))

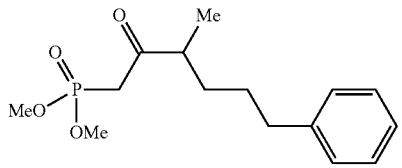 [SMILES: COP(=O)(CC(=O)C(C)CCCc1ccccc1)OC]

A mixture consisting of (±)-dimethyl (3-methyl-2-oxo-6-phenylhex-5-yn-1-yl)phosphonate (15db(i)/15dc(i)), (1.0 g, 3.4 mmol) and 10% palladium on activated carbon (15 mg) in methanol (30 mL) was stirred under an atmosphere of hydrogen overnight. The hydrogen was evacuated and the mixture was filtered through a micropore filter. The filtrate was concentrated in vacuo to afford the title compound (1.0 g, quantitative yield) as a clear oil; $^1$H-NMR (CDCl$_3$) δ 7.3-7.25 (m, 2H), 7.2-7.1 (m, 3H), 3.8-3.7 (m, 6H), 3.1 (d, 2H), 2.8-2.75 (m, 1H), 2.7-2.5 (m, 2H), 1.8-1.65 (m, 1H), 1.65-1.5 (m, 2H), 1.4-1.3 (m, 1H), 1.1 (d, 3H); MS (ESI$^+$) m/z 299 (M+1).

Preparation of (S)-(+)-dimethyl (3-methyl-2-oxo-6-phenylhexyl)phosphonate (15mb(i))

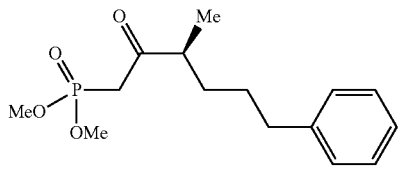 [SMILES: COP(=O)(CC(=O)[C@@H](C)CCCc1ccccc1)OC]

(S)-(+)-Dimethyl (3-methyl-2-oxo-6-phenylhexyl)phosphonate was prepared as a clear oil in the same manner as that described for the preparation of phosphonate 15mb(i)/15mc(i); $^1$H-NMR (CDCl$_3$) 7.3-7.2 (m, 2H), 7.2-7.1 (m, 3H), 3.8-3.7 (m, 6H), 3.12 (s, 1H), 3.07 (s, 1H), 2.8-2.7 (m, 1H), 2.7-2.5 (m, 2H), 1.8-1.7 (m, 2H), 1.7-1.5 (m, 2H), 1.1 (d, 3H); MS (ESI$^+$) m/z 299 (M+1).

Alternative preparation of (S)-(+)-dimethyl (3-methyl-2-oxo-6-phenylhexyl)phosphonate (15mb(i))

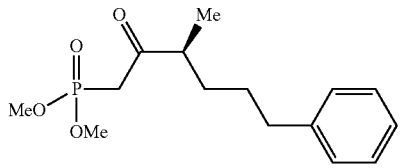 [SMILES: COP(=O)(CC(=O)[C@@H](C)CCCc1ccccc1)OC]

Scheme 7f, Step A: Preparation of (±)-2-methyl-5-phenylpentanoic acid (20mb(i)/20mc(i))

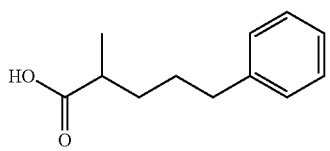

To a solution consisting of diisopropylamine (218.25 mL, 1557.3 mmol) in THF (400 mL) at −50° C. was added an n-butyllithium solution (628 mL, 393 mmol, 1.6 M solution in hexane). The reaction mixture was stirred for five minutes and was then allowed to warm to −20° C. To the reaction mixture was added dropwise a solution consisting of propionic acid (44.67 g, 603 mmol) in HMPA (102 mL). The reaction mixture was stirred at room temperature for 30 minutes, and subsequently cooled to 0° C., after which a mixture consisting of 1-bromo-3-phenylpropane (100 g, 502 mmol) in THF (200 mL) was added. The resulting reaction mixture stirred at room temperature for two hours. The reaction mixture was diluted with water and extracted with ethyl acetate. The aqueous layer was separated and then acidified with 2 M HCl until acidic. The aqueous layer was then extracted three times with ethyl acetate, and the organic layers were combined and dried over sodium sulfate, filtered, and concentrated to afford the title intermediate (105 g, quantitative yield) as a clear oil; TLC R$_f$ 0.44 (solvent system: 25:75:1 v/v/v ethyl acetate-heptane-acetic acid.

Scheme 7f, Step B: Preparation of (±)-2,5-dioxopyrrolidin-1-yl 2-methyl-5-phenylpentanoate (18mb(i))

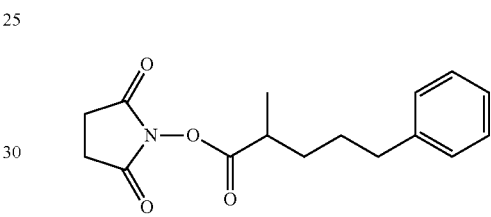

To a mixture consisting of (±)-2-methyl-5-phenylpentanoic acid (20mb(i)/20mc(i), 105.6 g, 549.1 mmol) in dichloromethane (800 mL) was added N-hydroxysuccinimide (69.5 g, 604 mmol), 4-dimethylaminopyridine (73.8 g, 604 mmol) and 1-ethyl-(3-dimethylaminopropyl) carbodiimide hydrochloride (115.8 g, 604.0 mmol) and the reaction mixture was stirred overnight at room temperature. The reaction mixture was extracted with dichloromethane and washed twice with brine, dried over sodium sulfate, filtered, and concentrated under vacuum. The residue was purified by silica gel chromatography. Elution with ethyl acetate-heptane (30:70 v/v) afforded the title intermediate (85.6 g, 54%); TLC R$_f$ 0.32 (solvent system 25:75 v/v ethyl acetate-heptane.

Scheme 7f, Steps C and D: Preparation of (S)—N—((R)-2-hydroxy-1-phenylethyl)-2-methyl-5-phenylpentanamide (19mb(i))

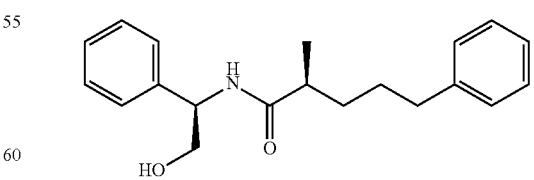

To a solution consisting of (±)-2,5-dioxopyrrolidin-1-yl 2-methyl-5-phenyl pentanoate (18mb(i), 85.6 g, 296 mmol) in THF (3000 mL) at 48° C. was added R-(−)-2-phenylglycinol (65.9 g, 480 mmol, Bridge Organics) in portions. The resulting reaction mixture was stirred at 48° C. for 40 hours.

A white precipitate formed, which was filtered from the reaction mixture and washed with THF. The filtrate was concentrated under vacuum and the residue, comprising the diastereomeric pair, was chromatographed on silica gel. Elution with ethyl acetate-heptane (50:50 v/v) afforded the pure diastereomer title compound (31.3 g, 34%) as a colorless solid; TLC $R_f$ 0.205 (solvent system: 50:50 v/v ethyl acetate-heptane); HPLC retention time 15.1 minutes, stationary phase: Gemini 5μ C18 250×4.6 mm, ultraviolet detector at 210 nm, mobile phase: 1 mL/min, 60:40:0.1 v/v methanol-water-acetic acid.

Scheme 7f, Step E1: Preparation of (S)-(+)-2-methyl-5-phenylpentanoic acid (20mb(i))

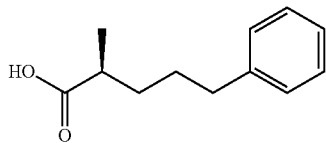

To a solution consisting of (S)—N—((R)-2-hydroxy-1-phenylethyl)-2-methyl-5-phenylpentanamide (19mb(i), 3.5 g, 11.24 mmol) in 1,4-dioxane (80 mL) was added aqueous sulfuric acid (36 mL, 3 N solution) and the mixture was stirred overnight at 80° C. The reaction mixture was extracted with ethyl acetate three times and the organic layers were combined, dried over sodium sulfate, filtered, and concentrated under vacuum. The residue was purified by silica gel chromatography. Elution with ethyl acetate-heptane-acetic acid (30:70:0.4 v/v/v) afforded the title compound (2.4 g, quantitative yield) as a clear oil; $R_f$ 0.48 (solvent system: 30:70:0.4 v/v/v ethyl acetate-heptane-acetic acid; HPLC retention time 26.0 minutes; Chiralpak IA, 5μ, 4.6×25 mm, ultraviolet detector at 208 nm 0.75 ml/min 99:1:0.5 v/v heptanes-2-propanol-acetic acid; MS (ESI) m/z 191.1 (M–H)$^-$; $^1$H-NMR (CDCl$_3$) δ 7.33-7.27 (m, 2H), 7.22-7.16 (m, 3H), 2.67-2.60 (m, 2H), 2.56-2.46 (m, 1H), 1.80-1.60 (m, 3H), 1.59-1.36 (m, 1H), 1.25-1.14 (m, 3H); $[α]^T_λ$=α/cl, $[α]^{21.9}_D$=+0.089/(0.01501 g/1.5 mL)(0.5)=+17.79° (c=1, CHCl$_3$).

Scheme 7f, Step F1: Preparation of (S)-(+)-ethyl 2-methyl-5-phenylpentanoate (14mb(i))

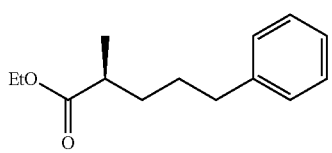 [SMILES: CCOC(=O)[C@@H](C)CCCc1ccccc1]

To a solution consisting of (S)-(+)-2-methyl-5-phenylpentanoic acid (20mb(i), 2.3 g, 12 mmol) in ethanol (200 mL) was added 4 drops of concentrated sulfuric acid. The stirring reaction mixture was brought to reflux overnight and was subsequently cooled and concentrated under vacuum. The residue was diluted with ethyl acetate and washed twice with brine. The organic layer was dried over sodium sulfate, filtered, and concentrated under vacuum to afford the title compound (2.4 g, 91%) as a clear oil; TLC $R_f$ 0.66 (solvent system: 15:85:1 v/v/v ethyl acetate-heptane-acetic; MS (ESI$^+$) m/z 221.2 (M+H)$^+$; $^1$H-NMR (CDCl$_3$) δ 7.29-7.25 (m, 2H), 7.21-7.13 (m, 3H), 4.12 (q, J=6.96 Hz, 2H), 2.64-2.57 (m, 2H), 2.48-2.39 (m, 1H), 1.75-1.54 (m, 3H), 1.52-1.41 (m, 1H), 1.24 (t, J=7.14 Hz, 3H) 1.16-1.11 (m, 3H); $[α]^T_λ$=α/cl, $[α]^{21.9}_D$=+0.101/(0.01506 g/1.5 ml)(0.5)=+20.12° (c=1, CHCl$_3$).

Scheme 6: Preparation of (S)-(+)-dimethyl (3-methyl-2-oxo-6-phenylhexyl)phosphonate (15mb (i))

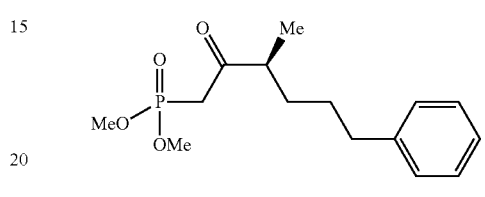

To a stirring solution consisting of dimethyl methylphosphonate (23.37 g, 188.4 mmol) in THF (400 mL) at –78° C. was slowly added n-butyllithium solution (112 mL, 179 mmol, 1.6 M solution in hexane). The reaction mixture was stirred for 30 minutes, after which time, (S)-(+)-ethyl 2-methyl-5-phenylpentanoate (14mb(i), 28.1 g, 94.2 mmol) in THF (100 mL) was slowly added. The resulting reaction mixture was stirred at –78° C. for two hours and was then allowed to rise to room temperature overnight. The reaction mixture was treated with 5% KHSO$_4$ and extracted with ethyl acetate three times. The organic layer was washed twice with 50:50 water-brine and the organic layer was dried over sodium sulfate, filtered, and concentrated under vacuum. The residue was purified by silica gel chromatography. Elution with ethyl acetate-heptane (60:40 v/v) afforded the title compound (11.9 g, 42%) as a clear oil, pure of unrelated components; TLC $R_f$ 0.22 (solvent system: 60:40 v/v ethyl acetate-heptane); HPLC retention time 14.5 minutes, 5 Chiralpak IA 250×4.6 mm, ultraviolet detector at 210 nm, 1 mL/min, chiral purity 97.8% (S), 2.19% (R); MS (ESI$^-$) m/z 297.1 (M–H)$^-$; $^1$H NMR (CDCl$_3$) δ 7.28-7.21 (m, 2H), 7.17-7.12 (m, 3H), 3.76-3.71 (m, 6H), 3.10 (d, J=2.20 Hz, 1H), 3.04 (d, J=2.20 Hz, 1H), 2.79-2.70 (m, 1H), 2.54-2.62 (m, 2H), 1.74-1.54 (m, 3H), 1.42-1.24 (m, 1H), 1.07 (d, J=6.96 Hz, 3H); $[α]^T_λ$=α/cl, $[α]^{21.9}_D$=+0.084/(0.0169 g/1.5 mL)(0.5)=+14.910 (c=1.13, CHCl$_3$).

The chromatography also provided additional title compound (8.3 g) with approximately 95% chemical purity based on visual observation of TLC; chiral purity 98.19% (S), 1.81% (R).

Second alternative preparation of (S)-(+)-dimethyl (3-methyl-2-oxo-6-phenylhexyl)phosphonate (15mb(i))

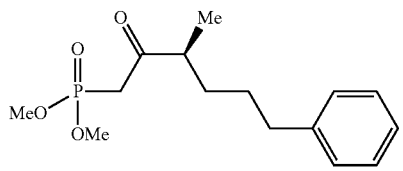 [SMILES: COP(=O)(CC(=O)[C@@H](C)CCCc1ccccc1)OC]

Scheme 7g, Step B: Preparation of (S)-4-benzyl-3-(5-phenylpentanoyl)oxazolidin-2-one (21ma)

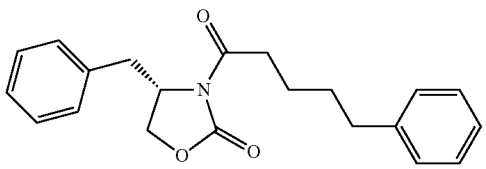 [SMILES: O=C(CCCCc1ccccc1)N1C(=O)OC[C@@H]1Cc1ccccc1]

To a stirring solution consisting of (S)-4-benzyloxazolidin-2-one (0.9 g, 5.08 mmol) in THF (20 mL) at −78° C. was slowly added n-butyllithium solution (3.5 mL, 5.6 mmol, 1.6 M solution in hexane). The reaction mixture was stirred at −78° C. for two hours, after which time 5-phenylpentanoyl chloride (1 g, 5 mmol, prepared by treatment of 5-phenylpentanoic acid with oxalyl chloride and catalytic DMF) was slowly added. The reaction mixture was stirred at −78° C. for two hours and was then allowed to rise to room temperature overnight. The reaction mixture was acidified with 5% KHSO$_4$ and extracted twice with ethyl acetate. The organic phase was washed with brine, dried over sodium sulfate, filtered, and concentrated under vacuum. The residue was purified by silica gel chromatography. Elution with ethyl acetate-heptane (25:75 v/v) afforded the title compound (1.4 g, 82%) as a clear oil; TLC R$_f$ 0.40 (solvent system: 25:75 v/v ethyl acetate-heptane); MS (ESI$^+$) m/z 337.4 (M+H)$^+$, 360.2 (M+Na)$^+$.

Scheme 7g, Step C: Preparation of (S)-4-benzyl-3-((S)-2-methyl-5-phenylpentanoyl)oxazolidin-2-one (21mb(i))

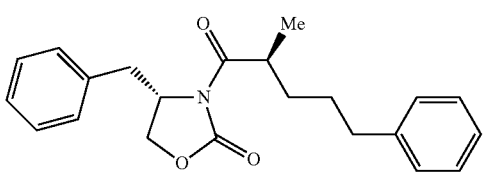 [SMILES: C[C@@H](CCCc1ccccc1)C(=O)N1C(=O)OC[C@@H]1Cc1ccccc1]

To a stirring solution consisting of (S)-4-benzyl-3-(5-phenylpentanoyl)oxazolidin-2-one (21ma, 1.24 g, 3.68 mmol) in THF (20 mL) at −78° C. was slowly added lithium bis-(trimethylsilyl)amide solution (4.41 mL, 4.41 mmol, 1 M solution in THF). The reaction mixture was stirred at −78° C. for one hour, after which time iodomethane (0.27 mL, 4.2 mmol) was slowly added. The resulting reaction mixture was allowed to rise to room temperature with stirring overnight. The mixture was acidified with 5% KHSO$_4$ and extracted twice with ethyl acetate. The organic layer was washed twice with brine, dried over sodium sulfate, filtered, and concentrated under vacuum. The residue was purified by silica gel chromatography. Elution with ethyl acetate-heptane (25:75 v/v) afforded the title compound (563 mg, 43.6%) as a clear oil; TLC R$_f$ 0.53 (solvent system: 25:75 v/v ethyl acetate-heptane; MS (ESI$^+$) m/z 352.3 (M+H)$^+$ 374.2 (M+Na)$^+$.

Scheme 7g, Step D: Preparation of (S)-2-methyl-5-phenylpentanoic acid (20mb(i))

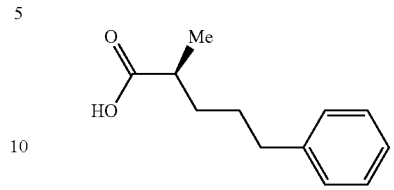

To a stirring aqueous mixture cooled to 0° C. comprising (S)-4-benzyl-3-((S)-2-methyl-5-phenylpentanoyl)oxazolidin-2-one (21mb(i), 563 mg, 1.60 mmol) was added hydrogen peroxide and lithium hydroxide. The resulting reaction mixture was stirred for four hours. The reaction mixture was acidified with 5% KHSO$_4$ and extracted twice with ethyl acetate, the organic layer was washed twice with brine, dried over sodium sulfate, and concentrated under vacuum. The residue was purified by silica gel chromatography. Elution with ethyl acetate-heptane-acetic acid (25:75:0.4) afforded the title compound (293 mg, 95%) as a colorless oil; TLC R$_f$ 0.35 (solvent system: 25:75:0.4 v/v/v ethyl acetate-heptane-acetic acid); HPLC retention time 12.08 min, stationary phase: Chiralpak IA 4.6×25 mm 5μ, ultraviolet detector at 210 nm, mobile phase: 1 mL/min 99:1:0.1 heptane:2-propanol:acetic acid, 97.22% (S), 2.78% (R).

Scheme 7g, Step E: Preparation of (S)-2,5-dioxopyrrolidin-1-yl 2-methyl-5-phenylpentanoate (18mb(i))

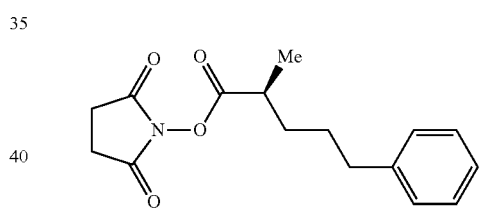

To a mixture consisting of (S)-2-methyl-5-phenylpentanoic acid (20mb(i), 290 mg, 1.51 mmol) in dichloromethane (20 mL) was added N-hydroxysuccinimide (191 mg, 1.66 mmol), 4-dimethylaminopyridine (203 mg, 1.66 mmol) and 1-ethyl-(3-dimethylaminopropyl)carbodiimide hydrochloride (318 mg, 1.66 mmol). The resulting reaction mixture was stirred for two hours at room temperature. The reaction mixture comprising 18mb(i) was carried on directly to the next step.

Scheme 7g, Step F and G: Preparation of (S)—N—((R)-2-hydroxy-1-phenylethyl)-2-methyl-5-phenylpentanamide (19mb(i))

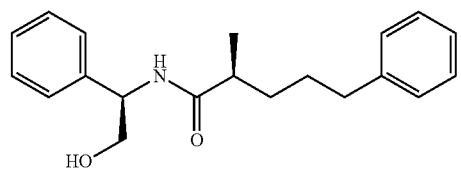 [SMILES: C[C@@H](CCCc1ccccc1)C(=O)N[C@@H](CO)c1ccccc1]

To the reaction mixture comprising 18mb(i) prepared as described above was added R-(−)-2-phenylglycinol, and the resulting reaction mixture was stirred overnight. The mixture was filtered and washed with THF. The combined filtrate and THF wash was concentrated under vacuum. The residue was purified by silca gel chromatography. Elution with ethyl acetate-heptane (60:40 v/v) provided a solid, which was crystallized from ethyl acetate-heptane to afford the highly-stereopure title compound (198 mg, 42%) as a white solid; TLC $R_f$ 0.21 (solvent system: 60:40 v/v ethyl acetate-heptane; HPLC retention time 14.68 minutes, stationary phase: Gemini, 5μ C18 250×4.6 mm, ultraviolet wavelength of 210 nm, mobile phase: 1 mL/min, 60:40:0.1 methanol-water-acetic acid, 100% (S); MS (ESI$^+$) m/z 312.2 (M+H)$^+$, 334.1 (M+Na)$^+$.

Preparation of (S)-(+)-dimethyl (3-methyl-2-oxo-6-phenylhexyl)phosphonate (15mb(i))

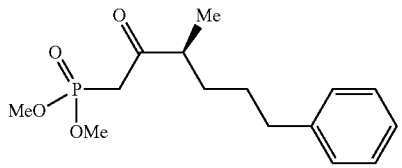 [SMILES: COP(=O)(CC(=O)[C@@H](C)CCCc1ccccc1)OC]

(S)-(+)-Dimethyl (3-methyl-2-oxo-6-phenylhexyl)phosphonate (15mb(i)) is prepared in three steps from the highly stereopure (S)—N—((R)-2-hydroxy-1-phenylethyl)-2-methyl-5-phenylpentanamide (19mb(i)) prepared by the Scheme 7g route as it is from the 19mb(i) derived from the reaction sequence of Scheme 7f starting from (±)-2-methyl-5-phenylpentanoic acid (20mb(i)/20mc(i)).

Preparation of (R)-(−)-dimethyl (3-methyl-2-oxo-6-phenylhexyl)phosphonate (15mc(i))

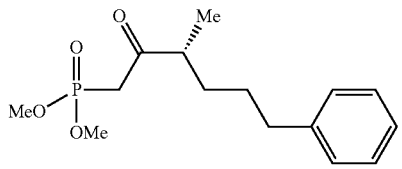

Preparation of (−)—(R)—N—((R)-2-hydroxy-1-phenylethyl)-2-methyl-5-phenylpentanamide (19mc(i))

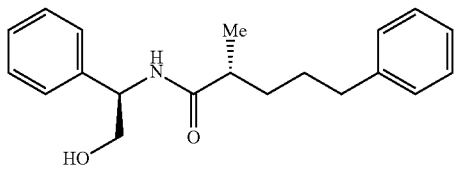 [SMILES: C[C@H](CCCc1ccccc1)C(=O)N[C@@H](CO)c1ccccc1]

(−)-(R)—N—((R)-2-Hydroxy-1-phenylethyl)-2-methyl-5-phenylpentanamide was prepared from (±)-2-methyl-5-phenylpentanoic acid (20mb(i)/20mc(i)) in the same manner as (S)—N—((R)-2-hydroxy-1-phenylethyl)-2-methyl-5-phenylpentanamide (19mb(i)) described above. Silica gel chromatography provided separation of the title compound from its diastereomer (19mb(i)) to provide the desired product (30.2 g, 33%) as a white solid; TLC $R_f$ 0.33 (solvent system: 50:50 v/v ethyl acetate-heptane); HPLC retention time 13.25 minutes, Gemini 5μ C18 250×4.6 mm, at ultraviolet wavelength of 210 nm, 1 mL/min, 60:40:0.1 methanol-water-acetic acid, purity 99.36% (R), 0.64% (S); $[\alpha]^T_\lambda = \alpha/cl$, $[\alpha]^{21.9}_D = -0.066/(0.01573 \text{ g}/2 \text{ mL})(0.5) = -16.78°$ (c=0.7865, CHCl$_3$).

Preparation of (R)-(−)-2-methyl-5-phenylpentanoic acid (20mc(i))

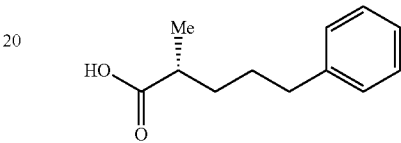

R)-(−)-2-Methyl-5-phenylpentanoic acid was prepared from 19mc(i) (30 g) in the same manner (S)-(+)-2-methyl-5-phenylpentanoic acid was prepared from 19mb(i) as described above. The residue was purified by silica gel chromatography. Elution with ethyl acetate-heptane-acetic acid (20:80:0.4 v/v/v) afforded the title compound (20.8 g) as a clear oil; TLC $R_f$ 0.51 (solvent system: 30:70:1 v/v/v ethyl aceate-hepatane-acetic acid; HPLC retention time 24.46 min; Chiralpak IA 4.6×25 mm 5μ, at a wavelength of 208 nm 0.75 mL/min, 99:1:0.5 heptane:2-propanol:acetic acid, chiral purity 99.32% (R), 0.68% (S); MS (ESI$^−$) in/z 191.1 (M−H)$^−$; $^1$H-NMR (CDCl$_3$) δ 7.31-7.26 (m, 2H), 7.21-7.15 (m, 3H), 2.67-2.57 (m, 2H), 2.54-2.44 (m, 1H), 1.79-1.59 (m, 3H) 1.58-1.41 (m, 1H), 1.18 (d, J=6.96 Hz, 3H).

Preparation of (R)-(−)-ethyl 2-methyl-5-phenylpentanoate (14mc(i))

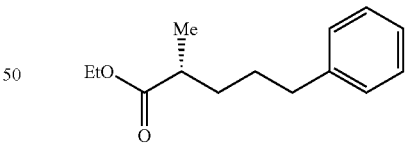

(R)-(−)-Ethyl 2-methyl-5-phenylpentanoate was prepared from 20mc(i) (20.8 g) in the same manner (S)-(+)-ethyl 2-methyl-5-phenylpentanoate was prepared from 20mb(i) as described above. The residue was purified by silica gel chromatography. Elution with ethyl acetate-heptane (5:95 v/v) afforded the title compound (21.0 g, 88%) as a clear oil; TLC $R_f$ 0.66 (solvent system: 15:85:1 v/v/v ethyl acetate-heptane-acetic acid); MS (ESI$^+$) m/z 221.2 (M+H)$^+$; $^1$H-NMR (CDCl$_3$) δ 7.32-7.26 (m, 2H), 7.20-7.14 (m, 3H), 4.11 (q, J=7.32 Hz, 2H), 2.64-2.57 (m, 2H), 2.48-2.39 (m, 1H), 1.75-1.53 (m, 3H), 1.52-1.41 (m, 1H), 1.27-1.21 (m, 3H), 1.13 (d, J=6.96 Hz, 3H); $[\alpha]^T_\lambda = \alpha/cl$, $[\alpha]^{21.9}_D = -0.114/(0.01771 \text{ g}/1.5 \text{ mL})(0.5) = -19.310$ (c=1.18, CHCl$_3$).

Preparation of (R)-(−)-dimethyl (3-methyl-2-oxo-6-phenylhexyl)phosphonate (15mc(i))

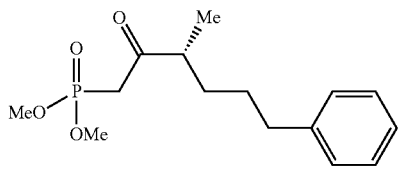 [SMILES: COP(=O)(CC(=O)[C@H](C)CCCc1ccccc1)OC]

(R)-(−)-Dimethyl (3-methyl-2-oxo-6-phenylhexyl)phosphonate was prepared from 14mc(i) (93 mg) in the same manner (S)-(+)-dimethyl (3-methyl-2-oxo-6-phenylhexyl) phosphonate was prepared from 14mb(i) as described above. The residue was purified by silica gel chromatography. Elution with ethyl acetate-heptane (70:30 v/v) afforded the title compound (83 mg, 66%) as a colorless oil; TLC $R_f$ 0.22 (solvent system: 70:30 v/v ethyl acetate-heptane); HPLC retention time 12.36 min, 5μ Chiralpak OJ-H 4.6×250 mm, at ultraviolet wavelength of 210 nm, 90:10:0.1 heptane-ethanol:acetic acid) 1 mL/min, chiral purity 100% (R); MS (ESI⁻) m/z 297.1 (M−H)⁻; ¹H NMR (CDCl$_3$) δ 7.29 (d, J=6.51 Hz, 2H), 7.22-7.16 (m, 3H), 3.77 (d, J=11.35 Hz, 3H), 3.78 (d, J=11.35 Hz, 3H), 3.13 (d, J=1.83 Hz, 1H), 3.08 (d, J=1.83 Hz, 1H), 2.78 (d, J=6.96 Hz, 1H), 2.67-2.56 (m, 2H), 1.61-1.52 (m, 3H), 1.45-1.32 (m, 1H), 1.11 (d, J=6.96 Hz, 3H); $[α]^T_λ=α/cl$, $[α]^{21.9}_D=−0.080/(0.01742\ g/1.5\ mL)$ (0.5)=−13.78° (c=1.16, CHCl$_3$).

Dimethyl (2-oxohept-5-yn-1-yl)phosphonate (15aa)

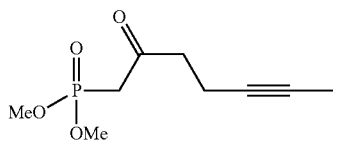

Scheme 7a, Step A: Preparation of diethyl 2-(but-2-yn-1-yl)malonate (16a)

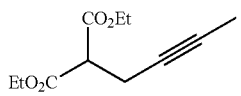

To a stirring mixture consisting of diethyl malonate (24.3 g, 141 mmol) in THF (140 mL) was added sodium hydride (60% dispersion in oil, 2.8 g, 70 mmol) and the resulting reaction mixture was stirred for 50 minutes. To the reaction mixture was added 1-bromobut-2-yne (GFS, 6.2 g, 47 mmol), and the mixture was stirred for two hours. The reaction mixture was treated carefully with 0.5 N HCl and extracted with ethyl acetate. The organic phase was washed with water, then brine, dried over magnesium sulfate, filtered, and concentrated. The residue was purified by silica gel chromatography. Elution with ethyl acetate-heptane (5:95 to 15:85 v/v) afforded the title intermediate (11.5 g, quantitative yield) as a clear oil.

Preparation of dimethyl (2-oxohept-5-yn-1-yl)phosphonate (15aa)

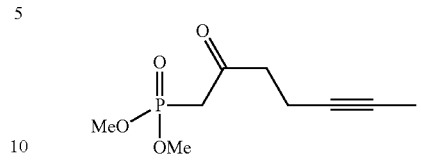

Dimethyl (2-oxohept-5-yn-1-yl)phosphonate was prepared in two steps from diethyl 2-(but-2-yn-1-yl)malonate in the same manner as that described for intermediate 15ab(i)/15ac(i) to afford the title phosphonate intermediate (2.5 g) as a clear oil; ¹H-NMR (CDCl$_3$) δ 3.78 (d, 6H, J=11.5 Hz), 3.1 (d, 2H, J=22.5 Hz), 2.80 (t, 2H), 2.42-2.35 (m, 2H), 1.73 (t, 3H).

Preparation of dimethyl (2-oxooct-5-yn-1-yl)phosphonate (15ba)

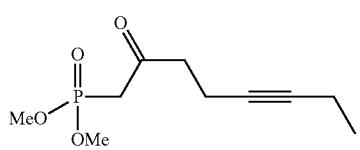

Dimethyl (2-oxooct-5-yn-1-yl)phosphonate was prepared in the same manner as that described for the preparation of intermediate 15aa except that 1-bromopent-2-yne (GFS, 6.9 g, 47 mmol) was used instead of 1-bromobut-2-yne to afford the title phosphonate intermediate (4.0 g) as a clear oil; ¹H-NMR (CDCl$_3$) δ 3.78 (d, 6H, J=11.1 Hz), 3.11 (d, 2H, J=22.8 Hz), 2.81 (t, 2H), 2.45-2.38 (m, 2H), 2.28-2.36 (m, 2H), 1.08 (t, 3H).

Preparation of dimethyl (2-oxonon-5-yn-1-yl)phosphonate (15ca)

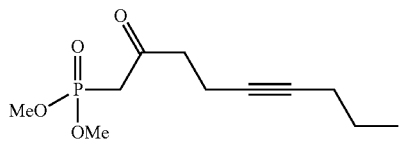

Dimethyl (2-oxonon-5-yn-1-yl)phosphonate is prepared in the same manner as that described for the preparation of intermediate 15aa except that 1-bromohex-2-yne is used instead of 1-bromobut-2-yne.

Preparation of dimethyl (2-oxo-6-phenylhex-5-yn-1-yl)phosphonate (15da)

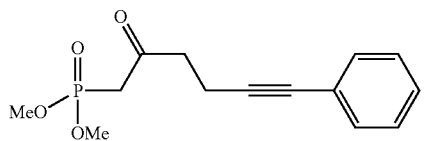 [SMILES: COP(=O)(CC(=O)CCC#Cc1ccccc1)OC]

Scheme 7a, Step A: Preparation of diethyl 2-(hex-2-yn-1-yl)malonate (16d)

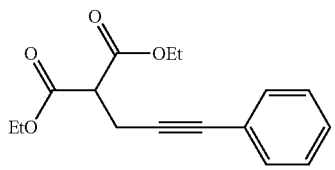

To a stirring suspension consisting of sodium hydride (1.22 g, 51.3 mmol) in THF (100 mL) at 0° C. was added dropwise a solution consisting of diethyl malonate (12.3 g, 76.9 mmol) in THF (20 mL) and the reaction mixture was stirred for 30 minutes. To the 0° C. reaction mixture was added a solution consisting of (3-bromoprop-1-yn-1-yl)benzene (5.0 g, 26 mmol, prepared from the corresponding commercially available alcohol using $PBr_3$/pyridine) in THF (30 mL) and the mixture was allowed to warm to room temperature for one hour. The reaction mixture was quenched with an aqueous solution of sodium chloride (500 mL) and extracted with diethyl ether (500 mL). The organic phase was washed with brine (300 mL), dried over sodium sulfate, filtered, and concentrated to afford the title intermediate (10.6 g) which was used as is in the next step immediately below; TLC $R_f$ 0.47 (solvent system: 1:5 v/v ethyl acetate-heptane).

Preparation of dimethyl (2-oxo-6-phenylhex-5-yn-1-yl)phosphonate (15da)

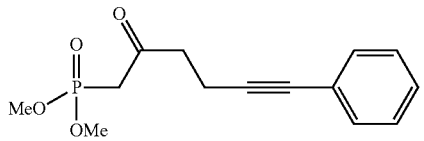 [SMILES: COP(=O)(CC(=O)CCC#Cc1ccccc1)OC]

Dimethyl (2-oxo-6-phenylhex-5-yn-1-yl)phosphonate was prepared in two steps from diethyl 2-(hex-2-yn-1-yl) malonate in the same manner as that described for the preparation of intermediate 15ab(i)/15ac(i) to afford 2.12 g; TLC $R_f$ 0.22 (solvent system: 4:1 v/v ethyl acetate-heptane); $^1$H-NMR (CDCl$_3$) δ 7.31-7.41 (m, 2H), 6.68-7.28 (m, 3H), 3.76-3.81 (m, 6H), 3.17 (s, 1H), 3.12 (s, 1H), 2.92-2.98 (m, 2H), 2.65-2.71 (m, 2H); MS (ESI$^+$) m/z 281 (M+1).

Preparation of dimethyl (2-oxo-6-phenylhexyl)phosphonate (15ma)

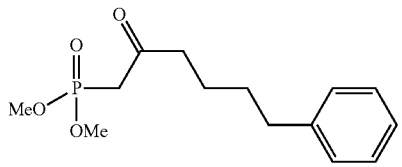 [SMILES: COP(=O)(CC(=O)CCCCc1ccccc1)OC]

Dimethyl (2-oxo-6-phenylhexyl)phosphonate was prepared in the same manner as that described for the preparation of intermediate 15ab(i)/15ac(i) except that methyl 5-phenylpentanoate (Sigma-Aldrich) was used instead of (±)-ethyl 2-methylhex-4-ynoate; $^1$H-NMR (CDCl$_3$) δ 7.29-7.23 (m, 2H), 7.19-7.13 (m, 3H), 3.76 (d, 6H, J=11.1 Hz), 3.06 (d, 2H, J=22.6 Hz), 2.55-2.7 (m, 4H), 1.55-1.7 (m, 4H).

Scheme 6: Preparation of dimethyl (3,3-dimethyl-2-oxoheptyl)phosphonate (15hd(i))

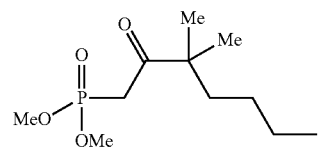 [SMILES: CCCCC(C)(C)C(=O)CP(=O)(OC)OC]

Dimethyl (3,3-dimethyl-2-oxoheptyl)phosphonate was prepared in the same manner as that described for the preparation of intermediate 15ab(i)/15ac(i) except that methyl 2,2-dimethylhexanoate (prepared by the acid (p-toluenesulfonic acid) catalyzed esterification of 2,2-dimethylhexanoic acid) was used instead of (±)-ethyl 2-methylhex-4-ynoate; MS (ESI$^+$) m/z 251 (M+1).

Scheme 6: Preparation of dimethyl (2-oxohex-3-yn-1-yl)phosphonate (15p)

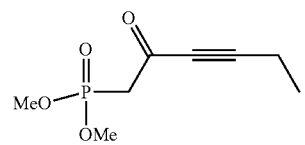

Dimethyl (2-oxohex-3-yn-1-yl)phosphonate was prepared in the same manner as that described for the preparation of intermediate 15ab(i)/15ac(i) except that ethyl pent-2-ynoate was used instead of (±)-ethyl 2-methylhex-4-ynoate; MS (ESI$^+$) m/z 205 (M+1).

Scheme 6: Preparation of dimethyl (2-oxo-4-phenylbut-3-yn-1-yl)phosphonate (15q)

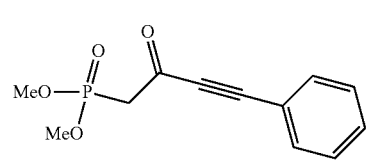 [SMILES: COP(=O)(CC(=O)C#Cc1ccccc1)OC]

Dimethyl (2-oxo-4-phenylbut-3-yn-1-yl)phosphonate was prepared in the same manner as that described for the preparation of intermediate 15ab(i)/15ac(i) except that ethyl 3-phenylpropiolate was used instead of (±)-ethyl 2-methylhex-4-ynoate; MS (ESI$^+$) m/z 253 (M+1).

(S)-dimethyl (2-oxo-3-phenylbutyl)phosphonate (15jb(i))

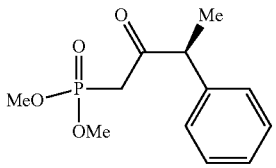 [SMILES: COP(=O)(CC(=O)[C@@H](C)c1ccccc1)OC]

Preparation of (S)-ethyl 2-phenylpropanoate (15jb(i))

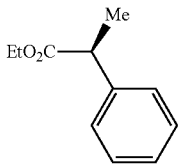

To a solution consisting of (S)-2-phenylpropanoic acid (1.0 g, 6.7 mmol, from Chem-Impex) in ethanol (30 mL) was added concentrated sulfuric acid (4 drops). The reaction mixture was stirred at reflux overnight in a vessel equipped with a Dean-Stark condenser. To the mixture was added solid sodium bicarbonate and the resulting mixture was filtered and concentrated under vacuum to afford the title compound (1.0 g, 84%) as a colorless oil; TLC $R_f$ 0.5 (solvent system: 15:85:1 v/v/v ethyl acetate-heptane-acetic acid). The product was carried directly onto the next step without further purification.

Preparation of (S)-(+)-dimethyl (2-oxo-3-phenylbutyl)phosphonate (15jb(i))

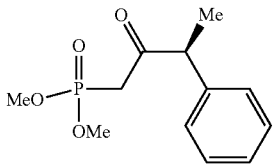 [SMILES: COP(=O)(CC(=O)[C@@H](C)c1ccccc1)OC]

To a stirring solution consisting of dimethyl methylphosphonate (1.392 g, 11.22 mmol) in THF (20 mL) at −78° C. was slowly added n-butyllithium solution (6.6 mL, 11 mmol, 1.6 M solution in hexane). The mixture was stirred for 30 minutes, after which time a mixture consisting of (S)-ethyl 2-phenylpropanoate (1.0 g, 5.6 mmol) in THF (10 mL) was slowly added, and the mixture stirred at −78° C. for two hours before being allowed to rise to room temperature overnight. The reaction mixture was treated with 5% aqueous $KHSO_4$ and extracted with ethyl acetate three times. The combined organic layer was twice washed with a solution of 50:50 water-brine, dried over sodium sulfate, and concentrated under vacuum. The residue was purified by silica gel chromatography. Elution with ethyl acetate-heptane (80:20 v/v) afforded the title compound (1.03 g, 72%) as a colorless oil; TLC $R_f$ 0.4 (solvent system 80:20 v/v ethyl acetate-heptane); MS (ESI$^+$) nm/z 257.1 (M+H)$^+$; $^1$H NMR (CD$_3$OD) δ 7.37-7.22 (m, 5H), 4.01 (q, J=6.71 Hz, 1H), 3.74-3.69 (m, 6H), 3.27-3.2 (m, 1H), 3.09-2.97 (m, 1H), 1.37-1.34 (m, 3H); $[\alpha]^T_\lambda$=α/cl, $[\alpha]^{21.9}_D$=0.946/(0.01859 g/1.5 mL)(0.5)=+152.6° (c=1.24, CHCl$_3$).

(S)-(+)-dimethyl (3-methyl-2-oxo-4-phenylbutyl)phosphonate (15kb(i))

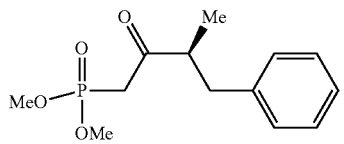 [SMILES: COP(=O)(CC(=O)[C@@H](C)Cc1ccccc1)OC]

(S)-(+)-Dimethyl (3-methyl-2-oxo-4-phenylbutyl)phosphonate was prepared in the same manner as the second alternative preparation of (S)-(+)-dimethyl (3-methyl-2-oxo-6-phenylhexyl)phosphonate (15mb(i)) using the same sequence of reactions except that benzyl bromide was used instead of (3-bromopropyl)benzene. The crude product was purified by silica gel chromatography. Elution with ethyl acetate-heptane (80:20 v/v) afforded the title compound (680 mg) as a colorless oil; TLC $R_f$ 0.35 (solvent system: 80:20 v/v ethyl acetate:heptanes; MS (ESI$^+$) m/z 271.1 (M+H)$^+$; $^1$H-NMR (CDCl$_3$) δ 7.29-7.14 (m, 5H), 3.71 (dd, 6H, J=10.99, 19.04 Hz), 3.12-2.89 (m, 4H), 2.58 (dd, 1H, J=7.69, 13.55 Hz), 1.11 (d, 3H, J=6.96 Hz); $[\alpha]^T_\lambda$=α/cl, $[\alpha]^{21.9}_D$=0.249/(0.01501 g/1.5 mL)(0.5)=+49.8° (c=1, CHCl$_3$).

Preparation of (S)-(+)-dimethyl (3-methyl-2-oxo-5-phenylpentyl)phosphonate (15lb(i))

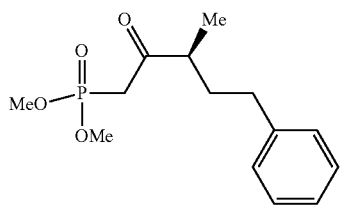 [SMILES: COP(=O)(CC(=O)[C@@H](C)CCc1ccccc1)OC]

(S)-Dimethyl (3-methyl-2-oxo-5-phenylpentyl)phosphonate was prepared in the same manner as the second alternative preparation of (S)-(+)-dimethyl (3-methyl-2-oxo-6-phenylhexyl)phosphonate (15mb(i)) using the same sequence of reactions except that (2-bromoethyl)benzene was used instead of (3-bromopropyl)benzene. The crude product was purified by silica gel chromatography. Elution with ethyl acetate-heptane (50:50 v/v) afforded the title compound (460 mg) as a colorless oil; TLC $R_f$ 0.14 (solvent system: 50:50 v/v ethyl acetate:heptanes); MS (ESI$^+$) m/z 285.1 (M+H)$^+$; $^1$H-NMR (CDCl$_3$) δ 7.30-7.24 (m, 2H), 7.21-7.14 (m, 3H), 3.76 (d, J=14.65 Hz, 3H), 3.76 (d, J=8.06 Hz, 3H), 3.16-3.03 (m, 2H), 2.77 (q, J=6.84 Hz, 1H), 2.64-2.56 (m, 2H), 2.03 (ddt, 1H), 1.16 (d, J=6.96 Hz, 3H); $[\alpha]^T_\lambda$=α/cl, $[\alpha]^{21.9}_D$=0.052/(0.01998 g/1.5 mL)(0.5)=+7.81° (c=1.33, CHCl$_3$).

Preparation of (S)-(+)-dimethyl (3-methyl-2-oxo-7-phenylheptyl)phosphonate (15nb(i))

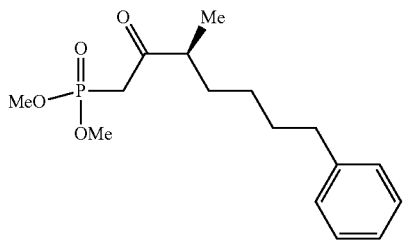 [SMILES: COP(=O)(CC(=O)[C@@H](C)CCCCc1ccccc1)OC]

(S)-Dimethyl (3-methyl-2-oxo-7-phenylheptyl)phosphonate was prepared in the same manner as the second alternative preparation of (S)-(+)-dimethyl (3-methyl-2-oxo-6-phenylhexyl)phosphonate (15mb(i)) using the same sequence of reactions except that (4-bromobutyl)benzene was used instead of (3-bromopropyl)benzene. The crude product was purified by silica gel chromatography. Elution with ethyl acetate-heptane (50:50 v/v) afforded the title compound (2.84 g) as a colorless oil; TLC $R_f$ 0.54 (solvent system: 100 v ethyl acetate); MS (ESI$^+$) m/z 313.1 (M+H)$^+$; $^1$H-NMR (CDCl$_3$) δ 7.22-7.17 (m, 2H), 7.12-7.07 (m, 3H), 3.82-3.68 (m, 6H), 3.07 (s, 1H), 3.01 (s, 1H), 2.71-2.62 (m, 1H), 2.53 (t, J=7.69 Hz, 2H), 1.66-1.47 (m, 4H), 1.28-1.22 (m, 2H), 1.02 (d, J=6.96 Hz, 3H); $[\alpha]^T_\lambda = \alpha/cl$, $[\alpha]^{21.9}_D = 0.052/(0.01998 \text{ g}/1.5 \text{ mL})(0.5) = +7.81°$ (c=1.017, CHCl$_3$).

Preparation of (S)-(+)-dimethyl (3-methyl-2-oxo-8-phenyloctyl)phosphonate (15ob(i))

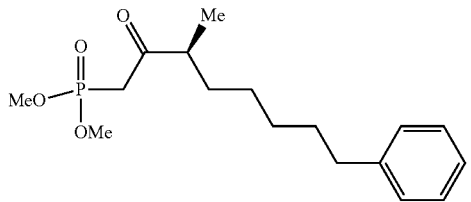 [SMILES: COP(=O)(CC(=O)[C@@H](C)CCCCCc1ccccc1)OC]

(S)-Dimethyl (3-methyl-2-oxo-8-phenyloctyl)phosphonate was prepared in the same manner as the second alternative preparation of (S)-(+)-dimethyl (3-methyl-2-oxo-6-phenylhexyl)phosphonate (15mb(i)) using the same sequence of reactions except that (5-bromopentyl)benzene was used instead of (3-bromopropyl)benzene. The crude product was purified by silica gel chromatography. Elution with ethyl acetate-heptane (50:50 v/v) afforded the title compound (1.06 g) as a colorless oil; TLC $R_f$ 0.22 (solvent system: 50:50 v/v ethyl acetate:heptanes); MS (ESI$^+$) m/z 327.1 (M+H)$^+$; $^1$H-NMR (CDCl$_3$) δ 7.27-7.24 (m, 2H), 7.19-7.14 (m, 3H), 3.79-3.76 (m, 6H), 3.13 (s, 1H), 3.08 (s, 1H), 2.76-2.68 (m, 1H), 2.61-2.56 (m, 2H), 1.68-1.56 (m, 4H), 1.35-1.28 (m, 4H), 1.09 (d, J=6.96 Hz, 3H); $[\alpha]^T_\lambda = \alpha/cl$, $[\alpha]^{21.9}_D = 0.074/(0.01534 \text{ g}/1.5 \text{ mL})(0.5) = +14.10°$ (c=1.02, CHCl$_3$).

Aspects of the present invention may be prepared utilizing a Horner-Emmons-Wadsworth-type procedure, according to the routes described below in Schemes 9 and 10. The coupling of an aldehyde intermediate, such as those for which their preparations are described and illustrated above (13a-f), with an organic phosphonate, such as those that are commercially available or for which their preparations are described and illustrated above (15), by way of Horner-Emmons-Wadsworth olefination reaction, (Scheme 9, Step A) provides an α,β-unsaturated ketone compound intermediate (22a-f). The C15-oxo group may be chemo- and stereoselectively reduced to the corresponding C15-hydroxyl group as stereoisomeric alcohol mixtures (two or more diastereomers, not necessarily of equal quantity) 23a-f (Scheme 9, Step B), which may be subsequently separated by HPLC (Step C) to provide a pure, single C15α-hydroxy diastereomer (24a-f) and a pure, single C15β-hydroxy (25a-f) diastereomers. The ester intermediates resulting from these transformations may be subsequently subjected to deesterification conditions, such as base-catalyzed hydrolysis. Base-catalyzed hydrolysis of the esters provides the corresponding carboxylic acid embodiments (26a-f and 27a-f). Organic β-keto phosphonates bearing a single chiral center, such as any of 15(a-o)b(i-viii) and 15(a-o)c(i-viii), when coupled with aldehydes like 13a-f in Scheme 9, Step A, followed by the stereoselective reduction (Step B), affords a set of four diastereomers which can be separated using HPLC to isolate each of its components (28a-f through 31a-f), C15α-C16β, C15α-C16α, C15α-C$_{16}$β, and C$_{15}$β-C16α as illustrated in Scheme 10. The carboxylic acids (32a-f through 35a-f) of each of these four diastereomers may be obtained by base-catalyzed hydrolysis of the corresponding esters using excess lithium hydroxide, potassium hydroxide or sodium hydroxide. Detailed procedures for preparing the sets of diastereomers are described below.

Scheme 9

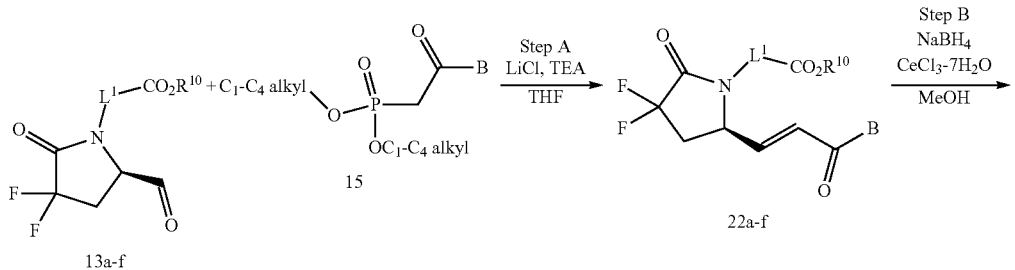

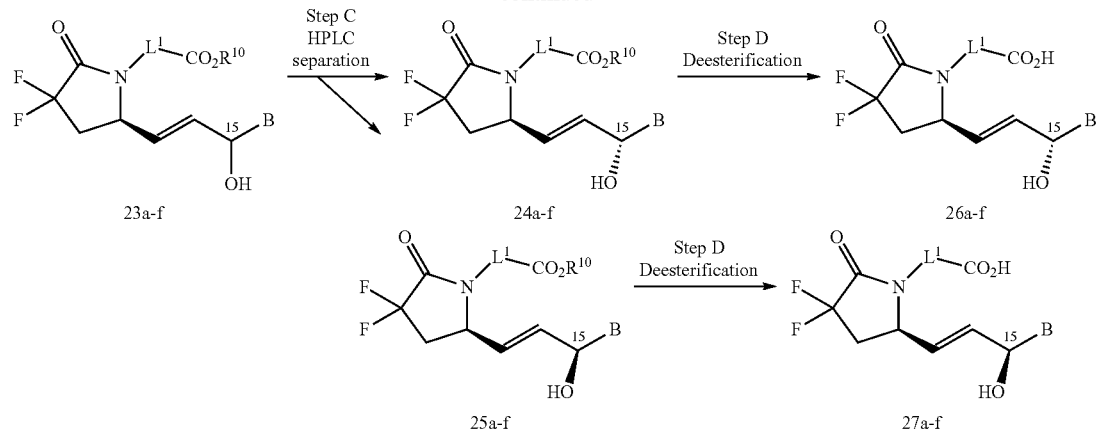
L = a, b, c, d, e, or f, as defined in Scheme 3
Scheme 10
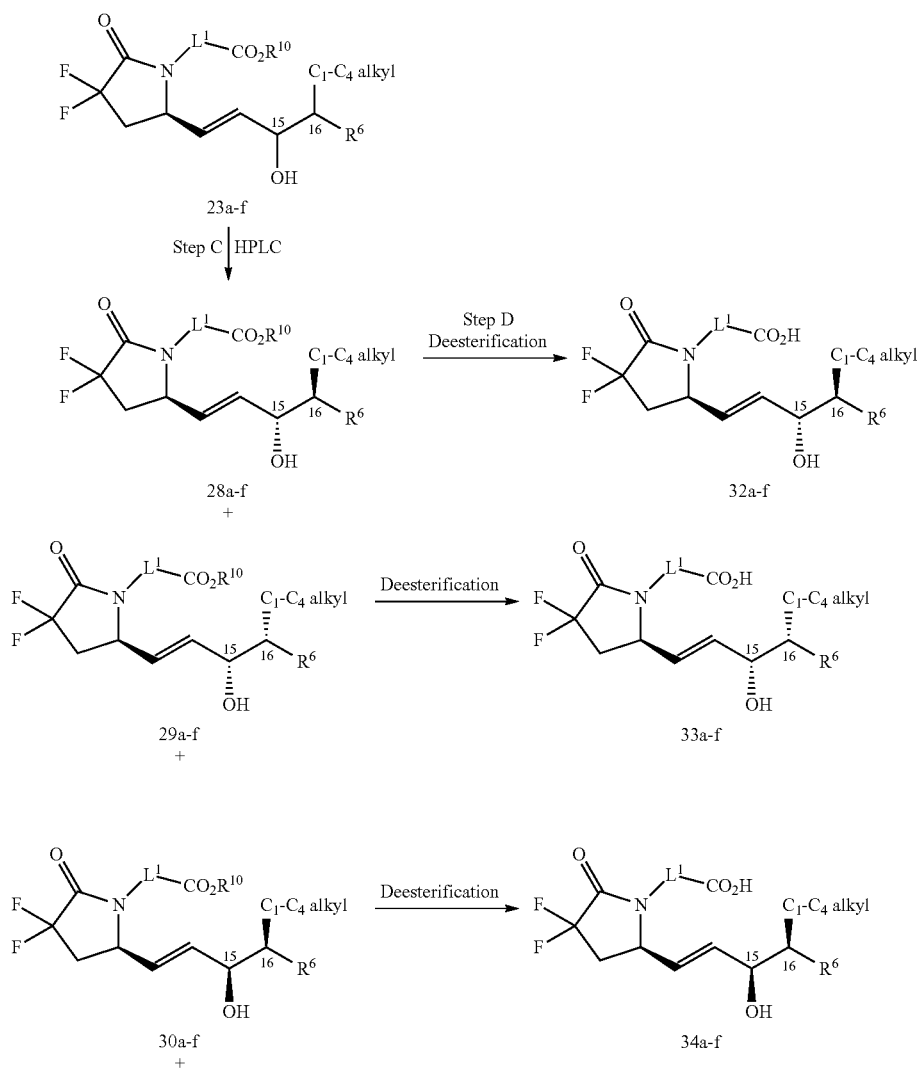

-continued

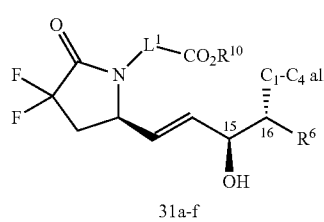

31a-f

Deesterification →

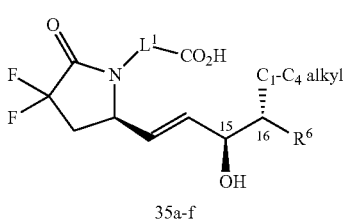

35a-f

Aspects of the present invention may include compounds of formula (I) wherein $R^1$ is a carboxylic acid or carboxylic acid derivative, including, but not limited to, esters, amides, and N-(alkylsulfonyl)amides. Carboxylic acid derivatives may be prepared from the corresponding carboxylic acids by methods known in the art. General methods utilized for carrying out these transformations are illustrated in Scheme 11.

Scheme 11

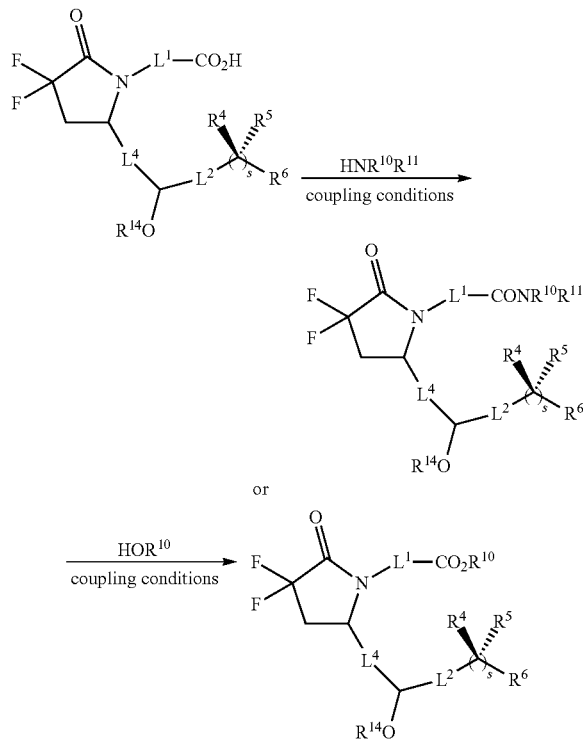

$R^{14}$ is hydrogen or an oxygen protecting group. If $R^{14}$ is an oxygen protecting group, it it may be removed after the amide coupling procedure to provide exemplary embodiments.

Compounds of formula (I), wherein $R^1$ is an amide or N-(alkylsulfonyl)amide, may be prepared from the corresponding compound of formula (I), wherein $R^1$ is a carboxylic acid, by methods known in the art. Methods and strategies for amide bond formation have been reviewed by Montalbetti, G. N. and Falque, V. in *Tetrahedron*, 2005, 61, 10827-10852. Amides and N-(alkylsulfonyl)amides may be prepared from the corresponding carboxylic acids by proceeding through a carboxyl activation and subsequent amide bond formation by methods known in the art. Such procedures may comprise forming a mixture comprising the carboxylic acid (limiting reagent), about one molar equivalent of an amine coupling partner, $HNR^{10}R^{11}$, about one molar equivalent to about a 50% molar excess of a coupling, condensing, or activating agent such as, but not limited to, N,N-dicyclohexylcarbodiimide (DCC), N,N-diisopropylcarbodiimide (DIC), carbonyl diimidazole (CDI), or 1-ethyl-3-(3'-dimethylamino)carbodiimide hydrochloride (EDC or EDAC), benzotriazol-1-yl-oxy-tris-(dimethylamino)-phosphonium hexafluorophosphate (BOP), benzotriazol-1-yl-oxy-tris-pyrrolidino-phosphonium hexafluorophosphate (PyBOP), O-(1H-benzotriazol-1-yl)-N,N,N',N'-tetramethyluronium hexafluorophosphate (HBTU), or O-(1H-benzotriazol-1-yl)-N,N,N',N'-tetramethyluronium tetrafluoroborate (TBTU), and a solvent, such as, but not limited to, DMF, NMP, dichloromethane, THF, 1,4-dioxane, acetonitrile, or DME. The mixture may further comprise about one to two molar equivalents of an amine base such as diisopropylethylamine (DIEA), triethylamine (TEA), or pyridine. The mixtures comprising an amine base may further comprise a catalytic amount of an additive such as DMAP. The mixtures comprising DCC, DIC, or EDC may further comprise about one molar equivalent of HOBt. The mixtures may be stirred at room temperature or may be warmed to promote the coupling reaction for the time necessary to effect completion of the desired coupling reaction. Reactions may be worked up and the amide or N-(alkylsulfonyl)amide product purified and isolated by methods known in the art.

Compounds of formula (I), wherein $R^1$ is an ester, may be prepared from the corresponding compound of formula (I), wherein $R^1$ is a carboxylic acid, by methods known in the art. A variety of methods that may be used is described by Larock, R. C. in *Comprehensive Organic Transformations*, VCH Publishers, Inc., New York, 1989, pp. 966-972, and references therein.

Aspects of the present invention may include compounds of formula (I) wherein $R^1$ is tetrazol-5-yl. Compounds of formula (I), wherein $R^1$ is tetrazol-5-yl, may be prepared from the corresponding compound of formula (I), wherein $R^1$ is cyano, by using conditions and methods known in the art, two of which are illustrated in Scheme 12.

Scheme 12

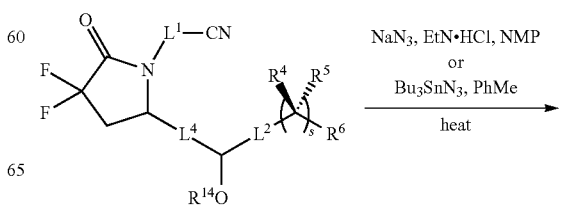

147

-continued

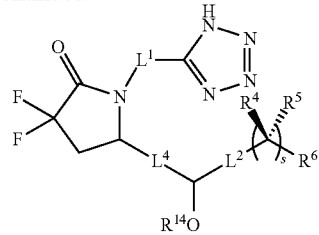

$R^{14}$ is hydrogen or an oxygen protecting group. If $R^{14}$ is an oxygen protecting group, it may be removed after the amide coupling procedure to provide exemplary embodiments.

Aspects of the present invention may include compounds of formula (I) wherein $L^4$ is an ethylene group. These compounds may be obtained by subjecting compounds of formula (I), wherein $L^4$ is ethenylene or ethynylene, to catalytic hydrogenation conditions, such as those known in the art. Catalytic hydrogenation methods have been reviewed by Rylander, P. N. in *Hydrogenation Methods*, Academic Press: New York, 1985, Chapters 2-3.

Aspects of the present invention may further include compounds of formula (I), wherein $L^4$ is —CH$_2$—CH$_2$— (ethylene), and $L^1$ comprises at least one moiety or functional group, such as an alkenyl, alkynyl, or halogen group, that may reduce under typical catalytic hydrogenation conditions. Preparation of these compounds may comprise a synthetic route wherein the lower chain is first installed onto the difluorolactam ring scaffold by, for example, an olefination or alkynylation reaction, as described herein, and the resulting 8+lower chain intermediate, wherein $L^4$ is ethenylene or ethynylene, is subsequently reduced by catalytic hydrogenation to provide the corresponding 8+lower chain intermediate wherein $L^4$ is ethylene. Subsequent installation and, if necessary, chemical modification, of the upper chain would provide the corresponding compound of formula (I) wherein $L^4$ is ethylene.

The following Examples were prepared based on the reaction Schemes 9, Steps A-D and Scheme 10, Steps C and D.

Examples 1A-1I

Step A: Preparation of methyl 7-((5R)-3,3-difluoro-5-((E)-4-methyl-3-oxooct-1-en-6-yn-1-yl)-2-oxopyrrolidin-1-yl)heptanoate

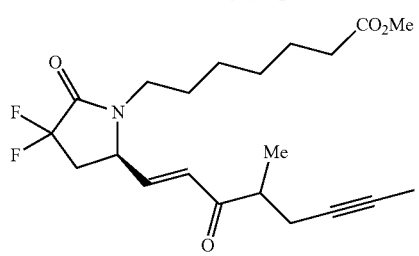 [SMILES: CC#CCC(C)C(=O)/C=C/[C@H]1CC(F)(F)C(=O)N1CCCCCCC(=O)OC]

To an ice cooled mixture consisting of dimethyl (3-methyl-2-oxohept-5-yn-1-yl)phosphonate (76 mg, 0.33 mmol) and (R)-methyl 7-(3,3-difluoro-5-formyl-2-oxopyrrolidin-1-yl) heptanoate (13a, 80 mg, 0.28 mmol) in THF (3 mL) was added lithium chloride (35 mg, 0.83 mmol) followed by triethylamine (55 µL, 0.42 mmol) and the reaction stirred overnight, warming to room temperature. The reaction was quenched with the addition of a saturated solution of aqueous ammonium chloride and extracted with ethyl acetate. The combined organic phase was dried over sodium sulfate and concentrated to a golden oil. The residue was purified by silica gel chromatography. Elution with methanol:dichloromethane (1:300 v/v) to afford the title compound (76.6 mg) as a clear oil; TLC $R_f$ 0.80 (solvent system: 5:95 v/v methanol-dichloromethane); $^1$H-NMR (CDCl$_3$) δ 6.7-6.5 (m, 1H), 6.4 (d, 1H), 4.3-4.2 (m, 2H), 3.0-2.8 (m, 1H), 2.8-2.6 (m, 1H) 2.5-2.2 (m, 6H), 1.8 (s, 3H), 1.7-1.4 (m, 4H), 1.4-1.2 (m, 4H), 1.2 (d, 3H); MS (ESI$^+$) m/z 398.1 (M+1), 420.1 (M+Na), (ESI$^-$) m/z 396.1 (M−1).

Step B: Preparation of four-diastereomer mixture methyl 7-((5R)-3,3-difluoro-5-((E)-3-hydroxy-4-methyloct-1-en-6-yn-1-yl)-2-oxopyrrolidin-1-yl)heptanoate

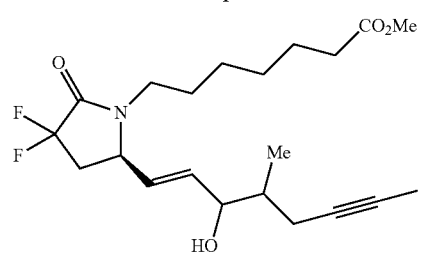

To a −40° C. solution consisting of methyl 7-((5R)-3,3-difluoro-5-((E)-4-methyl-3-oxooct-1-en-6-yn-1-yl)-2-oxopyrrolidin-1-yl)heptanoate (76 mg, 0.20 mmol) in methanol (5 mL) was added cerium chloride heptahydrate (75 mg, 0.20 mmol) in one portion. The reaction mixture was stirred for 15 minutes, and cooled to −78° C. for 20 minutes. Sodium borohydride (15 mg, 0.40 mmol) was added and the reaction was stirred for 3 hours, quenched with equal parts water and saturated ammonium chloride and warmed to room temperature. The reaction mixture was extracted with ethyl acetate. The combined organic phase was dried over sodium sulfate and concentrated to a cloudy white oil. The residue was purified by silica gel chromatography. Elution with methanol-dichloromethane (1:200 v:v) to afford the title compound (70 mg) as a clear oil. $R_f$ 0.50 (solvent system: 5:95 v/v methanol:dichloromethane).

Step C: Preparation of methyl 7-((R)-3,3-difluoro-5-((3S,4S,E)-3-hydroxy-4-methyloct-1-en-6-yn-1-yl)-2-oxopyrrolidin-1-yl)heptanoate (Example 1A), methyl 7-((R)-3,3-difluoro-5-((3S,4R,E)-3-hydroxy-4-methyloct-1-en-6-yn-1-yl)-2-oxopyrrolidin-1-yl) heptanoate (Example 1B), methyl 7-((R)-3,3-difluoro-5-((3R,4S,E)-3-hydroxy-4-methyloct-1-en-6-yn-1-yl)-2-oxopyrrolidin-1-yl)heptanoate (Example 1D) and methyl 7-((R)-3,3-difluoro-5-((3R,4R,E)-3-hydroxy-4-methyloct-1-en-6-yn-1-yl)-2-oxopyrrolidin-1-yl)heptanoate (Example 1E)

Example 1A

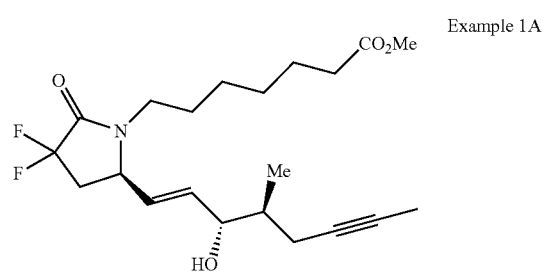

-continued

Example 1B

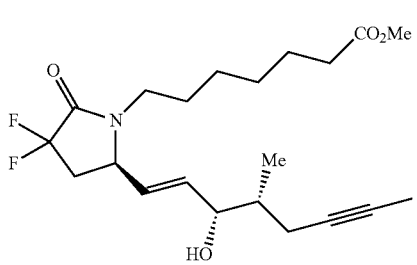 [SMILES: CC#CCC(C)C(O)/C=C/[C@H]1CC(F)(F)C(=O)N1CCCCCCC(=O)OC]

Example 1C

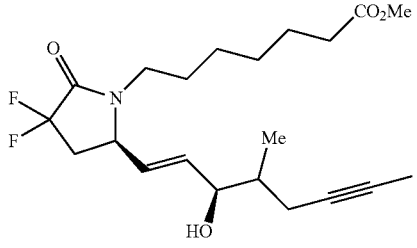

From the stereoisomeric mixture comprising the four-diastereomer mixture methyl 7-((5R)-3,3-difluoro-5-((E)-3-hydroxy-4-methyloct-1-en-6-yn-1-yl)-2-oxopyrrolidin-1-yl)heptanoate (70 mg, prepared in Step B of this Example above) were separated the single isomers methyl 7-((R)-3,3-difluoro-5-((3S,4S,E)-3-hydroxy-4-methyloct-1-en-6-yn-1-yl)-2-oxopyrrolidin-1-yl)heptanoate (Example 1A) and methyl 7-((R)-3,3-difluoro-5-((3S,4R,E)-3-hydroxy-4-methyloct-1-en-6-yn-1-yl)-2-oxopyrrolidin-1-yl)heptanoate (Example 1B), and the diastereomeric mixture (at C16) methyl 7-((5R)-3,3-difluoro-5-((3R,E)-3-hydroxy-4-methyloct-1-en-6-yn-1-yl)-2-oxopyrrolidin-1-yl)heptanoate (Example 1C) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (96:4 v/v).

Example 1A (7.6 mg); a clear oil; prep HPLC retention time 24.1-25.0 minutes; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Example 1B (5.8 mg); a clear oil; prep HPLC retention time 22.5-23.6 minutes; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Example 1D

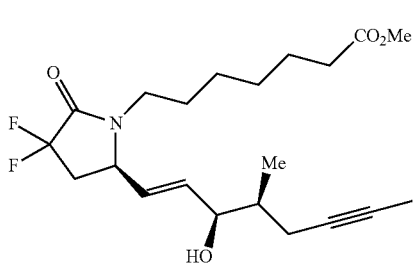

Example 1E

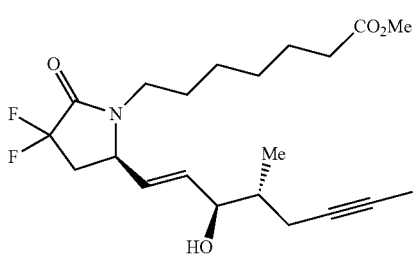

The diastereomeric mixture methyl 7-((5R)-3,3-difluoro-5-((3R,E)-3-hydroxy-4-methyloct-1-en-6-yn-1-yl)-2-oxopyrrolidin-1-yl)heptanoate (Example 1C) was separated to afford the pure diastereomers methyl 7-((R)-3,3-difluoro-5-((3R,4S,E)-3-hydroxy-4-methyloct-1-en-6-yn-1-yl)-2-oxopyrrolidin-1-yl)heptanoate (Example 1D), and methyl 7-((R)-3,3-difluoro-5-((3R,4R,E)-3-hydroxy-4-methyloct-1-en-6-yn-1-yl)-2-oxopyrrolidin-1-yl)heptanoate (Example 1E), by prep HPLC.

Agilent Semi-Prep instrument; ultraviolet detector at 205 nm; Luna Silica 5μ 250×10 mm column; mobile phase of heptanes-ethanol (98:2 v/v).

Example 1D (15.5 mg); a clear oil; HPLC retention time 48.4-55.7 min; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Example 1E (4.3 mg); a clear oil; HPLC retention time 42.7-47.3 min; $^1$H-NMR (CDCl$_3$) δ 6.9-6.8 (m, 1H), 6.6-6.5 (m, 1H), 4.2-4.1 (m, 1H), 3.7 (s, 1H), 3.6-3.5 (m, 1H) 3.1-2.9 (m, 1H), 2.8-2.6 (br, 1H) 2.4-2.0 (m, 7H), 1.8 (s, 3H), 1.7-1.4 (m, 4H), 1.4-1.2 (m, 4H), 1.0-0.9 (d, 3H); MS (ESI$^+$) m/z 400.2 (M+1), 422.1 (M+Na).

Step D1: Preparation of 7-((R)-3,3-difluoro-5-((3S,4S,E)-3-hydroxy-4-methyloct-1-en-6-yn-1-yl)-2-oxopyrrolidin-1-yl)heptanoic acid (Example 1F)

Example 1F

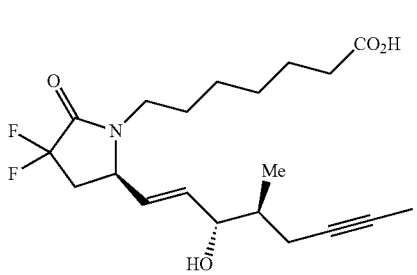

To a solution of methyl 7-((R)-3,3-difluoro-5-((3S,4S,E)-3-hydroxy-4-methylnon-1-en-6-yn-1-yl)-2-oxopyrrolidin-1-yl)heptanoate (Example 1A, 5.6 mg, 0.014 mmol) in methanol (0.15 mL) was added lithium hydroxide (1M in H$_2$O, 0.06 mL, 0.06 mmol) and the reaction mixture was stirred overnight. The reaction was quenched with the addition of KHSO$_4$ and brine and the organic material was extracted with ethyl acetate. The organic phase was concentrated, redissolved in ethyl acetate, filtered, and concentrated to give 5.7 mg of a clear oil; TLC R$_f$ 0.45 (solvent system: 90:10:1 v/v dichloromethane-methanol-acetic acid); $^1$H-NMR (CDCl$_3$) δ 6.9-6.8 (m, 1H), 6.6-6.5 (m, 1H), 4.4-4.3 (m, 1H), 4.2-4.1 (m, 1H), 3.6-3.5 (m, 1H) 3.1-2.9 (m, 1H), 2.8-2.6 (br, 1H) 2.4-2.0 (m, 7H), 1.9-1.7 (s, 3H), 1.7-1.4 (m, 4H), 1.4-1.1 (m, 4H), 1.0-0.9 (d, 3H); MS (ESI$^+$) m/z 368.1 (M+1), 408.1 (M+Na).

Step D2: Preparation of 7-((R)-3,3-difluoro-5-((3S, 4R,E)-3-hydroxy-4-methyloct-1-en-6-yn-1-yl)-2-oxopyrrolidin-1-yl)heptanoic acid (Example 1G)

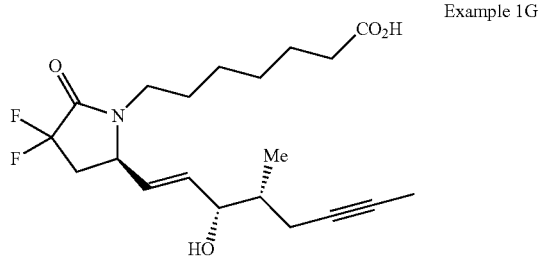 [SMILES: CC#CC[C@@H](C)[C@H](O)/C=C/[C@H]1CC(F)(F)C(=O)N1CCCCCCC(=O)O]

Example 1G

Hydrolysis of methyl 7-((R)-3,3-difluoro-5-((3S,4R,E)-3-hydroxy-4-methyloct-1-en-6-yn-1-yl)-2-oxopyrrolidin-1-yl)heptanoate, done in the same manner as Step D1 above, afforded 5.4 mg of a clear oil; TLC R$_f$ 0.45 (solvent system: 90:10:1 v/v dichloromethane-methanol-acetic acid); $^1$H-NMR (CDCl$_3$) δ 6.9-6.8 (m, 1H), 6.6-6.5 (m, 1H), 4.4-4.3 (m, 1H), 4.2-4.1 (m, 1H), 3.6-3.5 (m, 1H) 3.1-2.9 (m, 1H), 2.8-2.6 (br, 1H) 2.4-2.0 (m, 7H), 1.9-1.7 (s, 3H), 1.7-1.4 (m, 4H), 1.4-1.1 (m, 4H), 1.0-0.9 (d, 3H); MS (ESI$^+$) m/z 368.1 (M+1), 408.1 (M+Na).

Step D3: Preparation of 7-((R)-3,3-difluoro-5-((3R, 4S,E)-3-hydroxy-4-methyloct-1-en-6-yn-1-yl)-2-oxopyrrolidin-1-yl)heptanoic acid (Example 1H)

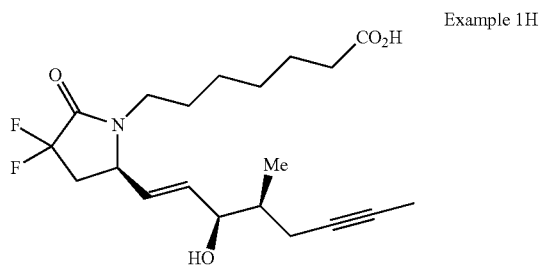 [SMILES: CC#CC[C@H](C)[C@@H](O)/C=C/[C@H]1CC(F)(F)C(=O)N1CCCCCCC(=O)O]

Example 1H

Step D4: Preparation of 7-((R)-3,3-difluoro-5-((3R, 4R,E)-3-hydroxy-4-methyloct-1-en-6-yn-1-yl)-2-oxopyrrolidin-1-yl)heptanoic acid (Example 1I)

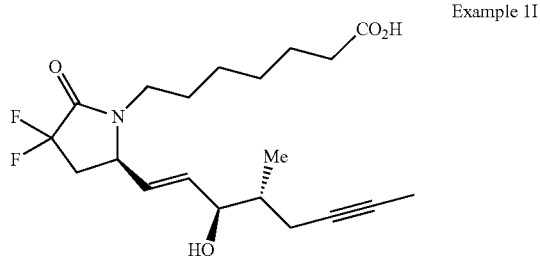 [SMILES: CC#CC[C@@H](C)[C@@H](O)/C=C/[C@H]1CC(F)(F)C(=O)N1CCCCCCC(=O)O]

Example 1I

The hydrolysis of each of the following carboxylic ester Examples were performed in the same manner as described in Example 1, Step D1, using aqueous lithium hydroxide (though in some cases sodium hydroxide or potassium hydroxide can and was used instead of lithium hydroxide) to afford the analogous carboxylic acid Examples.

Examples 2A-2D

Step A, B and C, Preparation of methyl 7-((R)-3,3-difluoro-5-((3S,4S,E)-3-hydroxy-4-methylnon-1-en-6-yn-1-yl)-2-oxopyrrolidin-1-yl)heptanoate (Example 2A) and methyl 7-((R)-3,3-difluoro-5-((3R, 4S,E)-3-hydroxy-4-methylnon-1-en-6-yn-1-yl)-2-oxopyrrolidin-1-yl)heptanoate (Example 2B)

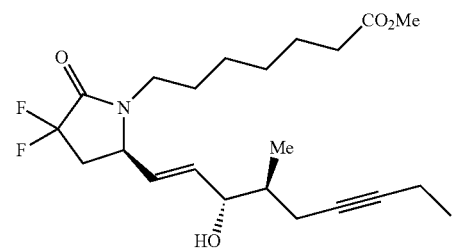

Example 2A

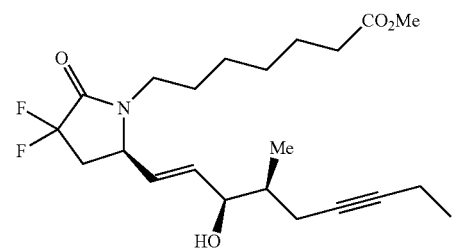

Example 2B

Methyl 7-((5R)-3,3-difluoro-5-((4S,E)-3-hydroxy-4-methylnon-1-en-6-yn-1-yl)-2-oxopyrrolidin-1-yl)heptanoate (61 mg) was prepared by the method described in Example 1, Steps A and B, except that (S)-(+)-dimethyl (3-methyl-2-oxooct-5-yn-1-yl)phosphonate (15bc(i)) was used instead of (+_)-dimethyl (3-methyl-2-oxohept-5-yn-1-yl)phosphonate (15ab(i)/15ac(i)) in Step A.

Step C: The pure diastereomers of Example 2A and Example 2B were isolated following separation by prep HPLC. Agilent Semi-Prep instrument; ultraviolet detector at 233 nm; Chiralpak IA 250×4.6 mm column; mobile phase of heptane-ethanol (98:2 v/v).

Example 2A (8.1 mg); a clear oil; HPLC retention time 57 min; MS (ESI$^+$) m/z 414.1 (M+1) (ESI$^-$) m/z 412.1 (M−1).

Example 2B (20.5 mg); a clear oil; HPLC retention time 42 min; MS (ESI$^+$) m/z 414.1 (M+1) (ESI$^-$) m/z 412.1 (M−1).

Step B: Alternative preparation of methyl 7-((R)-3, 3-difluoro-5-((3S,4S,E)-3-hydroxy-4-methylnon-1-en-6-yn-1-yl)-2-oxopyrrolidin-1-yl)heptanoate (Example 2A) and methyl 7-((R)-3,3-difluoro-5-((3S, 4R,E)-3-hydroxy-4-methylnon-1-en-6-yn-1-yl)-2-oxopyrrolidin-1-yl)heptanoate (Example 2B)

To a solution consisting of methyl 7-((R)-3,3-difluoro-5-((S,E)-4-methyl-3-oxonon-1-en-6-yn-1-yl)-2-oxopyrrolidin-1-yl)heptanoate (169 mg, 0.460 mmol) and (R)—Corey-Bakshi-Shibata catalyst (1 M in THF, 0.46 mmol) in dichloromethane (100 mL) at −40° C. was added catechol borane (1 M in THF, 0.46 mmol) dropwise over 10 minutes. The reaction mixture was stirred overnight, warming to room temperature, then quenched with 1 N HCl (10 mL). The reaction mixture was extracted with ethyl acetate. The combined organic phase was dried over sodium sulfate and concentrated to a cloudy brown oil. The residue was purified by silica gel chromatography. Elution with methanol:dichloromethane (1:200 v:v) afforded a mixture of 2A and 2B (52 mg) as a clear oil; $R_f$ 0.65 (solvent system: 7:93 v/v methanol:dichloromethane).

The diastereomers were separated and purified diastereomer 2A (15.2 mg) was isolated using the prep HPLC method described in Step C of the original preparation of this compound above.

Step D1: Preparation of 7-((R)-3,3-difluoro-5-((3S,4S,E)-3-hydroxy-4-methylnon-1-en-6-yn-1-yl)-2-oxopyrrolidin-1-yl)heptanoic acid (Example 2C)

Example 2C

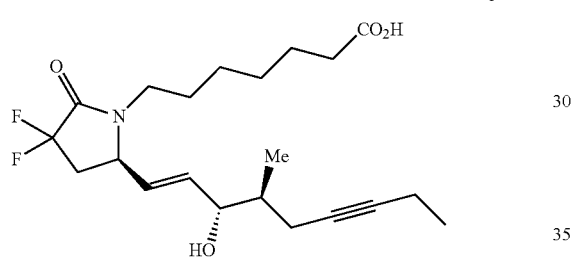

5.9 mg of a clear oil; TLC $R_f$ 0.45 (solvent system: 95:5:1 v/v dichloromethane-methanol-acetic acid); $^1$H-NMR (CDCl$_3$) δ 5.9-5.8 (m, 1H), 5.6-5.5 (m, 1H), 4.2-4.1 (m, 2H), 3.7-3.5 (m, 1H), 3.1-2.9 (m, 1H), 2.8-2.7 (br s, 1H), 2.4-2.3 (t, 2H), 2.3-2.1 (m, 5H), 1.9-1.8 (m, 1H), 1.7-1.5 (m, 5H), 1.4-1.2 (m, 4H), 1.1 (t, 3H), 1.0 (d, 3H); $^{19}$F-NMR (CDCl$_3$) δ −103.5 (d, 1F), −105.5 (d, 1F); MS (ESI$^+$) m/z 400 (M+1), MS (ESI$^-$) m/z 398 (M−1).

Step D2: Preparation of 7-((R)-3,3-difluoro-5-((3R,4S,E)-3-hydroxy-4-methylnon-1-en-6-yn-1-yl)-2-oxopyrrolidin-1-yl)heptanoic acid (Example 2D)

Example 2D

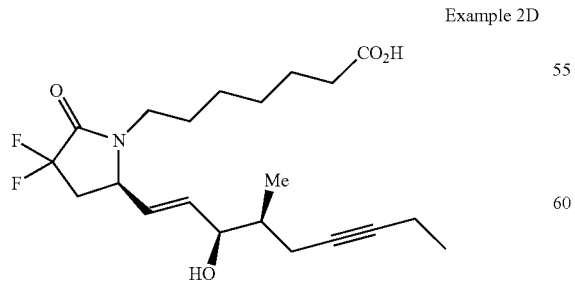

14.8 mg of a clear oil; TLC $R_f$ 0.45 (solvent system: 95:5:1 v/v dichloromethane-methanol-acetic acid); MS (ESI$^+$) m/z 400 (M+1), MS (ESI$^-$) m/z 398 (M−1).

Example 3

Methyl 7-((5R)-3,3-difluoro-5-((E)-3-hydroxy-4-methyldec-1-en-6-yn-1-yl)-2-oxopyrrolidin-1-yl)heptanoate

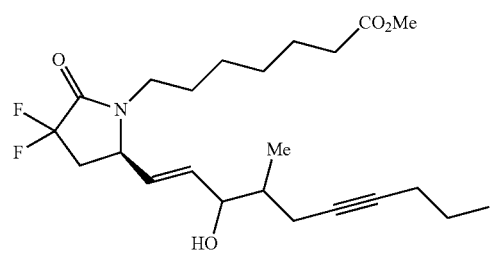 [SMILES: CCCC#CCC(C)C(O)/C=C/[C@H]1CC(F)(F)C(=O)N1CCCCCCC(=O)OC]

Example 4

Methyl 7-((5R)-3,3-difluoro-5-((E)-3-hydroxy-4-methyl-7-phenylhept-1-en-6-yn-1-yl)-2-oxopyrrolidin-1-yl)heptanoate

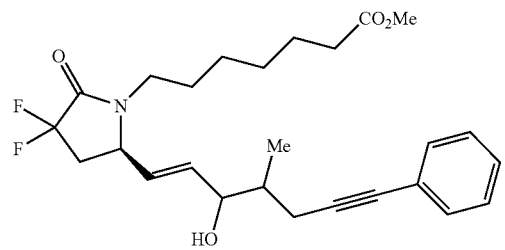 [SMILES: COC(=O)CCCCCCN1C(=O)C(F)(F)C[C@@H]1/C=C/C(O)C(C)CC#Cc1ccccc1]

Example 5

Methyl 7-((5R)-3,3-difluoro-5-((E)-3-hydroxy-4-methyloct-1-en-1-yl)-2-oxopyrrolidin-1-yl)heptanoate

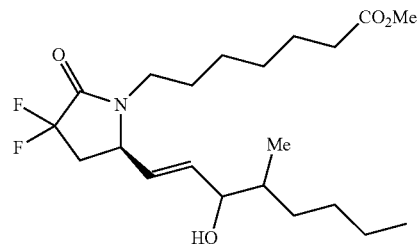 [SMILES: CCCCC(C)C(O)/C=C/[C@H]1CC(F)(F)C(=O)N1CCCCCCC(=O)OC]

Examples 6A-6F

Steps A, B, and C: Preparation of methyl 7-((R)-3,3-difluoro-5-((3S,4S,E)-3-hydroxy-4-methyl-7-phenylhept-1-en-1-yl)-2-oxopyrrolidin-1-yl)heptanoate (Example 6A), methyl 7-((R)-3,3-difluoro-5-((3S,4R,E)-3-hydroxy-4-methyl-7-phenylhept-1-en-1-yl)-2-oxopyrrolidin-1-yl)heptanoate (Example 6B), and methyl 7-((5R)-3,3-difluoro-5-((3R,E)-3-hydroxy-4-methyl-7-phenylhept-1-en-1-yl)-2-oxopyrrolidin-1-yl)heptanoate (Example 6C)

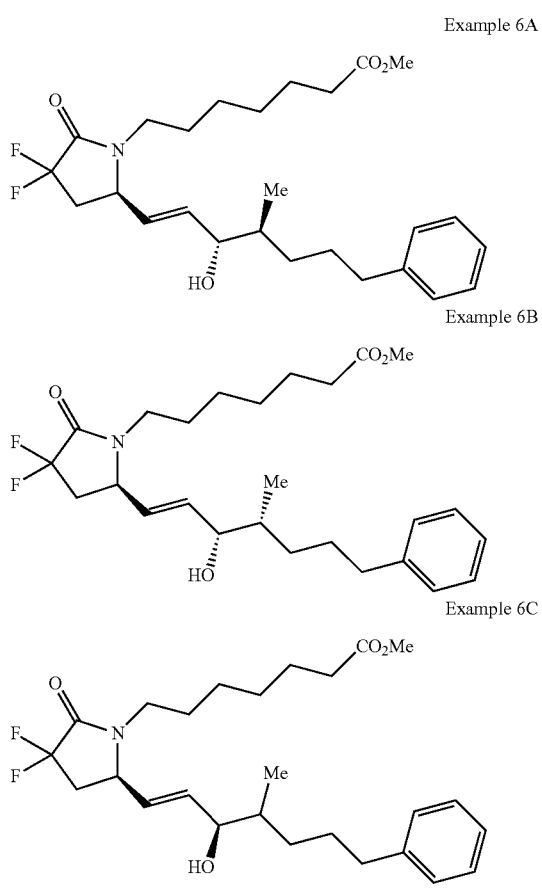

Example 6A

Example 6B

Example 6C

Methyl 7-((5R)-3,3-difluoro-5-((E)-3-hydroxy-4-methyl-7-phenylhept-1-en-1-yl)-2-oxopyrrolidin-1-yl)heptanoate was prepared by the method described in Example 1, Steps A and B, except that (±)-dimethyl (3-methyl-2-oxo-6-phenylhexyl)phosphonate (15mb(i)/15mc(i)) was used instead of (±)-dimethyl (3-methyl-2-oxohept-5-yn-1-yl)phosphonate (15ab(i)/15ac(i)) in Step A.

Step C: From the stereoisomeric mixture comprising the four-diastereomer mixture methyl 7-((5R)-3,3-difluoro-5-((E)-3-hydroxy-4-methyl-7-phenylhept-1-en-1-yl)-2-oxopyrrolidin-1-yl)heptanoate were separated the single isomers methyl 7-((R)-3,3-difluoro-5-((3S,4S,E)-3-hydroxy-4-methyl-7-phenylhept-1-en-1-yl)-2-oxopyrrolidin-1-yl)heptanoate (Example 6A) and methyl 7-((R)-3,3-difluoro-5-((3S,4R,E)-3-hydroxy-4-methyl-7-phenylhept-1-en-1-yl)-2-oxopyrrolidin-1-yl)heptanoate (Example 6B), and the diastereomeric mixture (at C16) methyl 7-((5R)-3,3-difluoro-5-((3R,E)-3-hydroxy-4-methyl-7-phenylhept-1-en-1-yl)-2-oxopyrrolidin-1-yl)heptanoate (Example 6C) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (96:4 v/v).

Example 6A (3.3 mg); a clear oil; prep HPLC retention time 20.9-21.8 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI$^+$) m/z 466.4 (M+1), 488.5 (M+Na).

Example 6B (10.1 mg); a clear oil; prep HPLC retention time 19.6-20.7 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI$^+$) m/z 466.4 (M+1), 488.5 (M+Na).

Example 6C (57.7 mg); a clear oil; prep HPLC retention time 16.2-18.6 minutes; $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 1H), 3.7 (s, 3H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (d, 3H); MS (ESI$^+$) nm/z 466.4 (M+1), 488.5 (M+Na).

Step D1: Preparation of 7-((R)-3,3-difluoro-5-((3S,4S,E)-3-hydroxy-4-methyl-7-phenylhept-1-en-1-yl)-2-oxopyrrolidin-1-yl)heptanoic acid (Example 6D)

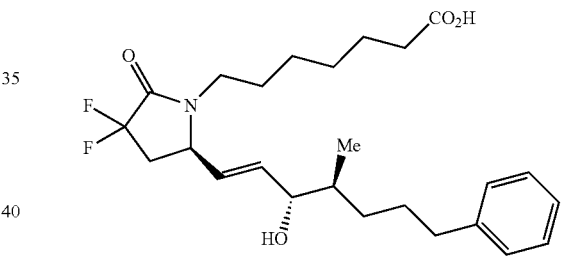

3.0 mg of a clear oil; TLC R$_f$ 0.45 (solvent system: 90:10:1 v/v dichloromethane-methanol-acetic acid); $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI$^+$) m/z 466.2 (M+1), 488.2 (M+Na).

Step D2: Preparation of 7-((R)-3,3-difluoro-5-((3S,4R,E)-3-hydroxy-4-methyl-7-phenylhept-1-en-1-yl)-2-oxopyrrolidin-1-yl)heptanoic acid (Example 6E)

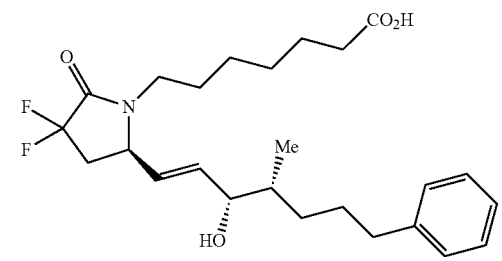 [SMILES: C[C@H](CCCc1ccccc1)[C@H](O)/C=C/[C@H]1CC(F)(F)C(=O)N1CCCCCCC(=O)O]

7.7 mg of a clear oil; TLC $R_f$ 0.45 (solvent system: 90:10:1 v/v dichloromethane-methanol-acetic acid); H-NMR (CDCl$_3$) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI$^+$) m/z 466.2 (M+1), 488.2 (M+Na).

Step D3: Preparation of 7-((5R)-3,3-difluoro-5-((3R,E)-3-hydroxy-4-methyl-7-phenylhept-1-en-1-yl)-2-oxopyrrolidin-1-yl)heptanoic acid (Example 6F)

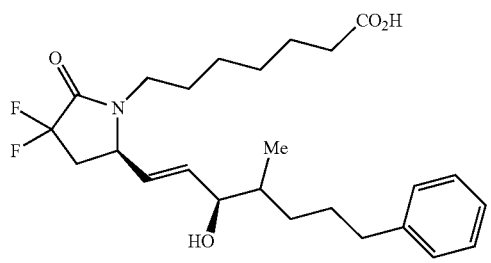 [SMILES: CC(CCCc1ccccc1)[C@@H](O)/C=C/[C@H]1CC(F)(F)C(=O)N1CCCCCCC(=O)O]

8.9 mg of a clear oil; TLC $R_f$ 0.45 (solvent system: 90:10:1 v/v dichloromethane-methanol-acetic acid); $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br, 1H), 2.6 (t, 2H), 2.4-2.0 (m, 6H), 1.8-1.4 (m, 7H), 1.4-1.0 (m, 6H), 0.9 (dt, 3H); MS (ESI$^+$) m/z 466.2 (M+1), 488.2 (M+Na).

Example 7

Methyl 7-((5R)-3,3-difluoro-5-((E)-3-hydroxynon-1-en-6-yn-1-yl)-2-oxopyrrolidin-1-yl)heptanoate

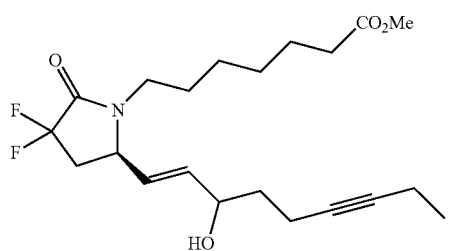 [SMILES: CCC#CCCC(O)/C=C/[C@H]1CC(F)(F)C(=O)N1CCCCCCC(=O)OC]

Example 8

Methyl 7-((5R)-3,3-difluoro-5-((E)-3-hydroxy-7-phenylhept-1-en-6-yn-1-yl)-2-oxopyrrolidin-1-yl)heptanoate

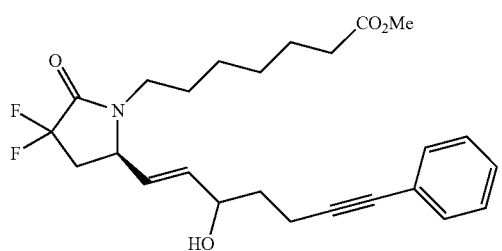 [SMILES: COC(=O)CCCCCCN1C(=O)C(F)(F)C[C@@H]1/C=C/C(O)CCC#Cc1ccccc1]

Examples 9A-9D

Steps A, B, and C: Preparation of methyl 7-((R)-3,3-difluoro-5-((S,E)-3-hydroxyoct-1-en-1-yl)-2-oxopyrrolidin-1-yl)heptanoate (Example 9A) and methyl 7-((R)-3,3-difluoro-5-((R,E)-3-hydroxyoct-1-en-1-yl)-2-oxopyrrolidin-1-yl)heptanoate (Example 9B)

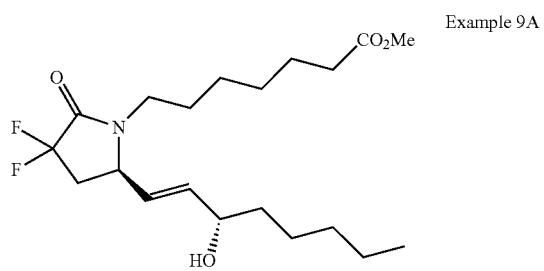

Example 9A

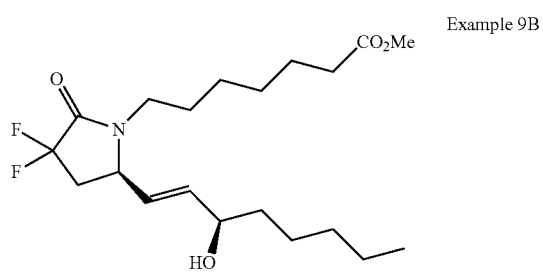

Example 9B

Methyl 7-((5R)-3,3-difluoro-5-((E)-3-hydroxyoct-1-en-1-yl)-2-oxopyrrolidin-1-yl)heptanoate was prepared by the method described in Examples 1, Steps A and B, except that dimethyl (2-oxoheptyl)phosphonate (15ga) was used instead of (±)-dimethyl (3-methyl-2-oxohept-5-yn-1-yl)phosphonate (15ab(i)/15ac(i)) in Step A.

Step C: From the diastereomeric mixture methyl 7-((5R)-3,3-difluoro-5-((E)-3-hydroxyoct-1-en-1-yl)-2-oxopyrrolidin-1-yl)heptanoate were separated the single isomers methyl 7-((R)-3,3-difluoro-5-((S,E)-3-hydroxyoct-1-en-1-yl)-2-oxopyrrolidin-1-yl)heptanoate (Example 9A) and methyl 7-((R)-3,3-difluoro-5-((R,E)-3-hydroxyoct-1-en-1-yl)-2-oxopyrrolidin-1-yl)heptanoate (Example 9B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (93:7 v/v).

Example 9A (21.6 mg); a clear oil; prep HPLC retention time 12.1-12.9 minutes; $^1$H-NMR (CDCl$_3$) δ 6.9-6.8 (m, 1H), 6.6-6.4 (m, 1H), 4.3-4.1 (m, 2H), 3.7 (s, 3H), 3.6-3.5 (m, 1H), 3.1-2.9 (m, 1H), 2.8-2.6 (m, 1H), 2.4-2.1 (m, 4H), 2.0-1.7 (br, 1H) 1.7-1.4 (m, 6H), 1.4-1.2 (m, 10H), 0.9 (t, 3H); MS (ESI$^+$) m/z 390.2 (M+1).

Example 9B (46.5 mg); a clear oil; prep HPLC retention time 10.6-11.5 minutes; 1H-NMR (CDCl$_3$) δ 6.9-6.8 (m, 1H), 6.6-6.4 (m, 1H), 4.3-4.1 (m, 2H), 3.7 (s, 3H), 3.6-3.5 (m, 1H), 3.1-2.9 (m, 1H), 2.8-2.6 (m, 1H), 2.4-2.1 (m, 4H), 2.0-1.7 (br, 1H) 1.7-1.4 (m, 6H), 1.4-1.2 (m, 10H), 0.9 (t, 3H); MS (ESI$^+$) m/z 390.2 (M+1).

Step D1: Preparation of 7-((R)-3,3-difluoro-5-((S,E)-3-hydroxyoct-1-en-1-yl)-2-oxopyrrolidin-1-yl)heptanoic acid (Example 9C)

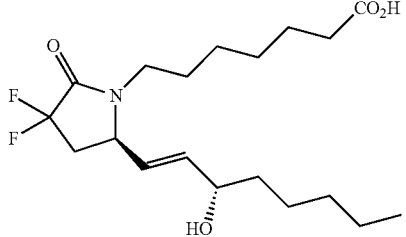 [SMILES: CCCCC[C@H](O)/C=C/[C@H]1CC(F)(F)C(=O)N1CCCCCCC(=O)O]

14.5 mg of a clear oil; TLC $R_f$ 0.40 (solvent system: 90:10:1 v/v dichloromethane-methanol-acetic acid); $^1$H-NMR (CDCl$_3$) δ 6.9-6.8 (m, 1H), 6.5-6.4 (m, 1H), 4.2-4.0 (m, 2H), 3.6-3.5 (m, 1H), 3.1-3.0 (m, 1H), 2.8-2.6 (m, 1H), 2.4-2.0 (m, 4H), 1.7-1.5 (m, 6H), 1.5-1.0 (m, 10H), 0.9 (t, 3H); MS (ESI$^+$) m/z 376.2 (M+1), 398.1 (M+Na).

Step D2: Preparation of 7-((R)-3,3-difluoro-5-((R,E)-3-hydroxyoct-1-en-1-yl)-2-oxopyrrolidin-1-yl)heptanoic acid (Example 9D)

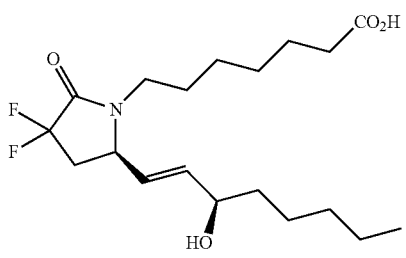 [SMILES: CCCCC[C@@H](O)/C=C/[C@H]1CC(F)(F)C(=O)N1CCCCCCC(=O)O]

14.0 mg of a clear oil; TLC $R_f$ 0.40 (solvent system: 90:10:1 v/v dichloromethane-methanol-acetic acid); $^1$HNMR (CDCl$_3$) δ 6.9-6.8 (m, 1H), 6.5-6.4 (m, 1H), 4.2-4.0 (m, 2H), 3.6-3.5 (m, 1H), 3.1-3.0 (m, 1H), 2.8-2.6 (m, 1H), 2.4-2.0 (m, 4H), 1.7-1.5 (m, 6H), 1.5-1.0 (m, 10H), 0.9 (t, 3H); MS (ESI$^+$) m/z 376.2 (M+1), 398.1 (M+Na).

Examples 10A-10D

Steps A, B, and C: Preparation of methyl 7-((R)-3,3-difluoro-5-((S,E)-3-hydroxy-7-phenylhept-1-en-1-yl)-2-oxopyrrolidin-1-yl)heptanoate (Example 10A) and methyl 7-((R)-3,3-difluoro-5-((R,E)-3-hydroxy-7-phenylhept-1-en-1-yl)-2-oxopyrrolidin-1-yl)heptanoate Example 10A

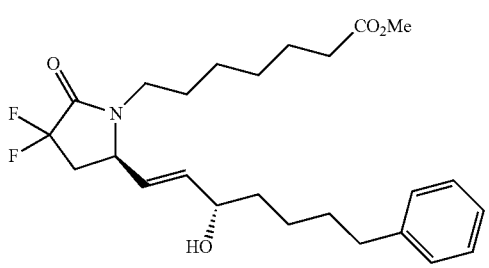 [SMILES: O=C(O)CCCCCCN1C(=O)C(F)(F)C[C@@H]1/C=C/[C@@H](O)CCCCc1ccccc1]

Example 10B

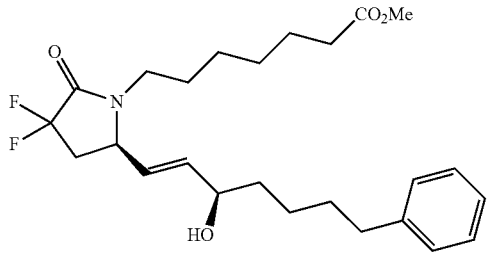 [SMILES: O=C(O)CCCCCCN1C(=O)C(F)(F)C[C@@H]1/C=C/[C@H](O)CCCCc1ccccc1]

Methyl 7-((5R)-3,3-difluoro-5-((E)-3-hydroxy-7-phenyl-hept-1-en-1-yl)-2-oxopyrrolidin-1-yl)heptanoate was prepared by the method described in Examples 1, Steps A and B, except that dimethyl (2-oxo-6-phenylhexyl)phosphonate (15ma) was used instead of (±)-dimethyl (3-methyl-2-oxo-hept-5-yn-1-yl)phosphonate (15ab(i)/15ac(i)) in Step A.

Step C: From the diastereomeric mixture methyl 7-((5R)-3,3-difluoro-5-((E)-3-hydroxy-7-phenylhept-1-en-1-yl)-2-oxopyrrolidin-1-yl)heptanoate were separated the single isomers methyl 7-((R)-3,3-difluoro-5-((S,E)-3-hydroxy-7-phenylhept-1-en-1-yl)-2-oxopyrrolidin-1-yl)heptanoate (Example 10A) and methyl 7-((R)-3,3-difluoro-5-((R,E)-3-hydroxy-7-phenylhept-1-en-1-yl)-2-oxopyrrolidin-1-yl)heptanoate (Example 10B) by prep HPLC. The separations were performed on an Agilent Semi-Prep instrument equipped with an ultraviolet detector at 205 nm and using ultraviolet detector at 205 nm; Luna Silica 5 250×10 mm column eluting with a mobile phase of heptanes-ethanol (93:7 v/v).

Example 10A (14.4 mg); a clear oil; prep HPLC retention time 15.8-17.0 minutes; $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.65 (s, 3H), 3.6-3.5 (m, 1H), 3.0-2.9 (m, 1H), 2.6 (t, 3H), 2.3 (t, 3H), 1.9-1.7 (br, 1H), 1.7-1.5 (m, 8H) 1.4-1.2 (m, 6H); $^{19}$F-NMR (CDCl$_3$) δ 8-103.5 (d, 1F), −105.5 (d, 1F); MS (ESI$^+$) m/z 452.2 (M+1) 474.2 (M+Na).

Example 10B (42.2 mg); a clear oil; prep HPLC retention time 13.7-15.1 minutes; $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.65 (s, 3H), 3.6-3.5 (m, 1H), 3.0-2.9 (m, 1H), 2.6 (t, 3H), 2.3 (t, 3H), 1.9-1.7 (br, 1H), 1.7-1.5 (m, 8H) 1.4-1.2 (m, 6H); 19F-NMR (CDCl$_3$) δ −103.5 (d, 1F), −105.5 (d, 1F); MS (ESI$^+$) m/z 452.2 (M+1) 474.2 (M+Na).

Step D1: Preparation of 7-((R)-3,3-difluoro-5-((S,E)-3-hydroxy-7-phenylhept-1-en-1-yl)-2-oxopyrrolidin-1-yl)heptanoic acid (Example 10C)

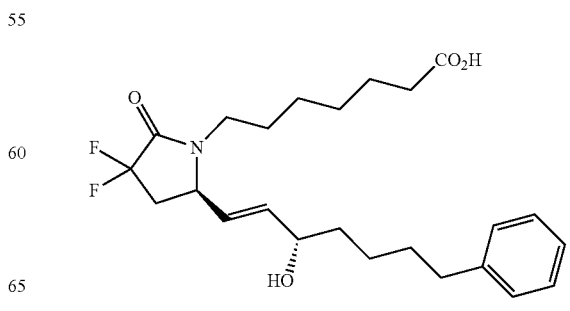

16.5 mg of a clear oil; TLC $R_f$ 0.35 (solvent system: 90:10:1 v/v dichloromethane-methanol-acetic acid); $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.6=3.5 (m, 1H), 3.0-2.9 (m, 1H), 2.6 (t, 3H), 2.2 (t, 3H), 2.2-2.1 (m, 1H), 1.7-1.5 (m, 8H), 1.5-1.1 (m, 6H); $^{19}$F-NMR (CDCl$_3$) δ −103.5 (d, 1F), −105.5 (d, 1F); MS (ES$^-$) m/z 436.2 (M−1).

Step D2: Preparation of 7-((R)-3,3-difluoro-5-((R, E)-3-hydroxy-7-phenylhept-1-en-1-yl)-2-oxopyrrolidin-1-yl)heptanoic acid (Example 10D)

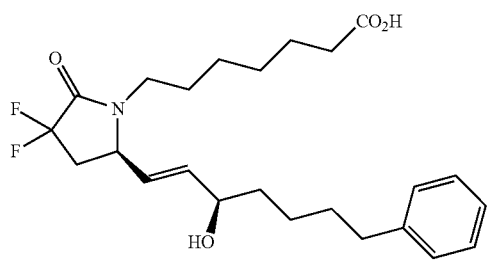

30.3 mg of a clear oil; TLC $R_f$ 0.35 (solvent system: 90:10:1 v/v dichloromethane-methanol-acetic acid); $^1$H-NMR (CDCl$_3$) δ 7.3-7.2 (m, 2H), 7.2-7.1 (m, 3H), 5.9-5.8 (m, 1H), 5.5-5.4 (m, 1H), 4.2-4.1 (m, 1H), 4.1-4.0 (m, 1H), 3.6-3.5 (m, 1H), 3.0-2.9 (m, 1H), 2.6 (t, 3H), 2.2 (t, 3H), 2.2-2.1 (m, 1H), 1.7-1.5 (m, 8H), 1.5-1.1 (m, 6H); $^{19}$F-NMR (CDCl$_3$) δ −103.5 (d, 1F), −105.5 (d, 1F); MS (ESI$^-$) m/z 436.2 (M−1).

Example 11

4-(2-((R)-3,3-Difluoro-5-((3S,4S,E)-3-hydroxy-4-methyloct-1-en-6-yn-1-yl)-2-oxopyrrolidin-1-yl)ethyl)benzoic acid

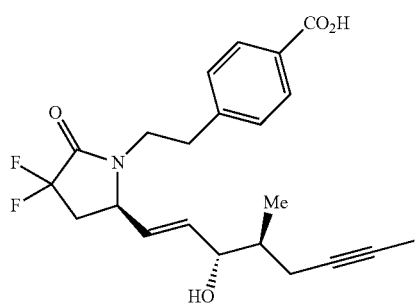 [SMILES: CC#CC[C@H](C)[C@H](O)/C=C/[C@H]1CC(F)(F)C(=O)N1CCc1ccc(C(=O)O)cc1]

Examples 12A-12F

Steps A, B, and C: Preparation of methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate (Example 12A), methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate (Example 12B), and methyl 4-(2-((5R)-3,3-difluoro-5-((3R,E)-3-hydroxy-4-methylnon-1-en-6-yn-1-yl)-2-oxopyrrolidin-1-yl)ethyl)benzoate (Example 12C)

Example 12A

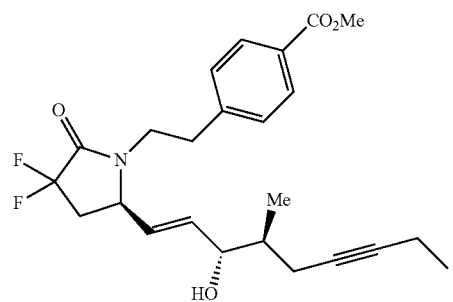 [SMILES: CCC#CC[C@H](C)[C@H](O)/C=C/[C@H]1CC(F)(F)C(=O)N1CCc1ccc(C(=O)O)cc1]

Example 12B

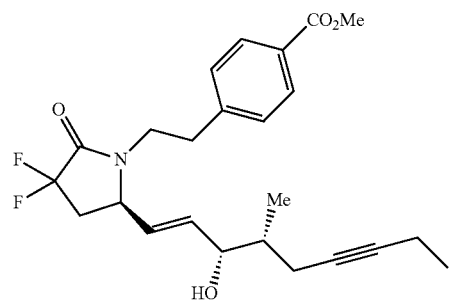

Example 12C

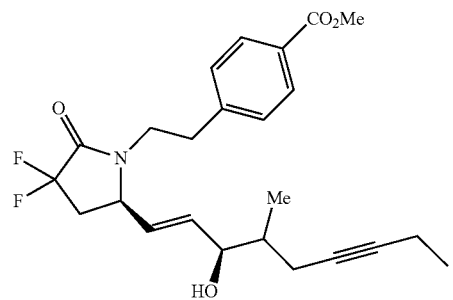

Methyl 4-(2-((5R)-3,3-difluoro-5-((E)-3-hydroxy-4-methylnon-1-en-6-yn-1-yl)-2-oxopyrrolidin-1-yl)ethyl)benzoate was prepared by the method described in Example 1, Steps A and B, except that (R)-methyl 4-(2-(3,3-difluoro-5-formyl-2-oxopyrrolidin-1-yl)ethyl)benzoate (13b) was used instead of (R)-methyl 7-(3,3-difluoro-5-formyl-2-oxopyrrolidin-1-yl) heptanoate (13a) and (±)-dimethyl (3-methyl-2-oxooct-5-yn-1-yl)phosphonate (15bb(i)/15bc(i)) was used instead of (±)-dimethyl (3-methyl-2-oxohept-5-yn-1-yl) phosphonate (15ab(i)/15ac(i)) in Step A.

Step C: From the stereoisomeric mixture comprising the four-diastereomer mixture methyl 4-(2-((5R)-3,3-difluoro-5-((E)-3-hydroxy-4-methylnon-1-en-6-yn-1-yl)-2-oxopyrrolidin-1-yl)ethyl)benzoate were separated the single isomers methyl 4-(2-((R)-3,3-difluoro-5-((3S,4S,E)-3-hydroxy-4-methylnon-1-en-6-yn-1-yl)-2-oxopyrrolidin-1-yl)ethyl)benzoate (Example 12A) and methyl 4-(2-((R)-3,3-difluoro-5-((3S,4R,E)-3-hydroxy-4-methylnon-1-en-6-yn-1-yl)-2-oxopyrrolidin-1-yl)ethyl)benzoate (Example 12B), and the diastereomeric mixture (at C16) methyl 4-(2-((5R)-3,3-difluoro-5-((3R,E)-3-hydroxy-4-methylnon-1-en-6-yn-1-yl)-2-oxopyrrolidin-1-yl)ethyl)benzoate (Example 12C) by prep HPLC.

Agilent Semi-Prep instrument; ultraviolet detector at 205 nm; Luna Silica 5µ 250 mm×10 mm column; mobile phase of heptane-ethanol (98:2 v/v).

Example 12A (6.0 mg); a clear oil; HPLC retention time 78.9-83.9 minutes; $^1$H-NMR (CDCl$_3$) δ 8.0 (d, 2H), 7.3-7.2 (m, 2H), 5.7-5.6 (m, 1H), 5.5-5.4 (m, 1H), 4.2-4.1 (m, 1H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Example 12B (7.0 mg); a clear oil; HPLC retention time 72.7-77.6 minutes; $^1$H-NMR (CDCl$_3$) δ 8.0 (d, 2H), 7.3-7.2 (m, 2H), 5.7-5.6 (m, 1H), 5.5-5.4 (m, 1H), 4.3-4.2 (m, 1H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Example 12C (20.0 mg); a clear oil; HPLC retention time 59.6-68.8 minutes; $^1$H-NMR (CDCl$_3$) δ 8.0 (d, 2H), 7.3-7.2 (m, 2H), 5.7-5.6 (m, 1H), 5.5-5.4 (m, 1H), 4.3-4.2 (m, 0.5H), 4.2-4.1 (m, 0.5H), 3.9 (s, 3H), 3.9-3.8 (m, 1H), 3.8-3.7 (m, 1H), 3.3-3.2 (m, 1H), 3.1-3.0 (m, 1H), 3.0-2.9 (m, 1H), 2.7-2.5 (m, 1H), 2.2-2.1 (m, 6H), 1.2-1.1 (t, 3H), 1.0-0.9 (d, 3H); MS (ESI$^+$) m/z 456.1 (M+Na).

Step D1: Preparation of 4-(2-((R)-3,3-difluoro-5-((3S,4S,E)-3-hydroxy-4-methylnon-1-en-6-yn-1-yl)-2-oxopyrrolidin-1-yl)ethyl)benzoic acid (Example 12D)

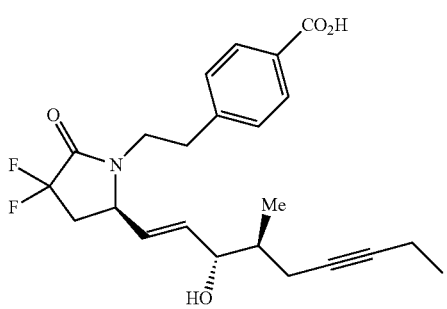

5.0 mg as a colorless oil; TLC R$_f$ 0.30 (solvent system: 96:4:1 v/v dichloromethane-methanol-acetic acid); $^1$H-NMR (CDCl$_3$) δ 8.0 (d, 2H), 7.4-7.3 (m, 2H), 5.9-5.8 (m, 1H), 5.5-5.4 (m, 1H), 4.2-4.0 (m, 2H), 3.9-3.8 (m, 1H), 3.4-3.3 (m, 1H), 3.1-3.0 (m, 1H), 3.0-2.9 (m, 1H), 2.8-2.7 (m, 1H), 2.3-2.2 (m, 2H), 2.2-2.1 (m, 2H), 2.1-2.0 (m, 1H), 1.8-1.7 (m, 1H) 1.2-1.1 (t, 3H), 1.0-0.9 (d, 3H); MS (ESI$^+$) m/z 442.1 (M+Na), (ESI$^-$) m/z 418.2.

Step D2: Preparation of 4-(2-((R)-3,3-difluoro-5-((3S,4R,E)-3-hydroxy-4-methylnon-1-en-6-yn-1-yl)-2-oxopyrrolidin-1-yl)ethyl)benzoic acid (Example 12E)

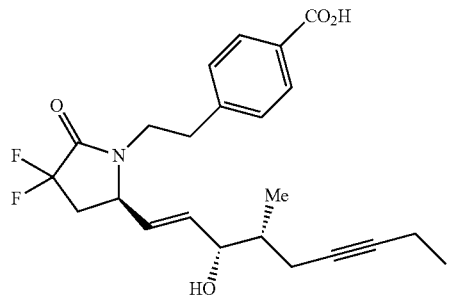 [SMILES: CCC#CC[C@@H](C)[C@H](O)/C=C/[C@H]1CC(F)(F)C(=O)N1CCc1ccc(C(=O)O)cc1]

4.8 mg as a colorless oil; TLC R$_f$ 0.30 (solvent system: 96:4:1 v/v dichloromethane-methanol-acetic acid); $^1$H-NMR (CDCl$_3$) δ 8.0 (d, 2H), 7.4-7.3 (m, 2H), 5.9-5.8 (m, 1H), 5.5-5.4 (m, 1H), 4.2-4.0 (m, 2H), 3.9-3.8 (m, 1H), 3.4-3.3 (m, 1H), 3.1-3.0 (m, 1H), 3.0-2.9 (m, 1H), 2.8-2.7 (m, 1H), 2.3-2.2 (m, 2H), 2.2-2.1 (m, 2H), 2.1-2.0 (m, 1H), 1.8-1.7 (m, 1H) 1.2-1.1 (t, 3H), 1.0-0.9 (d, 3H); MS (ESI$^+$) m/z 442.1 (M+Na), (ESI$^-$) m/z 418.2.

Step D3: Preparation of 4-(2-((5R)-3,3-difluoro-5-((3R,E)-3-hydroxy-4-methylnon-1-en-6-yn-1-yl)-2-oxopyrrolidin-1-yl)ethyl)benzoic acid (Example 12F)

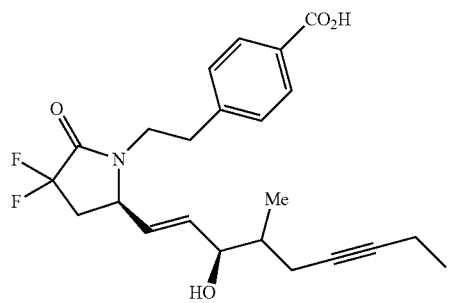 [SMILES: CCC#CCC(C)[C@@H](O)/C=C/[C@H]1CC(F)(F)C(=O)N1CCc1ccc(C(=O)O)cc1]

14.6 mg as a colorless oil; TLC R$_f$ 0.30 (solvent system: 96:4:1 v/v dichloromethane-methanol-acetic acid); $^1$H-NMR (CDCl$_3$) δ 8.0 (2H, d), 7.4-7.3 (2H, m), 5.9-5.8 (1H, m), 5.5-5.4 (1H, m), 4.2-4.0 (2H, m), 3.9-3.8 (1H, m), 3.4-3.3 (1H, m), 3.1-3.0 (1H, m), 3.0-2.9 (1H, m), 2.8-2.7 (1H, m), 2.3-2.2 (2H, m), 2.2-2.1 (2H, m), 2.1-2.0 (1H, m), 1.8-1.7 (1H, m) 1.2-1.1 (3H, t), 1.0-0.9 (3H, d); MS (ESI$^+$) m/z 442.1 (M+Na), (ESI$^-$) m/z 418.2.

Example 13D 4-(2-((R)-3,3-Difluoro-5-((3S,4S,E)-3-hydroxy-4-methyldec-1-en-6-yn-1-yl)-2-oxopyrrolidin-1-yl)ethyl)benzoic acid

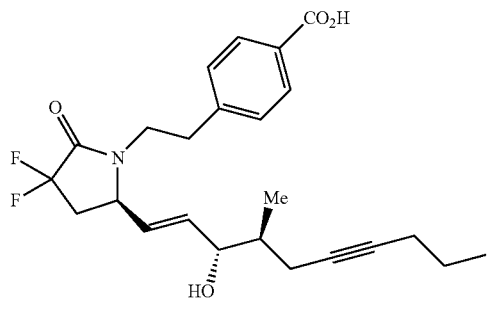 [SMILES: CCCC#CC[C@H](C)[C@H](O)/C=C/[C@H]1CC(F)(F)C(=O)N1CCc1ccc(C(=O)O)cc1]

Example 14D 4-(2-((R)-3,3-Difluoro-5-((3S,4S,E)-3-hydroxy-4-methyl-7-phenylhept-1-en-6-yn-1-yl)-2-oxopyrrolidin-1-yl)ethyl)benzoic acid

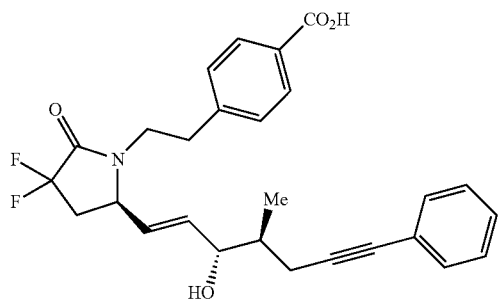 [SMILES: C[C@@H](CC#Cc1ccccc1)[C@H](O)/C=C/[C@H]1CC(F)(F)C(=O)N1CCc1ccc(C(=O)O)cc1]

Example 15D 4-(2-((R)-3,3-difluoro-5-((3S,4S,E)-3-hydroxy-4-methyloct-1-en-1-yl)-2-oxopyrrolidin-1-yl)ethyl)benzoic acid

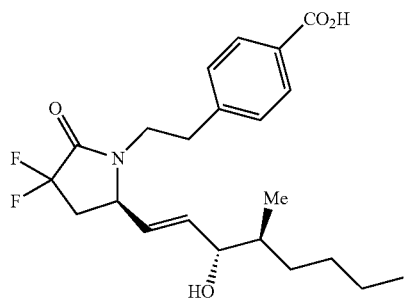 [SMILES: CCCC[C@H](C)[C@H](O)/C=C/[C@H]1CC(F)(F)C(=O)N1CCc1ccc(C(=O)O)cc1]

Example 16D 4-(2-((R)-3,3-Difluoro-5-((3S,4S,E)-3-hydroxy-4-methyl-7-phenylhept-1-en-1-yl)-2-oxopyrrolidin-1-yl)ethyl)benzoic acid

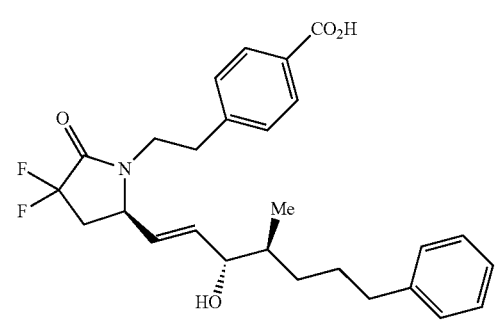 [SMILES: C[C@@H](CCCc1ccccc1)[C@H](O)/C=C/[C@H]1CC(F)(F)C(=O)N1CCc1ccc(C(=O)O)cc1]

Example 17C 4-(2-((R)-3,3-Difluoro-5-((S,E)-3-hydroxyoct-1-en-6-yn-1-yl)-2-oxopyrrolidin-1-yl)ethyl)benzoic acid

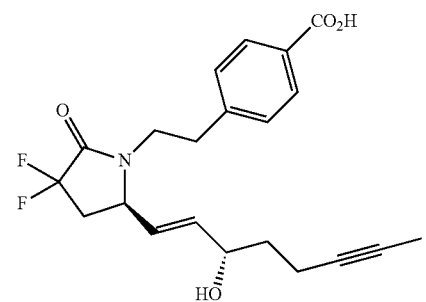 [SMILES: CC#CCC[C@H](O)/C=C/[C@H]1CC(F)(F)C(=O)N1CCc1ccc(C(=O)O)cc1]

Example 18C 4-(2-((R)-3,3-Difluoro-5-((S,E)-3-hydroxynon-1-en-6-yn-1-yl)-2-oxopyrrolidin-1-yl)ethyl)benzoic acid

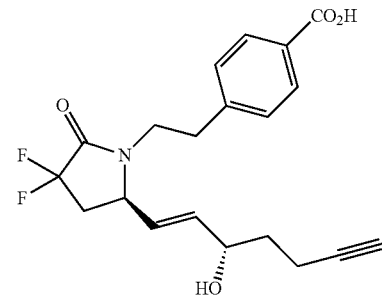

Example 19C 4-(2-((R)-3,3-Difluoro-5-((S,E)-3-hydroxydec-1-en-6-yn-1-yl)-2-oxopyrrolidin-1-yl)ethyl)benzoic acid

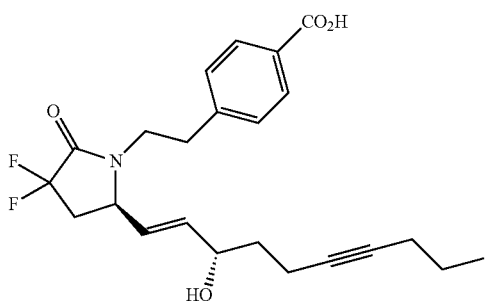 [SMILES: CCCC#CCC[C@H](O)/C=C/[C@H]1CC(F)(F)C(=O)N1CCc1ccc(C(=O)O)cc1]

Example 20C 4-(2-((R)-3,3-Difluoro-5-((S,E)-3-hydroxy-7-phenyl-hept-1-en-6-yn-1-yl)-2-oxopyrrolidin-1-yl)ethyl)benzoic acid

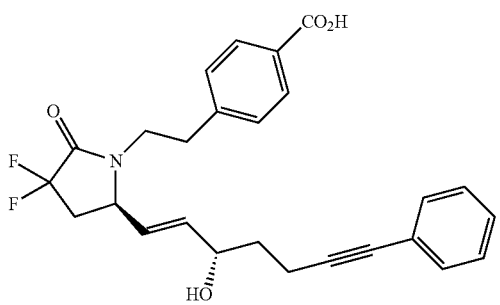 [SMILES: O=C(O)c1ccc(CCN2C(=O)C(F)(F)C[C@@H]2/C=C/[C@@H](O)CCC#Cc2ccccc2)cc1]

Examples 21A-21D

Steps A, B, and C: Preparation of methyl 4-(2-((R)-3,3-difluoro-5-((S,E)-3-hydroxyoct-1-en-1-yl)-2-oxopyrrolidin-1-yl)ethyl)benzoate (Example 21A) and methyl 4-(2-((R)-3,3-difluoro-5-((R,E)-3-hydroxyoct-1-en-1-yl)-2-oxopyrrolidin-1-yl)ethyl)benzoate (Example 21B)

Example 21A

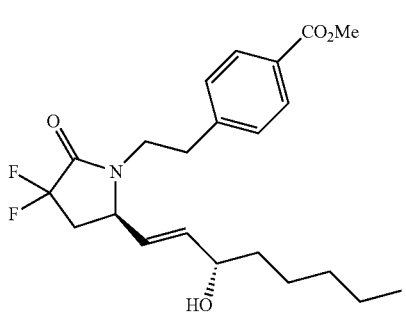 [SMILES: CCCCC[C@H](O)/C=C/[C@H]1CC(F)(F)C(=O)N1CCc1ccc(C(=O)O)cc1]

Example 21B

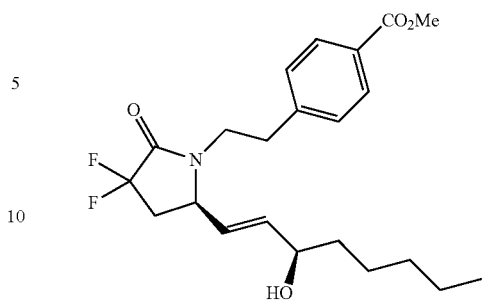

Methyl 4-(2-((R)-3,3-difluoro-5-((S,E)-3-hydroxyoct-1-en-1-yl)-2-oxopyrrolidin-1-yl)ethyl)benzoate was prepared by the method described in Example 9, Steps A and B, except that (R)-methyl 4-(2-(3,3-difluoro-5-formyl-2-oxopyrrolidin-1-yl)ethyl)benzoate (13b) was used instead of (R)-methyl 7-(3,3-difluoro-5-formyl-2-oxopyrrolidin-1-yl)heptanoate (13a) in Step A.

Step C: From the diastereomeric mixture methyl 4-(2-((5R)-3,3-difluoro-5-((E)-3-hydroxyoct-1-en-1-yl)-2-oxopyrrolidin-1-yl)ethyl)benzoate were separated the single isomers methyl 4-(2-((R)-3,3-difluoro-5-((S,E)-3-hydroxyoct-1-en-1-yl)-2-oxopyrrolidin-1-yl)ethyl)benzoate (Example 21A) and methyl 4-(2-((R)-3,3-difluoro-5-((R,E)-3-hydroxyoct-1-en-1-yl)-2-oxopyrrolidin-1-yl)ethyl)benzoate (Example 21B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (94:6 v/v).

Example 21A (12 mg); a clear oil; prep HPLC retention time 15.9-16.3 minutes; $^1$H-NMR (CDCl$_3$) δ 8.0 (d, 2H), 7.3-7.2 (m, 2H), 5.7-5.6 (m, 1H), 5.4-5.3 (m, 1H), 4.2-4.1 (m, 1H), 3.9 (s, 3H), 3.9-3.8 (m, 1H), 3.8-3.7 (m, 1H), 3.3-3.2 (m, 1H), 3.0-2.9 (m, 2H), 2.6-2.5 (m, 1H), 2.2-2.1 (m, 1H), 1.6 (br, 1H), 1.6-1.5 (m, 2H), 1.4-1.3 (m, 6H), 0.95-0.85 (m, 3H); MS (ESI$^+$) m/z 432.2 (M+Na).

Example 21B (24.0 mg); a clear oil; prep HPLC retention time 14.2-14.6 minutes; $^1$H-NMR (CDCl$_3$) δ 8.0 (d, 2H), 7.3-7.2 (m, 2H), 5.7-5.6 (m, 1H), 5.4-5.3 (m, 1H), 4.2-4.1 (m, 1H), 3.9 (s, 3H), 3.9-3.8 (m, 1H), 3.8-3.7 (m, 1H), 3.3-3.2 (m, 1H), 3.0-2.9 (m, 2H), 2.6-2.5 (m, 1H), 2.2-2.1 (m, 1H), 1.6 (br, 1H), 1.6-1.5 (m, 2H), 1.4-1.3 (m, 6H), 0.95-0.85 (m, 3H); MS (ESI$^+$) m/z 432.2 (M+Na).

Step D1: Preparation of 4-(2-((R)-3,3-difluoro-5-((S,E)-3-hydroxyoct-1-en-1-yl)-2-oxopyrrolidin-1-yl)ethyl)benzoic acid (Example 21C)

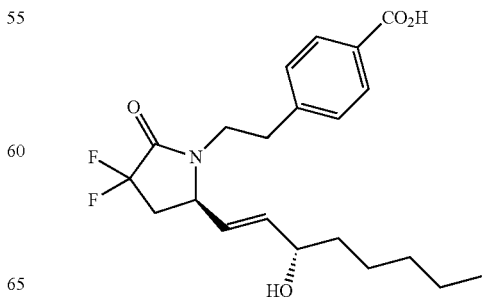

8.0 mg of a clear oil; TLC R$_f$ 0.35 (solvent system: 96:4:1 v/v dichloromethane-methanol-acetic acid); $^1$H-NMR (CDCl$_3$) δ 8.0 (d, 2H), 7.8 (d, 2H) 5.9-5.8 (m, 1H), 5.4-5.3 (m, 1H), 4.1-4.0 (m, 2H), 3.8-3.7 (m, 1H), 3.4-3.3 (m, 1H), 3.0-2.9 (m, 2H), 2.8-2.7 (m, 1H), 2.3-2.2 (m, 1H), 1.6-1.2 (m, 9H), 1.0-0.9 (m, 3H); MS (ESI$^-$) m/z 394 (M−1).

Step D2: Preparation of 4-(2-((R)-3,3-difluoro-5-((R,E)-3-hydroxyoct-1-en-1-yl)-2-oxopyrrolidin-1-yl)ethyl)benzoic acid (Example 21 D)

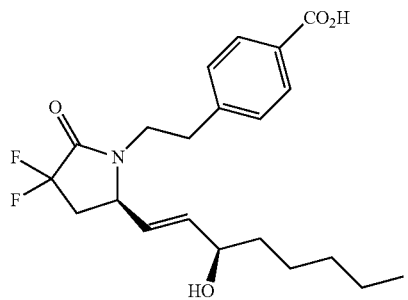 [SMILES: CCCCC[C@@H](O)/C=C/[C@H]1CC(F)(F)C(=O)N1CCc1ccc(C(=O)O)cc1]

16.6 mg of a clear oil; TLC R$_f$ 0.35 (solvent system: 96:4:1 v/v dichloromethane-methanol-acetic acid); $^1$H-NMR (CDCl$_3$) δ 8.0 (d, 2H), 7.8 (d, 2H) 5.9-5.8 (m, 1H), 5.4-5.3 (m, 1H), 4.1-4.0 (m, 2H), 3.8-3.7 (m, 1H), 3.4-3.3 (m, 1H), 3.0-2.9 (m, 2H), 2.8-2.7 (m, 1H), 2.3-2.2 (m, 1H), 1.6-1.2 (m, 9H), 1.0-0.9 (m, 3H); MS (ESI$^-$) m/z 394 (M−1).

Example 22C 4-(2-((R)-3,3-Difluoro-5-((S,E)-3-hydroxy-7-phenyl-hept-1-en-1-yl)-2-oxopyrrolidin-1-yl)ethyl)benzoic acid

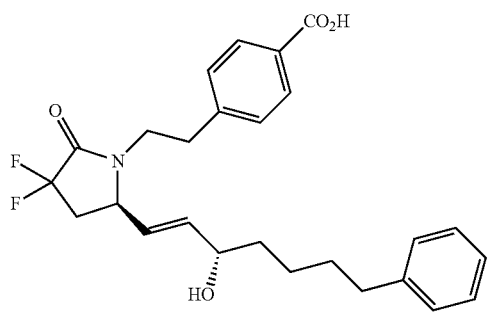 [SMILES: O=C(O)c1ccc(CCN2C(=O)C(F)(F)C[C@@H]2/C=C/[C@@H](O)CCCCc2ccccc2)cc1]

Example 23D 5-(3-((R)-3,3-Difluoro-5-((3S,4S,E)-3-hydroxy-4-methyloct-1-en-6-yn-1-yl)-2-oxopyrrolidin-1-yl)propyl)thiophene-2-carboxylic acid

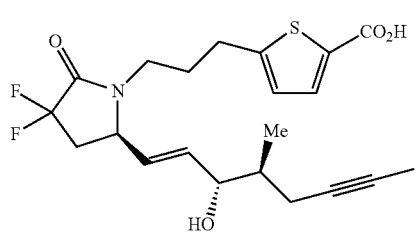 [SMILES: CC#CC[C@H](C)[C@H](O)/C=C/[C@H]1CC(F)(F)C(=O)N1CCCc1ccc(C(=O)O)s1]

Example 24A-24F

Step A, B, and C: Preparation of methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate (Example 24A), methyl 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylate (Example 24B), and methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate (Example 24C)

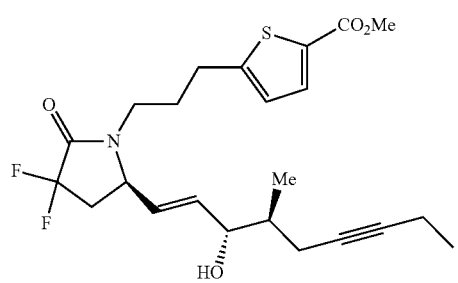 [SMILES: CCC#CC[C@H](C)[C@H](O)/C=C/[C@H]1CC(F)(F)C(=O)N1CCCc1ccc(C(=O)O)s1]
Example 24A

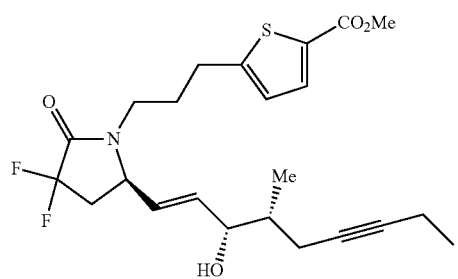 [SMILES: CCC#CC[C@@H](C)[C@H](O)/C=C/[C@H]1CC(F)(F)C(=O)N1CCCc1ccc(C(=O)O)s1]
Example 24B

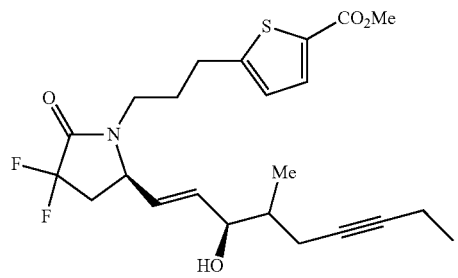 [SMILES: CCC#CCC(C)[C@@H](O)/C=C/[C@H]1CC(F)(F)C(=O)N1CCCc1ccc(C(=O)O)s1]
Example 24C

Methyl 5-(3-((5R)-3,3-difluoro-5-((E)-3-hydroxy-4-methylnon-1-en-6-yn-1-yl)-2-oxopyrrolidin-1-yl)propyl)thiophene-2-carboxylate was prepared by the method described in Examples 12, Steps A and B, except that (R)-methyl 5-(3-(3,3-difluoro-5-formyl-2-oxopyrrolidin-1-yl)propyl)thiophene-2-carboxylate (13f) was used instead of (R)-methyl 4-(2-(3,3-difluoro-5-formyl-2-oxopyrrolidin-1-yl)ethyl)benzoate (13b) in Step A.

Step C: From the stereoisomeric mixture comprising the four-diastereomer mixture methyl 5-(3-((5R)-3,3-difluoro-5-((E)-3-hydroxy-4-methylnon-1-en-6-yn-1-yl)-2-oxopyrrolidin-1-yl)propyl)thiophene-2-carboxylate were separated the single isomers methyl 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylate (Example 24A)

and methyl 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylate (Example 24B), and the diastereomeric mixture (at C16) methyl 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylate (Example 24C) by prep HPLC.

Agilent Semi-Prep instrument; ultraviolet detector at 205 nm; Luna Silica 5μ 250 mm×10 mm column; mobile phase of heptane-ethanol (98:2 v/v).

Example 24A (4.0 mg); a clear oil; HPLC retention time 78.9-83.9 minutes; $^1$H-NMR (CDCl$_3$) δ 7.6 (d, 1H), 6.8 (d, 1H), 5.9-5.8 (m, 1H), 5.6-5.5 (m, 1H), 4.2-4.1 (m, 2H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ −103.5 (d, 1F), −105.5 (d, 1F); MS (ESI$^+$) m/z 471.1 (M+Na).

Example 24B (5.0 mg); a clear oil; HPLC retention time 72.7-77.6 minutes; $^1$H-NMR (CDCl$_3$) δ 7.6 (d, 1H), 6.8 (d, 1H), 5.9-5.8 (m, 1H), 5.6-5.5 (m, 1H), 4.4-4.2 (m, 1H), 4.2-4.1 (m, 1H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ −103.5 (d, 1F), −105.5 (d, 1F); MS (ESI$^+$) m/z 471.1 (M+Na).

Example 24C (16.4 mg); a clear oil; HPLC retention time 59.6-68.8 minutes; 1H-NMR (CDCl$_3$) δ 7.6 (d, 1H), 6.8 (d, 1H), 5.9-5.8 (m, 1H), 5.6-5.5 (m, 1H), 4.4-4.2 (m, 0.5H), 4.2-4.1 (m, 1.5H), 3.85 (s, 3H), 3.7-3.6 (m, 1H), 3.1-3.0 (m, 1H), 2.9-2.8 (t, 2H), 2.7-2.6 (m, 1H), 2.3-2.1 (m, 6H), 2.0-1.9 (m, 2H), 1.8-1.7 (m, 1H), 1.2-1.1 (t, 3H), 1.0-0.9 (d, 3H); $^{19}$F-NMR (CDCl$_3$) δ −103.5 (d, 1F), −105.5 (d, 1F); MS (ESI$^+$) m/z 471.1 (M+Na).

Step D1: Preparation of 5-(3-((R)-3,3-difluoro-5-((3S,4S,E)-3-hydroxy-4-methylnon-1-en-6-yn-1-yl)-2-oxopyrrolidin-1-yl)propyl)thiophene-2-carboxylic acid (Example 24D)

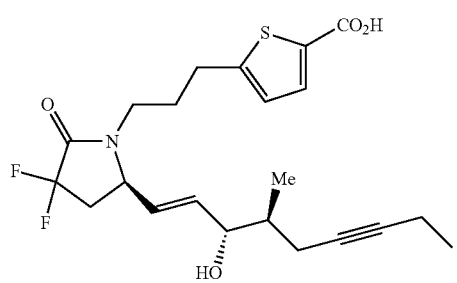

2.9 mg as a colorless oil; TLC R$_f$ 0.40 (solvent system: 95:5:1 v/v dichloromethane-methanol-acetic acid); MS (ESI$^+$) m/z 457.1 (M+Na).

Step D2: Preparation of 5-(3-((R)-3,3-difluoro-5-((3S,4R,E)-3-hydroxy-4-methylnon-1-en-6-yn-1-yl)-2-oxopyrrolidin-1-yl)propyl)thiophene-2-carboxylic acid (Example 24E)

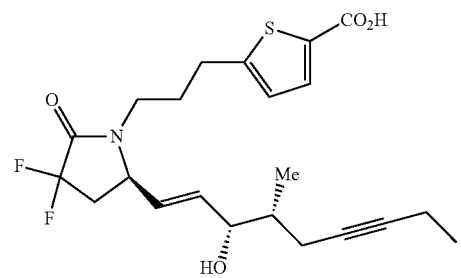

Step D3: Preparation of 5-(3-((5R)-3,3-difluoro-5-((3R,E)-3-hydroxy-4-methylnon-1-en-6-yn-1-yl)-2-oxopyrrolidin-1-yl)propyl)thiophene-2-carboxylic acid (Example 24F)

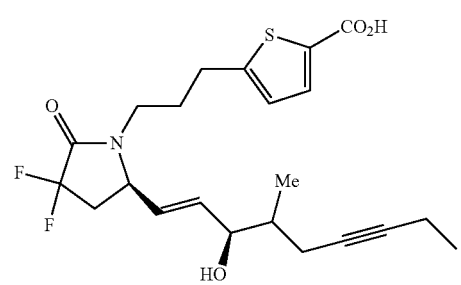

Example 25D 5-(3-((R)-3,3-Difluoro-5-((3S,4S,E)-3-hydroxy-4-methyldec-1-en-6-yn-1-yl)-2-oxopyrrolidin-1-yl)propyl)thiophene-2-carboxylic acid

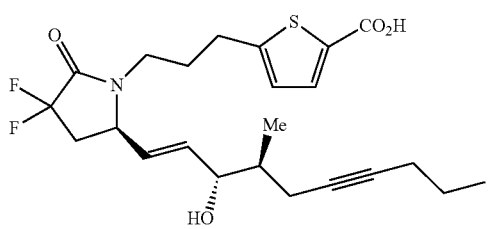 [SMILES: CCCC#CC[C@H](C)[C@H](O)/C=C/[C@H]1CC(F)(F)C(=O)N1CCCc1ccc(C(=O)O)s1]

Example 26D 5-(3-((R)-3,3-Difluoro-5-((3S,4S,E)-3-hydroxy-4-methyl-7-phenylhept 1-en-6-yn-1-yl)-2-oxopyrrolidin-1-yl)propyl)thiophene-2-carboxylic acid

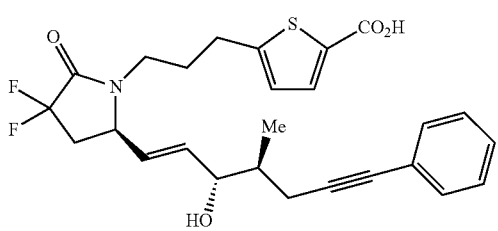 [SMILES: C[C@@H](CC#Cc1ccccc1)[C@H](O)/C=C/[C@H]1CC(F)(F)C(=O)N1CCCc1ccc(C(=O)O)s1]

Example 27D 5-(3-((R)-3,3-Difluoro-5-((3S,4S,E)-3-hydroxy-4-methyloct 1-en-1-yl)-2-oxopyrrolidin-1-yl)propyl) thiophene-2-carboxylic acid

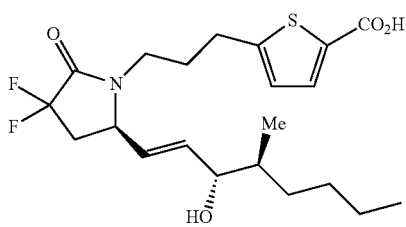 [SMILES: CCCC[C@H](C)[C@H](O)/C=C/[C@H]1CC(F)(F)C(=O)N1CCCc1ccc(C(=O)O)s1]

Examples 28A-28H

Steps A and B: Preparation of methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (28A) and methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (Example 28B)

Example 28A

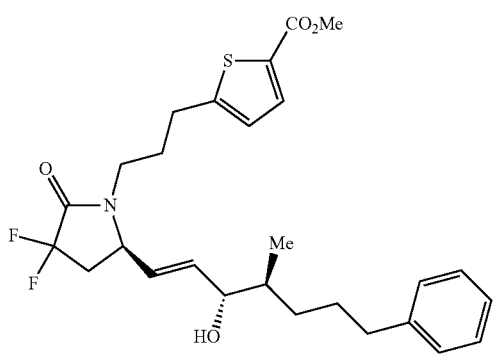

Example 28B

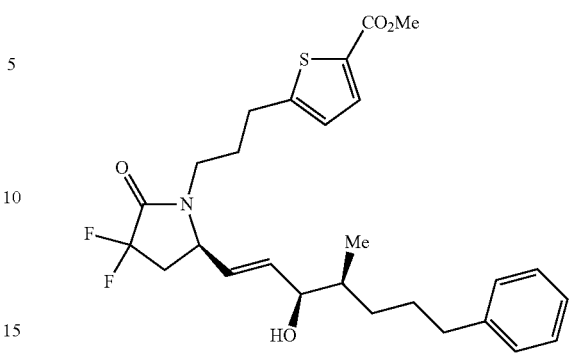

Methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate was prepared by the method described in Examples 24, Steps A and B, except that (S)-dimethyl (3-methyl-2-oxo-6-phenylhexyl)phosphonate (15mb(i)) was used in place of (±)-dimethyl (3-methyl-2-oxooct-5-yn-1-yl)phosphonate (15bb(i)/15bc(i)) in Step A.

Step C: From the stereoisomeric mixture comprising the two-diastereomer mixture methyl 5-(3-((5R)-3,3-difluoro-5-((4S,E)-3-hydroxy-4-methyl-7-phenylhept-1-en-1-yl)-2-oxopyrrolidin-1-yl)propyl)thiophene-2-carboxylate were separated the single isomers methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (28A) and methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (Example 28B) by prep HPLC.

Agilent Semi-Prep instrument; ultraviolet detector at 205 nm; Luna Silica 5μ 250 mm×10 mm column; mobile phase of heptane-ethanol (93:7 v/v).

Example 28A (3.6 mg); a clear oil; HPLC retention time 12.9-13.6 minutes; $^1$H-NMR (CDCl$_3$, 400 MHz) δ 7.6 (d, 1H), 7.3-7.2 (m, 2H), 7.2-7.1 (m, 3H), 6.8 (d, 1H), 5.8-5.7 (m, 1H), 5.5-5.4 (m, 1H), 4.1-4.0 (m, 2H), 3.85 (s, 3H), 3.7-3.5 (m, 1H), 3.1-3.0 (m, 1H), 2.9-2.8 (t, 2Ht), 2.7-2.5 (m, 3H), 2.3-2.1 (m, 1H), 2.0-1.8 (m, 2H), 1.8-1.5 (m, 5H), 1.5-1.4 (m, 1H), 1.3-1.2 (m, 1H), 1.2-1.1 (t, 1H), 0.85 (d, 3H); MS (ESI$^+$) m/z 528.2 (M+Na).

Example 28B (19.6 mg); a clear oil; HPLC retention time 12.0-12.9 minutes; $^1$H-NMR (CDCl$_3$, 400 MHz) δ 7.6 (d, 1H), 7.3-7.2 (m, 2H), 7.2-7.1 (m, 3H), 6.8 (d, 1H), 5.8-5.7 (m, 1H), 5.5-5.4 (m, 1H), 4.1-4.0 (m, 2H), 3.85 (s, 3H), 3.7-3.5 (m, 1H), 3.1-3.0 (m, 1H), 2.9-2.8 (t, 2H), 2.7-2.5 (m, 3H), 2.3-2.1 (m, 1H), 2.0-1.8 (m, 2H), 1.8-1.5 (m, 5H), 1.5-1.4 (m, 1H), 1.3-1.2 (m, 1H), 1.2-1.1 (t, 1H), 0.85 (d, 3H); MS (ESI$^+$) m/z 528.2 (M+Na).

Alternative Preparations of Example 28A from methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate (Enone intermediate 22f-mb(i))

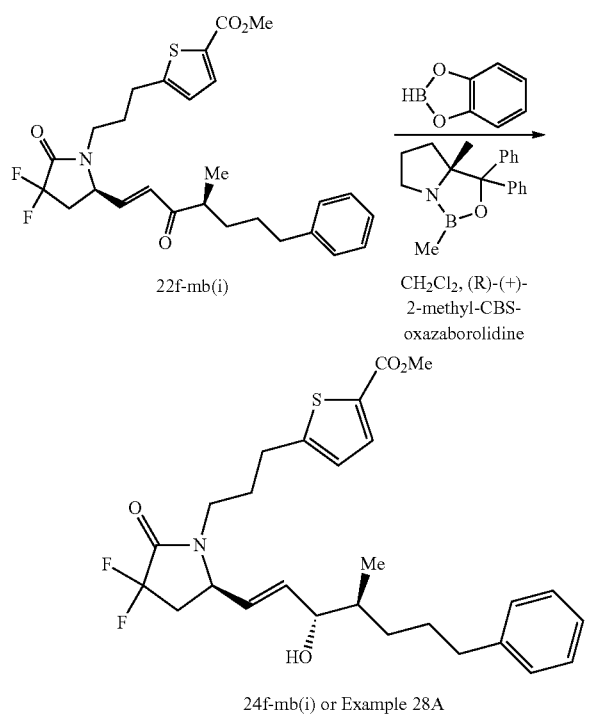

Enone 22f-mb(i) was prepared by reacting aldehyde 13f with β-keto phosphonate ester 15mb(i) using a Horner-Wadsworth-Emmons procedure similar to the protocol described in Step A for the preparation of Example 1A above.

Alternative Preparation 1:

To a stirring solution consisting of 22f-mb(i) (50 mg, 0.10 mmol) and R)-(+)-2-methyl-CBS-oxazaborolidine (0.12 mL, 0.12 mmol, 1 M in toluene) in dichloromethane (1 mL) was added a solution consisting of catecholborane (0.1 mL, 0.1 mmol, 1 M in THF) in dichloromethane (5 mL) over 15 minutes. The reaction was stirred for two hours. The reaction was quenched with 1 M HCl and extracted with ethyl acetate. The combined organic phase was sequentially washed with a 50% saturated aqueous solution of sodium chloride and a saturated aqueous solution of sodium chloride, dried over sodium sulfate, filtered, and concentrated to provide a residue comprising a diastereomeric mixture of Examples 28A and 28B, which was purified by silica gel chromatography. Elution with methanol-dichloromethane (1:250 v/v) afforded a purified diastereomeric mixture comprising Example 28A and Example 28B (23 mg) as a clear oil; TLC $R_f$ 0.50 (solvent system: 97:3 v/v dichloromethane:methanol).

Alternative Preparation 2:

A diastereomeric mixture comprising Example 28A and Example 28B, was prepared by the method as described above in Alternative preparation 1, except 4 molar equivalents of catecholborane (0.4 mL, 0.4 mmol, 1M in THF) were used instead of 1 molar equivalent to afford a second purified diastereomeric mixture comprising Example 28A and Example 28B (70 mg) as a clear oil; TLC $R_f$ 0.50 (solvent system: 3:97 v/v dichloromethane-methanol).

Alternative Preparation 3:

A diastereomeric mixture comprising Example 28A and Example 28B, was prepared by the method as described above in Alternative preparation 1, except on a larger scale. The reaction mixture comprising 22f-mb(i) (553 mg, 1.1 mmol), (R)-(+)-2-methyl-CBS-oxazaborolidine (1.32 mL, 1.32 mmol, 1M in toluene) and catecholborane (1.1 mL, 1.1 mmol, 1 M in THF) afforded a third purified diastereomeric mixture comprising Example 28A and Example 28B (226 mg) as a clear oil; TLC $R_f$ 0.50 (solvent system: 3:97 v/v dichloromethane-methanol).

Isolation of single diastereomer Example 28A by separation of a pooled mixture comprising the three purified diastereomeric mixtures generated from the three alternative Example 28A preparations above: *The pooled mixture was injected onto the Agilent* 1100 *prep HPLC*; stationary phase Luna 5m Silica 250×21.2 mm column; mobile phase 96:4 heptane-ethanol; Example 28A eluent collected at retention time 26-29 minutes and concentrated to afford the single diastereomer Example 28A (110 mg, 17%) as a white solid; TLC $R_f$ 0.50 (solvent system: 97:3 v/v dichloromethane:methanol); analytical HPLC, retention time 16.3 min, Agilent 1100 ultraviolet detector at 210 nm, stationary phase, Phenomenex Luna Silica, 5μ, 4.6×250 mm, mobile phase, 95:5 heptane-ethanol, flow rate 1 mL/min; $^1$H-NMR (CDCl$_3$) δ 7.6 (d, 1H), 7.3-7.2 (m, 2H), 7.2-7.1 (m, 3H), 6.8 (d, 1H), 5.75 (dd, 1H), 5.4 (dd, 1H), 4.1-4.0 (m, 2H), 3.82 (s, 3H), 3.6-3.5 (m, 1H), 3.0-2.9 (m, 1H), 2.80 (t, 2H), 2.6-2.5 (m, 3H), 2.2-2.1 (m, 1H), 2.1-2.0 (m, 1H), 1.9-1.8 (m, 2H), 1.7-1.4 (m, 4H), 1.2-1.1 (m, 1H), 0.84 (d, 3H); $^{19}$F-NMR (CDCl$_3$, 376 Hz) δ −103.6 (ddd, J=270, 15.3 Hz, 1F), −105.6 (ddd, J=271, 17, 15 Hz, 1F).

Alternative Preparation 4:

To a solution consisting of 22f-mb(i) (10 mg, 0.02 mmol) and (R)-(+) 2-methyl-CBS-oxazaborolidine (0.040 mL, 0.040 mmol, 1 M in toluene) in dichloromethane (1 mL) was added catecholborane (0.060 mL, 0.060 mmol, 1M in THF) in dichloromethane (1 mL) over 15 minutes. The reaction mixture was stirred for two hours and was subsequently quenched with 1 M HCl and extracted with ethyl acetate. The crude product, as a clear oil, was analyzed by HPLC (Phenomenex Luna 5μ Silica (2) 4.6×250 mm column at 30° C.; mobile phase 95:5:0.1 hexanes-isopropanol-acetic acid): diastereomeric ratio Example 28A-Example 28B=64:36 by area; TLC $R_f$ 0.50 (solvent system: 3:97 v/v dichloromethane-methanol).

Step D1: Preparation of 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid (Example 28C)

Example 28C

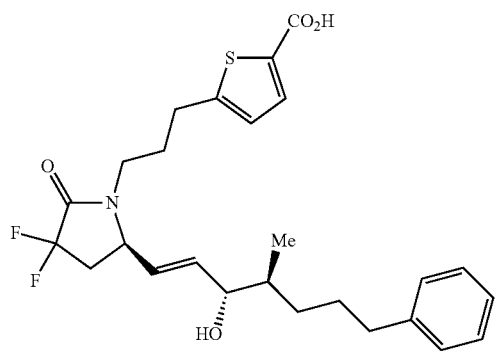

TLC $R_f$ 0.55 (solvent system: 96:4:1 v/v dichloromethane-methanol-acetic acid); MS (ESI⁻) m/z 490.2 (M−1).

Step D2: Preparation of 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylic acid (Example 28D)

Example 28D

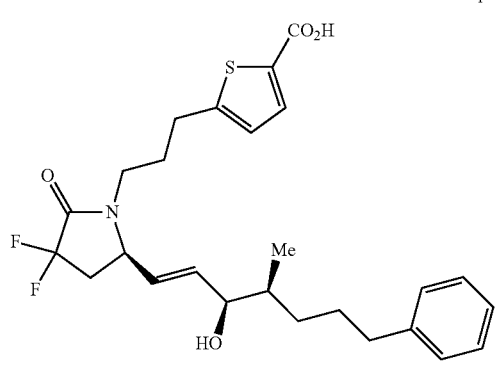

TLC $R_f$ 0.55 (solvent system: 96:4:1 v/v dichloromethane-methanol-acetic acid); MS (ESI⁻) m/z 490.2 (M−1).

Example 28E and 28F

Steps A, B, and C: Preparation of methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (Example 28E) and methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate (Example 28F)

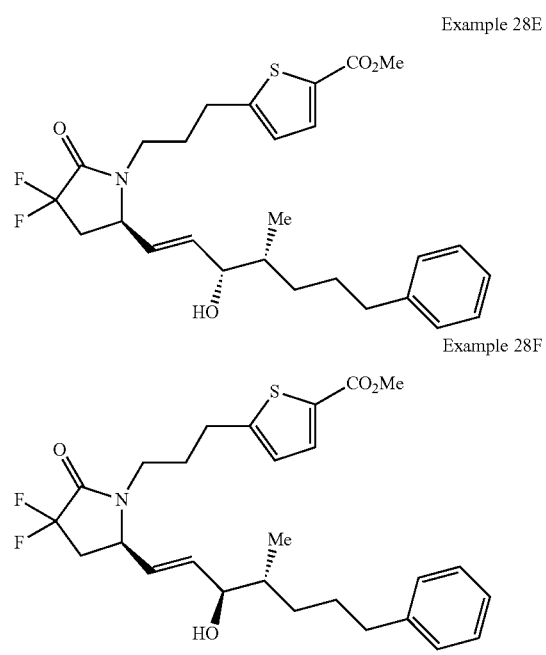

Methyl 5-(3-((5R)-3,3-difluoro-5-((4R,E)-3-hydroxy-4-methyl-7-phenylhept-1-en-1-yl)-2-oxopyrrolidin-1-yl)propyl)thiophene-2-carboxylate was prepared by the method described in Example 28, Steps A and B, except that (R)-dimethyl (3-methyl-2-oxo-6-phenylhexyl)phosphonate (15mc(i)) was used instead of (S)-dimethyl (3-methyl-2-oxo-6-phenylhexyl)phosphonate (15mb(i)) in Step A.

Step C: The pure diastereomers of Example 28E and Example 28F were isolated following separation by prep HPLC; Gilson Prep HPLC, Luna silica 51µ 21.2×250 mm, ultraviolet detector 210 nm, mobile phase 96:4:0.1 heptane-ethanol-acetic acid, 21.2 ml/min.

Example 28E: 175 mg as a clear oil; TLC $R_f$ 0.31 (solvent system: 35:65 v/v ethyl acetate-heptane); HPLC retention time 39 min; MS (ESI⁺) m/z 528 (M+Na)⁺; ¹H NMR (CD₃OD) δ 7.62 (d, J=3.66 Hz, 1H), 7.25-7.10 (m, 5H), 6.91 (d, J=3.92 Hz, 1H), 5.81 (dd, J=6.23, 15.38 Hz, 1H), 5.42 (dd, J=9.34, 15.20 Hz, 1H), 4.25 (dd, J=4.58, 7.87 Hz, 1H), 3.99-3.89 (m, 1H), 3.80 (s, 3H), 3.55-3.47 (m, 1H), 3.34 (s, 1H), 3.16-3.03 (m, 1H), 2.85 (dt, J=3.48, 7.42 Hz, 3H), 2.71-2.51 (m, 2H), 2.32-2.19 (m, 1H), 1.99-1.85 (m, 2H), 1.71-1.44 (m, 4H), 1.11 (s, 1H), 0.86 (d, J=6.96 Hz, 3H); ¹⁹F NMR (CD₃OD) δ −104.4 (ddd, 1F), −107.3 (ddd, 1F); $[\alpha]^T_\lambda = \alpha/cl$, $[\alpha]^{21.9}_D = -0.004/(0.01568 \text{ g}/1.5 \text{ mL})(0.5) = -0.765°$ (c=1.045, CHCl₃).

Example 28F: 580 mg as a clear oil; TLC $R_f$ 0.31 (solvent system: 35:65 v/v ethyl acetate-heptane); HPLC retention time 35 min; MS (ESI⁺) m/z 528 (M+Na)⁺; ¹H NMR (CD₃OD) δ 7.63-7.61 (m, 1H), 7.25-7.10 (m, 5H), 6.92 (d, J=3.91 Hz, 1H), 5.85 (dd, J=5.68, 15.20 Hz, 1H), 5.43 (dd, J=9.34, 15.20 Hz, 1H), 4.29-4.22 (m, 1H), 3.96 (dt, J=1.46, 5.49 Hz, 1H), 3.82-3.80 (m, 3H), 3.59-3.47 (m, 1H), 3.36-3.32 (m, 1H), 3.11 (dd, J=6.04, 7.87 Hz, 1H), 2.85 (t, J=7.51 Hz, 2H), 2.79-2.67 (m, 1H), 2.59 (t, J=7.51 Hz, 2H), 2.28-2.15 (m, 1H), 1.99-1.86 (m, 2H), 1.75-1.52 (m, 3H), 1.47 (td, J=5.17, 13.46 Hz, 1H), 1.17-1.07 (m, 1H), 0.85 (d, J=6.59 Hz, 3H); $^{19}$F NMR (CD$_3$OD) δ −104.5 (ddd, 1F), −107.2 (ddd, 1F).

Alternative Preparation of Example 28E from methyl 5-(3-((R)-3,3-difluoro-5-((R,E)-4-methyl-3-oxo-7-phenylhept-1-en-1-yl)-2-oxopyrrolidin-1-yl) propyl)thiophene-2-carboxylate (Enone Intermediate 22f-mc(i))

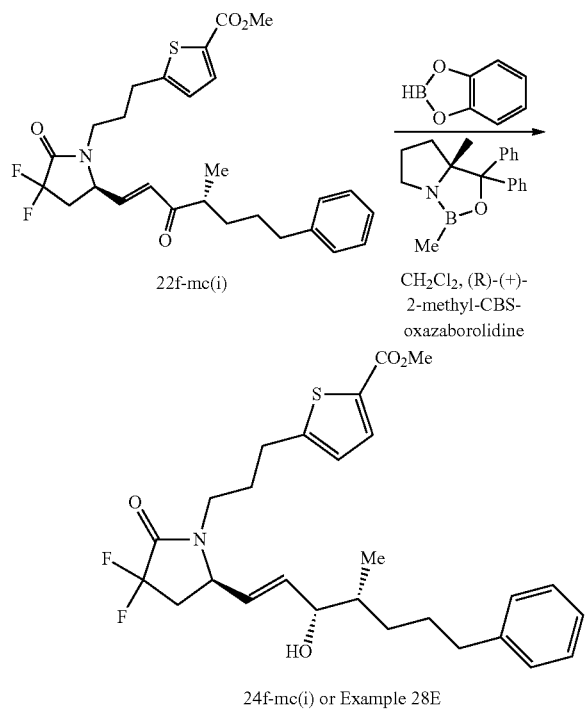

To a solution consisting of methyl 5-(3-((R)-3,3-difluoro-5-((R,E)-4-methyl-3-oxo-7-phenylhept-1-en-1-yl)-2-oxopyrrolidin-1-yl)propyl)thiophene-2-carboxylate (10 mg, 0.02 mmol) and (R)-(+) 2-methyl-CBS-oxazaborolidine (0.040 mL, 0.040 mmol, 1 M in toluene) in dichloromethane (1 mL) was added catecholborane (0.060 mL, 0.060 mmol, 1M in THF) in dichloromethane (1 mL) over 15 minutes. The reaction mixture was stirred for two hours and was subsequently quenched with 1 M HCl and extracted with ethyl acetate. The crude product, as a clear oil, was analyzed by HPLC (Phenomenex Luna 5μ Silica (2) 4.6×250 mm column at 30° C.; mobile phase 95:5:0.1 hexanes-isopropanol-acetic acid):diastereomeric ratio Example 28E-Example 28F=99:1 by area; TLC R$_f$ 0.50 (solvent system: 3:97 v/v dichloromethane-methanol).

Enone 22f-mc(i) was prepared by reacting aldehyde 13f with β-keto phosphonate ester 15mc(i) using a Horner-Wadsworth-Emmons procedure similar to the protocol described in Step A for the preparation of Example 1A above.

Step D1: Preparation of 5-(3-((R)-3,3-difluoro-5-((3S,4R,E)-3-hydroxy-4-methyl-7-phenylhept-1-en-1-yl)-2-oxopyrrolidin-1-yl)propyl)thiophene-2-carboxylic acid (Example 28G)

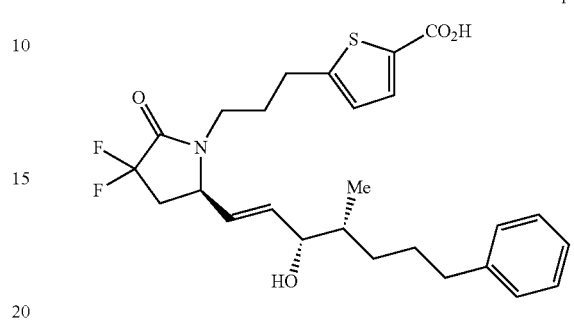

Example 28G 60 mg (44%) of the title compound as a colorless oil; TLC R$_f$ 0.45 (solvent system: 60:40:1 v/v/v ethyl acetate-heptane-acetic acid); MS (ESI$^-$) m/z 490 (M−H)$^-$; $^1$H NMR (CD$_3$OD) δ 7.58 (d, J=4.03 Hz, 1H), 7.25-7.10 (m, 5H), 6.89 (d, J=4.02 Hz, 1H), 5.81 (dd, J=6.23, 15.38 Hz, 1H), 5.42 (dd, J=9.34, 15.20 Hz, 1H), 4.30-4.21 (m, 1H), 3.93 (t, J=5.49 Hz, 1H), 3.62-3.42 (m, 1H), 3.15-3.04 (m, 1H), 2.89-2.68 (m, 4H), 2.65-2.51 (m, 2H), 2.32-2.14 (m, 1H), 2.01-1.85 (m, 2H), 1.71-1.44 (m, 4H), 1.19-1.05 (m, 1H), 0.92-0.83 (m, 3H); $^{19}$F NMR (CD$_3$OD) δ −104.3 (ddd, 1F), −107.2 (ddd, 1F); $[α]^T_λ$=α/cl, $[α]^{21.9}_D$=−0.011/(0.0163 g/1.5 mL)(0.5)=−2.03° (c=1.09, CHCl$_3$).

Step D2: Preparation of 5-(3-((R)-3,3-difluoro-5-((3R,4R,E)-3-hydroxy-4-methyl-7-phenylhept-1-en-1-yl)-2-oxopyrrolidin-1-yl)propyl)thiophene-2-carboxylic acid (Example 28H)

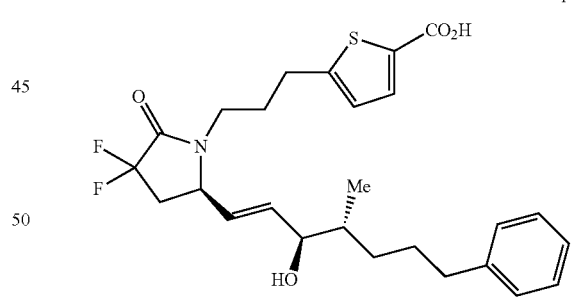

Example 28H 510 mg (94%) of the title compound as a white solid; TLC R$_f$ 0.47 (solvent system: 50:50:1 v/v/v ethyl acetate-heptane-acetic acid); MP 133-134° C.; MS (ESI$^-$) m/z 490 (M−H)$^-$; $^1$H-NMR (CD$_3$OD) δ 7.58 (d, J=3.66 Hz, 1H), 7.26-7.10 (m, 5H), 6.90 (d, J=3.86 Hz, 1H), 5.85 (dd, J=5.49, 15.38 Hz, 1H), 5.43 (dd, J=9.15, 15.38 Hz, 1H), 4.30-4.22 (m, 1H), 3.97 (dt, J=1.46, 5.49, Hz, 1H), 3.59-3.51 (m, 1H), 3.16-3.07 (m, 1H), 2.88-2.67 (m, 4H), 2.59 (t, J=7.51 Hz, 2H), 2.21 (dtd, 1H), 2.00-1.86 (m, 2H), 1.76-1.52 (m, 3H), 1.51-1.41 (m, 1H), 1.17-1.07 (m, 1H), 0.86 (d, J=6.59 Hz, 3H); $^{19}$F-NMR (CD$_3$OD) δ −104.5 (ddd, 1F), −107.2 (ddd, 1F); $[α]^T_λ$=α/cl, $[α]^{21.9}_D$=−0.140/(0.0194 g/2.5 mL)(0.5)=−36.08° (c=0.776, CHCl$_3$).

Example 28C-H₂

Preparation of 5-(3-((S)-3,3-difluoro-5-((3R,4S)-3-hydroxy-4-methyl-7-phenylheptyl)-2-oxopyrrolidin-1-yl)propyl)thiophene-2-carboxylic acid (Example 28C-H₂)

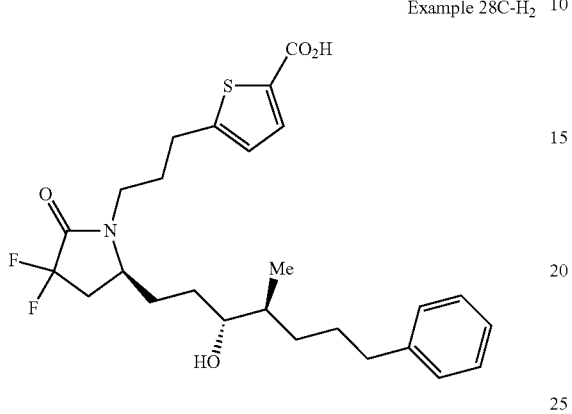

Example 28C-H₂

To a solution consisting of 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid (15.2 mg, 0.031 mmol) in ethanol (12 mL) and covered with an atmosphere of nitrogen was added palladium (12 mg, 10% on activated carbon). The nitrogen atmosphere was replaced with hydrogen and the reaction mixture was stirred vigorously for 5 hours at room temperature. The hydrogen was replaced with nitrogen and mixture was filtered through a small pad of celite which was washed with ethanol. The combined filtrate was concentrated under vacuum and the residue was purified by silica gel chromatography eluting with ethyl acetate-heptane-acetic acid (45:55:0.4 v/v/v) to give 9.5 mg (62%) of the title compound as a colorless oil; TLC $R_f$ 0.29 (solvent system: 45:55:1 v/v/v ethyl acetate-heptane-acetic acid); MS (ESI⁻) m/z 492.2 (M–H)⁻; ¹H NMR (CD₃OD) δ 7.47 (d, J=3.66 Hz, 1H), 7.18-7.01 (m, 5H), 6.80 (d, J=3.30 Hz, 1H), 3.72-3.63 (m, 1H), 3.16-3.03 (m, 1H), 2.79 (t, J=7.32 Hz, 2H), 2.61-2.45 (m, 3H), 2.19-2.05 (m, 1H), 1.98-1.78 (m, 2H), 1.78-1.57 (m, 2H), 1.53-1.39 (m, 4H), 1.34-1.14 (m, 5H), 1.10-1.00 (m, 1H), 0.81-0.76 (m, 3H); ¹⁹F NMR (CD₃OD) δ –103.2 (ddd, 1F), –105.9 (ddd, 1F).

Example 29C 5-(3-((R)-3,3-Difluoro-5-((S,E)-3-hydroxyoct-1-en-6-yn-1-yl)-2-oxopyrrolidin-1-yl)propyl)thiophene-2-carboxylic acid

Example 30C 5-(3-((R)-3,3-Difluoro-5-((S,E)-3-hydroxynon-1-en-6-yn-1-yl)-2-oxopyrrolidin-1-yl)propyl)thiophene-2-carboxylic acid

Example 31C 5-(3-((R)-3,3-Difluoro-5-((S,E)-3-hydroxydec-1-en-6-yn-1-yl)-2-oxopyrrolidin-1-yl)propyl)thiophene-2-carboxylic acid

Example 32C 5-(3-((R)-3,3-Difluoro-5-((S,E)-3-hydroxy-7-phenyl-hept-1-en-6-yn-1-yl)-2-oxopyrrolidin-1-yl)propyl)thiophene-2-carboxylic acid

Examples 33A-33D

Steps A, B, and C: Preparation of methyl 5-(3-((R)-3,3-difluoro-5-((S,E)-3-hydroxyoct-1-en-1-yl)-2-oxopyrrolidin-1-yl)propyl)thiophene-2-carboxylate (Example 33A) and methyl 5-(3-((R)-3,3-difluoro-5-((R,E)-3-hydroxyoct-1-en-1-yl)-2-oxopyrrolidin-1-yl)propyl)thiophene-2-carboxylate (Example 33B)

Example 33A

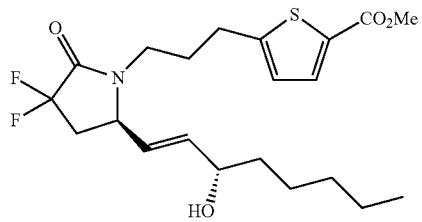

Example 33B

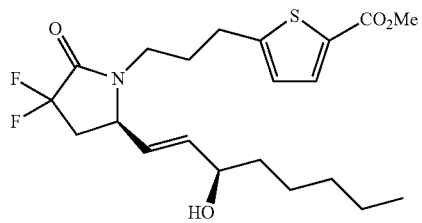

Methyl 5-(3-((5R)-3,3-difluoro-5-((E)-3-hydroxyoct-1-en-1-yl)-2-oxopyrrolidin-1-yl)propyl)thiophene-2-carboxylate was prepared by the method described in Example 9, Steps A and B, except that (R)-methyl 5-(3-(3,3-difluoro-5-formyl-2-oxopyrrolidin-1-yl)propyl)thiophene-2-carboxylate (13f) was used instead of (R)-methyl 7-(3,3-difluoro-5-formyl-2-oxopyrrolidin-1-yl) heptanoate (13a).

Step C: From the diastereomeric mixture methyl 5-(3-((5R)-3,3-difluoro-5-((E)-3-hydroxyoct-1-en-1-yl)-2-oxopyrrolidin-1-yl)propyl)thiophene-2-carboxylate were separated the single isomers methyl 5-(3-((R)-3,3-difluoro-5-((S,E)-3-hydroxyoct-1-en-1-yl)-2-oxopyrrolidin-1-yl)propyl)thiophene-2-carboxylate (Example 33A) and methyl 5-(3-((R)-3,3-difluoro-5-((R,E)-3-hydroxyoct-1-en-1-yl)-2-oxopyrrolidin-1-yl)propyl)thiophene-2-carboxylate (Example 33B) by prep HPLC. The separations were performed on an Agilent Semi-Prep instrument equipped with an ultraviolet detector at 205 nm and using ultraviolet detector at 205 nm; Luna Silica 5μ 250×10 mm column eluting with a mobile phase of heptanes-ethanol (94:6 v/v).

Example 33A (10.2 mg); a clear oil; prep HPLC retention time 15.9-16.3 minutes; $^1$H-NMR (CDCl$_3$) δ 7.6 (d, 1H), 6.8 (d, 1H), 5.9-5.7 (m, 1H), 5.5-5.4 (m, 1H), 4.2-4.1 (m, 1H), 4.1-4.0 (m, 1H), 3.9 (s, 3H), 3.7-3.6 (m, 1H), 3.2-3.0 (m, 1H), 2.8 (t, 2H), 2.8-2.6 (m, 1H), 2.3-2.1 (m, 1H), 2.0-1.8 (m, 2H), 1.8-1.7 (br, 1H), 1.6-1.5 (m, 2H), 1.4-1.2 (m, 6H), 0.9 (t, 3H); MS (ESI$^+$) m/z 452.0 (M+Na).

Example 33B (24.0 mg); a clear oil; prep HPLC retention time 14.2-14.6 minutes; $^1$H-NMR (CDCl$_3$) δ 7.6 (d, 1H), 6.8 (d, 1H), 5.9-5.7 (m, 1H), 5.5-5.4 (m, 1H), 4.2-4.1 (m, 1H), 4.1-4.0 (m, 1H), 3.9 (s, 3H), 3.7-3.6 (m, 1H), 3.2-3.0 (m, 1H), 2.8 (t, 2H), 2.8-2.6 (m, 1H), 2.3-2.1 (m, 1H), 2.0-1.8 (m, 2H), 1.8-1.7 (br, 1H), 1.6-1.5 (m, 2H), 1.4-1.2 (m, 6H), 0.9 (t, 3H); MS (ESI$^+$) m/z 452.0 (M+Na).

Step D1: Preparation of 5-(3-((R)-3,3-difluoro-5-((S,E)-3-hydroxyoct-1-en-1-yl)-2-oxopyrrolidin-1-yl)propyl)thiophene-2-carboxylic acid (Example 33C)

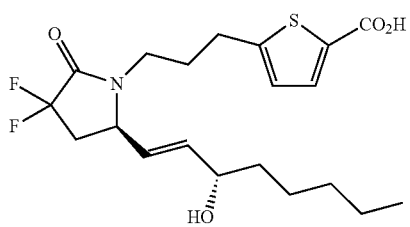 [SMILES: CCCCC[C@H](O)/C=C/[C@H]1CC(F)(F)C(=O)N1CCCc1ccc(C(=O)O)s1]

10.0 mg of a clear oil; TLC R$_f$ 0.40 (solvent system: 90:10:1 v/v dichloromethane-methanol-acetic acid); $^1$H-NMR (CDCl$_3$) δ 7.7 (d, 1H), 6.9 (d, 1H), 5.9-5.8 (m, 1H), 5.5-5.4 (m, 1H), 4.2-4.1 (m, 1H), 4.1-4.0 (m, 1H), 3.7-3.5 (m, 1H), 3.2-3.0 (m, 1H), 2.9 (t, 2H), 2.8-2.6 (m, 1H), 2.3-2.1 (m, 1H), 2.0-1.8 (m, 2H), 1.8-1.0 (m, 9H), 0.8 (t, 3H); MS (ESI$^+$) m/z 438.0 (M+Na) (ESI$^-$) m/z 414.2 (M−1).

Step D2: Preparation of 5-(3-((R)-3,3-difluoro-5-((R,E)-3-hydroxyoct-1-en-1-yl)-2-oxopyrrolidin-1-yl)propyl)thiophene-2-carboxylic acid (Example 33D)

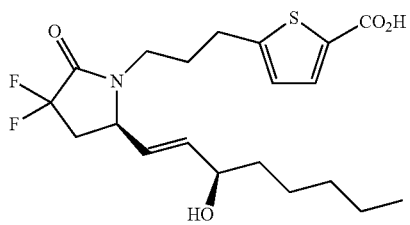 [SMILES: CCCCC[C@@H](O)/C=C/[C@H]1CC(F)(F)C(=O)N1CCCc1ccc(C(=O)O)s1]

10.0 mg of a clear oil; TLC R$_f$ 0.40 (solvent system: 90:10:1 v/v dichloromethane-methanol-acetic acid); $^1$H-NMR (CDCl$_3$) δ 7.7 (d, 1H), 6.9 (d, 1H), 5.9-5.8 (m, 1H), 5.5-5.4 (m, 1H), 4.2-4.1 (m, 1H), 4.1-4.0 (m, 1H), 3.7-3.5 (m, 1H), 3.2-3.0 (m, 1H), 2.9 (t, 2H), 2.8-2.6 (m, 1H), 2.3-2.1 (m, 1H), 2.0-1.8 (m, 2H), 1.8-1.0 (m, 9H), 0.8 (t, 3H); MS (ESI$^+$) m/z 438.0 (M+Na) (ESI$^-$) in/z 414.2 (M−1).

Example 34C 5-(3-((R)-3,3-Difluoro-5-((S,E)-3-hydroxy-7-phenyl-hept-1-en-1-yl)-2-oxopyrrolidin-1-yl)propyl)thiophene-2-carboxylic acid

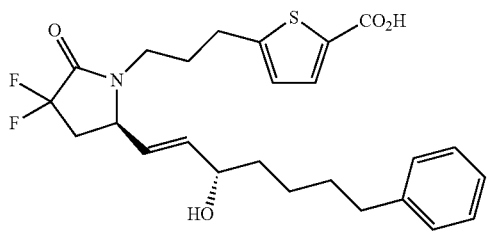 [SMILES: O=C(O)c1ccc(CCCN2C(=O)C(F)(F)C[C@@H]2/C=C/[C@@H](O)CCCCc2ccccc2)s1]

Examples 35A-35D

Steps A, B, and C: Preparation of methyl 5-(3-((R)-3,3-difluoro-5-((3R,4S,E)-3-hydroxy-4-phenylpent-1-en-1-yl)-2-oxopyrrolidin-1-yl)propyl)thiophene-2-carboxylate (Example 35A) and methyl 5-(3-((R)-3,3-difluoro-5-((3S,4S,E)-3-hydroxy-4-phenylpent-1-en-1-yl)-2-oxopyrrolidin-1-yl)propyl)thiophene-2-carboxylate (Example 35B)

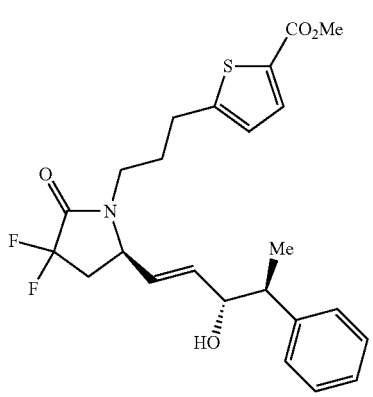

Example 35A

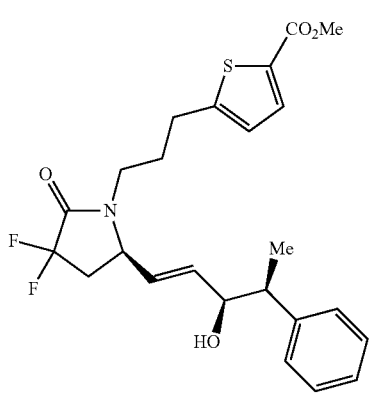

Example 35B

Methyl 5-(3-((R)-3,3-difluoro-5-((4S,E)-3-hydroxy-4-phenylpent-1-en-1-yl)-2-oxopyrrolidin-1-yl)propyl)thiophene-2-carboxylate was prepared by the method described in Example 28, Steps A and B, except that (S)-dimethyl (2-oxo-3-phenylbutyl)phosphonate (15jb) was used instead of (S)-dimethyl (3-methyl-2-oxo-6-phenylhexyl)phosphonate (15mb(i)) in Step A.

Methyl 5-(3-((R)-3,3-difluoro-5-((4S,E)-3-hydroxy-4-phenylpent-1-en-1-yl)-2-oxopyrrolidin-1-yl)propyl)thiophene-2-carboxylate was prepared by the method described in Example 28, Steps A and B, except that (S)-dimethyl (2-oxo-3-phenylbutyl)phosphonate (15jb) was used instead of (S)-dimethyl (3-methyl-2-oxo-6-phenylhexyl)phosphonate (15mb(i)) in Step A.

The pure diastereomers of Example 35A and Example 35B were isolated following separation by prep HPLC.

Agilent Semi Prep, Chiralpak IA 250×10 mm, ultraviolet detector at 210 nm; mobile phase 90:10 heptane-ethanol, flowrate 21.2 mL/min, Example 35A (peak 2): 4 mg; colorless oil; HPLC retention time 21 min; TLC $R_f$ 0.23 (solvent system: 35:65 v/v ethyl acetate-heptane).

Example 35B (peak 1): 9 mg; colorless oil; HPLC retention time 16 min; TLC $R_f$ 0.23 (solvent system: 35:65 v/v ethyl acetate-heptane).

Step D1: Preparation of 5-(3-((R)-3,3-difluoro-5-((3R,4S,E)-3-hydroxy-4-phenylpent-1-en-1-yl)-2-oxopyrrolidin-1-yl)propyl)thiophene-2-carboxylic acid (Example 35C)

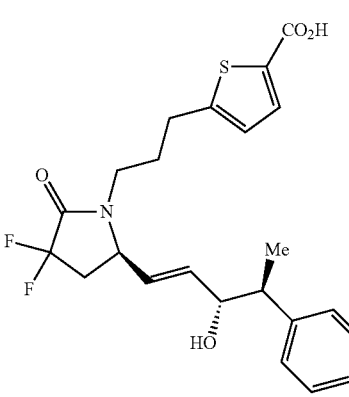

Example 35C 1.8 mg (46%); colorless oil; TLC $R_f$ 0.35 (solvent system: 55:45:1 v/v ethyl acetate-heptane-acetic acid); MS (ESI⁻) m/z 448.2 (M–H)⁻; ¹H NMR (CD₃OD) δ 7.48 (s, 1H), 7.27-7.16 (m, 5H), 6.84 (s, 1H), 5.85 (dd, J=5.49, 15.38 Hz, 1H), 5.36 (dd, J=9.15, 15.75 Hz, 1H), 3.26-3.11 (m, 1H), 2.81-2.58 (m, 5H), 1.93-1.74 (m, 2H), 1.73-1.48 (m, 4H), 0.95-0.85 (m, 3H); ¹⁹F NMR (CD₃OD) δ –104.3 (ddd, 1F), –107.2 (ddd, 1F).

Step D2: Preparation of 5-(3-((R)-3,3-difluoro-5-((3S,4S,E)-3-hydroxy-4-phenylpent-1-en-1-yl)-2-oxopyrrolidin-1-yl)propyl)thiophene-2-carboxylic acid (Example 35D)

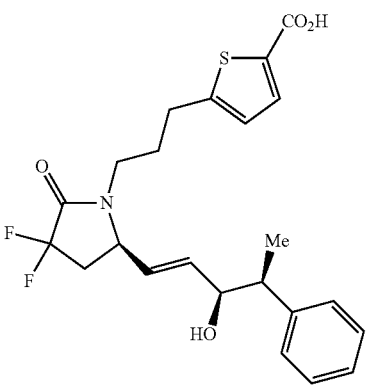

Example 35D 8.7 mg (100% not pure product); colorless oil; TLC $R_f$ 0.35 (solvent system: 55:45:1 v/v ethyl acetate-heptane-acetic acid); MS (ESI⁻) m/z 448.2 (M–H)⁻.

Examples 36A-36D

Steps A, B, and C: Preparation of methyl 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylate (Example 36A) and methyl 5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylate (Example 36B)

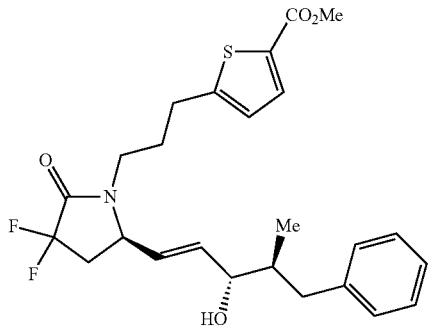

Example 36A

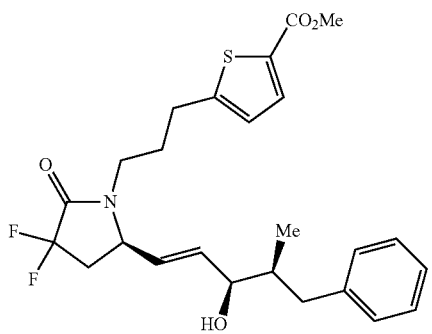

Example 36B

Methyl 5-(3-((5R)-3,3-difluoro-5-((4S,E)-3-hydroxy-4-methyl-5-phenylpent-1-en-1-yl)-2-oxopyrrolidin-1-yl)propyl)thiophene-2-carboxylate was prepared by the method described in Example 28, Steps A and B, except that (S)-dimethyl (3-methyl-2-oxo-4-phenylbutyl)phosphonate (15kb(i)) was used instead of (S)-dimethyl (3-methyl-2-oxo-6-phenylhexyl)phosphonate (15mb(i)) in Step A.

Step C: The pure diastereomers of Example 36A and Example 36B were isolated following separation by prep HPLC; Gilson Prep instrument; ultraviolet detector at 210 nm; Luna silica 5μ 21.2×250 mm column; mobile phase of heptane-ethanol (96:4 v/v), 21.2 mL/min.

Example 36A (39 mg); a clear oil; HPLC retention time 36 min; TLC $R_f$ 0.18 (solvent system: 35:65 v/v ethyl acetate-heptane); MS (ESI$^+$) m/z 500 (M+Na)$^+$; $^1$H-NMR (CD$_3$OD) δ 7.59 (d, J=4.03H, z1H), 7.27-7.22 (m, 2H), 7.19-7.10 (m, 3H), 6.91 (d, J=3.90 Hz, 1H), 5.90 (dd, J=6.41, 15.20 Hz, 1H), 5.49 (dd, J=9.34, 15.20 Hz, 1H), 4.30 (tt, J=4.17, 8.28 Hz, 1H), 3.96-3.91 (m, 1H), 3.80 (s, 3H), 3.63-3.54 (m, 1H), 3.13 (td, J=6.50, 13.37 Hz, 1H), 2.94-2.71 (m, 5H), 2.36-2.23 (m, 2H), 2.05-1.82 (m, 3H), 0.76 (d, J=6.96 Hz, 3H); 19F NMR (CD$_3$OD) δ −104.4 (ddd, 1F), −107.2 (ddd, 1F).

Example 36B (120 mg); a colorless oil; HPLC retention time 34 min; $R_f$ 0.23 (solvent system: 35:65 v/v ethyl acetate-heptane); MS (ESI$^+$) m/z 500 (M+Na)$^+$; $^1$H-NMR (CD$_3$OD) δ 7.60 (d, J=4.03 Hz, 1H), 7.30-7.20 (m, 2H), 7.18-7.13 (m, 3H), 6.91 (d, J=3.50 Hz, 1H), 5.91 (dd, J=4.94, 15.20 Hz, 1H), 5.54-5.46 (m, 1H), 4.33-4.26 (m, 1H), 4.05-4.00 (m, 1H), 3.81 (s, 3H), 3.63-3.54 (m, 1H), 3.21-3.11 (m, 1H), 2.91-2.70 (m, 5H), 2.36-2.21 (m, 2H), 2.05-1.81 (m, 3H), 0.79 (d, J=6.59 Hz, 3H); $^{19}$F NMR (CD$_3$OD) δ −104.5 (ddd, 1F), −107.2 (ddd, 1F).

Step D1: Preparation of 5-(3-((R)-3,3-difluoro-5-((3S,4S,E)-3-hydroxy-4-methyl-5-phenylpent-1-en-1-yl)-2-oxopyrrolidin-1-yl)propyl)thiophene-2-carboxylic acid (Example 36C)

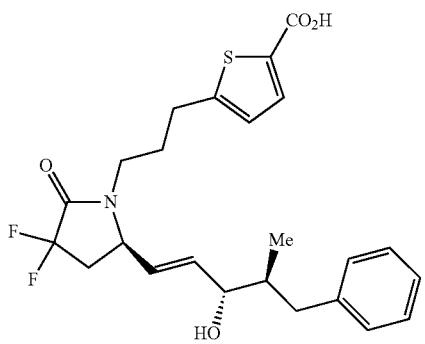

Example 36C 30 mg (97%), colorless oil; TLC $R_f$ 0.23 (solvent system: 50:50:1 v/v/v ethyl acetate-heptane-acetic acid; MS (ESI$^-$) m/z 462.1 (M−H)$^-$; $^1$H NMR (CD$_3$OD) δ 7.56 (d, J=3.66 Hz, 1H), 7.27-7.22 (m, 2H), 7.17-7.12 (m, 3H), 6.89 (d, J=4.12, 8.33 Hz, 1H), 5.91 (dd, J=6.23, 15.38 Hz, 1H), 5.49 (dd, J=9.34, 15.20 Hz, 1H), 4.30 (tt, J=4.12, 8.33 Hz, 1H), 3.95 (dt, J=1.10, 6.04 Hz, 1H), 3.63-3.55 (m, 1H), 3.19-3.09 (m, 1H), 2.94-2.61 (m, 5H), 2.36-2.23 (m, 2H), 2.06-1.82 (m, 3H), 0.77 (d, J=6.59 Hz, 3H); $^{19}$F NMR (CD$_3$OD) δ −104.3 (ddd, 1F), −107.2 (ddd, 1F); $[\alpha]^T_\lambda$=α/cl, $[\alpha]^{21.9}_D$=0.025/(0.01501 g/2 mL)(0.5)=+6.66 (c=0.75, CHCl$_3$).

Step D2: Preparation of 5-(3-((R)-3,3-difluoro-5-((3R,4S,E)-3-hydroxy-4-methyl-5-phenylpent-1-en-1-yl)-2-oxopyrrolidin-1-yl)propyl)thiophene-2-carboxylic acid (Example 36D)

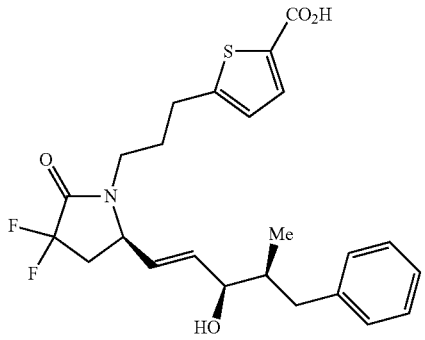

Example 36D 68 mg, colorless oil; TLC $R_f$ 0.256 (solvent system: 50:50:1 v/v/v ethyl acetate-heptane-acetic acid; MS (ESI$^-$)

m/z 462.1 (M−H)⁻; ¹H NMR (CD₃OD) δ 7.57 (d, J=3.66 1H, Hz), 7.30-7.20 (m, 2H), 7.18-7.12 (m, 3H), 6.89 (d, J=3.91 Hz, 1H), 5.91 (dd, J=4.94, 15.20 Hz, 1H), 5.50 (dd, J=9.34, 15.20 Hz, 1H), 4.33-4.27 (m, 1H), 4.05-4.01 (m, 1H), 3.64-3.55 (m, 1H), 3.27-3.12 (m, 1H), 2.91-2.69 (m, 5H), 2.37-2.15 (m, 2H), 2.05-1.81 (m, 3H), 0.80 (d, J=6.59 Hz, 3H); ¹⁹F NMR (CD₃OD) δ −104.4 (ddd, 1F), −107.2 (ddd, 1F); [α]$^T_\lambda$=α/cl, [α]$^{21.9}_D$=−0.142/(0.01838 g/1.5 mL) (0.5)=−23.17 (c=1.22, CHCl₃).

Examples 37A-37D

Steps A, B, and C: Preparation of methyl 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylate (Example 37A) and methyl 5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylate (Example 37B)

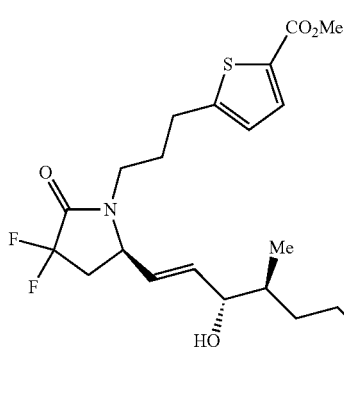

Example 37A

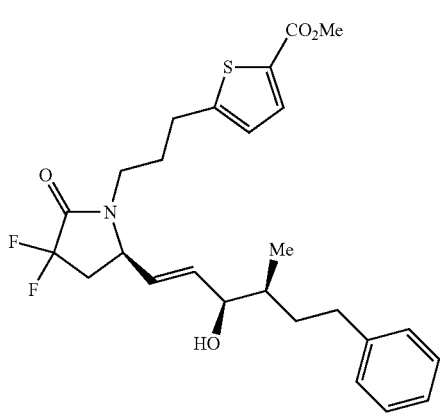

Example 37B

Methyl 5-(3-((R)-3,3-difluoro-5-((4S,E)-3-hydroxy-4-methyl-6-phenylhex-1-en-1-yl)-2-oxopyrrolidin-1-yl)propyl)thiophene-2-carboxylate was prepared by the method described in Example 28, Steps A and B, except that (S)-dimethyl (3-methyl-2-oxo-5-phenylpentyl)phosphonate (151b(i)) was used instead of (S)-dimethyl (3-methyl-2-oxo-6-phenylhexyl)phosphonate (15mb(i)) in Step A.

Step C: The pure diastereomers of Example 37A and Example 37B were isolated following separation by prep HPLC; Gilson Prep instrument; ultraviolet detector at 210 nm; Luna silica 5μ 21.2×250 mm column; mobile phase of heptane-ethanol (96:4 v/v), 21.2 mL/min.

Example 37A (35 mg): as a colorless oil; HPLC retention time 19 min; TLC R$_f$ 0.18 (solvent system: 35:65 v/v ethyl acetate-heptane); MS (ESI⁺) in/z 514.2 (M+Na)⁺; ¹H NMR (CD₃OD) δ 7.61 (d, J=3.83 Hz, 1H), 7.25-7.21 (m, 2H), 7.17-7.10 (m, 3H), 6.89 (d, J=3.83 Hz, 1H), 5.82 (dd, J=6.59, 15.38 Hz, 1H), 5.45 (dd, J=9.34, 15.20 Hz, 1H), 4.95-4.87 (m, 1H), 4.27 (tt, J=4.21, 8.24 Hz, 1H), 3.95 (t, J=6.23 Hz, 1H), 3.82 (s, 3H), 3.58-3.41 (m, 1H), 3.13-3.04 (m, 1H), 2.90-2.67 (m, 5H), 2.52 (ddd, J=6.59, 9.98, 13.82 Hz, 1H), 2.34-2.24 (m, 1H), 2.00-1.86 (m, 2H), 1.79-1.70 (m, 1H), 1.64-1.56 (m, 1H), 1.40-1.23 (m, 1H), 0.91 (d, J=6.59 Hz, 3H); ¹⁹F NMR (CD₃OD) δ−104.4 (ddd, 1F), −107.1 (ddd, 1F).

Example 37B (164 mg): colorless oil; HPLC retention time 16 min; TLC R$_f$ 0.22 (solvent system: 35:65 v/v ethyl acetate-heptane); MS (ESI⁺) m/z 514.2 (M+Na)⁺; ¹H NMR (CD₃OD) δ 7.61 (d, J=3.66 Hz, 1H), 7.25-7.10 (m, 5H), 6.88 (d, J=3.97 Hz, 1H), 5.89 (dd, J=4.94, 15.20 Hz, 1H), 5.47 (dd, J=9.34, 15.20 Hz, 1H), 4.32-4.25 (m, 1H), 4.08-4.01 (m, 1H), 3.83-3.82 (m, 3H), 3.59-3.47 (m, 1H), 3.12 (dddd, J=1.46, 5.77, 7.87, 13.82 Hz, 1H), 2.87-2.65 (m, 5H), 2.61-2.52 (m, 1H), 2.25 (dtd, 1H), 2.00-1.75 (m, 3H), 1.59 (dtt, 1H), 1.43-1.32 (m, 1H), 0.95-0.90 (m, 3H); ¹⁹F NMR (CD₃OD) δ −104.6 (ddd, 1F), −107.1 (ddd, 1F).

Step D1: Preparation of 5-(3-((R)-3,3-difluoro-5-((3S,4S,E)-3-hydroxy-4-methyl-6-phenylhex-1-en-1-yl)-2-oxopyrrolidin-1-yl)propyl)thiophene-2-carboxylic acid (Example 37C)

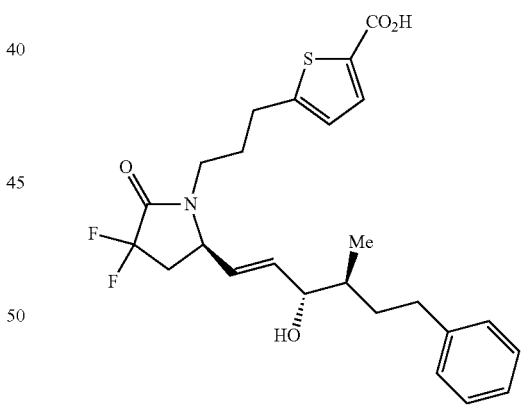

Example 37C 21 mg (81%), colorless oil; TLC R$_f$ 0.24 (solvent system: 50:50:1 v/v/v ethyl acetate-heptane-acetic acid); MS (ESI⁻) m/z 477.56 (M−H)⁻; ¹H NMR (CD₃OD) δ 7.57 (d, J=3.66 Hz, 1H), 7.25-7.10 (m, 5H), 6.86 (d, J=3.88 Hz, 1H), 5.88-5.80 (m, 1H), 5.44 (dd, J=9.15, 15.38 Hz, 1H), 4.27 (tt, J=4.21, 8.42 Hz, 1H), 3.98-3.93 (m, 1H), 3.59-3.46 (m, 1H), 3.13-3.04 (m, 1H), 2.90-2.67 (m, 5H), 2.53 (ddd, J=6.59, 9.80, 13.64 Hz, 1H), 2.34-2.21 (m, 1H), 2.03-1.84 (m, 2H), 1.80-1.71 (m, 1H), 1.65-1.55 (m, 1H), 1.42-1.28 (m, 1H), 0.92 (d, J=6.59 Hz, 3H); ¹⁹F NMR (CD₃OD) δ −104.5 (ddd, 1F), −107.2 (ddd, 1F); [α]$^T_\lambda$=α/cl, [α]$^{21.9}_D$=−0.049/(0.0158 g/1.5 mL)(0.5)=−9.30 (c=1.05, CHCl₃).

Step D2: Preparation of 5-(3-((R)-3,3-difluoro-5-((3R,4S,E)-3-hydroxy-4-methyl-6-phenylhex-1-en-1-yl)-2-oxopyrrolidin-1-yl)propyl)thiophene-2-carboxylic acid (Example 37D)

Example 37D

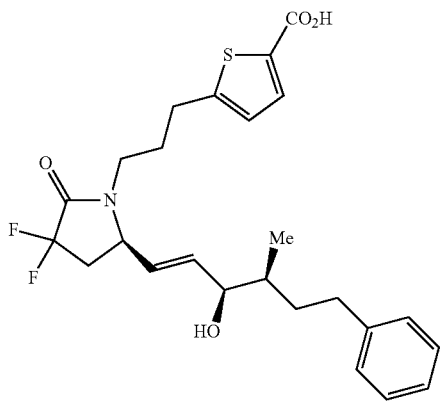

64 mg (43%); colorless oil; TLC $R_f$ 0.24 (solvent system: 50:50:1 v/v/v ethyl acetate-heptane-acetic acid); MS (ESI) m/z 477.56 (M–H)$^-$; $^1$H NMR (CD$_3$OD) δ 7.58 (d, J=3.66 Hz, 1H), 7.26-7.10 (m, 5H), 6.87 (d, J=3.66 Hz, 1H), 5.89 (dd, J=5.13, 15.38 Hz, 1H), 5.48 (dd, J=9.34, 15.20 Hz, 1H), 4.29 (tt, J 4.35, 8.28 Hz, 1H), 4.05 (t, J=4.03 Hz, 1H), 3.60-3.52 (m, 1H), 3.17-3.07 (m, 1H), 2.87-2.65 (m, 5H), 2.57 (ddd, J=6.41, 9.89, 13.73 Hz, 1H), 2.32-2.19 (m, 1H), 2.02-1.75 (m, 3H), 1.64-1.55 (m, 1H), 1.44-1.32 (m, 1H), 0.97-0.88 (m, 3H); $^{19}$F NMR (CD$_3$OD) δ –104.4 (ddd, 1F), –107.1 (ddd, 1F); $[\alpha]^T_\lambda = \alpha/cl$, $[\alpha]^{21.9}_D = -0.170/(0.01556$ g/1.5 mL)(0.5)=–32.755 (c=1.04, CHCl$_3$).

Examples 38A-38D

Steps A, B, and C: Preparation of methyl 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylate (Example 38A) and methyl 5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylate (Example 38B)

Example 38A

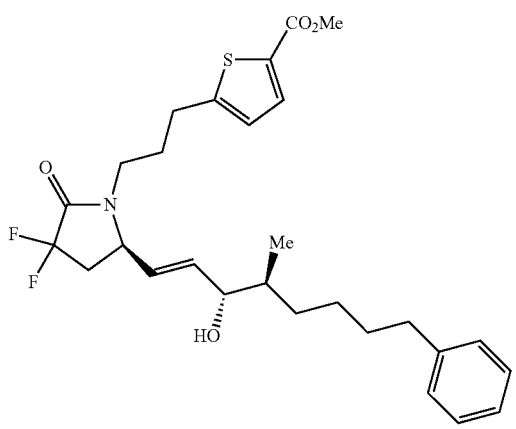

Example 38B

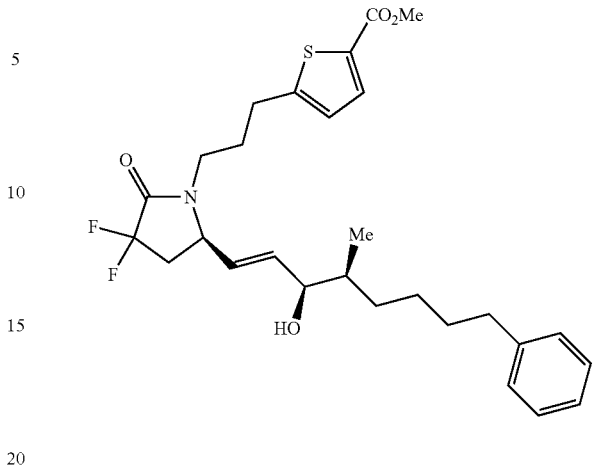

Methyl 5-(3-((5R)-3,3-difluoro-5-((4S,E)-3-hydroxy-4-methyl-8-phenyloct-1-en-1-yl)-2-oxopyrrolidin-1-yl)propyl)thiophene-2-carboxylate was prepared by the method described in Example 28, Steps A and B, except that (S)-dimethyl (3-methyl-2-oxo-7-phenylheptyl)phosphonate (15nb(i)) was used instead of (S)-dimethyl (3-methyl-2-oxo-6-phenylhexyl)phosphonate (15mb(i)) in Step A.

Step C: The pure diastereomers of Example 38A and Example 38B were isolated following separation by prep HPLC.

Agilent 1100 Prep instrument; ultraviolet detector at 210 nm; Luna silica 5μ 21.2×250 mm column; mobile phase of heptane-ethanol (96:4 v/v), 21.2 mL/min.

Example 38A (61 mg); a clear oil; HPLC retention time 29 min; $R_f$ 0.22 (solvent system: 35:65 v/v ethyl acetate-heptane); MS (ESI$^+$) m/z 542.2 (M+Na)$^+$; $^1$H NMR (CD$_3$OD) δ 7.61 (d, J=3.66 Hz, 1H), 7.26-7.19 (m, 2H), 7.17-7.10 (m, 3H), 6.91 (d, J=3.66 Hz, 1H), 5.82 (dd, J=6.59, 15.38 Hz, 1H), 5.42 (dd, J=9.15, 15.38 1H, Hz), 4.30-4.24 (m, 1H), 3.90 (t, J=6.04 Hz, 1H), 3.82 (s, 3H), 3.59-3.47 (m, 1H), 3.16-3.02 (m, 1H), 2.93-2.73 (m, 3H), 2.65-2.53 (m, 2H), 2.34-2.20 (m, 1H), 2.02-1.87 (m, 2H), 1.62-1.36 (m, 5H), 1.35-1.20 (m, 2H), 1.16-1.04 (m, 1H), 0.81 (d, J=6.59 Hz, 3H); $^{19}$F NMR (CD$_3$OD) δ –104.4 (ddd, 1F), –107.2 (ddd, 1F).

Example 38B (222 mg); a colorless oil; HPLC retention time 34 min; $R_f$ 0.26 (solvent system: 35:65 v/v ethyl acetate-heptane); MS (ESI$^+$) m/z 542.2 (M+Na); $^1$H NMR (CD$_3$OD) δ 7.62 (d, J=4.03 Hz, 1H), 7.26-7.18 (m, 2H), 7.16-7.09 (m, 3H), 6.91 (d, J=3.94 Hz, 1H), 5.88 (dd, J=5.13, 15.38 Hz, 1H), 5.46 (dd, J=9.34, 15.56 Hz, 1H), 4.32-4.25 (m, 1H), 4.01-3.96 (m, 1H), 3.82 (s, 3H), 3.61-3.53 (m, 1H), 3.17-3.09 (m, 1H), 2.90-2.68 (m, 3H), 2.58 (t, J=7.69 Hz, 2H), 2.32-2.18 (m, 1H), 2.02-1.88 (m, 2H), 1.64-1.47 (m, 3H), 1.40-1.24 (m, 4H), 1.11-0.99 (m, 1H), 0.84 (d, J=6.96 Hz, 3H); $^{19}$F NMR (CD$_3$OD) δ –104.5 (ddd, 1F), –107.2 (ddd, 1F).

Step D1: Preparation of 5-(3-((R)-3,3-difluoro-5-((3S,4S,E)-3-hydroxy-4-methyl-8-phenyloct-1-en-1-yl)-2-oxopyrrolidin-1-yl)propyl)thiophene-2-carboxylic acid (Example 38C)

Example 38C

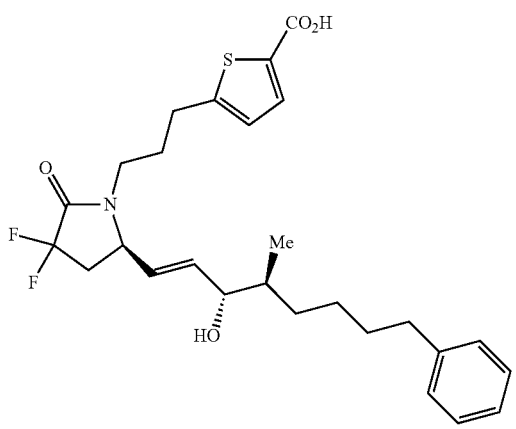

28 mg, colorless oil; TLC $R_f$ 0.21 (solvent system: 50:50:1 v/v/v ethyl acetate-heptane-acetic acid; MS (ESI⁻) m/z 504.1 (M–H)⁻; ¹H NMR (CD₃OD) δ 7.58 (d, J=3.66 Hz, 1H), 7.27-7.09 (m, 5H), 6.89 (d, J=3.99 Hz, 1H), 5.84 (dd, J=6.59, 15.01 Hz, 1H), 5.43 (dd, J=9.15, 15.38 Hz, 1H), 4.32-4.25 (m, 1H), 3.92 (t, J=6.07 Hz, 1H), 3.61-3.45 (m, 1H), 3.17-3.02 (m, 1H), 2.94-2.70 (m, 4H), 2.60 (dt, J=3.84, 7.60 Hz, 2H), 2.35-2.21 (m, 1H), 2.05-1.88 (m, 2H), 1.63-1.37 (m, 5H), 1.34-1.22 (m, 1H), 1.17-1.04 (m, 1H), 0.83 (d, J=6.59 Hz, 3H); ¹⁹F NMR (CD₃OD) δ –100.5 (ddd, 1F), –103.2 (ddd, 1F); $[\alpha]^T_\lambda$=α/cl, $[\alpha]^{21.9}_D$=–0.032/(0.01617 g/1.5 mL)(0.5)=–5.937 (c=1.08, CHCl₃).

Step D2: Preparation of 5-(3-((R)-3,3-difluoro-5-((3R,4S,E)-3-hydroxy-4-methyl-8-phenyloct-1-en-1-yl)-2-oxopyrrolidin-1-yl)propyl)thiophene-2-carboxylic acid (Example 38D)

Example 38D

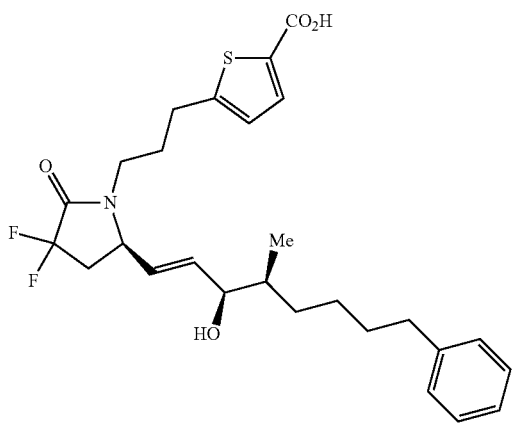

170 mg (88%), colorless oil; TLC $R_f$ 0.19 (solvent system: 50:50:1 v/v/v ethyl acetate-heptane-acetic acid; MS (ESI) m/z 504.1 (M–H)⁻; ¹H NMR (CD₃OD) δ 7.58 (d, J=3.66 Hz, 1H), 7.26-7.18 (m, 2H), 7.16-7.09 (m, 3H), 6.89 (d, J=3.66 Hz, 1H), 5.89 (dd, J=5.13, 15.38 Hz, 1H), 5.46 (dd, J=8.79, 15.38 Hz, 1H), 4.29 (tt, J=4.26, 8.38 Hz, 1H), 3.99 (dt, J=1.46, 4.76 Hz, 1H), 3.62-3.51 (m, 1H), 3.18-3.09 (m, 1H), 2.92-2.67 (m, 4H), 2.58 (t, J=7.69 Hz, 2H), 2.25 (dtd, 1H), 2.03-1.88 (m, 2H), 1.54-1.26 (m, 6H), 1.12-0.89 (m, 1H), 0.84 (d, J=6.96 Hz, 3H); ¹⁹F NMR (CD₃OD) δ –104.4 (ddd, 1F), –107.2 (ddd, 1F); $[\alpha]^T_\lambda$=α/cl, $[\alpha]^{21.9}_D$=–0.134/(0.017 g/2 mL)(0.5)=–31.53 (c=0.85, CHCl₃).

Example 39A-39D

Steps A, B, and C: Preparation of methyl 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylate (Example 39A) and methyl 5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylate (Example 39B)

Example 39A

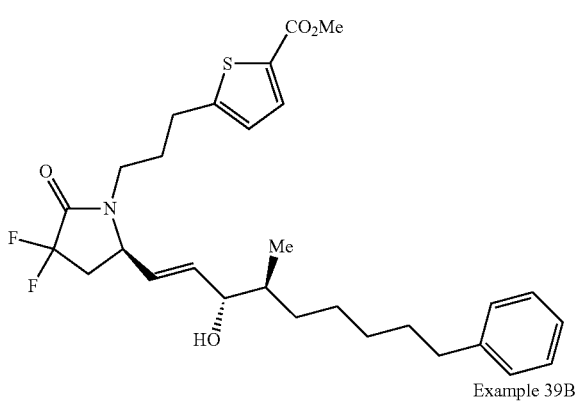

Example 39B

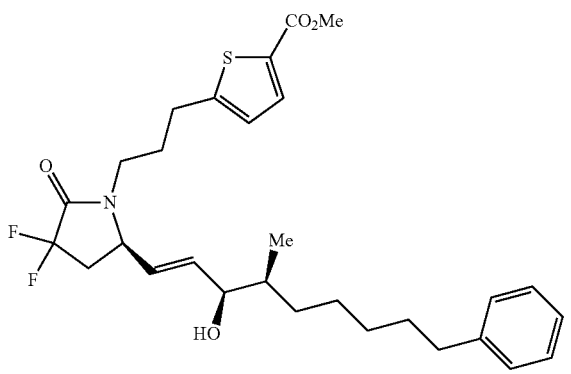

Methyl 5-(3-((R)-3,3-difluoro-5-((4S,E)-3-hydroxy-4-methyl-9-phenylnon-1-en-1-yl)-2-oxopyrrolidin-1-yl)propyl)thiophene-2-carboxylate was prepared by the method described in Example 28, Steps A and B, except that (S)-dimethyl (3-methyl-2-oxo-8-phenyloctyl)phosphonate (15ob(i)) was used instead of (S)-dimethyl (3-methyl-2-oxo-6-phenylhexyl)phosphonate (15mb(i)) in Step A.

Step C: The pure diastereomers of Example 39A and Example 39B were isolated following separation by prep HPLC.

Gilson Prep instrument; ultraviolet detector at 210 nm; Luna silica 5 21.2×250 mm column; mobile phase of heptane-ethanol (96:4 v/v), 21.2 mL/min.

Example 39A: 46 mg; colorless oil; HPLC retention time 22.5 min; TLC $R_f$ 0.24 (solvent system: 35:65 v/v ethyl acetate-heptane); MS (ESI⁺) m/z 556.2 (M+Na); ¹H NMR (CD₃OD) 7.62 (d, J=3.66 Hz, 1H), 7.25-7.19 (m, 2H), 7.16-7.10 (m, 3H), 6.90 (d, J=3.86 Hz, 1H), 5.82 (dd, J=6.59, 15.38 Hz, 1H), 5.44 (dd, J=9.15, 15.38 Hz, 1H), 4.30-4.24 (m, 1H), 3.93-3.89 (m, 1H), 3.82 (s, 3H), 3.58-3.47 (m, 1H), 3.13-3.05 (m, 1H), 2.91-2.73 (m, 3H), 2.58 (t, J=7.51 Hz, 2H), 2.27 (dtd, 1H), 2.01-1.87 (m, 2H), 1.64-1.51 (m, 3H), 1.44-1.21 (m, 6H), 1.03 (q, J=9.03 Hz, 1H), 0.82 (d, J=6.96 Hz, 3H); $^{19}F$ NMR (CD$_3$OD) δ −104.4 (ddd, 1F), −107.2 (ddd, 1F).

Example 39B: 211 mg; colorless oil; HPLC retention time 19 min; TLC R$_f$ 0.27 (solvent system: 35:65 v/v ethyl acetate-heptane); MS (ESI$^+$) m/z 556.2 (M+Na)$^+$.

Step D1: Preparation of 5-(3-((R)-3,3-difluoro-5-((3S,4S,E)-3-hydroxy-4-methyl-9-phenylnon-1-en-1-yl)-2-oxopyrrolidin-1-yl)propyl)thiophene-2-carboxylic acid (Example 39C)

Example 39C

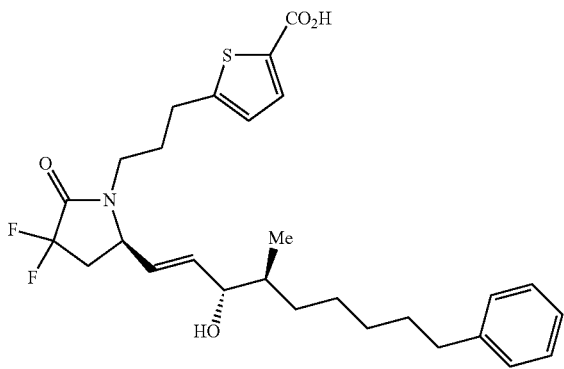

3 mg (8%); colorless oil; TLC R$_f$ 0.13 (solvent system: 50:50:1 v/v/v ethyl acetate-heptane-acetic acid; MS (ESI$^-$) m/z 518.2 (M−H)$^-$; $^1$H NMR (CD$_3$OD) δ 7.51 (d, J=3.66 Hz, 1H), 7.28-7.18 (m, 2H), 7.17-7.08 (m, 3H), 6.84 (d, J=3.66 Hz, 1H), 5.83 (dd, J=6.59, 15.38 Hz, 1H), 5.44 (dd, J=9.15, 15.38 Hz, 1H), 4.27 (tt, J=4.17, 8.47 Hz, 1H), 3.91 (t, J=6.04 Hz, 1H), 3.57-3.43 (m, 1H), 3.17-2.99 (m, 1H), 2.89-2.71 (m, 3H), 2.65-2.51 (m, 2H), 2.29-2.19 (m, 1H), 2.03-1.88 (m, 2H), 1.36-1.20 (m, 9H), 1.12-1.01 (m, 1H), 0.89-0.82 (m, 3H); $^{19}F$ NMR (CD$_3$OD) δ −104.4 (ddd, 1F), −107.2 (ddd, 1F).

Step D2: Preparation of 5-(3-((R)-3,3-difluoro-5-((3R,4S,E)-3-hydroxy-4-methyl-9-phenylnon-1-en-1-yl)-2-oxopyrrolidin-1-yl)propyl)thiophene-2-carboxylic acid (Example 39D)

Example 39D

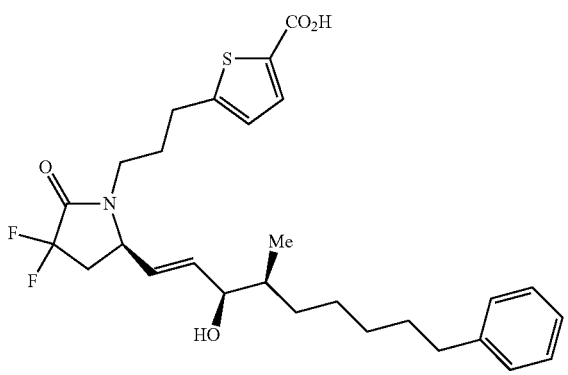

90 mg (46%); colorless oil; TLC R$_f$ 0.2 (solvent system: 50:50:1 v/v/v ethyl acetate-heptane-acetic acid; MS (ESI$^-$) m/z 518.2 (M−H)$^-$; [α]$^T_λ$=α/cl, [α]$^{21.9}_D$=−0.177/(0.026 g/2 mL)(0.5)=−27.23° (c=1.3, CHCl$_3$).

Compounds wherein X═H may generally be prepared using procedures and methods analogous to those hereinabove described for preparing compounds where X═F. Additional procedures and methods that may be used to prepare compounds wherein X═H are described hereinbelow.

The aldehydes 6a'-f' may be prepared from commercially available (R)-di-tert-butyl 2-aminopentanedioate 7' according to the route illustrated in Scheme 1'. Condensation of 7' with bromides 3a'-f provides 8a'-f', respectively (Step A). Subsequent ring closure provides pyrrolidinone intermediates 9a'-f (Step B). Removal of the tert-butyl group with TFA (Step C) unmasks the carboxylic acid moiety of intermediates 10a'-f'. Mixed anhydride formation by reacting these carboxylic acids with isobutyl chloroformate and subsequent reduction of the mixed anhydride with sodium borohydride (Step D) provides alcohol intermediates 5a'-f'. Controlled oxidation of the alcohol group of each of the compounds 5a'-f' provides aldehydes 6a'-f'.

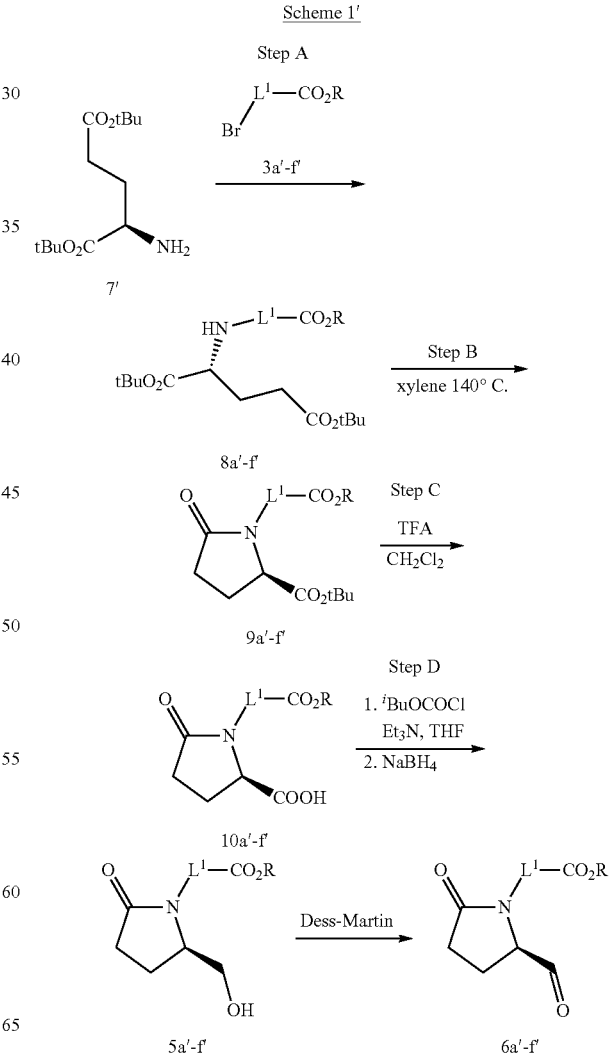

Scheme 1'

-continued

L¹ =

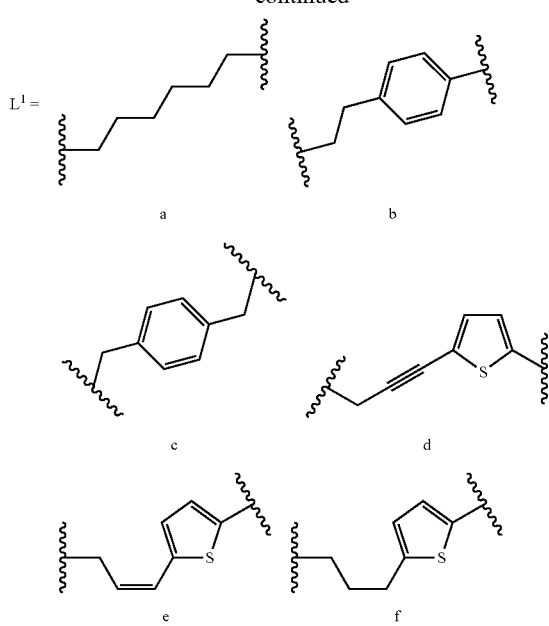

a  b  c  d  e  f

The aldehyde (R)-methyl 4-(2-(2-formyl-5-oxopyrrolidin-1-yl)ethyl)benzoate (6b') may be prepared from commercially available (R)-di-tert-butyl 2-aminopentanedioate (7') and aldehyde 11' according to the method described by Yufang X. et al. in Bioorganic and Medicinal Chemistry Letters, 2008, 18, 821-824, where the key reductive alkylation step is shown below in Scheme 2'. Condensation of 7' with methyl 4-(2-oxoethyl)benzoate (11') accompanied with subsequent ring closure provides pyrrolidinone intermediate 9b' (Step A and B). Deesterification of 9b' followed by reduction and subsequent controlled oxidation produces aldehyde 6b'.

Scheme 2'

Step A

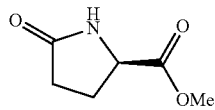

Step B
xylene, reflux

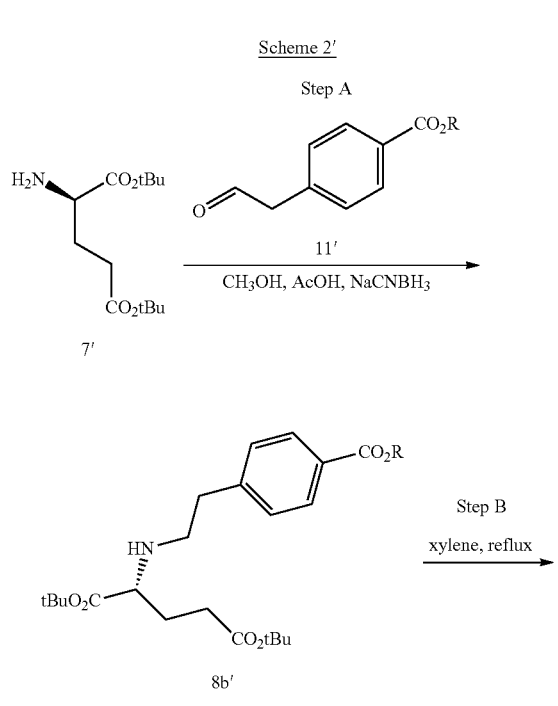

-continued

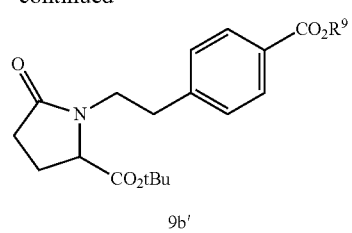

9b'

Preparation of (R)-methyl 5-oxopyrrolidine-2-carboxylate (D-pyroglutamic acid methyl ester) from (R)-5-oxopyrrolidine-2-carboxylic acid (D-pyroglutamic acid)

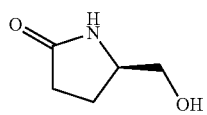

To a solution consisting of (R)-5-oxopyrrolidine-2-carboxylic acid (D-pyroglutamic acid from Chem-Impex International, 12.6 g, 97.4 mmol) in methanol (100 mL) was added sulfuric acid (1 mL) and the mixture was stirred at room temperature for 24 hours. The solvent was evaporated from the mixture, and the residue was purified by silica gel chromatography. Elution with acetone-dichloromethane (3:7 v/v) afforded the title intermediate (13.3 g, 95%) as a clear oil; TLC $R_f$ 0.42 (solvent system: 3:7 v/v acetone-dichloromethane); $^1$H-NMR (CDCl$_3$) δ 4.25 (t, 1H), 3.73 (s, 3H), 2.5-2.2 (m, 4H).

Preparation of (R)-5-(hydroxymethyl)pyrrolidin-2-one

To a solution consisting of (R)-methyl 5-oxopyrrolidine-2-carboxylate (D-pyroglutamic acid methyl ester, 13.2 g, 115 mmol) in methanol (100 mL) at 0° C. was added sodium borohydride (10.5 g, 278 mmol) in portions. The reaction mixture was stirred at 0° C. until completion, at which time, acetic acid (3 mL) was added. The reaction mixture was concentrated and the residue was purified on silica gel, eluting with methanol-chloroform (1:9 v/v) to afford the title intermediate (12.9 g, 97%) as a colorless solid; TLC $R_f$ 0.33 (solvent system: 1:9 v/v methanol-chloroform); $^1$H-NMR (CDCl$_3$) δ 7.17 (s, 1H), 3.92 (s, 1H), 3.85-3.75 (m, 1H), 3.64-3.40 (m, 2H), 2.42-2.35 (m, 2H), 2.2-2.05 (m, 1H), 1.88-1.7 (m, 1H).

Preparation of (5R)-5-((1-ethoxyethoxy)methyl)pyrrolidin-2-one

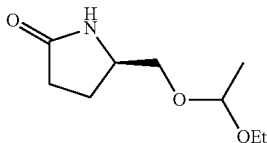

To a solution consisting of (R)-5-(hydroxymethyl)pyrrolidin-2-one (21.7 g, 188 mmol) in dichloromethane (250 mL) was added ethyl vinyl ether (36.2 mL, 376 mmol) followed by trichloroacetic acid (0.878 g, 5.37 mmol). The reaction mixture was stirred at room temperature for 16 hours. To the reaction mixture was added a saturated solution of sodium bicarbonate (400 mL) and the organic phase was separated. The organic phase was subsequently washed with water (200 mL) and brine (200 mL), dried over anhydrous sodium sulfate, filtered, and concentrated. The residue was purified by silica gel chromatography eluting with methanol-chloroform (1:9 v/v) to afford the title intermediate (13.0 g, 37%) as a clear oil; TLC $R_f$ 0.56 (solvent system: 1:9 v/v methanol-chloroform); $^1$H-NMR (CDCl$_3$) δ 4.69 (quartet, 1H), 3.83-3.2 (m, 5H), 2.35 (t, 2H), 2.25-2.19 (m, 1H), 1.8-1.7 (m, 1H), 1.38 (d, 3H), 1.21 (t, 3H).

Preparation of (R)-5-(((tert-butyldimethylsilyl)oxy)methyl)-pyrrolidin-2-one

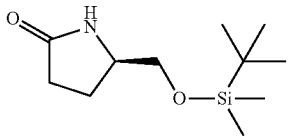

To a solution consisting of (R)-5-(hydroxymethyl)pyrrolidin-2-one (5.7 g, 50 mmol) in dimethylsulfoxide (50 mL) was added tert-butyldimethylchlorosilane (9.71 g, 64.5 mmol) followed by imidazole (4.39 g, 64.5 mmol). The reaction mixture was stirred at room temperature overnight. The reaction mixture was quenched with water (50 mL) and extracted with ethyl acetate (3×100 mL). The combined organic phase was dried over anhydrous sodium sulfate, filtered, and concentrated. The residue was purified by silica gel chromatography eluting with methanol-chloroform (5:95 v/v) to afford the title intermediate (10.0 g, 85%) as a clear oil; TLC $R_f$ 0.37 (solvent system: 5:95 v/v methanol-chloroform).

Preparation of methyl 7-((2R)-2-((1-ethoxyethoxy)methyl)-5-oxopyrrolidin-1-yl)heptanoate

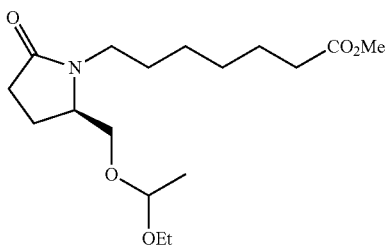 [SMILES: CCOC(C)OC[C@H]1CCC(=O)N1CCCCCCC(=O)OC]

To an ice-chilled suspension consisting of sodium hydride (60% in mineral oil, 1.07 g, 26.7 mmol) and sodium iodide (4.40 g, 29.4 mmol) in hexamethylphosphoramide (30 mL) was added dropwise a solution consisting of (5R)-5-((1-ethoxyethoxy)methyl)-pyrrolidin-2-one (5.00 g, 26.7 mmol) in hexamethylphosphoramide (20 mL). The mixture was stirred at room temperature for two hours followed by 50° C. for 20 minutes. To the reaction mixture was added dropwise methyl 7-bromoheptanoate (commercially available from Alfa Aesar, 7.15 g, 32.0 mmol) and stirred overnight at 50° C. The mixture was diluted with ethyl acetate (300 mL). Concentrated aqueous hydrochloric acid (10 mL) was subsequently added followed by water (50 mL). The aqueous phase was separated and the organic layer was washed with 5% aqueous sodium thiosulfate (100 mL), water (200 mL), and brine (300 mL), and was dried over anhydrous sodium sulfate, filtered and evaporated to provide the crude title intermediate, which was carried on to the next step without further purification or characterization.

Preparation of (R)-methyl 7-(2-(hydroxymethyl)-5-oxopyrrolidin-1-yl)heptanoate

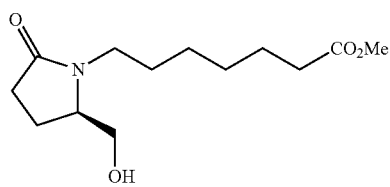 [SMILES: COC(=O)CCCCCCN1C(=O)CC[C@@H]1CO]

To a solution consisting of the crude methyl 7-((2R)-2-((1-ethoxyethoxy)methyl)-5-oxopyrrolidin-1-yl)heptanoate in methanol (50 mL) was added p-toluenesulfonic acid monohydrate (10 mg) and the mixture was stirred at room temperature for 18 hours. To the reaction mixture was added a saturated aqueous solution of sodium bicarbonate and the organic material was extracted with ethyl acetate. The organic phase was separated and washed with brine, dried over anhydrous sodium sulfate, filtered, and concentrated. The residue was purified by silica gel chromatography eluting with methanol-ethyl acetate (3:97 v/v) to afford the title intermediate (1.24 g, 18% over two steps) as a pale yellow oil; TLC $R_f$ 0.24 (solvent system: 3:97 v/v methanol-ethyl acetate); MS (APCI$^+$) m/z 258 (M+1).

Preparation of (R)-methyl 7-(2-formyl-5-oxopyrrolidin-1-yl)heptanoate

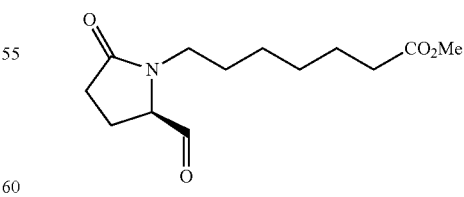

To a solution consisting of (R)-methyl 7-(2-(hydroxymethyl)-5-oxopyrrolidin-1-yl)heptanoate (1.24 g, 4.82 mmol) in dichloromethane (25 mL) was added Dess-Martin periodinane (2.04 g, 4.82 mmol) in portions and the mixture was stirred at room temperature until completion as monitored by TLC. The volatiles were evaporated, and to the residual mixture was added diethyl ether (50 mL). The solid material was filtered through a thin pad of Celite and the filtrate was concentrated. The residue was purified on silica gel eluting with methanol-ethyl acetate (3:97 v/v) to afford the title intermediate (1.1 g, 89%) as a pale yellow oil; TLC $R_f$ 0.33 (solvent system: 3:97 v/v methanol-ethyl acetate).

Preparation of (R)-tert-butyl 1-(4-(methoxycarbonyl)-phenethyl)-5-oxopyrrolidine-2-carboxylate

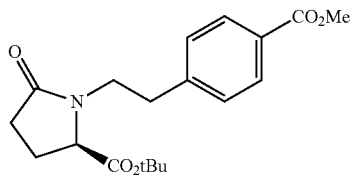 [SMILES: COC(=O)c1ccc(CCN2C(=O)CC[C@@H]2C(=O)OC(C)(C)C)cc1]

Step A

To a solution consisting of (R)-di-tert-butyl 2-aminopentanedioate (H-D-Glu(OtBu)-OtBu, commercially available from Life ProTein (3.50 g, 15.6 mmol) in methanol (100 mL) was added methyl 4-(2-oxoethyl)benzoate (synonym: 4-carbomethoxyphenylacetaldehyde, reagent; obtained from methyl 4-formyl benzoate as described in Nair et al., *J. Med. Chem.*, 1989, 32, 1277-1283; 2.80 g, 15.6 mmol), acetic acid (1.05 mL, 2.67 mmol), and sodium cyanoborohydride (1.45 g, 23.1 mmol), and the mixture was stirred at room temperature for three hours. The reaction mixture was diluted with ethyl acetate and washed with water and brine, dried over sodium sulfate, filtered, and concentrated under reduced pressure.

Step B:

The residue was diluted with xylene and the solution refluxed for 5 hours and concentrated. The residue was purified by silica gel chromatography eluting with ethyl acetate-heptane (1:1) to afford the title compound (2.0 g, 37%) as a white solid; TLC $R_f$ 0.45 (solvent system 1:1 v/v ethyl acetate-heptane).

Preparation of (R)-1-(4-(methoxycarbonyl)phenethyl)-5-oxopyrrolidine-2-carboxylic acid

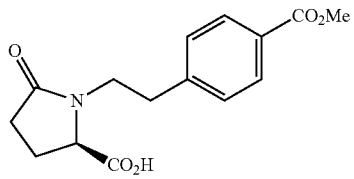 [SMILES: COC(=O)c1ccc(CCN2C(=O)CC[C@@H]2C(=O)O)cc1]

A mixture consisting of (R)-tert-butyl 1-(4-(methoxycarbonyl)phenethyl)-5-oxopyrrolidine-2-carboxylate (2.0 g, 5.7 mmol), trifluoroacetic acid (25 mL), and water (0.125 mL) was stirred for three hours at room temperature and was subsequently concentrated in vacuo to afford the crude title intermediate (2.26 g) as a yellow oil, which was used in the next step without purification.

Preparation of (R)-methyl 4-(2-(2-(hydroxymethyl)-5-oxopyrrolidin-1-yl)ethyl)benzoate

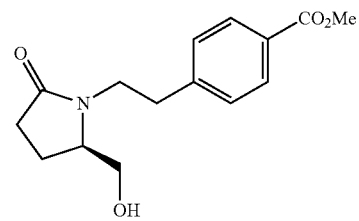 [SMILES: COC(=O)c1ccc(CCN2C(=O)CC[C@@H]2CO)cc1]

To a stirring mixture consisting of crude (R)-1-(4-(methoxycarbonyl)phenethyl)-5-oxopyrrolidine-2-carboxylic acid (2.26 g, 8.14 mmol) in THF (40 mL) at −10° C. was added N-methylmorpholine (0.9 mL, 8 mmol). After stirring for five minutes, isobutyl chloroformate (1.08 mL, 8.25 mmol) was added dropwise and the reaction mixture was stirred for an additional thirty minutes and was subsequently filtered through a pad of Celite. The filtrate was cooled to −10° C., and a solution consisting of sodium borohydride (0.434 g, 11.5 mmol) predissolved in water (15 mL) was added. The resulting mixture was stirred at 0° C. for one hour and then at room temperature for one hour. The mixture was poured into a separatory funnel and diluted with ethyl acetate (200 mL). The organic layer was washed sequentially with 1N hydrochloric acid solution, saturated sodium bicarbonate solution, and brine, was dried over sodium sulfate, filtered, and concentrated. The residue was purified by silica gel chromatography eluting with methanol-ethyl acetate (3:97 v/v) to afford the title compound as an off white solid; TLC $R_f$ 0.19 (solvent system 3:97 v/v methanol-ethyl acetate); MS (APCI) m/z 278 (M+1).

Preparation of (R)-methyl 4-(2-(2-formyl-5-oxopyrrolidin-1-yl)ethyl)benzoate

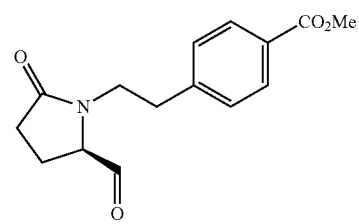 [SMILES: COC(=O)c1ccc(CCN2C(=O)CC[C@@H]2C=O)cc1]

(R)-Methyl 4-(2-(2-(2-formyl-5-oxopyrrolidin-1-yl)ethyl)benzoate was prepared from (R)-methyl 4-(2-(2-(hydroxymethyl)-5-oxopyrrolidin-1-yl)ethyl)benzoate by oxidation with Dess-Martin periodinane as described above; TLC $R_f$ 0.29 (solvent system 3:97 v/v methanol-ethyl acetate).

Preparation of (R)-di-tert-butyl 2-((4-(2-methoxy-2-oxoethyl)benzyl)amino)pentanedioate

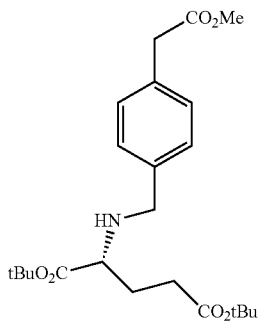 [SMILES: COC(=O)Cc1ccc(CN[C@H](CCC(=O)OC(C)(C)C)C(=O)OC(C)(C)C)cc1]

A stirring mixture consisting of (R)-di-tert-butyl 2-aminopentanedioate (H-D-Glu(OtBu)-OtBu, 5.0 g, 16.9 mmol), methyl 2-(4-(bromomethyl)phenyl)acetate (4.52 g, 18.6 mmol; prepared in 99% yield from the corresponding carboxylic acid and trimethylsilyldiazomethane according to known methods such as those described in Leggio, A. et al., *Chemical Biology & Drug Design*, 2009, 73(3), 287-291), diisopropylethylamine (8.83 mL, 50.7 mmol), and sodium iodide (2.53 g, 16.9 mmol) in dry hexamethylphosphoramide (50 mL) was heated at 55° C. for 15 hours. The reaction mixture was cooled, diluted with ethyl acetate (1.5 L), and washed sequentially with an aqueous solution of ammonium chloride and a saturated aqueous solution of sodium chloride. The organic phase was dried over sodium sulfate and concentrated in vacuo. The residue was purified by silica gel chromatography eluting with a gradient of ethyl acetate-heptane (1:20 to 1:5 v/v) to afford the title intermediate (5.78 g, 81%) as a colorless oil; TLC $R_f$ 0.45 (solvent system 1:3 v/v ethyl acetate-heptane); MS (APCI$^+$) m/z 422 (M+1).

Preparation of (R)-tert-butyl 1-(4-(2-methoxy-2-oxoethyl)benzyl)-5-oxopyrrolidine-2-carboxylate

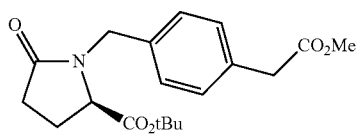 [SMILES: COC(=O)Cc1ccc(CN2C(=O)CC[C@@H]2C(=O)OC(C)(C)C)cc1]

A stirring mixture consisting of (R)-di-tert-butyl 2-((4-(2-methoxy-2-oxoethyl)benzyl)amino)pentanedioate (5.75 g, 13.6 mmol) in o-xylene (40 mL) was heated at 100° C. for three days. The solvent was evaporated under reduced pressure and the residue was purified by silica gel chromatography eluting with a gradient of ethyl acetate-heptane (1:20 to 1:1 v/v) to afford the title intermediate (3.09 g, 65.2%) as a colorless oil; TLC $R_f$ 0.6 (solvent system 4:6 v/v ethyl acetate-heptane); MS (APCI$^+$) m/z 370 (M+23, Na$^+$).

Preparation of (R)-1-(4-(2-methoxy-2-oxoethyl)benzyl)-5-oxopyrrolidine-2-carboxylic acid

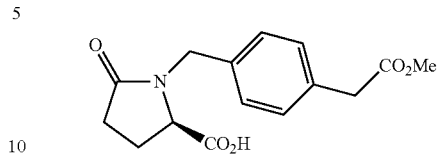

A stirring mixture consisting of (R)-tert-butyl 1-(4-(2-methoxy-2-oxoethyl)benzyl)-5-oxopyrrolidine-2-carboxylate (2.93 g, 8.43 mmol) and trifluoroacetic acid (4.55 mL, 59.0 mmol) in dichloromethane (30 mL) was heated at 45° C. for seven hours with subsequent stirring at room temperature overnight. The reaction mixture was diluted with ethanol and evaporated under reduced pressure. The crude residue (2.44 g) was carried onto the next step without purification.

Preparation of (R)-methyl 2-(4-((2-(hydroxymethyl)-5-oxopyrrolidin-1-yl)methyl)phenyl)acetate

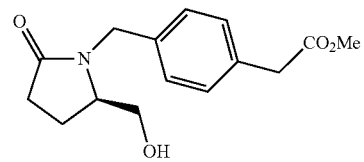 [SMILES: COC(=O)Cc1ccc(CN2C(=O)CC[C@@H]2CO)cc1]

(R)-Methyl 2-(4-((2-(hydroxymethyl)-5-oxopyrrolidin-1-yl)methyl)phenyl)acetate was prepared from (R)-1-(4-(2-methoxy-2-oxoethyl)benzyl)-5-oxopyrrolidine-2-carboxylic acid as described above for (R)-methyl 4-(2-(2-(hydroxymethyl)-5-oxopyrrolidin-1-yl)ethyl)benzoate; TLC $R_f$ 0.5 (solvent system 5:95 v/v methanol-dichloromethane); $^1$H-NMR (CDCl$_3$) δ 7.3-7.2 (m, 4H), 4.9 (d, 1H), 4.2 (d, 1H), 3.8-3.7 (m, 1H), 3.7 (s, 3H), 3.6 (s, 2H), 3.6-3.4 (m, 2H), 2.6-2.4 (m, 2H), 2.1-1.9 (m, 2H).

Preparation of (R)-methyl 2-(4-((2-formyl-5-oxopyrrolidin-1-yl)methyl)phenyl)acetate

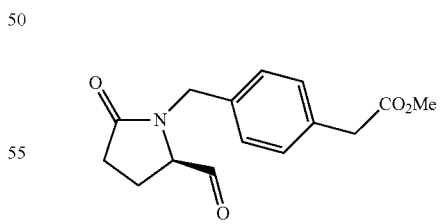

(R)-Methyl 2-(4-((2-formyl-5-oxopyrrolidin-1-yl)methyl)phenyl)acetate (0.2 g, 90%) was prepared from (R)-methyl 2-(4-((2-(hydroxymethyl)-5-oxopyrrolidin-1-yl)methyl)phenyl)acetate by oxidation with Dess-Martin periodinane as described above; MS (ESI$^-$) m/z 274 (M−1); $^1$H-NMR (CDCl$_3$) δ 9.4 (d, 1H), 7.3-7.1 (m, 4H), 5.0-4.8 (m, 2H), 4.2-4.0 (m, 1H), 3.7 (s, 3H), 3.6 (s, 2H), 2.6-1.9 (m, 4H).

Preparation of methyl 5-bromo-2-thiophene carboxylate

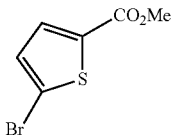

To an ice-cooled mixture consisting of 5-bromo-2-thiophene carboxylic acid (5.25 g, 25.4 mmol) in ethyl acetate (200 mL) and methanol (20 mL) was added trimethylsilyldiazomethane (2M in diethyl ether, 20 mL, 40 mmol) over 20 minutes. The reaction mixture was stirred for 24 hours. The solvent was removed and the residue was purified by silica gel chromatography eluting with ethyl acetate-heptanes (1:50 v/v) to afford the title intermediate (5.5 g, 98%) as a white solid; TLC $R_f$ 0.60 (solvent system 1:9 v/v ethyl acetate-heptanes); $^1$H-NMR (CDCl$_3$) δ 7.5 (d, 1H), 7.1 (d, 1H), 4.9 (s, 3H).

Preparation of methyl 5-(3-hydroxyprop-1-yn-1-yl)thiophene-2-carboxylate

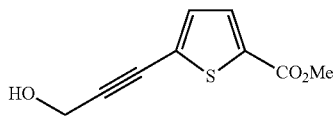 [SMILES: COC(=O)c1ccc(C#CCO)s1]

To a covered mixture consisting of methyl 5-bromo-2-thiophene carboxylate (5.6 g, 25 mmol) in benzene (60 mL) was added a suspension consisting of tetrakis(triphenylphosphine)palladium (0) (1.4 g, 1.3 mmol) in benzene (10 mL), and the reaction mixture was stirred for 30 minutes. To the reaction mixture was then added copper(I) iodide (480 mg, 2.52 mmol) and n-butylamine (5 mL, 50 mmol) in one portion each, followed by propargyl alcohol (2.2 mL, 38 mmol) in benzene (30 mL) over 15 minutes, and the reaction was stirred for 24 hours. To the reaction mixture was added a saturated solution of ammonium chloride (200 mL) and the organic material was extracted with ethyl acetate. The organic phase was washed with water, then brine, dried over sodium sulfate, filtered, and concentrated. The residue was purified by silica gel chromatography eluting with ethyl acetate-heptanes (1:10 v/v) to afford the title intermediate (3.8 g, 78%); TLC $R_f$ 0.7 (solvent system 1:1 v/v ethyl acetate-heptanes); $^1$H-NMR (CDCl$_3$) δ 7.6 (d, 1H), 7.1 (d, 1H), 4.5 (s, 2H), 3.9 (s, 3H), 2.0 (br s, 1H).

Preparation of methyl 5-(3-bromoprop-1-yn-1-yl)thiophene-2-carboxylate

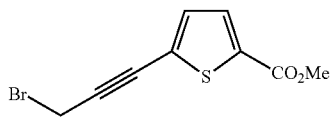 [SMILES: COC(=O)c1ccc(C#CCBr)s1]

To an ice cooled solution of methyl 5-(3-hydroxyprop-1-yn-1-yl)thiophene-2-carboxylate (1.32 g, 6.73 mmol) in dichloromethane (25 ml) was added carbon tetrabromide (3.1 g, 9.42 mmol) and triphenylphosphine (2.5 g, 9.42 mmol) and the mixture stirred for 4 hours. The solvent was removed and the residue was purified by silica gel chromatography eluting with ethyl acetate:heptanes (1:25 v:v) to afford the title compound (1.5 g). TLC $R_f$ 0.65 (solvent system 80:20 v/v heptanes:ethyl acetate); H-NMR (CDCl$_3$) δ 7.6 (d, 1H), 7.1 (d, 1H), 4.1 (s, 2H), 3.9 (s, 3H).

Preparation of (R)-di-tert-butyl 2-((3-(5-(methoxycarbonyl)-thiophen-2-yl)prop-2-yn-1-yl)amino)pentanedioate

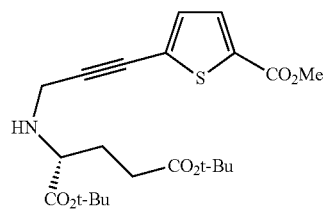 [SMILES: COC(=O)c1ccc(C#CCN[C@H](CCC(=O)OC(C)(C)C)C(=O)OC(C)(C)C)s1]

(R)-Di-tert-butyl 2-((3-(5-(methoxycarbonyl)thiophen-2-yl)prop-2-yn-1-yl)amino)pentanedioate was prepared from methyl 5-(3-bromoprop-1-yn-1-yl)thiophene-2-carboxylate using the method described above for preparing (R)-di-tert-butyl 2-((4-(2-methoxy-2-oxoethyl)benzyl)amino)pentanedioate; TLC $R_f$ 0.45 (solvent system 80:20 v/v heptanes:ethyl acetate); $^1$H-NMR (CDCl$_3$) δ 7.7 (d, 1H), 6.9 (d, 1H), 3.9 (s, 3H), 3.3-3.2 (m, 1H), 3.2 (s, 2H), 2.4 (t, 2H), 2.0-1.8 (m, 2H), 1.45 (d, 18H).

Preparation of (R)-tert-butyl 1-(3-(5-(methoxycarbonyl)-thiophen-2-yl)prop-2-yn-1-yl)-5-oxopyrrolidine-2-carboxylate

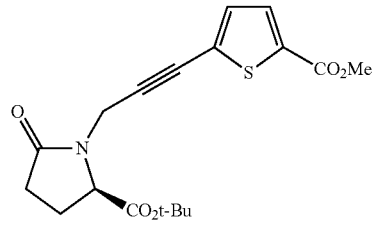 [SMILES: COC(=O)c1ccc(C#CCN2C(=O)CC[C@@H]2C(=O)OC(C)(C)C)s1]

(R)-Tert-butyl 1-(3-(5-(methoxycarbonyl)thiophen-2-yl)prop-2-yn-1-yl)-5-oxopyrrolidine-2-carboxylate was prepared from (R)-di-tert-butyl 2-((3-(5-(methoxycarbonyl)thiophen-2-yl)prop-2-yn-1-yl)amino)pentanedioate using the method described above for preparing (R)-tert-butyl 1-(4-(2-methoxy-2-oxoethyl)benzyl)-5-oxopyrrolidine-2-carboxylate; TLC $R_f$ 0.25 (solvent system 60:40 v/v heptanes:ethyl acetate); $^1$H-NMR (CDCl$_3$) δ 7.7 (d, 1H), 6.9 (d, 1H), 4.5-4.4 (m, 1H), 4.2-4.0 (m, 2H), 3.85 (s, 3H), 2.6-2.5 (m, 1H), 2.4-2.2 (m, 2H), 2.1-2.0 (m, 1H), 1.4 (s, 9H).

Preparation of (R)-1-(3-(5-(methoxycarbonyl)thiophen-2-yl)prop-2-yn-1-yl)-5-oxopyrrolidine-2-carboxylic acid

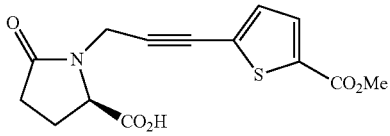 [SMILES: COC(=O)c1ccc(C#CCN2C(=O)CC[C@@H]2C(=O)O)s1]

A solution of (R)-tert-butyl 1-(3-(5-(methoxycarbonyl)thiophen-2-yl)prop-2-yn-1-yl)-5-oxopyrrolidine-2-carboxylate (1.1 g, 3.03 mmol) and trifluoroacetic acid (4 mL, 51.9 mmol) in dichloromethane (45 mL) was heated at 50° C. overnight. The reaction mixture was diluted with ethanol and toluene and evaporated under reduced pressure to produce a residue that was used in the next step with no further purification; TLC $R_f$ 0.10 (solvent system 60:40 v/v heptanes:ethyl acetate).

Preparation of (R)-methyl 5-(3-(2-(hydroxymethyl)-5-oxopyrrolidin-1-yl)prop-1-yn-1-yl)thiophene-2-carboxylate

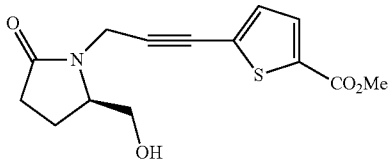 [SMILES: COC(=O)c1ccc(C#CCN2C(=O)CC[C@@H]2CO)s1]

(R)-Methyl 5-(3-(2-(hydroxymethyl)-5-oxopyrrolidin-1-yl)prop-1-yn-1-yl)thiophene-2-carboxylate was prepared from (R)-1-(3-(5-(methoxycarbonyl)thiophen-2-yl)prop-2-yn-1-yl)-5-oxopyrrolidine-2-carboxylic acid using the method described above for preparing (R)-methyl 4-(2-(2-(hydroxymethyl)-5-oxopyrrolidin-1-yl)ethyl)benzoate; TLC $R_f$ 0.30 (solvent system 95:5 v/v dichloromethane:methanol); $^1$H-NMR (CDCl$_3$); δ 7.6 (d, 1H), 6.9 (d, 1H), 4.1-4.0 (m, 1H), 3.85 (s, 3H), 3.8 (s, 2H) 3.6-3.5 (s, 1H), 3.2-3.0 (br s, 1H), 2.6-2.4 (m, 1H), 2.4-2.3 (m, 1H), 2.2-2.0 (m, 1H), 2.0-1.9 (m, 1H); MS (ESI$^+$) m/z 294.0 (M+1), (ESI$^-$) m/z 292.0 (M−1).

Preparation of (R)-methyl 5-(3-(2-formyl-5-oxopyrrolidin-1-yl)prop-1-yn-1-yl)thiophene-2-carboxylate

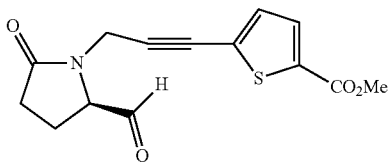 [SMILES: COC(=O)c1ccc(C#CCN2C(=O)CC[C@@H]2C=O)s1]

(R)-Methyl 5-(3-(2-formyl-5-oxopyrrolidin-1-yl)prop-1-yn-1-yl)thiophene-2-carboxylate was prepared from (R)-methyl 5-(3-(2-(hydroxymethyl)-5-oxopyrrolidin-1-yl)prop-1-yn-1-yl)thiophene-2-carboxylate by oxidation with Dess-Martin periodinane as described above; TLC $R_f$ 0.30 (solvent system 95:5 v/v dichloromethane:methanol).

Preparation of (Z)-methyl 5-(3-hydroxyprop-1-en-1-yl)thiophene-2-carboxylate

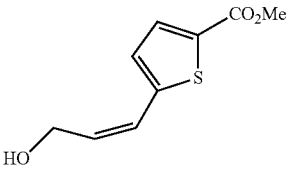 [SMILES: COC(=O)c1ccc(/C=C\CO)s1]

To a mixture consisting of methyl 5-(3-hydroxyprop-1-yn-1-yl)thiophene-2-carboxylate (1.9 g, 9.7 mmol) in ethyl acetate (50 mL) and methanol (5 mL) was added palladium on calcium carbonate (5%, 1.5 g). The reaction flask was evacuated and backfilled with hydrogen gas and the reaction mixture was subsequently stirred for 2 hours while maintaining a hydrogen atmosphere. The mixture was then filtered through Celite and the solvent removed. The residue was purified by silica gel chromatography eluting with ethyl acetate-heptanes (1:10 v/v) to afford the title intermediate (1.5 g); TLC $R_f$ 0.65 (solvent system 1:1 v/v ethyl acetate-heptanes); MS (ESI$^+$) m/z 221 (M+Na$^+$); $^1$H-NMR (CDCl$_3$) δ 7.7 (d, 1H), 6.9 (d, 1H), 6.6 (d, 1H), 6.0-5.9 (m, 1H), 4.6 (d, 2H), 3.9 (s, 3H), 1.9 (br s, 1H).

Preparation of (Z)-methyl 5-(3-bromoprop-1-en-1-yl)thiophene-2-carboxylate

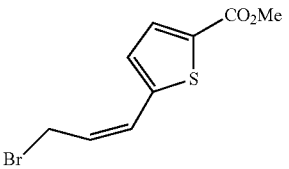 [SMILES: COC(=O)c1ccc(/C=C\CBr)s1]

(Z)-Methyl 5-(3-bromoprop-1-en-1-yl)thiophene-2-carboxylate (2.56 g) was from (Z)-methyl 5-(3-hydroxyprop-1-en-1-yl)thiophene-2-carboxylate using the method described above for methyl 5-(3-bromoprop-1-yn-1-yl)thiophene-2-carboxylate; TLC $R_f$ 0.60 (solvent system 20:80 v/v ethyl acetate-heptanes); MS (ESI$^+$) m/z 261 (M+1); $^1$H-NMR (CDCl$_3$) δ 7.7 (d, 1H), 7.2 (d, 1H), 6.6 (d, 1H), 6.2-6.0 (m, 1H), 4.3 (d, 2H), 3.9 (s, 3H).

Preparation of (R,Z)-di-tert-butyl 2-((3-(5-(methoxycarbonyl)-thiophen-2-yl)allyl)amino)pentanedioate

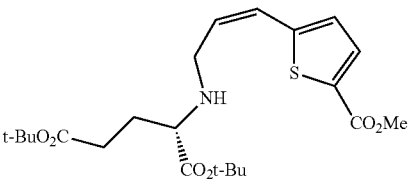

(R,Z)-Di-tert-butyl 2-((3-(5-(methoxycarbonyl)thiophen-2-yl)allyl)amino)-pentanedioate was prepared from (Z)-methyl 5-(3-bromoprop-1-en-1-yl)thiophene-2-carboxylate using the method described above for (R)-di-tert-butyl 2-((4-(2-methoxy-2-oxoethyl)benzyl)amino)pentanedioate; TLC $R_f$ 0.30 (solvent system 1:4 v/v ethyl acetate-heptanes); MS (ESI$^+$) m/z 440 (M+1); $^1$H-NMR (CDCl$_3$) δ 7.7 (d, 1H), 6.9 (d, 1H), 6.6 (d, 1H), 5.9-5.8 (m, 1H), 3.9 (s, 3H), 3.7-3.5 (s, 2H), 3.3-3.2 (m, 1H), 2.4 (t, 2H), 2.0-1.8 (m, 2H), 1.5 (s, 9H), 1.4 (s, 9H).

Preparation of (R,Z)-tert-butyl 1-(3-(5-(methoxycarbonyl)-thiophen-2-yl)allyl)-5-oxopyrrolidine-2-carboxylate

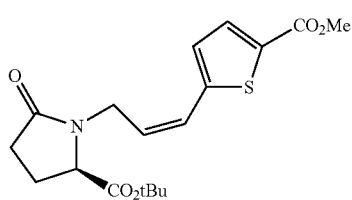 [SMILES: COC(=O)c1ccc(/C=C\CN2C(=O)CC[C@@H]2C(=O)OC(C)(C)C)s1]

(R,Z)-tert-Butyl 1-(3-(5-(methoxycarbonyl)thiophen-2-yl)allyl)-5-oxopyrrolidine-2-carboxylate was prepared from (R,Z)-di-tert-butyl 2-((3-(5-(methoxycarbonyl)thiophen-2-yl)allyl)amino)pentanedioate using the method described above for (R)-tert-butyl 1-(4-(2-methoxy-2-oxoethyl)benzyl)-5-oxopyrrolidine-2-carboxylate; TLC $R_f$ 0.20 (solvent system 2:3 v/v ethyl acetate-heptanes); MS (ESI$^+$) m/z 366 (M+1), 388 (M+Na$^+$); $^1$H-NMR (CDCl$_3$) δ 7.7 (d, 1H), 6.9 (d, 1H), 6.6 (d, 1H), 5.7-5.6 (m, 1H), 4.5-4.4 (m, 1H), 4.2-4.0 (m, 2H), 3.85 (s, 3H), 2.6-2.5 (m, 1H), 2.4-2.2 (m, 2H), 2.1-2.0 (m, 1H), 1.4 (s, 9H).

Preparation of (R,Z)-1-(3-(5-(methoxycarbonyl) thiophen-2-yl)allyl)-5-oxopyrrolidine-2-carboxylic acid

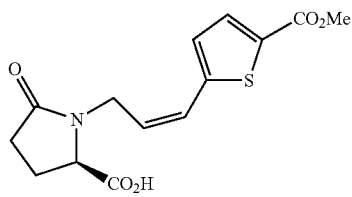 [SMILES: COC(=O)c1ccc(/C=C\CN2C(=O)CC[C@@H]2C(=O)O)s1]

A stirring mixture consisting of (R,Z)-tert-butyl 1-(3-(5-(methoxycarbonyl)-thiophen-2-yl)allyl)-5-oxopyrrolidine-2-carboxylate (2.05 g, 5.61 mmol) and trifluoroacetic acid (5.0 mL, 65 mmol) in dichloromethane (40 mL) was heated at 45° C. overnight. The reaction mixture was diluted with ethanol and evaporated under reduced pressure to provide a residue (2.44 g) that was used in the next step without further purification; TLC $R_f$ 0.25 (solvent system 50:50:1 v/v ethyl acetate-heptanes-acetic acid).

Preparation of (R,Z)-methyl 5-(3-(2-(hydroxymethyl)-5-oxopyrrolidin-1-yl)prop-1-en-1-yl)thiophene-2-carboxylate

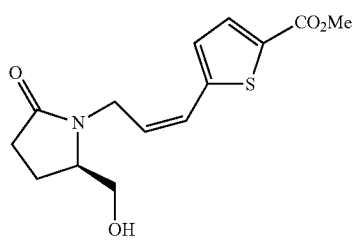 [SMILES: COC(=O)c1ccc(/C=C\CN2C(=O)CC[C@@H]2CO)s1]

(R,Z)-Methyl 5-(3-(2-(hydroxymethyl)-5-oxopyrrolidin-1-yl)prop-1-en-1-yl)thiophene-2-carboxylate was prepared from (R,Z)-1-(3-(5-(methoxycarbonyl)thiophen-2-yl)allyl)-5-oxopyrrolidine-2-carboxylic acid using the method described above for (R)-methyl 4-(2-(2-(hydroxymethyl)-5-oxopyrrolidin-1-yl)ethyl)benzoate; TLC $R_f$ 0.20 (solvent system 50:50:1 v/v ethyl acetate-heptanes-acetic acid); MS (ESI$^+$) m/z 296 (M+1), 318 (M+Na$^+$); $^1$H-NMR (CDCl$_3$) δ 7.6 (d, 1H), 6.9 (d, 1H), 6.6 (d, 1H), 6.1-5.6 (m, 1H), 4.5-4.3 (m, 1H), 4.1-4.0 (m, 1H), 3.85 (s, 3H), 3.7 (s, 2H) 3.6-3.5 (m, 1H), 3.2-3.0 (br s, 1H), 2.6-2.4 (m, 1H), 2.4-2.3 (m, 1H), 2.2-2.0 (m, 1H), 2.0-1.9 (m, 1H).

Preparation of (R,Z)-methyl 5-(3-(2-formyl-5-oxopyrrolidin-1-yl)prop-1-en-1-yl)thiophene-2-carboxylate

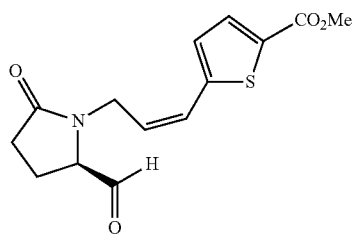 [SMILES: COC(=O)c1ccc(/C=C\CN2C(=O)CC[C@@H]2C=O)s1]

(R,Z)-Methyl 5-(3-(2-formyl-5-oxopyrrolidin-1-yl)prop-1-en-1-yl)thiophene-2-carboxylate was prepared from (R,Z)-methyl 5-(3-(2-(hydroxymethyl)-5-oxopyrrolidin-1-yl)prop-1-en-1-yl)thiophene-2-carboxylate by oxidation with Dess-Martin periodinane as described above; TLC $R_f$ 0.40 (solvent system 1:1 v/v ethyl acetate-heptanes).

Preparation of (R)-methyl 5-(3-(2-(hydroxymethyl)-5-oxopyrrolidin-1-yl)propyl)thiophene-2-carboxylate

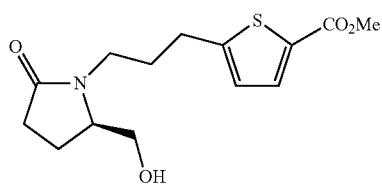 [SMILES: COC(=O)c1ccc(CCCN2C(=O)CC[C@@H]2CO)s1]

To a solution of (R,Z)-methyl 5-(3-(2-(hydroxymethyl)-5-oxopyrrolidin-1-yl)prop-1-en-1-yl)thiophene-2-carboxylate (496 mg) in ethyl acetate (40 mL) and methanol (4 mL) was added palladium on carbon (10%, 40 mg) and the flask evacuated and exposed to hydrogen for 4 hours. The mixture was then filtered through Celite and the solvent removed to afford the title intermediate in a quantitative yield, which was used without purification; TLC $R_f$ 0.25 (solvent system 95:5 v/v dichloromethane:methanol); $^1$H-NMR (CDCl$_3$); δ 7.6 (d, 1H), 6.6 (d, 1H), 3.85 (s, 3H), 3.8 (dd, 1H) 3.75-3.65 (m, 2H), 3.6 (dd, 1H), 3.1 (m, 1H), 2.85 (t, 2H), 2.7-2.4 (br s, 1H), 2.5-2.4 (m, 1H), 2.35-2.25 (m, 1H), 2.1-1.8 (m, 4H); MS (ESI$^+$) m/z 298.0 (M+1), 320.0 (M+Na$^+$).

Preparation of (R)-methyl 5-(3-(2-formyl-5-oxopyrrolidin-1-yl)propyl)thiophene-2-carboxylate

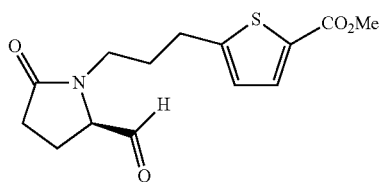 [SMILES: COC(=O)c1ccc(CCCN2C(=O)CC[C@@H]2C=O)s1]

(R)-Methyl 5-(3-(2-formyl-5-oxopyrrolidin-1-yl)propyl) thiophene-2-carboxylate was prepared from (R)-methyl 5-(3-(2-(hydroxymethyl)-5-oxopyrrolidin-1-yl)propyl)thiophene-2-carboxylate by oxidation with Dess-Martin periodinane as described above; TLC $R_f$ 0.25 (solvent system 95:5 v/v dichloromethane:methanol).

Examples 1A'-F'

Methyl 7-((2R)-2-((4R/S,E)-4-methyl-3-oxooct-1-en-6-yn-1-yl)-5-oxopyrrolidin-1-yl)heptanoate

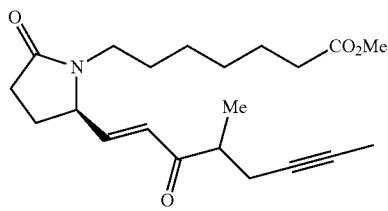 [SMILES: CC#CCC(C)C(=O)/C=C/[C@H]1CCC(=O)N1CCCCCCC(=O)OC]

To a stirring mixture consisting of (R)-methyl 7-(2-formyl-5-oxopyrrolidin-1yl)heptanoate (0.500 g, 1.96 mmol) and (+)-dimethyl (3-methyl-2-oxohept-5-yn-1-yl) phosphonate (0.438 g, 1.89 mmol) in THF (40 mL) at 0° C. was added lithium chloride (280 mg, 6.61 mmol) and triethylamine (0.30 g, 3.0 mmol). The reaction mixture was stirred at room temperature overnight. To the reaction mixture was added a saturated solution of ammonium chloride (30 mL) and organic material was extracted with ethyl acetate (100 mL). The organic layer was separated, washed with brine (50 mL), dried over sodium sulfate, filtered, and concentrated in vacuo. The residue was purified by silica gel chromatography eluting with ethyl acetate-heptane (7:3 v/v) to afford the title compound (360 mg, 51%); TLC $R_f$ 0.44 (solvent system: ethyl acetate); MS (APCI$^+$) m/z 362 (M+1).

Preparation of four-diastereomer mixture methyl 7-((2R)-2-((E)-3-hydroxy-4-methyloct-1-en-6-yn-1-yl)-5-oxopyrrolidin-1-yl)heptanoate

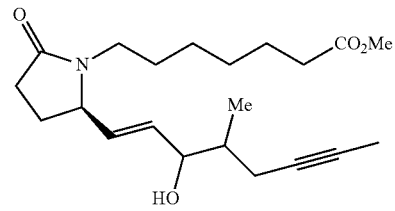 [SMILES: CC#CCC(C)C(O)/C=C/[C@H]1CCC(=O)N1CCCCCCC(=O)OC]

To a mixture consisting of methyl 7-((2R)-2-((4R/S,E)-4-methyl-3-oxooct-1-en-6-yn-1-yl)-5-oxopyrrolidin-1-yl) heptanoate (0.36 g, 1.0 mmol) in methanol (10 mL) at −40° C. was added cerium (III) chloride heptahydrate (0.373 g, 1.00 mmol). The reaction mixture was cooled to −78° C. and stirred for one hour. To the reaction mixture was added sodium borohydride (0.076 g, 2.0 mmol), and the reaction mixture stirred for two hours. Acetone was added and the mixture was stirred for 15 minutes at −78° C., after which time the mixture was elevated to room temperature. To the room temperature reaction mixture was added a saturated aqueous solution of ammonium chloride (30 mL) and the organic material was extracted with ethyl acetate (100 mL). The organic layer was separated and washed with brine (50 mL), dried over sodium sulfate, filtered, and concentrated in vacuo. The residue was purified by silica gel chromatography eluting with ethyl acetate-heptanes (7:3 v/v) to afford the title compound (450 mg) as a stereoisomeric mixture of four diastereomeric components with regard to the configurations of the C15-OH and C16-Me positions.

Preparation of methyl 7-((2R)-2-((3S,4R/S,E)-3-hydroxy-4-methyloct-1-en-6-yn-1-yl)-5-oxopyrrolidin-1-yl)heptanoate (Example 1A') and methyl 7-((2R)-2-((3R,4R/S,E)-3-hydroxy-4-methyloct-1-en-6-yn-1-yl)-5-oxopyrrolidin-1-yl)heptanoate (Example 1B')

Example 1A'

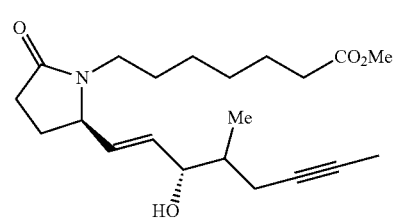

Example 1B'

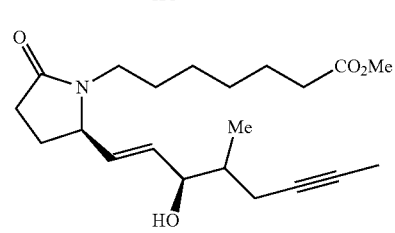

From the stereoisomeric mixture comprising the four methyl 7-((2R)-2-((3R/S,4R/S,E)-3-hydroxy-4-methyloct-1-en-6-yn-1-yl)-5-oxopyrrolidin-1-yl)heptanoate diastereomers (450 mg) were separated the methyl 7-((2R)-2-((3S,4R/S,E)-3-hydroxy-4methyloct-1-en-6-yn-1-yl)-5-oxopyrrolidin-1-yl)heptanoate disatereomeric pair from the methyl 7-((2R)-2-((3R,4R/S,E)-3-hydroxy-4-methyloct-1-en-6-yn-1-yl)-5-oxopyrrolidin-1-yl)heptanoate disatereomeric pair by prep HPLC. The separations were performed on an Agilent Semi-Prep instrument equipped with an ultraviolet detector at 210 nm and using a Chiralpak IA 250 mm×20 mm column eluting with a mobile phase of heptanes-ethanol (90:10 v/v) at a flow rate of 18 mL/min. Each of the two diastereomeric mixtures, Examples 1A' and 1B', was isolated as a clear oil.

Example 1A' (89 mg); prep HPLC retention time 22-25 minutes; TLC $R_f$ 0.20 (solvent system: ethyl acetate); MS (APCI+) m/z 364 (M+1).

Example 1B' (191 mg); prep HPLC retention time 16-19 minutes; TLC $R_f$ 0.27 (solvent system: ethyl acetate); MS (APCI+) in/z 364 (M+1).

Preparation of 7-((2R)-2-((3S,4R/S,E)-3-hydroxy-4-methyloct-1-en-6-yn-1-yl)-5-oxopyrrolidin-1-yl)heptanoic acid (Example 1C')

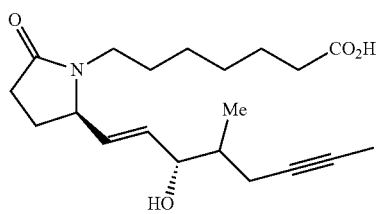 [SMILES: CC#CCC(C)[C@H](O)/C=C/[C@H]1CCC(=O)N1CCCCCCC(=O)O]

To a mixture consisting of methyl 7-((2R)-2-((3S,4R/S,E)-3-hydroxy-4-methyloct-1-en-6-yn-1-yl)-5-oxopyrrolidin-1-yl)heptanoate (0.089 g, 0.24 mmol, prepared as Example 1A' above) in methanol (3 mL) was added 2N sodium hydroxide (6 drops). The reaction mixture was stirred at room temperature for three hours. To the reaction mixture was added a solution of 5% potassium hydrogen sulfate-brine (1:1) to achieve an acidic pH, and the organic material was extracted with ethyl acetate. The organic phase was dried over sodium sulfate, filtered, and concentrated in vacuo. The residue was purified on silica gel eluting with ethyl acetate-acetic acid (100:0.4 v/v) to afford the title compound (62 mg, 75%) as a nearly colorless solid; TLC $R_f$ 0.27 (solvent system: 80:20:1 v/v ethyl acetate-heptane-acetic acid); MS (ESI−) m/z 348 (M−1); $^1$H-NMR (CDCl$_3$) δ 5.7 (dd, 1H), 5.5 (dd, 1H), 4.25 (t, 1H), 3.6-3.5 (m, 1H), 2.9-2.8 (m, 1H), 2.5-1.2 (m, 20H), 0.95 (dd, 3H).

Preparation of 7-((2R)-2-((3R,4R/S,E)-3-hydroxy-4-methyloct-1-en-6-yn-1-yl)-5-oxopyrrolidin-1-yl)heptanoic acid (Example 1D')

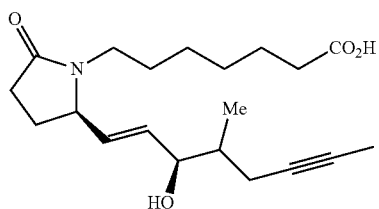 [SMILES: CC#CCC(C)[C@@H](O)/C=C/[C@H]1CCC(=O)N1CCCCCCC(=O)O]

The title compound was prepared from methyl 7-((2R)-2-((3R,4R/S,E)-3-hydroxy-4-methyloct-1-en-6-yn-1-yl)-5-oxopyrrolidin-1-yl)heptanoate (0.191 g, 0.525 mmol) according to the procedure described for the preparation of Example 1C'. The title compound was obtained (146 mg, 79.6%) as a yellow oil; TLC $R_f$ 0.31 (solvent system: 80:20:1 v/v ethyl acetate-heptane-acetic acid); MS (ESI−) m/z 348 (M−1).

Preparation of 7-((R)-2-((3S,4S,E)-3-hydroxy-4-methyloct-1-en-6-yn-1-yl)-5-oxopyrrolidin-1-yl)heptanoic acid (Example 1E') and 7-((R)-2-((3S,4R,E)-3-hydroxy-4-methyloct-1-en-6-yn-1-yl)-5-oxopyrrolidin-1-yl)heptanoic acid (Example 1F')

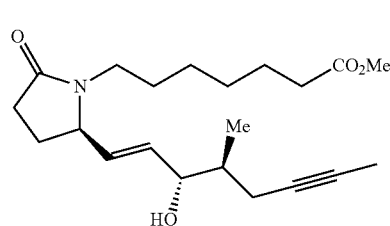

Example 1E'

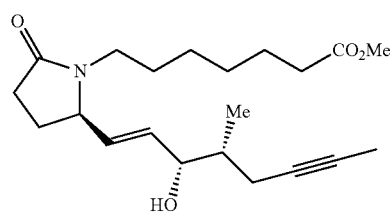

Example 1F'

From the stereoisomer mixture comprising 7-((2R)-2-((3S,4R/S,E)-3-hydroxy-4-methyloct-1-en-6-yn-1-yl)-5-oxopyrrolidin-1-yl)heptanoic acid (Example 1C', 35 mg) were separated the pure stereoisomers 7-((R)-2-((3S,4S,E)-3-hydroxy-4-methyloct-1-en-6-yn-1-yl)-5-oxopyrrolidin-1-yl)heptanoic acid (Example 1E') and 7-((R)-2-((3S,4R,E)-3-hydroxy-4-methyloct-1-en-6-yn-1-yl)-5-oxopyrrolidin-1-yl)heptanoic acid (Example 1F') by prep HPLC. Each pure stereoisomer was isolated as a colorless solid. The separation was performed on a Gilson Semi-Prep instrument equipped with an ultraviolet detector at 205 nm and using a Luna Silica 5μ 250 mm×10 mm column eluting with a mobile phase of heptane-ethanol (92:8 v/v).

Example 1E' (5 mg); a colorless solid; HPLC retention time 52 minutes; TLC $R_f$ 0.31 (solvent system: 80:20:1 v/v ethyl acetate-heptane-acetic acid); MS (ESI−) m/z 348 (M−1); melting point 113-114° C.

Example 1F' (9 mg); a colorless solid; HPLC retention time 49 minutes; TLC $R_f$ 0.31 (solvent system: 80:20:1 v/v ethyl acetate-heptane-acetic acid); MS (ESI−) nm/z 348 (M−1); melting point 100-101° C.

Examples 2A'-2F'

Preparation of methyl 7-((2R)-2-((4R/S,E)-4-methyl-3-oxonon-1-en-6-yn-1-yl)-5-oxopyrrolidin-1-yl)heptanoate

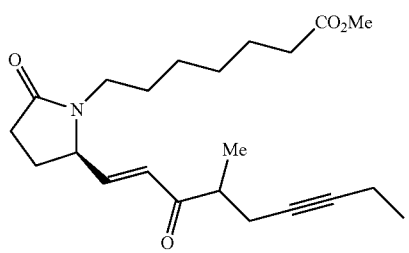 [SMILES: CCC#CCC(C)C(=O)/C=C/[C@H]1CCC(=O)N1CCCCCCC(=O)OC]

Methyl 7-((2R)-2-((4R/S,E)-4-methyl-3-oxonon-1-en-6-yn-1-yl)-5-oxopyrrolidin-1-yl)heptanoate (648 mg) was prepared analogously to the above procedures. TLC $R_f$ 0.33 (solvent system: 4:1 v/v ethyl acetate-heptane).

Preparation of methyl 7-((2R)-2-((3S,4R/S,E)-3-hydroxy-4-methylnon-1-en-6-yn-1-yl)-5-oxopyrrolidin-1-yl)heptanoate (Example 2A') and methyl 7-((2R)-2-((3R,4R/S,E)-3-hydroxy-4-methylnon-1-en-6-yn-1-yl)-5-oxopyrrolidin-1-yl)heptanoate (Example 2B')

Example 2A'
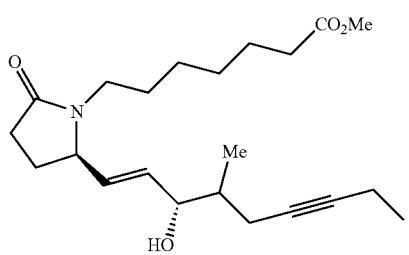

Example 2B'
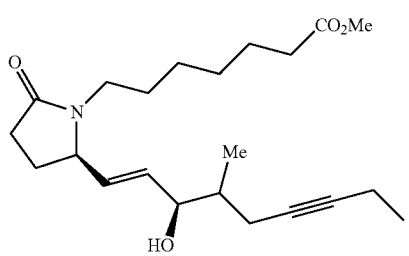

Methyl 7-((2R)-2-((E)-3-hydroxy-4-methylnon-1-en-6-yn-1-yl)-5-oxopyrrolidin-1-yl)heptanoate (570 mg), consisting of the four diastereomers, was prepared by the above methods. Both diastereomeric pairs methyl 7-((2R)-2-((3S,4R/S,E)-3-hydroxy-4-methylnon-1-en-6-yn-1-yl)-5-oxopyrrolidin-1-yl)heptanoate (Example 2A') and methyl 7-((2R)-2-((3R,4R/S,E)-3-hydroxy-4-methylnon-1-en-6-yn-1-yl)-5-oxopyrrolidin-1-yl)heptanoate (Example 2'B) were isolated following separation by prep HPLC. The separation was performed on a Gilson Prep instrument equipped with an ultraviolet detector at 210 nm and using a Luna Silica 250×42.5 mm column eluting with a mobile phase of 9:1 v/v heptane-n-propanol.

Example 2A' (70 mg); a clear oil; HPLC retention time of 7 min; TLC $R_f$ 0.35 (solvent system: ethyl acetate); MS (ESI$^+$) m/z 378 (M+1).

Example 2B' (240 mg); a clear oil; HPLC retention time of 6 min; TLC $R_f$ 0.44 (solvent system: ethyl acetate); MS (ESI$^+$) m/z 378 (M+1).

Preparation of 7-((2R)-2-((3S,4R/S,E)-3-hydroxy-4-methylnon-1-en-6-yn-1-yl)-5-oxopyrrolidin-1-yl)heptanoic acid (Example 2C')

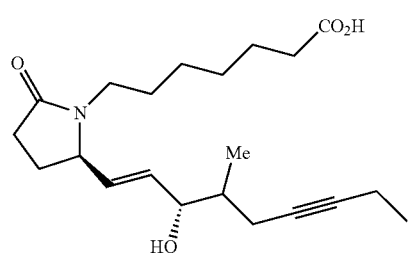 [SMILES: CCC#CCC(C)[C@H](O)/C=C/[C@H]1CCC(=O)N1CCCCCCC(=O)O]

7-((2R)-2-((3S,4R/S,E)-3-Hydroxy-4-methylnon-1-en-6-yn-1-yl)-5-oxopyrrolidin-1-yl)heptanoic acid (Example 2C') was prepared from methyl 7-((2R)-2-((3S,4R/S,E)-3-hydroxy-4-methylnon-1-en-6-yn-1-yl)-5-oxopyrrolidin-1-yl)heptanoate (Example 2A') using the above methods to obtain the title compound (58 mg, 91%) as a nearly colorless solid; melting point 123-124° C.; MS (ESI$^-$) m/z 362 (M−1); $^1$HNMR (CDCl$_3$) δ 5.76 (dd, 1H), 5.64 (dd, 1H), 4.25 (t, 1H), 4.2-4.0 (m, 1H), 3.6-3.4 (m, 1H), 3.0-2.9 (m, 1H), 2.5-1.15 (m, 19H), 1.15 (t, 3H), 0.9 (dd, 3H).

Preparation of 7-((2R)-2-((3R,4R/S,E)-3-hydroxy-4-methylnon-1-en-6-yn-1-yl)-5-oxopyrrolidin-1-yl)heptanoic acid (Example 2D')

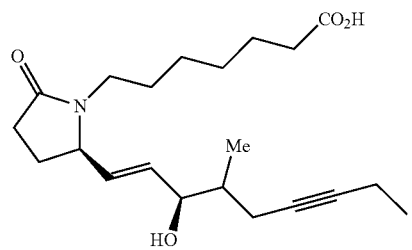 [SMILES: CCC#CCC(C)[C@@H](O)/C=C/[C@H]1CCC(=O)N1CCCCCCC(=O)O]

7-((2R)-2-((3R,4R/S,E)-3-Hydroxy-4-methylnon-1-en-6-yn-1-yl)-5-oxopyrrolidin-1-yl)heptanoic acid (Example 2D') was prepared from methyl 7-((2R)-2-((3R,4R/S,E)-3-hydroxy-4-methylnon-1-en-6-yn-1-yl)-5-oxopyrrolidin-1-yl)heptanoate (Example 2B') using the above methods to obtain the title compound (223 mg) as a nearly colorless solid; MS (ESI$^-$) m/z 362 (M−1); melting point 56-57° C.

Preparation of 7-((R)-2-((3S,4S,E)-3-hydroxy-4-methylnon-1-en-6-yn-1-yl)-5-oxopyrrolidin-1-yl)heptanoic acid (Example 2E') and 7-((R)-2-((3S,4R,E)-3-hydroxy-4-methylnon-1-en-6-yn-1-yl)-5-oxopyrrolidin-1-yl)heptanoic acid (Example 2F')

Preparation of diastereomeric mixture methyl 7-((2R)-2-((3S,4S,E)-3-hydroxy-4-methylnon-1-en-6-yn-1-yl)-5-oxopyrrolidin-1-yl)heptanoate (Example 2G') and methyl 7-((2R)-2-((3R,4S,E)-3-hydroxy-4-methylnon-1-en-6-yn-1-yl)-5-oxopyrrolidin-1-yl)heptanoate (Example 2G'-15-epi)

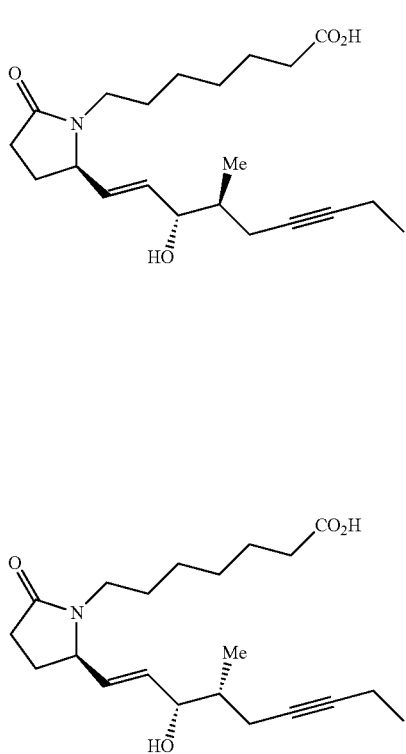

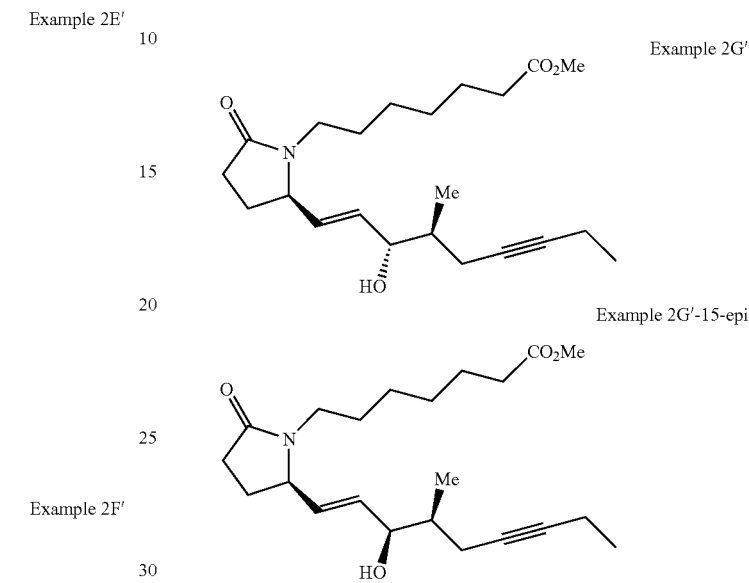

7-((2R)-2-((3S,4R/S,E)-3-hydroxy-4-methylnon-1-en-6-yn-1-yl)-5-oxopyrrolidin-1-yl)heptanoic acid (Example 2C', 143 mg) was separated into the stereoisomers 7-((R)-2-((3S,4S,E)-3-hydroxy-4-methylnon-1-en-6-yn-1-yl)-5-oxopyrrolidin-1-yl)heptanoic acid (Example 2E') and 7-((R)-2-((3S,4R,E)-3-hydroxy-4-methylnon-1-en-6-yn-1-yl)-5-oxopyrrolidin-1-yl)heptanoic acid (Example 2F') by prep HPLC. Each stereoisomer was isolated as a colorless solid. The separation was performed on an Agilent 1200 Prep instrument equipped with an ultraviolet detector at 210 nm and using a Luna Silica 21.2×250 mm column eluting with a mobile phase of heptanes-ethanol (95:5 v/v).

Example 2E' (24 mg); white solid; prep HPLC retention time 67 minutes; MS (ESI) m/z 362 (M−1); melting point 138-139° C.

Example 2F' (30 mg); white solid; prep HPLC retention time 62 minutes; MS (ESI⁻) m/z 362 (M−1); melting point 112-113° C.

Example 2E', Alternate Route

Methyl 7-((2R)-2-((S,E)-4-methyl-3-oxonon-1-en-6-yn-1-yl)-5-oxopyrrolidin-1-yl)heptanoate was prepared by the above methods using (S)-(+)-dimethyl (3-methyl-2-oxooct-5-yn-1-yl)phosphonate; TLC $R_f$ 0.33 (solvent system: 4:1 v/v ethyl acetate-heptane).

To a room temperature solution consisting of methyl 7-((2R)-2-((S,E)-4-methyl-3-oxonon-1-en-6-yn-1-yl)-5-oxopyrrolidin-1-yl)heptanoate (695 mg, 1.85 mmol) was treated with (R)-(+)-2-methyl-CBS-oxazaborolidine (1.85 mL, 1.85 mmol, 1M solution in toluene). The reaction mixture was cooled to −40° C. and to the mixture was added catecholborane (6.1 mL, 6.1 mmol, 1M solution in THF). The reaction mixture was allowed to warm to room temperature and stirred for one hour followed by the addition of 1 mL of 1N HCl and stirring over night. To the reaction mixture was added methanol and the organic material was extracted with ethyl acetate. The organic phase was washed with brine, dried over sodium sulfate and concentrated. The residue was chromatographed on a silica gel column eluted with 80:20 ethyl acetate-heptane to afford (280 mg) the diastereomeric mixture of alcohols; TLC $R_f$ 0.17 (solvent system: 4:1 v/v ethyl acetate-heptane).

From the diastereomeric mixture of methyl 7-((2R)-2-((4S,E)-3-hydroxy-4-methylnon-1-en-6-yn-1-yl)-5-oxopyrrolidin-1-yl)heptanoate (approximately 95:5 ratio of Example 2G' to Example 2G'-15-epi) were separated the pure stereoisomers methyl 7-((R)-2-((3S,4S,E)-3-hydroxy-4-methylnon-1-en-6-yn-1-yl)-5-oxopyrrolidin-1-yl)heptanoate (Example 2G') and methyl 7-((R)-2-((3R,4S,E)-3-hydroxy-4-methylnon-1-en-6-yn-1-yl)-5-oxopyrrolidin-1-yl)heptanoate (Example 2G'-15-epi) by prep HPLC. The separation was performed on an Agilent 1200 Prep instrument equipped with an ultraviolet detector at 210 nm and using a CN 5g 250×21.2 mm column eluting with a mobile phase of heptanes-ethanol (92:8 v/v).

Example 2G' (57 mg); a clear oil; prep HPLC retention time 19 minutes; TLC $R_f$ 0.35 (solvent system: ethyl acetate); MS (ESI⁺) r/z 378 (M+1).

Preparation of 7-((R)-2-((3S,4S,E)-3-hydroxy-4-methylnon-1-en-6-yn-1-yl)-5-oxopyrrolidin-1-yl)heptanoic acid (Example 2E')

7-((R)-2-((3S,4S,E)-3-hydroxy-4-methylnon-1-en-6-yn-1-yl)-5-oxopyrrolidin-1-yl)heptanoic acid (Example 2E') was prepared from methyl 7-((2R)-2-((3S,4S,E)-3-hydroxy-4-methylnon-1-en-6-yn-1-yl)-5-oxopyrrolidin-1-yl)heptanoate (Example 2G') by the above methods to obtain the title compound MS (ESI−) r/z 362 (M−1); $^1$H-NMR (MeOD-d$_4$) δ 5.76 (dd, 1H), 5.55 (dd, 1H), 4.17-4.23 (m, 1H), 4.02 (t, 1H), 3.43-3.51 (m, 1H), 2.95 (ddd, 1H), 2.21-2.41 (m, 6H), 2.08-2.18 (m, 3H), 1.68-1.82 (m, 2H), 1.43-1.64 (m, 4H), 1.25-1.4 (m, 5H), 1.1 (t, 3H), 0.96 (d, 3H).

Example 2F', Alternate Route

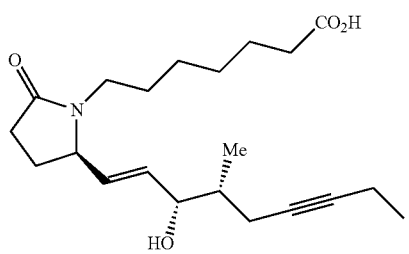 [SMILES: CCC#CC[C@@H](C)[C@H](O)/C=C/[C@H]1CCC(=O)N1CCCCCCC(=O)O]

7-((R)-2-((3S,4R,E)-3-hydroxy-4-methylnon-1-en-6-yn-1-yl)-5-oxopyrrolidin-1-yl)heptanoic acid (Example 2F') is prepared according to the alternative route to Example 2E' presented immediately above.

The following Examples were prepared by the methods described in Example 1A'-1F', using the appropriate aldehyde (6a'-f') and the appropriate β-keto phosphonate ester as described above followed by selective reduction of the α,β-unsaturated ketone. The isomers were isolated by the use of HPLC and the esters were hydrolyzed using aqueous base such as lithium, potassium or sodium hydroxide.

Examples 3A'-3D'

Methyl 7-((2R)-2-((3S,4R/S,E)-3-hydroxy-4-methyldec-1-en-6-yn-1-yl)-5-oxopyrrolidin-1-yl)heptanoate (Example 3A') and methyl 7-((2R)-2-((3R,4R/S,E)-3-hydroxy-4-methyldec-1-en-6-yn-1-yl)-5-oxopyrrolidin-1-yl)heptanoate (Example 3B')

Example 3A'

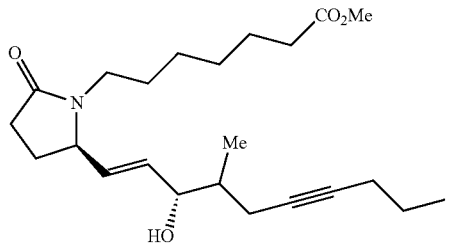

Example 3B'

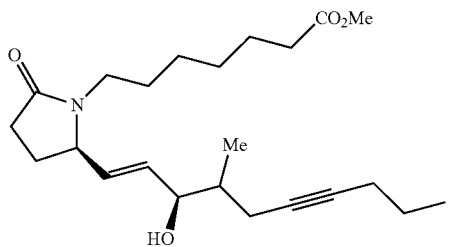

The diastereomeric mixtures of Example 3A' and Example 3B' were isolated following separation by prep HPLC.

Gilson Prep instrument; ultraviolet detector at 210 nm; Luna 5µ Silica 250×21.2 mm column; mobile phase of heptane-ethanol (9:1 v/v) with a flow rate of 21 mL/min.

Example 3A' (80 mg); a clear oil; HPLC retention time 19 min; TLC R$_f$ 0.69 (solvent system: ethyl acetate); MS (ESI$^+$) m/z 392 (M+1).

Example 3B' (180 mg); a colorless solid; HPLC retention time 14.5 min; TLC R$_f$ 0.74 (solvent system: ethyl acetate); MS (ESI$^+$) m/z 392 (M+1).

7-((2R)-2-((3S,4R/S,E)-3-hydroxy-4-methyldec-1-en-6-yn-1-yl)-5-oxopyrrolidin-1-yl)heptanoic acid (Example 3C')

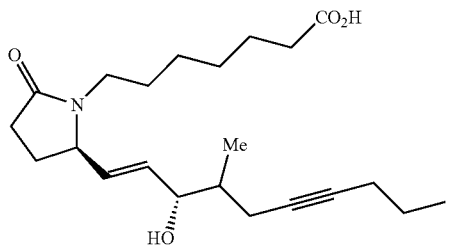 [SMILES: CCCC#CCC(C)[C@H](O)/C=C/[C@H]1CCC(=O)N1CCCCCCC(=O)O]

71 mg (92%) as a white solid; melting point 104-105° C.; TLC R$_f$ 0.22 (solvent system: 85:15:1 v/v ethyl acetate-heptane-acetic acid); MS (ESI−) m/z 376.2 (M−1); $^1$H-NMR (CDCl$_3$) δ 5.76 (dd, 2H), 4.26 (t, 1H), 4.1-4.15 (m, 1H), 3.4-3.5 (m, 1H), 2.9-2.98 (m, 1H), 2.1-2.5 (m, 9H), 1.75-1.84 (m, 2H), 1.25-1.66 (m, 10H), 0.92-1.1 (m, 6H).

7-((2R)-2-((3R,4R/S,E)-3-hydroxy-4-methyldec-1-en-6-yn-1-yl)-5-oxopyrrolidin-1-yl)heptanoic acid (Example 3D')

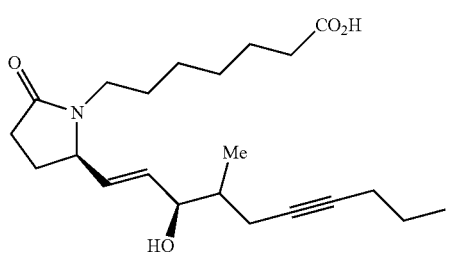 [SMILES: CCCC#CCC(C)[C@@H](O)/C=C/[C@H]1CCC(=O)N1CCCCCCC(=O)O]

87 mg (91%) as a clear oil; TLC R$_f$ 0.28 (solvent system: 85:15:1 v/v ethyl acetate-heptane-acetic acid); MS (ESI$^-$) m/z 376 (M–1).

Examples 4A'-4D'

Methyl 7-((2R)-2-((3S,4R/S,E)-3-hydroxy-4-methyl-7-phenylhept-1-en-6-yn-1-yl)-5-oxopyrrolidin-1-yl)heptanoate (Example 4A') and methyl 7-((2R)-2-((3R,4R/S,E)-3-hydroxy-4-methyl-7-phenylhept-1-en-6-yn-1-yl)-5-oxopyrrolidin-1-yl)heptanoate (Example 4B')

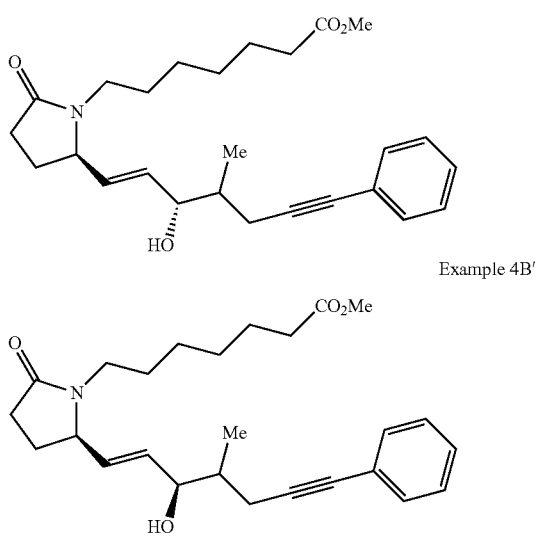

Example 4A'

Example 4B'

The diastereomeric mixtures of Example 4A' and Example 4B' were isolated following separation by prep HPLC.

Agilent Prep 1100 instrument; ultraviolet detector at 233 nm; Chiralpak IA 250×20 mm column; mobile phase of heptane-ethanol (88:12 v/v) with a flow rate of 18 mL/min.

Example 4A' (100 mg); a clear oil; HPLC retention time 28 min; TLC R$_f$ 0.30 (solvent system: 9:1 v/v ethyl acetate-heptane); MS (ESI$^+$) m/z 426 (M+1).

Example 4B' (195 mg); a clear oil; HPLC retention time 20 min; TLC R 0.36 (solvent system: 9:1 v/v ethyl acetate-heptane); MS (ESI$^+$) in/z 426 (M+1).

Preparation of 7-((2R)-2-((3S,4R/S,E)-3-hydroxy-4-methyl-7-phenylhept 1-en-6-yn-1-yl)-5-oxopyrrolidin-1-yl)heptanoic acid (Example 4C')

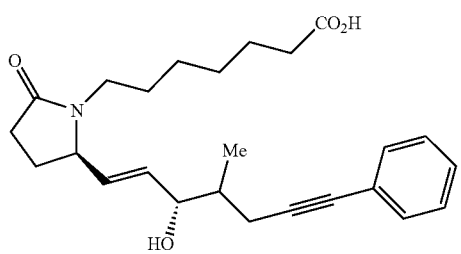 [SMILES: CC(CC#Cc1ccccc1)[C@H](O)/C=C/[C@H]1CCC(=O)N1CCCCCCC(=O)O]

95 mg (100%) as a pale yellow oil; TLC R$_f$ 0.28 (solvent system: 50:50:1 v/v acetone-heptane-acetic acid); MS (ESI$^+$) m/z 412 (M+1).

Preparation of 7-((2R)-2-((3R,4R/S,E)-3-hydroxy-4-methyl-7-phenylhept-1-en-6-yn-1-yl)-5-oxopyrrolidin-1-yl)heptanoic acid (Example 4D')

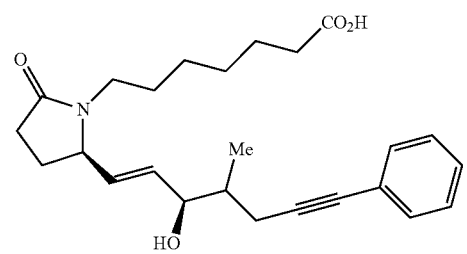 [SMILES: CC(CC#Cc1ccccc1)[C@@H](O)/C=C/[C@H]1CCC(=O)N1CCCCCCC(=O)O]

175 mg (93%) as a pale yellow oil; TLC R$_f$ 0.32 (solvent system: 50:50:1 v/v acetone-heptane-acetic acid); MS (ESI$^+$) in/z 412 (M+1).

Examples 5A'-5D'

Preparation of methyl 7-((2R)-2-((3S,E)-3-hydroxy-7-phenylhept-1-en-6-yn-1-yl)-5-oxopyrrolidin-1-yl)heptanoate (Example 5A') and methyl 7-((2R)-2-((3R,E)-3-hydroxy-7-phenylhept-1-en-6-yn-1-yl)-5-oxopyrrolidin-1-yl)heptanoate (Example 5B')

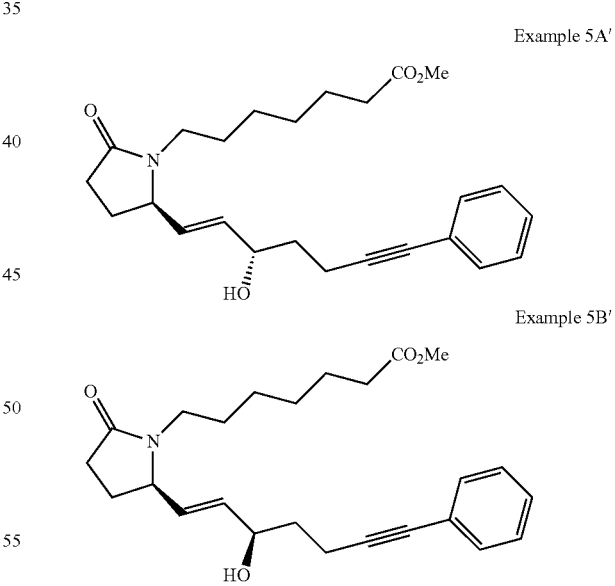

Example 5A'

Example 5B'

The single diastereomers of Example 5A' and Example 5B' were isolated following separation by prep HPLC.

Gilson Prep instrument; ultraviolet detector at 210 nm; Luna 5μ Silica 250×21.2 mm column; mobile phase of heptanes-ethanol (90:10 v/v) with a flow rate of 21.2 mL/min.

Example 5A' (47 mg): a clear oil; HPLC retention time 27 min; TLC R$_f$ 0.36 (solvent system: 8:2 v/v ethyl acetate-heptane); MS (ESI$^+$) m/z 412 (M+1).

Example 5B' (67 mg); a clear oil; HPLC retention time 21 min; TLC $R_f$ 0.41 (solvent system: 8:2 v/v ethyl acetate-heptane); MS (ESI$^+$) m/z 412 (M+1).

Preparation of 7-((R)-2-((3S,E)-3-hydroxy-7-phenylhept-1-en-6-yn-1-yl)-5-oxopyrrolidin-1-yl)heptanoic acid (Example 5C')

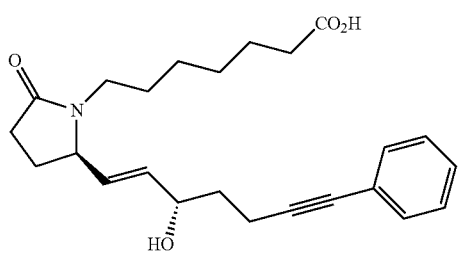 [SMILES: O=C(O)CCCCCCN1C(=O)CC[C@@H]1/C=C/[C@@H](O)CCC#Cc1ccccc1]

37 mg (100%); clear oil; TLC $R_f$ 0.25 (solvent system: 80:20:1 v/v ethyl acetate-heptane-acetic acid); MS (ESI$^-$) m/z 397 (M−1); $^1$H-NMR (MeOH-$d_4$) δ 7.26-7.36 (m, 5H), 5.81 (dd, 1H), 5.6 (dd, 1H), 4.3 (q, 1H), 4.07-4.22 (m, 2H), 3.4-3.49 (m, 1H), 2.97 (ddd, 1H), 2.34-2.53 (m, 4H), 2.21-2.33 (m, 3H), 1.73-1.84 (m, 3H), 1.5-1.62 (m, 3H), 1.21-1.38 (m, 5H)

Preparation of 7-((R)-2-((3R,E)-3-hydroxy-7-phenylhept-1-en-6-yn-1-yl)-5-oxopyrrolidin-1-yl)heptanoic acid (Example 5D')

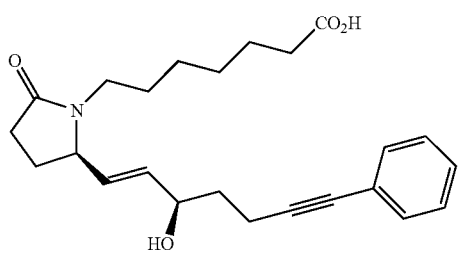 [SMILES: O=C(O)CCCCCCN1C(=O)CC[C@@H]1/C=C/[C@H](O)CCC#Cc1ccccc1]

55 mg (100%); clear oil; TLC $R_f$ 0.33 (solvent system: 80:20:1 v/v ethyl acetate-heptane-acetic acid); MS (ESI$^-$) m/z 397 (M−1).

Examples 6A'-6D'

Preparation of methyl 7-((R)-2-((R,E)-3-hydroxyhept-1-en-4-yn-1-yl)-5-oxopyrrolidin-1-yl)heptanoate (Example 6A') and methyl 7-((R)-2-((S,E)-3-hydroxyhept-1-en-4-yn-1-yl)-5-oxopyrrolidin-1-yl)heptanoate (Example 6B')

Example 6A'

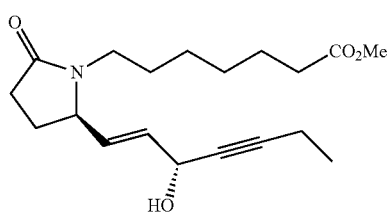

Example 6B'

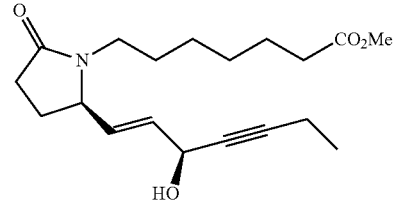

From the diastereomeric mixture (404 mg), the single diastereomers Example 6A' and Example 6B' were isolated following separation by prep HPLC.

Agilent 1100 Prep instrument; ultraviolet detector at 210 nm; Luna 5t Silica 250×21.2 mm column; mobile phase of heptanes-ethanol (92:8 v/v) with a flow rate of 21.2 mL/min.

Example 6A' (40 mg); a clear oil; HPLC retention time 26 min; TLC $R_f$ 0.34 (solvent system 4:1 v/v ethyl acetate-heptane); MS (ESI$^+$) in/z 336 (M+1);

Example 6B' (90 mg); a clear oil; HPLC retention time 24 min; TLC $R_f$ 0.39 (solvent system 4:1 v/v ethyl acetate-heptane); MS (ESI$^+$) m/z 336 (M+1).

Preparation of 7-((R)-2-((R,E)-3-hydroxyhept-1-en-4-yn-1-yl)-5-oxopyrrolidin-1-yl)heptanoic acid (Example 6C')

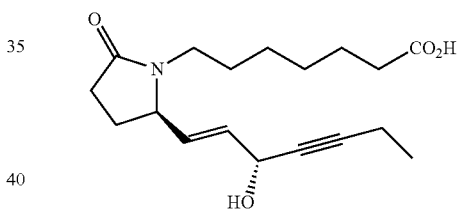

27 mg (70%) as a clear oil; TLC $R_f$ 0.22 (solvent system 85:15:1 v/v ethyl acetate-heptane-acetic acid); MS (ESI$^+$) m/z 322 (M+1); $^1$H-NMR (CDCl$_3$) δ 5.8 (dd, 2H), 4.90 (d, 1H), 4.12 (t, 1H), 1.2-2.58 (m, 18H), 1.08 (t, 3H).

Preparation of 7-((R)-2-((S,E)-3-hydroxyhept-1-en-4-yn-1-yl)-5-oxopyrrolidin-1-yl)heptanoic acid (Example 6D')

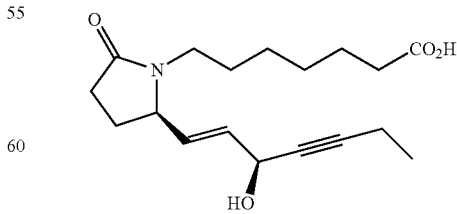

40 mg (46%) as a clear oil; TLC $R_f$ 0.25 (solvent system 85:15:1 v/v ethyl acetate-heptane-acetic acid); MS (ESI$^+$) m/z 322 (M+1).

Examples 7A'-7D'

Preparation of methyl 7-((R)-2-((R,E)-3-hydroxy-5-phenylpent-1-en-4-yn-1-yl)-5-oxopyrrolidin-1-yl)heptanoate (Example 7A') and methyl 7-((R)-2-((S,E)-3-hydroxy-5-phenylpent-1-en-4-yn-1-yl)-5-oxopyrrolidin-1-yl)heptanoate (Example 7B')

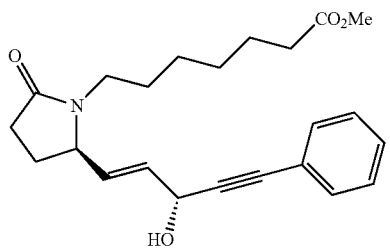
Example 7A'

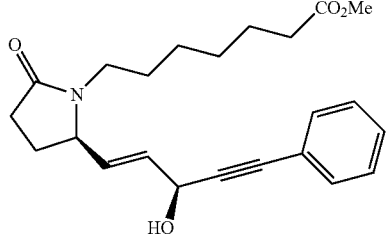
Example 7B'

The single diastereomers Example 7A' and Example 7B' were isolated following separation by prep HPLC.

Agilent 1100 Prep instrument; ultraviolet detector at 210 nm; Luna Silica 250×21.2 mm column; mobile phase of heptanes-ethanol (92:8 v/v) with a flow rate of 21.2 mL/min.

Example 7A' (40 mg); a clear oil; HPLC retention time 20.9 min;

Example 7B' (90 mg); a yellow oil; HPLC retention time 19.4 min.

Preparation of 7-((R)-2-((R,E)-3-hydroxy-5-phenylpent-1-en-4-yn-1-yl)-5-oxopyrrolidin-1-yl)heptanoic acid (Example 7C')

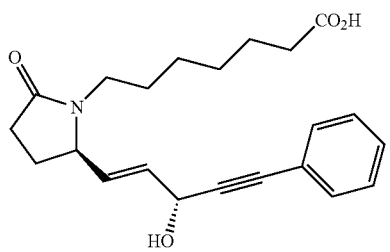 [SMILES: O=C(O)CCCCCCN1C(=O)CC[C@@H]1/C=C/[C@@H](O)C#Cc1ccccc1]

27 mg (71%) as a yellow solid; MS (ESI⁻) m/z 368 (M−1); ¹H-NMR (CDCl₃) δ 7.5-7.2 (m, 5H), 5.9 (dd, 1H), 5.8 (dd, 1H), 5.19 (d, 1H), 4.1-4.0 (m, 1H), 3.6-3.4 (m, 1H), 3.0-2.9 (m, 1H), 2.45-1.2 (m, 14H).

Step D2: Preparation of 7-((R)-2-((S,E)-3-hydroxy-5-phenylpent-1-en-4-yn-1-yl)-5-oxopyrrolidin-1-yl)heptanoic acid (Example 7D')

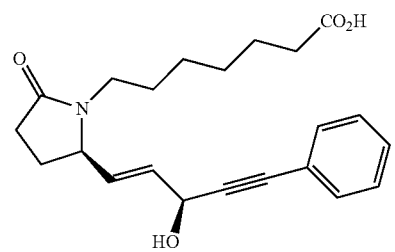 [SMILES: O=C(O)CCCCCCN1C(=O)CC[C@@H]1/C=C/[C@H](O)C#Cc1ccccc1]

40 mg (47%) as a yellow oil; TLC R_f 0.22 (solvent system 90:10:1 v/v ethyl acetate-heptane-acetic acid); MS (ESI⁻) m/z 368 (M−1).

Examples 8A'-8D'

Preparation of methyl 4-(2-((2R)-2-((3S,4R/S,E)-3-hydroxy-4-methyloct-1-en-6-yn-1-yl)-5-oxopyrrolidin-1-yl)ethyl)benzoate (Example 8A') and methyl 4-(2-((2R)-2-((3R,4R/S,E)-3-hydroxy-4-methyloct-1-en-6-yn-1-yl)-5-oxopyrrolidin-1-yl)ethyl)benzoate (Example 8B')

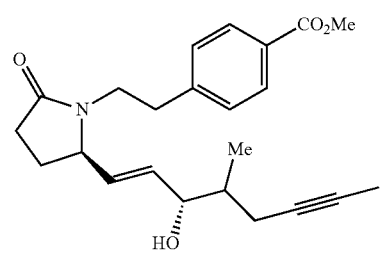 [SMILES: CC#CCC(C)[C@H](O)/C=C/[C@H]1CCC(=O)N1CCc1ccc(C(=O)O)cc1]
Example 8A'

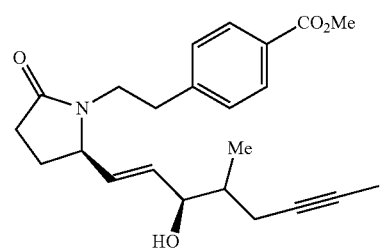 [SMILES: CC#CCC(C)[C@@H](O)/C=C/[C@H]1CCC(=O)N1CCc1ccc(C(=O)O)cc1]
Example 8B'

The diastereomeric mixtures of Example 8A' and Example 8B' were isolated following separation by prep HPLC.

Agilent Semi-Prep instrument; ultraviolet detector at 210 nm; Chiralpak IA 250 mm×10 mm column; mobile phase of heptanes-ethanol (9:1 v/v) with a flow rate of 5 mL/min.

Example 8A' (30 mg of a clear oil); prep HPLC retention time 19.3-21.1 minutes; TLC R_f 0.69 (solvent system: ethyl acetate); MS (ESI⁺) m/z 406 (M+23);

Example 8B' (40 mg of a colorless solid); prep HPLC retention time 14.9-16.1 minutes; TLC R_f 0.72 (solvent system: ethyl acetate); MS (ESI⁺) m/z 406 (M+23).

Preparation of 4-(2-((2R)-2-((3S,4R/S,E)-3-hydroxy-4-methyloct-1-en-6-yn-1-yl)-5-oxopyrrolidin-1-yl)ethyl)benzoic acid (Example 8C')

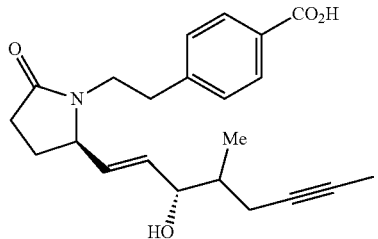

16.5 mg (59%) as a colorless solid; TLC $R_f$ 0.28 (solvent system 90:10:1 v/v ethyl acetate-heptane-acetic acid); melting point 183-185° C.; MS (ESI⁻) m/z 368 (M−1); ¹H-MNR (CDCl₃) δ 8.0 (d, 2H), 7.2 (d, 2H), 5.6 (dd, 2H), 5.4 (dd, 2H) 4.2 (t, 1H), 4.1-4.0 (m, 1H), 3.85-3.75 (m, 1H), 3.2-3.1 (m, 1H), 2.4-1.2 (m, 12H), 0.9 (dd, 3H).

Preparation of 4-(2-((2R)-2-((3R,4R/S,E)-3-hydroxy-4-methyloct-1-en-6-yn-1-yl)-5-oxopyrrolidin-1-yl)ethyl)benzoic acid (Example 8D')

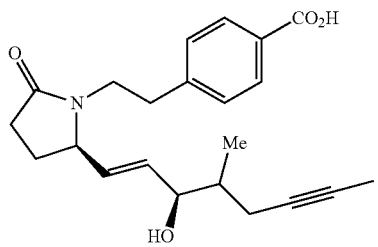

10 mg (26%) as an off-white solid; TLC $R_f$ 0.29 (solvent system 90:10:1 v/v ethyl acetate-heptane-acetic acid); MS (ES⁻) m/z 368 (M−1).

Examples 9A'-9D'

Preparation of ethyl 4-(2-((R)-2-((3S,4S,E)-3-hydroxy-4-methylnon-1-en-6-yn-1-yl)-5-oxopyrrolidin-1-yl)ethyl)benzoate (Example 9A') and ethyl 4-(2-((R)-2-((3R,4S,E)-3-hydroxy-4-methylnon-1-en-6-yn-1-yl)-5-oxopyrrolidin-1-yl)ethyl)benzoate (Example 9'B)

Example 9A'

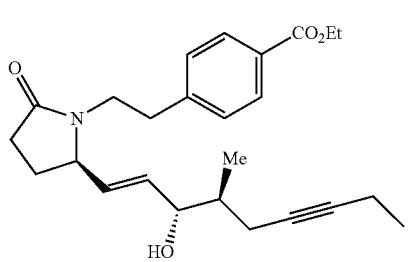

Example 9B'

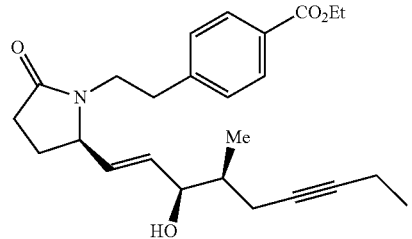

Mixture ethyl 4-(2-((2R)-2-((4S,E)-3-hydroxy-4-methyl-non-1-en-6-yn-1-yl)-5-oxopyrrolidin-1-yl)ethyl)benzoate (217 mg), consisting of the two diastereomers, was prepared by methods described hereinabove utilizing the appropriate aldehyde and β-keto phosphonate ester. Both C15-hydroxy diastereomers ethyl 4-(2-((R)-2-((3S,4S,E)-3-hydroxy-4-methylnon-1-en-6-yn-1-yl)-5-oxopyrrolidin-1-yl)ethyl)benzoate (Example 9A') and ethyl 4-(2-((R)-2-((3R,4S,E)-3-hydroxy-4-methylnon-1-en-6-yn-1-yl)-5-oxopyrrolidin-1-yl)ethyl)benzoate (Example 9B') were isolated following separation by prep HPLC. The separation was performed on an Agilent Semi-Prep instrument; ultraviolet detector at 210 nm; Luna Silica 250 mm×10 mm column; mobile phase of heptane-ethanol-acetic acid (93:7:0.1 v/v) with a flow rate of 5 mL/min.

Example 9A'; a clear oil, HPLC retention time 26 minutes; TLC $R_f$ 0.39 (solvent system: 3:1 v/v ethyl acetate-heptane); MS (ESI⁺) m/z 434 (M+23(Na⁺));

Example 9B'; a clear oil, HPLC retention time 18 minutes; TLC $R_f$ 0.45 (solvent system: 3:1 v/v ethyl acetate-heptane); MS (ESI⁺) m/z 434 (M+23(Na⁺)).

4-(2-((R)-2-((3S,4S,E)-3-hydroxy-4-methylnon-1-en-6-yn-1-yl)-5-oxopyrrolidin-1-yl)ethyl)benzoic acid (Example 9C')

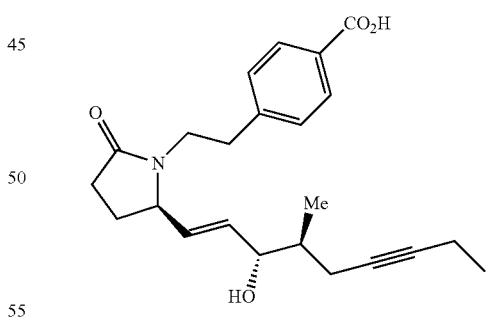

42 mg (100%) as a colorless solid; TLC $R_f$ 0.31 (solvent system 100:1 v/v ethyl acetate-acetic acid); melting point 173-174° C.; MS (ESI⁻) m/z 382 (M−1); ¹H-NMR (MeOH-d₄) δ 7.94-7.96 (d, 2H), 7.32-7.34 (d, 2H), 5.66-5.71 (dd, 1H), 5.46-5.52 (dd, 1H) 3.98-4.09 (m, 2H), 3.71-3.8 (m, 1H), 3.14-3.29 (m, 1H), 2.8-2.98 (m, 2H), 2.3-2.39 (m, 2H), 2.09-2.29 (m, 6H), 1.67-1.79 (m, 2H), 1.09 (t, 3H), 0.91-1.03 (m, 3H)

4-(2-((R)-2-((3R,4S,E)-3-hydroxy-4-methylnon-1-en-6-yn-1-yl)-5-oxopyrrolidin-1-yl)ethyl)benzoic acid (Example 9D')

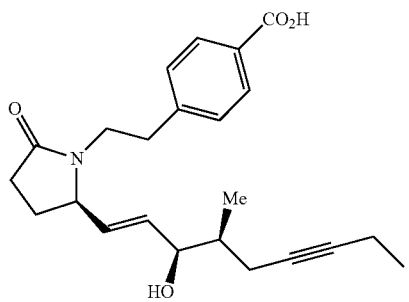 [SMILES: CCC#CC[C@H](C)[C@@H](O)/C=C/[C@H]1CCC(=O)N1CCc1ccc(C(=O)O)cc1]

111 mg (100%) as a colorless solid; TLC $R_f$ 0.42 (solvent system 100:1 v/v ethyl acetate-acetic acid); MS (ESI$^-$) m/z 382 (M−1).

Examples 10A'-10D'

Preparation of ethyl 4-(2-((R)-2-((3S,4R/S,E)-3-hydroxy-4-methyldec-1-en-6-yn-1-yl)-5-oxopyrrolidin-1-yl)ethyl)benzoate (Example 10A') and ethyl 4-(2-((R)-2-((3R,4R/S,E)-3-hydroxy-4-methyldec-1-en-6-yn-1-yl)-5-oxopyrrolidin-1-yl)ethyl)benzoate (Example 10B')

Example 10A'

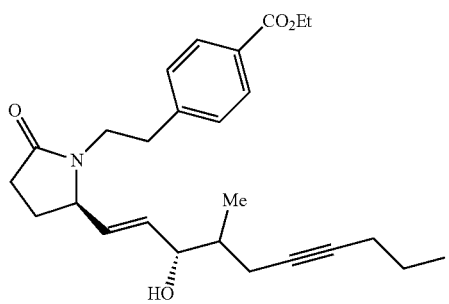

Example 10B'

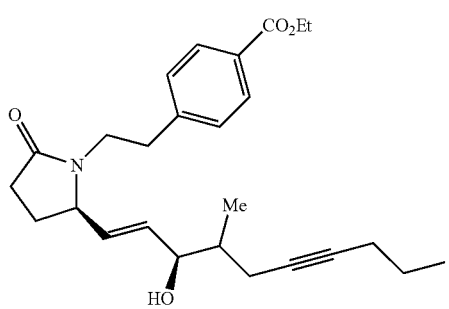

The diastereomeric mixtures of Example 10A' and Example 10B' were isolated following separation by prep HPLC.

Gilson Semi-Prep instrument; ultraviolet detector at 210 nm; Luna Silica 250 mm×21.2 mm column; mobile phase of heptane-ethanol (94:6 v/v) with a flow rate of 21.2 mL/min.

Example 10A' (161 mg); a clear oil; HPLC retention time 24 minutes; TLC $R_f$ 0.36 (solvent system: 3:1 v/v ethyl acetate-heptane); MS (ESI$^+$) m/z 448 (M+23(Na$^+$));

Example 10B' (97 mg); a clear oil; HPLC retention time 39 minutes; TLC $R_f$ 0.43 (solvent system: 3:1 v/v ethyl acetate-heptane); MS (ESI$^+$) m/z 448 (M+23(Na$^+$)).

4-(2-((2R)-2-((3S,E)-3-hydroxy-4-methyldec-1-en-6-yn-1-yl)-5-oxopyrrolidin-1-yl)ethyl)benzoic acid (Example 10C')

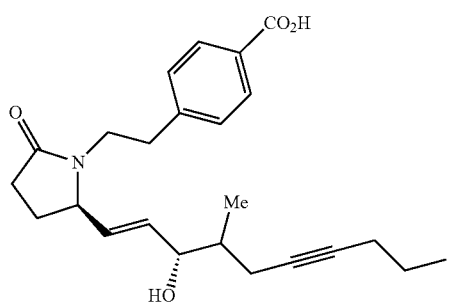 [SMILES: CCCC#CCC(C)[C@H](O)/C=C/[C@H]1CCC(=O)N1CCc1ccc(C(=O)O)cc1]

61 mg (96%) as a colorless solid; TLC $R_f$ 0.47 (solvent system 80:20:1 v/v ethyl acetate-heptane-acetic acid); melting point 109-111° C.; MS (ESI$^-$) m/z 396 (M−1)); $^1$H-NMR (MeOH-d$_4$) δ 7.94-7.96 (d, 2H), 7.32-7.34 (dd, 2H), 5.66-5.73 (m, 1H), 5.45-5.54 (m, 1H), 4.-4.09 (m, 2H), 3.71-3.79 (m, 1H), 3.14-3.29 (m, 1H), 2.8-2.98 (m, 2H), 2.09-2.38 (m, 7H), 1.66-1.79 (m, 2H), 1.48 (m, 2H), 0.93-1.04 (m, 6H).

4-(2-((2R)-2-((3R,E)-3-hydroxy-4-methyldec-1-en-6-yn-1-yl)-5-oxopyrrolidin-1-yl)ethyl)benzoic acid (Example 10D')

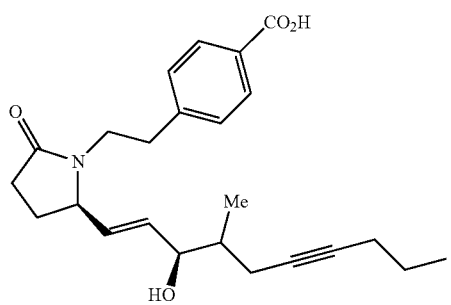 [SMILES: CCCC#CCC(C)[C@@H](O)/C=C/[C@H]1CCC(=O)N1CCc1ccc(C(=O)O)cc1]

113 mg (75%) as a colorless solid; TLC $R_f$ 0.51 (solvent system 80:20:1 v/v ethyl acetate-heptane-acetic acid); MS (ESI) m/z 396 (M−1).

Examples 11A'-11D'

Preparation of methyl 4-(2-((2R)-2-((3S,4R/S,E)-3-hydroxy-4-methyl-7-phenylhept-1-en-6-yn-1-yl)-5-oxopyrrolidin-1-yl)ethyl)benzoate (Example 11A') and methyl 4-(2-((2R)-2-((3R,4R/S,E)-3-hydroxy-4-methyl-7-phenylhept-1-en-6-yn-1-yl)-5-oxopyrrolidin-1-yl)ethyl)benzoate (Example 11B')

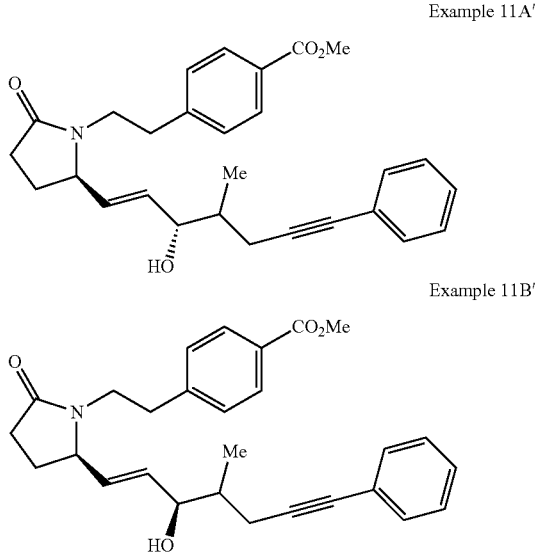

Example 11A'

Example 11B'

The diastereomeric mixtures of Example 11A' and Example 11B' were isolated following separation by prep HPLC.

Gilson Semi-Prep instrument; ultraviolet detector at 240 nm; Luna Silica 5μ 250 mm×10 mm column; mobile phase of heptane-ethanol (9:1 v/v) with a flow rate of 5 mL/min.

Example 11A' (64 mg); HPLC retention time 18 minutes; TLC $R_f$ 0.15 (solvent system: 4:1 v/v ethyl acetate-heptane); MS (ESI$^+$) m/z 446 (M+1);

Example 11B' (90 mg); HPLC retention time 15.5 minutes; TLC $R_f$ 0.18 (solvent system: 4:1 v/v ethyl acetate-heptane); MS (ESI$^+$) m/z 446 (M+1).

Preparation of 4-(2-((2R)-2-((3S,4R/S,E)-3-hydroxy-4-methyl-7-phenylhept-1-en-6-yn-1-yl)-5-oxopyrrolidin-1-yl)ethyl)benzoic acid (Example 11C')

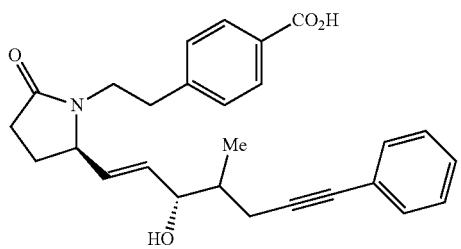 [SMILES: CC(CC#Cc1ccccc1)[C@H](O)/C=C/[C@H]1CCC(=O)N1CCc1ccc(C(=O)O)cc1]

60 mg (100%) as a clear oil; TLC $R_f$ 0.31 (solvent system 50:50:1 v/v acetone-heptane-acetic acid); MS (ESI$^-$)/z 430 (M−1); $^1$H-NMR (400 MHz, CDCl$_3$) δ 8.0 (d, 2H), 7.35-7.45 (m, 2H), 7.25-7.32 (m, 5H), 5.6 (dd, 2H), 4.3 (t, 1H), 4.15-4.2 (m, 2H), 3.2-3.1 (m, 2H) 2.6-1.3 (m, 9H) 1.1 (dd, 3H); $^{13}$CNMR (100 MHz, CDCl$_3$) δ 175.18, 170.16, 145.05, 134.89, 134.70, 130.84, 130.35, 128.88, 128.26, 127.82, 123.44, 87.91, 87.80, 82.43, 74.94, 74.15, 60.92, 50.81, 41.82, 38.29, 33.83, 29.96, 25.88, 23.27, 22.64, 15.81, 14.30.

Preparation of 4-(2-((2R)-2-((3R,4R/S,E)-3-hydroxy-4-methyl-7-phenylhept-1-en-6-yn-1-yl)-5-oxopyrrolidin-1-yl)ethyl)benzoic acid (Example 11D')

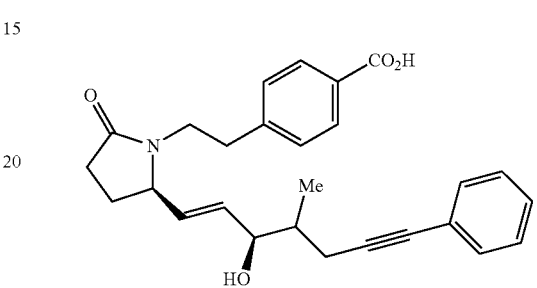

45 mg (51%) as a clear oil; TLC $R_f$ 0.36 (solvent system: 50:50:1 v/v acetone-heptane-acetic acid); MS (ESI$^-$) m/z 430 (M−1).

Examples 12A'-12D'

Preparation of methyl 2-(4-(((2R)-2-((3S,4R/S,E)-3-hydroxy-4-methyloct-1-en-6-yn-1-yl)-5-oxopyrrolidin-1-yl)methyl)phenyl)acetate (Example 12A') and methyl 2-(4-(((2R)-2-((3R,4R/S,E)-3-hydroxy-4-methyloct-1-en-6-yn-1-yl)-5-oxopyrrolidin-1-yl)methyl)phenyl)acetate (Example 12B')

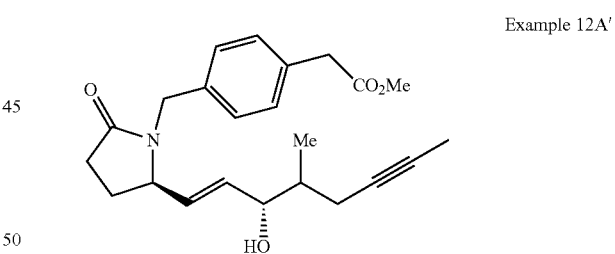

Example 12A'

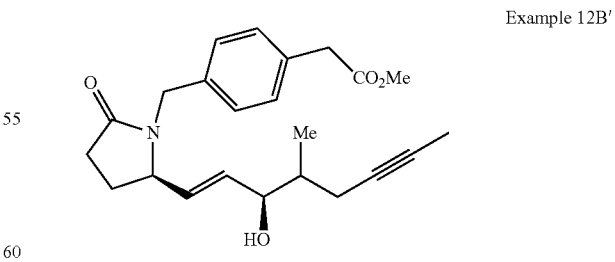

Example 12B'

The diastereomeric mixtures of Example 12A' and Example 12B' were isolated following separation by prep HPLC.

Agilent Semi-Prep instrument; ultraviolet detector at 210 nm; Chiralpak IA 250 mm×10 mm column; mobile phase of heptane-ethanol (9:1 v/v).

Example 12A' (11.2 mg); prep HPLC retention time 18.1-19.5 minutes; TLC R_f 0.5 (solvent system 5:95:1 v/v methanol-dichloromethane-acetic acid);

Example 12B' (7.3 mg); prep HPLC retention time 15.0-16.0 minutes; TLC R_f 0.45 (solvent system 5:95:1 v/v methanol-dichloromethane-acetic acid).

Preparation of 2-(4-(((2R)-2-((3S,4R/S,E)-3-hydroxy-4-methyloct-1-en-6-yn-1-yl)-5-oxopyrrolidin-1-yl)methyl)phenyl)acetic acid (Example 12C')

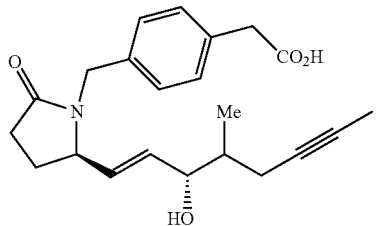 [SMILES: CC#CCC(C)[C@H](O)/C=C/[C@H]1CCC(=O)N1Cc1ccc(CC(=O)O)cc1]

3.5 mg as an oil; TLC R_f 0.25 (solvent system: 5:95:1 v/v methanol-dichloromethane-acetic acid); MS (ESI$^-$) m/z 368 (M−1); $^1$H-NMR (400 MHz, CDCl$_3$) δ 7.2 (quartet, 4H), 5.6-5.4 (m, 2H), 4.8 (t, 1H), 4.2 (t, 1H), 4.0-3.9 (m, 2H), 3.7 (s, 2H), 2.6-2.3 (m, 2H), 2.3-2.1 (m, 2H), 2.1-2.0 (m, 2H), 1.8-1.7 (m, 5H), 0.9 (t, 3H).

Preparation of 2-(4-(((2R)-2-((3R,4R/S,E)-3-hydroxy-4-methyloct-1-en-6-yn-1-yl)-5-oxopyrrolidin-1-yl)methyl)phenyl)acetic acid (Example 12D')

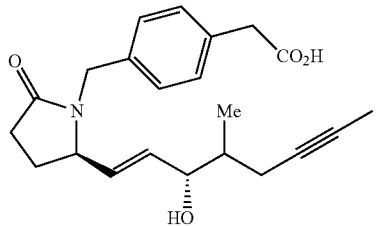 [SMILES: CC#CCC(C)[C@H](O)/C=C/[C@H]1CCC(=O)N1Cc1ccc(CC(=O)O)cc1]

8.4 mg as an oil; TLC R_f 0.2 (solvent system: 5:95:1 v/v methanol-dichloromethane-acetic acid); $^1$H-NMR (400 MHz, CDCl$_3$) δ 7.2 (quartet, 4H), 5.6-5.4 (m, 2H), 4.8 (t, 1H), 4.2 (t, 1H), 4.0-3.9 (m, 2H), 3.7 (s, 2H), 2.6-2.3 (m, 2H), 2.3-2.1 (m, 2H), 2.1-2.0 (m, 2H), 1.8-1.7 (m, 5H), 0.9 (t, 3H).

Examples 13A'-13D'

Preparation of methyl 5-(3-((2R)-2-((3S,E)-3-hydroxy-4-methylnon-1-en-6-yn-1-yl)-5-oxopyrrolidin-1-yl)prop-1-yn-1-yl)thiophene-2-carboxylate (Example 13A') and methyl 5-(3-((2R)-2-((3R,E)-3-hydroxy-4-methylnon-1-en-6-yn-1-yl)-5-oxopyrrolidin-1-yl)prop-1-yn-1-yl)thiophene-2-carboxylate (Example 13B')

Example 13A'

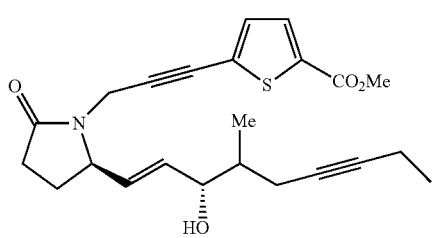

Example 13B'

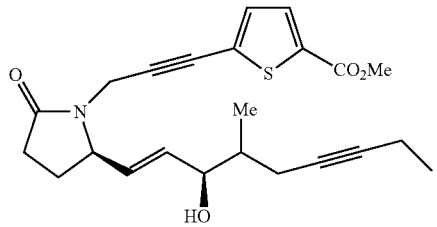

From the diastereomeric mixture of four isomers (76 mg), the diastereomeric mixtures of Example 13A' and Example 13B' were isolated following separation by prep HPLC.

Agilent Semi-Prep instrument; ultraviolet detector at 205 nm; Luna Silica 5μ 250 mm×10 mm column; mobile phase of 9:1 v/v heptane:ethanol.

Example 13A' (18.7 mg); as a clear oil; HPLC retention time of 16.1-18.1 minutes; MS (APCI$^+$) m/z 436.1 (M+23 (Na$^+$))

Example 13B' (46.6 mg); as a clear oil; HPLC retention time of 13.4-15.1 minutes; MS (APCI$^+$) m/z 436.1 (M+23 (Na$^+$))

Preparation of 5-(3-((2R)-2-((3S,E)-3-hydroxy-4-methylnon-1-en-6-yn-1-yl)-5-oxopyrrolidin-1-yl)prop-1-yn-1-yl)thiophene-2-carboxylic acid (Example 13C')

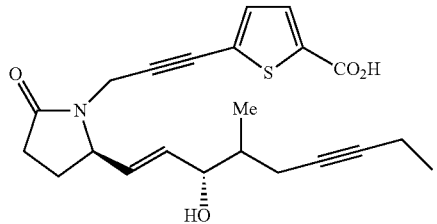 [SMILES: CCC#CCC(C)[C@H](O)/C=C/[C@H]1CCC(=O)N1CC#Cc1ccc(C(=O)O)s1]

10.7 mg as an oil; TLC R 0.35 (solvent system 96:4:1 v/v dichloromethane-methanol-acetic acid); MS (ESI$^+$)/z 400.1 (M+1) (ESI$^-$) m/z 398.0 (M−1)

Preparation of 5-(3-((2R)-2-((3R,E)-3-hydroxy-4-methylnon-1-en-6-yn-1-yl)-5-oxopyrrolidin-1-yl)prop-1-yn-1-yl)thiophene-2-carboxylic acid (Example 13D')

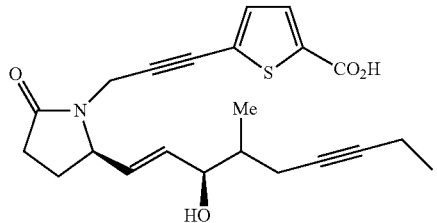 [SMILES: CCC#CCC(C)[C@@H](O)/C=C/[C@H]1CCC(=O)N1CC#Cc1ccc(C(=O)O)s1]

35.6 mg as an oil; TLC R_f 0.35 (solvent system 96:4:1 v/v dichloromethane-methanol-acetic acid); MS (ESI$^+$) m/z 400.1 (M+1) (ESI) m/z 398.1 (M−1)

Example 14A'-14D'

Preparation of methyl 5-(3-((2R)-2-((3S,E)-3-hydroxy-4-methyl-7-phenylhept-1-en-6-yn-1-yl)-5-oxopyrrolidin-1-yl)prop-1-yn-1-yl)thiophene-2-carboxylate (14A') and methyl 5-(3-((2R)-2-((3R,E)-3-hydroxy-4-methyl-7-phenylhept-1-en-6-yn-1-yl)-5-oxopyrrolidin-1-yl)prop-1-yn-1-yl)thiophene-2-carboxylate (14B')

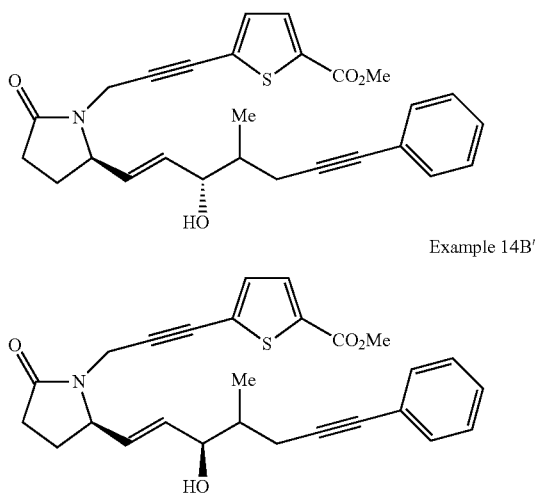

Example 14A'

Example 14B'

The diastereomeric mixtures of Example 14A' and Example 14B' were isolated following separation by prep HPLC.

Agilent Semi-Prep instrument; ultraviolet detector at 205 nm; Luna Silica 5μ 250 mm×10 mm column; mobile phase of 9:1 v/v heptane:ethanol.

Example 14A' (18.7 mg); as a clear oil; HPLC retention time of 16.1-18.1 minutes; MS (APCI+) m/z 436.1 (M+23 (Na+))

Example 14B' (50.1 mg); as a clear oil; HPLC retention time of 13.4-15.1 minutes; MS (APCI+) m/z 436.1 (M+23 (Na+))

Preparation of 5-((Z)-3-((2R)-2-((3S,E)-3-hydroxy-4-methyl-7-phenylhept-1-en-6-yn-1-yl)-5-oxopyrrolidin-1-yl)prop-1-en-1-yl)thiophene-2-carboxylic acid (Example 14C')

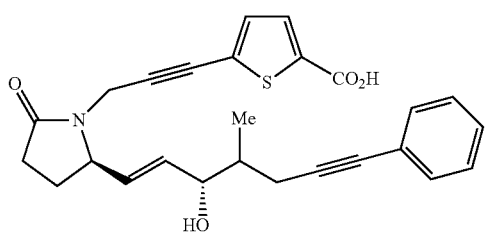 [SMILES: CC(CC#Cc1ccccc1)[C@H](O)/C=C/[C@H]1CCC(=O)N1CC#Cc1ccc(C(=O)O)s1]

14.4 mg as an oil; TLC R$_f$ 0.35 (solvent system 96:4:1 v/v dichloromethane-methanol-acetic acid); MS (ESI+) m/z 400.1 (M+1) (ESI−) m/z 398.0 (M−1)

Preparation of 5-((Z)-3-((2R)-2-((3R,E)-3-hydroxy-4-methyl-7-phenylhept-1-en-6-yn-1-yl)-5-oxopyrrolidin-1-yl)prop-1-en-1-yl)thiophene-2-carboxylic acid (Example 14D')

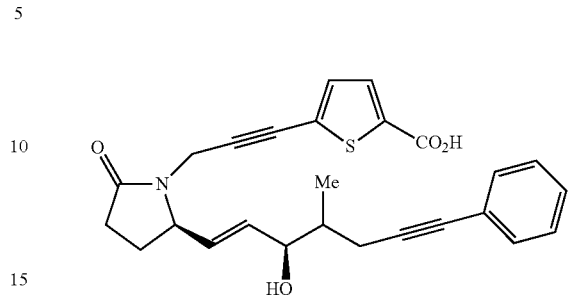

36.1 mg as an oil; TLC R$_f$ 0.35 (solvent system 96:4:1 v/v dichloromethane-methanol-acetic acid); MS (ESI+) m/z 400.1 (M+1) (ESI−) m/z 398.1 (M−1)

Examples 15A'-15D'

Preparation of methyl 5-((Z)-3-((2R)-2-((3S,4R/S,E)-3-hydroxy-4-methylnon-1-en-6-yn-1-yl)-5-oxopyrrolidin-1-yl)prop-1-en-1-yl)thiophene-2-carboxylate (Example 15A') and methyl 5-((Z)-3-((2R)-2-((3R,4R/S,E)-3-hydroxy-4-methylnon-1-en-6-yn-1-yl)-5-oxopyrrolidin-1-yl)prop-1-en-1-yl)thiophene-2-carboxylate (Example 15B')

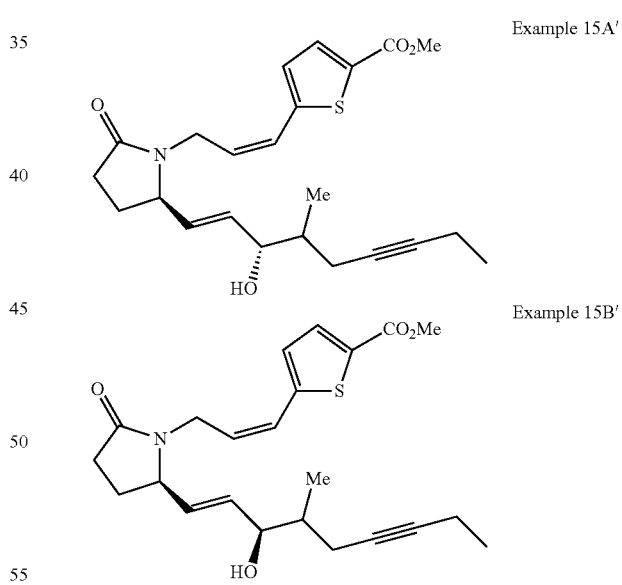

Example 15A'

Example 15B'

The diastereomeric mixtures of Example 15A' and Example 15B' were isolated following separation by prep HPLC.

Agilent Semi-Prep instrument; ultraviolet detector at 205 nm; Luna Silica 5μ 250 mm×10 mm column; mobile phase of heptane-ethanol (93:7 v/v).

Example 15A' (6.3 mg); a clear oil; prep HPLC retention time 27-29.8 minutes; MS (APCI+) m/z 438 (M+23(Na+));

Example 15B' (2.7 mg); a clear oil; prep HPLC retention time 23.5-24.8 minutes; MS (APCI+) m/z 438 (M+23(Na+)).

Preparation of 5-((Z)-3-((2R)-2-((3S,4R/S,E)-3-hydroxy-4-methylnon-1-en-6-yn-1-yl)-5-oxopyrrolidin-1-yl)prop-1-en-1-yl)thiophene-2-carboxylic acid (Example 15C')

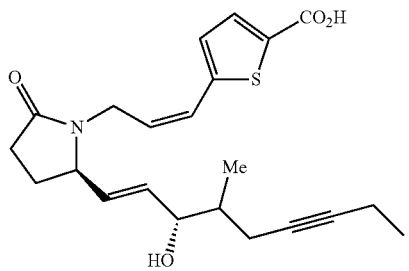 [SMILES: CCC#CCC(C)[C@H](O)/C=C/[C@H]1CCC(=O)N1C/C=C\c1ccc(C(=O)O)s1]

3.0 mg as a colorless oil; TLC $R_f$ 0.30 (solvent system: 95:5:1 v/v dichloromethane-methanol-acetic acid); MS (ESI⁺) m/z 424 (M+Na).

Preparation of 5-((Z)-3-((2R)-2-((3R,4R/S,E)-3-hydroxy-4-methylnon-1-en-6-yn-1-yl)-5-oxopyrrolidin-1-yl)prop-1-en-1-yl)thiophene-2-carboxylic acid (Example 15D')

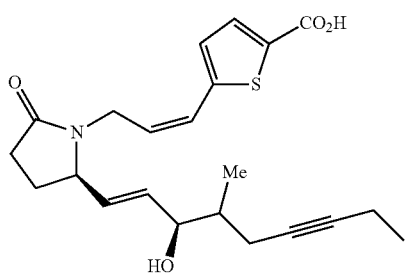 [SMILES: CCC#CCC(C)[C@@H](O)/C=C/[C@H]1CCC(=O)N1C/C=C\c1ccc(C(=O)O)s1]

2.5 mg as a colorless oil; TLC $R_f$ 0.30 (solvent system: 95:5:1 v/v dichloromethane-methanol-acetic acid); MS (ESI⁺) m/z 424 (M+23(Na⁺)).

Examples 16A'-16D'

Preparation of methyl 5-((Z)-3-((2R)-2-((3S,4R/S,E)-3-hydroxy-4-methyl-7-phenylhept-1-en-6-yn-1-yl)-5-oxopyrrolidin-1-yl)prop-1-en-1-yl)thiophene-2-carboxylate (Example 16A') and methyl 5-((Z)-3-((2R)-2-((3R,4R/S,E)-3-hydroxy-4-methyl-7-phenylhept-1-en-6-yn-1-yl)-5-oxopyrrolidin-1-yl)prop-1-en-1-yl)thiophene-2-carboxylate (Example 16B')

Example 16A'

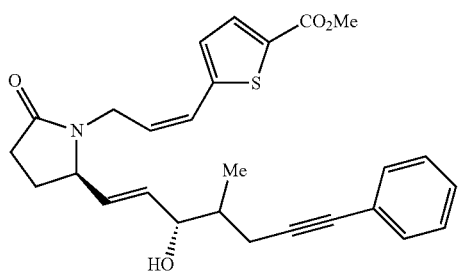 [SMILES: CC(CC#Cc1ccccc1)[C@H](O)/C=C/[C@H]1CCC(=O)N1C/C=C\c1ccc(C(=O)O)s1]

Example 16B'

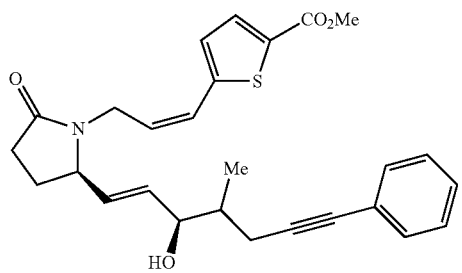 [SMILES: CC(CC#Cc1ccccc1)[C@@H](O)/C=C/[C@H]1CCC(=O)N1C/C=C\c1ccc(C(=O)O)s1]

The diastereomeric mixtures of Example 16A' and Example 16B' were isolated following separation by prep HPLC.

Agilent Semi-Prep instrument; ultraviolet detector at 205 nm; Luna Silica 5 µ250 mm×10 mm column; mobile phase of heptane-ethanol (93:7 v/v).

Example 16A' (23 mg); a clear oil; prep HPLC retention time 26.5-28.2 minutes; MS (APCI⁺) m/z 464 (M+1);

Example 16B' (7.5 mg); a clear oil; prep HPLC retention time 23-24.8 minutes; MS (APCI⁺) m/z 464 (M+1).

Preparation of 5-((Z)-3-((2R)-2-((3S,4R/S,E)-3-hydroxy-4-methyl-7-phenylhept-1-en-6-yn-1-yl)-5-oxopyrrolidin-1-yl)prop-1-en-1-yl)thiophene-2-carboxylic acid (Example 16C')

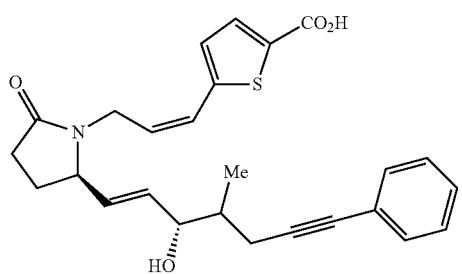

3.0 mg as a colorless oil; TLC $R_f$ 0.35 (solvent system: 95:5:1 v/v dichloromethane-methanol-acetic acid); MS (ESI⁺) m/z 472 (M+23(Na⁺)).

Preparation of 5-((Z)-3-((2R)-2-((3R,4R/S,E)-3-hydroxy-4-methyl-7-phenylhept-1-en-6-yn-1-yl)-5-oxopyrrolidin-1-yl)prop-1-en-1-yl)thiophene-2-carboxylic acid (Example 16D')

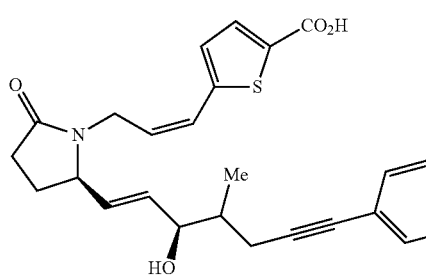

2.5 mg as a colorless oil; TLC R_f 0.35 (solvent system: 95:5:1 v/v dichloromethane-methanol-acetic acid); MS (ESI⁻) m/z 448 (M−1).

Examples 17A'-17E'

Preparation of methyl 5-(3-((R)-2-((3S,4S,E)-3-hydroxy-4-methylnon-1-en-6-yn-1-yl)-5-oxopyrrolidin-1-yl)propyl)thiophene-2-carboxylate (Example 17A') and methyl 5-(3-((R)-2-((3S,4R,E)-3-hydroxy-4-methylnon-1-en-6-yn-1-yl)-5-oxopyrrolidin-1-yl)propyl)thiophene-2-carboxylate (Example 17B') and methyl 5-(3-((2R)-2-((3R,E)-3-hydroxy-4-methylnon-1-en-6-yn-1-yl)-5-oxopyrrolidin-1-yl)propyl)thiophene-2-carboxylate (Example 17C')

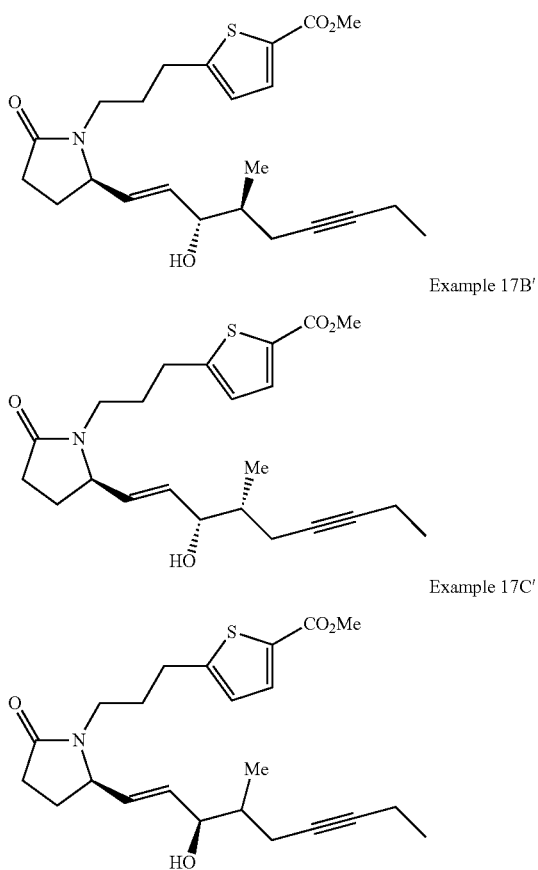

Example 17A'

Example 17B'

Example 17C'

The stereoisomeric mixtures of Examples 17A', 17B', and 17C' were isolated from the diastereomeric mixture of methyl 5-(3-((2R)-2-((E)-3-hydroxy-4-methylnon-1-en-6-yn-1-yl)-5-oxopyrrolidin-1-yl)propyl)thiophene-2-carboxylate following separation by prep HPLC.

Agilent Semi-Prep instrument; ultraviolet detector at 205 nm; Luna Silica 5μ 250 mm×10 mm column; mobile phase of heptane-ethanol (95:5 v/v).

Example 17A' (4.9 mg); a clear oil; HPLC retention time 48.8-51.8 minutes; ¹H-NMR (CDCl₃) δ 7.6 (d, 1H), 6.8 (d, 1H), 5.7-5.6 (m, 1H), 5.6-5.5 (m, 1H), 4.2-4.1 (m, 2H), 3.85 (s, 3H), 3.7-3.5 (m, 1H), 3.0-2.9 (m, 1H), 2.9-2.8 (t, 2H), 2.5-2.1 (m, 6H), 2.0-1.7 (m, 5H), 1.1 (t, 3H), 0.95 (d, 3H); MS (ESI⁺) m/z 418.1 (M+1), 440.1 (M+23(Na⁺)).

Example 17B' (7.2 mg); a clear oil; HPLC retention time 45.9-48.4 minutes; ¹H-NMR (CDCl₃) δ 7.6 (d, 1H), 6.8 (d, 1H), 5.7-5.6 (m, 1H), 5.6-5.5 (m, 1H), 4.3-4.2 (m, 1H), 4.1-4.2 (m, 1H), 3.85 (s, 3H), 3.7-3.5 (m, 1H), 3.0-2.9 (m, 1H), 2.9-2.8 (t, 2H), 2.5-2.1 (m, 6H), 2.0-1.7 (m, 5H), 1.1 (t, 3H), 0.95 (d, 3H); MS (ESI⁺) m/z 418.1 (M+1), 440.1 (M+23(Na⁺)).

Example 17C' (26.7 mg); a clear oil; HPLC retention time 34.1-36.9 minutes; ¹H-NMR (CDCl₃) δ 7.6 (d, 1H), 6.8 (d, 1H), 5.7-5.6 (m, 1H), 5.6-5.5 (m, 1H), 4.3-4.2 (m, 0.5H), 4.1-4.2 (m, 1.5H), 3.85 (s, 3H), 3.7-3.5 (m, 1H), 3.0-2.9 (m, 1H), 2.9-2.8 (t, 2H), 2.5-2.1 (m, 6H), 2.0-1.7 (m, 5H), 1.1 (t, 3H), 0.95 (d, 3H); MS (ESI⁺) m/z 418.1 (M+1), 440.1 (M+23(Na⁺)).

Preparation of 5-(3-((R)-2-((3S,4S,E)-3-hydroxy-4-methylnon-1-en-6-yn-1-yl)-5-oxopyrrolidin-1-yl)propyl)thiophene-2-carboxylic acid (Example 17D')

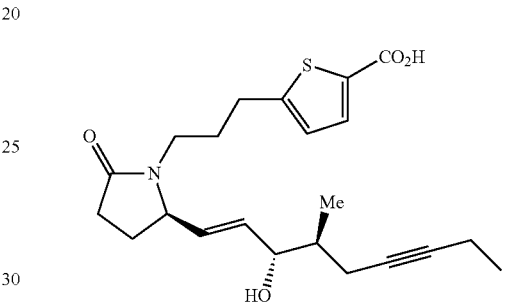

5-(3-((R)-2-((3S,4S,E)-3-Hydroxy-4-methylnon-1-en-6-yn-1-yl)-5-oxopyrrolidin-1-yl)propyl)thiophene-2-carboxylic acid (Example 17D') was prepared from methyl 5-(3-((R)-2-((3S,4S,E)-3-hydroxy-4-methylnon-1-en-6-yn-1-yl)-5-oxopyrrolidin-1-yl)propyl)thiophene-2-carboxylate (Example 17A') by the above methods to obtain the title compound (3.7 mg) as a colorless oil; TLC R_f 0.35 (solvent system: 96:4:1 v/v dichloromethane-methanol-acetic acid); ¹H-NMR (CDCl₃) δ 7.7 (d, 1H, J=3.6 Hz), 6.8 (d, 1H, J=3.6 Hz), 5.8-5.7 (m, 1H), 5.6-5.5 (m, 1H), 4.3-4.2 (m, 0.5H), 4.2-4.0 (m, 1.5H), 3.7-3.5 (m, 1H), 3.1-3.0 (m, 1H), 2.9-2.8 (m, 2H), 2.6-2.3 (m, 2H), 2.3-2.1 (m, 5H), 2.0-1.7 (m, 4H), 1.2-1.0 (m, 3H), 1.0-0.9 (m, 3H); MS (ESI⁺) m/z 404.1 (M+1), (ESI⁻) m/z 402.1 (M−1).

Preparation of 5-(3-((R)-2-((3S,4R,E)-3-hydroxy-4-methylnon-1-en-6-yn-1-yl)-5-oxopyrrolidin-1-yl)propyl)thiophene-2-carboxylic acid (Example 17E')

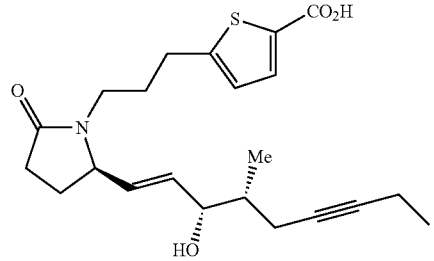 [SMILES: CCC#CC[C@@H](C)[C@H](O)/C=C/[C@H]1CCC(=O)N1CCCc1ccc(C(=O)O)s1]

5-(3-((R)-2-((3S,4R,E)-3-hydroxy-4-methylnon-1-en-6-yn-1-yl)-5-oxopyrrolidin-1-yl)propyl)thiophene-2-carboxylic acid (Example 17E') is prepared from methyl 5-(3-((R)-

2-((3S,4R,E)-3-hydroxy-4-methylnon-1-en-6-yn-1-yl)-5-oxopyrrolidin-1-yl)propyl)thiophene-2-carboxylate (Example 17B') by the above methods.

Preparation of 5-(3-((R)-2-((3S,E)-3-hydroxy-4-methylnon-1-en-6-yn-1-yl)-5-oxopyrrolidin-1-yl)propyl)thiophene-2-carboxylic acid (Example 17F')

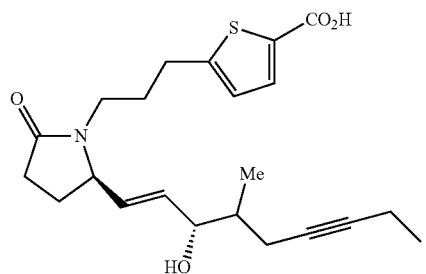 [SMILES: CCC#CCC(C)[C@H](O)/C=C/[C@H]1CCC(=O)N1CCCc1ccc(C(=O)O)s1]

5-(3-((R)-2-((3S,E)-3-Hydroxy-4-methylnon-1-en-6-yn-1-yl)-5-oxopyrrolidin-1-yl)propyl)thiophene-2-carboxylic acid (Example 17F') was prepared from methyl 5-(3-((R)-2-((3S,E)-3-Hydroxy-4-methylnon-1-en-6-yn-1-yl)-5-oxopyrrolidin-1-yl)propyl)thiophene-2-carboxylate by the above methods to obtain the title compound as a colorless oil; $^1$H-NMR (CDCl$_3$) δ 7.7 (d, 1H, J=3.6 Hz), 6.8 (d, 1H, J=3.6 Hz), 5.8-5.7 (m, 1H), 5.6-5.5 (m, 1H), 4.3-4.2 (m, 0.5H), 4.2-4.0 (m, 1.5H), 3.7-3.5 (m, 1H), 3.1-3.0 (m, 1H), 2.9-2.8 (m, 2H), 2.6-2.3 (m, 2H), 2.3-2.1 (m, 5H), 2.0-1.7 (m, 4H), 1.2-1.0 (m, 3H), 1.0-0.9 (m, 3H); MS (ESI$^-$) m/z 402.1 (M−1).

Preparation of 5-(3-((R)-2-((3R,E)-3-hydroxy-4-methylnon-1-en-6-yn-1-yl)-5-oxopyrrolidin-1-yl)propyl)thiophene-2-carboxylic acid (Example 17G')

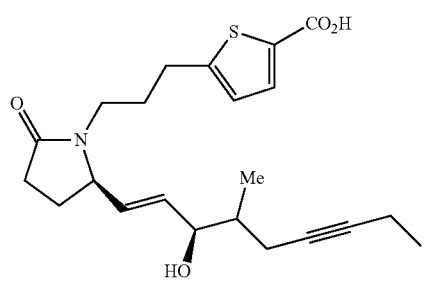 [SMILES: CCC#CCC(C)[C@@H](O)/C=C/[C@H]1CCC(=O)N1CCCc1ccc(C(=O)O)s1]

5-(3-((R)-2-((3R,E)-3-Hydroxy-4-methylnon-1-en-6-yn-1-yl)-5-oxopyrrolidin-1-yl)propyl)thiophene-2-carboxylic acid (Example 17G') was prepared from methyl 5-(3-((R)-2-((3R,E)-3-Hydroxy-4-methylnon-1-en-6-yn-1-yl)-5-oxopyrrolidin-1-yl)propyl)thiophene-2-carboxylate (Example 17C') by the above methods to obtain the title compound as a colorless oil; $^1$H-NMR (CDCl$_3$) δ 7.7 (d, 1H, J=3.6 Hz), 6.8 (d, 1H, J=3.6 Hz), 5.8-5.7 (m, 1H), 5.6-5.5 (m, 1H), 4.2-4.0 (m, 1H), 3.7-3.5 (m, 1H), 3.1-3.0 (m, 1H), 2.9-2.8 (m, 2H), 2.6-2.3 (m, 2H), 2.3-2.1 (m, 5H), 2.0-1.7 (m, 4H), 1.2-1.0 (m, 3H), 1.0-0.9 (m, 3H); MS (ESI$^-$) m/z 402.1 (M−1).

Examples 18A'-18D'

Preparation of methyl 5-(3-((2R)-2-((3S,E)-3-hydroxy-4-methyl-7-phenylhept-1-en-6-yn-1-yl)-5-oxopyrrolidin-1-yl)propyl)thiophene-2-carboxylate (Example 18A') and methyl 5-(3-((2R)-2-((3R,E)-3-hydroxy-4-methyl-7-phenylhept-1-en-6-yn-1-yl)-5-oxopyrrolidin-1-yl)propyl)thiophene-2-carboxylate (Example 18B')

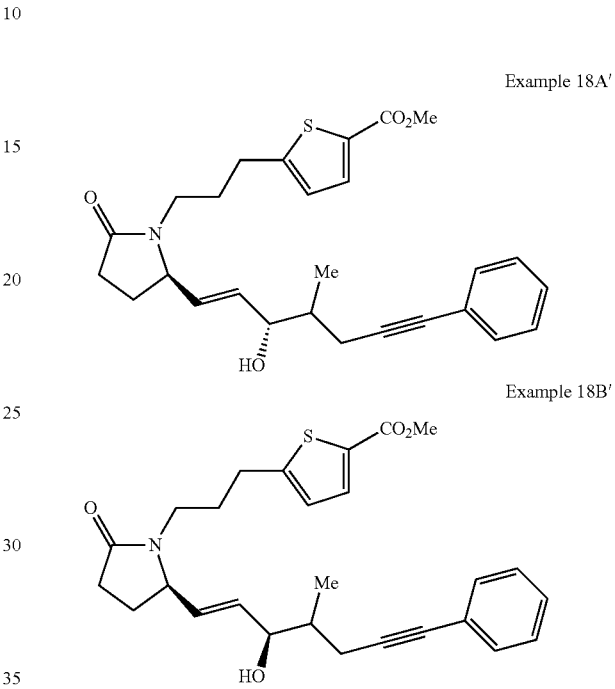

The diastereomeric mixtures of Example 18A' and Example 18B' were isolated following separation by prep HPLC.

Agilent Semi-Prep instrument; ultraviolet detector at 205 nm; Luna Silica 5μ 250 mm×10 mm column; mobile phase of heptane-ethanol (90:10 v/v).

Example 18A' (15.4 mg); a clear oil; prep HPLC retention time 21.5-24.5 minutes; MS (ESI$^+$)/z 466.1 (M+1), 488.1 (M+23(Na$^+$))

Example 18B' (38.2 mg); a clear oil; prep HPLC retention time 17.1-20.2 minutes; MS (ESI$^+$) m/z 466.1 (M+1), 488.1 (M+23(Na$^+$))

5-(3-((2R)-2-((3S,E)-3-hydroxy-4-methyl-7-phenylhept-1-en-6-yn-1-yl)-5-oxopyrrolidin-1-yl)propyl)thiophene-2-carboxylic acid (Example 18C')

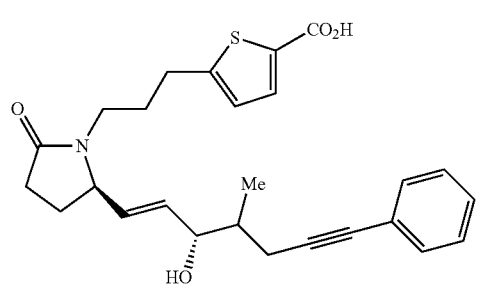 [SMILES: CC(CC#Cc1ccccc1)[C@H](O)/C=C/[C@H]1CCC(=O)N1CCCc1ccc(C(=O)O)s1]

9.8 mg as a colorless oil; TLC R$_f$ 0.35 (solvent system: 96:4:1 v/v dichloromethane-methanol-acetic acid); MS (ESI$^-$) m/z 450.1 (M−1).

5-(3-((2R)-2-((3R,E)-3-hydroxy-4-methyl-7-phenyl-hept-1-en-6-yn-1-yl)-5-oxopyrrolidin-1-yl)propyl)thiophene-2-carboxylic acid (Example 18D')

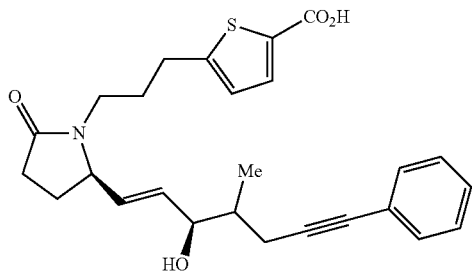 [SMILES: CC(CC#Cc1ccccc1)[C@@H](O)/C=C/[C@H]1CCC(=O)N1CCCc1ccc(C(=O)O)s1]

28.9 mg as a colorless oil; TLC R$_f$ 0.35 (solvent system: 96:4:1 v/v dichloromethane-methanol-acetic acid); MS (ESI$^-$) m/z 450.1 (M−1).

Examples 1A"-7D"

Preparation of (R,E)-methyl 7-(2-oxo-5-(3-oxo-7-phenylhept-1-en-1-yl)pyrrolidin-1-yl)heptanoate

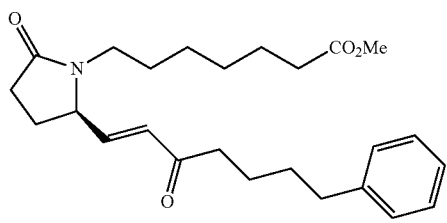 [SMILES: COC(=O)CCCCCCN1C(=O)CC[C@@H]1/C=C/C(=O)CCCCc1ccccc1]

To a stirring mixture consisting of (R)-methyl 7-(2-formyl-5-oxopyrrolidin-1yl)heptanoate (0.200 g, 0.78 mmol) and dimethyl (2-oxo-6-phenylhexyl)phosphonate (0.16 g, 0.56 mmol) in THF (20 mL) at 0° C. was added lithium chloride (83 mg, 1.96 mmol) and triethylamine (0.13 mL, 0.94 mmol). The reaction mixture was stirred at room temperature overnight. To the reaction mixture was added a saturated solution of ammonium chloride (30 mL) and organic material was extracted with ethyl acetate (100 mL). The organic layer was separated, washed with brine (50 mL), dried over sodium sulfate, filtered, and concentrated in vacuo. The residue was purified by silica gel chromatography eluting with ethyl acetate-heptane (7:3 v/v) to afford the title compound (182 mg, 56%); TLC R$_f$ 0.55 (solvent system: 75:25 v/v ethyl acetate-heptane).

Preparation of methyl 7-((R)-2-((S,E)-3-hydroxy-7-phenylhept-1-en-1-yl)-5-oxopyrrolidin-1-yl)heptanoate (Example 1A") and methyl 7-((R)-2-((R,E)-3-hydroxy-7-phenylhept-1-en-1-yl)-5-oxopyrrolidin-1-yl)heptanoate (Example 1B")

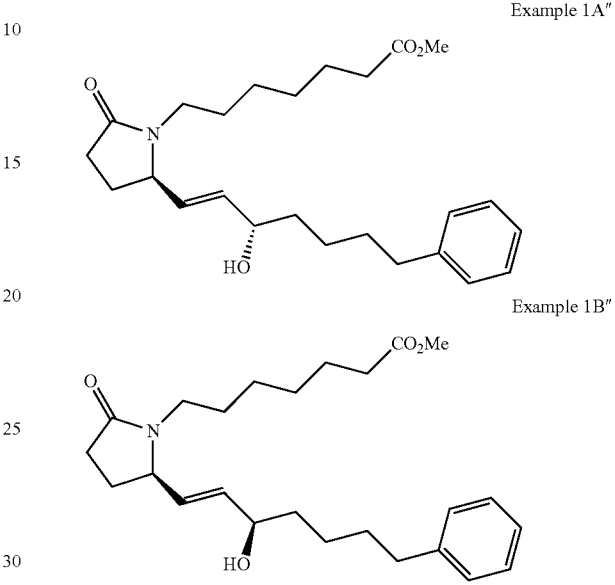

To a mixture consisting of (R,E)-methyl 7-(2-oxo-5-(3-oxo-7-phenylhept-1-en-1-yl)pyrrolidin-1-yl)heptanoate (182 mg, 0.47 mmol) in methanol (15 mL) at −40° C. was added cerium (III) chloride heptahydrate (176 mg, 0.47 mmol). The reaction mixture was cooled to −78° C. and stirred for one hour. To the reaction mixture was added sodium borohydride (36 mg, 0.94 mmol), and the reaction mixture stirred for two hours. Acetone was added and the mixture was stirred for 15 minutes at −78° C., after which time the mixture was allowed to warm to room temperature. To the room temperature reaction mixture was added a saturated aqueous solution of ammonium chloride (30 mL) and the organic material was extracted with ethyl acetate (100 mL). The organic layer was separated and washed with brine (50 mL), dried over sodium sulfate, filtered, and concentrated in vacuo. The residue was purified by silica gel chromatography eluting with ethyl acetate-heptanes (7:3 v/v) to afford the title compound (163 mg, 89%) as an epimeric mixture with regard to the configuration of the C15-OH position.

From the epimeric mixture (163 mg), the single epimers of Example 1A" and Example 1B" were isolated following separation by prep HPLC.

Gilson Semi-Prep instrument; ultraviolet detector at 210 nm; Luna 5μ Silica 250×21.2 mm column; mobile phase of heptanes-ethanol (92:8 v/v).

Example 1A" (40 mg): a clear oil; HPLC retention time 23 min; TLC R$_f$ 0.36 (solvent system: 3:1 v/v ethyl acetate-heptane); MS (FIA/ESI$^+$) m/z 415.6 (M+1).

Example 1B" (78 mg); a clear oil; HPLC retention time 18 min; TLC R$_f$ 0.42 (solvent system: 3:1 v/v ethyl acetate-heptane); MS (FIA/ESI$^+$) m/z 415.6 (M+1).

Preparation of 7-((R)-2-((S,E)-3-hydroxy-7-phenyl-hept-1-en-1-yl)-5-oxopyrrolidin-1-yl)heptanoic acid (Example 1C")

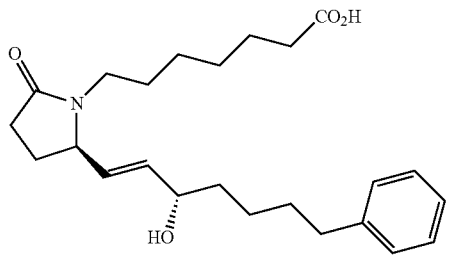 [SMILES: O=C(O)CCCCCCN1C(=O)CC[C@@H]1/C=C/[C@@H](O)CCCCc1ccccc1]

To a mixture consisting of methyl 7-((R)-2-((S,E)-3-hydroxy-7-phenylhept-1-en-1-yl)-5-oxopyrrolidin-1-yl)heptanoate (40 mg, 0.096 mmol, prepared as Example 1A" above) in methanol (2 mL) was added 2 N sodium hydroxide (1 mL). The reaction mixture was stirred at room temperature for three hours. To the reaction mixture was added a solution of 5% potassium hydrogen sulfate-brine (1:1) to achieve an acidic pH, and the organic material was extracted with ethyl acetate. The organic phase was dried over sodium sulfate, filtered, and concentrated in vacuo. The residue was purified on silica gel eluting with ethyl acetate-acetic acid (100:0.4 v/v) to afford the title compound (33 mg, 85%) as a colorless oil; TLC $R_f$ 0.14 (solvent system: 100:1 v/v ethyl acetate-acetic acid); MS (ESI⁻) m/z 400 (M−1); ¹HNMR (methanol-$d_4$) δ 7.21-7.27 (m, 2H), 7.12-7.18 (m, 3H), 5.71 (dd, 1H) 5.48 (dd, 1H) 4.04-4.18 (m, 2H), 3.34-3.47 (m, 2H), 2.82-2.9 (m, 1H), 2.62 (t, 2H), 2.2-2.4 (m, 5H), 1.49-1.68 (m, 7H), 1.25-1.48 (m, 8H).

Preparation of 7-((R)-2-((R,E)-3-hydroxy-7-phenyl-hept-1-en-1-yl)-5-oxopyrrolidin-1-yl)heptanoic acid (Example 1D")

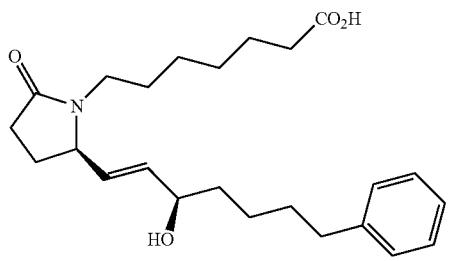 [SMILES: O=C(O)CCCCCCN1C(=O)CC[C@@H]1/C=C/[C@H](O)CCCCc1ccccc1]

7-((R)-2-((R,E)-3-Hydroxy-7-phenylhept-1-en-1-yl)-5-oxopyrrolidin-1-yl)heptanoic acid was prepared from the corresponding carboxylic ester, Example 1B", in the same manner as its epimer 7-((R)-2-((S,E)-3-hydroxy-7-phenyl-hept-1-en-1-yl)-5-oxopyrrolidin-1-yl)heptanoic acid, Example 1C", to obtain 69 mg (75%) of a clear oil; TLC $R_f$ 0.20 (solvent system: 100:1 v/v ethyl acetate-acetic acid); MS (ESI$^L$) m/z 400 (M−1).

Preparation of methyl 7-((2R)-2-((E)-4-methyl-3-oxo-7-phenylhept-1-en-1-yl)-5-oxopyrrolidin-1-yl)heptanoate

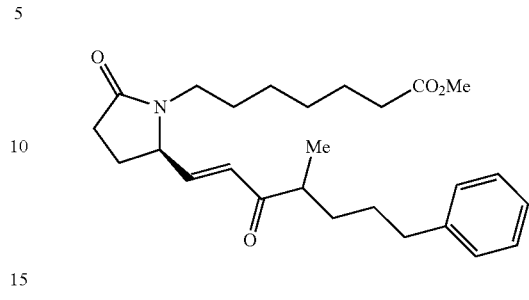

Methyl 7-((2R)-2-((E)-4-methyl-3-oxo-7-phenylhept-1-en-1-yl)-5-oxopyrrolidin-1-yl)heptanoate (182 mg, 56%) was prepared in the same manner as (R,E)-methyl 7-(2-oxo-5-(3-oxo-7-phenylhept-1-en-1-yl)pyrrolidin-1-yl)heptanoate as described above. TLC $R_f$ 0.55 (solvent system: 75:25 v/v ethyl acetate-heptane).

Preparation of methyl 7-((2R)-2-((3S,E)-3-hydroxy-4-methyl-7-phenylhept-1-en-1-yl)-5-oxopyrrolidin-1-yl)heptanoate (Example 2A") and methyl 7-((2R)-2-((3R,E)-3-hydroxy-4-methyl-7-phenyl-hept-1-en-1-yl)-5-oxopyrrolidin-1-yl)heptanoate (Example 2B")

Example 2A"

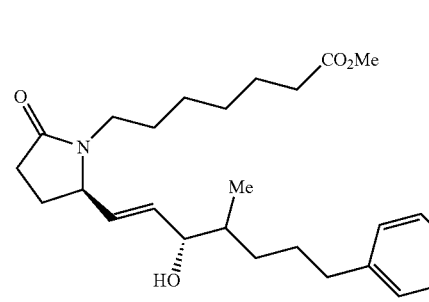

Example 2B"

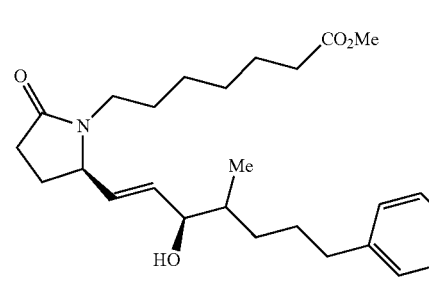

The set of four diastereomers of methyl 7-((2R)-2-((E)-3-hydroxy-4-methyl-7-phenylhept-1-en-1-yl)-5-oxopyrrolidin-1-yl)heptanoate was prepared from methyl 7-((2R)-2-((E)-4-methyl-3-oxo-7-phenylhept-1-en-1-yl)-5-oxopyrrolidin-1-yl)heptanoate in the same manner as described in Example 1A"-1D" above utilizing cerium (III) chloride heptahydrate and sodium borohydride.

From the diastereomeric mixture of four isomers, the epimeric mixtures of Example 2A" and Example 2B" were isolated following separation by prep HPLC.

Gilson Prep instrument; ultraviolet detector at 210 nm; Luna Silica 5µ 250 mm×21.2 mm column; mobile phase of heptane-ethanol (92:8 v/v), 21.2 mL/min.

Example 2A"; a clear oil; HPLC retention time 18 min; TLC R_f 0.38 (solvent system: 4:1 v/v ethyl acetate-heptane); MS (ESI$^+$) m/z 430.2 (M+1).

Example 2B"; a clear oil; HPLC retention time 14.5 min; TLC R_f 0.46 (solvent system: 4:1 v/v ethyl acetate-heptane); MS (ESI$^+$) m/z 430.2 (M+1).

Preparation of 7-((2R)-2-((3S,E)-3-hydroxy-4-methyl-7-phenylhept-1-en-1-yl)-5-oxopyrrolidin-1-yl)heptanoic acid (Example 2C")

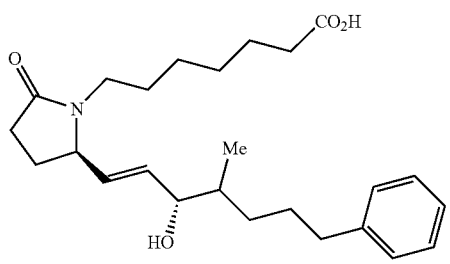 [SMILES: CC(CCCc1ccccc1)[C@H](O)/C=C/[C@H]1CCC(=O)N1CCCCCCC(=O)O]

7-((2R)-2-((3S,E)-3-Hydroxy-4-methyl-7-phenylhept-1-en-1-yl)-5-oxopyrrolidin-1-yl)heptanoic acid was prepared from the corresponding carboxylic ester, Example 2A", in the same manner as 7-((R)-2-((S,E)-3-hydroxy-7-phenylhept-1-en-1-yl)-5-oxopyrrolidin-1-yl)heptanoic acid, Example 1C", to obtain 49 mg (100%) of a clear oil; TLC R 0.22 (solvent system: 85:15:1 v/v ethyl acetate-heptane-acetic acid); MS (ESI$^-$) m/z 414.2 (M−1); $^1$H-NMR (CDCl$_3$) δ 7.18-7.35 (m, 5H), 5.4-5.7 (dd, 2H), 4.1-4.15 (m, 1H), 0.83-2.95 (m, 26H).

Preparation of 7-((2R)-2-((3R,E)-3-hydroxy-4-methyl-7-phenylhept-1-en-1-yl)-5-oxopyrrolidin-1-yl)heptanoic acid (Example 2D")

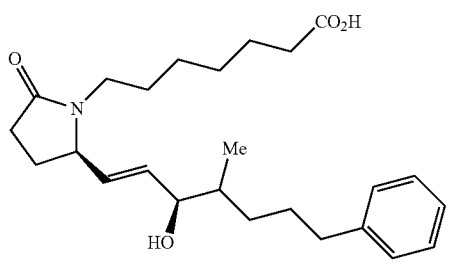 [SMILES: CC(CCCc1ccccc1)[C@@H](O)/C=C/[C@H]1CCC(=O)N1CCCCCCC(=O)O]

7-((2R)-2-((3R,E)-3-Hydroxy-4-methyl-7-phenylhept-1-en-1-yl)-5-oxopyrrolidin-1-yl)heptanoic acid was prepared from the corresponding carboxylic ester, Example 2B", in the same manner as its epimer 7-((2R)-2-((3S,E)-3-hydroxy-4-methyl-7-phenylhept-1-en-1-yl)-5-oxopyrrolidin-1-yl) heptanoic acid (Example 2C"), to obtain 134 mg (100%) of a clear oil; TLC R_f 0.32 (solvent system: 85:15:1 v/v ethyl acetate-heptane-acetic acid); $^1$H-NMR (CD$_3$OD) δ 7.26-7.10 (m, 5H), 5.71 (td, 1H, J=5.86, 15.38 Hz), 5.52-5.44 (m, 1H), 4.18-4.12 (m, 1H), 3.98-3.94 (m, 1H), 3.46 (td, 1H, J=7.69, 13.55 Hz), 2.91 (ddd, J=5.49, 8.15, 13.46 Hz), 2.66-2.53 (m, 2H), 2.43-2.15 (m, 6H), 1.73-1.44 (m, 9H), 1.39-1.23 (m, 4H), 1.18-1.07 (m, 1H), 0.89 (dd, 3H, J=6.77, 10.07 Hz); MS (ESI$^-$) m/z 414.2 (M−1).

Preparation of 7-((R)-2-((3S,4S,E)-3-hydroxy-4-methyl-7-phenylhept-1-en-1-yl)-5-oxopyrrolidin-1-yl)heptanoic acid (Example 2E")

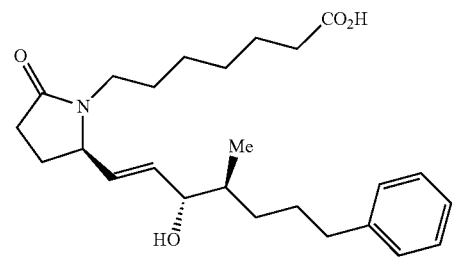 [SMILES: C[C@@H](CCCc1ccccc1)[C@H](O)/C=C/[C@H]1CCC(=O)N1CCCCCCC(=O)O]

The title compound is prepared from (R)-methyl 7-(2-formyl-5-oxopyrrolidin-1-yl)heptanoate with the same sequence of chemical steps used to prepare Example 1A".

Preparation of 7-((R)-2-((3S,4R,E)-3-hydroxy-4-methyl-7-phenylhept-1-en-1-yl)-5-oxopyrrolidin-1-yl)heptanoic acid (Example 2F")

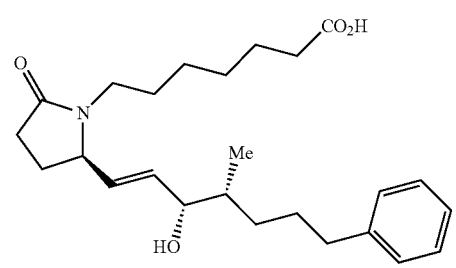

The title compound is prepared from (R)-methyl 7-(2-formyl-5-oxopyrrolidin-1-yl)heptanoate in the manner used to prepare Example 2E" using dimethyl (R)-(−)-(3-methyl-2-oxo-6-phenylhexyl)phosphonate in the Horner-Wadsworth-Emmons step.

Preparation of methyl 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylate (3A") and methyl 5-(3-((2R)-2-((3R,E)-3-hydroxy-4-methyl-7-phenylhept-1-en-1-yl)-5-oxopyrrolidin-1-yl)prop-1-yn-1-yl)thiophene-2-carboxylate (3B")

Example 3A"

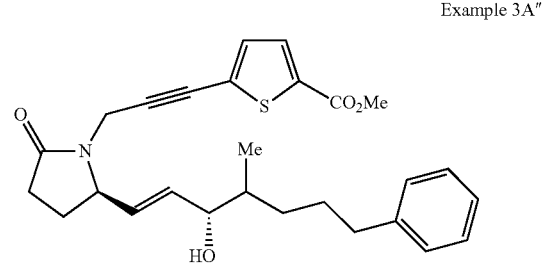

Example 3B''

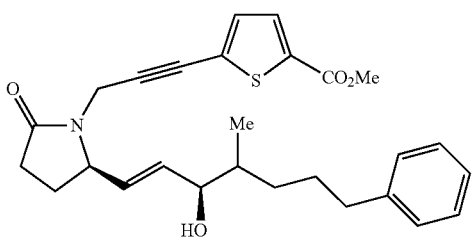

The set of four diastereomers of methyl 5-(3-((2R)-2-((E)-3-hydroxy-4-methyl-7-phenylhept-1-en-1-yl)-5-oxopyrrolidin-1-yl)prop-1-yn-1-yl)thiophene-2-carboxylate was prepared in the same manner as described in Example 2A''-2D'' using (R)-methyl 5-(3-(2-formyl-5-oxopyrrolidin-1-yl)prop-1-yn-1-yl)thiophene-2-carboxylate.

From the diastereomeric mixture of four isomers (85 mg), the epimeric mixtures of Example 3A'' and Example 3B'' were isolated following separation by prep HPLC.

Agilent Semi-Prep instrument; ultraviolet detector at 205 nm; Luna Silica 5μ 250 mm×10 mm column; mobile phase of heptane-ethanol (90:10 v/v).

Example 3A'' (17.1 mg); a clear oil; prep HPLC retention time 17.1-19.5 minutes; $^1$H-NMR (CDCl$_3$) δ 7.6 (d, 1H), 7.3-7.25 (m, 2H), 7.2-7.15 (m, 3H), 7.1 (d, 1H), 5.85-5.75 (m, 1H), 5.55-5.5 (m, 1H), 4.7-4.65 (m, 1H), 4.25-4.2 (m, 1H), 4.1-4.0 (m, 1H), 3.87 (s, 3H) 3.85-3.75 (m, 1H), 2.6 (t, 2H), 2.45-2.25 (m, 3H), 1.75-1.5 (m, 4H), 1.2-1.1 (m, 2H), 0.91 (d, 3H); MS (ESI$^+$) m/z 466.1 (M+1), 488.0 (M+Na).

Example 3B'' (52 mg); a clear oil; prep HPLC retention time 13.8-16.9 minutes; $^1$H-NMR (CDCl$_3$) δ 7.6 (d, 1H), 7.3-7.25 (m, 2H), 7.2-7.15 (m, 3H), 7.1 (d, 1H), 5.85-5.75 (m, 1H), 5.55-5.5 (m, 1H), 4.7-4.65 (m, 1H), 4.25-4.2 (m, 1H), 4.1-4.0 (m, 1H), 3.87 (s, 3H) 3.85-3.75 (m, 1H), 2.6 (t, 2H), 2.45-2.25 (m, 3H), 1.75-1.5 (m, 4H), 1.2-1.1 (m, 2H), 0.91 (d, 3H); MS (ESI$^+$) m/z 466.1 (M+1), 488.0 (M+Na).

Preparation of 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylic acid (Example 3C'')

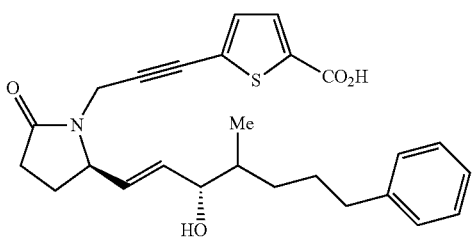 [SMILES: CC(CCCc1ccccc1)[C@H](O)/C=C/[C@H]1CCC(=O)N1CC#Cc1ccc(C(=O)O)s1]

5-(3-((2R)-2-((3S,E)-3-Hydroxy-4-methyl-7-phenylhept-1-en-1-yl)-5-oxopyrrolidin-1-yl)prop-1-yn-1-yl)thiophene-2-carboxylic acid was prepared from the corresponding carboxylic ester, Example 3A'', in the same manner as 7-((R)-2-((S,E)-3-hydroxy-7-phenylhept-1-en-1-yl)-5-oxopyrrolidin-1-yl)heptanoic acid, Example 1C'', to obtain 13.8 mg; TLC R$_f$ 0.40 (solvent system: 96:4:1 v/v dichloromethane-methanol-acetic acid); $^1$H-NMR (CDCl$_3$) δ 7.6 (d, 1H), 7.25-7.15 (m, 2H), 7.1-7.05 (m, 3H), 7.05 (d, 1H), 5.8-5.7 (m, 1H), 5.5-5.4 (m, 1H), 4.65-4.55 (m, 1H), 4.25-4.15 (m, 1H), 4.05-3.95 (m, 1H), 3.8-3.7 (m, 1H), 2.5 (t, 2H), 2.45-2.3 (m, 2H), 2.3-2.15 (m, 1H), 1.75-1.4 (m, 4H), 1.2-1.1 (m, 2H), 0.85 (d, 1.5H) 0.83 (d, 1.5H); MS ((ESI$^+$) m/z 452.1 (M+1) (ESI$^-$) m/z 450.1 (M−1).

Preparation of 5-(3-((2R)-2-((3R,E)-3-hydroxy-4-methyl-7-phenylhept-1-en-1-yl)-5-oxopyrrolidin-1-yl)prop-1-yn-1-yl)thiophene-2-carboxylic acid (Example 3D'')

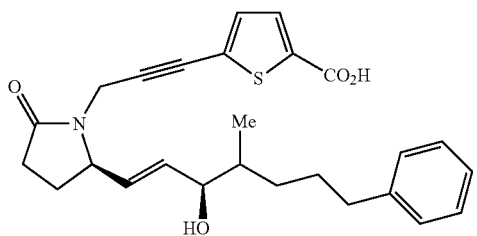 [SMILES: CC(CCCc1ccccc1)[C@@H](O)/C=C/[C@H]1CCC(=O)N1CC#Cc1ccc(C(=O)O)s1]

5-(3-((2R)-2-((3R,E)-3-Hydroxy-4-methyl-7-phenylhept-1-en-1-yl)-5-oxopyrrolidin-1-yl)prop-1-yn-1-yl)thiophene-2-carboxylic acid was prepared from the corresponding carboxylic ester, Example 3B'', in the same manner as its epimer 5-(3-((2R)-2-((3S,E)-3-hydroxy-4-methyl-7-phenylhept-1-en-1-yl)-5-oxopyrrolidin-1-yl)prop-1-yn-1-yl)thiophene-2-carboxylic acid (Example 3C''), to obtain 40.4 mg; TLC R$_f$ 0.40 (solvent system: 96:4:1 v/v dichloromethane-methanol-acetic acid); $^1$H-NMR (CDCl$_3$) δ 7.6 (d, 1H), 7.25-7.15 (m, 2H), 7.1-7.05 (m, 3H), 7.05 (d, 1H), 5.8-5.7 (m, 1H), 5.5-5.4 (m, 1H), 4.65-4.55 (m, 1H), 4.25-4.15 (m, 1H), 4.05-3.95 (m, 1H), 3.8-3.7 (m, 1H), 2.5 (t, 2H), 2.45-2.3 (m, 2H), 2.3-2.15 (m, 1H), 1.75-1.4 (m, 4H), 1.2-1.1 (m, 2H), 0.85 (d, 1.5H) 0.83 (d, 1.5H); MS ((ESI$^+$) nm/z 452.1 (M+1) (ESI$^-$) m/z 450.1 (M−1).

Preparation of methyl 5-(3-((2R)-2-((3S,E)-3-hydroxy-4-methyl-7-phenylhept-1-en-1-yl)-5-oxopyrrolidin-1-yl)propyl)thiophene-2-carboxylate (Example 4A'') and methyl 5-(3-((2R)-2-((3R,E)-3-hydroxy-4-methyl-7-phenylhept-1-en-1-yl)-5-oxopyrrolidin-1-yl)propyl)thiophene-2-carboxylate (Example 4B'')

Example 4A''

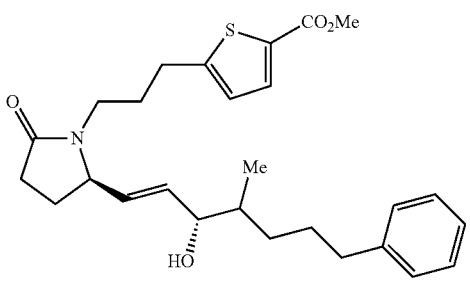

Example 4B″

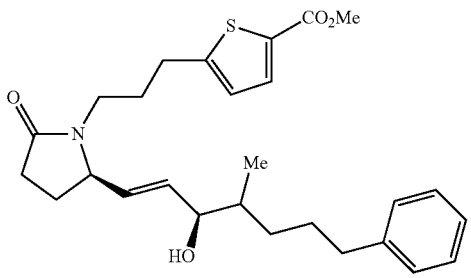

The set of four diastereomers of methyl 5-(3-((2R)-2-((E)-3-hydroxy-4-methyl-7-phenylhept-1-en-1-yl)-5-oxopyrrolidin-1-yl)propyl)thiophene-2-carboxylate was prepared in the same manner as described in Example 2A″-2D″ using (R)-methyl 5-(3-(2-formyl-5-oxopyrrolidin-1-yl)propyl)thiophene-2-carboxylate.

From the diastereomeric mixture of four isomers, the epimeric mixtures of Example 4A″ and Example 4B″ were isolated following separation by prep HPLC.

Agilent Semi-Prep instrument; ultraviolet detector at 205 nm; Luna Silica 5μ 250 mm×10 mm column; mobile phase of heptane-ethanol (90:10 v/v).

Example 4A″ (9.6 mg); a clear oil; prep HPLC retention time 19.0-21.5 minutes; $^1$H-NMR (CDCl$_3$) δ 7.6 (d, 1H), 7.3-7.2 (m, 2H), 7.2-7.1 (m, 3H), 6.8 (d, 1H), 5.65 (dd, 1H), 5.5-5.45 (m, 1H), 4.05-4.0 (m, 2H), 3.85 (s, 3H), 3.6-3.55 (1H, m), 3.0-2.95 (m, 1H), 2.8 (t, 2H), 2.6-2.5 (m, 2H), 2.5-2.3 (m, 2H), 2.3-2.1 (m, 1H), 1.9-1.8 (m, 2H), 1.7-1.4 (m, 5H), 1.2-1.1 (m, 1H), 0.86 (d, 1.5H), 0.85 (d, 1.5H); MS (ESI$^+$) m/z 492.1 (M+Na)

Example 4B″ (32.6 mg); a clear oil; prep HPLC retention time 15.6-18.0 minutes; $^1$H-NMR (CDCl$_3$) δ 7.6 (d, 1H), 7.3-7.2 (m, 2H), 7.2-7.1 (m, 3H), 6.8 (d, 1H), 5.65 (dd, 1H), 5.5-5.45 (m, 1H), 4.05-4.0 (m, 2H), 3.85 (s, 3H), 3.6-3.55 (1H, m), 3.0-2.95 (m, 1H), 2.8 (t, 2H), 2.6-2.5 (m, 2H), 2.5-2.3 (m, 2H), 2.3-2.1 (m, 1H), 1.9-1.8 (m, 2H), 1.7-1.4 (m, 5H), 1.2-1.1 (m, 1H), 0.86 (d, 1.5H), 0.85 (d, 1.5H); MS (ESI$^+$) m/z 492.1 (M+Na)

5-(3-((2R)-2-((3S,E)-3-hydroxy-4-methyl-7-phenyl-hept-1-en-1-yl)-5-oxopyrrolidin-1-yl)propyl)thio-phene-2-carboxylic acid (Example 4C″)

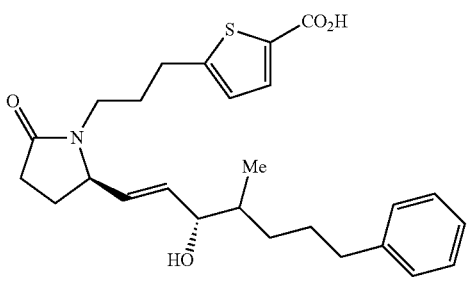

5-(3-((2R)-2-((3S,E)-3-Hydroxy-4-methyl-7-phenylhept-1-en-1-yl)-5-oxopyrrolidin-1-yl)propyl)thiophene-2-carboxylic acid was prepared from the corresponding carboxylic ester, Example 4A″, in the same manner as 7-((R)-2-((S,E)-3-hydroxy-7-phenylhept-1-en-1-yl)-5-oxopyrrolidin-1-yl)heptanoic acid, Example 1C″, to obtain 7.8 mg as a colorless oil; TLC R$_f$ 0.40 (solvent system: 96:4:1 v/v dichloromethane-methanol-acetic acid); $^1$H-NMR (CDCl$_3$) δ 7.6 (d, 1H), 7.3-7.2 (m, 2H), 7.2-7.1 (m, 3H), 6.75 (d, 1H), 5.6 (dd, 1H), 5.45-5.35 (m, 1H), 4.1-3.9 (m, 2H), 3.55-3.45 (1H, m), 2.95-2.9 (m, 1H), 2.75 (t, 2H), 2.6-2.45 (m, 2H), 2.45-2.3 (m, 2H), 2.3-2.1 (m, 1H), 1.85-1.75 (m, 2H), 1.65-1.35 (m, 5H), 1.2-1.0 (m, 1H), 0.80 (d, 1.5H), 0.79 (d, 1.5H); MS (ESI$^-$) m/z 454.1 (M−1).

5-(3-((2R)-2-((3R,E)-3-hydroxy-4-methyl-7-phenyl-hept-1-en-1-yl)-5-oxopyrrolidin-1-yl)propyl)thio-phene-2-carboxylic acid (Example 4D″)

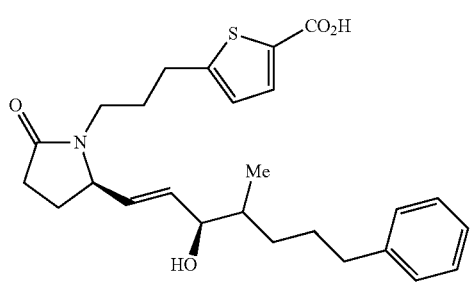 [SMILES: CC(CCCc1ccccc1)[C@@H](O)/C=C/[C@H]1CCC(=O)N1CCCc1ccc(C(=O)O)s1]

5-(3-((2R)-2-((3R,E)-3-Hydroxy-4-methyl-7-phenylhept-1-en-1-yl)-5-oxopyrrolidin-1-yl)propyl)thiophene-2-carboxylic acid was prepared from the corresponding carboxylic ester, Example 4B″, in the same manner as its epimer 5-(3-((2R)-2-((3S,E)-3-hydroxy-4-methyl-7-phenylhept-1-en-1-yl)-5-oxopyrrolidin-1-yl)propyl)thiophene-2-carboxylic acid (Example 4C″), to obtain 26.8 mg as a colorless oil; TLC R$_f$ 0.40 (solvent system: 96:4:1 v/v dichloromethane-methanol-acetic acid); $^1$H-NMR (CDCl$_3$) δ 7.6 (d, 1H), 7.3-7.2 (m, 2H), 7.2-7.1 (m, 3H), 6.75 (d, 1H), 5.6 (dd, 1H), 5.45-5.35 (m, 1H), 4.1-3.9 (m, 2H), 3.55-3.45 (1H, m), 2.95-2.9 (m, 1H), 2.75 (t, 2H), 2.6-2.45 (m, 2H), 2.45-2.3 (m, 2H), 2.3-2.1 (m, 1H), 1.85-1.75 (m, 2H), 1.65-1.35 (m, 5H), 1.2-1.0 (m, 1H), 0.80 (d, 1.5H), 0.79 (d, 1.5H); MS (ESI$^-$) m/z 454.1 (M−1).

5-(3-((R)-2-((3S,4S,E)-3-hydroxy-4-methyl-7-phenylhept-1-en-1-yl)-5-oxopyrrolidin-1-yl)propyl)thio-phene-2-carboxylic acid (Example 4E″)

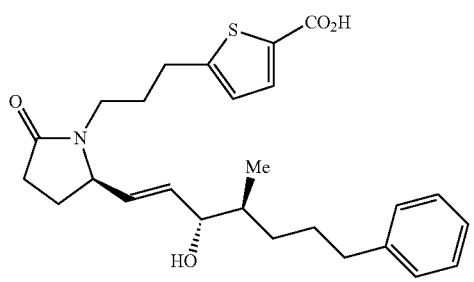 [SMILES: C[C@@H](CCCc1ccccc1)[C@H](O)/C=C/[C@H]1CCC(=O)N1CCCc1ccc(C(=O)O)s1]

The title compound is prepared from (R)-methyl 5-(3-(2-formyl-5-oxopyrrolidin-1-yl)propyl)thiophene-2-carboxylate with the same sequence of chemical steps used to prepare Example 1E″.

5-(3-((R)-2-((3S,4R,E)-3-hydroxy-4-methyl-7-phenylhept-1-en-1-yl)-5-oxopyrrolidin-1-yl)propyl)thiophene-2-carboxylic acid (Example 4F")

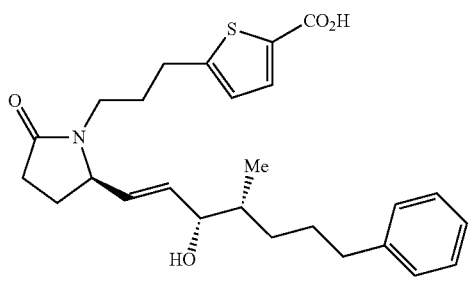 [SMILES: C[C@H](CCCc1ccccc1)[C@H](O)/C=C/[C@H]1CCC(=O)N1CCCc1ccc(C(=O)O)s1]

The title compound is prepared from (R)-methyl 5-(3-(2-(formyl-5-oxopyrrolidin-1-yl)propyl)thiophene-2-carboxylate with the same sequence of chemical steps used to prepare Example 1F".

Preparation of 5-(3-((R)-2-((3S,4S,E)-3-hydroxy-4-methyl-6-phenylhex-1-en-1-yl)-5-oxopyrrolidin-1-yl)propyl)thiophene-2-carboxylic acid (Example 5A") and 5-(3-((R)-2-((3R,4S,E)-3-hydroxy-4-methyl-6-phenylhex-1-en-1-yl)-5-oxopyrrolidin-1-yl)propyl)thiophene-2-carboxylic acid (Example 5B")

Example 5A"

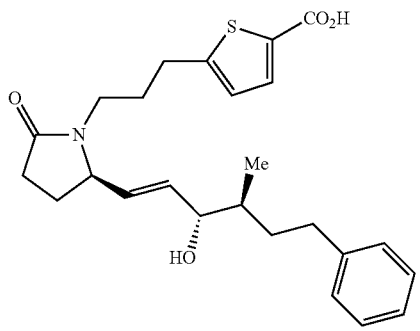

Example 5B"

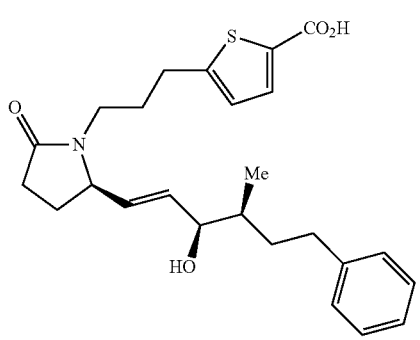

The title compounds are prepared according to the methods used to prepare Examples 1C" and 1D".

Preparation of 5-(3-((R)-2-((3S,4R,E)-3-hydroxy-4-methyl-6-phenylhex-1-en-1-yl)-5-oxopyrrolidin-1-yl)propyl)thiophene-2-carboxylic acid (Example 5C") and 5-(3-((R)-2-((3R,4R,E)-3-hydroxy-4-methyl-6-phenylhex-1-en-1-yl)-5-oxopyrrolidin-1-yl)propyl)thiophene-2-carboxylic acid (Example 5D")

Example 5C"

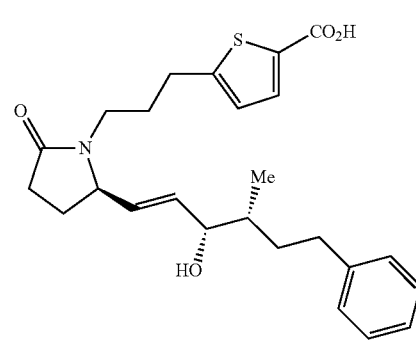

Example 5D"

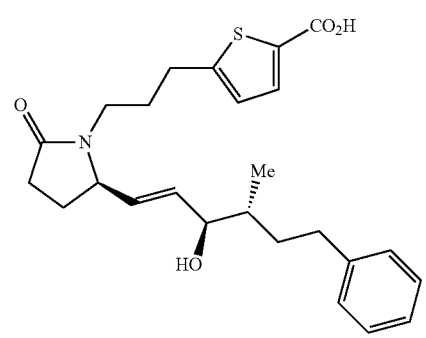

The title compounds are prepared according to the methods used to prepare Examples 1C" and 1D".

Preparation of 5-(3-((R)-2-((3S,4S,E)-3-hydroxy-4-methyl-8-phenyloct-1-en-1-yl)-5-oxopyrrolidin-1-yl)propyl)thiophene-2-carboxylic acid (Example 6A") and 5-(3-((R)-2-((3R,4S,E)-3-hydroxy-4-methyl-8-phenyloct-1-en-1-yl)-5-oxopyrrolidin-1-yl)propyl)thiophene-2-carboxylic acid (Example 6B")

Example 6A"

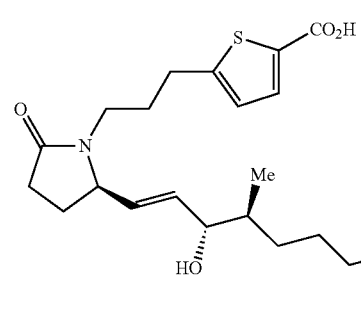

Example 6B″

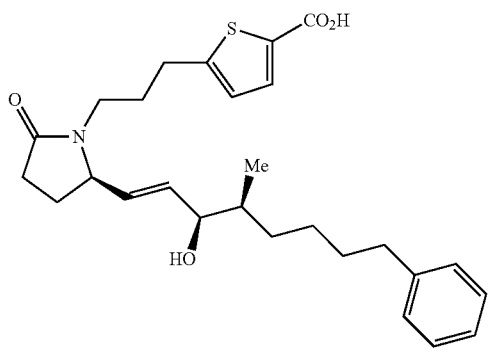

The title compounds are prepared according to the methods used to prepare Examples 1C″ and 1D″.

Preparation of 5-(3-((R)-2-((3S,4R,E)-3-hydroxy-4-methyl-8-phenyloct-1-en-1-yl)-5-oxopyrrolidin-1-yl)propyl)thiophene-2-carboxylic acid (Example 6C″) and 5-(3-((R)-2-((3R,4R,E)-3-hydroxy-4-methyl-8-phenyloct-1-en-1-yl)-5-oxopyrrolidin-1-yl)propyl)thiophene-2-carboxylic acid (Example 6D″)

Example 6C″

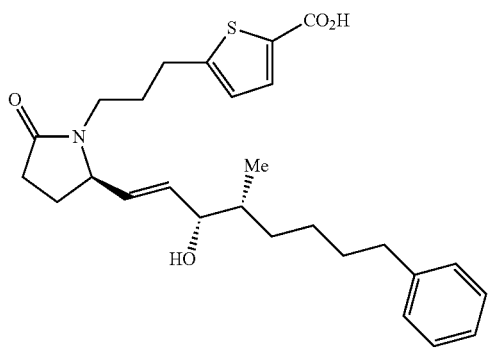

Example 6D″

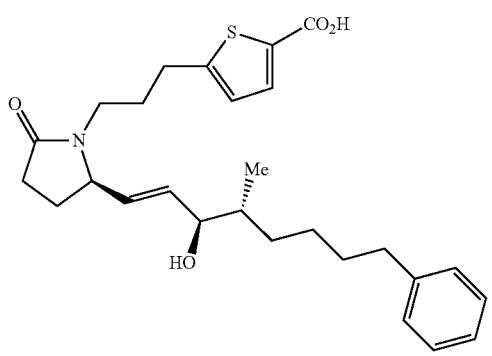

The title compounds are prepared according to the methods used to prepare Examples 1C″ and 1D″.

Preparation of 5-(3-((R)-2-((3S,4S,E)-3-hydroxy-4-methyl-9-phenylnon-1-en-1-yl)-5-oxopyrrolidin-1-yl)propyl)thiophene-2-carboxylic acid (Example 7A″) and 5-(3-((R)-2-((3R,4S,E)-3-hydroxy-4-methyl-9-phenylnon-1-en-1-yl)-5-oxopyrrolidin-1-yl)propyl)thiophene-2-carboxylic acid (Example 7B″)

Example 7A″

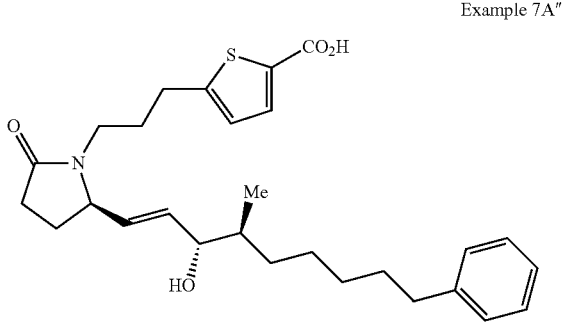

Example 7B″

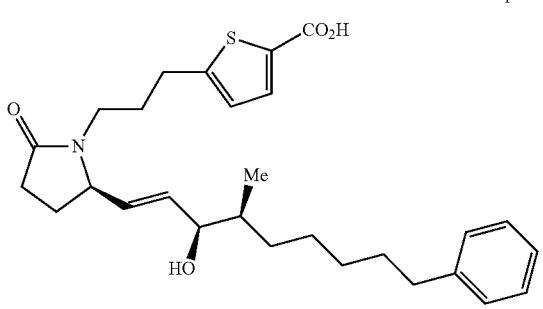

The title compounds are prepared according to the methods used to prepare Examples 1C″ and 1D″.

Preparation of 5-(3-((R)-2-((3S,4R,E)-3-hydroxy-4-methyl-9-phenyloctnon-1-en-1-yl)-5-oxopyrrolidin-1-yl)propyl)thiophene-2-carboxylic acid (Example 7C″) and 5-(3-((R)-2-((3R,4R,E)-3-hydroxy-4-methyl-9-phenylnon-1-en-1-yl)-5-oxopyrrolidin-1-yl)propyl)thiophene-2-carboxylic acid (Example 7D″)

Example 7C″

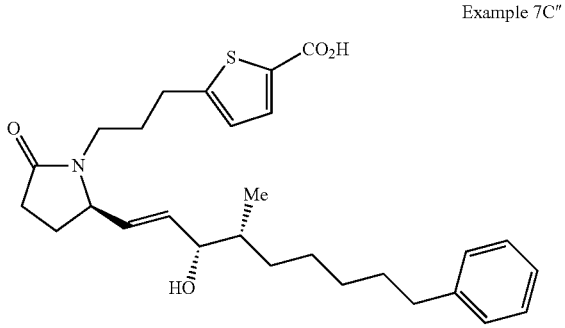

Example 7D″

The title compounds are prepared according to the methods used to prepare Examples 1C″ and 1D″.

Example 92

Radioligand Binding Assay for the Evaluation of the Affinity of Compounds for the Agonist Site of the Human Prostanoid EP4 Receptor in Transfected HEK-293 Cells Assay Volume and Format:

200 µl in 96-well plate

Cell membrane homogenates (20 µg protein) are incubated for 120 min at 22° C. with 0.5 nM [$^3$H]PGE$_2$ in the absence or presence of the test compound in a buffer containing 10 mM MES/KOH (pH 6.0), 10 mM MgCl$_2$ and 1 mM EDTA.

Nonspecific binding is determined in the presence of 10 µM PGE2.

Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The standard reference compound is PGE$_2$, which is tested in each experiment at several concentrations to obtain a competition curve from which its IC$_{50}$ is calculated.

Example 93

Functional Cellular Assays (STEP Plate Format)

Both SEAP activity assay and cAMP level assay for EP$_2$ or EP$_4$ agonist were performed on EP$_2$/EP$_4$ STEP (Surface Transfection and Expression Protocol) plates (from Originus®) which are coated with both rat EP$_2$ or EP$_4$ receptor and secreted alkaline phosphatase (SEAP) reporter constructs. Cells grown on the STEP complex will express EP$_2$ or EP$_4$ at the cell surface. Binding of agonists to EP$_2$ or EP$_4$ initiates a signal transduction cascade results in a transient increase in cAMP and an increase in expression of SEAP which is secreted into the cell culture media. cAMP levels were then measured with an ELISA assay and SEAP activity was measured with a luminescence-based alkaline phosphatase substrate.

Procedure of SEAP Activity Assay for EP2/EP4 Agonist

1. Seed cells on an EP$_2$ or EP$_4$ STEP plate at a density of 40,000-80,000 cells/well in 200 µl of reduced serum medium containing 0.5% FBS. Place the plate in a 37° C. incubator with 5% CO$_2$ and incubate overnight.

2. After 16-18 hours of incubation, aspirate the culture media from each well.

3. Add 200 µl of culture medium containing different concentration of test compounds to the assigned wells. For each test compound, at least 8 concentrations starting at highest 10 µM and lowest 0.01 pM were tested. In addition each concentration had triplicates. A PGE$_2$ curve (concentrations from lowest to highest, 0 pM, 0.384 pM, 1.92 pM, 9.6 pM, 48 pM, 240 pM, 1200 pM, and 6000 pM) was always run in parallel with test compounds.

4. After 6-8 hours of stimulation with test compounds and PGE$_2$, 10 µl of culture media from each well was transferred to a corresponding well of a 96-well solid black plate. Cover the plate with the lid.

5. Inactivate the endogenous alkaline phosphatase by heating the samples at 65° C. for 30 minutes.

6. Add 50 µl of luminescence-based alkaline phosphatase substrate (Michigan Diagnostics, LLC, Cat # SAP450101) to each well.

7. Measure the SEAP activity by reading the luminescent signal from each well.

8. The data was analyzed and the EC$_{50}$ for PGE$_2$ and each test compound was calculated using GraphPad Prism 5.

Procedure of cAMP Assay for EP2/EP4 Agonist

1. Seed cells on an EP$_2$ or EP$_4$ STEP plate at a density of 40,000-80,000 cells/well in 200 µL of reduced serum medium containing 0.5% FBS. Place the plate in a 37° C. incubator with 5% CO$_2$ and incubate overnight.

2. After 16-18 hours of incubation, aspirate the culture media from each well.

3. Add 200 µl of culture medium containing 500 µM IBMX (an inhibitor of cAMP phosphodiesterase) and different concentration of test compounds to the assigned wells. For each test compound, at least 8 concentrations starting at highest 10 µM and lowest 0.01 pM were tested. In addition each concentration had triplicates. A PGE$_2$ curve (concentrations from lowest to highest, 0 pM, 0.384 pM, 1.92 pM, 9.6 pM, 48 pM, 240 pM, 1200 pM, and 6000 pM) was always run in parallel with test compounds.

4. Incubate the cells in a cell culture incubator for 30 minutes.

5. Centrifuge the plate at 1,000×rpm for 10 minutes.

6. Aspirate the supernatant.

7. Add 100 µL of EIA assay buffer to each well and put the plate with the lid in a −80° C. freezer. Freeze the sample in the −80° C. for at least one hour.

8. Take the plate out from the −80° C. freezer and leave it at room temperature to thaw completely.

9. Centrifuge the plate at 1,000×rpm for 10 minutes.

10. Pick up 50 µl of supernatant from each well for cAMP level measurement, using an ELISA assay kit from Cayman chemical, Item #581001.

11. The data was analyzed and the EC$_{50}$ for PGE$_2$ and each test compound was calculated using GraphPad Prism 5.

Specificity of EP$_2$/EP$_4$ Agonist on the Receptors

Compounds demonstrating potency in SEAP or cAMP functional assays were confirmed for receptor agonist specificity by incubation of the cells with the compound together with an EP$_2$ specific antagonist AH-6809 or an EP$_4$ specific antagonist L-161,982. Compounds that showed agonist activity for either EP$_2$ or EP$_4$ are specific if the stimulation effect was diminished when incubated together with their receptor specific antagonist.

| Example No. | hEP$_4$ receptor binding (nM) | | STEP cell functional assay EC$_{50}$ (nM) | | |
|---|---|---|---|---|---|
| | IC$_{50}$ | Ki | cAMP/EP$_4$ | SEAP/EP$_4$ | SEAP/EP$_2$ |
| PGE$_2$ | 0.38 ± 0.07 | 0.14 ± 0.02 | 0.48 ± 0.36 | 0.05 ± 0.03 | 59 ± 17 |
| 1F | 1.2 | 0.44 | 0.15 | 0.059 | |
| 2C | 1.3 | 0.49 | 0.24 ± 0.08 | 0.038 ± 0.037 | >1000 |
| 6D | 2.4 | 0.89 | 0.023 ± 0.019 | <0.001 | >1000 |
| 9C | 0.57 | 0.21 | 0.37 | 0.059 | 205 ± 124 |
| 10C | 4.9 | 1.8 | 1.10 | 0.010 | |
| 12D | 0.32 | 0.12 | 0.047 | 0.035 | 1,630 |
| 21C | 0.22 | 0.082 | 0.61 | 0.075 | 1,960 |
| 24D | 3.3 | 1.2 | 0.73 ± 0.31 | 0.11 | 763 |
| 28C | 0.74 | 0.28 | 0.010 ± 0.021 | | 148 ± 5 |
| 28D | | | 5.68 | | |
| 28E | | | 50.8 | | |
| 28F | | | >1000 | | |
| 28G | | | 0.016 | | 65 |
| 28H | | | 3.15 | | |
| 28C-H2 | | | 0.0029 ± 0.0008 | | |
| 33C | 0.28 | 0.10 | 0.079 | 0.063 | 326 |
| 35C | | | 62 | | |
| 36A | | | 5.02 | | |
| 36B | | | >1,000 | | |
| 36C | | | 0.038 | | 1,000 |
| 37A | | | 8.09 | | |
| 37C | | | 0.15 | | |
| 37D | | | 198 | | 743 |
| 38A | | | >1,000 | | |
| 38B | | | >1,000 | | |
| 38C | | | 1.4 × 10$^{-7}$ | | 157 |
| 38D | | | 0.37 | | >10,000 |
| 39A | | | >1,000 | | |
| 39B | | | >1,000 | | |
| 39C | | | 2.7 × 10$^{-6}$ | | 1,020 |
| 39D | | | 0.059 | | 79,000 |
| 1C' | 86% @100 | | | 0.67 | 760 |
| 1D' | 11% @100 | | | 4.82 | >10,000 |
| 1E' | 3.9 | 1.5 | 2.98 | 0.57 | 800 |
| 1F' | 18 | 6.9 | 5.79 | | 184 |
| 2C' | 4.0 | 1.5 | | 0.064 | 905 |
| 2D' | | | | 0.145 | 1,420 |
| 2E' | 3.0 | 1.1 | 0.96 ± 0.46 | 0.19 ± 0.07 | >1,000 |
| 2F' | | | | 1.06 | |
| 3A' | | | | 8.64 | 2,485 |
| 3B' | | | | 223.1 | >10,000 |
| 3C' | | | | 0.085 | 2,260 |
| 3D' | | | | 29.03 | >10,000 |
| 4C' | | | | 2.49 | 830 |
| 5A' | | | | 77.7 | >10,000 |
| 5B' | | | | 41.5 | >5,000 |
| 5C' | | | | 110.9 | >1,000 |
| 5D' | | | | 46.8 | >5,000 |
| 6A' | | | | 6.71 | >3,000 |
| 6B' | | | | | >2,000 |
| 6C' | | | | 4.73 | >1,000 |
| 6D' | | | | 4.79 | >1,000 |
| 7C' | | | | 22.3 | >1,000 |
| 8A' | | | | 6.74 | 364 |
| 8B' | | | | 1,640 | |
| 8C' | 1.3 | 0.47 | | 0.19 | 120 |
| 8D' | | | | 13.4 | 1,130 |
| 9C' | 0.67 | 0.25 | 0.31 | 0.020 ± 0.017 | >1,000 |
| 11C' | | | | 0.054 | 2,960 |
| 11D' | | | | 3.51 | 1,750 |
| 12C' | | | | 2,290 | >10,000 |
| 12D' | | | | >10,000 | >10,000 |
| 13C' | | | | 18.3 | >10,000 |
| 14C' | | | | >100 | >10,000 |
| 15C' | | | | 947 | >10,000 |
| 15D' | | | | 1,600 | >10,000 |
| 16C' | | | | 67.2 | >10,000 |
| 16D' | | | | 1,200 | >10,000 |
| 17D' | 6.1 | 2.3 | 1.54 | 0.32 | 5,300 |
| 17F' | | | | 0.091 | >10,000 |
| 17G' | | | | 18.4 | >10,000 |
| 18C' | | | | <0.01 | >10,000 |
| 18D' | | | | 2.03 | >10,000 |
| 1C" | 10 | 3.8 | 1.37 | 0.014 | >1,000 |
| 2C" | 5.7 | 2.1 | 0.007 | 0.001 | >1,000 |

-continued

| Example No. | hEP$_4$ receptor binding (nM) | | STEP cell functional assay EC$_{50}$ (nM) | | |
|---|---|---|---|---|---|
| | IC$_{50}$ | Ki | cAMP/EP$_4$ | SEAP/EP$_4$ | SEAP/EP$_2$ |
| 3C" | | | | 0.019 | >10,000 |
| 3D" | | | | 31.5 | >10,000 |
| 4C" | | | | 0.003 | 2,280 |

Example 94

Accelerated Healing of a Calvarial Bone Defect by Example 2C

The rat calvarial defect model is a widely used model through which the ability of a treatment agent to induce bone formation is assessed (Aghaloo et al., The effect of NELL1 and bone morphogenetic protein-2 on calvarial bone regeneration, J. Oral Maxillofac. Surg. 2010: 68:300-308; Mark et al., Repair of calvarial nonunions by osteogenin, a bone-inductive protein, Plast. Reconstr. Surg. 1990: 86:623-30).

Bone defects are created by removal of bone from the cranium of female Sprague Dawley rats by a bone trephine (cranial defect). Cranial defects are 2.6 mm in diameter and the cranium approximately 1 mm thick. A matrix of approximately 2 mm thickness is applied to the defect. Thus the dosing volume for each defect is calculated as π*r$^2$*matrix thickness=3.14*1.3$^2$*2=10.61 µl and rounded to 11 µl for purposes of dose calculation.

EXAMPLE 2C is delivered set inside calcium phosphate cement that, after loading with drug and setting, is ground to a fine powder and suspended in demineralized bone matrix at a ratio of 1:8 (weight/volume). EXAMPLE 2C is tested at seven doses with five rats in each group. These are 3, 10, 30, 100 and 300 µg/ml and 1 and 3 mg/ml. A negative control group treated with dosing matrix containing no drug (Vehicle) as well as a positive control group treated with 50 µg/ml recombinant human bone morphogenetic protein 2 (BMP-2) are also included in the study.

Calcium Phosphate cement powders may be combinations of α-tri-Calcium phosphate, β-tri-Calcium phosphate and hydroxyapatite; combinations of Dicalcium Phosphate and Tetracalcium Phosphate; or a commercially available calcium phosphate cement. Commercially available Human demineralized bone matrix, Puros Demineralized Bone Matrix Putty manufactured by RTI Biologics (Alachua, Fla.) using the Urist & Dowell method, is used in the studies described. Demineralized bone matrix can also be made by the method described by Urist & Dowell (Inductive Substratum for Osteogenesis in Pellets of Particulate Bone Matrix, Clin. Orthop. Relat. Res., 1968, 61, 61-78.)

Dosing solutions are made from a 5 mg/ml EXAMPLE 2C stock which is made by dissolving 1.5 mg of neat EXAMPLE 2C in 300 µl of 100% ethanol.

The dosing volume of a single defect is 11 µl. Thus for each group of five rats the total treatment volume is 55 µl. The ratio of calcium phosphate cement to volume is 1:8 thus for each group of five rats 6.8 mg of calcium phosphate cement was used.

The dosing solutions were made up by adding 5 mg/ml Example 2C dissolved in ethanol onto 6.8 mg of calcium phosphate cement using the volumes shown in the table below. The 10 µg/ml dose and the 3 µg/ml dose were not made directly from the 5 mg/ml stock but were made with 5.5 µl of a further 1:50 dilution of the stock and 3.3 µl of a 1:100 stock dilution respectively.

| | mg/defect =Dose * (11/1000) | mg/group =(mg/defect) * 5 | µl of 5 mg/ml stock/group =(mg/group)/ (5/1000) |
|---|---|---|---|
| Vehicle | 0 | 0 | 0 |
| BMP-2 | 0 | 0 | 0 |
| 3 mg/ml | 0.033 | 0.165 | 33 |
| 1 mg/ml | 0.011 | 0.055 | 11 |
| 300 µg/ml | 0.0033 | 0.0165 | 3.3 |
| 100 µg/ml | 0.0011 | 0.0055 | 1.1 |
| 30 µg/ml | 0.00033 | 0.00165 | 0.33 |
| 10 µg/ml | 0.00011 | 0.00055 | 5.5 µl of 1:50 stock dilution in ethanol |
| 3 µg/ml | 0.000033 | 0.000165 | 3.3 µl of 1:100 stock dilution in ethanol |

After the ethanol has been vented off, the cement is wetted with a setting solution and mixed thoroughly for 1 minute as the cement begins to set. Calcium phosphate cement containing no Example 2C is also made up for the Vehicle and BMP-2 groups. The cement-drug mixture is allowed to set overnight at room temperature before being ground to a fine powder in a mortar and pestle.

Following grinding the cement is added to 55 µl of demineralized bone matrix (DBM) and thoroughly mixed using two spatulas. The cement-DBM mix is rolled into a single length of material of equal thickness and using a ruler as a guide cut into five equal length pieces. The dosing matrix is placed in a test subject within four hours of mixing the cement with the DBM.

Immediately after creation the bone defect is filled with dosing matrix containing either no drug, 50 µg/ml BMP-2 or a defined concentration of Example 2C. The operation area is closed and sutured and the animal allowed to recover. Eight weeks after the beginning of treatment each rat is anaesthetized with isoflurane and the defect area is imaged using a cone beam dental CT scanner (Vatech Pax-Duo3D).

The area measured each week is compared to that of the first week and the degree of repair calculated by the following formula:

(original area−current area)/original area*100

The mean repair for each group after eight weeks of treatment is shown in the FIG. 1.

Example 95

Accelerated Healing of a Calvarial Bone Defect by Example 2E'

Dosing solutions are made from a 10 mg/ml Example 2E' stock which is made by dissolving 2.07 mg of neat Example 2E' in 207 µl of 100% ethanol.

The dosing volume of a single defect is 11 µl. Thus for each group of five rats the total treatment volume is 55 µl. The ratio of calcium phosphate cement to volume is 1:8 thus for each group of five rats 6.8 mg of calcium phosphate cement was used.

The dosing solution for Example 2E' was made by adding 18 μL of the 5 mg/ml stock to 6.8 mg of calcium phosphate cement powder. The Vehicle dosing solution was made by adding 18 μl of ethanol containing no Example 2E' to 6.8 mg of calcium phosphate cement powder.

After the ethanol had been vented off, the cement was wetted with a setting solution and mixed thoroughly for 1 minute as the cement begins to set. The cement was allowed to set overnight at room temperature before being ground to a fine powder in a mortar and pestle.

Following grinding the cement was added to 55 μl of demineralized bone matrix (DBM) and thoroughly mixed using two spatulas. The cement-DBM mix was rolled into a single length of material of equal thickness and using a ruler as a guide cut into five equal length pieces. The dosing matrix was placed in a test subject within four hours of mixing the cement with the DBM.

Immediately after creation the bone defect was filled with dosing matrix containing no drug (Vehicle) or 3 mg/ml of Example 2E'. The operation area was closed and sutured and the animal was allowed to recover. Eight weeks after the beginning of treatment each rat was anaesthetized with isoflurane and the defect area was imaged using a cone beam dental CT scanner (Vatech Pax-Duo3D).

The area measured at eight weeks was compared to the area of the original defect and the degree of repair calculated by the following formula:

(original area−current area)/original area*100

Figure 2:
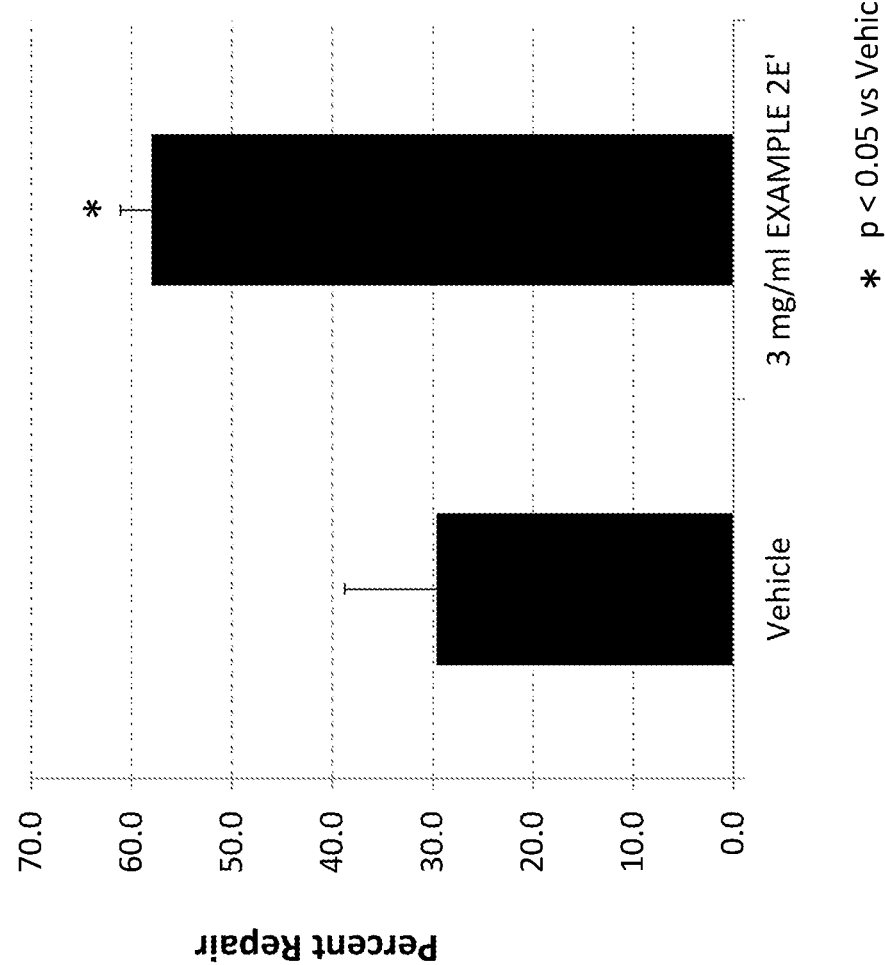
FIG. 2 depicts data showing the effect of Compound 2E' on stimulation of bone growth in the rat calvarial defect model using a demineralized bone matrix putty.

The mean repair for each group after eight weeks of treatment is shown in FIG. 2.

The above description of the examples and embodiments of the invention is merely exemplary in nature and, thus, variations thereof are not to be regarded as a departure from the spirit and scope of the invention.

Example 96

Accelerated Healing of a Calvarial Bone Defect by Example 2E' Loaded into Intact Demineralized Bone Matrix.

Bone defects are created by removal of bone from the cranium of female Sprague Dawley rats by a bone trephine (cranial defect). Cranial defects are 5.0 mm in diameter and the cranium approximately 1 mm thick.

EXAMPLE 2E' is delivered inside calcium phosphate cement that, after loading with drug set inside three voids each of approximately 1.0 mm in diameter drilled into a solid demineralized bone matrix circular block of 5.0 mm in diameter and 1 mm thickness. EXAMPLE 2E' is tested at 10 mg/gm of cement. A negative control group treated with dosing matrix containing no drug (Vehicle) is also included in the study.

Dosing solutions are made from a 5 mg/ml EXAMPLE 2E' stock which is made by dissolving 2.08 mg of neat EXAMPLE 2E' in 416 μl of 100% ethanol.

The volume of each dosing void is $\pi*r^2*$matrix thickness=$3.14*0.5^2*1=0.8$ μl. Thus a 5 mm solid demineralized matrix with three voids filled with cement contains 2.4 μl of loading cement. The cement that is used weighs 107 mg for 100 μl volume. Thus 2.4 ul of volume is occupied by 2.6 mg of cement. A 10 mg/gm dosing cement provides 26 ug of EXAMPLE 2E' for each 5 mm intact demineralized bone matrix block.

The dosing solution is made up by adding 30 μl of 5 mg/ml EXAMPLE 2E' dissolved in ethanol onto 15 mg of calcium phosphate cement.

After the ethanol has been vented off, the cement is wetted with a setting solution and mixed thoroughly for 1 minute as the cement begins to set. Calcium phosphate cement containing no EXAMPLE 2E' is also made up for the Vehicle group. The cement-drug mixture is transferred to the demineralized bone matrix block and mechanically inserted into the voids using a spatula. Once the voids have been filled with cement any surplus cement is removed from the demineralized bone matrix by gentle scraping of the surface. The cement-drug mixture is allowed to set overnight inside the demineralized bone matrix at 4° C. in a water saturated atmosphere.

Following setting the drug-cement loaded demineralized bone matrix is stored at 4° C. in a water saturated atmosphere until it is implanted into a recipient rat within 5 days.

Immediately after creation the bone defect is filled with intact demineralized bone matrix. The defect is imaged using a cone beam dental CT scanner (Vatech Pax-Duo3D). The operation area is closed and sutured and the animal allowed to recover. Four weeks after the beginning of treatment each rat is anaesthetized with isoflurane and the defect area is imaged again.

The area measured each week is compared to that of the first week and the degree of repair calculated by the following formula:

(original area−current area)/original area*100

Figure 4:
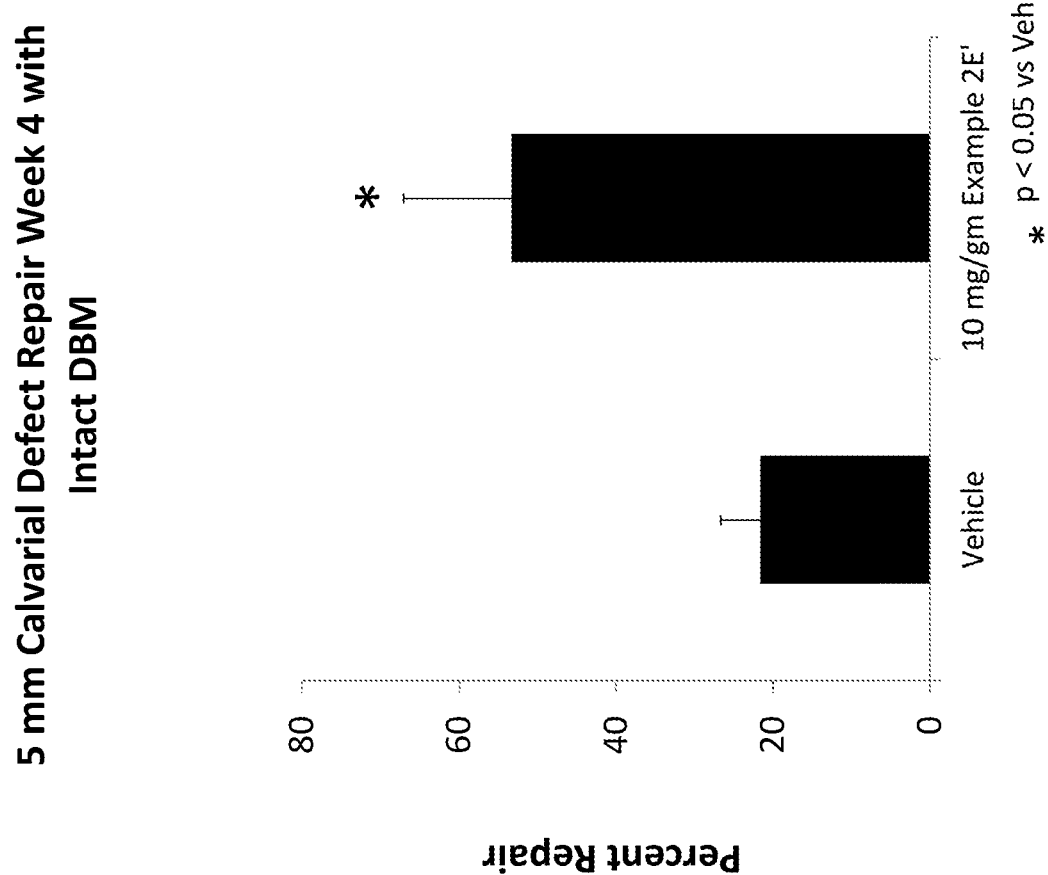
FIG. 4 depicts the effect of Compound 2E' on stimulation of bone growth in the rat calvarial defect model using intact demineralized bone matrix.

The mean repair for both groups after four weeks of treatment is shown in FIG. 4.

Example 97

Increased Bone Density of Osteoporotic Femur Treated by Example 2E'

Dosing solutions are made from a 5 mg/ml Example 2E' stock which is made by dissolving 2.08 mg of neat Example 2E' in 416 μl of 100% ethanol.

The dosing solution for Example 2E' was made by adding 44.4 μL of the 5 mg/ml stock to 22.2 mg of calcium phosphate cement powder. The Vehicle dosing solution was made by adding 50.4 μl of ethanol containing no Example 2E' to 25.2 mg of calcium phosphate cement powder.

After the ethanol has been vented off, the cement is wetted with a setting solution and mixed thoroughly for 1 minute as the cement begins to set. The cement is separated into five aliquots and placed on a glass microscope slide. A second microscope slide separated by 1 mm spacer is placed on the slide containing the drug-cement aliquots and the cement allowed to set between the glass slides overnight.

The cement-drug blocks are stored at room temperature until insertion into a recipient animal with one week.

The ovaries of four month old Female Sprague Dawley rats are removed and the animal allowed to recover. Eight months after removal of the ovaries, the right femur is exposed and a 1 mm osteotomy drilled mid shaft from the anterior surface of the femur through to the bone marrow cavity.

The thickness of the femur is approximately 1 mm. Thus the dosing volume for each osteotomy is $\pi*r^2*$bone thickness=$3.14*0.5^2*1=0.8$ μl Immediately after creation of the osteotomy a dosing cement block is trimmed with a scalpel into a cylinder of 1 mm diameter and 1 mm thickness. The cement contains either no drug (Vehicle) or 10 mg/gm of Example 2E'. The operation area is closed and sutured. The femur is imaged using a cone beam dental CT scanner (Vatech Pax-Duo3D)

and the animal is allowed to recover. Three weeks later the rat is anaesthetized with isoflurane and the femur imaged again.

To account for variability in density measurements that are due to variability of the CT scanner an additional 5 mm diameter piece of rat calvaria (phantom) is placed in the field of view (FOV) during imaging of the femur.

After obtaining the CT image the cross sectional density of the bone 3 mm dorsal to the implant site is measured in three places and the measurements averaged. The density of the phantom is measured at the same time and is compared to the phantom measurement on week 0. The apparent density of the phantom on week 3 is divided by the apparent density of the phantom on week zero to determine the normalization factor. After calculating the normalization factor the bone density measurements on week 3 are then divided by the same factor.

After the week 3 density data has been normalized it is expressed as a percentage of the density measurement taken on week 0.

For example the density of the femur of a vehicle treated rat imaged on week 0 is measured at 3028, 3597 and 3329 units (average=3318) and the phantom measured 4209 units. On week three the femur density measurements are 2809, 3478 and 3353 (average=3213) units and the phantom measurement is 4004 units. The ratio of week 3 to week 0 phantom measurement is 4004/4209=0.95. The week 3 bone density values are divided by 0.95 to give 2952,3656, 3525 (average=3378). The relative density on bone at week 3 compared to week 0 is then calculated as:

$$\text{average week } 3_{normalized}/\text{average week } 0*100=3378/3318*100=101.8\%$$

Figure 5:
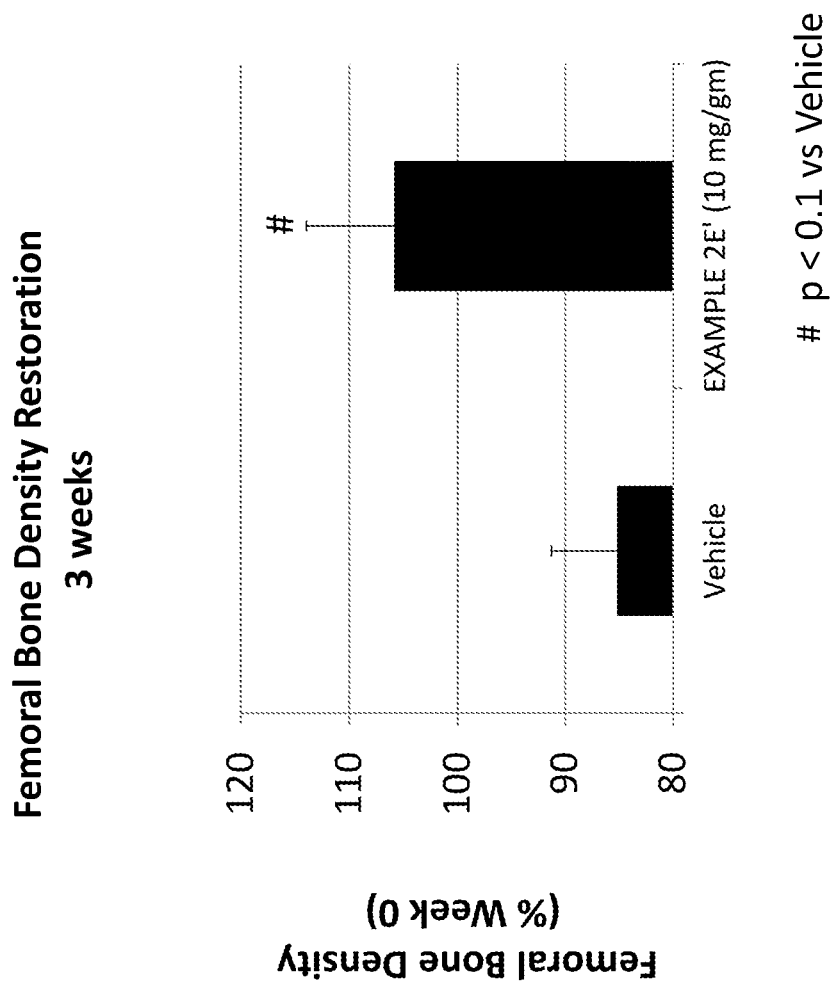
FIG. 5 depicts the effect of Compound 2E' on bone mineral density in a rat femur following an osteotomy.

The mean change in bone density of both groups after three weeks of treatment is shown in FIG. 5.

Example 98

Effect of Varying Concentrations of $\alpha$ and $\beta$TCP on Dissolution Rate

Five different cements varying in their $\alpha$TCP content from 0 (100% $\beta$TCP) to 100% $\alpha$TCP were prepared. After setting for 24 hrs the cements were ground to a powder and incubated for 2 days at 37° C. in phosphate buffered saline (PBS). After the two days the samples were spun at low speed to precipitate the large granular material (pellet). The supernatant was then spun again at high speed to precipitate the fine material (super). The weight of the granular material and the fine material was added and subtracted from the original weight of the cement. The difference was calculated to be cement that had dissolved into the PBS during the 48 hrs in the PBS. The results are depicted in FIG. 3.

Example 99

Increased Bone Density of Osteoporotic Femur Treated by Example 28C

Dosing solutions are made from a 5 mg/ml Example 28C stock which is made by dissolving 2.08 mg of neat Example 28C in 416 µl of 100% ethanol.

The 300 µg/gm dosing solution for Example 28C is made by adding 1.49 µL of the 5 mg/ml stock to 24.8 mg of calcium phosphate cement powder. The 100 µg/gm dosing solution for Example 28C is made by diluting the 5 mg/ml stock ten-fold in 100% ethanol to give a final concentration of 0.5 mg/ml and then adding 7.44 µL of the 0.5 mg/ml stock to 37.2 mg of calcium phosphate cement powder. The Vehicle dosing solution is made by adding 50.4 µl of ethanol containing no Example 28C to 30.1 mg of calcium phosphate cement powder.

After the ethanol has been vented off, the cement is wetted with a setting solution and mixed thoroughly for 1 minute as the cement begins to set. The cement is separated into five aliquots and placed on a glass microscope slide. A second microscope slide separated by 1 mm spacer is placed on the slide containing the drug-cement aliquots and the cement allowed to set between the glass slides overnight.

The cement-drug blocks are stored at room temperature until insertion into a recipient animal within one week.

The ovaries of four month old Female Sprague Dawley rats are removed and the animal allowed to recover. Eight months after removal of the ovaries the right femur is exposed and a 1 mm osteotomy drilled mid shaft from the anterior surface of the femur through to the bone marrow cavity.

The thickness of the femur is approximately 1 mm. Thus the dosing volume for each osteotomy is $\pi*r^2*\text{bone thickness}=3.14*0.5^2*1=0.8$ µl.

Immediately after creation of the osteotomy a dosing cement block is trimmed with a scalpel into a cylinder of 1 mm diameter and 1 mm thickness. The cement contains either no drug (Vehicle), 100 µg/gm or 300 µg/gm of Example 28C. The operation area is closed and sutured. The femur is imaged using a cone beam dental CT scanner (Vatech Pax-Duo3D) and the animal is allowed to recover. Twenty weeks later the rat is anaesthetized with isoflurane and the femur imaged again.

To account for variability in density measurements that are due to variability of the CT scanner an additional 5 mm diameter piece of rat calvaria (phantom) is placed in the field of view (FOV) during imaging of the femur.

After obtaining the CT image the cross sectional density of the bone 3 mm dorsal to the implant site is measured in three places and the measurements averaged. The density of the phantom is measured at the same time and is compared to the phantom measurement on week 0. The apparent density of the phantom on week 20 is divided by the average measured density of the phantom from all of the images taken to determine the normalization factor. After calculating the normalization factor the bone density measurements on week 20 are then divided by the same factor.

After the week 20 density data has been normalized it is expressed as a percentage of the density measurement taken on week 0.

For example the density of the femur of a vehicle treated rat imaged on week 0 is measured at 3838, 3878 and 3152 units (average=3623) and the phantom measured at 3678 units. On week twenty the femur density measurements are 4032, 4155 and 3038 (average=3742) units and the phantom measurement is 4021 units. The average phantom measurement from all images is 3965. The ratio of week 20 phantom to the average phantom measurement is 4021/3965=1.02. The week 20 bone density value is divided by 1.02 to give 3689. Likewise the week 0 density value of 3623 is divided by the product of the phantoms (3678/3965=0.93) to give 3905. The relative density on bone at week 20 compared to week 0 is then calculated as:

$$\text{average week } 20_{normalized}/\text{average week } 0_{normalized}*100=3689/3905*100=94\%$$

Figure 6:
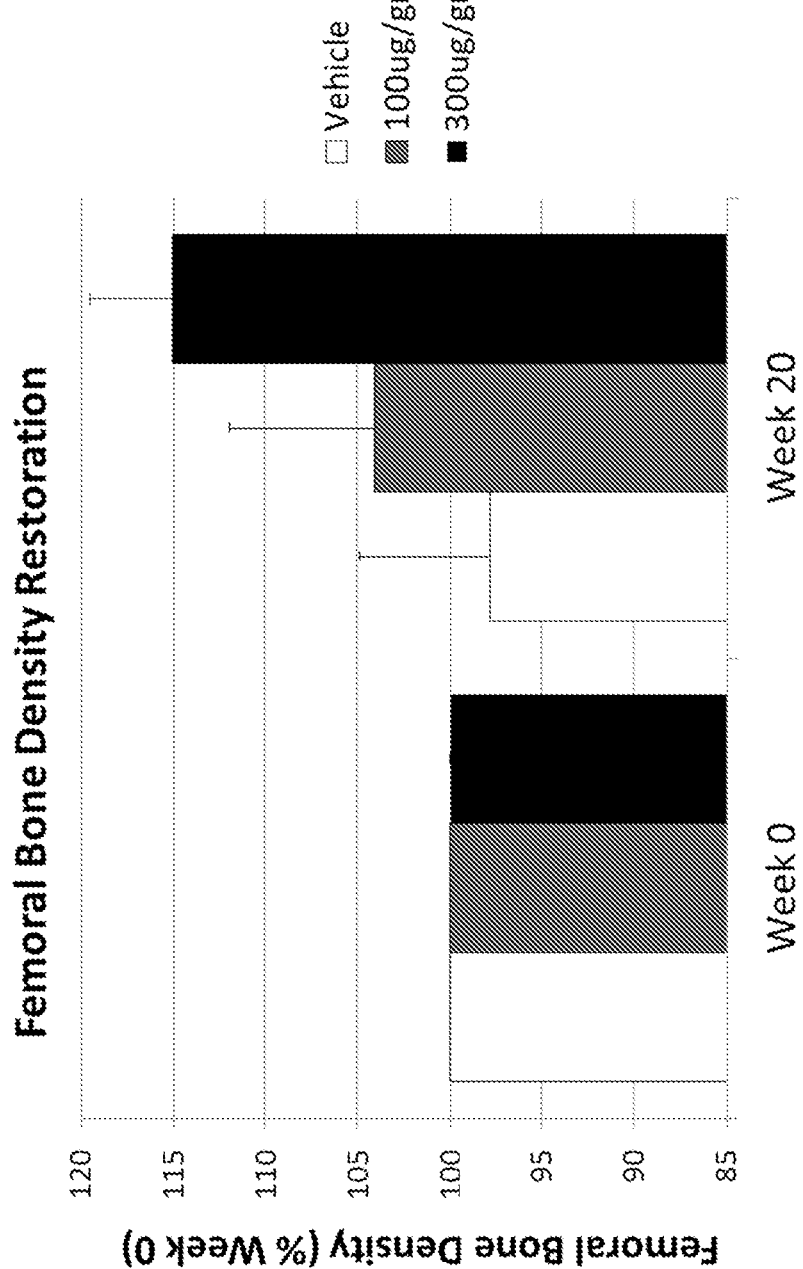
FIG. 6 depicts the effect of Compound 28C on femoral bone density in a rat following an osteotomy.

The mean change in bone density of both groups after twenty weeks of treatment is shown in the FIG. 6.

We claim:
1. A bone composition comprising:
   a drug-carrier mixture, the drug-carrier mixture comprising a calcium phosphate cement and a therapeutically effective amount of a compound of Formula (Ia):

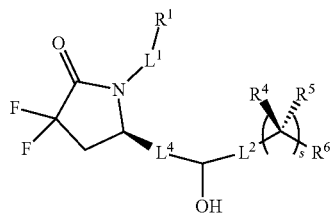

(Ia)

or a pharmaceutically acceptable salt thereof, wherein
$L^1$ is
   a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;
   b) —(CH$_2$)$_t$-G-(CH$_2$)$_p$—; wherein t is 0, 1, or 2, p is 0, 1, 2, or 3, and t+p=0, 1, 2, 3, or 4; or
   c) —(CH$_2$)$_n$-G$^1$-(CH$_2$)$_p$—, —(CH$_2$)$_n$-G$^2$-(CH$_2$)$_p$—, —(CH$_2$)$_n$—C≡C-G$^2$-, or —(CH$_2$)$_n$—C(R$^{13}$)═C(R$^{13}$)-G$^2$-, wherein n is 1, 2, 3, 4, or 5, p is 0, 1, 2, or 3, and n+p=1, 2, 3, 4, 5, or 6;
G is

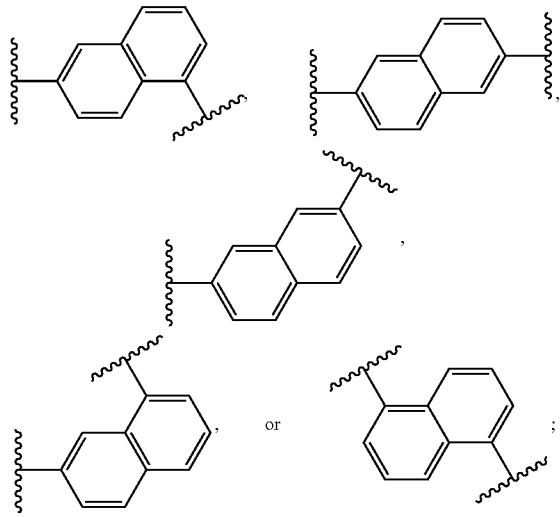

$G^1$ is O, C(O), S, S(O), S(O)$_2$, or NR$^8$; wherein R$^8$ is H, $C_1$-$C_4$ alkyl, or $C_1$-$C_4$alkylcarbonyl;
$G^2$ is

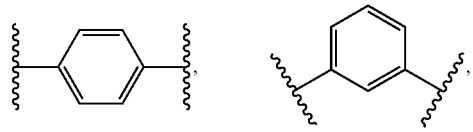

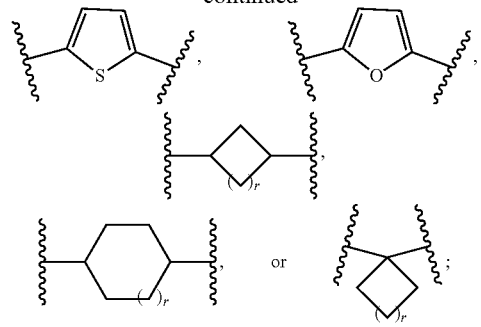

wherein $G^2$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;
$R^1$ is COOR$^{10}$, CONR$^{10}$R$^{11}$, CH$_2$OR$^{10}$, SO$_3$R$^{10}$, SO$_2$NR$^{10}$R$^{11}$, PO(OR$^{10}$)$_2$, or tetrazol-5-yl;
$R^{10}$ is H, $C_1$-$C_4$ alkyl, or aryl;
$R^{11}$ is H, $C_1$-$C_4$ alkyl, COR$^{12}$, OR$^{10}$, or SO$_2$R$^{12}$;
$R^{12}$ is $C_1$-$C_4$ alkyl;
$R^{13}$, at each occurrence, is independently H or $C_1$-$C_4$alkyl;
$L^4$ is —C(R$^2$)$_2$—C(R$^3$)$_2$—, —C(R$^2$)═C(R$^3$)—, —C≡C—, or

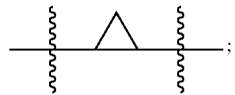

wherein R$^2$ and R$^3$ are each H, CH$_3$, fluoro, or chloro;
$L^2$ is —CH$_2$— or a bond;
$R^4$ and $R^5$ are each independently H, F, CF$_3$, or $C_1$-$C_4$ alkyl; or $R^4$ and $R^5$ together with the carbon to which they are attached form a $C_3$-$C_5$ cycloalkyl,

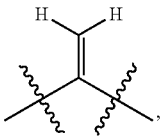

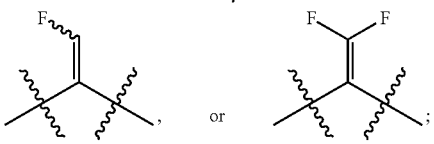

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or L$^3$-R$^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy; and wherein the $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, and $C_3$-$C_{10}$haloalkynyl are optionally substituted with a substituent selected from the group consisting of COOR$^{10'}$, CONR$^{10'}$R$^{11'}$, CH$_2$OR$^{10'}$, SO$_3$R$^{10'}$, SO$_2$NR$^{10'}$R$^{11'}$, PO(OR$^{10'}$)$_2$, and tetrazol-5-yl;

$R^{10'}$ is H, $C_1$-$C_4$ alkyl, or aryl;

$R^{11'}$ is H, $C_1$-$C_4$ alkyl, $COR^{12'}$, $OR^{10'}$, or $SO_2R^{12'}$;

$R^{12'}$ is $C_1$-$C_4$ alkyl;

$L^3$ is $C_1$-$C_6$alkylene, $C_2$-$C_6$alkenylene, $C_2$-$C_6$alkynylene, —$(CH_2)_m$-$G^3$-$(CH_2)_q$—, —$(CH_2)_m$-$G^4$-$(CH_2)_q$—, or -$G^5$-C≡C—; wherein the $C_1$-$C_6$alkylene, $C_2$-$C_6$alkenylene, and $C_2$-$C_6$alkynylene are optionally substituted with 1, 2, 3, or 4 fluoro substituents; and wherein m and q are each independently 0, 1, 2, or 3 and m+q=0, 1, 2, 3, or 4;

$G^3$ is O, C(O), S, S(O), S(O)$_2$, or $NR^9$; wherein $R^9$ is H, $C_1$-$C_4$ alkyl, or $C_1$-$C_4$alkylcarbonyl;

$G^4$ is

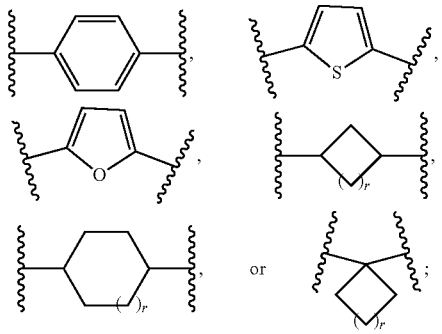

wherein $G^4$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$G^5$ is

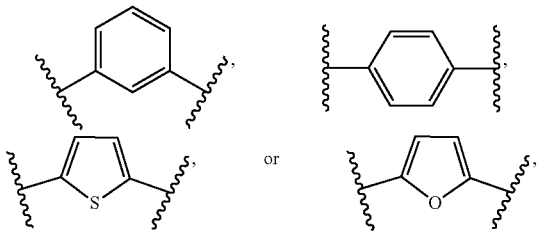

wherein $G^5$ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy;

r is 0 or 1; and s is 0 or 1; and a collagen sponge or a bone matrix, the bone matrix being at least partially demineralized.

2. The bone composition of claim 1, wherein the calcium phosphate cement is produced from setting one or more of α-tricalcium phosphate, β-tricalcium phosphate, hydroxyapatite, dicalcium phosphate, or tetracalcium phosphate.

3. The bone composition of claim 1, wherein the calcium phosphate cement is non-ceramic.

4. The bone composition of claim 1, wherein the bone matrix is fully demineralized.

5. The bone composition of claim 1, wherein the bone matrix is partially demineralized.

6. The bone composition of claim 4, wherein the bone matrix is in a ground form.

7. The bone composition of claim 1, wherein the bone matrix is in intact form.

8. The bone composition of claim 7, wherein the composition is in the form of chips.

9. The bone composition of claim 7, wherein the composition is in the form of strips.

10. The bone composition of claim 1, further comprising at least one of an organic bisphosphonate; a cathepsin K inhibitor; an estrogen or an estrogen receptor modulator; calcitonin; an inhibitor of osteoclast proton ATPase; an inhibitor of HMG-CoA reductase; an αvβ3integrin receptor antagonist; a bone morphogenic protein; a RANKL inhibitor; parathyroid hormone; Vitamin D or a synthetic Vitamin D analogue; an androgen or an androgen receptor modulator; an activator of Wnt/β-catenin signaling; bortezomib; strontium ranelate; platelet-derived growth factor; and the pharmaceutically acceptable salts and mixtures thereof.

11. The bone composition of claim 1, wherein the compound of Formula (Ia) activates osteoblasts.

12. The bone composition of claim 1, wherein the compound of Formula (Ia) inhibits osteoclasts.

13. The bone composition of claim 1, comprising at least one drug that activates osteoblasts and at least one drug that inhibits osteoclasts.

14. The bone composition of claim 1, wherein the compound of Formula (Ia) activates osteoblasts and inhibits osteoclasts.

15. A bone composition comprising:

a solid insert comprising a therapeutically effective amount of a compound of Formula (Ia):

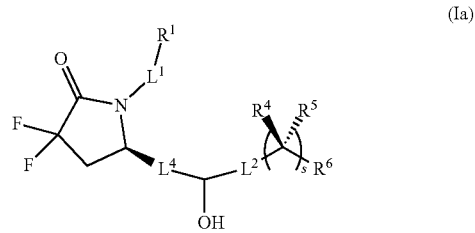

(Ia)

or a pharmaceutically acceptable salt thereof, wherein:

$L^1$ is a) $C_3$-$C_7$alkylene, $C_3$-$C_7$alkenylene, or $C_3$-$C_7$alkynylene, wherein the $C_3$-$C_7$alkylene, $C_3$-$C_7$alkenylene, or $C_3$-$C_7$alkynylene are each optionally substituted with 1, 2, 3, or 4 fluoro substituents;

b) —$(CH_2)_t$-G-$(CH_2)_p$—; wherein t is 0, 1, or 2, p is 0, 1, 2, or 3, and t+p=0, 1, 2, 3, or 4; or c) —$(CH_2)_n$-$G^1$-$(CH_2)_p$—, —$(CH_2)_n$-$G^2$-$(CH_2)_p$—, —$(CH_2)_n$—C≡C-$G^2$-, or —$(CH_2)_n$—C($R^{13}$)=C($R^{13}$)-$G^2$-, wherein n is 1, 2, 3, 4, or 5, p is 0, 1, 2, or 3, and n+p=1, 2, 3, 4, 5, or 6;

G is

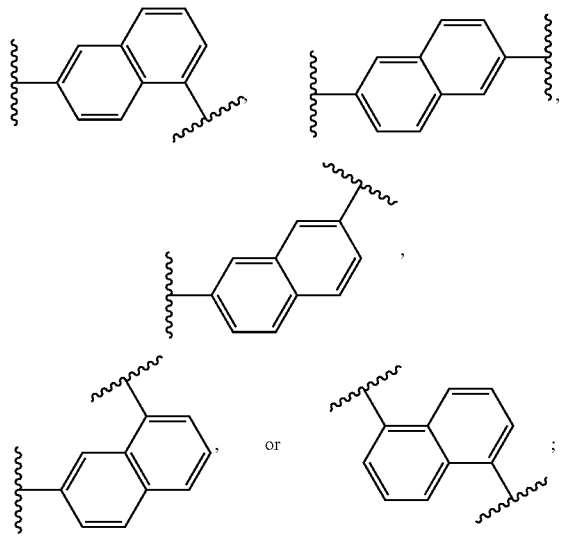

$G^1$ is O, C(O), S, S(O), S(O)$_2$, or NR$^8$; wherein R$^8$ is H, C$_1$-C$_4$ alkyl, or C$_1$-C$_4$alkylcarbonyl;

$G^2$ is

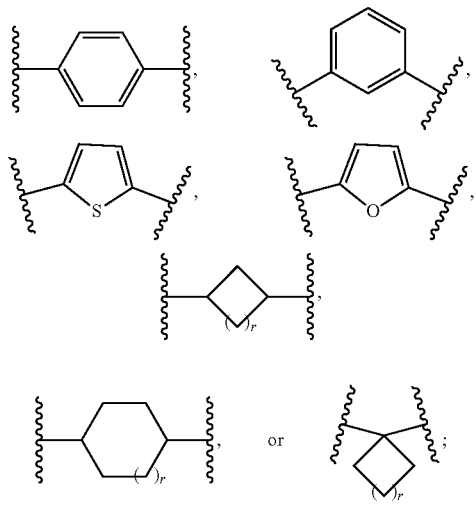

wherein G$^2$ is optionally substituted with 1, 2, or 3 substituents selected from the group consisting of C$_1$-C$_4$alkyl, C$_1$-C$_3$haloalkyl, cyano, halogen, C$_1$-C$_3$alkoxy, and C$_1$-C$_3$haloalkoxy;

R$^1$ is COOR$^{10}$, CONR$^{10}$R$^{11}$, CH$_2$OR$^{10}$, SO$_3$R$^{10}$, SO$_2$NR$^{10}$R$^{11}$, PO(OR$^{10}$)$_2$, or tetrazol-5-yl;

R$^{10}$ is H, C$_1$-C$_4$ alkyl, or aryl;

R$^{11}$ is H, C$_1$-C$_4$ alkyl, COR$^{12}$, OR$^{10}$, or SO$_2$R$^{12}$;

R$^{12}$ is C$_1$-C$_4$ alkyl;

R$^{13}$, at each occurrence, is independently H or C$_1$-C$_4$alkyl;

L$^4$ is —C(R$^2$)$_2$—C(R$^3$)$_2$—, —C(R$^2$)=C(R$^3$)—, —C≡C—, or

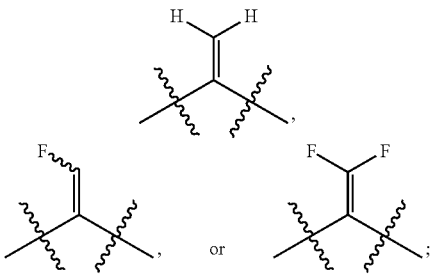

wherein R$^2$ and R$^3$ are each H, CH$_3$, fluoro, or chloro;

L$^2$ is —CH$_2$— or a bond;

R$^4$ and R$^5$ are each independently H, F, CF$_3$, or C$_1$-C$_4$ alkyl; or R$^4$ and R$^5$ together with the carbon to which they are attached form a C$_3$-C$_5$ cycloalkyl,

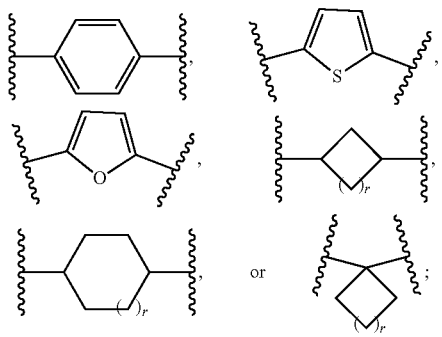

R$^6$ is aryl, heteroaryl, C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, C$_3$-C$_{10}$haloalkynyl, or L$^3$-R$^7$; wherein the aryl and heteroaryl are optionally substituted with 1, 2, 3, or 4 substituents selected from the group consisting of C$_1$-C$_4$alkyl, C$_1$-C$_3$haloalkyl, cyano, halogen, C$_1$-C$_3$alkoxy, C$_1$-C$_3$haloalkoxy; and —C$_1$-C$_3$alkylene-C$_1$-C$_3$alkoxy; and wherein the C$_3$-C$_{10}$alkyl, C$_3$-C$_{10}$alkenyl, C$_3$-C$_{10}$alkynyl, C$_3$-C$_{10}$haloalkyl, C$_3$-C$_{10}$haloalkenyl, and C$_3$-C$_{10}$haloalkynyl are optionally substituted with a substituent selected from the group consisting of COOR$^{10'}$, CONR$^{10'}$R$^{11'}$, CH$_2$OR$^{10'}$, SO$_3$R$^{10'}$, SO$_2$NR$^{10'}$R$^{11'}$, PO(OR$^{10'}$)$_2$, and tetrazol-5-yl;

R$^{10'}$ is H, C$_1$-C$_4$ alkyl, or aryl;

R$^{11'}$ is H, C$_1$-C$_4$ alkyl, COR$^{12'}$, OR$^{10'}$, or SO$_2$R$^{12'}$;

R$^{12'}$ is C$_1$-C$_4$ alkyl;

L$^3$ is C$_1$-C$_6$alkylene, C$_2$-C$_6$alkenylene, C$_2$-C$_6$alkynylene, —(CH$_2$)$_m$-G$^3$-(CH$_2$)$_q$—, —(CH$_2$)$_m$-G$^4$-(CH$_2$)$_q$—, or -G$^5$-C≡C—; wherein the C$_1$-C$_6$alkylene, C$_2$-C$_6$alkenylene, and C$_2$-C$_6$alkynylene are optionally substituted with 1, 2, 3, or 4 fluoro substituents; and wherein m and q are each independently 0, 1, 2, or 3 and m+q=0, 1, 2, 3, or 4;

G$^3$ is O, C(O), S, S(O), S(O)$_2$, or NR$^9$; wherein R$^9$ is H, C$_1$-C$_4$ alkyl, or C$_1$-C$_4$alkylcarbonyl;

G$^4$ is wherein G⁴ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

G⁵ is

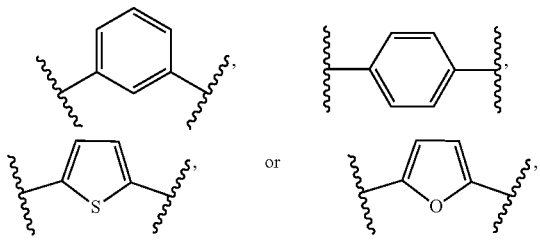

wherein G⁵ is optionally substituted with 1, 2, or 3 substituents selected from the group consisting of $C_1$-$C_4$alkyl, $C_1$-$C_3$haloalkyl, cyano, halogen, $C_1$-$C_3$alkoxy, and $C_1$-$C_3$haloalkoxy;

R⁷ is $C_3$-$C_8$cycloalkyl, aryl, heteroaryl, or heterocyclyl; wherein R⁷ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy;

r is 0 or 1; and s is 0 or 1;

the compound of Formula (Ia) being disposed in a set non-ceramic calcium phosphate cement, the compound of Formula (Ia) being embedded substantially homogeneously throughout the set non-ceramic calcium phosphate cement.

16. The bone composition of claim 15, wherein the calcium phosphate cement prior to setting comprises one or more of α-tricalcium phosphate, β-tricalcium phosphate, hydroxyapatite, dicalcium phosphate, or tetracalcium phosphate.

* * * * *